US007851637B2

(12) United States Patent
Castro et al.

(10) Patent No.: US 7,851,637 B2
(45) Date of Patent: *Dec. 14, 2010

(54) COMPOUNDS AND METHODS FOR INHIBITING THE INTERACTION OF BCL PROTEINS WITH BINDING PARTNERS

(75) Inventors: Alfredo C. Castro, Winchester, MA (US); Wei Deng, Lexington, MA (US); Kristopher M. Depew, Acton, MA (US); Michael A. Foley, Chestnut Hill, MA (US); Christian C. Fritz, Natick, MA (US); Asimina T. Georges Evangelinos, Andover, MA (US); Michael J. Grogan, Arlington, MA (US); Nafeeza Hafeez, West Roxbury, MA (US); Edward B. Holson, Newton Highlands, MA (US); Brian T. Hopkins, Brookline, MA (US); Nii O. Koney, Somerville, MA (US); Tao Liu, Ashland, MA (US); David A. Mann, Swampscott, MA (US); Lisa A. Marcaurelle, Arlington, MA (US); Daniel A. Snyder, Cambridge, MA (US); Dennis J. Underwood, Jamaica Plain, MA (US); Andrew A. Wylie, Brookline, MA (US); Lin-Chen Yu, Wollaston, MA (US); Linping Zhang, Lexington, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 46 days.

This patent is subject to a terminal disclaimer.

(21) Appl. No.: 11/156,364

(22) Filed: Jun. 17, 2005

(65) Prior Publication Data

US 2006/0025460 A1 Feb. 2, 2006

Related U.S. Application Data

(60) Provisional application No. 60/580,616, filed on Jun. 17, 2004, provisional application No. 60/659,301, filed on Mar. 7, 2005.

(51) Int. Cl.
*C07D 261/02* (2006.01)
*A61K 31/42* (2006.01)

(52) U.S. Cl. ...................... 548/240; 514/378
(58) Field of Classification Search ................ 548/240; 514/378
See application file for complete search history.

(56) References Cited

U.S. PATENT DOCUMENTS

| 5,294,617 | A | 3/1994 | Venkatesan et al. |
| 5,514,505 | A | 5/1996 | Limburg et al. |
| 6,221,865 | B1 * | 4/2001 | Sebti et al. ............. 514/235.5 |
| 6,747,050 | B1 | 6/2004 | Kim et al. |

FOREIGN PATENT DOCUMENTS

| DE | 3643012 A1 | 6/1988 |
| EP | 0769296 A1 | 4/1997 |
| EP | 0970950 A2 | 1/2000 |
| JP | 11343285 A | 12/1999 |
| WO | WO-95/24398 A1 | 9/1995 |
| WO | WO 98/08694 | 2/1998 |
| WO | WO 98/16830 | 4/1998 |
| WO | WO 01/16115 A1 | 3/2001 |
| WO | WO-02/097053 | 12/2002 |
| WO | WO 03/105788 A1 | 2/2003 |
| WO | WO-2006/009869 | 1/2006 |

OTHER PUBLICATIONS

Blanarikova-Hlobilova et al. (Tetrahedron, 59(2003), 3333-3339).*
Kubinyi (3D QSAR in Drug Design: Ligand-Protein Interactions and Molecular Similarity, vol. 2-3, Springer, 1998, 800 pages).*
Byrn et al., Pharm. Res., v. 12, n. 7, p. 945-54, 1995.*
Tan, D. S. et al., "Stereoselective Synthesis of over Two Million Compounds Having Structural Features Both Reminiscent of Natural Products and Compatible with Miniaturized Cell-Based Assays", *J. Am. Chem. Soc.*, 120:8565-8566 (1998).
Banerji. A. et a., "1.3-Dipolar cycloadditions: Part VII—Cycloaddition of C.N-diarytnitrones to ethyl crotonate", *Ind. Journ. of Chem.*, 43B:1925-1933 (Sep. 2004).
Dugović , B., et al., "Reversal of Regioselectivity of Nitrone Cycloadditions by Lewis Acids", *Helvetica Chimica Acta*, 88:1432-1443 (2005).
Inouye, Y., et al., "Regioselective Effects of the Allylic Heteroatoms in 1,3-Dipolar Cycloaddition of Nitrones to Several Allyl Derivatives", *Heterocycles*, 25:109-111 (1987).
Jen, W. S., et al., "New Strategies for Organic Catalysis: The First Enantioselective Organocatalytic 1,3-Dipolar Cycloaddition", *J. Am. Chem. Soc.*, 122:9874-9875 (2000).
Kanemasa, S. et al., "Metal Ion-Mediated Diastereoface-Selective Nitrone Cycloadditions. Reaction Mechanism for the Reversal of Regioselectivity Observed in the Magnesium and Zinc Ion-Mediated Nitrone Cycloadditions of Allylic Alcohols", *Tetrahedron Letters*, 38(28):5019-5022 (1995).
Kanemasa. S. et al., "Metallic Base-Induced and Lewis Acid-Catalyzed Nitrone Cycloadditions to Allyl Alcohol Dipolarophiles. Highly Effective Regio- and Stereocontrol", *Tetrahedron Letters*, 34(1):87-90 (1993).

(Continued)

*Primary Examiner*—Robert Havlin
(74) *Attorney, Agent, or Firm*—Foley Hoag LLP

(57) ABSTRACT

One aspect of the present invention relates to heterocyclic compounds that bind to bcl proteins and inhibit Bcl function. Another aspect of the present invention relates to compositions comprising a heterocyclic compound of the invention. The present invention provides methods for treating and modulating disorders associated with hyperproliferation, such as cancer.

17 Claims, 1 Drawing Sheet

OTHER PUBLICATIONS

Kano, T. et al., "Asymmetric 1,3-Dipolar Cycloaddition Reaction of Nitrones and Acrolein with a Bis-Titanium Catalyst as Chiral Lewis Acid", *J. Am. Chem. Soc.*, 127:11926-11927 (2005).

Merino, P. et al., "1,3-Dipolar Cycloadditions of N-Benzyl Furfuryl Nitrones with Electron-rich Alkenes", *Molecules*, 5:132-152 (2000).

Merino, P. et al., "A DFT Study on the 1,3-Dipolar Cycloaddition Reactions of C-(methylcarbonyl)-$N$-methyl nitrone with methyl acrylate and vinyl acetate", *Tetrahedron*, 59:3581-3592 (2003).

Niu, D. et al., "Non-Cycloaddition Approach to Regioselective Synthesis of Isoxazolidines", *Synlett*, 979-980 (Sep. 1998).

Puglisi, A. et al., "Enantioselective 1,3-Dipolar Cycloadditions of Unsaturated Aldehydes Promoted by a Poly(ethylene glycol)-Supported Organic Catalyst", *Eur. J. Org. Chem.*, 567-573 (2004).

Ratts, K. W. et al., "Chemistry of Resonance-Stabilized Sulfonium Ylids", *J. Org. Chem.*, 1689-1693 (Jun. 1966).

Revuelta, J. et al., "Samarium(II) iodide reduction of isoxazolidines", *Tetrahedron Letters*, 45:8375-8377 (2004).

Saito. T. et al., "Evaluation of chiral bidentate ligand-metal complexes in asymmetric 1,3 dipolar cycloaddition reaction of nitrones with 3-alkenoyl-2-oxazolidinones", *Tetrahedron Letters*, 45:9581-9584 (2004).

Sibi, M. P. et al., "Exo Selective Enantiosetective Nitrone Cycloadditions", *J. Am. Chem. Soc.*, 128:718-719 (2004).

"Infinity Pharmaceuticals—ACS Prospectives Conference Series", PowerPoint Presentation Sep. 22, 2003.

"Infinity Pharmaceuticals—Cambridge Health Institute's Conference on Diversity-Oriented Synthesis (DOS) and Natural Product Chemistry", PowerPoint Presentation Oct. 9, 2003.

Foley, M., "Infinity Pharmaceuticals—ACS Short Course on Drug Discovery in the 21st Century—Arrayed Split-Pool Libraries: Developing a Platform for Chemical Genetic Studies", PowerPoint Presentation Jul. 10, 2002.

Foley, M., "Infinity Pharmaceuticals—Chemical Genomics-Linking the Genome to Therapies", PowerPoint Presentation Jun. 11, 2002.

Foley, M., "Infinity Pharmaceuticals—Infiniplex Libraries: Developing a Platform for Chemical Genetic Studies", PowerPoint Presentation Oct. 2, 2002.

Akmanova, N. A. et al., "Dipolar Addition to Carbamoyl Nitrones", *Zhurnal Organicheskoi Khimii*, 15(10):2061-2065 (Oct. 1979) (English translation).

Baell, J. et al., "Prospects for targeting the Bcl-2 family of proteins to develope novel cytotoxic drugs", *Biochem. Pharmacol.*, 64:851-863 (2002).

Ding, X. et al., "Catalytic Asymmetric 1,3-Dipolar Cycloaddition of a Nitrone Bearing a Bulky Amide Moiety to γ-Substituted Allylic Alcohols", *Chemistry Letters*, 2002:302-303 (2002).

Ratts, K. W. et al., "Chemistry of Resonance-Stabilized Sulfonium Ylids", *Journal of Organic Chemistry*, 31(6):1689-1693 (1966).

International Search Report dated Dec. 16, 2005.

\* cited by examiner

COMPOUNDS AND METHODS FOR INHIBITING THE INTERACTION OF BCL PROTEINS WITH BINDING PARTNERS

RELATED APPLICATIONS

This application claims the benefit of priority to U.S. Provisional Patent Applications Ser. Nos. 60/580,616, filed Jun. 17, 2004; and 60/659,301, filed Mar. 7, 2005, both applications are incorporated in their entirety.

FIELD OF THE INVENTION

The invention is in the field of cancer therapeutics. Specifically, the present invention is in the field of cancer therapeutics that promote apoptosis in tumor cells using isoxazolidine analogs. The isoxazolidine compounds of the invention bind to Bcl proteins and block Bcl anti-apoptotic function in cancer cells and tumor tissue expressing the Bcl proteins. The compounds, and pharmaceutical compositions comprising these compounds, may be used in the treatment of cancerous disease either alone or in combination with chemotherapeutics or other drugs.

BACKGROUND OF THE INVENTION

Apoptosis, or programmed cell death, is important for normal embryological/ananatomical development, host defense and suppression of oncogenesis. Faulty regulation of apoptosis has been implicated in cancer and many other human diseases which result from an imbalance between the process of cell division and cell death. Bcl-2 was originally identified at the chromosomal breakpoint of t(14;1 8)-bearing B-cell lymphomas and belongs to a growing family of proteins which regulate apoptosis. (Gross, A; McDonnell, J M; Korsmeyer, S. J. BCL-2family members and the mitochondria in apoptosis. Genes & Development 1999, 13, 1899-1911, Cory, S.; Huang, D. C. S.; Adams, J. M. The Bcl-2 family: roles in cell survival and oncogenesis. Oncogene, 2003 22, 8590-8607. Danial, N. N.; Korsmeyer, S. J. Cell death: Critical control points. Cell 2004, 116, 205-218. Chao, D. T.; Korsmeyer, S. J. Bcl-2 family: regulators of cell death. Annu. Rev. Immunol. 1998, 16, 395-419). Apoptosis, Christopher Potten, James Wilson, Cambridge University Press, 2004). The Bcl-2 family of proteins include both anti-apoptotic molecules, such as Bcl-2 and Bcl-XL, and pro-apoptotic molecules, such as Bax, Bak, Bid and Bad. Bcl-2 contributes to cancer cell progression by preventing normal cell turnover caused by physiological cell-death mechanisms. Over-expression of Bcl-2 has been observed in 70% of breast cancer and many other forms of cancer (Buolaniwini, J. K. Novel anticancer drug discovery. Curr. Opin. Chem. Biol. 1999, 3, 500-509). The expression levels of Bcl-2 proteins also correlate with resistance to a wide spectrum of chemotherapeutic drugs and γ-radiation therapy (Reed, J. C.; Miyashita, T.; Takayama, S.; Wang, H. G.; Sato, T.; Krajewski, S.; Aime-Sempe, C.; Bodrug, S.; Kitada, S.; Hanada, M. Bcl-2 family proteins: Regulators of cell-death involved in the pathogenesis of cancer and resistance to therapy. J. Cell. Biochem. 1996, 60, 23-32; Reed, J. C. Bcl-2 family proteins: strategies for overcoming chemoresistance in cancer. Advances in Pharmocology 1997, 41, 501-553; Strasser, A.; Huang, D. C. S.; Vaux, D. L. The role of the Bcl-2/ced-9 gene family in cancer and general implications of defects in cell death control for tumorigenesis and resistance to chemotherapy. Biochem. Biophys. Acta 1997,1333, F151-F189; DiPaola, R. S.; Aisner, J. Overcoming Bcl-2- and p53-mediated resistance in prostate cancer. Semin. Oncol. 1999, 26, 112-116).

Members of the Bcl-2 family of proteins represent key regulators of apoptosis, with pro-apoptotic (e.g., Bax, Bak, Bid, Bim, Noxa, Puma) and anti-apoptotic function (e.g., Bcl-2, Bcl-xL, Mcl-1). Selective and competitive dimerization between pro-and anti-apoptotic members of the family determines the fate of a cell given pro-apoptotic stimulus. Although the precise roles of Bcl-2 and Bcl-xL in cancer are not completely understood, there are several lines of evidence that suggest that Bcl-2 and Bcl-xL not only contribute to cancer progression by preventing normal cell turnover, but also play a role in the resistance of cancer cells to current cancer treatments. Experimental over-expression of Bcl-2 (Bcl-xL) renders cancer cells resistant to a wide spectrum of chemotherapeutic agents and radiation (Bcl-2 family proteins: Regulators of cell-death involved in the pathogenesis of cancer and resistance to therapy. J. Cell. Biochem. 1996, 60, 23-32; Reed, J. C). Bcl-2 and/or Bcl-xL are over-expressed in more than 50% of all tumors as shown below (from Wang, S.; Yang, D.; Lippman, M. E. Targeting Bcl-2 and Bcl-xL with nonpeptidic small-molecule antagonists. Seminars in Oncology, 2003, 5, 133-142).

| Cancer type | Bcl-2 over-expression (%) | Bcl-xL over-expression (%) |
|---|---|---|
| Prostate | 20-40 | 100 |
| hormone resistant | 80-100 | — |
| Breast | 60-80 | 40-60 |
| Non-small cell lung | 20-40 | — |
| Small cell lung | 60-80 | — |
| Colorectal | 50-100 | 83 |
| Melanoma | 65 | 90 |
| Multiple myeloma (at relapse) | — | 77 |
| Head and Neck | 13 | 52-75 |
| Pancreatic | 23 | 90 |
| Hepatocellular carcinoma | — | 80 |

Biological approaches to modulating Bcl-2 function using anti-sense oligonucleotides or single-chain antibodies have been shown to enhance tumor cell chemosensitivity (Ziegler, A.; Luedke, G. H.; Fabbro, D.; Altmann, K. H.; Stahel, R. A.; Zangemeister-Wittke, U. Induction of apoptosis in small-cell lung cancer cells by an antisense oligodeoxynucleotide targeting the Bcl-2coding sequence. J. Natl. Cancer. Inst. 1997, 89, 1027-1036; Webb, A.; Cunningham, D.; Cotter, F.; Clarke, P. A.; Di Stefano, F.; Ross, P.; Corpo, M.; Dziewanowska, Z. Bcl-2 antisense therapy in patients with non-hodgkin lymphoma. Lancet 1997, 349, 1137-1141; Cotter, F. E. Phase I clinical and pharmacokinetic study of Bcl-2 antisense oligonucleotide therapy in patients with non-hodgkin's lymphoma. J. Clin. Oncol. 2000, 18, 1812-1823; Piche, A.; Grim, J.; Rancourt, C.; Gomez-Navarro, J.; Reed, J. C.; Curiel, D. T. Modulation of Bcl-2 protein levels by an intracellular anti-Bcl-2 single-chain antibody increases drug-induced cytotoxicity in the breast cancer cell line MCF-7. Cancer Res. 1998, 58, 2134-2140).

It has been shown that an anti-sense oligonucleotide (G3139) (Raynaud, F. I.; Orr, R. M.; Goddard, P. M.; Lacey, H. A.; Lancashire, H.; Judson, I. R.; Beck, T.; Bryan, B.; Cotter, F. E. Pharmacokinetics of G3139, a phosphorothioate oligodeoxynucleotide antisense to Bcl-2, after intravenous administration or continuous subcutaneous infusion to mice. J. Pharmacol. Exp. Ther. 1997, 281, 420-427), designed to hybridize to sequence in Bcl-2 MRNA, inhibits Bcl-2expression, induces apoptosis and inhibits cell growth in human breast cancer cells having Bcl-2 over-expression (Chen, H. X., Marchall, J. L., Trocky, N., Baidas, S., Rizvi, N., Ling,Y., Bhagava, P., Lippman, M. E., Yang, D., and Hayes, D. F. A Phase I study of Bcl-2 antisense G3139 (Genta) and weekly docetaxel in patients with advanced breast cancer and other solid tumors. Proceedings of American Society of Clinical Oncology, 2000). Importantly, synergistic effects and complete tumor regression were observed in vivo in the combined treatments of G3139 with docetaxel. Therefore, Bcl-2 represents a highly attractive target for the development of a novel therapy for the treatment of many forms of cancers.

Limitations associated with the use of large molecules, such as oligonucleotides, proteins and polypeptides, as therapeutic agents include poor oral availability, poor in vivo stability, and high cost. More desirable therapeutics would be non-peptide, cell-permeable small molecules that bind to Bcl-2 and block the anti-apoptotic function in cancer and promote cell-death in tumors.

Various small molecules have been shown to inhibit the function of Bcl-2. For example, acyl sulfonamides were shown to inhibit the function of Bcl-2 and Bcl-xL in biochemical and in vitro assays. *Nature* (2005) 435, 677-681. Nevertheless, the need exists for additional small organic molecules that bind to Bcl-2 and block its anti-apoptotic function in cancer and promote cell death in tumors. The present invention fulfills this need and has other related advantages.

SUMMARY OF THE INVENTION

One aspect of the present invention relates to isoxazolidine compounds. In certain instances, the nitrogen atom of the isoxazolidine ring is bonded to a substituted aralkyl group. In certain instances, the substituted aralkyl group is a substituted benzyl group. In certain instances, the isoxazolidine ring is substituted with a hydroxy methyl or hydroxy ethyl group. In certain instances, the isoxazolidine ring is substituted with a hydroxy methyl and a hydroxy ethyl group. In certain instances, the isoxazolidine ring is substituted with an amide group. The present invention further provides pharmaceutically active salts of the above-mentioned isoxazolidine compounds. Another aspect of the present invention relates to pharmaceutical compositions comprising an isoxazolidine compound of the invention. Another aspect of the present invention relates to a method of using the above compounds, or pharmaceutically active salts thereof, alone or in combination with other agents to treat cancer. Specifically, the invention provides a therapeutic method comprising treating a condition characterized by the pathological proliferation of mammalian cells, such as tumors cells, (e.g., breast cancer and myeloid leukemia), by administering to a mammal or a human afflicted with such a condition an effective amount of a compound of the present invention. In certain instances, the compound of the present invention is administered with a pharmaceutically acceptable carrier.

BRIEF DESCRIPTION OF THE INVENTION

Figure 1:
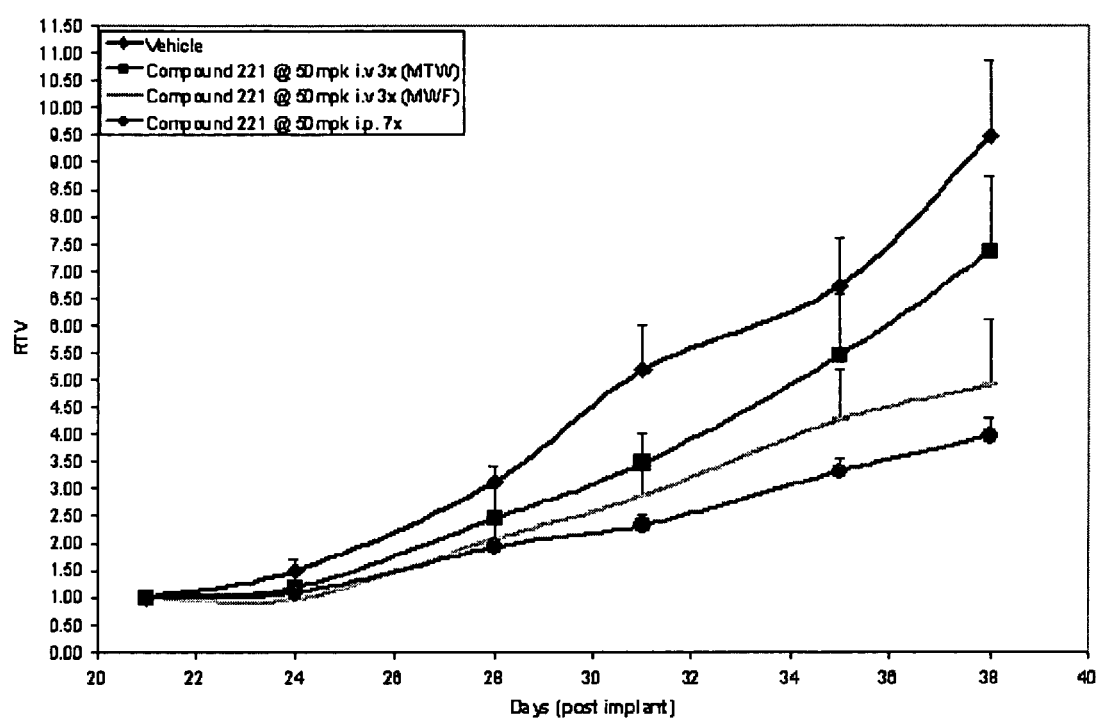
FIG. 1 depicts the results of an efficacy study of compound 221 in an RL tumor xenograft model in SCID/NOD mice.

The present invention generally relates to isoxazolidine compounds useful for treating cancer. The isoxazolidine compounds of the invention bind to one or more Bcl proteins and block Bcl anti-apoptotic function in cancer cells and tumor tissue that express the Bcl protein. In certain embodiments, certain compounds of the invention selectively inhibit the anti-apoptotic activity of only one member of the Bcl-2 subfamily of anti-apoptotic proteins. The isoxazolidine compounds of the invention can be used to treat a patient suffering from a disease related to Bcl. In certain instances, the isoxazolidine compounds of the invention are used to treat a patient suffering from cancer. The isoxazolidine compounds of the invention can be administered to a patient in the form of a pharmaceutical composition. The pharmaceutical composition comprises an isoxazolidine compound of the invention and one or more pharmaceutically acceptable excipients. In certain instances, the pharmaceutical composition comprises an isoxazolidine compound of the invention, a chemotherapeutic agent, and one or more pharmaceutically acceptable excipients. In certain instances, the chemotherapetic agent is Docetaxel, Paclitaxel, cisplatin, 5-FU, Doxrubincin, epipodophyllotoxin, camptothecin, 17-AAG, or cyclophosphamide.

Synthesis of Isoxazolidine Compounds

The isoxazolidine compounds of the invention can be prepared using a [3+2] cycloaddition reaction between a nitrone and an alkene. The nitrone substrate and alkene may contain functional groups suitable for chemical derivatization following synthesis of the isoxazolidine core. In certain instances, a Lewis acid is added to the reaction. In a preferred embodiment, the Lewis acid is $Ti(Oi-Pr)_4$. In certain instances, the reaction mixture is subjected to microwave radiation. In general, the subject reactions are carried out in a liquid reaction medium, but can be carried out on a solid support. The reactions may be conducted in an aprotic solvent, preferably one in which the reaction ingredients are substantially soluble. Suitable solvents include ethers, such as diethyl ether, 1,2-dimethoxyethane, diglyme, t-butyl methyl ether, tetrahydrofuran and the like; halogenated solvents, such as chloroform, dichloromethane, dichloroethane, chlorobenzene, carbon tetrachloride, and the like; aliphatic or aromatic hydrocarbon solvents, such as benzene, xylene, toluene, hexane, pentane and the like; esters and ketones, such as ethyl acetate, acetone, and 2-butanone; polar aprotic solvents, such as acetonitrile, dimethylsulfoxide, dimethylformamide, pyridine, and the like; or combinations of two or more solvents. The reactions can be conducted at a variety of temperatures. Generally, reactions conducted at lower temperatures will take a longer to reach completion. In certain instances, the cycloaddition reaction is conducted in the range of about 15° C. to about 60° C. In certain instances, the cycloaddition reaction is conducted in the range of about 15° C. to about 30° C. In certain instances, the cycloaddition reaction is conducted at about room temperature. In certain instances, the cycloaddition reaction is conducted in the range of about 80° C. to about 150° C. In certain instances, the cycloaddition reaction is conducted in the range of about 90° C. to about 120° C. In certain instances, the cycloaddition reaction is conducted in the range of about 95° C. to about 105° C. In certain instances, the cycloaddition reaction is conducted using a substrate attached to a solid support. Following synthesis of the isoxazolidine core, the isoxazolidine compound may be derivatized using a variety of functionalization reactions known in the art. Representative examples include palladium coupling reactions to alkenylhalides or aryl halides, oxidations, reductions, reactions with nucleophiles, reactions with electrophiles, pericyclic reactions, installation of protecting groups, removal of protecting groups, and the like.

Biological Activity Analysis

The following in vitro binding and cellular assays can be used to determine the activity and specificity of compounds of the present invention to bind to Bcl-2 and inhibit Bcl-2 function in a cell.

Bcl-2 Binding Assay

Bcl-2 and Bcl-xL binding can be determined using a variety of known methods. One such assay is a sensitive and quantitative in vitro binding assay using fluorescence polarization (FP) described by Wang, J. -L.; Zhang, Z -J.; Choksi, S.; Sjam. S.; Lu, Z.; Croce, C. M.; Alnenri, E. S.; Komgold, R.; Huang, Z. Cell permeable Bcl-2 binding peptides: a chemical approach to apoptosis induction in tumor cells. Cancer Res. 2000, 60, 1498-1502).

Cell Based Assays

The ability of isoxazolidine compounds of the present invention to inhibit cell-viability in cancer cells with Bcl-2 protein over-expression was demonstrated. When RL-cells are exposed to isoxazolidine compounds of the present invention, the inhibitors show a dose-dependent cell-killing in the Alamar blue cytoxicity assay with $IC_{50}$ values of from about 100 µM to about 1 µM (See Examples). When Panc1 cells are exposed to the isoxazolidine compounds of the present invention in combination with camptothecin, the inhibitors show a synergistic dose-dependent cell killing in the propidium iodide exclusion cell survival assay with $IC_{50}$ values of from about 100 µM to about 1 µM (See Examples).

Bcl-2 inhibitors have been shown to be active against a number of cancer cell lines as single agent, including, but not limited to, breast cancer (US 2003/0119894, published PCT applications WO 02/097053 and WO 02/13833), lymphomas (Nature (2005) 435, 677-681), small cell lung cancer (Nature (2005) 435, 677-681), head and neck cancer (published PCT application WO 02/097053), and leukemias (published PCT application WO 02/13833).

Bcl-2 inhibitors have been shown to be active against a number of cancer cell lines in combination with other anticancer agents and radiation, including, but not limited to, breast cancer (With docetaxel, published PCT application WO 02/097053), prostate cancer (With docetaxel, published PCT application WO 02/097053), head and neck cancer (With docetaxel, published PCT application WO 02/097053), and non small-cell lung cancer (With paclitaxel, Nature (2005) 435, 677-681). In addition to the aforementioned combination chemotherapeutics, small molecule inhibitors of Bcl-2 proteins display synergy with other anticancer agents, including, but not limited to etoposide, doxorubicin, cisplatin, paclitaxel, and radiation (Nature (2005) 435, 677-681).

Methods of Therapy and Treatment

The present invention further provides methods for treating and reducing the severity of cancer as well as other Bcl mediated disorders or conditions.

Cancers or neoplastic diseases and related disorders that can be treated by administration of compounds and compositions of the present invention, include, but are not limited to those listed in Table 1 (for a review of such disorders, see Fishman et al., 1985, Medicine, 2d Ed., J. B. Lippincott Co., Philadelphia):

TABLE 1

| CANCERS AND NEOPLASTIC DISORDERS |
| --- |
| Leukemia |
|   acute leukemia |
|   acute lymphocytic leukemia |
|   acute myelocytic leukemia |
|     myeloblastic |
|     promyelocytic |
|     myelomonocytic |
|     monocytic |
|     erythroleukemia |
|   chronic leukemia |

TABLE 1-continued

| CANCERS AND NEOPLASTIC DISORDERS |
| --- |
|   chronic myelocytic (granulocytic) leukemia |
|   chronic lymphocytic leukemia |
| Polycythemia vera |
| Lymphoma |
|   Hodgkin's disease |
|   non-Hodgkin's disease |
| Multiple myeloma |
| Waldenstrom's macroglobulinemia |
| Heavy chain disease |
| Solid tumors |
|   sarcomas and carcinomas |
|     fibrosarcoma |
|     myxosarcoma |
|     liposarcoma |
|     chondrosarcoma |
|     osteogenic sarcoma |
|     chordoma |
|     angiosarcoma |
|     lymphangiosarcoma |
|     lymphangioendotheliosarcoma |
|     synovioma |
|     mesothelioma |
|     Ewing's tumor |
|     leiomyosarcoma |
|     rhabdomyosarcoma |
|     colon carcinoma |
|     pancreatic cancer |
|     breast cancer |
|     ovarian cancer |
|     prostate cancer |
|     squamous cell carcinoma |
|     basal cell carcinoma |
|     adenocarcinoma |
|     sweat gland carcinoma |
|     sebaceous gland carcinoma |
|     papillary carcinoma |
|     papillary adenocarcinomas |
|     cystadenocarcinoma |
|     medullary carcinoma |
|     bronchogenic carcinoma |
|     renal cell carcinoma |
|     hepatoma |
|     bile duct carcinoma |
|     choriocarcinoma |
|     seminoma |
|     embryonal carcinoma |
|     Wilms' tumor |
|     cervical cancer |
|     uterine cancer |
|     testicular tumor |
|     lung carcinoma |
|     small cell lung carcinoma |
|     bladder carcinoma |
|     epithelial carcinoma |
|     glioma |
|     astrocytoma |
|     medulloblastoma |
|     craniopharyngioma |
|     ependymoma |
|     pinealoma |
|     hemangioblastoma |
|     acoustic neuroma |
|     oligodendroglioma |
|     meningioma |
|     melanoma |
|     neuroblastoma |
|     retinoblastoma |

In a preferred embodiment, the compounds of the present invention are used to treat cancers including, but not limited to lymphomas (preferably follicular lymphoma, diffuse large B-cell lymphoma, mantle cell lymphoma, or chronic lymphocytic leukemia), prostate cancer (more preferably hormone insensitive), breast cancer (preferably estrogen receptor positive), neuroblastoma, colorectal, endometrial, ovarian, lung (preferably small cell), hepatocellular carcinoma, multiple myeloma, head and neck or testicular cancer (preferably germ cell).

Treatment of Cancer in Combination with Chemotherapy or Radiotherapy

In certain embodiments, one or more compounds of the present invention are used to treat or prevent cancer or neoplastic disease in combination with one or more anti-cancer, chemotherapeutic agents including, but not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, prednisolone, dexamethasone, cytarbine, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In a preferred embodiment, one or more compound of the present invention is used to treat or prevent cancer or neoplastic disease in combination with one or more chemotherapeutic or other anti-cancer agents including, but not limited to those presented in Table 2.

TABLE 2

CHEMOTHERAPEUTICS AND OTHER ANTI-CANCER AGENTS

| Radiation: | γ-radiation |
|---|---|
| Alkylating agents | |
| Nitrogen mustards: | cyclophosphamide |
| | Ifosfamide |
| | trofosfamide |
| | Chlorambucil |
| | Estramustine |
| | melphalan |
| Nitrosoureas: | carmustine (BCNU) |
| | Lomustine (CCNU) |
| Alkylsulphonates | busulfan |
| | Treosulfan |
| Triazenes: | Dacarbazine |
| Platinum containing compounds: | Cisplatin |
| | carboplatin |
| | oxaplatin |
| Plant Alkaloids | |
| Vinca alkaloids: | vincristine |
| | Vinblastine |
| | Vindesine |
| | Vinorelbine |
| Taxoids: | paclitaxel |
| | Docetaxol |
| DNA Topoisomerase Inhibitors | |
| Epipodophyllins: | etoposide |
| | Teniposide |
| | Topotecan |
| | 9-aminocamptothecin |
| | campto irinotecan |
| | crisnatol |
| mytomycins | |
| mytomycin C | Mytomycin C |
| Anti-metabolites | |
| Anti-folates: | |
| DHFR inhibitors: | methotrexate |
| | Trimetrexate |
| IMP dehydrogenase Inhibitors: | mycophenolic acid |
| | Tiazofurin |
| | Ribavirin |
| | EICAR |
| Ribonucleotide reductase Inhibitors: | hydroxyurea |
| | deferoxamine |

TABLE 2-continued

CHEMOTHERAPEUTICS AND OTHER ANTI-CANCER AGENTS

| Pyrimidine analogs: | |
|---|---|
| Uracil analogs | 5-Fluorouracil |
| | Floxuridine |
| | Doxifluridine |
| | Ratitrexed |
| | capecitabine |
| Cytosine analogs | cytarabine (ara C) |
| | Cytosine arabinoside |
| | fludarabine |
| Purine analogs: | mercaptopurine |
| | Thioguanine |
| Hormonal therapies: | |
| Receptor antagonists: | |
| Anti-estrogens | Tamoxifen |
| | Raloxifene |
| | megestrol |
| LHRH agonists: | goscrelin |
| | Leuprolide acetate |
| Anti-androgens: | flutamide |
| | bicalutamide |
| Retinoids/Deltoids | |
| Vitamin D3 analogs: | EB 1089 |
| | CB 1093 |
| | KH 1060 |
| Photodyamic therapies: | vertoporfin (BPD-MA) |
| | Phthalocyanine |
| | photosensitizer Pc4 |
| | Demethoxy-hypocrellin A |
| | (2BA-2-DMHA) |
| Cytokines: | Interferon α |
| | Interferon γ |
| | Tumor necrosis factor |
| Others: | |
| Isoprenylation inhibitors: | Lovastatin |
| Dopaminergic neurotoxins: | 1-methyl-4-phenylpyridinium ion |
| Cell cycle inhibitors: | staurosporine |
| Actinomycins: | Actinomycin D |
| | Dactinomycin |
| Bleomycins: | bleomycin A2 |
| | Bleomycin B2 |
| | Peplomycin |
| Anthracyclines: | daunorubicin |
| | Doxorubicin (adriamycin) |
| | Idarubicin |
| | Epirubicin |
| | Pirarubicin |
| | Zorubicin |
| | Mitoxantrone |
| MDR inhibitors: | verapamil |
| $Ca^{2+}$ ATPase inhibitors: | thapsigargin |
| Antibodies | Avastin |
| | Erbitux |
| | Rituxan |
| Others | Prednisilone |
| | Imatinib |
| | Thalidomide |
| | Lenalidomide |
| | Bortezomib |
| | Gemcitabine |
| | Erlotinib |
| | Gefitinib |
| | Sorafenib |
| | Sutinib |

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, compounds of the present invention and the chemotherapeutic agent do not have to be administered in the same pharmaceutical composition, and may, because of different physical and chemical characteristics, have to be administered by different routes. For example, compounds of the present invention may be administered intravenously to generate and maintain good blood levels, while the chemotherapeutic agent may be administered orally. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of chemotherapeutic agent or radiation will depend upon the diagnosis of the attending physicians and their judgment of the condition of the patient and the appropriate treatment protocol.

A compound of the present invention, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with a compound of the present invention.

If a compound of the present invention, and the chemotherapeutic agent and/or radiation are not administered simultaneously or essentially simultaneously, then the optimum order of administration of the compound of the present invention, and the chemotherapeutic agent and/or radiation, may be different for different tumors. Thus, in certain situations the compound of the present invention may be administered first followed by the administration of the chemotherapeutic agent and/or radiation; and in other situations the chemotherapeutic agent and/or radiation may be administered first followed by the administration of a compound of the present invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of the present invention followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent, i.e., compound of the present invention, chemotherapeutic agent or radiation) of the treatment according to the individual patient's needs, as the treatment proceeds.

Definitions

For convenience, certain terms employed in the specification, examples, and appended claims are collected here.

The terms "co-administration" and "co-administering" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent at the same time.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated a liphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "haloalkyl", as used herein, refers to an alkyl group where anywhere from 1 to all hydgrogens have been replaced with a halide. A "perhaloalkyl" is where all of the hydrogens have been replaced with a halide.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that may be represented by the general formulas:

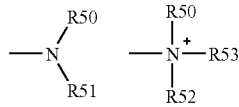

wherein R50, R51 and R52 each independently represent a hydrogen, an alkyl, an alkenyl, —(CH$_2$)$_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

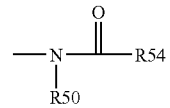

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

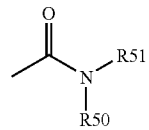

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carboxyl" is art recognized and includes such moieties as may be represented by the general formulas:

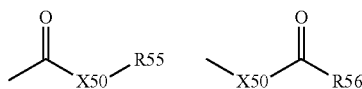

wherein X50 is a bond or represents an oxygen or a sulfur, and R55 and R56 represents a hydrogen, an alkyl, an alkenyl, —(CH$_2$)$_m$—R61or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

$$-\overset{\overset{O}{\|}}{\underset{\underset{O}{\|}}{S}}-OR_{41}$$

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "carbamoyl" refers to —O(C=O)NRR', where R and R' are independently H, aliphatic groups, aryl groups or heteroaryl groups.

The term "alkylamino" refers to —NHR, where R is an alkyl group.

The term "dialkylamino" refers to —NRR', where both R and R' are alkyl groups.

The term "hydroxyalkyl" refers to —R—OH, where R is an aliphatic group.

The term "aminoalkyl" refers to —R—$NH_2$, where R is an aliphatic group.

The term "alkylaminoalkyl" refers to —R—NH—R', where both R and R' are aliphatic groups.

The term "dialkylaminoalkyl" refers to —R—N(R')—R", where R, R', and R" are aliphatic groups.

The term "arylaminoalkyl" refers to —R—NH—R', where R is an aliphatic and R' is an aryl group.

The term "oxo" refers to a carbonyl oxygen (=O).

The term "diradical" or "bivalent" as used herein are used interchangeably and refer to any of a series of divalent groups from alkyl, alkenyl, alkynyl, alkylamino, alkoxyl, cycloalkyl, heterocycloalkyl, aryl, aralkyl, heterocyclyl, heteroaryl, and heteroaralkyl groups. For example,

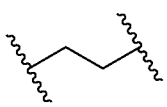

is a bivalent alkyl or alkyl diradical;

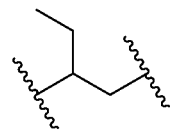

is also a bivalent alkyl or alkyl diradical;

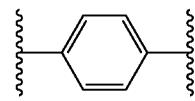

is a bivalent aryl or aryl diradical;

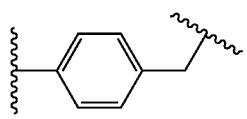

is a bivalent aralkyl or aralkyl diradical; and

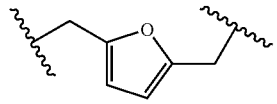

is a bivalent (alkyl)heteroaralkyl or (alkyl)heteroaralkyl diradical.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

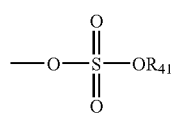

in which $R_{41}$ is as defined above.

The term "sulfonylamino" is art recognized and includes a moiety that can be represented by the general formula:

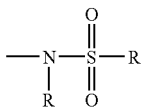

The term "sulfamoyl" is art-recognized and includes a moiety that can be represented by the general formula:

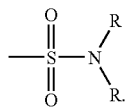

The term "sulfonyl", as used herein, refers to a moiety that can be represented by the general formula:

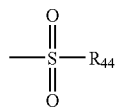

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

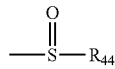

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P.G.M. *Protective Groups in Organic Synthesis*, 2$^{nd}$ ed.; Wiley: New York, 1991). Protected forms of the inventive compounds are included within the scope of this invention.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

The term "subject" as used herein, refers to an animal, typically a mammal or a human, that has been the object of treatment, observation, and/or experiment. When the term is used in conjunction with administration of a compound or drug, then the subject has been the object of treatment, observation, and/or administration of the compound or drug.

The term "therapeutically effective amount" as used herein, means that amount of active compound or pharmaceutical agent that elicits the biological or medicinal response in a cell culture, tissue system, animal, or human that is being sought by a researcher, veterinarian, clinician, or physician, which includes alleviation of the symptoms of the disease, condition, or disorder being treated. In the present invention, such an amount will be sufficient to bind to bcl-2 in a cell and inhibit at least part of the anti-apoptotic activity of the protein. Such an amount may be sufficient to provide therapeutic effectiveness in a patient or may serve to sensitize the cell to treatment with another anticancer agent.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The phrases "Bcl-mediated disorder" and "disorder mediated by cells expressing Bcl proteins" refer to pathological and disease conditions in which a Bcl protein plays a role. Such roles can be directly related to the pathological condition or can be indirectly related to the condition. The feature common to this class of conditions is that they can be ameliorated by inhibiting the activity of, function of, or association with Bcl proteins.

As used herein, the terms "Bcl" and "Bcl protein" are intended to encompass one or more of the Bcl-2 subfamily of anti-apoptotic proteins Bcl-2, Bcl-w, Mcl-1, Bcl-XL, A1, Bfl1, Bcl-B, BOO/DIVA, and their homologues.

Compounds Of The Invention

One aspect of the present invention relates to a compound represented by formula 1:

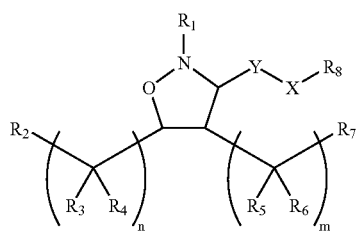

or pharmaceutically acceptable salts, solvates, or hydrates thereof, wherein

Y is $-C(R_9)_2-$, $-C(O)-$, $-C(S)-$, or $-C(=NR_{10})-$;

X is $-N(R_{11})-$, an optionally substituted phenyl group, or a bond;

X' represents independently for each occurrence O, $N(R_{10})$, or S;

m is 0, 1, 2, 3, 4, 5, or 6;

n represents independently for each occurrence 0, 1, 2, 3, 4, 5, or 6;

$R_1$ is alkyl, aralkyl, heteroaralkyl, has the formula 1a:

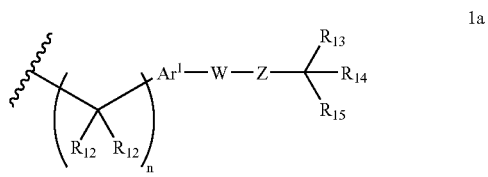

wherein $R_{12}$ represents independently for each occurrence H, alkyl, aryl, heteroaryl, or aralkyl; wherein any two instances of $R_{12}$ may be connected by a covalent bond;

$Ar^1$ is a monocyclic or bicyclic aryl with 6-14 ring atoms; or a monocyclic or bicyclic heteroaryl with 5-14 ring atoms, of which one, two or three ring atoms are independently S, O or N;

W is a bond; or bivalent alkyl, alkenyl, or alkynyl chain;

Z is a bond, $-(C(R_{12})_2)_n-$, or $-X'(C(R_{12})_2)_n-$;

$R_{13}$ and $R_{14}$ are independently H, alkyl, aryl, cycloalkyl, heterocycloalkyl, aralkyl, heteroaryl, heteroaralkyl, or $-A^1-A^2-A^3$; or $R_{13}$ and $R_{14}$ taken together form a monocyclic or polycyclic ring; or $R_{13}$ and $R_{14}$ taken together with $R_{15}$ form a cycloalkenyl ring, aromatic ring, or heteroaromatic ring;

$R_{15}$ is halide, hydroxyl, alkoxyl, aryl, aryloxy, acyloxy, $-N(R_{10})_2$, acylamino, aralkyl, nitro, acylthio, carboxamide, carboxyl, nitrile, $-COR_{10}$, $-CO_2R_{10}$, $-N(R_{10})CO_2R_{10}$, $-OC(O)N(R_{10})_2$, $-N(R_{10})SO_2R_{19}$, $-N(R_{10})C(X')N(R_{19})_2$, $-_{N(R10)}(C(R_9)_2)_n-A^1-A^2-A^3$, $-(C(R_9)_2)_n$-halogen, or $-CH_2O$-heterocyclyl; or $R_{15}$ taken together with $R_{13}$ and $R_{14}$ form a cycloalkenyl ring, aromatic ring, or heteroaromatic ring; or $R_1$ or $R_{15}$ are each represented independently by formula 1b:

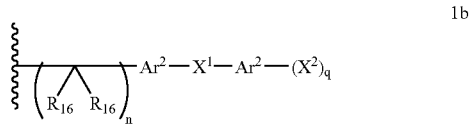

$R_{16}$ represents independently for each occurrence H, alkyl, cycloalkyl, heterocycloalkyl, aryl, aralkyl, halide, hydroxyl, alkoxyl, aryloxy, acyloxy, amino, alkylamino, arylamino, acylamino, aralkylamino, nitro, acylthio, carboxamide, carboxyl, nitrile, $-COR_{10}$, $-CO_2R_{10}$, $-N(R_{10})CO_2R_{10}$, $-OC(O)N(R_{10})_2$, $-N(R_{10})SO_2R_{10}$, or $-N(R_{10})C(X')N(R_{10})_2$; wherein any two instances of $R_{16}$ may be connected by a covalent bond to form a ring;

$Ar^2$ represents independently for each occurrence a monocyclic or bicyclic aryl with 6-14 ring atoms; or a monocyclic or bicyclic heteroaryl with 5-14 ring atoms, of which one, two or three ring atoms are independently S, O or N;

$X^1$ represents independently for each occurrence a bond, O, S, S(O), $S(O)_2$, $S(O)_3$, amino, alkylamino diradical, alkoxyl diradical, alkyl diradical, alkenyl diradical, alkynyl diradical, amido, carbonyl, —N(R$_{10}$)CO$_2$—, —OC(O)N(R$_{10}$)—, or —N(R$_{10}$)C(X')N(R$_{10}$)—;

X$^2$ represents independently for each occurrence H, halide, hydroxyl, alkoxyl, aryloxy, acyloxy, amino, alkylamino, arylamino, acylamino, aralkylamino, nitro, acylthio, carboxamide, carboxyl, nitrile, —COR$_{10}$, —CO$_2$R$_{10}$, —N(R$_{10}$)CO$_2$R$_{10}$, —OC(O)N(R$_{10}$)$_2$, —N(R$_{10}$)SO$_2$R$_{10}$, —N(R$_{10}$)C(X')N(R$_{10}$)$_2$, or —CH$_2$O-heterocyclyl; and q represents independently for each occurrence 1, 2, 3, 4, or 5;

R$_2$ and R$_7$ are independently H, hydroxyl, alkyl, alkoxyl, amino, alkylamino, or acylamino; or R$_2$ and R$_7$ taken together form a —OC(O)O— linkage, —N(R$_{10}$)C(O)N(R$_{10}$)— linkage, or an optionally substituted covalent linkage comprising 1 to 6 carbon atoms and 0, 1, or 2 nitrogen, oxygen, or sulfur atoms to form a 5-8 membered ring; or R$_7$ is a bond to R$_8$;

R$_3$ and R$_6$ each represent independently for each occurrence H, hydroxyl, or alkyl;

R$_4$ and R$_5$ each represent independently for each occurrence independently H or alkyl;

R$_8$ is H, a branched or unbranched alkyl or alkenyl, cycloalkyl, heterocycloalkyl, bicycloalkyl, a bond to R$_7$, heterocycloalkyl substituted with an aralkyl group, or has the formula 1c:

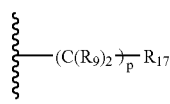

wherein p is 0, 1, 2, 3, 4, 5, or 6; and

R$_{17}$ is aryl, cycloalkyl, cycloalkenyl, heterocyclyl, alkoxyl, heteroaryl, —OR$_{18}$, —SR$_{18}$, —N(R$_{18}$)$_2$, —N(R$_{10}$)CO$_2$-alkyl, —CO$_2$R$_{10}$, —C(O)N(R$_{10}$)aryl, or a polycyclic ring containing 8-14 carbon atoms; wherein R$_{18}$ is independently for each occurrence H, alkyl, aryl, aralkyl, acyl, -A$^1$-A$^2$-A$^3$, or —CR$_9$=CR$_9$(C(R$_9$)$_2$)$_n$CR$_9$=C(R$_9$)$_2$; or two R$_{18}$ taken together form a ring;

R$^9$ represents independently for each occurrence H or alkyl;

R$_{10}$ and R$_{11}$ represent independently for each occurrence H, alkyl, aryl, cycloalkyl, aralkyl, heteroaryl, or heteroaralkyl;

R$_{19}$ represents independently for each occurrence H, alkyl, aryl, cycloalkyl, aralkyl, heteroaryl, heteroaralkyl, or -A$^1$-A$^2$-A$^3$;

A$^1$ and A$^3$ each represent independently for each occurrence alkyl, cycloalkyl, heterocycloalkyl, aryl, heteroaryl, aralkyl, or heteroaralkyl;

A$^2$ represents independently for each occurrence O, N(R$_{10}$), S, or a bond; and the stereochemical configuration at any stereocenter of a compound represented by 1 is R, S, or a mixture of these configurations.

In certain embodiments, the present invention relates to the aforementioned compound, wherein Y is —C(O)—, X is —N(R$_{11}$)—, R$_2$ and R$_7$ are hydroxyl, R$_6$ is methyl, ethyl, or propyl, and R$_3$, R$_4$, and R$_5$ are H.

In certain embodiments, the present invention relates to the aforementioned compound, wherein the compound has formula 1d:

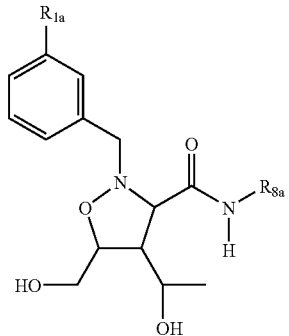

wherein

R$_{1a}$ has formula 1e:

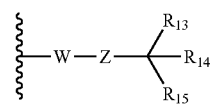

wherein

W is a bond; or bivalent alkyl, alkenyl, or alkynyl chain;

Z is a bond, —(C(R$_{12}$)$_2$)$_n$—, or —O(C(R$_{12}$)$_2$)$_n$—;

R$_{13}$ and R$_{14}$ are independently H, alkyl, aryl, cycloalkyl, heterocycloalkyl, aralkyl, heteroaryl, heteroaralkyl, or -A$^1$-A$^2$-A$^3$; or R$_{13}$ and R$_{14}$ taken together form a monocyclic or polycyclic ring; or R$_{13}$ and R$_{14}$ taken together with R$_{15}$ form a cycloalkenyl ring, aromatic ring, or heteroaromatic ring;

R$_{15}$ is halide, hydroxyl, alkoxyl, aryl, aryloxy, acyloxy, —N(R$_{10}$)$_2$, acylamino, aralkyl, nitro, acylthio, carboxamide, carboxyl, nitrile, —COR$_{10}$, —CO$_2$R$_{10}$, —N(R$_{10}$)CO$_2$R$_{10}$, —OC(O)N(R$_{10}$)$_2$, —N(R$_{10}$)SO$_2$R$_{19}$, —N(R$_{10}$)C(O)N(R$_{19}$)$_2$, —N(R$_{10}$)(C(R$_9$)$_2$)$_n$-A$^1$-A$^2$-A$^3$, —(C(R$_9$)$_2$)$_n$-halogen, or —CH$_2$O-heterocyclyl; or R$_{15}$ taken together with R$_{13}$ and R$_{14}$ form a cycloalkenyl ring, aromatic ring, or heteroaromatic ring; or has the formula 1f:

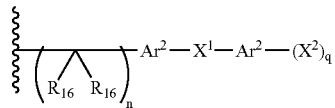

R$_{16}$ represents independently for each occurrence H, alkyl, cycloalkyl, heterocycloalkyl, aryl, aralkyl, halide, hydroxyl, alkoxyl, aryloxy, acyloxy, amino, alkylamino, arylamino, acylamino, aralkylamino, nitro, acylthio, carboxamide, carboxyl, nitrile, —COR$_{10}$, —CO$_2$R$_{10}$, —N(R$_{10}$)CO$_2$R$_{10}$, —OC(O)N(R$_{10}$)$_2$, —N(R$_{10}$)SO$_2$R$_{10}$, or —N(R$_{10}$)C(O)N(R$_{10}$)$_2$; wherein any two instances of R$_{16}$ may be connected by a covalent bond to form a ring;

Ar$^2$ represents independently for each occurrence a monocyclic or bicyclic aryl with 6-14 ring atoms; or a monocyclic or bicyclic heteroaryl with 5-14 ring atoms, of which one, two or three ring atoms are independently S, O or N;

X¹ is a bond, O, S, S(O), S(O)$_2$, S(O)$_3$, amino, alkylamino diradical, alkoxyl diradical, alkyl diradical, alkenyl diradical, alkynyl diradical, amido, carbonyl, —N(R$_{10}$)CO$_2$R$_{10}$, —OC(O)N(R$_{10}$)$_2$, or —N(R$_{10}$)C(O)N(R$_{10}$)$_2$;

X² represents independently for each occurrence H, halide, hydroxyl, alkoxyl, aryloxy, acyloxy, amino, alkylamino, arylamino, acylamino, aralkylamino, nitro, acylthio, carboxamide, carboxyl, nitrile, —COR$_{10}$, —CO$_2$R$_{10}$, —N(R$_{10}$)CO$_2$R$_{10}$, —C(O)N(R$_{10}$)$_2$, —N(R$_{10}$)SO$_2$R$_{10}$, —N(R$_{10}$)C(O)N(R$_{10}$)$_2$, or —CH$_2$O—heterocyclyl; and q is 1, 2, 3, 4, or 5; and R$_{8a}$ is H, a branched or unbranched alkyl or alkenyl, cycloalkyl, heterocycloalkyl, bicycloalkyl, a bond to R$_7$, heterocycloalkyl substituted with an aralkyl group, or has the formula 1g:

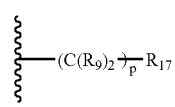

wherein p is 0, 1, 2, 3, 4, 5, or 6; and

R$_{17}$ is aryl, cycloalkyl, cycloalkenyl, heterocyclyl, alkoxyl, heteroaryl, —OR$_{18}$, —SR$_{18}$, —N(R$_{18}$)$_2$, —N(R$_{10}$)CO$_2$-alkyl, —CO$_2$R$_{10}$, —C(O)N(R$_{10}$)aryl, or a polycyclic ring containing 8-14 carbon atoms; wherein R$_{18}$ is independently for each occurrence H, alkyl, aryl, aralkyl, acyl, -A¹-A²-A³, or —CR$_9$=CR$_9$(C(R$_9$)$_2$)$_n$CR$_9$=C(R$_9$)$_2$; or two R$_{18}$ taken together form a ring;

In certain embodiments, the present invention relates to the aforementioned compound, wherein R$_{13}$ and R$_{14}$ are independently H, alkyl, or aryl; or R$_{13}$ and R$_{14}$ taken together form a monocyclic or polycyclic ring; or R$_{13}$ and R$_{14}$ taken together with R$_{15}$ form a cycloalkenyl ring or heteroaromatic ring;

R$_{15}$ is halide, hydroxyl, alkoxyl, aryl, aryloxy, acyloxy, —N(R$_{10}$)$_2$, acylamino, aralkyl, —N(R$_{10}$)SO$_2$R$_{19}$, or —N(R$_{10}$)C(O)N(R$_{19}$)$_2$; or R$_{15}$ taken together with R$_{13}$ and R$_{14}$ form a cycloalkenyl ring or heteroaromatic ring; or has the formula 1f:

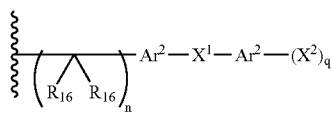

wherein

R$_{16}$ is H;

Ar² represents independently for each occurrence a monocyclic aryl with 6-14 ring atoms; or a monocyclic heteroaryl with 5-14 ring atoms, of which one, two or three ring atoms are independently S, O or N;

X¹ is a bond;

X² represents independently for each occurrence H, halide, hydroxyl, or alkoxyl; and q is 1 or 2.

In certain embodiments, the present invention relates to the aforementioned compound, wherein R$_8$ is bicycloalkyl, heterocycloalkyl substituted with an aralkyl group, or has the formula 1g:

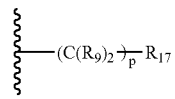

wherein p is 0, 1, 2, 3, 4, 5, or 6; and

R$_{17}$ is aryl, cycloalkyl, cycloalkenyl, heterocyclyl, alkoxyl, heteroaryl, —OR$_{18}$, —SR$_{18}$, —N(R$_{18}$)$_2$, or a polycyclic ring containing 8-14 carbon atoms; wherein R$_{18}$ is independently for each occurrence H, alkyl, aryl, aralkyl, acyl, or -A¹-A²-A³.

In certain embodiments, the present invention relates to the aforementioned compound, wherein W is an alkynyl chain and Z is a bond.

In certain embodiments, the present invention relates to the aforementioned compound, wherein R$_{13}$ and R$_{14}$ are H and R$_{15}$ is acylamino.

In certain embodiments, the present invention relates to the aforementioned compound, wherein R$_{13}$ and R$_{14}$ taken together form a cyclohexyl ring and R$_{15}$ is an amino group.

In certain embodiments, the present invention relates to the aforementioned compound, wherein R$_{8a}$ is a bicycloalkyl.

In certain embodiments, the present invention relates to the aforementioned compound, wherein R$_{8a}$ has formula 1g and R$_{17}$ is N(CH$_3$)Ph.

In certain embodiments, the present invention relates to the aforementioned compound, wherein R$_{1a}$ is:

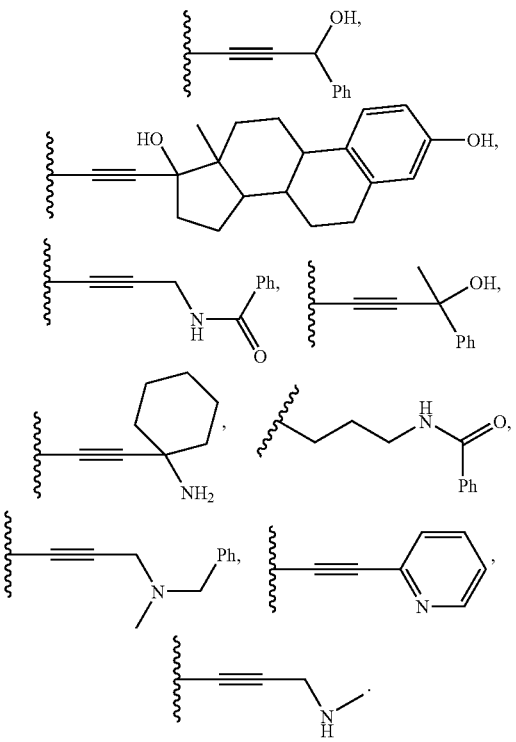

In certain embodiments, the present invention relates to the aforementioned compound, wherein R$_{8a}$ is:

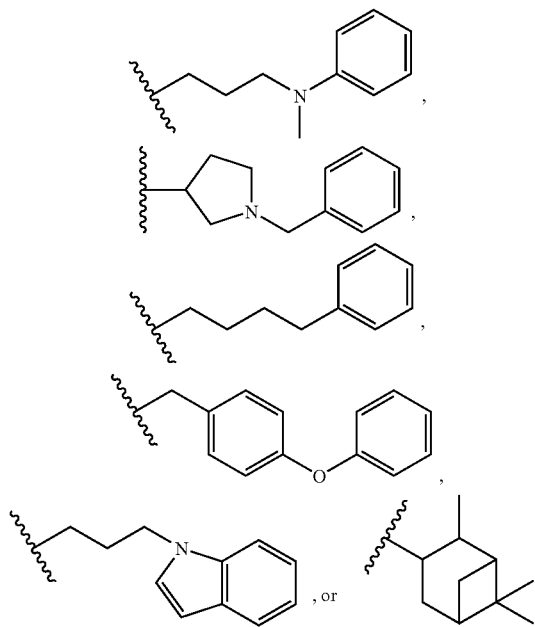
In certain embodiments, the present invention relates to the aforementioned compound, wherein $R_{8a}$ is
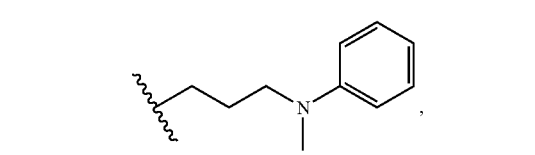
and $R_{1a}$ is:
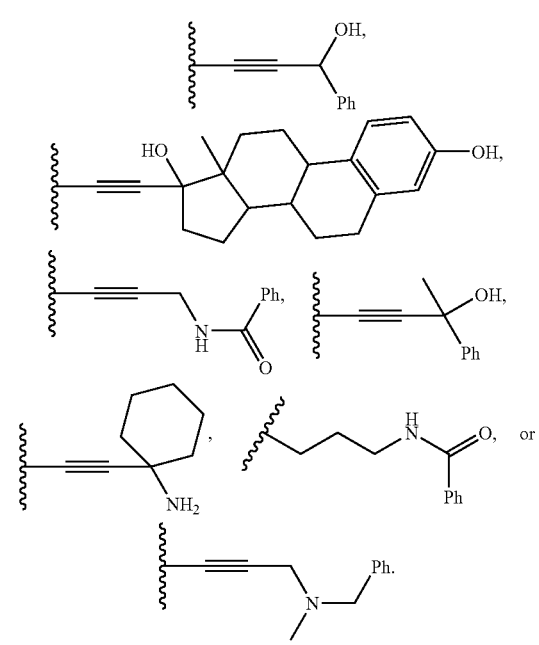
In certain embodiments, the present invention relates to the aforementioned compound, wherein $R_{1a}$ is
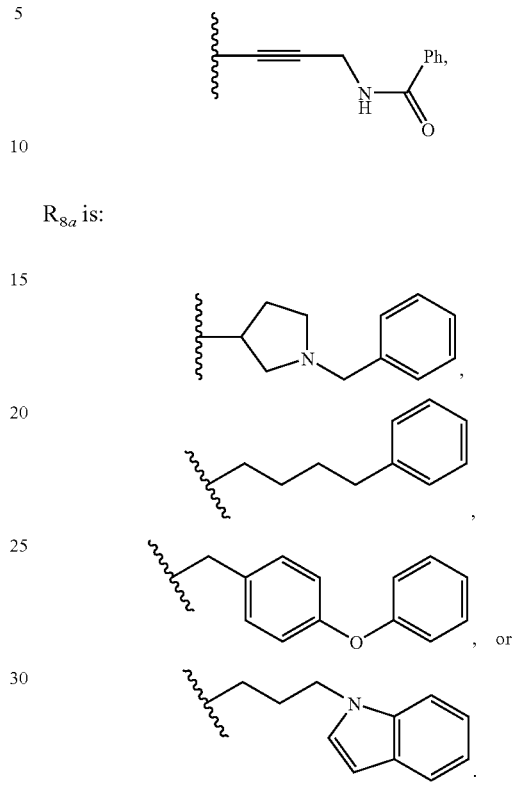
$R_{8a}$ is:
In certain embodiments, the present invention relates to the aforementioned compound, wherein $R_{8a}$ is
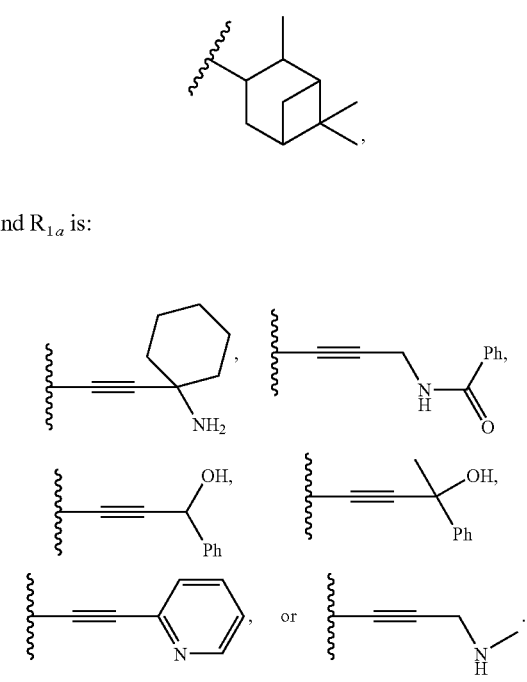
and $R_{1a}$ is:

In certain embodiments, the present invention relates to the aforementioned compound, wherein $R_{1a}$ is

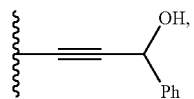

and $R_{8a}$ is

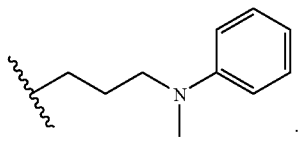

In certain embodiments, the present invention relates to the aforementioned compound, wherein $R_{1a}$ is

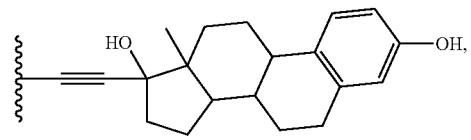

and $R_{8a}$ is

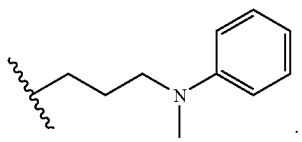

In certain embodiments, the present invention relates to the aforementioned compound, wherein $R_{1a}$ is

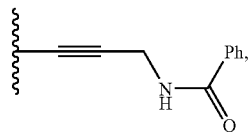

and $R_{8a}$ is

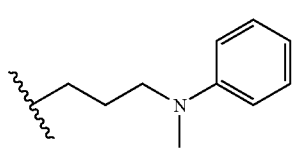

In certain embodiments, the present invention relates to the aforementioned compound, wherein $R_{1a}$ is

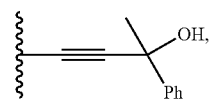

and $R_{8a}$ is

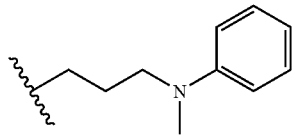

In certain embodiments, the present invention relates to the aforementioned compound, wherein $R_{1a}$ is

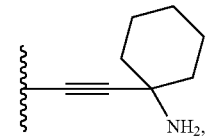

and $R_{8a}$ is

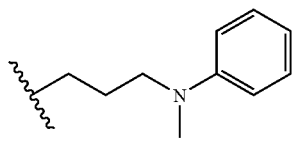

In certain embodiments, the present invention relates to the aforementioned compound, wherein $R_{1a}$ is

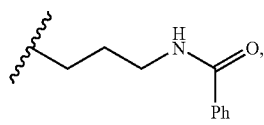

and $R_{8a}$ is

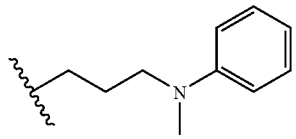

In certain embodiments, the present invention relates to the aforementioned compound, wherein $R_{1a}$ is

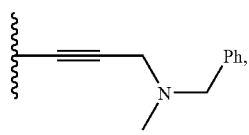

and $R_{8a}$ is

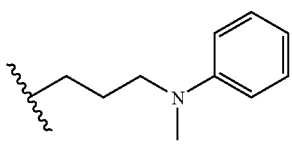

In certain embodiments, the present invention relates to the aforementioned compound, wherein $R_{1a}$ is

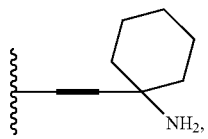

and $R_{8a}$ is

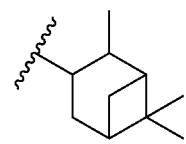

In certain embodiments, the present invention relates to the aforementioned compound, wherein $R_{1a}$ is

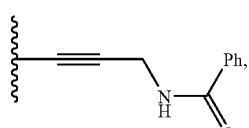

and $R_{8a}$ is

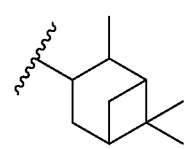

In certain embodiments, the present invention relates to the aforementioned compound, wherein $R_{1a}$ is

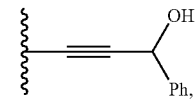

and $R_{8a}$ is

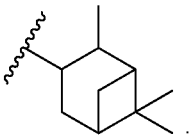

In certain embodiments, the present invention relates to the aforementioned compound, wherein $R_{1a}$ is

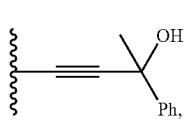

and $R_{8a}$ is

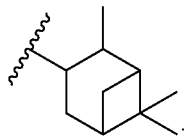

In certain embodiments, the present invention relates to the aforementioned compound, wherein $R_{1a}$ is

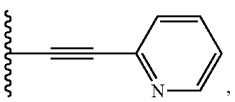

and $R_{8a}$ is

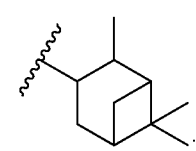

In certain embodiments, the present invention relates to the aforementioned compound, wherein $R_{1a}$ is

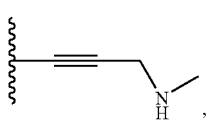

and R$_{8a}$ is

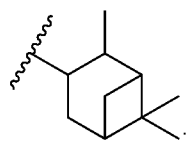

In certain embodiments, the present invention relates to the aforementioned compound, wherein R$_{1a}$ is

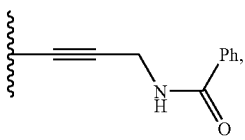

and R$_{8a}$ is

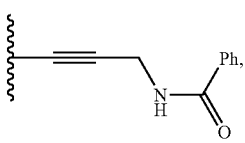

In certain embodiments, the present invention relates to the aforementioned compound, wherein R$_{1a}$ is

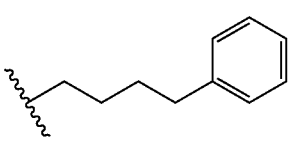

and R$_{8a}$ is

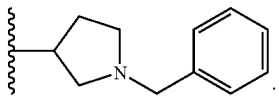

In certain embodiments, the present invention relates to the aforementioned compound, wherein R$_{1a}$ is

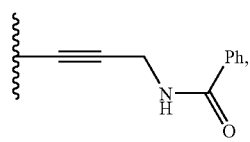

and R$_{8a}$ is

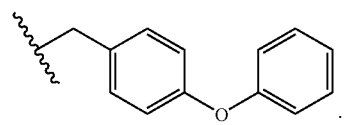

In certain embodiments, the present invention relates to the aforementioned compound, wherein R$_{1a}$ is

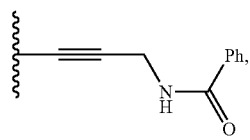

and R$_{8a}$ is

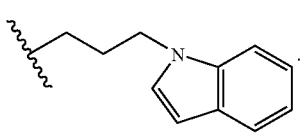

Another aspect of the present invention relates to a compound selected from the group consisting of:

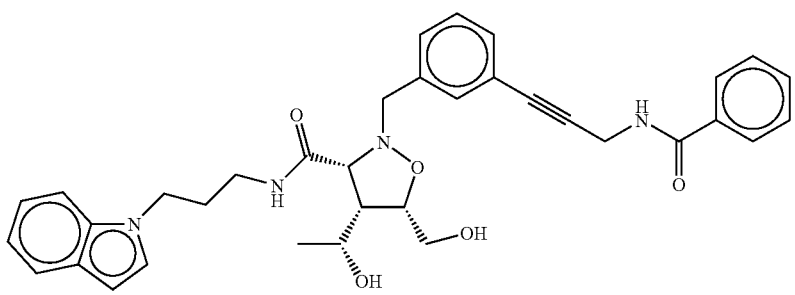

-continued
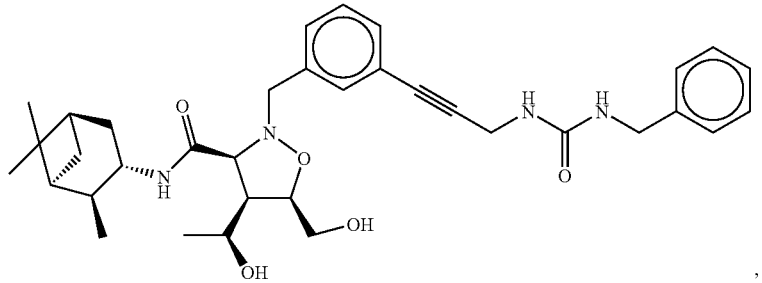
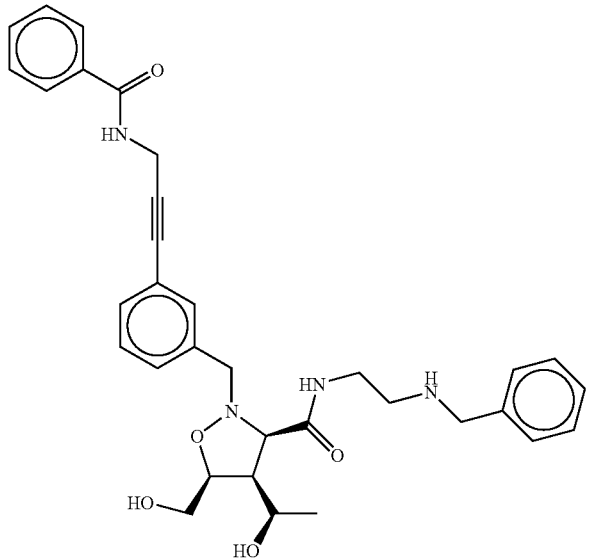
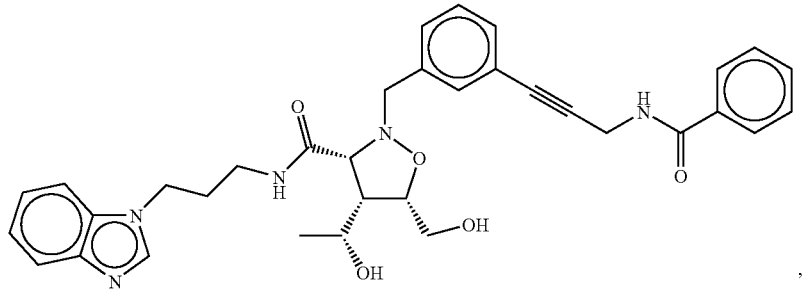
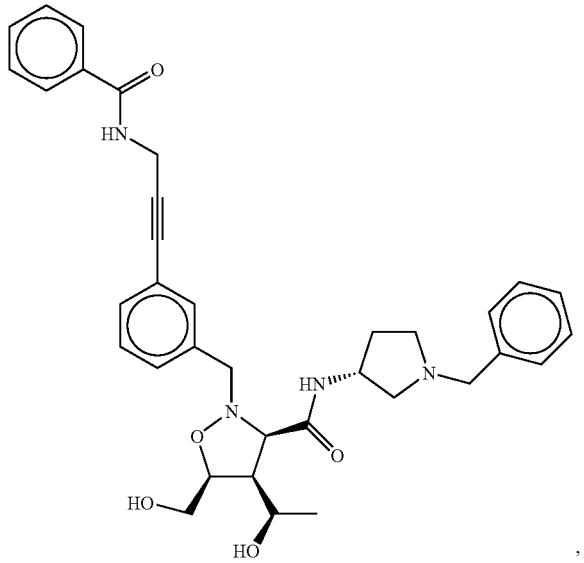
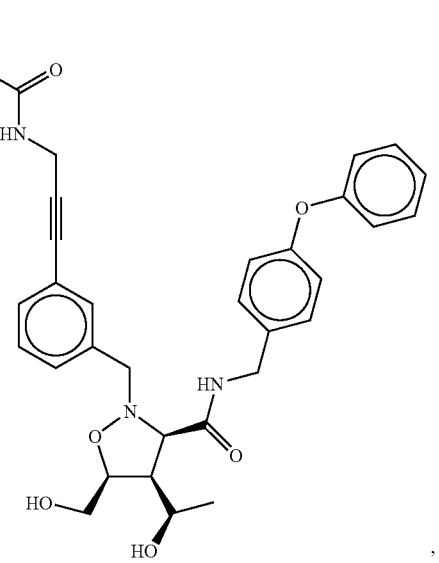

-continued
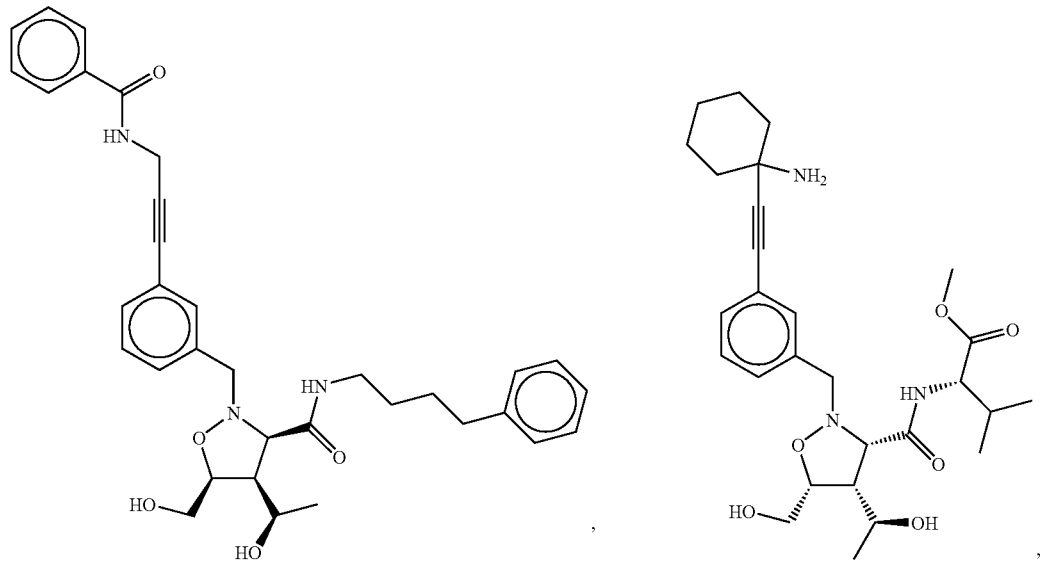
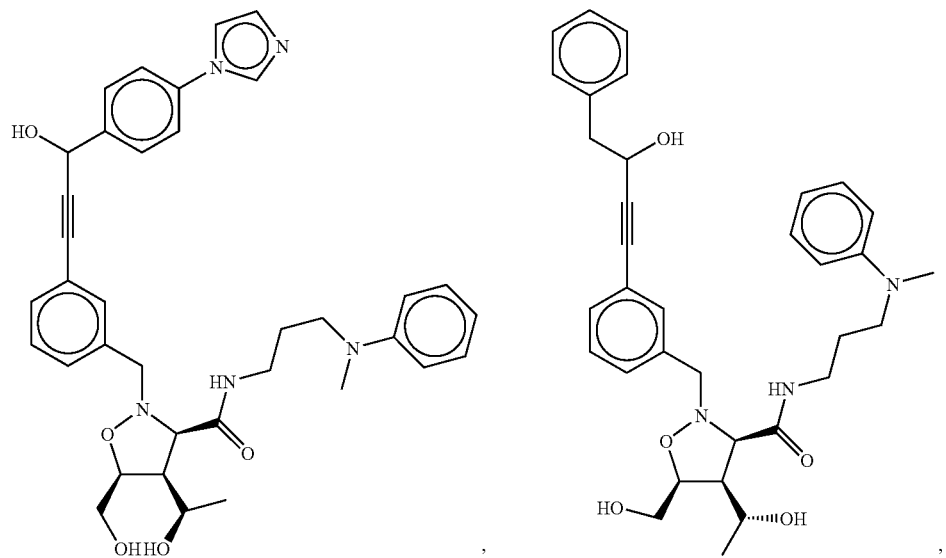
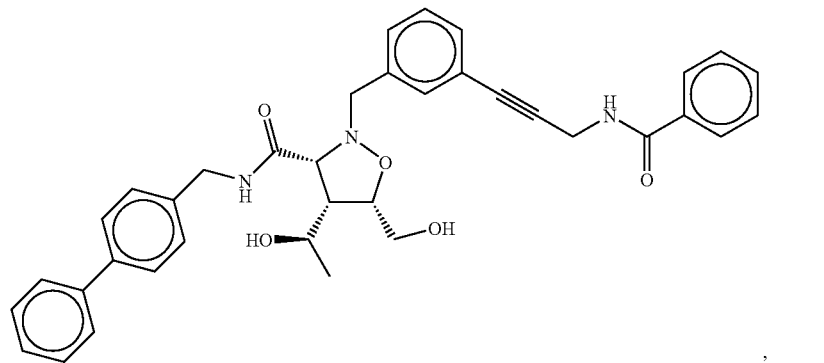

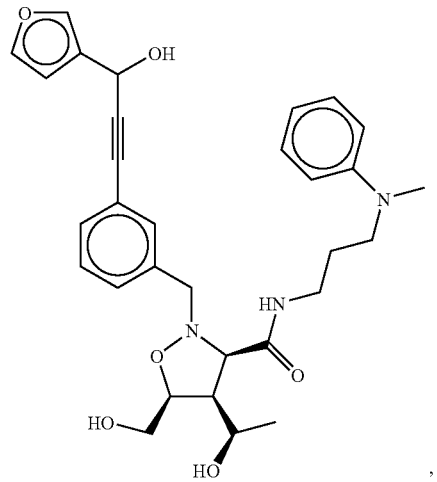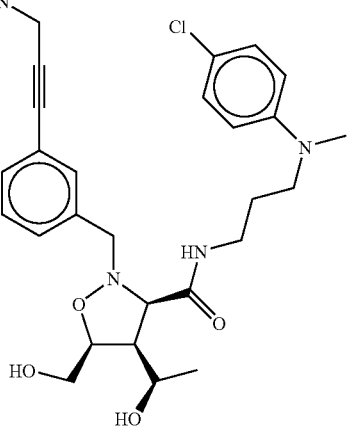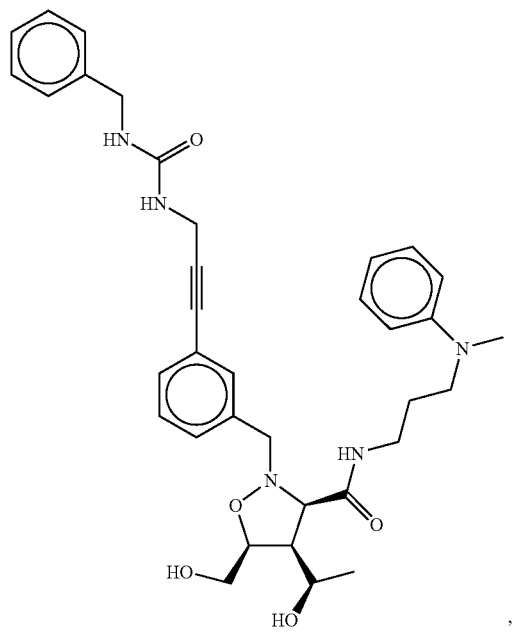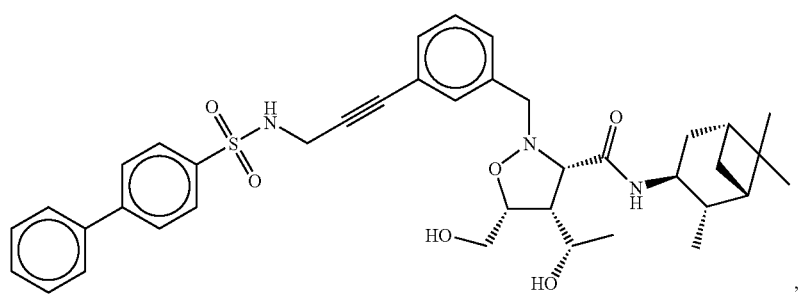

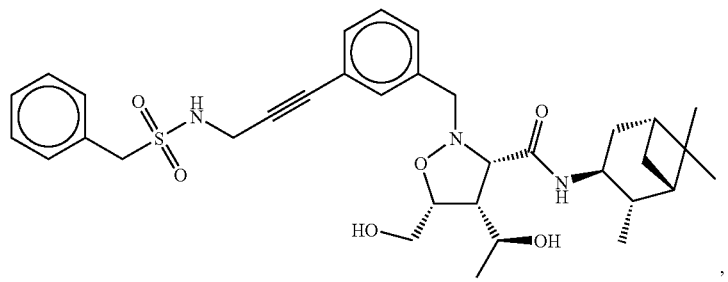
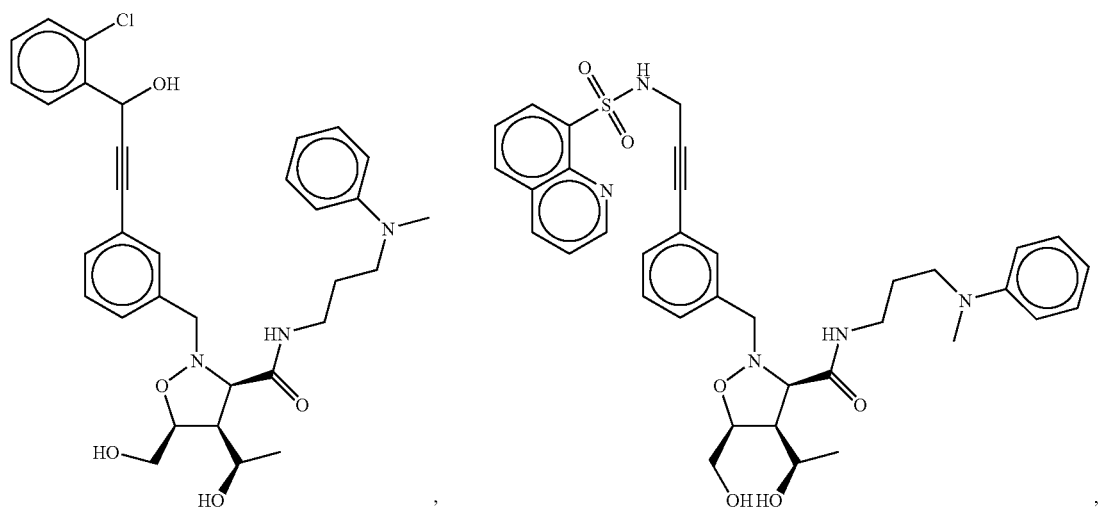
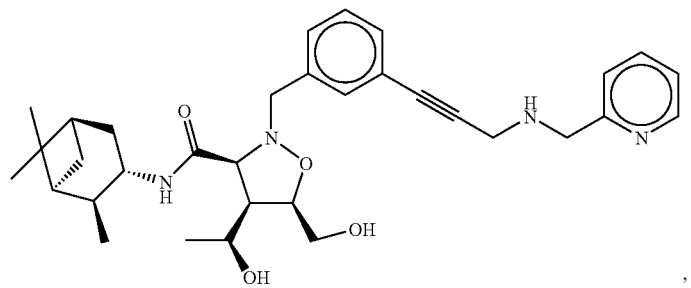
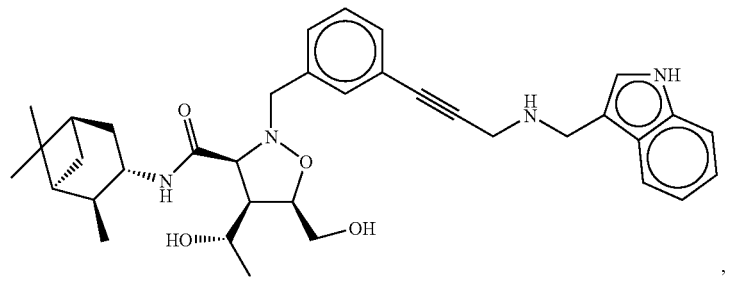

-continued
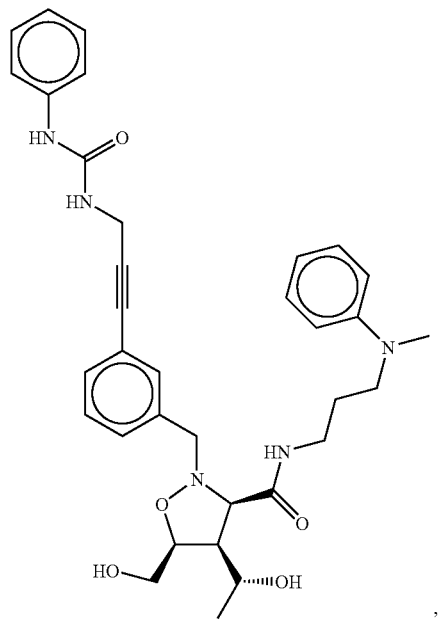
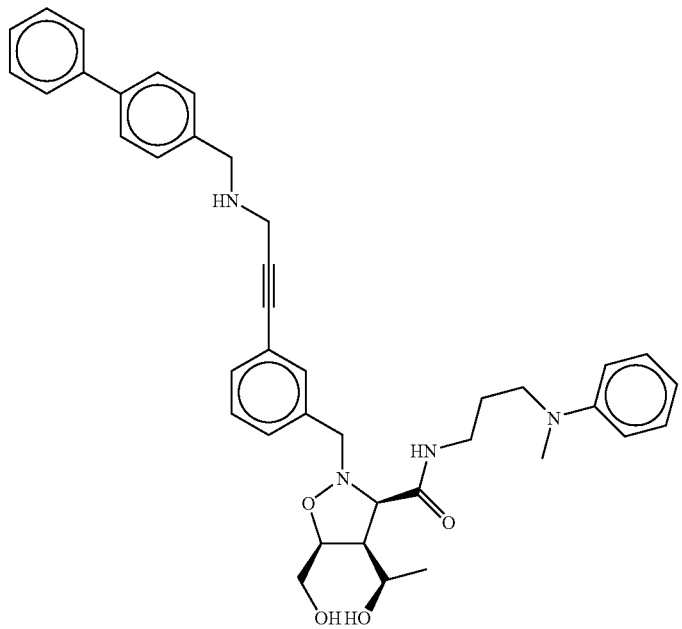
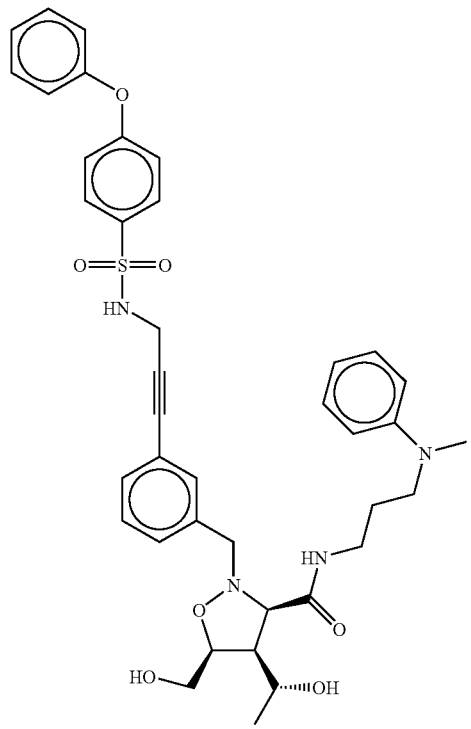
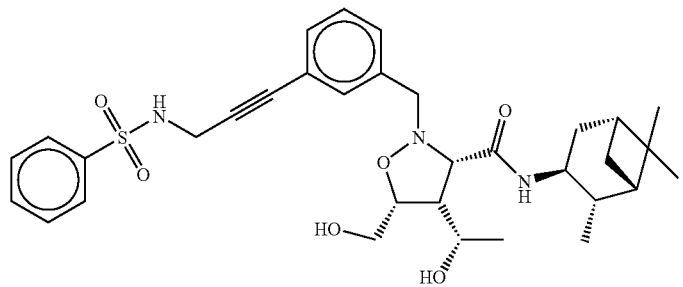

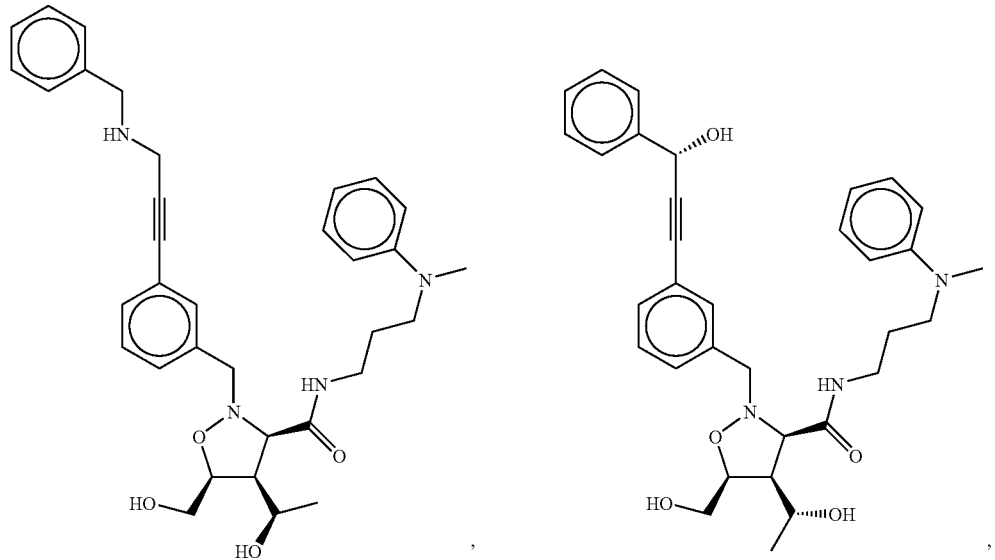
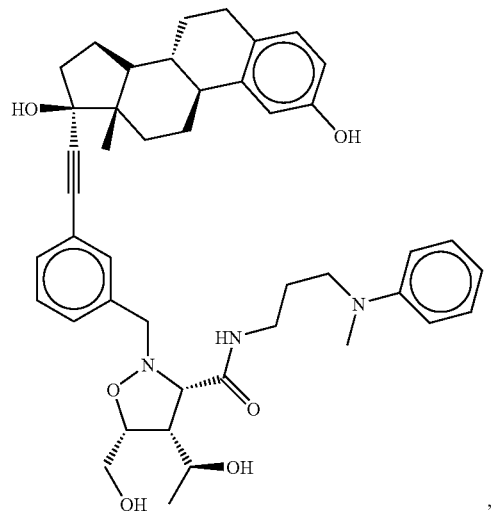
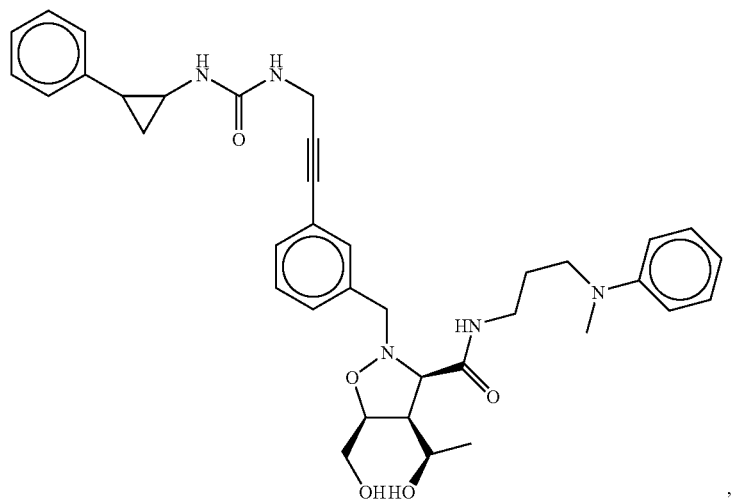

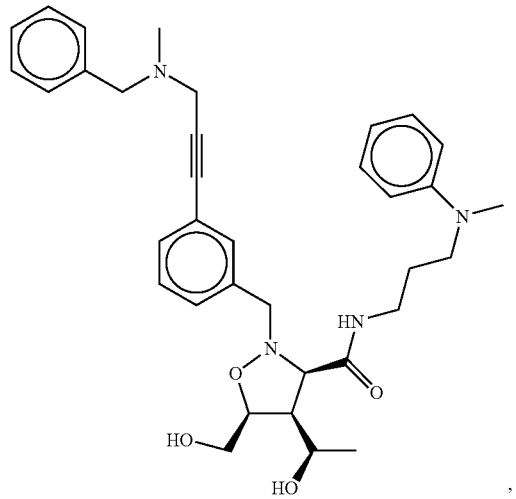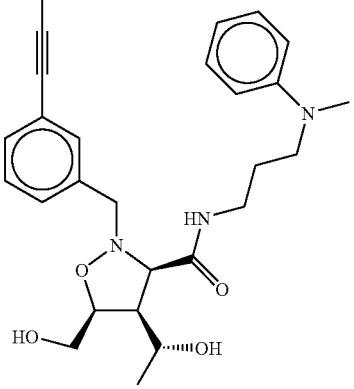
-continued
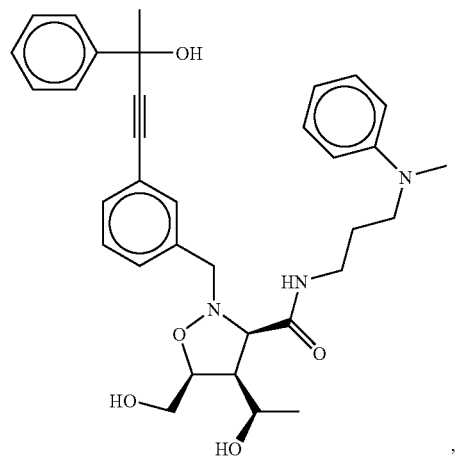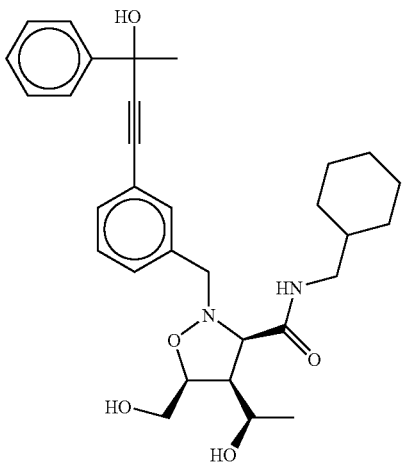
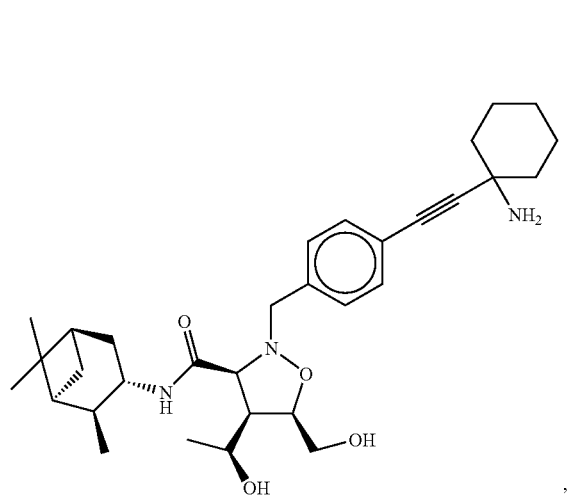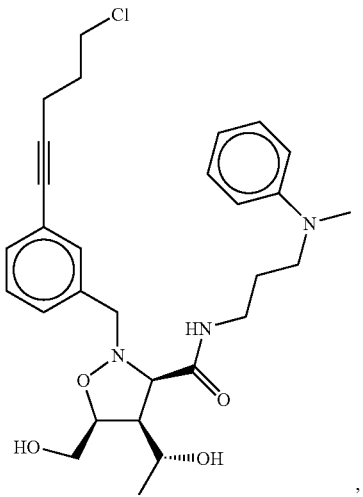

-continued
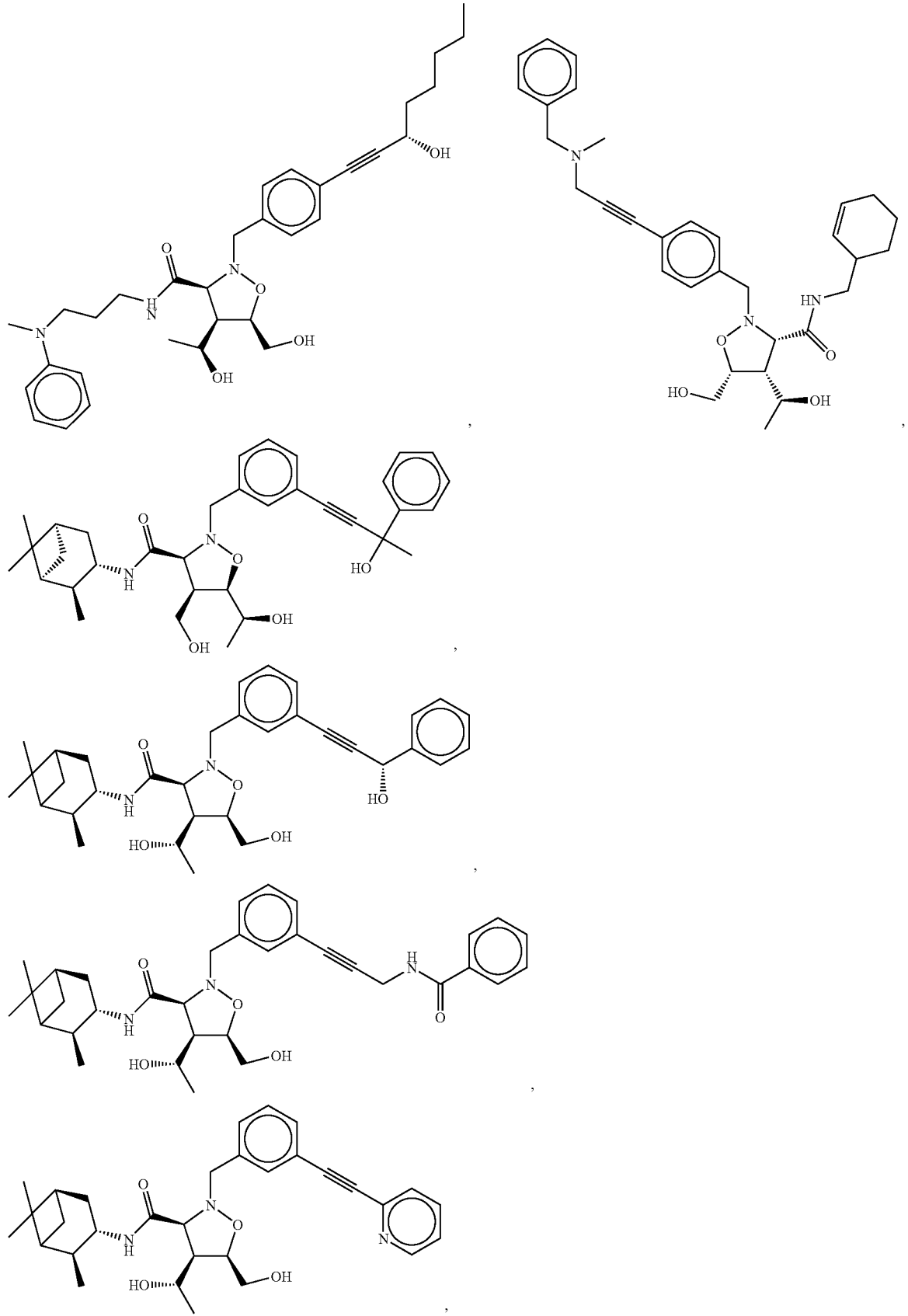

-continued
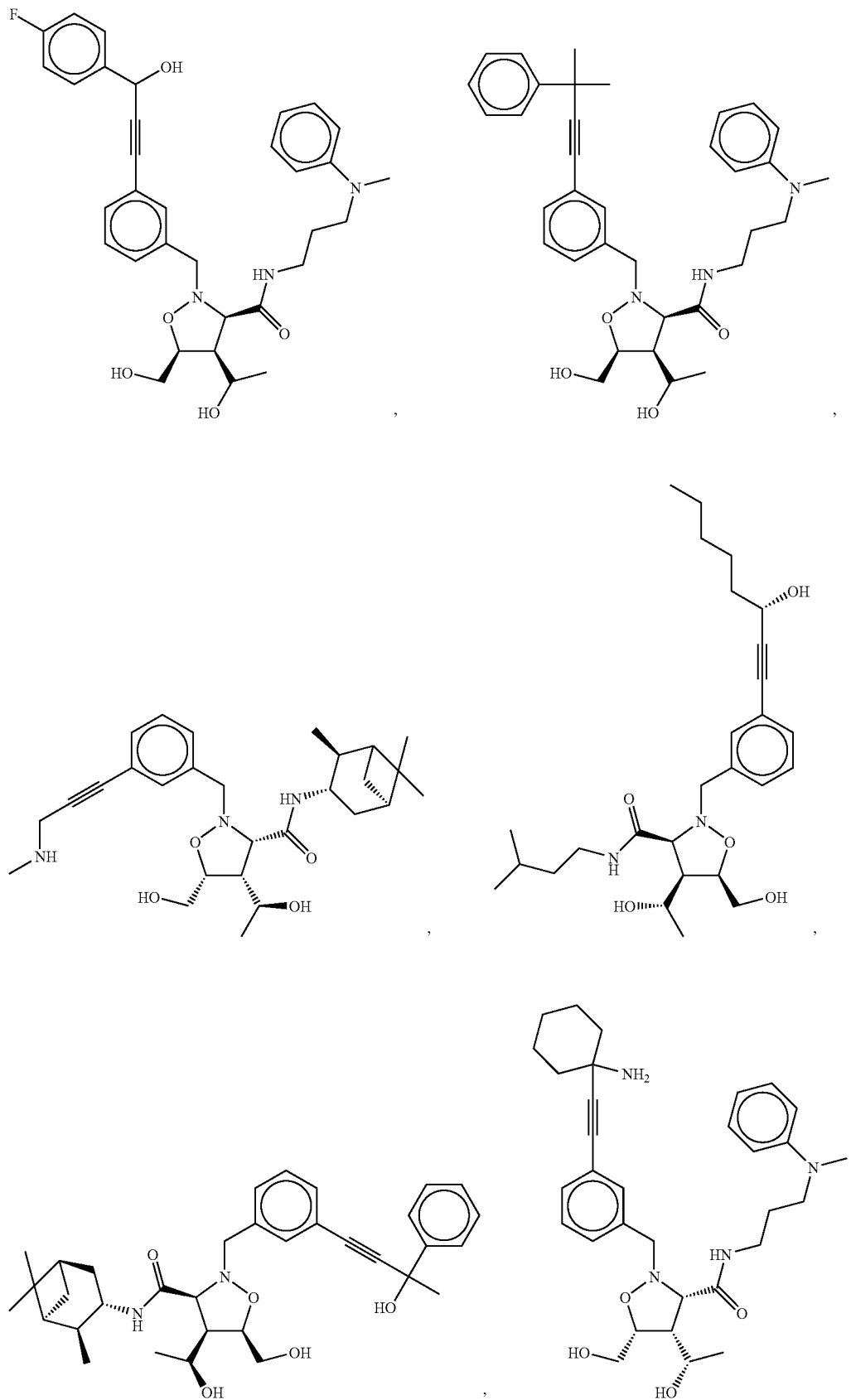

-continued

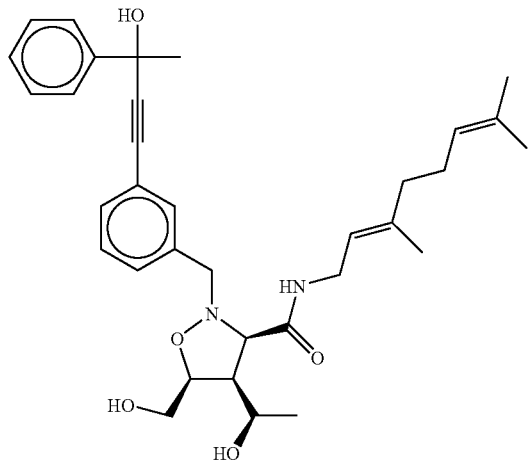
, and

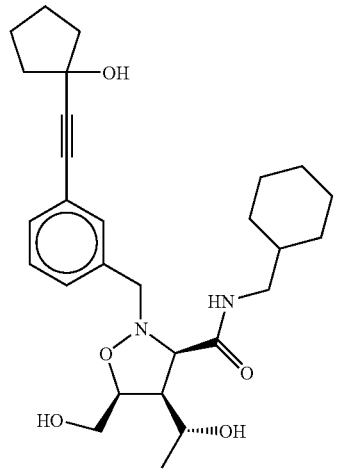
.

Another aspect of the present invention relates to a compound represented by formula 2:

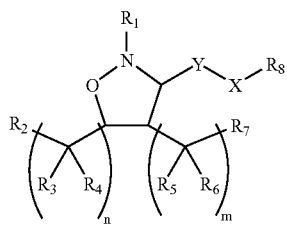
2 or pharmaceutically acceptable salts, solvates, or hydrates thereof,
wherein
Y is —C($R_9$)$_2$—, —C(O)—, —C(S)—, or —C(=N$R_{10}$)—;
X is O, S, aryl, —N($R_{11}$)—, or a bond;
m is 0, 1, 2, 3, 4, 5, or 6;
n represents independently for each occurrence 0, 1, 2, 3, 4, 5, or 6;
$R_1$ has the formula 2a:

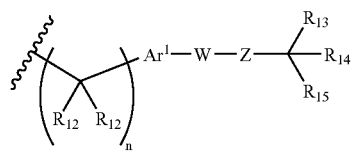
2a wherein
$R_{12}$ represents independently for each occurrence H or alkyl; wherein any two instances of $R_{12}$ may be connected by a covalent bond;
$Ar^1$ is a monocyclic or bicyclic aryl with 6-14 ring atoms; or a monocyclic or bicyclic heteroaryl with 5-14 ring atoms, of which one, two or three ring atoms are independently S, O or N;
W is a bond; or bivalent alkyl, alkenyl, or alkynyl chain;

Z is a bond, —(C($R_{12}$)$_2$)$_n$—, or —O(C($R_{12}$)$_2$)$_n$—;
$R_{13}$ and $R_{14}$ are independently H, alkyl, aryl, cycloalkyl, aralkyl, heteroaryl, heteroaralkyl, or -$A^1$-$A^2$-$A^3$; or $R_{13}$ and $R_{14}$ taken together form a monocyclic or polycyclic ring; or $R_{13}$ and $R_{14}$ taken together with $R_{15}$ form a cycloalkenyl ring, or heteroaromatic ring;
$R_{15}$ is halide, hydroxyl, alkoxyl, aryl, aryloxy, acyloxy, —N($R_{10}$)$_2$, acylamino, nitro, sulfhydryl, alkylthio, carboxamide, carboxyl, thioalkyl, nitrile, —CO$R_{10}$, —CO$_2R_{10}$, —N($R_{10}$)CO$_2R_{10}$, —OC(O)N($R_{10}$)$_2$, —N($R_{10}$)SO$_2R_{19}$, —N($R_{10}$)C(O)N($R_9$)$_2$, —N($R_{10}$)(C($R_9$)$_2$)$_n$-$A^1$-$A^2$-$A^3$, —(C($R_9$)$_2$)$_n$-halogen, or —CH$_2$O-heterocyclyl; or $R_{15}$ taken together with $R_{13}$ and $R_{14}$ form a cycloalkenyl ring or heteroaromatic ring; or has the formula 2b:

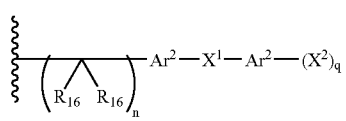
2b wherein
$R_{16}$ represents independently for each occurrence H or alkyl;
$Ar^2$ represents independently for each occurrence a monocyclic or bicyclic aryl with 6-14 ring atoms; or a monocyclic or bicyclic heteroaryl with 5-14 ring atoms, of which one, two or three ring atoms are independently S, O or N;
$X^1$ is a bond or O;
$X^2$ represents independently for each occurrence H, halide, hydroxyl, alkoxyl, amino, alkylamino, or arylamino; and
q is 1 or 2;
$R_2$ and $R_7$ are independently H, hydroxyl, alkyl, halide, alkoxyl, aryloxy, acyloxy, silyloxy, amino, alkylamino, arylamino, acylamino, aralklyamino, nitro, sulfhydryl, alkylthio, acylthio, carboxamide, carboxyl, phosphate, silyl, thioalkyl, alkylsulfonyl, arylsulfonyl, alkylsulfonyloxy, arylsulfonyloxy, nitrile, —COR, —CO$_2$R, or —CH$_2$O-heterocyclyl; or R$_2$ and R$_7$ taken together form a —OC(O)O— linkage or an optionally substituted alkyl linkage containing 1 to 6 carbon atoms; or R$_7$ is a bond to R$_8$;

R$_3$ and R$_6$ each represent independently for each occurrence H, halide, hydroxyl, amino, alkyl, aryl, cycloalkyl, aralkyl, heteroaryl, heteroaralkyl, alkoxyl, aryloxy, acyloxy, silyloxy, alkylamino, arylamino, acylamino, or aralklyamino;

R$_4$ and R$_5$ each represent independently for each occurrence H, halide, alkyl, aryl, cycloalkyl, aralkyl, heteroaryl, heteroaralkyl, alkoxyl, aryloxy, acyloxy, silyloxy, alkylamino, arylamino, acylamino, or aralklyamino;

R$_8$ is H, a branched or unbranched alkyl or alkenyl, cycloalkyl, heterocycloalkyl, bicycloalkyl, a bond to R$_7$, heterocycloalkyl substituted with an aralkyl group, or has the formula 2c:

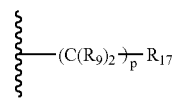

2c wherein p is 0, 1, 2, 3, 4, 5, or 6; and

R$_{17}$ is aryl, cycloalkyl, cycloalkenyl, heterocyclyl, alkoxyl, heteroaryl, —OR$_{18}$, —SR$_{18}$, —N(R$_{18}$)$_2$, —N(R$_{10}$)CO$_2$-alkyl, —CO$_2$R$_{10}$, —C(O)N(R$_{10}$)aryl, or a polycyclic ring containing 8-14 carbon atoms; wherein R$_{18}$ is independently for each occurrence H, alkyl, aryl, aralkyl, acyl, -A$^1$-A$^2$-A$^3$, or —CR$_9$=CR$_9$(C(R$_9$)$_2$)$_n$CR$_9$=C(R$_9$)$_2$; or two R$_{18}$ taken together form a ring;

R$^9$ represents independently for each occurrence H or alkyl;

R$_{10}$ and R$_{11}$ each represent independently for each occurrence H, alkyl, aryl, cycloalkyl, aralkyl, heteroaryl, or heteroaralkyl;

R$_{19}$ represents independently for each occurrence H, alkyl, aryl, cycloalkyl, aralkyl, heteroaryl, heteroaralkyl, or -A$^1$-A$^2$-A$^3$;

A$^1$ and A$^3$ each represent independently for each occurrence alkyl, cycloalkyl, heterocycloalkyl, aryl, heteroaryl, aralkyl, or heteroaralkyl;

A$^2$ represents independently for each occurrence O or a bond; and the stereochemical configuration at any stereocenter of a compound represented by 2 is R, S, or a mixture of these configurations.

In certain embodiments, the present invention relates to the aforementioned compound, wherein R$_2$ and R$_7$ are hydroxyl.

In certain embodiments, the present invention relates to the aforementioned compound, wherein R$_2$ and R$_7$ are hydroxyl; and R$_4$, R$_5$, and R$_6$ are H.

In certain embodiments, the present invention relates to the aforementioned compound, wherein R$_2$ and R$_7$ are hydroxyl; R$_4$, R$_5$, and R$_6$ are H; and m and n are 1.

In certain embodiments, the present invention relates to the aforementioned compound, wherein R$_2$ and R$_7$ are hydroxyl; R$_4$, R$_5$, R$_6$ are H; m and n are 1; and R$_3$ is methyl.

Another aspect of the present invention relates to a compound represented by formula 3:

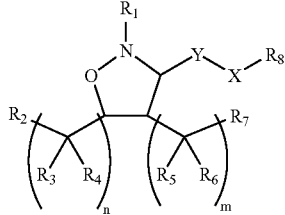

3 or pharmaceutically acceptable salts, solvates, or hydrates thereof, wherein

Y is —C(R$_9$)$_2$—, —C(O)—, —C(S)—, or —C(=NR$_{10}$)—;

X is —N(R$_{11}$)—, an optionally substituted phenyl group, or a bond;

m is 0, 1, 2, 3, 4, 5, or 6;

n represents independently for each occurrence 0, 1, 2, 3, 4, 5, or 6;

R$_1$ is alkyl, aralkyl, heteroaralkyl, has the formula 3a:

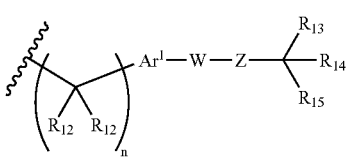

3a wherein

R$_{12}$ represents independently for each occurrence H or alkyl; wherein any two instances of R$_{12}$ may be connected by a covalent bond;

Ar$^1$ is a monocyclic or bicyclic aryl with 6-14 ring atoms; or a monocyclic or bicyclic heteroaryl with 5-14 ring atoms, of which one, two or three ring atoms are independently S, O or N;

W is a bond; or bivalent alkyl, alkenyl, or alkynyl chain;

Z is a bond, —(C(R$_{12}$)$_2$)$_n$—, or —O(C(R$_{12}$)$_2$)$_n$—;

R$_{13}$ and R$_{14}$ are independently H, alkyl, aryl, cycloalkyl, heterocycloalkyl, aralkyl, heteroaryl, heteroaralkyl, halide, alkenyl, alkynyl, aminoalkyl, thiol, thioalkyl, silyl, nitro, nitrile, alkoxyl, acyl, acylamino, —COR$_{10}$, —CO$_2$R$_{10}$, or -A$^1$-A$^2$-A$^3$; or R$_{13}$ and R$_{14}$ taken together form a monocyclic or polycyclic ring; or R$_{13}$ and R$_{14}$ taken together with R$_{15}$ form a cycloalkenyl ring, aromatic ring, or heteroaromatic ring;

R$_{15}$ is halide, hydroxyl, alkoxyl, aryl, aryloxy, acyloxy, —N(R$_{10}$)$_2$, acylamino, aralkyl, nitro, acylthio, carboxamide, carboxyl, nitrile, —COR$_{10}$, —CO$_2$R$_{10}$, —N(R$_{10}$)CO$_2$R$_{10}$, —OC(O)N(R$_{10}$)$_2$, —N(R$_{10}$)SO$_2$R$_{19}$, —N(R$_{20}$)C(O)N(R$_{19}$)$_2$, —N(R$_{10}$)(C(R$_9$)$_2$)$_n$-A$^1$-A$^2$-A$^3$, —(C(R$_9$)$_2$)$_n$-halogen, —CH$_2$O-heterocyclyl, alkyl, cycloalkyl, alkenyl, alkynyl, silyloxy, thiol, acylthio, phosphate, silyl, thioalkyl, alkylsulfonyl, arylsulfonyl, alkylsulfonyloxy, or arylsulfonyloxy; or R$_{15}$ taken together with R$_{13}$ and R$_{14}$ form a cycloalkenyl ring, aromatic ring, or heteroaromatic ring; or R$_1$ or R$_{15}$ are independently represented by formula 3b:

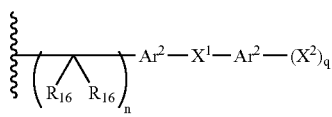

wherein $R_{16}$ represents independently for each occurrence H, alkyl, cycloalkyl, heterocycloalkyl, aryl, aralkyl, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{10}$, or —$N(R_{10})C(O)N(R_{10})_2$; wherein any two instances of $R_{16}$ may be connected by a covalent bond to form a ring;

$Ar^2$ represents independently for each occurrence a monocyclic or bicyclic aryl with 6-14 ring atoms; or a monocyclic or bicyclic heteroaryl with 5-14 ring atoms, of which one, two or three ring atoms are independently S, O or N;

$X^1$ represents independently for each occurrence a bond, O, S, S(O), S(O)$_2$, S(O)$_3$, amino, alkylamino diradical, alkoxyl diradical, alkyl diradical, alkenyl diradical, alkynyl diradical, amido, carbonyl, —$N(R_{10})CO_2R_{10}$, —$OC(O)N(R_{10})_2$, or —$N(R_{10})C(O)N(R_{10})_2$;

$X^2$ represents independently for each occurrence H, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{10}$, —$N(R_{10})C(O)N(R_{10})_2$, or —$CH_2O$-heterocyclyl; and q represents independently for each occurrence 1, 2, 3, 4, or 5;

$R_2$ and $R_7$ are independently H, hydroxyl, alkyl, halide, alkoxyl, aryloxy, acyloxy, silyloxy, amino, alkylamino, arylamino, acylamino, aralklyamino, nitro, sulfhydryl, alkylthio, acylthio, carboxamide, carboxyl, phosphate, silyl, thioalkyl, alkylsulfonyl, arylsulfonyl, alkylsulfonyloxy, arylsulfonyloxy, nitrile, —COR, —$CO_2R$, or —$CH_2O$-heterocyclyl; or $R_2$ and $R_7$ taken together form a —OC(O)O— linkage or an optionally substituted alkyl linkage containing 1 to 6 carbon atoms; or $R_7$ is bond to $R_8$;

$R_3$ and $R_6$ each represent independently for each occurrence H, halide, hydroxyl, amino, alkyl, aryl, cycloalkyl, aralkyl, heteroaryl, heteroaralkyl, alkoxyl, aryloxy, acyloxy, silyloxy, alkylamino, arylamino, acylamino, or aralklyamino;

$R_4$ and $R_5$ each represent independently for each occurrence H, halide, alkyl, aryl, cycloalkyl, aralkyl, heteroaryl, heteroaralkyl, alkoxyl, aryloxy, acyloxy, silyloxy, alkylamino, arylamino, acylamino, or aralklyamino;

$R_8$ is a branched or unbranched alkyl, bicycloalkyl, heterocycloalkyl substituted with an aralkyl group, or has the formula 3c:

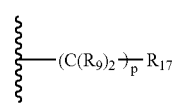

wherein p is 0, 1, 2, 3, 4, 5, or 6; and $R_{17}$ is aryl, cycloalkyl, cycloalkenyl, heterocyclyl, heteroaryl, —$N(R_{18})_2$, —$OR_{18}$, or —$CO_2R_{10}$; wherein $R_{18}$ is independently for each occurrence H, alkyl, aryl, aralkyl, -$A^1$-$A^2$-$A^3$, or —$CR_9$=$CR_9(C(R_9)_2)_nCR_9$=C$(R_9)_2$; or two $R_{18}$ taken together form a ring;

$R^9$ represents independently for each occurrence H or alkyl;

$R_{10}$ and $R_{11}$ each represent independently for each occurrence H, alkyl, aryl, cycloalkyl, aralkyl, heteroaryl, or heteroaralkyl;

$R_{19}$ represents independently for each occurrence H, alkyl, aryl, cycloalkyl, aralkyl, heteroaryl, heteroaralkyl, or -$A^1$-$A^2$-$A^3$;

$A^1$ and $A^3$ each represent independently for each occurrence alkyl, cycloalkyl, heterocycloalkyl, aryl, heteroaryl, aralkyl, or heteroaralkyl;

$A^2$ represents independently for each occurrence O or a bond; and the stereochemical configuration at any stereocenter of a compound represented by 3 is R, S, or a mixture of these configurations.

Another aspect of the present invention relates to compound represented by formula 4:

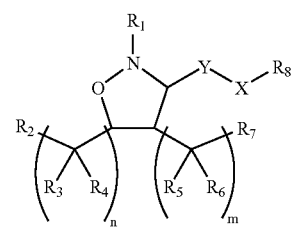

or pharmaceutically acceptable salts, solvates, or hydrates thereof, wherein

Y is —$C(R_9)_2$—, —C(O)—, —C(S)—, or —C(=$NR_{10}$)—;

X is O, S, —$N(R_{11})$—, aryl, or a bond;

m is 0, 1, 2, 3, 4, 5, or 6;

n represents independently for each occurrence 0, 1, 2, 3, 4, 5, or 6;

$R_1$ is alkyl, aralkyl, heteroaralkyl, has the formula 4a:

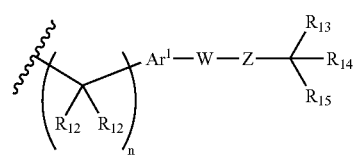

wherein $R_{12}$ represents independently for each occurrence H or alkyl; wherein any two instances of $R_{12}$ may be connected by a covalent bond;

$Ar^1$ is a monocyclic or bicyclic aryl with 6-14 ring atoms; or a monocyclic or bicyclic heteroaryl with 5-14 ring atoms, of which one, two or three ring atoms are independently S, O or N;

W is a bond; or bivalent alkyl, alkenyl, or alkynyl chain;

Z is a bond, —$(C(R_{12})_2)_n$—, or —$O(C(R_{12})_2)_n$—;

$R_{13}$ and $R_{14}$ are independently H, alkyl, aryl, cycloalkyl, heterocycloalkyl, aralkyl, heteroaryl, heteroaralkyl, halide, alkenyl, alkynyl, aminoalkyl, thiol, thioalkyl, silyl, nitro, nitrile, alkoxyl, acyl, acylamino, —$COR_{10}$, —$CO_2R_{10}$, or -$A^1$-$A^2$-$A^3$; or $R_{13}$ and $R_{14}$ taken together form a monocyclic or polycyclic ring; or $R_{13}$ and $R_{14}$ taken together with $R_{15}$ form a cycloalkenyl ring, aromatic ring, or heteroaromatic ring;

$R_{15}$ is halide, hydroxyl, alkoxyl, aryl, aryloxy, acyloxy, —$N(R_{10})_2$, acylamino, aralkyl, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{19}$, —$N(R_{10})C(O)N(R_{19})_2$, —$N(R_{10})(C(R_9)_2)_n$-$A^1$-$A^2$-$A^3$, —$(C(R_9)_2)_n$-halogen, —$CH_2O$-heterocyclyl, alkyl, cycloalkyl, alkenyl, alkynyl, silyloxy, thiol, acylthio, phosphate, silyl, thioalkyl, alkylsulfonyl, arylsulfonyl, alkylsulfonyloxy, or arylsulfonyloxy; or $R_{15}$ taken together with $R_{13}$ and $R_{14}$ form a cycloalkenyl ring, aromatic ring, or heteroaromatic ring; or $R_1$ or $R_{15}$ are represented by formula 4b:

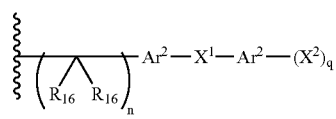

wherein $R_{16}$ represents independently for each occurrence H, alkyl, cycloalkyl, heterocycloalkyl, aryl, aralkyl, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{10}$, or —$N(R_{10})C(O)N(R_{10})_2$; wherein any two instances of $R_{16}$ may be connected by a covalent bond to form a ring;

$Ar^2$ represents independently for each occurrence a monocyclic or bicyclic aryl with 6-14 ring atoms; or a monocyclic or bicyclic heteroaryl with 5-14 ring atoms, of which one, two or three ring atoms are independently S, O or N;

$X^1$ represents independently for each occurrence a bond, O, S, S(O), $S(O)_2$, $S(O)_3$, amino, alkylamino diradical, alkoxyl diradical, alkyl diradical, alkenyl diradical, alkynyl diradical, amido, carbonyl, —$N(R_{10})CO_2R_{10}$, —$OC(O)N(R_{10})_2$, or —$N(R_{10})C(O)N(R_{10})_2$;

$X^2$ represents independently for each occurrence H, halide, hydroxyl, alkoxyl, aryloxy, acyloxy, amino, alkylamino, arylamino, acylamino, aralkylamino, nitro, acylthio, carboxamide, carboxyl, nitrile, —$COR_{10}$, —$CO_2R_{10}$, —$N(R_{10})CO_2R_{10}$, —$OC(O)N(R_{10})_2$, —$N(R_{10})SO_2R_{10}$, —$N(R_{10})C(O)N(R_{10)2}$, or —$CH_2O$-heterocyclyl; and q represents independently for each occurrence 1, 2, 3, 4, or 5;

$R_2$ and $R_7$ are independently hydroxyl or alkoxyl;

$R_3$, $R_4$, and $R_5$ are H;

$R_6$ is methyl, ethyl, or propyl;

$R_8$ is H, a branched or unbranched alkyl or alkenyl, cycloalkyl, heterocycloalkyl, bicycloalkyl, a bond to $R_7$, heterocycloalkyl substituted with an aralkyl group, or has the formula 4c:

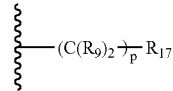

wherein p is 0, 1, 2, 3, 4, 5, or 6; and $R_{17}$ is aryl, cycloalkyl, cycloalkenyl, heterocyclyl, alkoxyl, heteroaryl, —$OR_{18}$, —$SR_{18}$, —$N(R_{18})_2$, —$N(R_{10})CO_2$-alkyl, —$CO_2R_{10}$, —$C(O)N(R_{10})$aryl, or a polycyclic ring containing 8-14 carbon atoms; wherein $R_{18}$ is independently for each occurrence H, alkyl, aryl, aralkyl, acyl, -$A^1$-$A^2$-$A^3$, or —$CR_9$=$CR_9(C(R_9)_2)CR_9$=$C(R_9)_2$; or two $R_{18}$ taken together form a ring;

$R^9$ represents independently for each occurrence H or alkyl;

$R_{10}$ and $R_{11}$ each represent independently for each occurrence H, alkyl, aryl, cycloalkyl, aralkyl, heteroaryl, or heteroaralkyl;

$R_{19}$ represents independently for each occurrence H, alkyl, aryl, cycloalkyl, aralkyl, heteroaryl, heteroaralkyl, or -$A^1$-$A^2$-$A^3$;

$A^1$ and $A^3$ each represent independently for each occurrence alkyl, cycloalkyl, heterocycloalkyl, aryl, heteroaryl, aralkyl, or heteroaralkyl;

$A^2$ represents independently for each occurrence O or a bond; and the stereochemical configuration at any stereocenter of a compound represented by 4 is R, S, or a mixture of these configurations.

Another aspect of the present invention relates to a compound represented by formula 5:

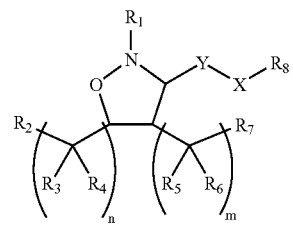

or pharmaceutically acceptable salts, solvates, or hydrates thereof, wherein:

Y is —$C(R_9)_2$—, —C(O)—, —C(S)—, or —C(=$NR_{10}$)—;

X is O, S, or —$N(R_{11})$—;

m is 0, 1, 2, 3, 4, 5, or 6;

n represents independently for each occurrence 0, 1, 2, 3, 4, 5, or 6;

$R_1$ is alkyl, aralkyl, heteroalkyl, or has the formula 5a or 5b:

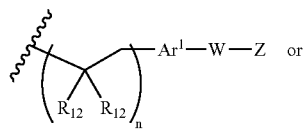

-continued

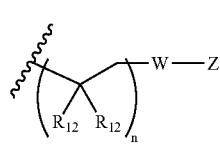

5b wherein:
$R_{12}$ represents independently for each occurrence H or alkyl; wherein any two instances of $R_{12}$ may be connected by a covalent bond;
$Ar^1$ is a monocyclic or bicyclic aryl with 6-14 ring atoms; or a monocyclic or bicyclic heteroaryl with 5-14 ring atoms, of which one, two or three ring atoms are independently S, O or N; or $Ar^1$ is represented by formua 5c:

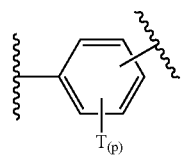

5c wherein,
T independently for each occurrence is H, halide, branched or unbranched alkyl, alkenyl, allyl, alkoxy, aryl, aralkyl, hydroxyl, amino, aminoalkyl, amido, carboxamide, cycloalkyl, cycloalkene, bycycloalkyl, bicycloalkene, cycloalkalkyl, heteroaromatic, heteroaralkyl, heterocyclyl, heterocyclalkyl, haloalkyl, ester; carboxylic, bis aryl, bis aryl ether, heterocyclic substituted aryl, or two T taken together form an aromatic or nonaromatic ring; and
p is 0, 1, 2, 3, or 4;
W is a bond; or bivalent alkyl, aryl, heteroaryl, or heterocyclyl group;
Z is a bond; H; —SR; —S(O)$_2$R; —NRSO$_2$R; —S(O)R; —N(R)$_2$; —C(O)R; —CO$_2$R; —C(O)N(R)$_2$; —C(S)N(R)$_2$; —CH$_2$C(O)heterocyclyl; —NRC(O)R; —NRCO$_2$R; —OC(O)N(R)$_2$; —NRC(O)(C(R$_9$)$_2$)$_n$N(R)$_2$; —NC(O)CH(R)$_2$; —C(=NR)N(R)$_2$; —C(=NR)R; hydroxyalkyl; or mono or bicyclic aryl, heteroaryl, or heterocyclyl;
wherein:
R independently for each occurrence is H, branched or unbranched alkyl, alkenyl, allyl, alkoxy, haloalkyl, acyl, mesylate, tosylate, ester, —(C(R$_9$)$_2$)$_n$T,—CH((C(R$_9$)$_2$)$_n$T)$_2$, or two R taken together form an aromatic or nonaromatic ring;
$R_2$ and $R_7$ are independently H, hydroxyl, alkyl, alkoxyl, amino, alkylamino, ester, or carboxamide;
$R_3$ and $R_6$ each represent independently for each occurrence H, hydroxyl, or alkyl;
$R_4$ and $R_5$ each represent independently for each occurrence H or alkyl; and
$R_8$ is H, a branched or unbranched alkyl or alkenyl, cycloalkyl, heterocycloalkyl, bicycloalkyl, a branched or unbranched aminoalkyl, or heterocycloalkyl substituted with an aralkyl group;
$R_9$, $R_{10}$, and $R_{11}$ represents independently for each occurrence H, alkyl, aryl, aralkyl, cycloalkyl, cycloalkalkyl, heteroaryl, or heteroaralkyl;
providing that $Ar^1$, W and Z may be further substituted with one or more groups selected from the following: halide, amido, alkoxy, ether, —NO$_2$, hydroxyl, —NR$_2$, or —CN;
that where applicable $Ar^1$, W, and Z, may be bonded to each other at the ortho, meta, or para positions; and
the stereochemical configuration at any stereocenter of a compound represented by 5 is R, S, or a mixture of these configurations.

In certain embodiments, the present invention relates to the aforementioned compound, wherein $R_2$ is OH.

In certain embodiments, the present invention relates to the aforementioned compound, wherein $R_6$ is methyl or ethyl and $R_7$ is hydroxyl.

In certain embodiments, the present invention relates to the aforementioned compound, wherein Y is —C(O)—, X is —N(R$_{11}$)—, and $R_8$ is bicycloalkyl.

In certain embodiments, the present invention relates to the aforementioned compound, wherein $R_1$ has formula 5a.

In certain embodiments, the present invention relates to the aforementioned compound, wherein $R_1$ has formula 5a, wherein $R_{12}$ is H or methyl.

In certain embodiments, the present invention relates to the aforementioned compound, wherein $R_1$ has formula 5a, wherein $Ar^1$ is a benzene ring.

In certain embodiments, the present invention relates to the aforementioned compound, wherein $R_1$ has formula 5a, wherein W is a bond, —CH$_2$—, or a benzene ring.

In certain embodiments, the present invention relates to the aforementioned compound, wherein $R_1$ has formula 5b, wherein $R_{12}$ is H or methyl.

In certain embodiments, the present invention relates to the aforementioned compound, wherein $R_1$ has formula 5b, wherein n is 4.

In certain embodiments, the present invention relates to the aforementioned compound, wherein $R_1$ has formula 5b and Z is N(R)$_2$.

In certain embodiments, the present invention relates to the aforementioned compound, wherein the compound has formula 5d or 5e:

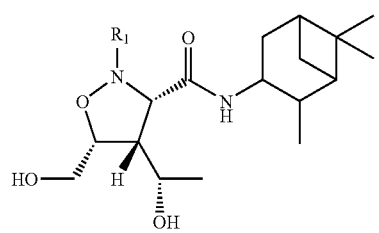

5d

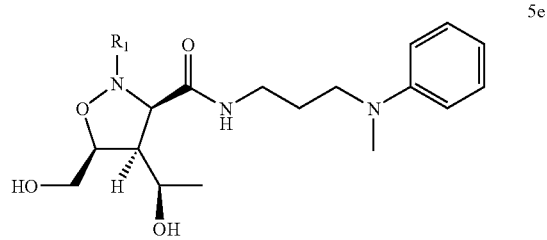

5e wherein:
$R_1$ has formula 5f:

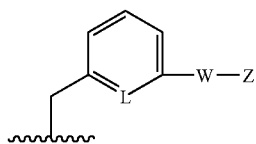

wherein:
L is N or CR; and
W, Z, $R_{13}$, $R_{14}$, $R_{15}$, and n are as defined above.

In certain embodiments, the present invention relates to the aforementioned compound, wherein L is CH, W is a benzene ring, and Z is —C(O)N(R)$_2$.

In certain embodiments, the present invention relates to the aforementioned compound, wherein L is CR, R is alkoxy, W is a benzene ring, and Z is —C(O)N(R)$_2$.

In certain embodiments, the present invention relates to the aforementioned compound, wherein L is COMe, W is a benzene ring, and Z is —C(O)N(R)$_2$.

In certain embodiments, the present invention relates to the aforementioned compound, wherein L is COEt, W is a benzene ring, and Z is —C(O)N(R)$_2$.

In certain embodiments, the present invention relates to the aforementioned compound, wherein L is COCH$_2$(cyclopropyl), W is a benzene ring, and Z is —C(O)N(R)$_2$.

In certain embodiments, the present invention relates to the aforementioned compound, wherein L is CH, W is a benzene ring, and Z is H.

In certain embodiments, the present invention relates to the aforementioned compound, wherein L is CH, W is —CH$_2$—, and Z is —N(R)$_2$.

In certain embodiments, the present invention relates to the aforementioned compound, wherein L is CH, W is a piperazine ring, and Z is —C(S)N(R)$_2$.

In certain embodiments, the present invention relates to the aforementioned compound, wherein L is CH, W is a piperazine ring, and Z is —C(O)N(R)$_2$.

In certain embodiments, the present invention relates to the aforementioned compound, wherein L is CH, W is a bond, and Z is N(R)$_2$.

In certain embodiments, the present invention relates to the aforementioned compound, wherein L is CH, W is a bond, and Z is —NRCO$_2$R or —OC(O)N(R)$_2$.

In certain embodiments, the present invention relates to the aforementioned compound, wherein L is CH, W is a bond, and Z is —NRC(O)(C(R$_9$)$_2$)$_n$N(R)$_2$.

In certain embodiments, the present invention relates to a compound or formula 5g:

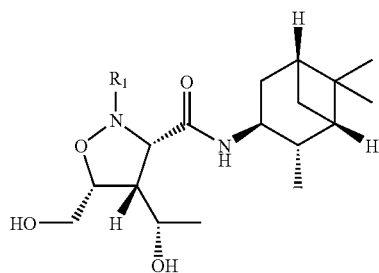

wherein $R_1$ is

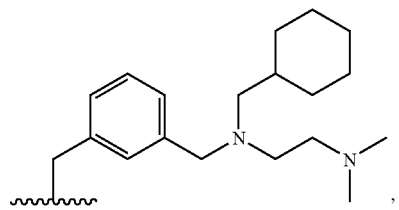

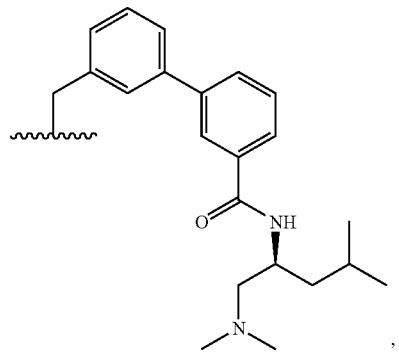

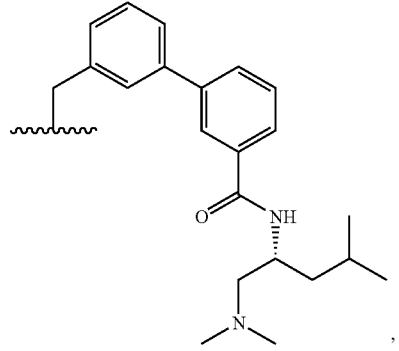

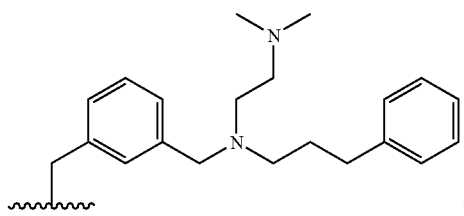

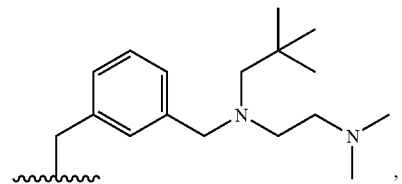

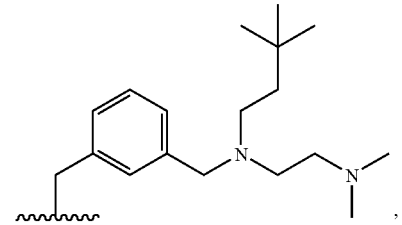

61
-continued
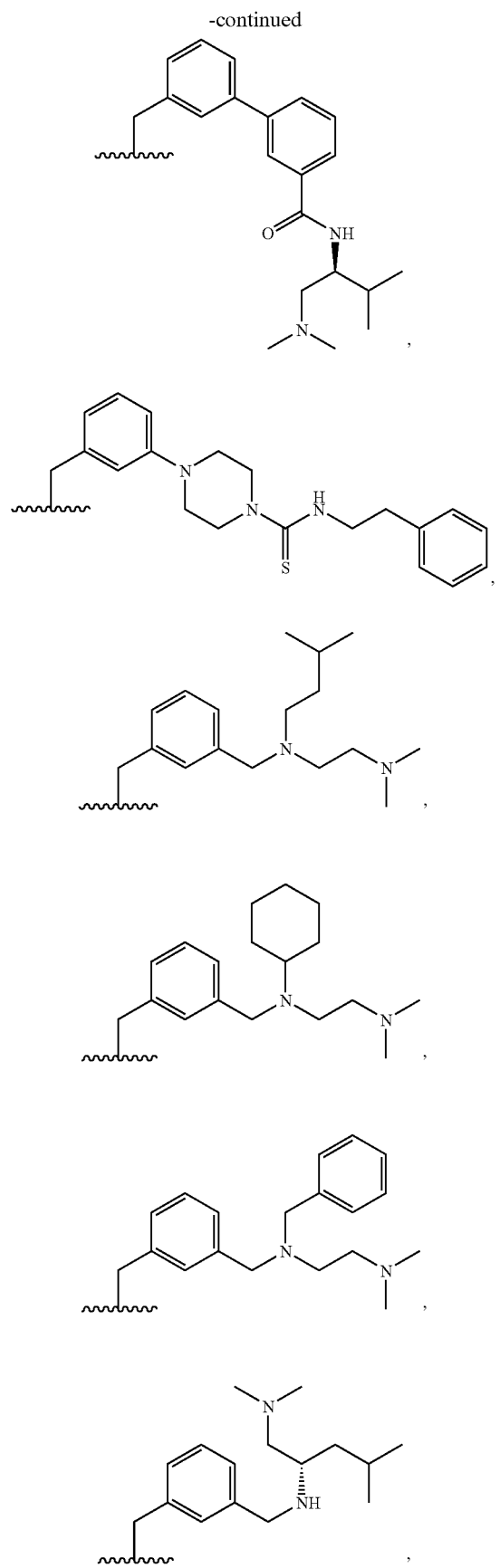
62
-continued
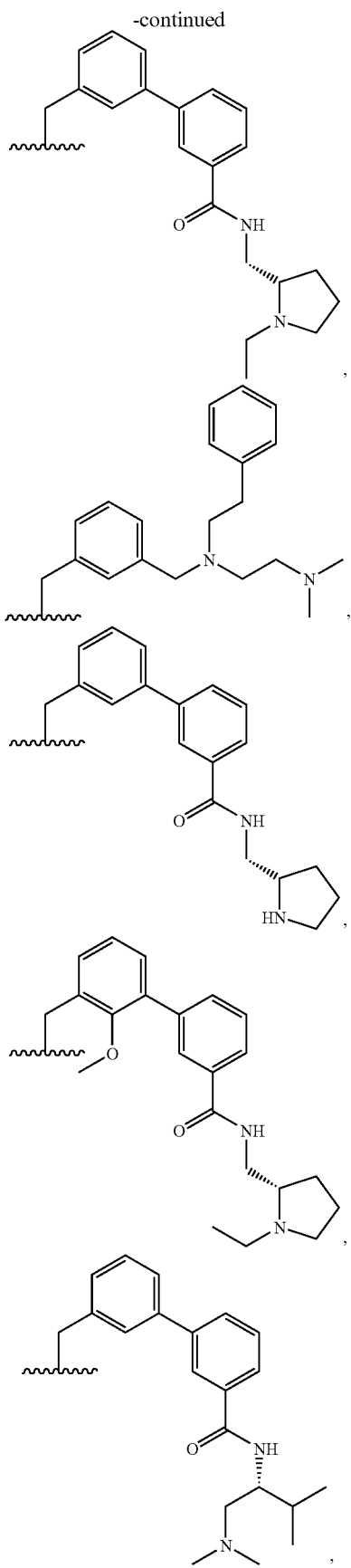

63
-continued
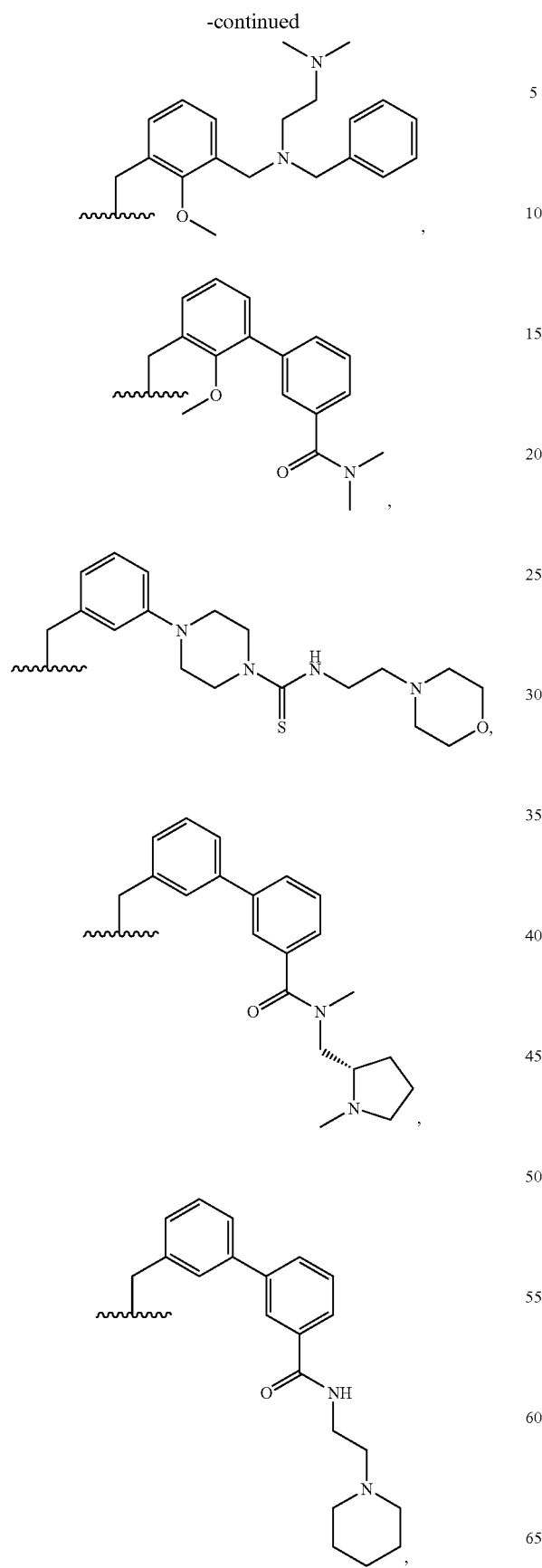
64
-continued
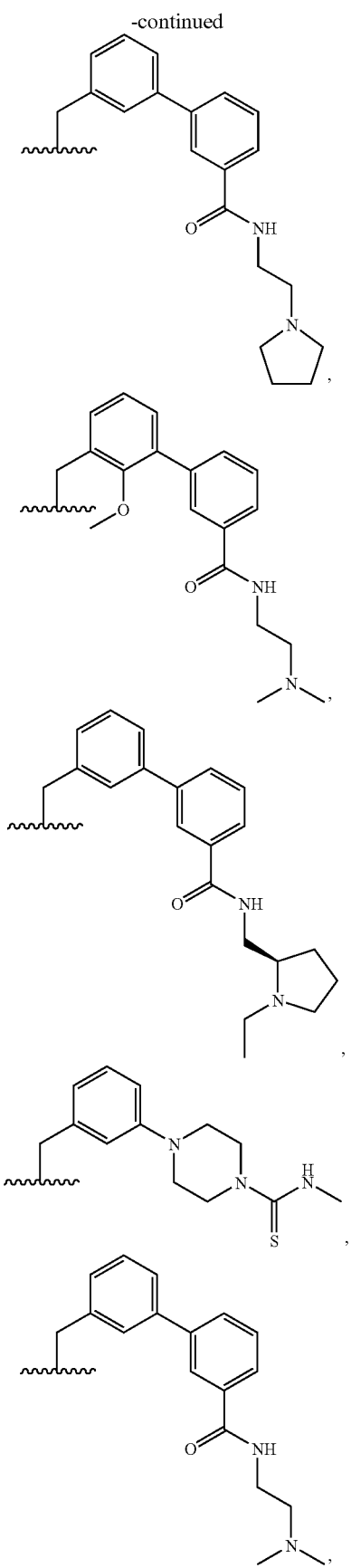

65
-continued
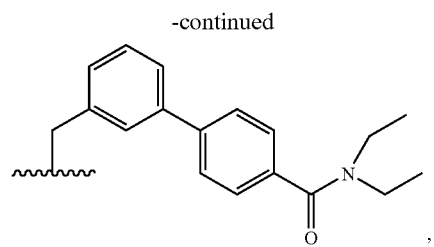
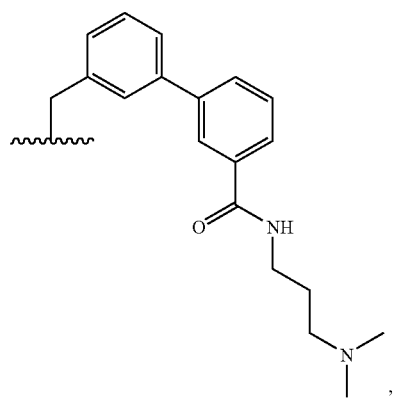
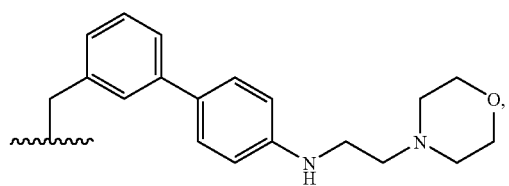
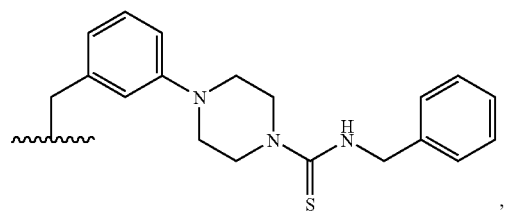
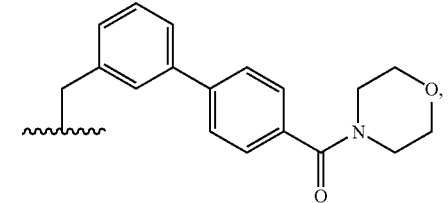
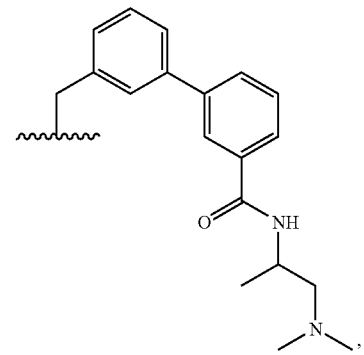
66
-continued
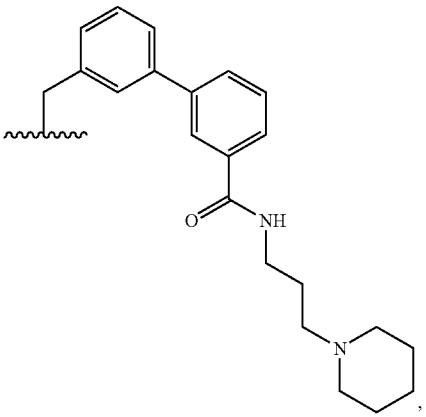
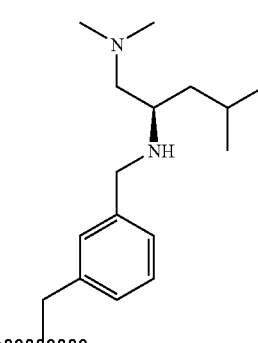
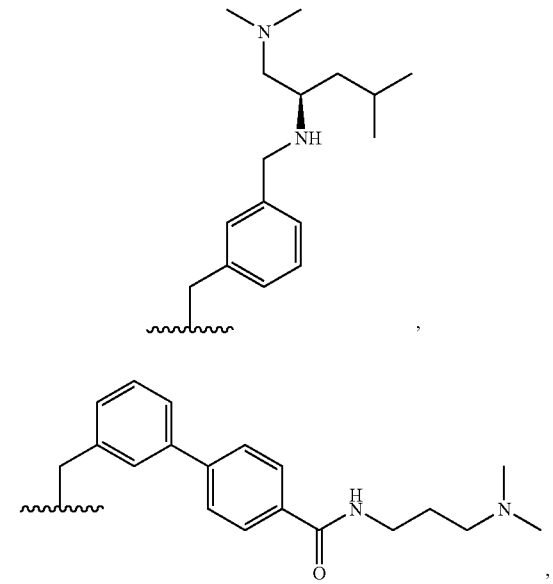
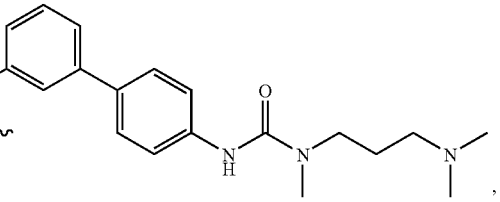
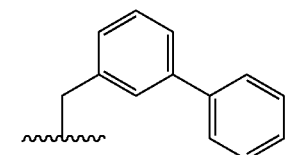
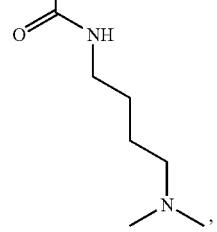

-continued
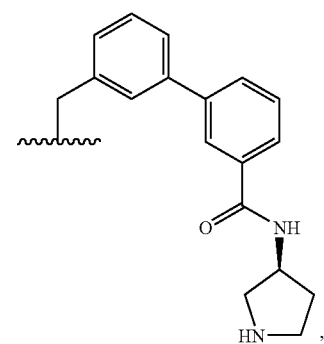
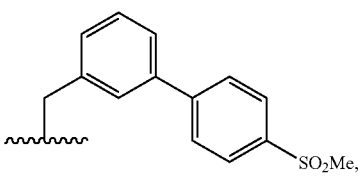
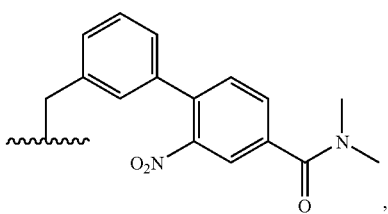
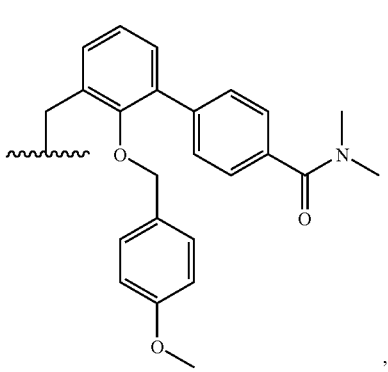
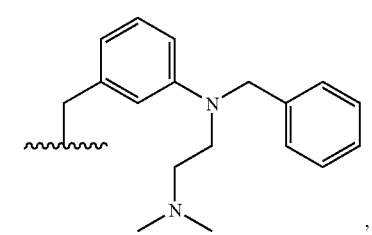
-continued
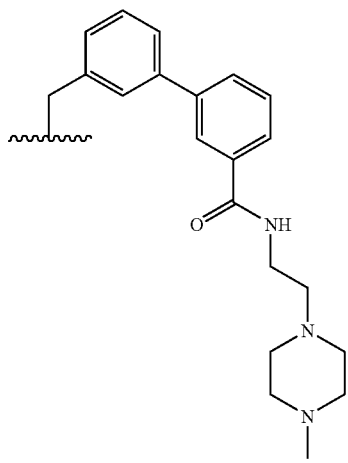
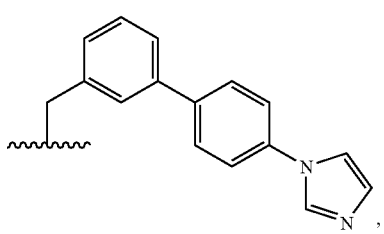
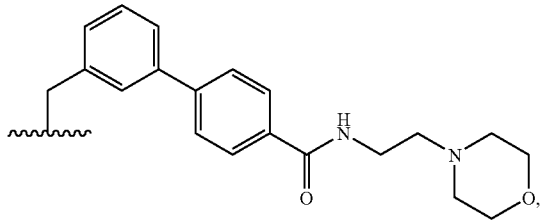
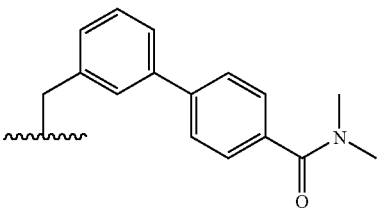
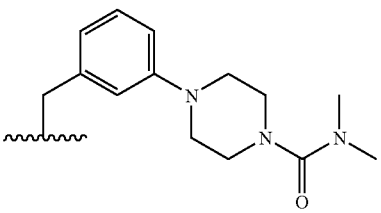
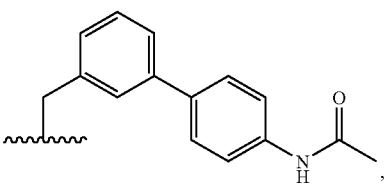

69
-continued
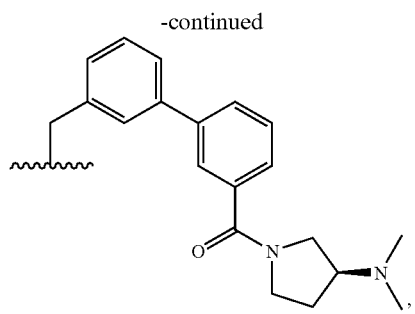
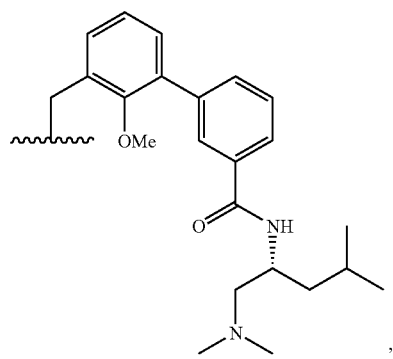
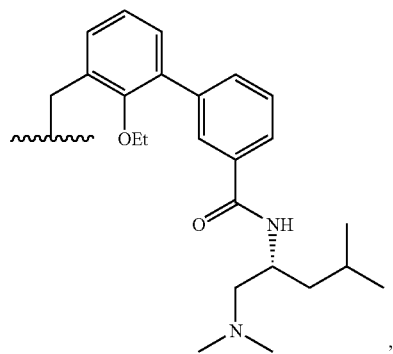
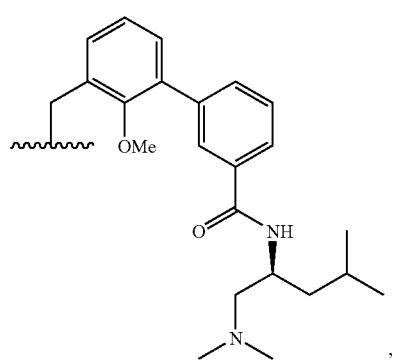
70
-continued
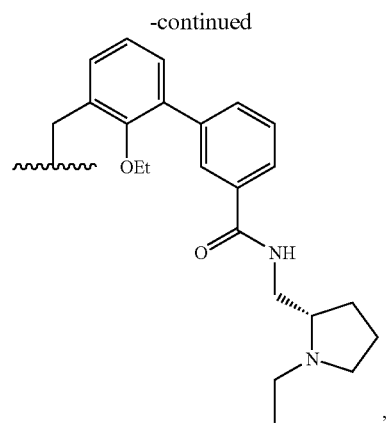
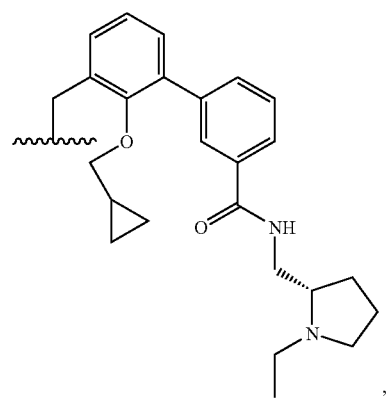
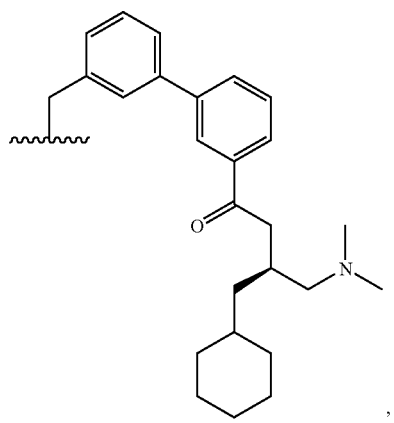
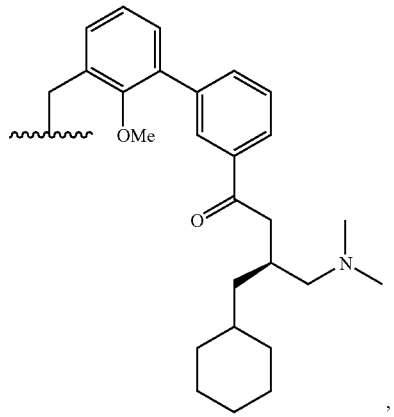

71
-continued
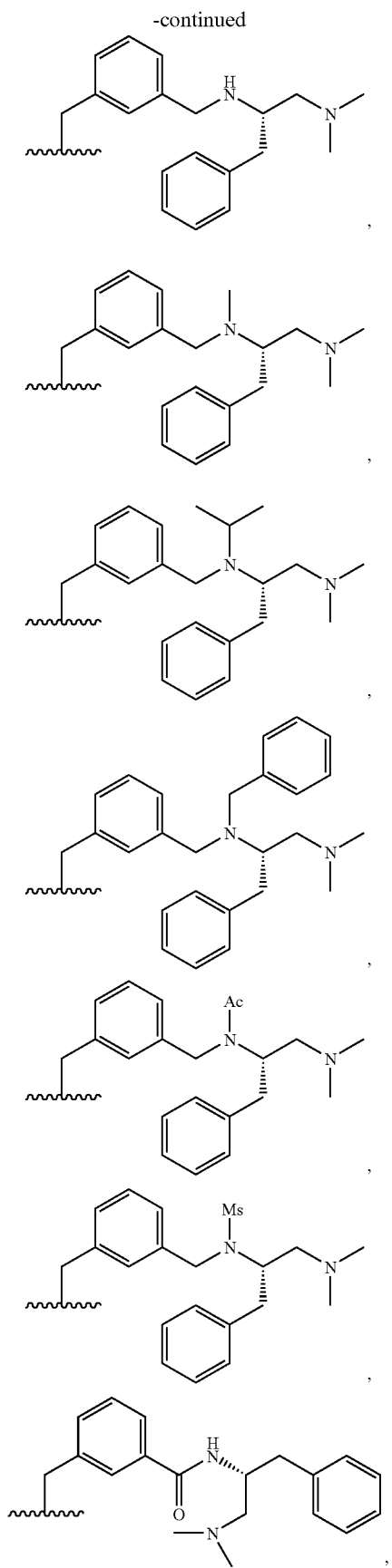
72
-continued
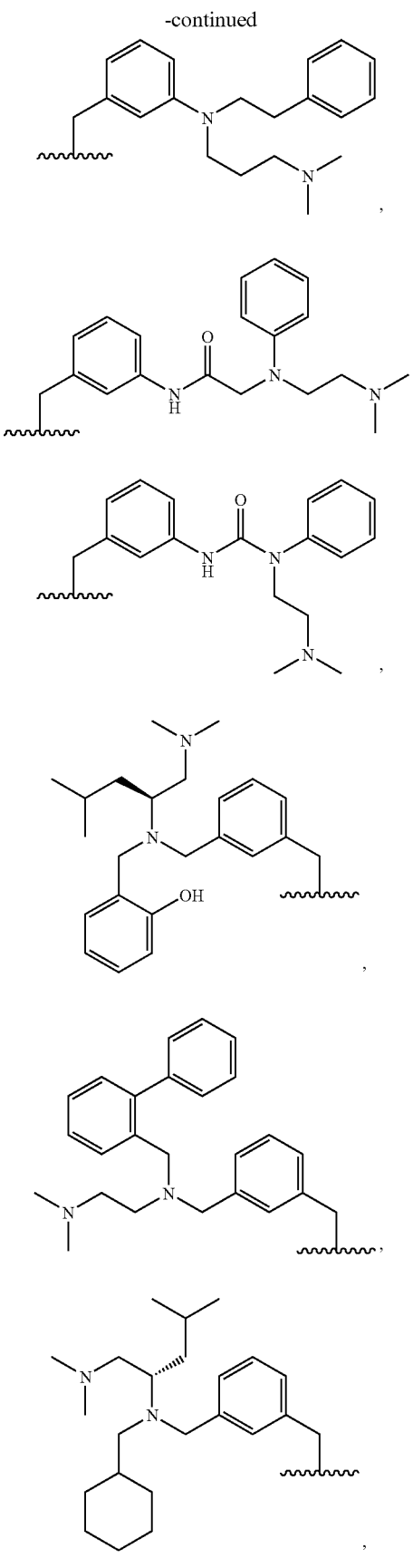

-continued
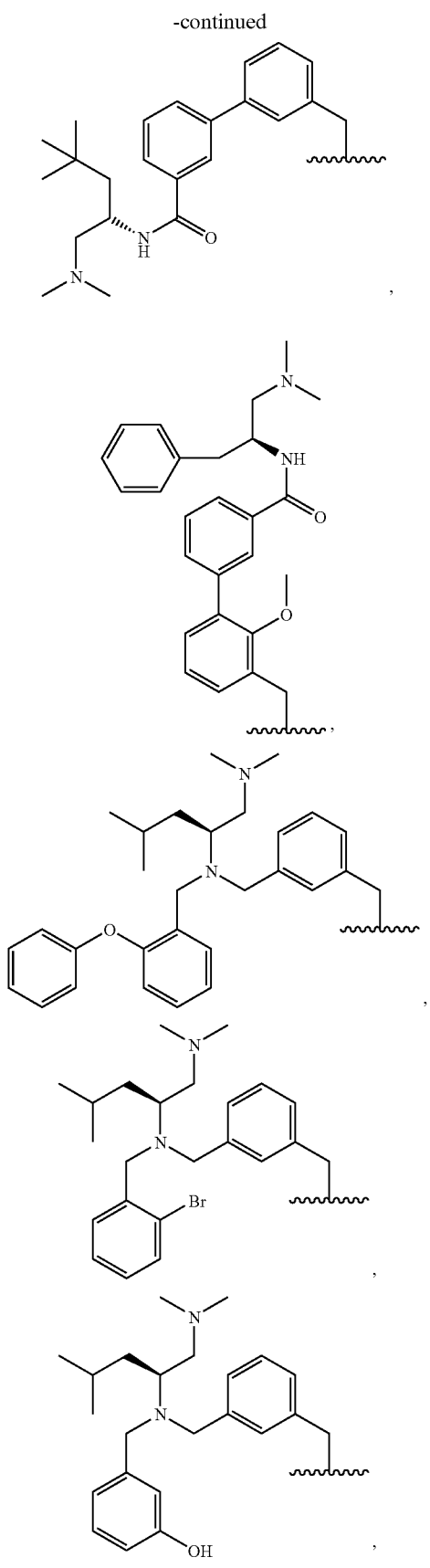
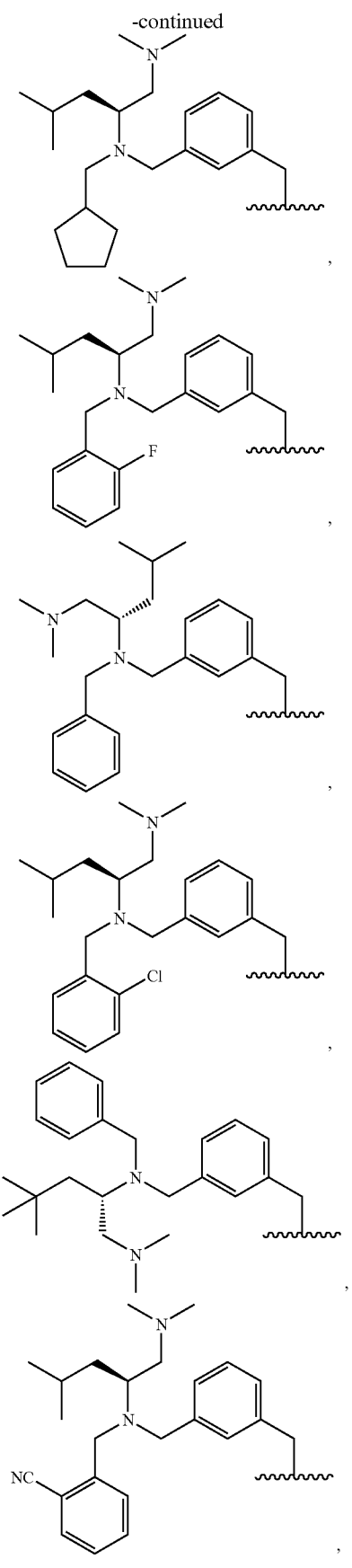

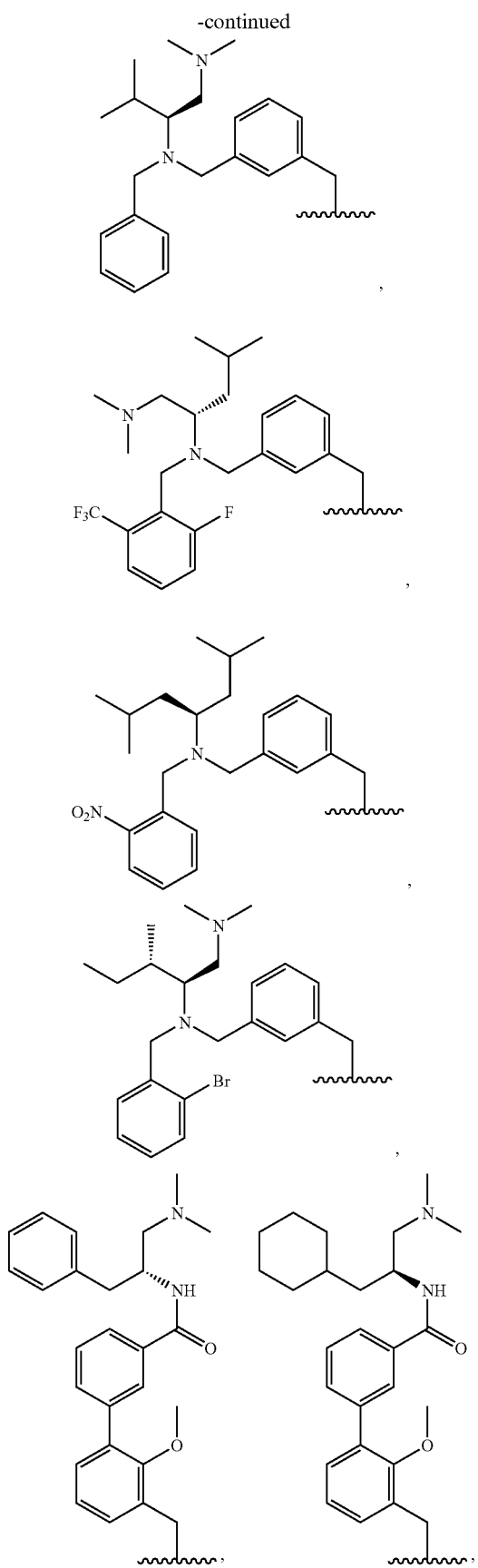
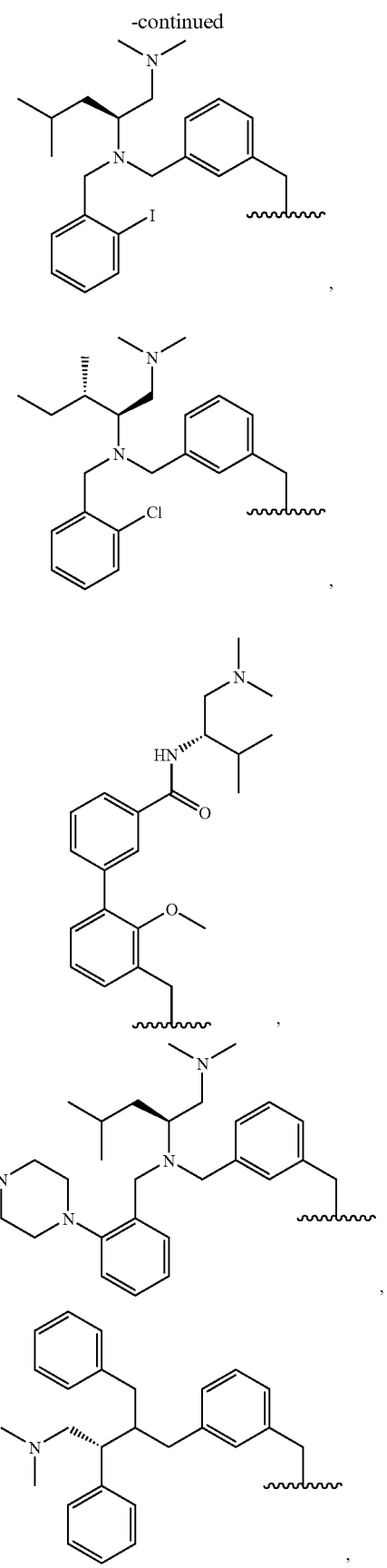

77
-continued
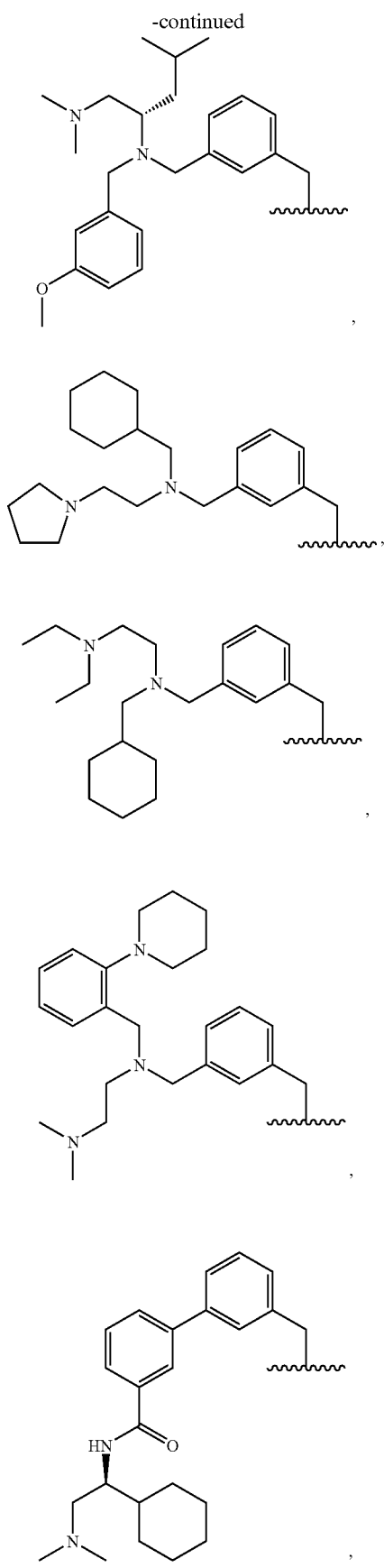
78
-continued
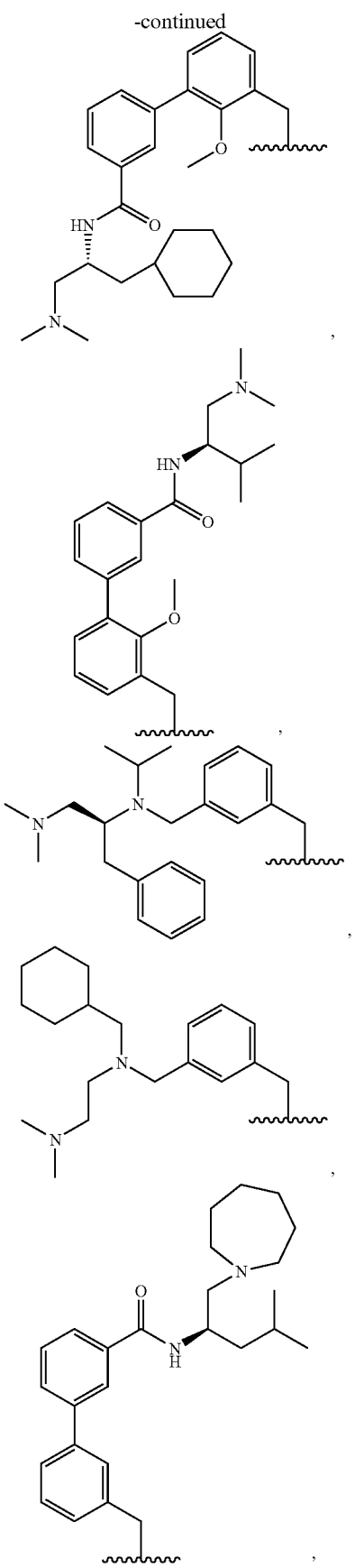

79
-continued
80
-continued
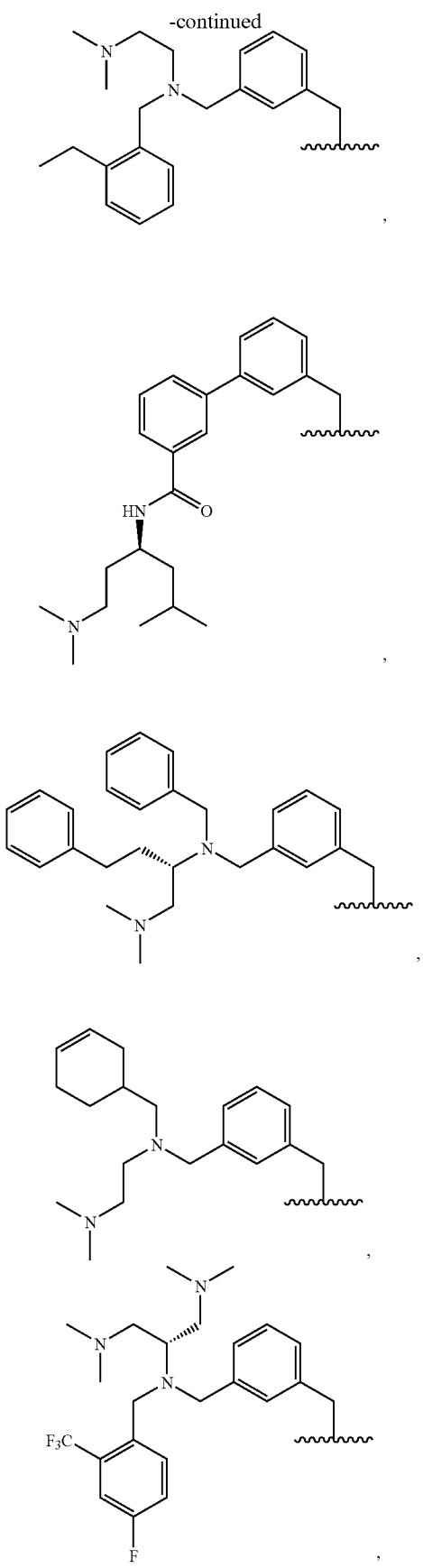
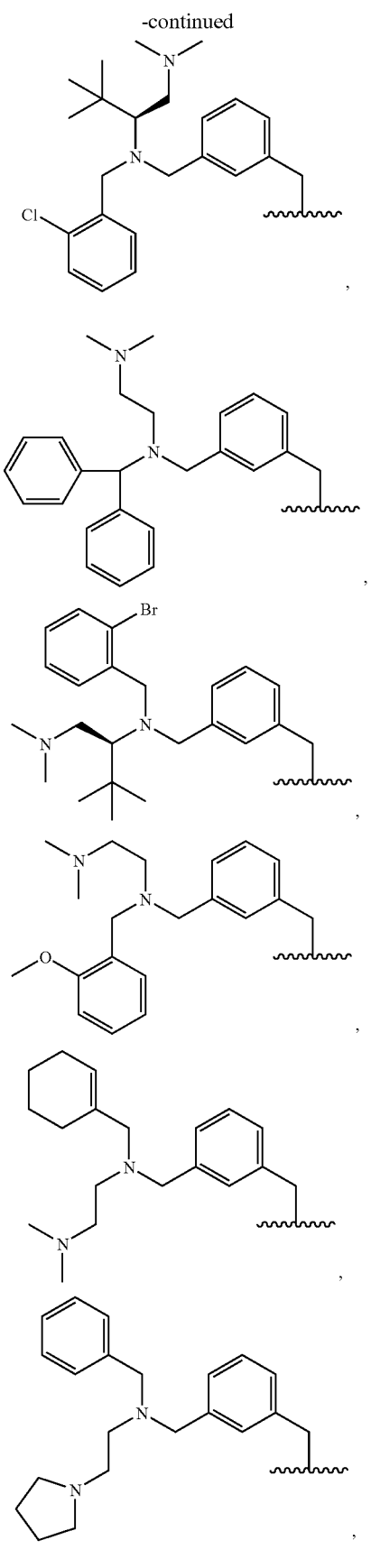

-continued
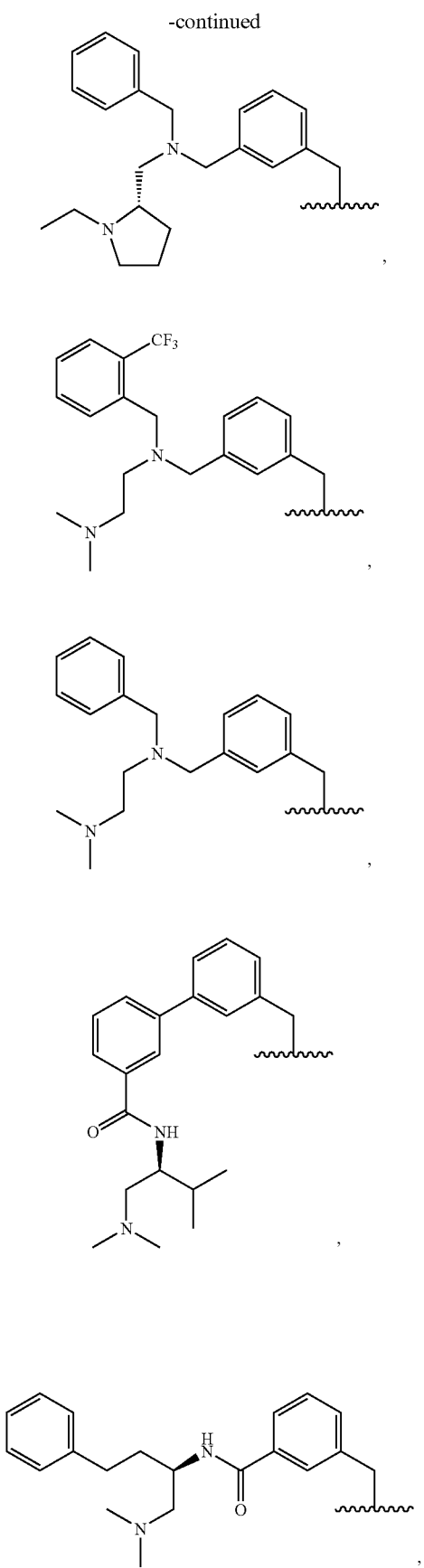
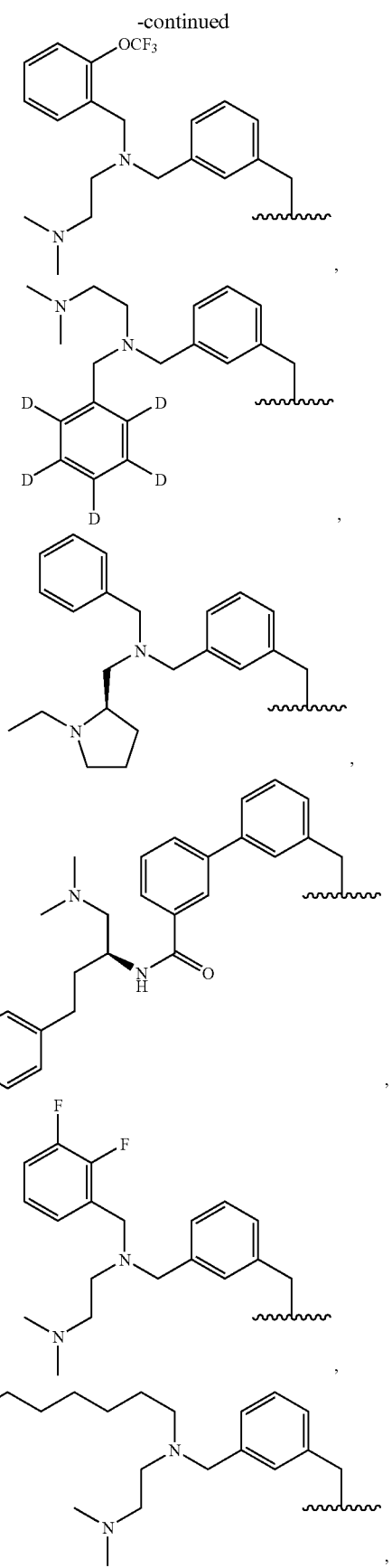

83 -continued
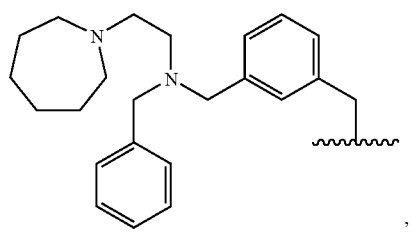
84 -continued
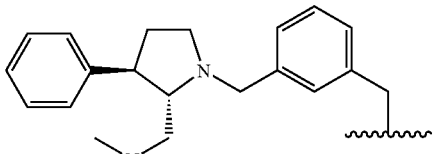
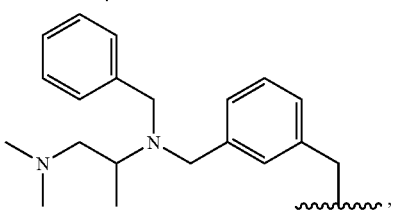
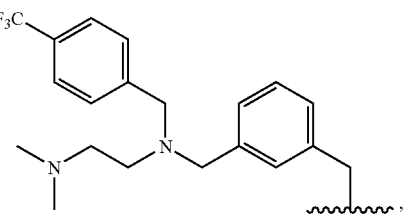
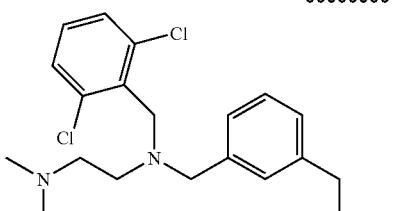
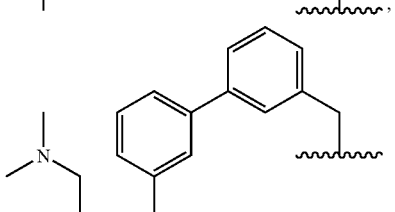
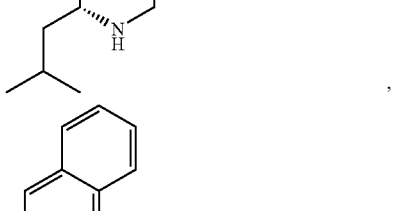
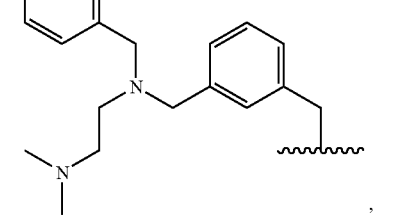
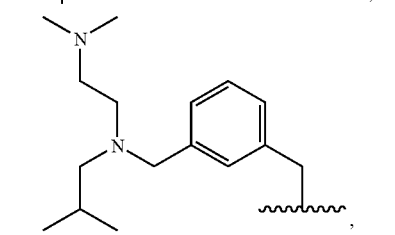

85
-continued
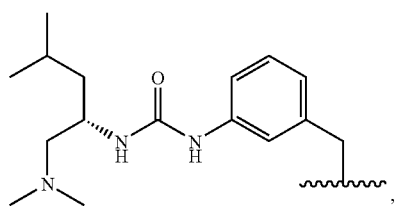
,
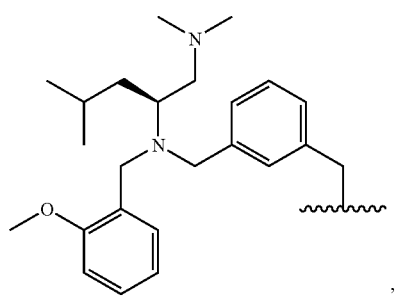
,
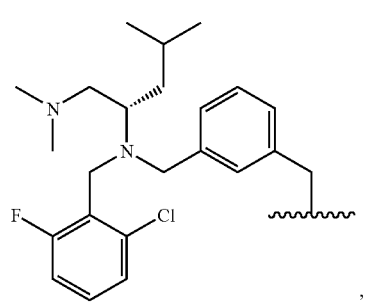
,
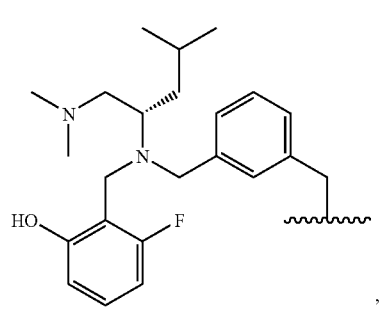
,
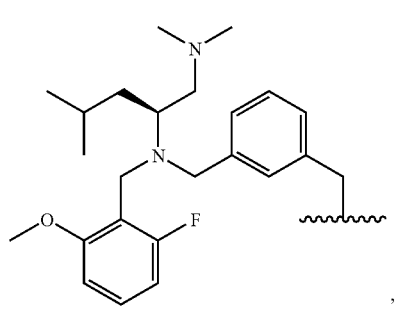
,
86
-continued
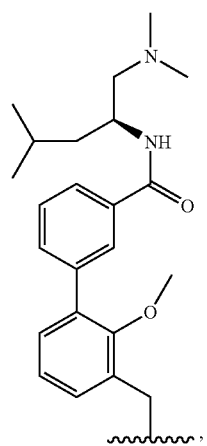
,
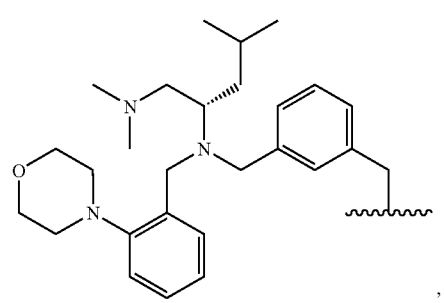
,
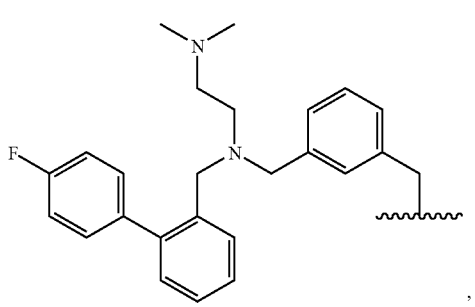
,
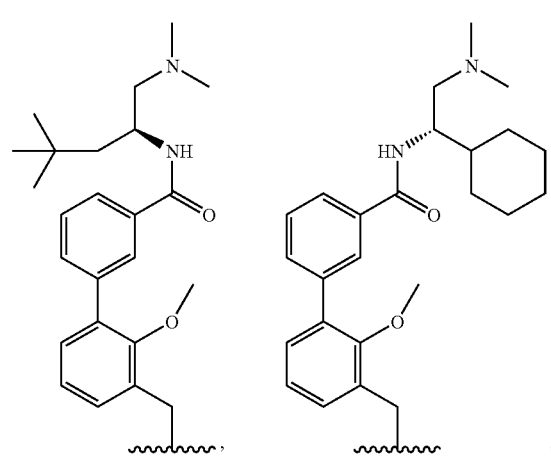
, -continued
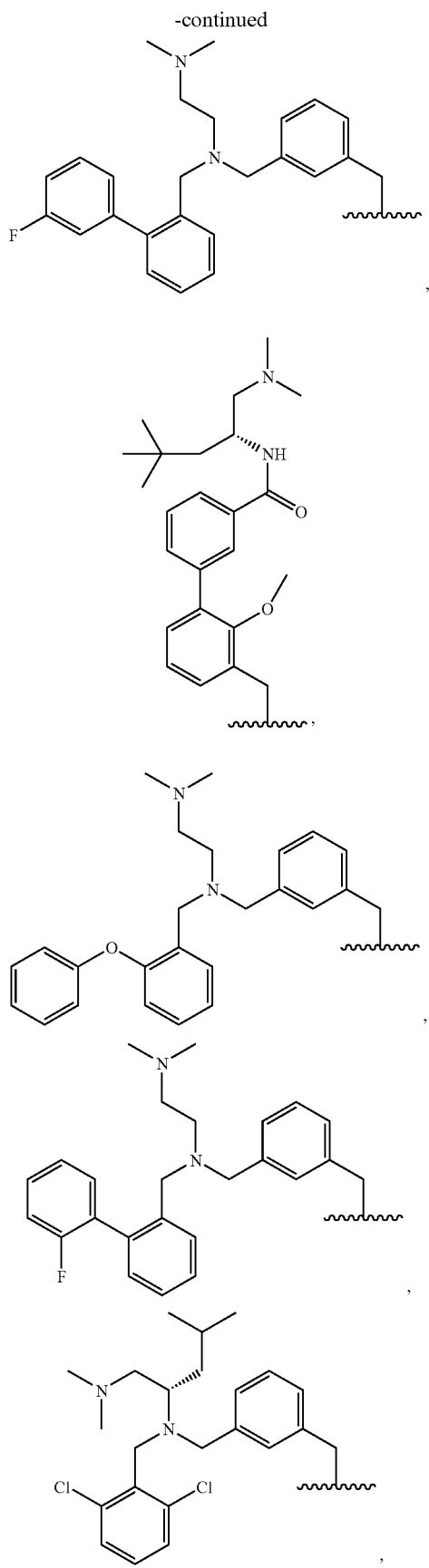
-continued
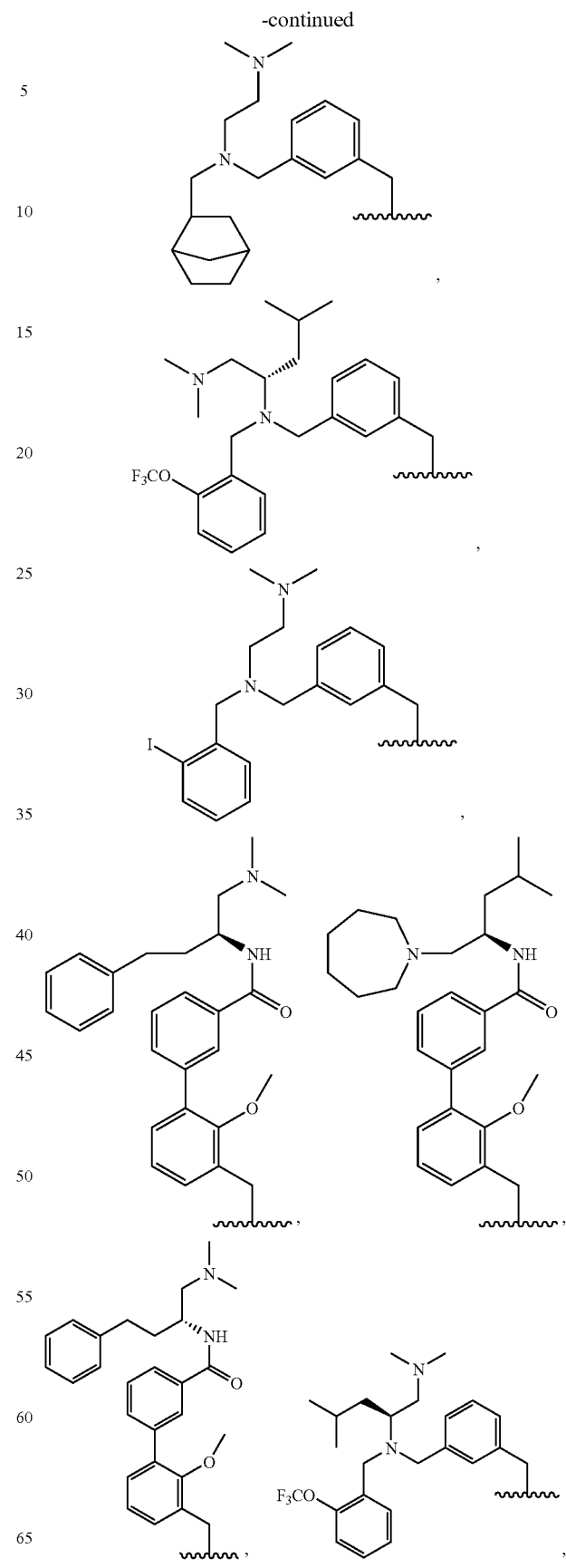

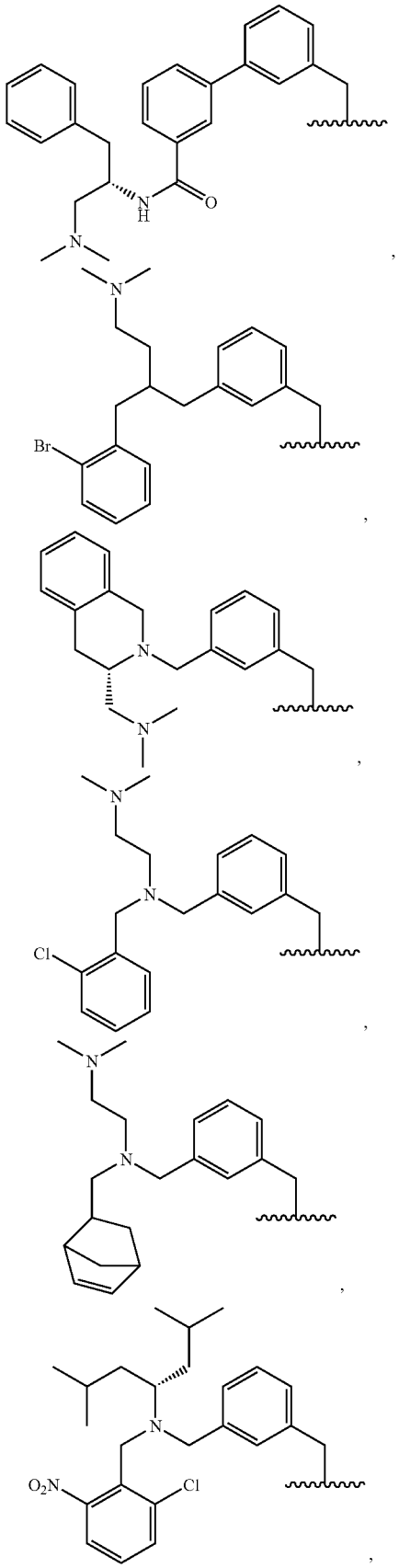
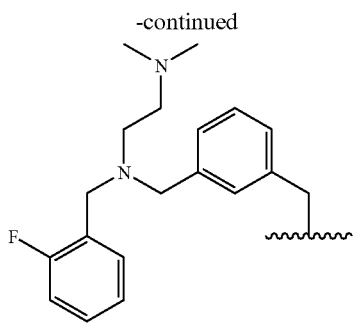
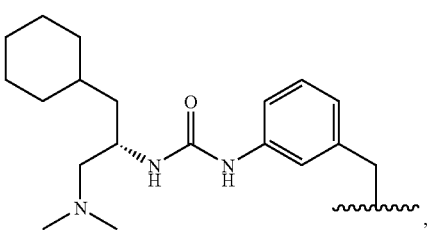
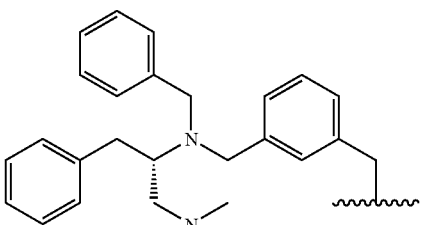
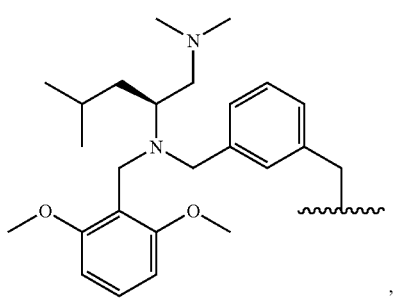
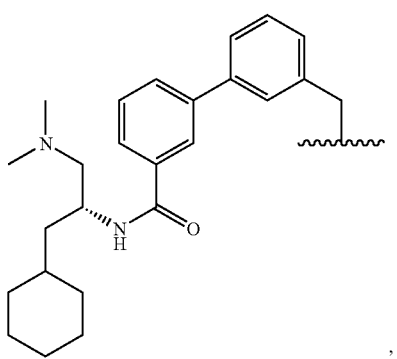

91
-continued
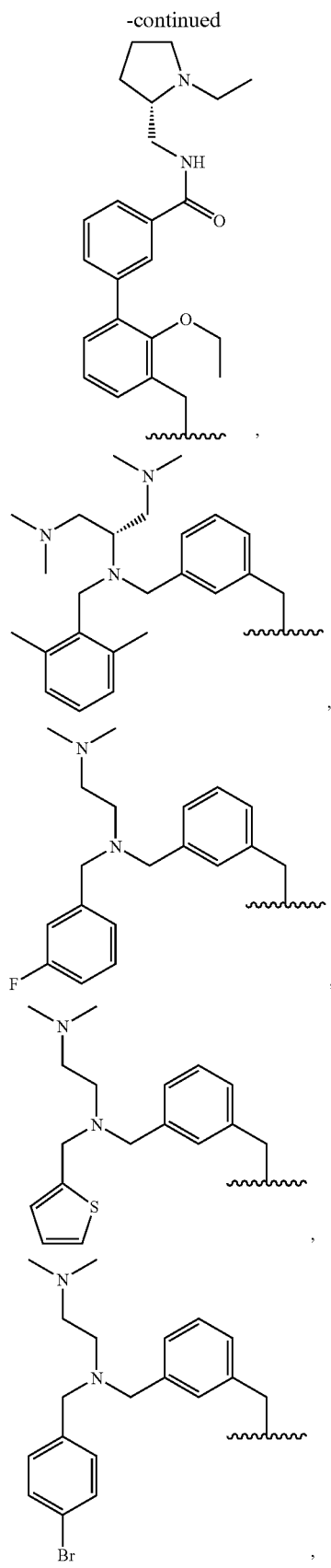
92
-continued
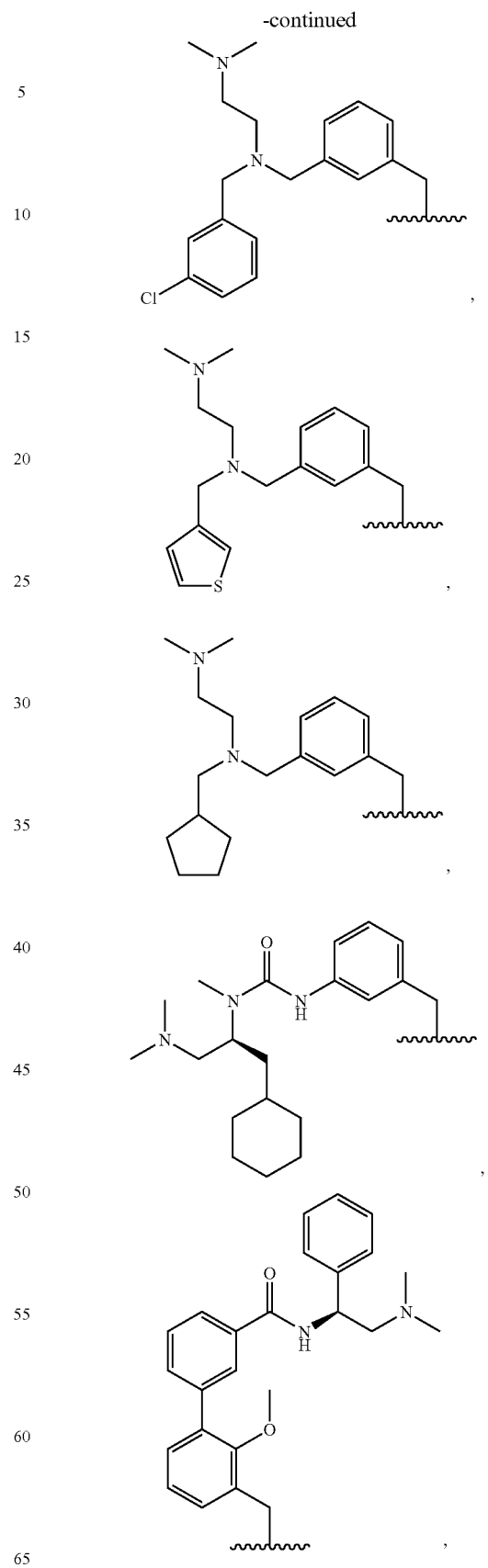

-continued
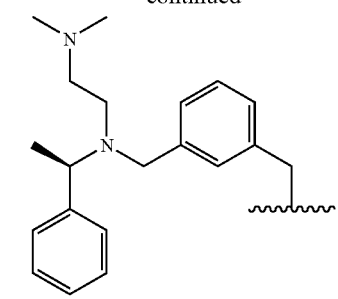
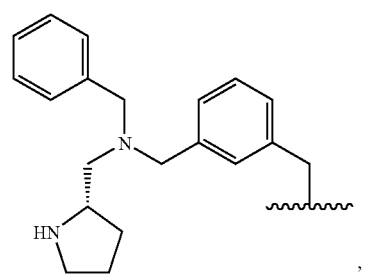
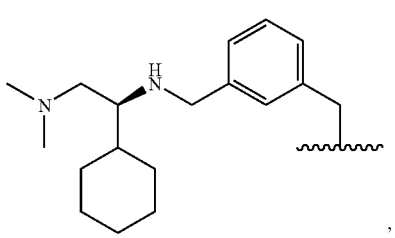
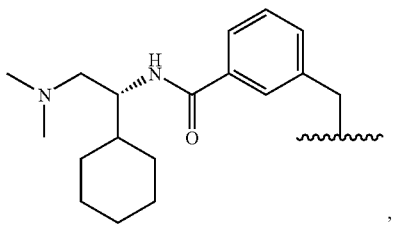
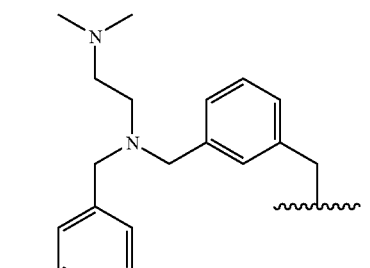
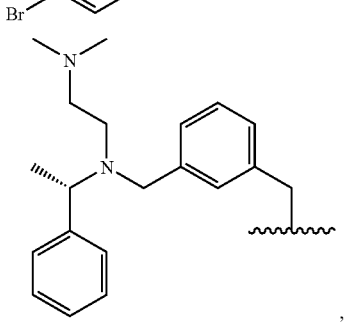
-continued
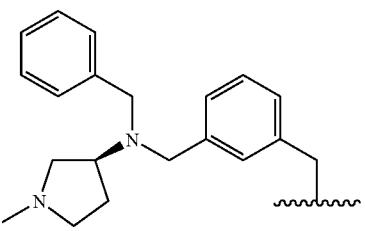
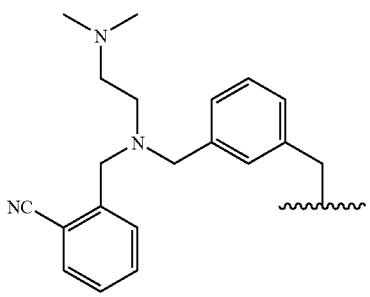
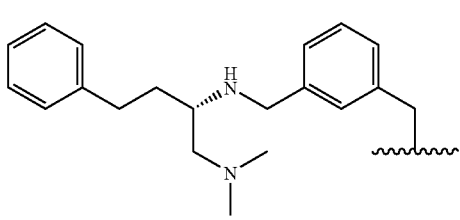
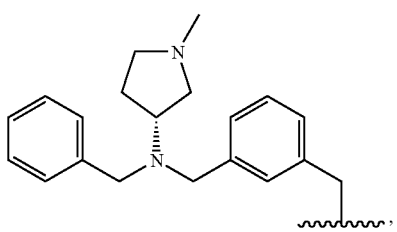
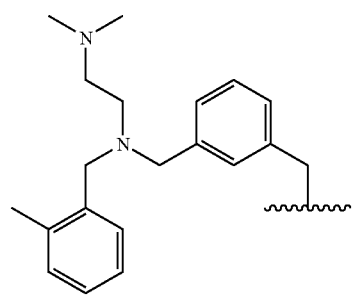
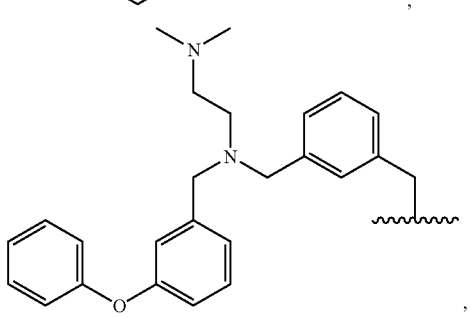

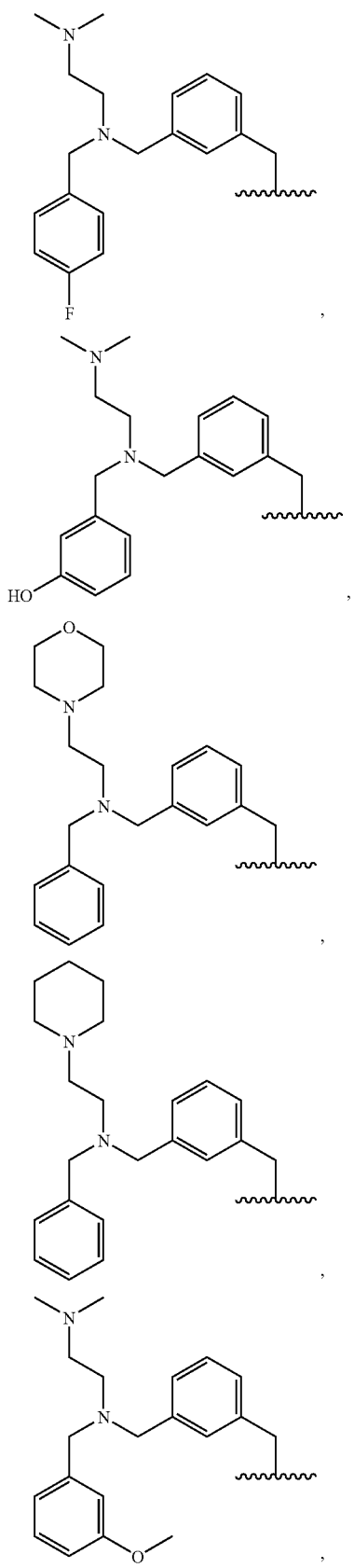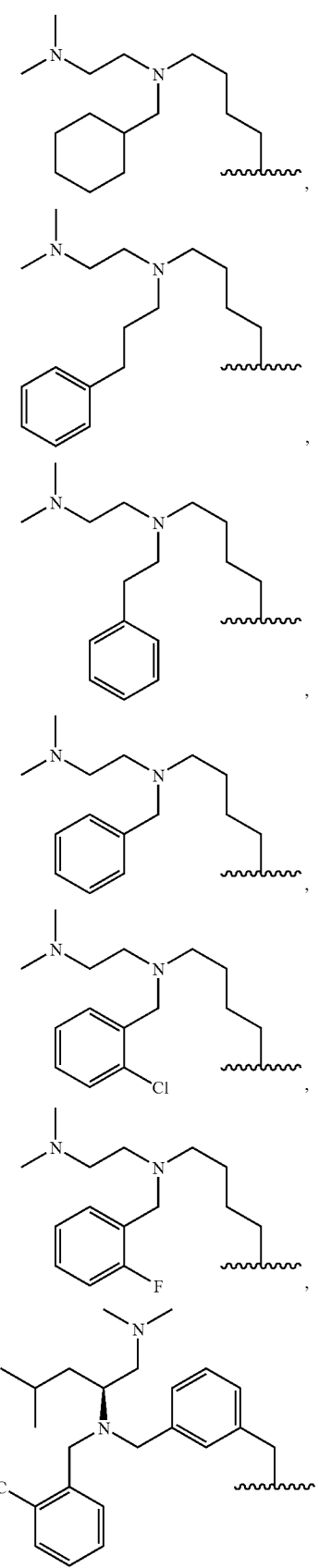

-continued
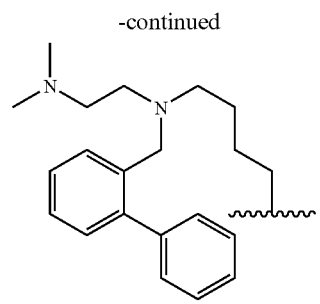
Another aspect of the present invention relates to a compound selected from the group consisting of:
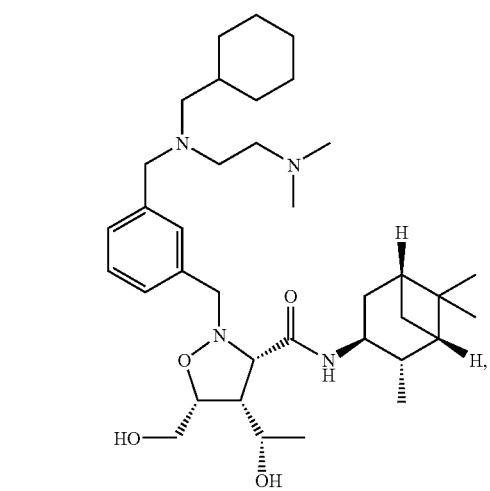
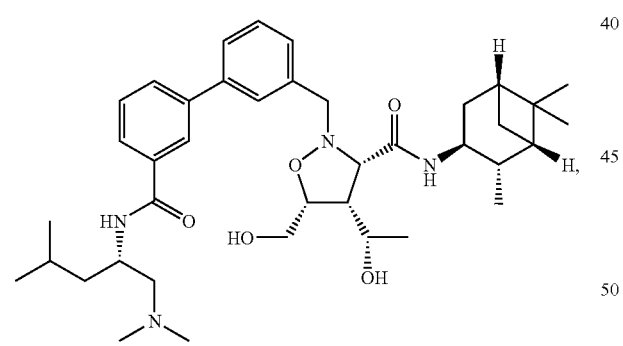
-continued
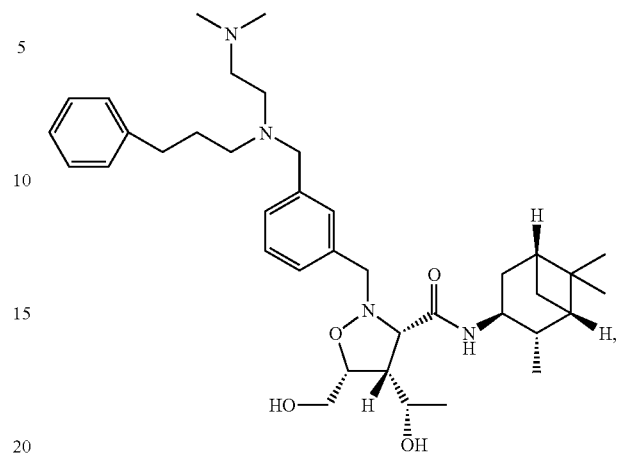
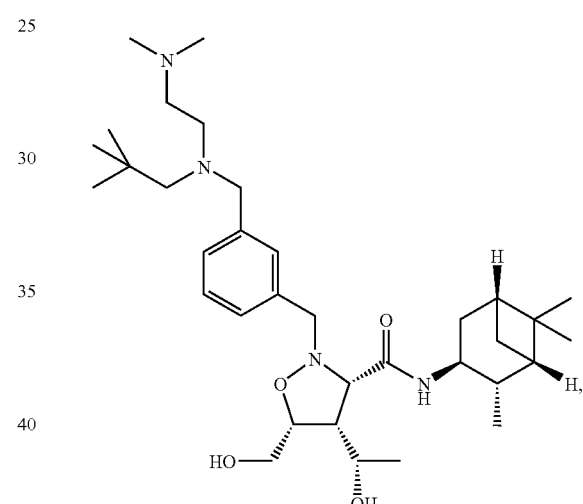
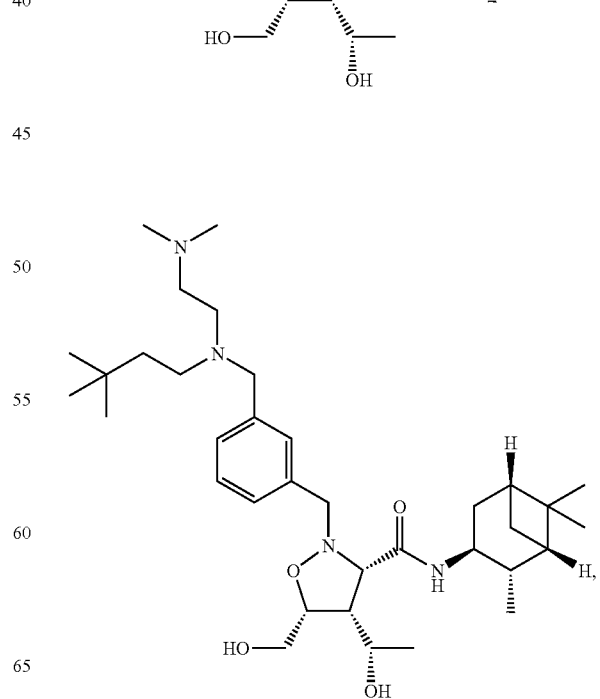

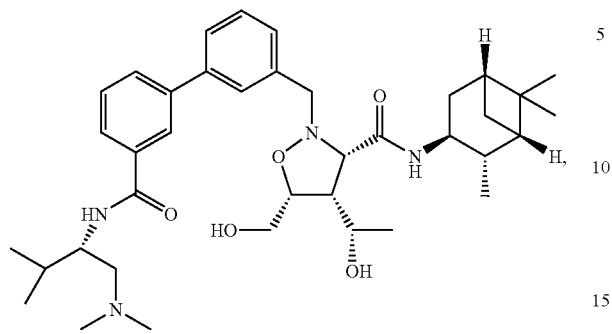
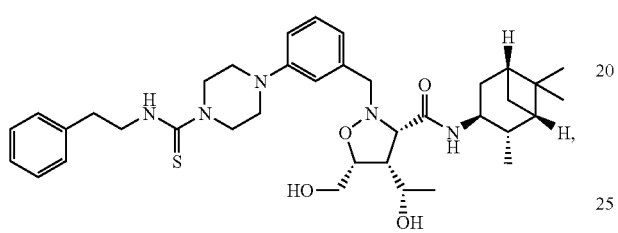
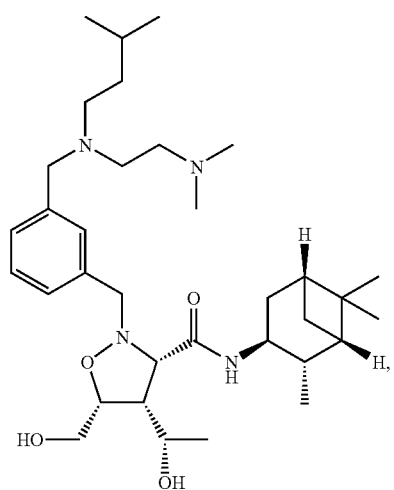
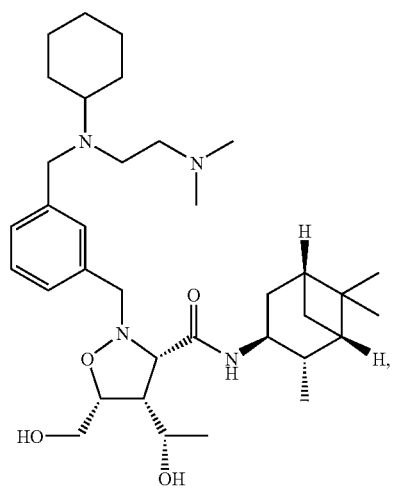
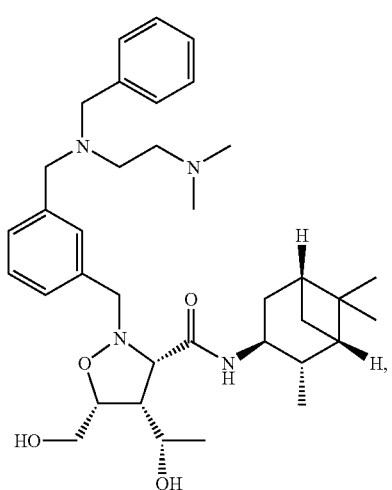
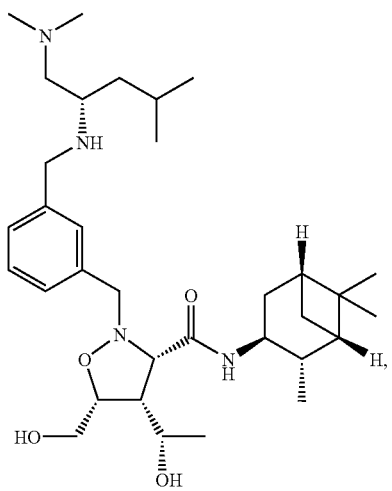
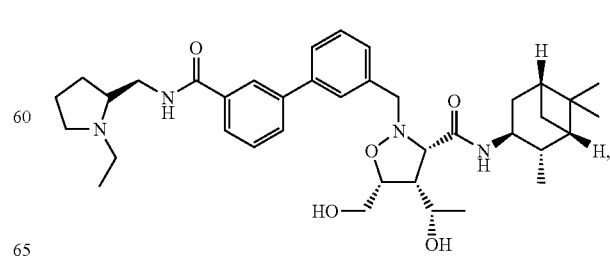

101
-continued
102
-continued
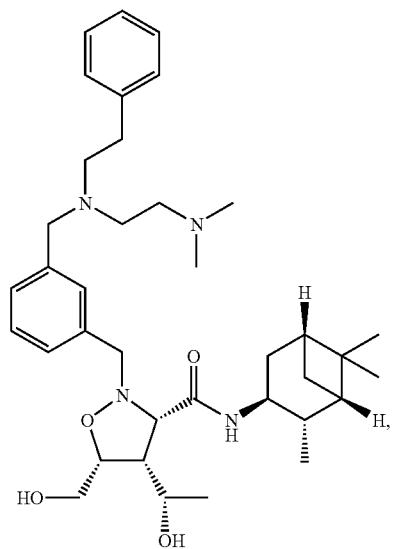
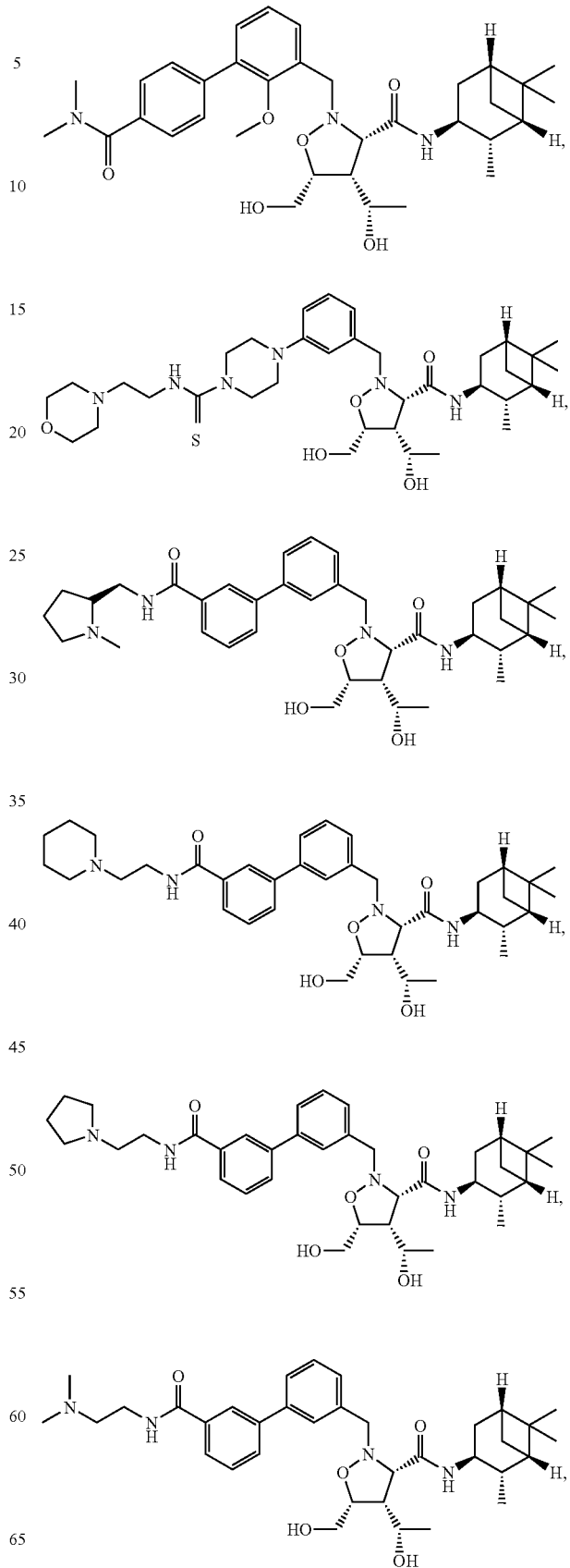

103
-continued
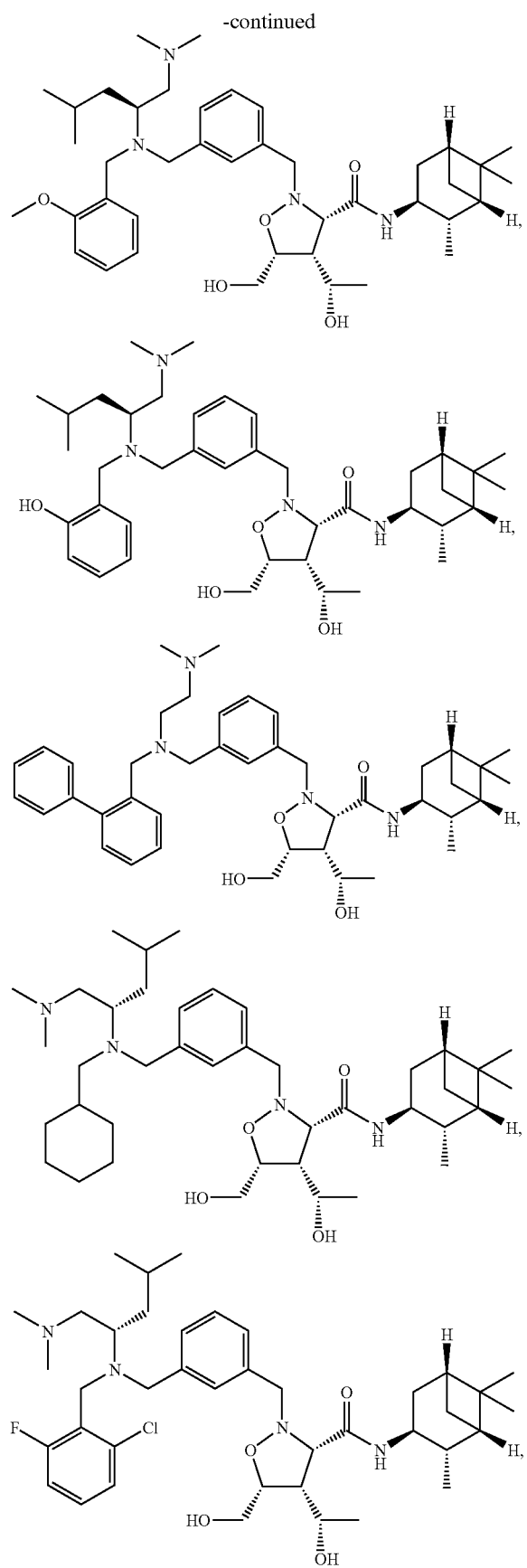
104
-continued
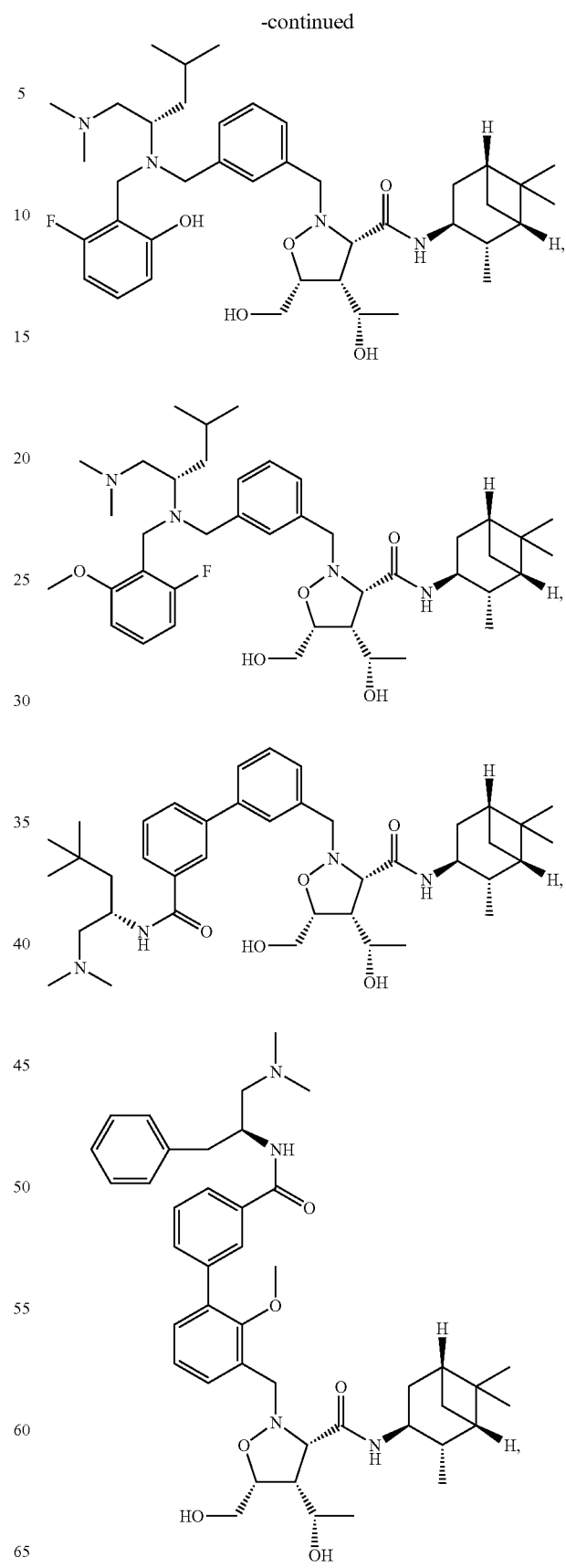

105
-continued
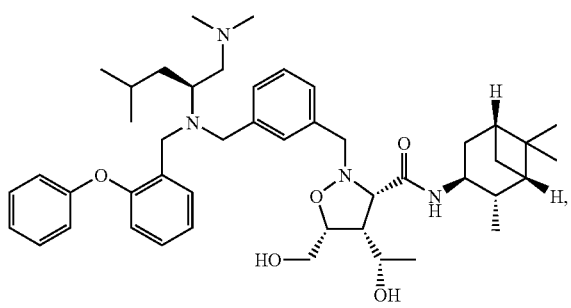
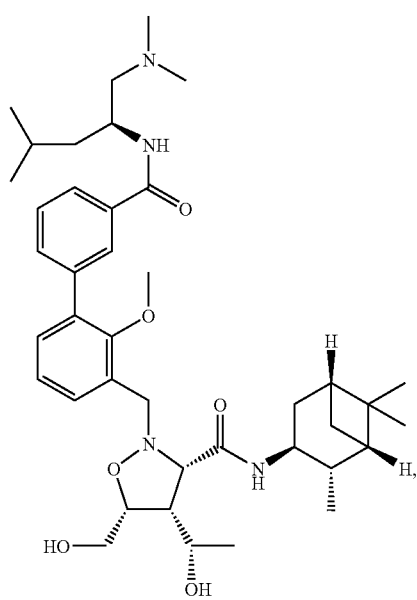
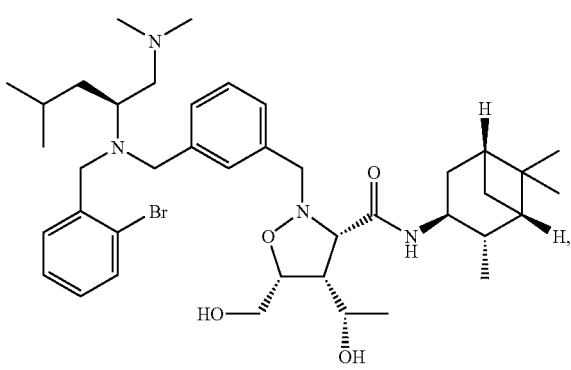
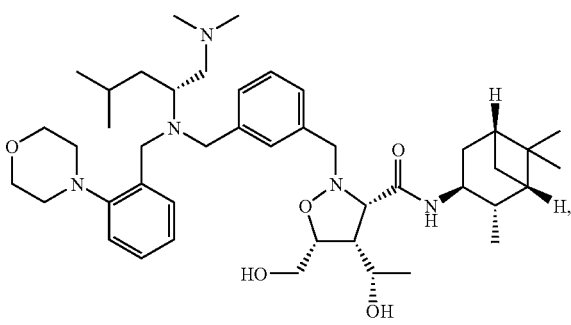
106
-continued
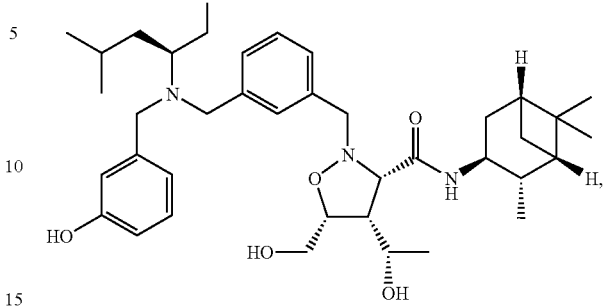
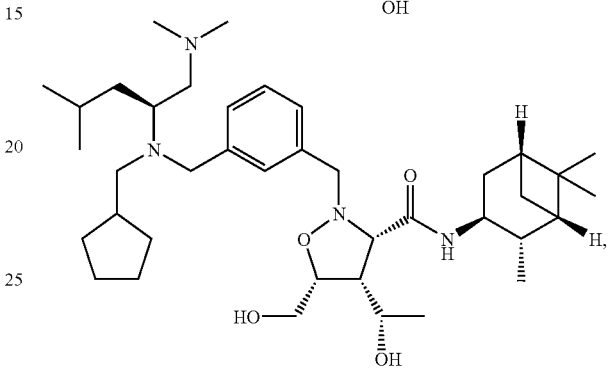
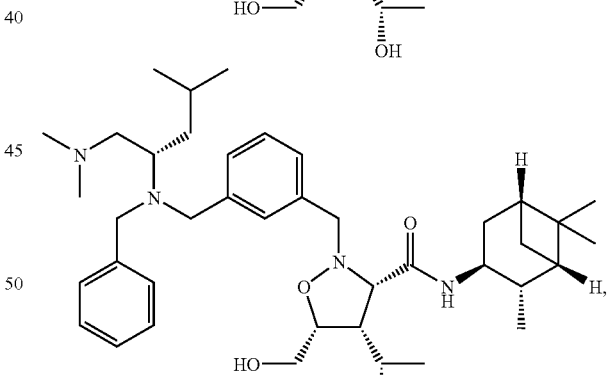
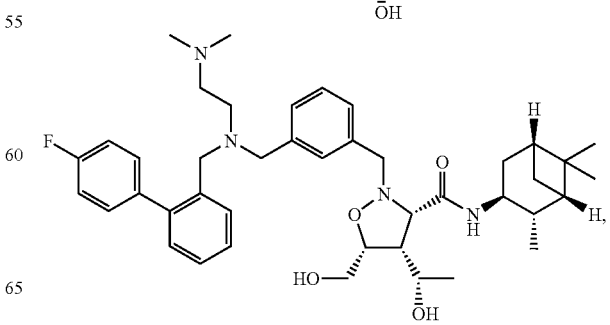

107
-continued
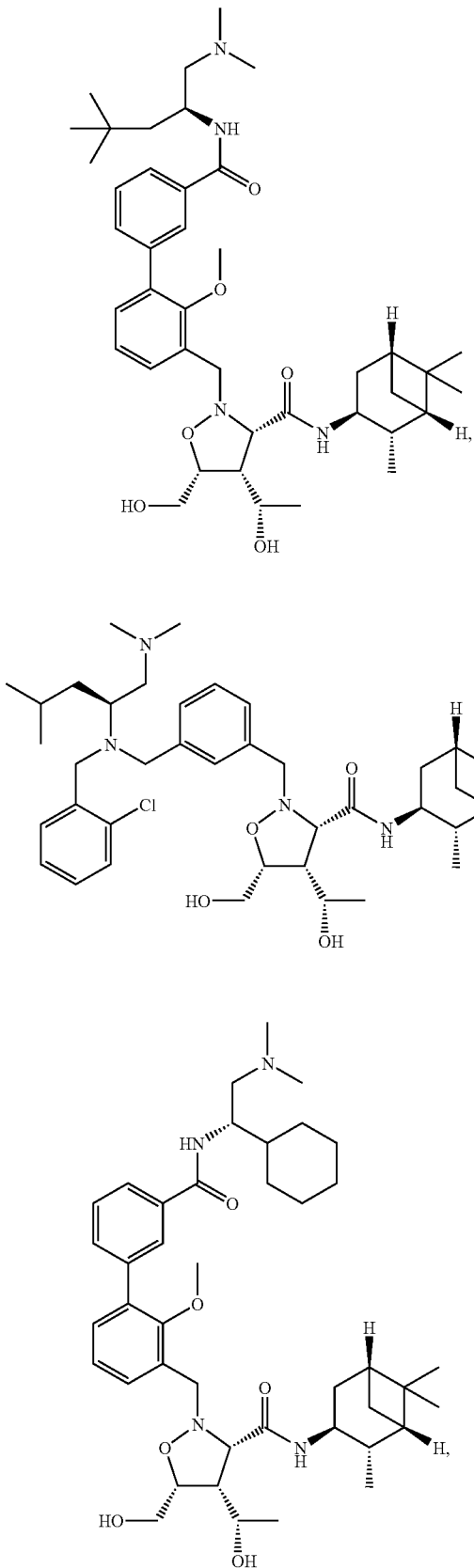
108
-continued
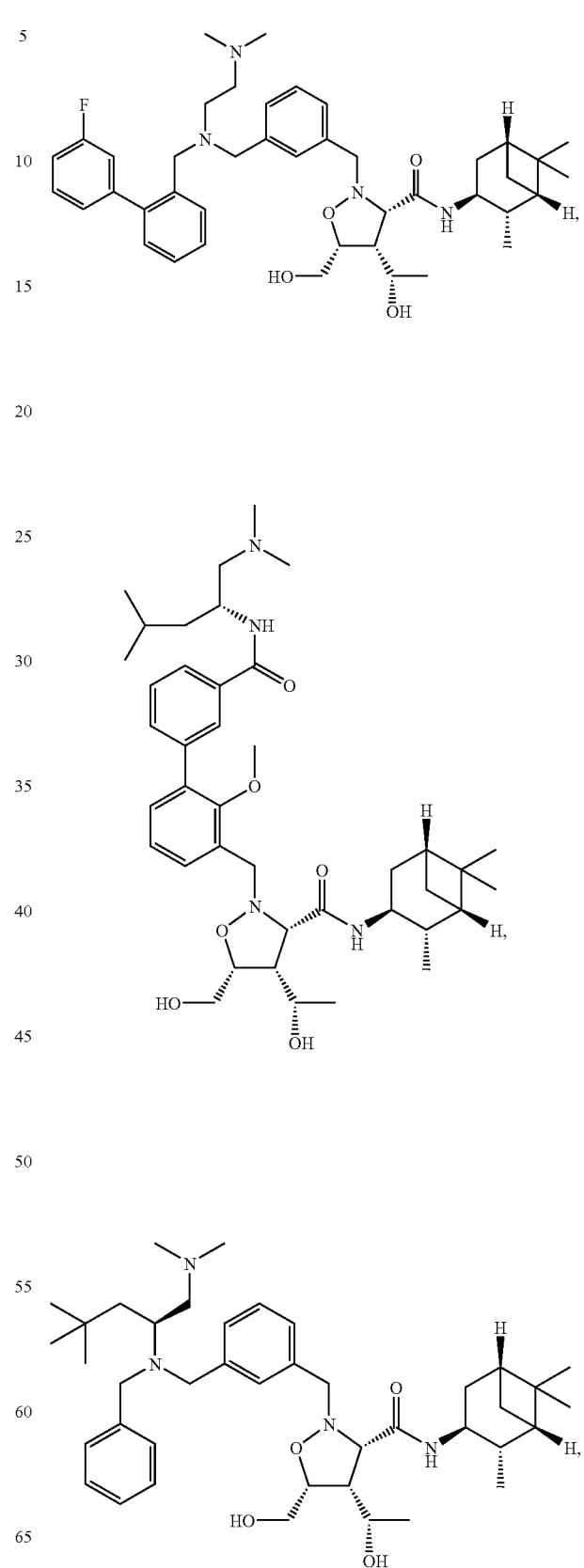

-continued

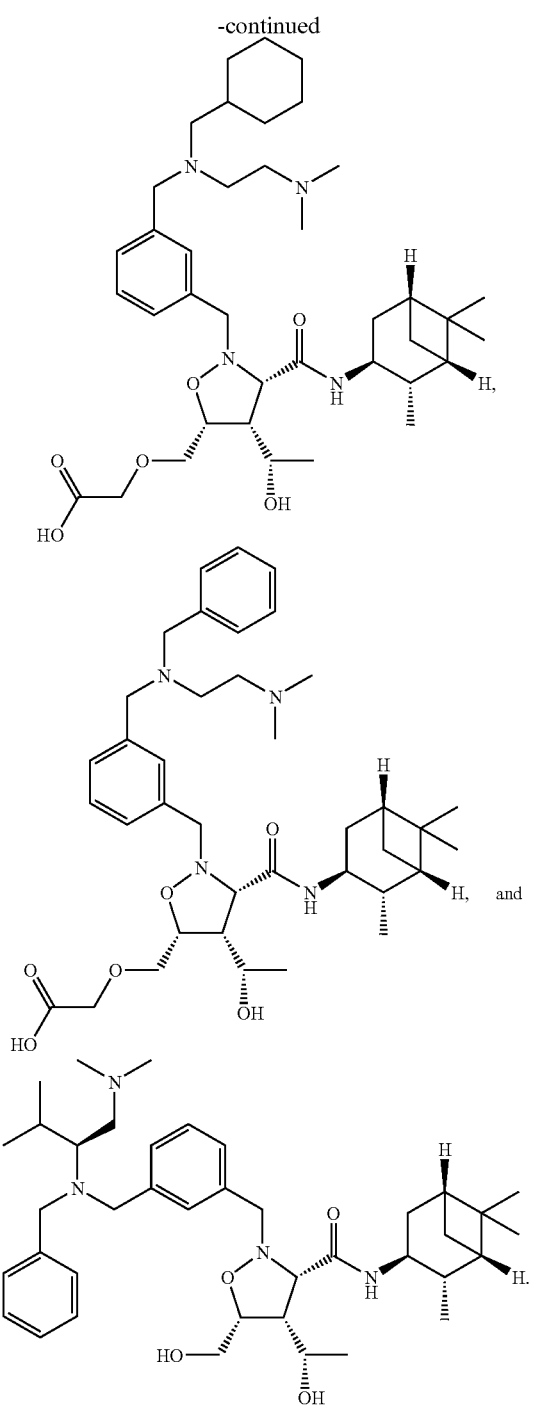

Another aspect of the present invention relates to a pharmaceutical composition comprising a compound of formula 1, 2, 3, 4, or 5 as described above and at least one pharmaceutically acceptable excipient.

METHODS OF THE INVENTION

One aspect of the present invention relates to a method of treating a Bcl-mediated disorder, comprising the step of:

administering to a patient in need thereof a therapeutically effective amount of a compound of formula 1, 2, 3, 4, or 5 as described above.

In certain embodiments, the present invention relates to the aforementioned method, wherein said Bcl-mediated disorder is cancer or neoplastic disease.

In certain embodiments, the present invention relates to the aforementioned method, wherein said cancer or neoplastic disease is selected from the group consisting of acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia Vera, Hodgkin's disease, non-Hodgkin's disease; multiple myeloma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and endometrial cancer.

In certain embodiments, the present invention relates to the aforementioned method, wherein said cancer is follicular lymphoma, diffuse large B-cell lymphoma, mantle cell lymphoma, chronic lymphocytic leukemia prostrate cancer, breast cancer, neuroblastoma, colorectal, endometrial, ovarian, lung cancer, hepatocellular carcinoma, multiple myeloma, head and neck or testicular cancer.

In certain embodiments, the present invention relates to the aforementioned method, wherein said cancer over-expresses a Bcl protein.

In certain embodiments, the present invention relates to the aforementioned method, wherein said cancer is dependent upon a Bcl protein for growth and survival.

In certain embodiments, the present invention relates to the aforementioned method, wherein said Bcl protein is Bcl-2.

In certain embodiments, the present invention relates to the aforementioned method, wherein said Bcl protein is Bcl-xL.

In certain embodiments, the present invention relates to the aforementioned method, wherein the cancer exhibits a t(14; 18) chromosomal translocation.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating a Bcl-mediated disorder, comprising the step of: administering to a patient in need thereof a therapeutically effective amount of a chemothereutic agent in combination with a therapeutically effective amount of a compound of compound of formula 1, 2, 3, 4, or 5 as described above.

In certain embodiments, the present invention relates to the aforementioned method, wherein said Bcl-mediated disorder is cancer or neoplastic disease.

In certain embodiments, the present invention relates to the aforementioned method, wherein said cancer or neoplastic disease is selected from the group consisting of acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia Vera, Hodgkin's disease, non-Hodgkin's disease; multiple myeloma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and endometrial cancer.

In certain embodiments, the present invention relates to the aforementioned method, wherein the cancer over-expresses a Bcl protein.

In certain embodiments, the present invention relates to the aforementioned method, wherein said cancer is dependent upon a Bcl protein for growth and survival.

In certain embodiments, the present invention relates to the aforementioned method, wherein said Bcl protein is Bcl-2.

In certain embodiments, the present invention relates to the aforementioned method, wherein said Bcl protein is Bcl-xL.

In certain embodiments, the present invention relates to the aforementioned method, wherein said cancer exhibits a t(14; 18) chromosomal translocation.

In certain embodiments, the present invention relates to the aforementioned method, wherein the amount of compound of formula 1, 2, 3, 4, or 5 is such that the cellular levels of Bcl client proteins are reduced, and the amount of said chemotherapeutic agent is such that said Bcl client proteins are effectively inhibited by said chemotherapeutic agent.

In certain embodiments, the present invention relates to the aforementioned methods, wherein said compound is administered parenterally.

In certain embodiments, the present invention relates to the aforementioned methods, wherein said compound is administered intramuscularly, intravenously, subcutaneously, orally, pulmonary, intrathecally, topically or intranasally.

In certain embodiments, the present invention relates to the aforementioned methods, wherein said compound is administered systemically.

In certain embodiments, the present invention relates to the aforementioned methods, wherein said patient is a mammal.

In certain embodiments, the present invention relates to the aforementioned methods, wherein said patient is a primate.

In certain embodiments, the present invention relates to the aforementioned methods, wherein said patient is a human.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 per cent to about ninety-nine percent of active ingredient, preferably from about 5 per cent to about 70 per cent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" 0 and B books, Corvallis, Oreg., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylaamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459, 731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, JRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of Benzyl Hydroxyamines

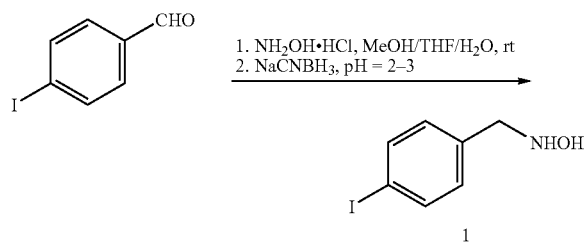

To a solution of 4-iodobenzaldehyde (0.025 mmol) in MeOH/THF (40 mL, 3:1) was added aqueous solution of $NH_2OH \cdot HCl$ (10 mL). The pH was adjusted to 9 using of 6 N KOH. The reaction was stirred at rt for 2 h and $NaCNBH_3$ (1.5 g, 0.025 mmol) was added followed by a crystal of methyl orange. The solution was acidified to a pH 2 and the resulting ruby red color was maintained for the duration of the reaction by the addition of 1 N HCl. After 2 h, another portion of $NaCNBH_3$ (1.5 g, 0.025 mmol) was added. The mixture was stirred for 14 h, at which point, ⅔ of solvent was evaporated and the pH was raised to 9-10 by addition of a 6 N KOH aqueous solution. This mixture was extracted with $CH_2Cl_2$ (3×100 mL). The organic layers were combined, washed with water then brine. The organic layer was dried ($MgSO_4$), filtered and evaporated in vacuo to afford 1 (5.7 g, 91%) an off-white solid.

Example 2

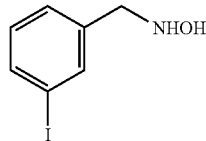

Hydroxyamine 2 was synthesized according to the procedure described in Example 1 using 3-iodobenzaldehyde in place of 4-iodobenzaldehyde affording a 90% yield of the desired product.

Example 3

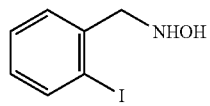

Hydroxyamine 3 was synthesized according to the procedure described in Example 1 using 2-iodobenzaldehyde in place of 4-iodobenzaldehyde affording a 85% yield of the desired product.

Example 4

Synthesis of Nitrone Acids for Use in [3+2] Cycloadditions

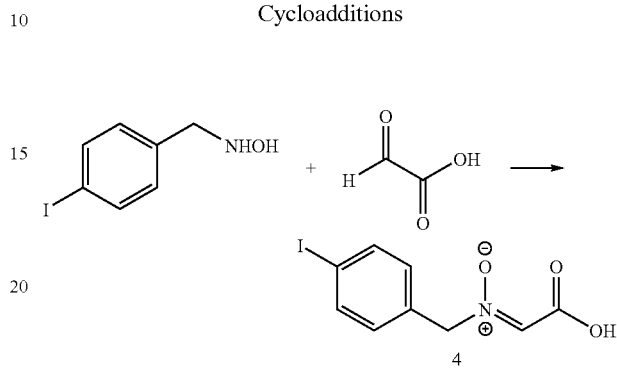

(Keirs, D.; Overton, K. Heterocycles 1989, 28, 841-848) To a suspension of N-(4-iodobenzyl)hydroxylamine (10 g, 42.5 m mol) in $CH_2Cl_2$ (200 mL) under nitrogen was added glyoxylic acid monohydrate (4.7 g, 51.1 mmol). The reaction mixture was stirred for 24 h at rt. The reaction mixture was washed with water (2×200 mL), brine, dried ($MgSO_4$), filtered and concentrated in vacuo. $Et_2O$ (50 mL) was added to the yellowish solid and the suspension was titrated and filtered to afford 4 as a cream colored solid. The mother liquor was concentrated in vacuo. and the solid was washed with $Et_2O$ and then filtered to afford 4 (11.8 g, 93% yield).

Example 5

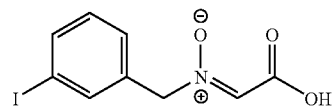

Nitrone acid 5 was synthesized according to the procedure described in Example 4 using N-(3-iodobenzyl)hydroxylamine in place of N-(4-iodobenzyl)hydroxylamine affording a 90% yield of the desired product.

Example 6

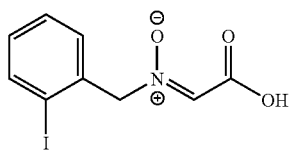

Nitrone acid 6 was synthesized according to the procedure described in Example 4 using N-(2-iodobenzyl)hydroxylamine in place of N-(4-iodobenzyl)hydroxylamine affording a 90% yield of the desired product.

Example 7

Synthesis of Nitrone Carboxylic Methyl Esters for use in [3+2] Cycloadditions

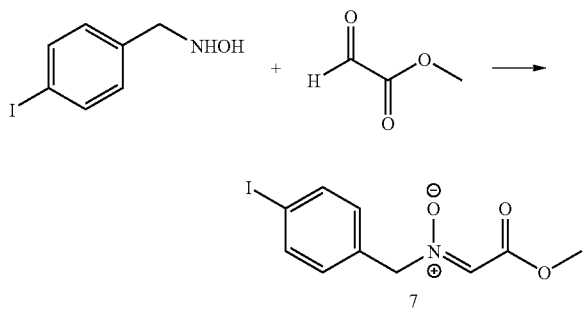

To a solution of N-(4-iodobenzyl)hydroxylamine (16 g, 64 mmol) in benzene (320 mL) was added the methyl glyoxylate (6.8 g, 80 mmol). The mixture was heated to 120° C. for 3 h using a Dean Stark trap. The solution was cooled to rt and the solvent was concentrated in vacuo to give 7 (19.1 g, 93%) as a yellow solid.

Example 8

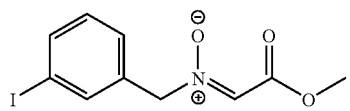

Nitrone methyl ester 8 was synthesized according to the procedure described in Example 7 using N-(3-iodobenzyl) hydroxylamine in place of N-(4-iodobenzyl)hydroxylamine affording a 85% yield of the desired product.

Example 9

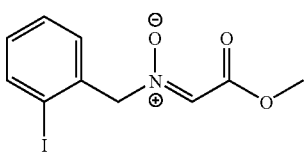

Nitrone methyl ester 9 was synthesized according to the procedure described in Example 7 using N-(2-iodobenzyl) hydroxylamine in place of N-(4-iodobenzyl)hydroxylamine affording a 90% yield of the desired product.

Example 10

Synthesis of Dipolarophiles

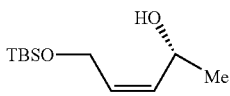

Part A

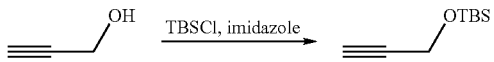

To a solution of TBSCl (215 g, 1.43 mol) in $CH_2Cl_2$ (1.2 L) at 0° C. was added imidazole (97 g, 1.43 mol). Propargylic alcohol (83 mL, 1.43 mol) was added dropwise and the suspension was allowed to warmed to rt and stirred for 60 min The reaction was quenched by the addition of water (500 mL). The mixture was concentrated in vacuo and the residue was extracted with hexanes (3×500 mL). The organic extracts were combined and washed with brine, dried ($MgSO_4$), filtered and concentrated in vacuo to afford an oil which was purified by distillation (70° C./~10 mm Hg) afforded the desired product (179 g, 74%).

Part B

TBSO—≡— $\xrightarrow{\text{n-BuLi, acetaldehyde}}$ TBSO—≡—CH(OH)Me

To a solution of tert-Butyldimethyl(2-propynyloxy)silane (freshly distilled, 27 g, 0.16 mol) in THF (300 mL) at −78° C. was added n-BuLi (119 mL of 1.6 M in heane, 0.19 mol). After 15 min acetaldehyde (10 mL, 0.19 mol.) was added. The reaction mixture was stirred for 30 min and quenched with an aqueous solution of 5% (m/v) $NH_4Cl$ (50 mL) and water (100 mL). A half volume of THF was evaporated in vacuo and the mixture was poured into water (150 mL). This mixture was extracted with hexanes (3×200 mL) and $Et_2O$ (100 mL). The combined extracts were dried ($Mg_2SO_4$) and concentrated in vacuo. The crude product was purified by distillation (115° C./1 mm Hg (bath temp. 155 ° C.) to afford the product (30 g, 88%).

Part C

TBSO—≡—CH(OH)Me $\xrightarrow{\text{Lipase CA, vinyl acetate}}_{\text{Cyclohexane}}$ -continued

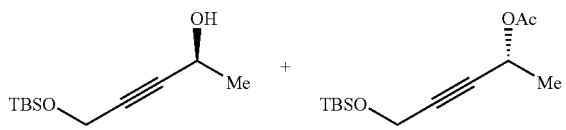

Lipase CA (Candida Antarctica immobilized on macropous acryl resin, Sigma L-4777 Lot 11K127) (1 g) was added to a mixture of the propargyl alcohol (10 g, 0.47 mol) and vinyl acetate (129 mL, 0.14 mol) in cyclohexane (380 mL). The reaction mixture was stirred for 48 h, then filtered and the resin was rinsed with EtOAc (50 mL). The filtrate and the rinses were combined and concentrated in vacuo. The crude material was purified by column chromatography (hexane/EtOAc, 95:5 to 80:20) to give 5.3 g of the alcohol and 6.5 g of the acetate (93% ee).

Part D

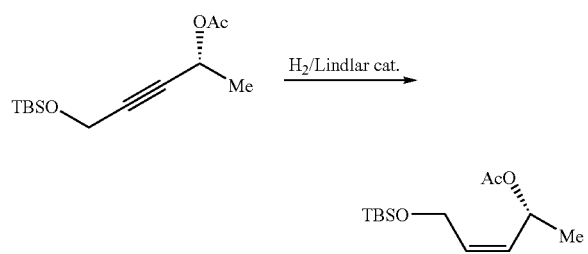

To a stirred solution of the propargyl acetate (60 g, 0.23 mmol) in EtOAc (700 mL) was added quinoline (30 mL) and Lindlar cat. (6 g) and placed under an atomsphere of $H_2$. After 9 hr the reaction mixture was filtered and the filtrate was concentrated in vacuo. The crude was purified by column chromatography (hexane/EtOAc 95:5) to afford of the desired product (57.5 g, 97%).

Part E

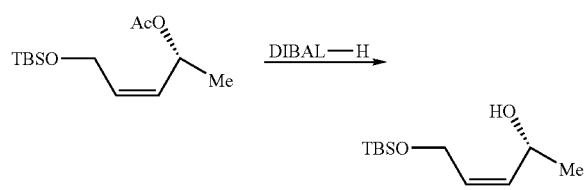

To a stirred solution of the allylic acatate (50 g, 0.19 mol) in $CH_2Cl_2$ (400 mL) at −78° C. was added DIBAL-H (426 mL of a 1 M solution in heptane, 0.43 mol). After 15 min the reaction was diluted with $Et_2O$ (400 mL) and quenched with brine (150 mL). The reaction mixture was warmed to rt and stirred for an additional 2 h. The reaction mixture was dried ($MgSO_4$), filtered and concentrated in vacuo. The crude mixture was purified by column chromatography (hexane/EtoAc, 80:20) to afford (41 g) of the desired product.

Example 11

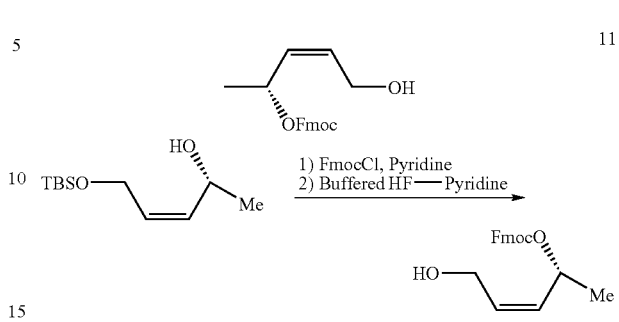

To a stirred solution of the allylic alcohol (40 g, 0.19 mol) in pyridine (400 mL) and $CH_2Cl_2$ (100 mL) at 0° C. was added Fmoc-Cl (62 g). The reaction was warmed to rt, stirred for an additional 30 min, and quenched with water (500 mL). The layers were separated and the water phase was extracted with $Et_2O$ (2×200 mL) and the combined extracts were washed with $CuSO_4$ (aq) water, brine, dried (MgSO4), filtered and concentrated in vacuo to give Fmoc-protected alcohol. The crude material was carried on to the next step without purification.

The crude product (35 g) was placed in a plastic bottle and THF (100 mL) was added followed by a solution of HF-pyridine (HF-Py (7.7 mL)/pyridine (15.4 mL)/THF (76.9 mL) The reaction mixture was kept at rt for 4 h and and treated with TMSOMe for 60 min and poured into water (500 mL). The layers were separated and the aqueous phase was extracted with $Et_2O$ (3×200 mL). The organic extracts were collected and washed with aqueous $NaHCO_3$, brine, dried ($MgSO_4$), filtered an d concentrated in vacuo to give the crude allylic alcohol. The crude material was purified by column chromatography to afford 14.4 g of the desired product.

Example 12

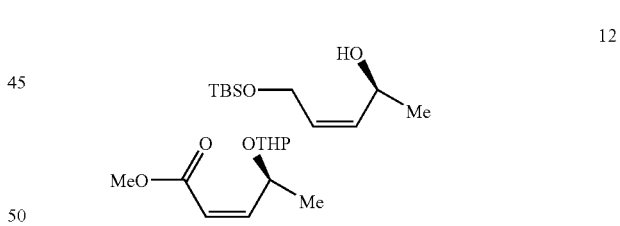

Part A Move Ester Structure below Part A

A solution of bis(2,2,2-trifluoroethyl)phosphonoacetic acid methyl ester (28 g, 0.1 mmol) and 18-crown-6 (132 g, 0.50 mmol) in THF (2 L) was cooled to −78° C. under nitrogen. To the cooled solution was added a 0.6 M solution of potassium bis(trimethylsilyl)amide in toluene (20 g, 0.1 mmol). (S)-2-(tetrahydropyranyloxy)propanal (synthesis described in *J. Chem. Soc., Perkin. Trans.* 1, 1994, 2791) (16 g, 0.1 mmol) was then added and the resulting mixture was stirred for 30 min at −78° C. Saturated ammonium chloride was then added and the product was extracted with $Et_2O$ (3×500 mL). The ether extracts were combined, dried over sodium sulfate, filtered and concentrated in vacuo. The crude material was purified via silica gel chromatography to yield 13.5 g of the product.

Part B

4(S)-(Tetrahydro-pyran-2-yloxy)-pent-2-enoic acid methyl ester (10 g, 46.7 mmol) was reduced with DIBAL-H according to the procedure described in *J. Chem. Soc., Perkin. Trans.* 1 1994, 2791 to yield 4(S)-(Tetrahydro-pyran-2-yloxy)-pent-2-en-1-ol in 88% yield.

Part C

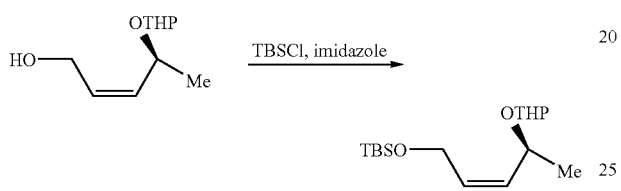

To a solution of 4(S)-(tetrahydro-pyran-2-yloxy)-pent-2-en-1-ol (4.0 g, 22 mmol) in THF (20 mL) was added imidazole (slowly) (3.66 g, 53.5 mmol) followed by TBSCl (1.2 eq., 3.89 g, 25.8 mmol). The reaction mixture was stirred at ambient temperature for 4 h, quenched with water (20 mL) and extracted with Et$_2$O (3×10 mL). The combined organic extracts were washed with water (5×50 mL), brine (1×50 mL), dried (MgSO$_4$), filtered and concentrated in vacuo. The oil was purified by column chromatography (2:1 Hexane/EtOAc) to give the desirded TBDMS ether (5.9 g, 92%) of a colorless oil.

Part D

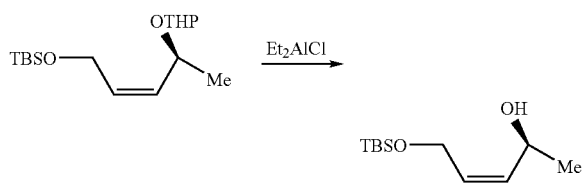

The THP protecting group was removed from t-butyl-dimethyl-[4(S)-(tetrahydro-pyran-2-yloxy)-pent-2-enyloxy]-silane (10 g, 33 mmol) according to the procedure described in *Tetrahedron Letters* 1984, 25, 663 to afford the product in 83% yield.

Example 13

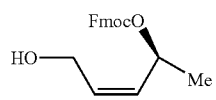

Part A

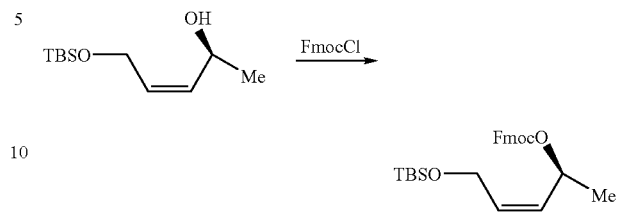

To a solution of 5-(tert-butyl-dimethyl-silanyloxy)-pent-3-en-2(S)-ol (3.95 g, 18.3 mmol) in pyridine (20 mL) was added FmocCl (6.14 g, 23.7 mmol, 1.3 eq.). The reaction mixture was stirred overnight at rt. The reaction mixture was slowly quenched with water (20 mL) and extracted with Et$_2$O (3×15 mL). The combined organic extracts were washed with water (3×50 mL), 5% KH$_2$PO$_4$ (3×50 mL), and brine (1×50 mL), dried over MgSO$_4$ and filtered. Concentration and column chromatography afforded 6.98 g (87 %) of a pale yellow oil.

Part B

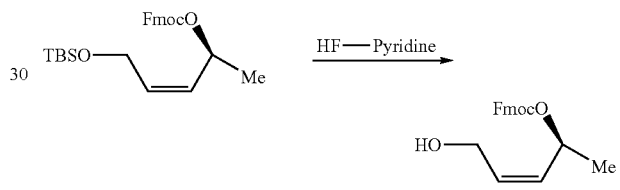

To a solution of carbonic acid 4-(tert-butyl-dimethyl-silanyloxy)-1-methyl-butyl-2(S)-enyl ester 9H-fluoren-9-yl methyl ester (700 mg, 1.60 mmol) in Et$_2$O (5 mL) in a plastic Wharton tube was added slowly in 6 portions HF/pyridine (70% HF in pyridine, 6 mL). The reaction was monitored by TLC. When the reaction was complete the mixture was cooled to 0° C. with an ice bath and then quenched with TMSOMe (10 mL). The reaction mixture was stirred for 30 min while warming to ambient temperature. The reaction mixture was poured into water (50 mL), the layers were separated and the aqueous layer was extracted with Et$_2$O (3×15 mL). The combined organic extracts were washed with water (3×30 mL), 5% KH$_2$PO$_4$ (3×30 mL), brine (1×30 mL), dried (Na$_2$SO$_4$) and filtered. Concentration and column chromatography gave 471 mg (91 %) of a clear colorless oil.

Example 14

General Procedures for [3+2] Cycloadditions

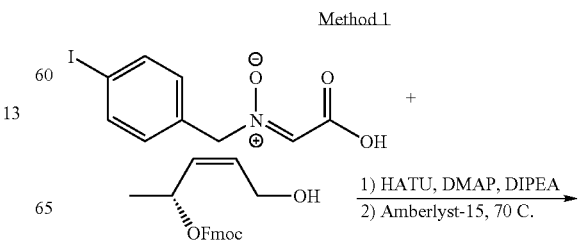

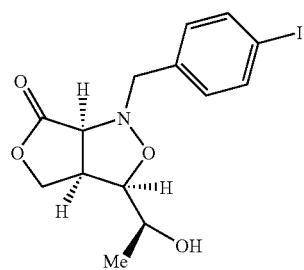

To a solution of nitronecarboxylic acid 4 (1.4 g, 3.1 mmol) in CH$_2$Cl$_2$ was added allylic alcohol 11 (1.0 g, 3.1 mmol), HATU (2.0 g, 6 mmol) and DMAP (0.56 g, 4.6 mmol). The solution was cooled in an ice-bath and stirred for 1.0 h. Diisopropylethyl amine (0.44 g, 0.6 mL, 4.6 mmol) was added dropwise over 15 min and the reaction was stirred at 0° C. for 1 h. The solution was diluted with CH$_2$Cl$_2$-5% NaHCO$_3$ (300 mL, 1:1) and the aqueous layer was extracted with CH$_2$Cl$_2$ (2×125 mL). The combined organic extracts were combined and washed with water (200 mL), dried (MgSO$_4$), filtered and concentrated in vacuo to afford an residue. The residue was suspended in THF (10 mL), diisopropylethylamine (0.12 g, 0.167 mL, 1 mmol) was added and the solution was heated at reflux for 1 hr, cooled to rt and concentrated in vacuo. The residue was taken up in THF (8 mL), 1.33 g of Amberlyst-15 was added and the mixture was heated at 70° C. for 2 h. Again the solution was cooled, filtered and concentrated in vacuo. The crude material was purified by flash chromatography to yield the desired product in 59% yield

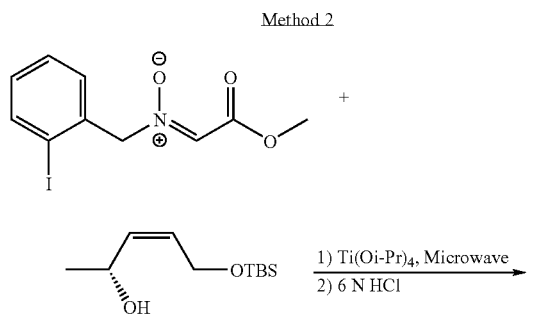

Method 2

To a solution of nitrone methyl ester 9 (8.1 g, 38 mmol) and secondary alcohol 10 (12 g, 38 mmol) in toluene (40 mL) was added Ti(OCH(CH$_3$)$_2$)$_4$ (16 g, 17 mL, 56 mmol). The suspension was heated in microwave oven to 140° C. for 30 min, and allowed to cool to rt. The solution was diluted with EtOAc (150 mL) and 3-(dimethylamino)-1,2-propanediol (7 g, 7 mL, 58 mmol) and stirred at rt for 8 h. To the solution was added water (100 mL) and the organic phase was separated, the aqueous was washed with EtOAc (3×30 mL). The combined organic extracts were washed with water (100 mL), brine (100 mL), dried (Na$_2$SO$_4$), filtered and concentrated in vacuo. The crude material was purified by flash chromatography (Et$_2$O/CH$_2$Cl$_2$, 1:29) to afford the lactone (13.5 g, 71%).

To a solution of isoxazolidine (13.5 g, 26 mmol) in THF (120 mL) was added 6 N HCl (67 mL). The solution was stirred at rt for 1.5 h, diluted water (25 mL) and extracted with EtOAc (3×80 mL), the organic extracts were combined and washed with saturated NaHCO$_3$ (50 mL), brine (50 mL), dried (Na$_2$SO$_4$) and concentrated in vacuo. The crude material was purified by chromatography on silica a gel (mesh 230-400) (Et$_2$O-CH$_2$Cl$_2$, a gradient of 1:4 to 1:2) to give desired product (9.5 g, 64% overall yield for 2 steps).

Rewrite these two procedures get help from Porter and Georges and Hopkins

Example 15

Synthesis of Isoxazolidine Cores

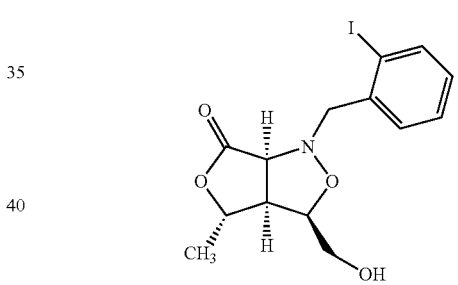

Isoxazolidine 14 w as synthesized according to general method 2 using nitrone methyl ester 9 in place of nitrone methyl ester 7 and allylic alcohol 12 in place of allylic alcohol 10. Yield: 40-60%.

Example 16

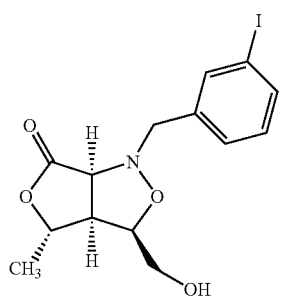

Isoxazolidine 15 was synthesized according to general method 2 using nitrone methyl ester 8 in place of nitrone methyl ester 7 and allylic alcohol 12 in place of allylic alcohol 10. Yield: 40-60%.

Example 17

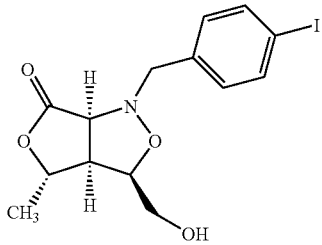

Isoxazolidine 16 was synthesized according to general method 2 using nitrone methyl ester 7 and allylic alcohol 12 in place of allylic alcohol 10. Yield: 40-60%.

Example 18

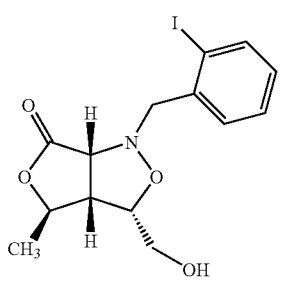

Isoxazolidine 17 was synthesized according to general method 2 using nitrone methyl ester 9 in place of nitrone methyl ester 7 and allylic alcohol 10. Yield: 40-60%.

Example 19

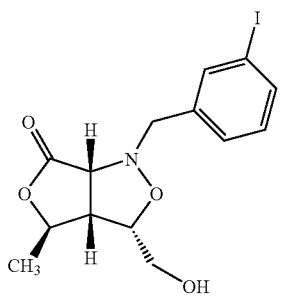

Isoxazolidine 18 was synthesized according to general method 2 using nitrone methyl ester 8 in place of nitrone methyl ester 7 allylic alcohol 10. Yield: 40-60%.

Example 20

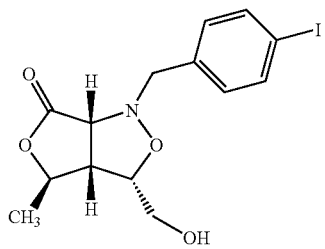

Isoxazolidine 19 was synthesized according to general method 2 using nitrone methyl ester 7 and allylic alcohol 10. Yield: 40-60%.

Example 21

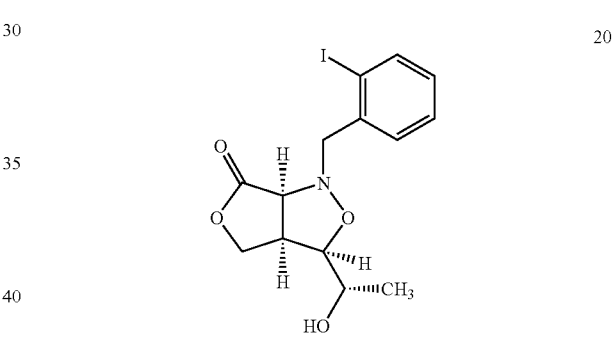

Isoxazolidine 20 was synthesized according to general method 1 using nitrone acid 6 in place of nitrone acid 4 and allylic alcohol 11. Yield: 50-60%.

Example 22

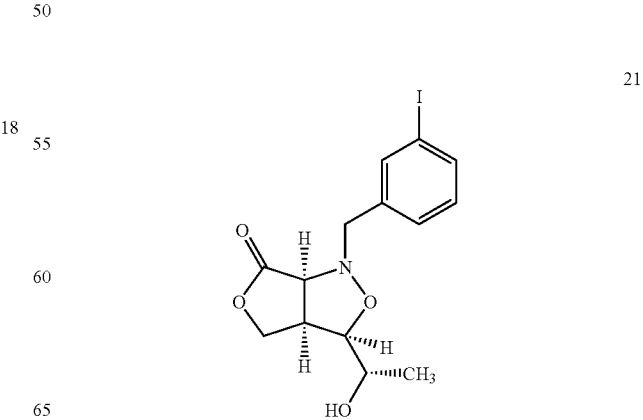

Isoxazolidine 21 was synthesized according to general method 1 using nitrone acid 5 in place of nitrone acid 4 and allylic alcohol 11. Yield: 50-60%.

Example 23

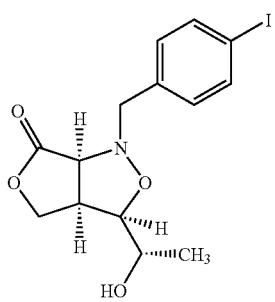

22

Isoxazolidine 22 was synthesized according to general method 1 using nitrone acid 4 and allylic alcohol 12. Yield: 50-60%.

Example 24

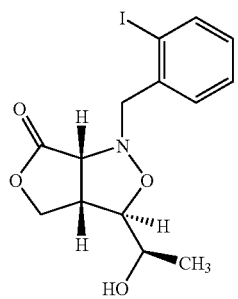

23

Isoxazolidine 23 was synthesized according to general method 1 using nitrone acid 6 in place of nitrone acid 4 and allylic alcohol 13 in place of allylic alcohol 11. Yield: 50-60%.

Example 25

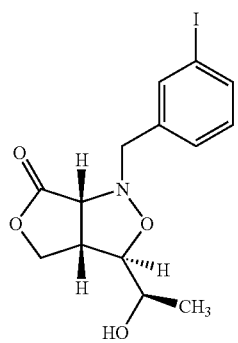

24

Isoxazolidine 24 was synthesized according to general method 1 using nitrone acid 5 in place of nitrone acid 4 and allylic alcohol 13 in place of allylic alcohol 11. Yield: 50-60%.

Example 26

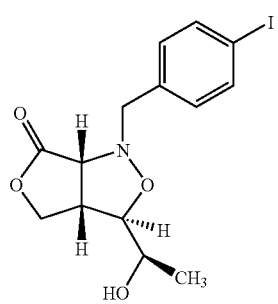

25

Isoxazolidine 25 was synthesized according to general method 1 using nitrone acid 4 and allylic alcohol 13 in place of allylic alcohol 11. Yield: 50-60%.

Example 27

Synthesis of the Allyl Silane Linker

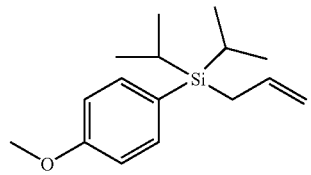

26

The allyl silane 26 was synthesized according to the procedure described in Tallarico et al., *J. Chem. Comb.* 2001, 3, 312-318.

Example 28

Modification of Mimotopes Lanterns with Silyl Linker

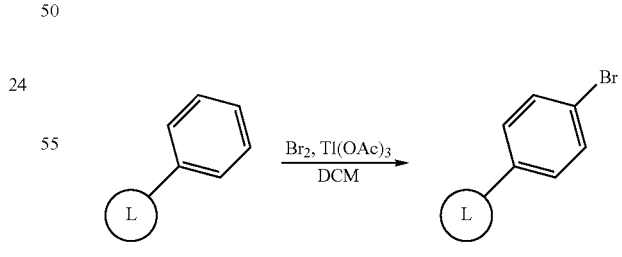

32,000 lanterns (2.22 mol of Ph rings, SynPhase-PS L-Series lanterns; Mimotopes, Clayton Victoria Australia) were added to a 22 L reactor flask containing a 5-neck detachable head and a Teflon®-screw bottom port. The head was connected to an air-driven overhead stirrer bearing a 16 cm-wide Teflon® paddle, an argon inlet, an addition funnel (250 mL), a temperature probe and an outlet for an HBr trap (1 L flask filled with 500 mL water). The reactor was flushed with argon for 15 min followed by the addition of anhydrous DCM (14.8 L). After 10 min, thallium acetate (76 g, 0.20 mol, 0.090 eq) was added. The reaction vessel was covered in aluminum foil and allowed to stir at ambient temperature for 150 min Bromine (177 g, 1.11 mol, 0.50 eq) in DCM (100 mL) was placed in the addition funnel and was added dropwise over the course of 15 min to the reactor, which warmed the reaction temperature from 19.3 to 27.0° C. Following bromine addition, the reaction was stirred for an additional 60 min The reaction was then quenched with MeOH (1.5 L) and was allowed to stir at ambient temperature overnight. The reaction solution was drained to waste and the lanterns were washed according to the following protocol: (12 L each for 10-20 min) DCM, 3:1 THF:IPA, 3:1 THF:water, water, and THF (2×). The lanterns were stripped of solvent under reduced pressure. Bromine elemental analysis of five lanterns indicated an average bromine loading level of 34.2±0.7 umol/lantern where 35.0 was the target (98% Br incorporation).

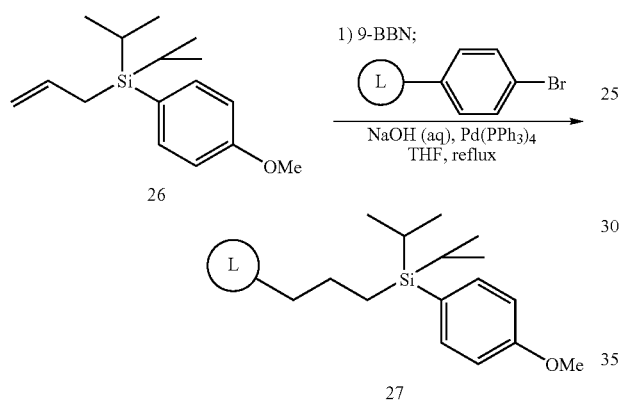

A 22 L reactor flask containing a Teflon®-screw bottom port with a detachable 5-neck head was connected to a solvent or argon inlet, an air-driven (sparkproof) overhead stirrer bearing a 16 cm-wide Teflon® paddle, a temperature probe, and two condensers. The reactor flask was placed in a 3-legged heating mantle stand and secured to the wall of a walk-in hood. Anhydrous THF (500 mL, 40 ppm H2O by KF test) was added to the flask and the solvent was stirred vigorously to rinse the flask walls in order to remove water. The solvent was drained out to waste through the bottom port under a flow of argon. The flask was flushed with argon for 10 min and then was charged with di-isopropyl(4-methoxyphenyl)allylsilane (353 g, 1.34 mol, 1.2 eq., Maybridge # MO01086ZZ). Anhydrous THF was added (11 L). Argon was bubbled vigorously through the solution for 20 min using ⅛"-wide Teflon( hose. Then, 9-BBN (167 g, 1.34 mol., 1.2 eq.) was added and the solution was stirred at ambient temperature under argon for 2 h. An in-process-check (NMR, CDCl3) revealed complete consumption of the allylsilane. The brominated lanterns (32,000, 1.11 mol Br, 1.0 eq.), Pd(PPh$_3$)$_4$ (65 g, 0.056 mol, 0.05 eq., Strem Chemical # 40-2150) and 2 N NaOH (1.34 L, 2.69 mol, 2.4 eq.) were added under a stream of argon. The reaction mixture was heated to an internal temperature of 65° C. under a positive flow of argon with stirring for 40 h. The reaction was cooled, drained and washed with the following solvents in this order (10 L, 10-20 min each): THF, 3:1 THF:IPA, 3:1 THF: 1 N NaCN (aqueous) (1 h or until all black color on lanterns is gone), water (2×), 3:1 THF:water, THF (2×) and DCM. The lanterns were stripped of solvent under reduced pressure. Silicon elemental analysis of five lanterns indicated an average silicon loading level of 22.2±2.2 umol/lantern. Bromine analysis indicated 5.5 umol/lantern of residual bromine.

Example 29

Loading and Modification of the Isoxazolidine Cores

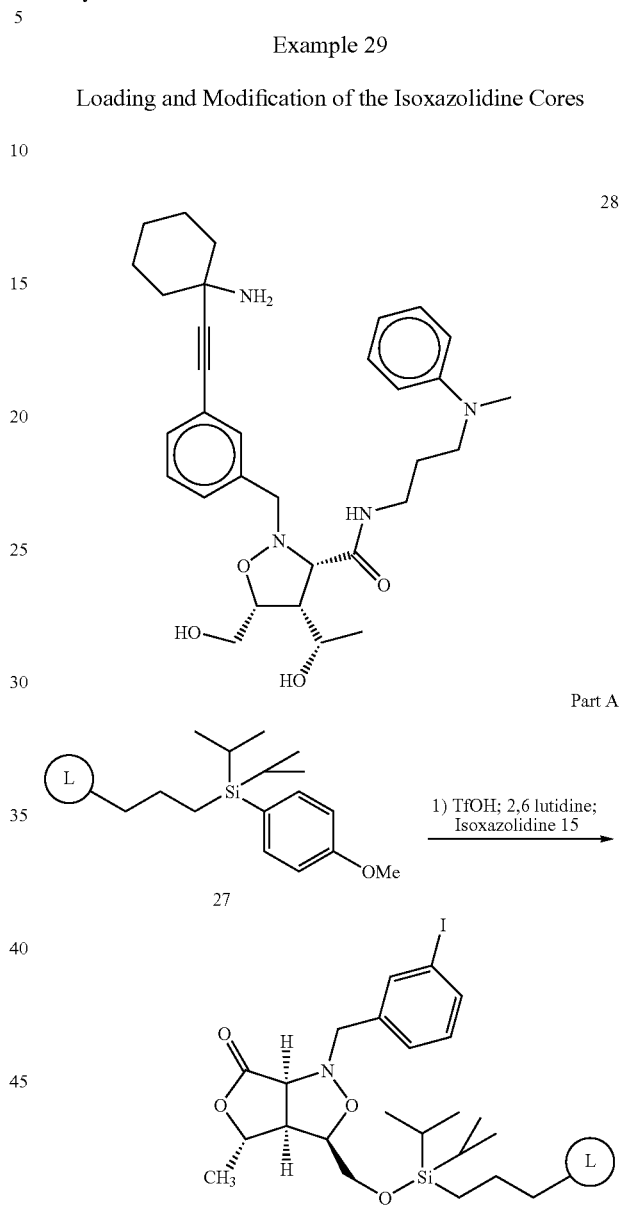

Part A 1808 lanterns were placed in a flame dried 2 L flask. A stir bar was added and the flask was purged with nitrogen and capped with a rubber septa. CH$_2$Cl$_2$ (1.2 L) was added to the flask and the lanterns were allowed to sit in this solution for 10 min when the solvent was removed. A 3% triflic acid solution in anhydrous CH$_2$Cl$_2$ (1.2 L, 393 mmol, 3%, v/v) was added and the lanterns were stirred gently for 20 min The triflic acid solution was then removed via canula. CH$_2$Cl$_2$ (1.2 L) and 2,6-lutidine (62 mL, 532 mmol) were added. The lanterns were stirred in this solution for 10 min Dry isoxazolidine 15 (10 g, 38 mmol) was then added. The resulting mixture was stirred for 18 h, at which point the solution was decanted and the lanterns were washed according to the following protocol: (2×10 min) CH$_2$Cl$_2$ (1.5 L), THF (1.5 L), THF:IPA (3:1, 1.5 L), THF:water (3:1, 1.5 L), THF:IPA (3:1, 1.5 L), and THF (1.5 L). The lanterns were then dried under reduced pressure overnight. Loading level determination: 5 lanterns were each placed into 5 mL polypropylene containers. To each container was added THF (300 μL) and HF-pyridine (50 μL). The lanterns were allowed to sit in this solution for 6 h, at which point TMSOMe (500 μL)was added and the lanterns were allowed to sit in this solution for an additional 15 min The reaction solution was then transferred to a tared glass round-bottomed flask and concentrated in vacuo to afford isoxazolidine 15. The isolated material was weighed and the average loading level was calculated to be 14 μmol/lantern.

Part B

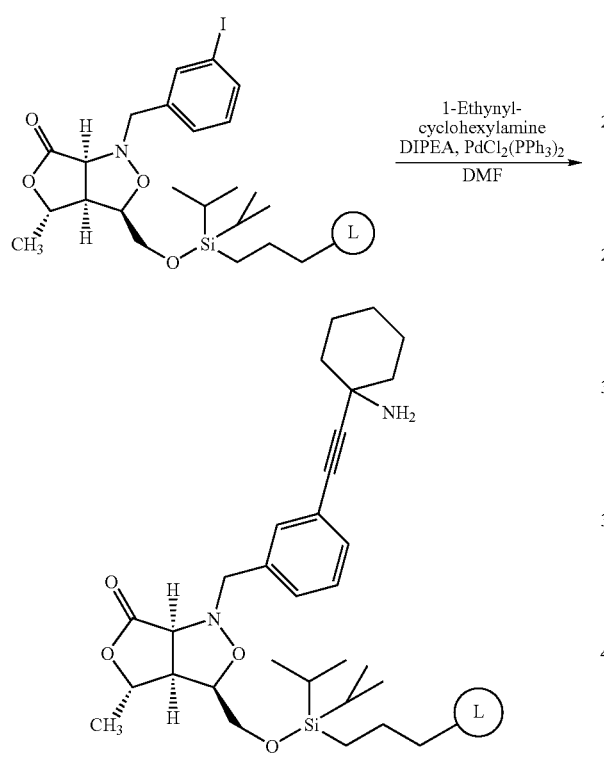

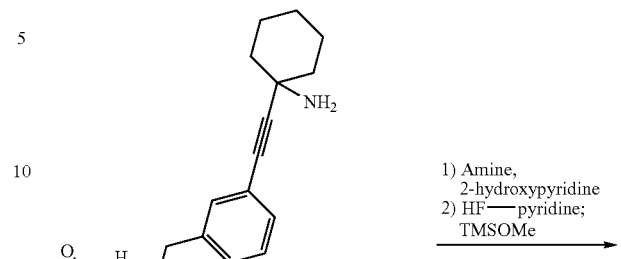

Part C

376 lanterns loaded with the isoxazolidine core were placed in a 500 mL flask. The flask was flushed with nitrogen and capped. Pd(PPh$_3$)$_2$Cl$_2$ (7.92 g, 11.3 mmol) and CuI (3.22 g, 16.9 mmol) were added to the flask. The reaction vessel was flushed with nitrogen again, capped, and anhydrous DMF (300 mL) was added. Diisopropylethylamine (30.0 mL, 172 mmol,) was added, followed by 1-ethynyl-cyclohexylamine (110 mmol) via syringe. The reaction vessel was then shaken gently for 2 h. The solution was then decanted and the lanterns were washed according to the following protocol: (2×10 min) DMF (300 mL), THF (300 mL), THF:IPA (3:1, 300 mL), THF:Water (3:1, 300 mL), THF:IPA (3:1, 300 mL), THF (300 mL), CH$_2$Cl$_2$ (300 mL). Reaction conversion determination: 1 lantern was placed into a 5 mL polypropylene container and treated with THF (300 μL) and HF-pyridine (50 μL). The lantern was allowed to sit in this solution for 6 h. At which point TMSOMe (500 μL)was added and the lantern was allowed to sit in this solution for an additional 15 min The reaction solution was then transferred to a glass round-bottomed flask and in vacuo to afford the sonogashira product.

374 lanterns were placed into a 500 mL round-bottomed flask followed by 2-hydroxypyridine (300 mL of a 0.35 M solution in THF, 105 mmol) was flushed with N$_2$ and capped with a rubber septum. N$^1$-methyl-N$^1$-phenyl-propane-1,3-diamine (279 mmol) was added and the reaction was heated to 50° C. for 16 h. The solvent was removed and the lanterns were washed according to the following protocol: (2×10 min) THF (300 mL), THF:IPA (3:1, 300 mL), THF:water (3:1, 300 mL), THF:IPA (3:1, 300 mL), THF (300 mL), CH$_2$Cl$_2$ (300 mL). Reaction conversion determination: 1 lantern was placed into a 5 mL polypropylene container and treated with THF (160 μL), pyridine (200 μL) and HF-pyridine (40 μL). The lantern was allowed to sit in this solution for 1 h, at which point TMSOMe (500 μL)was added and the lantern was allowed to sit in this solution for an additional 15 min The reaction solution was then transferred to a glass round-bottomed flask and concentrated under reduced pressure to afford the product.

Isoxazolidine 28 was characterized by LC-MS analysis. The general procedures and conditions used for analytical analysis used in this and other examples are presented below.

Conditions for LC-MS Analysis

| | |
|---|---|
| Mass Spectrometer: | Waters ZQ |
| HPLC: | Waters 2795 Alliance HT |
| Diode Array: | Waters 2696 |

Mass spectrometer conditions:

Mass spectrometer ionization mode: electro-spray with positive negative switching.

| | |
|---|---|
| Mass Range | 150-1000 Daltons |
| Capillary (KV) | 3.2 |
| Cone (V) | 35 |
| Extractor (V) | 3 |
| RF Lens | 0 |
| Source Temperature | 120° C. |
| Desolvation Temp. | 350° C. |
| Cone Gas | 25 L/H |
| Desolvation Gas | 550 L/H |

HPLC conditions:

| | | | | |
|---|---|---|---|---|
| Mobile phases: | A: Water 95% Acetonitrile 5% Formic Acid 0.1% | | | |
| | B: Water 5% Acetonitrile 95% Formic Acid 0.1% | | | |
| Flow rate: | 1.00 mL/minute | | | |
| Column: | Waters Symmetry 4.6 mm by 50 mm 5 micron C18 | | | |
| Column Temperature | 50° C. | | | |
| Gradient: | A | B | Time | Flow |
| | 85 | 15 | 0.0 | 1.0 |
| | 85 | 15 | 1.0 | 1.0 |
| | 0 | 100 | 5.0 | 1.0 |
| | 0 | 100 | 6.0 | 1.0 |
| | 85 | 15 | 6.1 | 1.5 |
| | 85 | 15 | 7.0 | 1.5 |
| | 85 | 15 | 8.0 | 1.0 |
| Injection volume: | 5 µL | | | |
| Diode Array conditions: | Wavelength array: 220 nm-400 nm | | | |
| | Resolution: 1.2 nm | | | |

Sample concentrations are normally run at 0.2 mg/mL unless otherwise stated.

Conditions for MS-TOF Analysis

| | |
|---|---|
| Mass Spectrometer: | Micromass LCT |
| HPLC: | Waters 2795 Alliance HT |
| Diode Array: | Waters 2696 |

Mass spectrometer conditions:

Mass spectrometer ionization mode: electro-spray positive

| | |
|---|---|
| Mass Range | 150-1000 Daltons |
| Capillary (KV) | 3.2 |
| Cone (V) | 35 |
| Extractor (V) | 3 |
| RF Lens | 0 |
| Source Temperature | 120° C. |
| Desolvation Temp. | 350° C. |
| Cone Gas | 25 L/H |
| Desolvation Gas | 450 L/H |

HPLC conditions:

| | | | | |
|---|---|---|---|---|
| Mobile phases: | A: Water with Formic Acid 0.1% | | | |
| | B: 65% Methanol/35% 2-Propanol with Formic Acid 0.1% | | | |
| Flow rate: | 1.00 mL/minute | | | |
| Column: | Varian Polaris 2.1 mm by 50 mm 5 micron C18 | | | |
| Column Temperature | 50° C. | | | |
| Gradient: | A | B | Time | Flow |
| | 90 | 10 | 0.0 | 1.0 |
| | 90 | 10 | 0.5 | 1.0 |
| | 10 | 90 | 3.2 | 1.0 |
| | 10 | 90 | 3.4 | 1.0 |
| | 0 | 100 | 3.5 | 1.0 |
| | 0 | 100 | 4.0 | 1.0 |

Injector system runs in two column regeneration mode so that column equilibration occurs during the rime of the next sample analyzed.

| | |
|---|---|
| Injection volume: | 5 µL |
| Diode Array conditions: | Wavelength array: 220 nm-400 nm |
| | Resolution: 1.2 nm |

Sample concentrations are normally run at 2.0 mg/mL unless otherwise stated.

Example 30

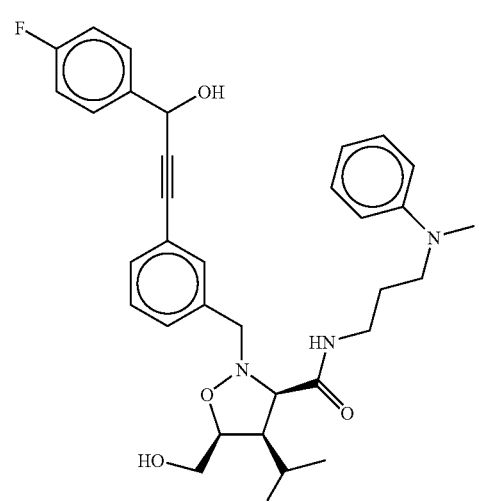

29

Compound 29 was synthesized according to the procedure described in Example 29 using isoxazolidine 18 in place of isoxazolidine 15, 1-(4-fluoro-phenyl)-prop-2-yn-1-ol in place of 1-ethynyl-cyclohexylamine and N¹-methyl-N¹-phenyl-propane-1,3-diamine. MS (ESI(+)) m/e 576.4 (M+H)⁺.

Example 31

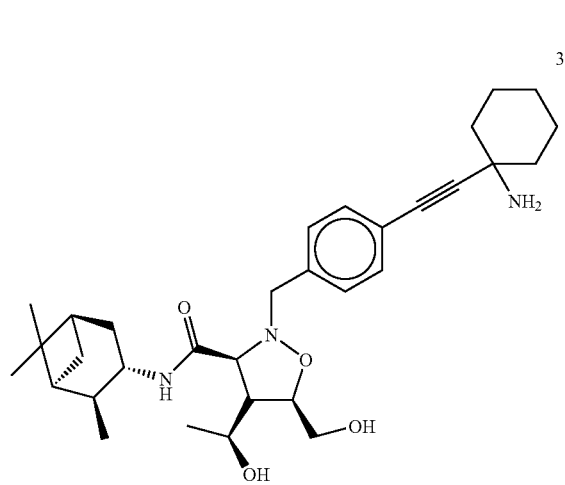

Compound 30 was synthesized according to the procedure described in Example 29 using isoxazolidine 18 in place of isoxazolidine 15, 1-(4-fluoro-phenyl)-prop-2-yn-1-ol in place of 1-ethynyl-cyclohexylamine and (+)-isopinocampheylamine in place of N¹-methyl-N¹-phenyl-propane-1,3-diamine. MS (ESI(+)) m/e 538.3 (M+H)⁺.

Example 32

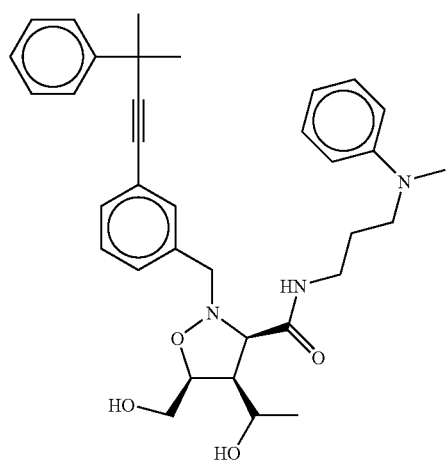

Compound 31 was synthesized according to the procedure described in Example 29 using isoxazolidine 15, (1,1-dimethyl-prop-2-ynyl)-benzene in place of 1-ethynyl-cyclohexylamine and N'-methyl-N'-phenyl-propane-1,3-diamine. MS (ESI(+)) m/e 570.4 (M+H)⁺.

Example 33

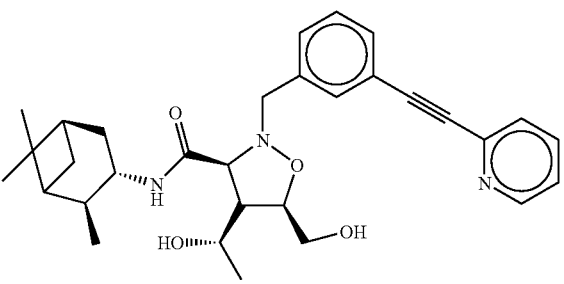

Compound 32 was synthesized according to the procedure described in Example 29 using isoxazolidine 15, 2-ethynyl-pyridine in place of 1-ethynyl-cyclohexylamine and (+)-isopinocampheylamine in place of N¹-methyl-N¹-phenyl-propane-1,3-diamine. MS (ESI(+)) m/e 518.4 (M+H)⁺.

Example 34

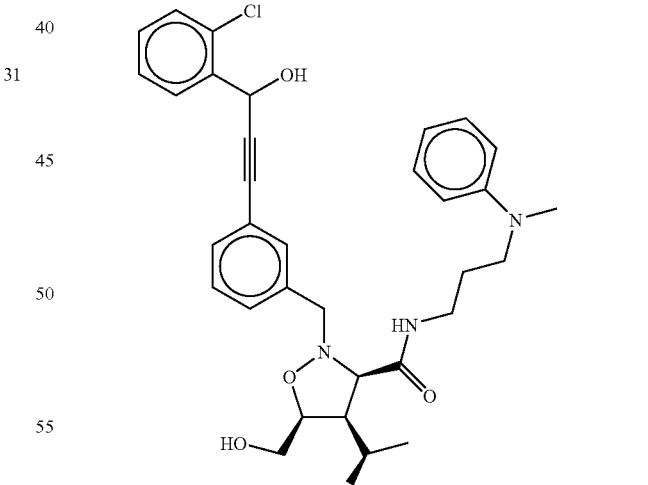

Compound 33 was synthesized according to the procedure described in Example 29 using isoxazolidine 18 in place of isoxazolidine 15, 1-(2-chloro-phenyl)-prop-2-yn-1-ol in place of 1-ethynyl-cyclohexylamine and N¹-methyl-N¹-phenyl-propane-1,3-diamine.

Example 35

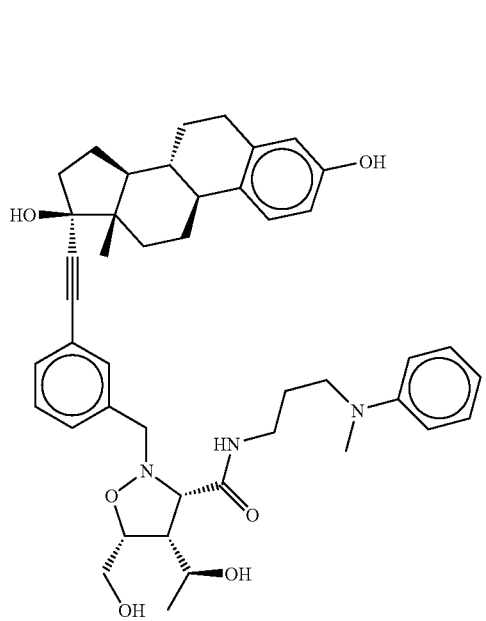

Compound 34 was synthesized according to the procedure described in Example 29 using isoxazolidine 15, 17 a-ethynylestradiol in place of 1-ethynyl-cyclohexylamine and $N^1$-methyl-$N^1$-phenyl-propane-1,3-diamine. MS (ESI(+)) m/e 722.4 (M+H)$^+$.

Example 36

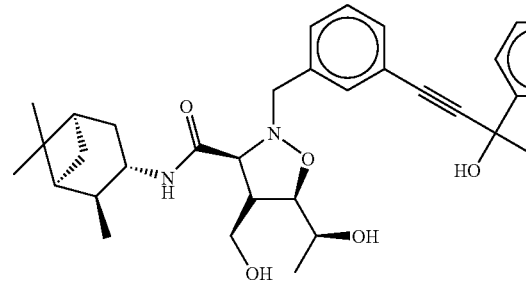

Compound 35 was synthesized according to the procedure described in Example 29 using isoxazolidine 15, 2-phenyl-but-3-yn-2-ol in place of 1-ethynyl-cyclohexylamine and (+)-isopinocampheylamine in place of $N^1$-methyl-$N^1$-phenyl-propane-1,3-diamine.

Example 37

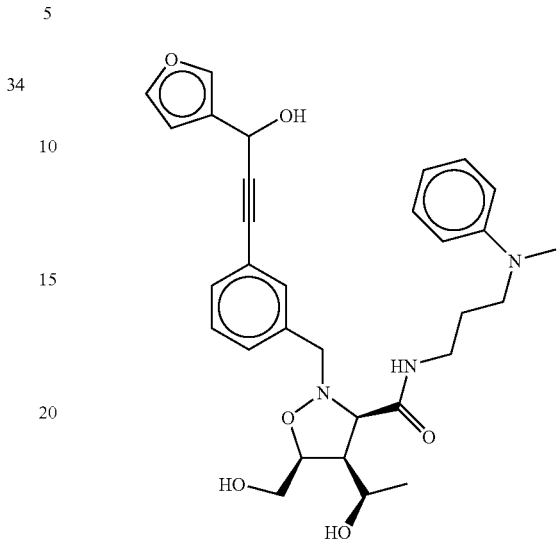

Compound 36 was synthesized according to the procedure described in Example 29 using isoxazolidine 18 in place of isoxazolidine 15, 1-furan-3-yl-prop-2-yn-1-ol in place of 1-ethynyl-cyclohexylamine and $N^1$-methyl-$N^1$-phenyl-propane-1,3-diamine.

Example 38

Compound 37 was synthesized according to the procedure described in Example 29 using isoxazolidine 18 in place of isoxazolidine 15, 2-phenyl-but-3-yn-2-ol in place of 1-ethynyl-cyclohexylamine and cyclohexyl-methylamine in place of $N^1$-methyl-$N^1$-phenyl-propane-1,3-diamine. MS (ESI(+)) m/e 521.6 (M+H)$^+$.

Example 39

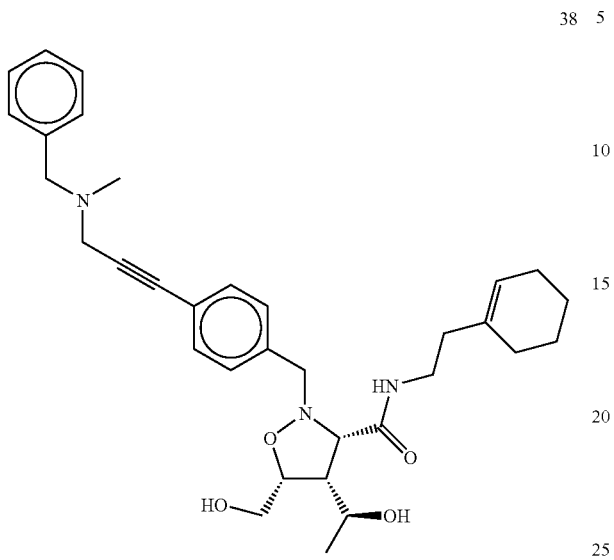

38

Compound 38 was synthesized according to the procedure described in Example 29 using isoxazolidine 16 in place of isoxazolidine 15, benzyl-methyl-prop-2-ynyl-amine in place of 1-ethynyl-cyclohexylamine and 2-cyclohex-1-enyl-ethylamine in place of $N^1$-methyl-$N^1$-phenyl-propane-1,3-diamine.

Example 41

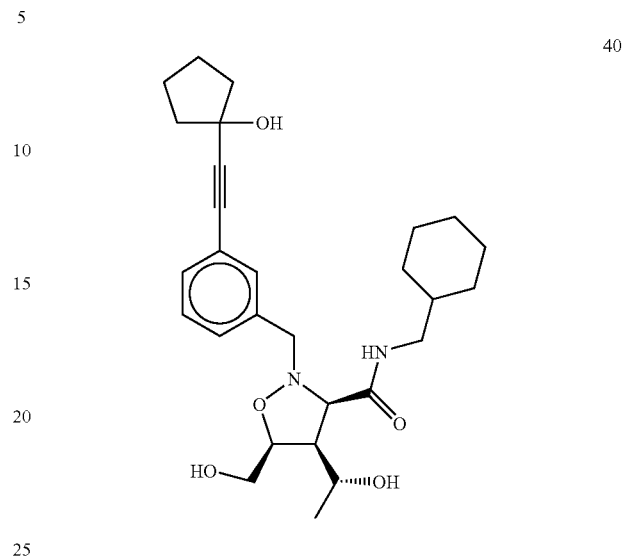

40

Compound 40 was synthesized according to the procedure described in Example 29 using isoxazolidine 18 in place of isoxazolidine 15, 1-ethynyl-cyclopentanol in place of 1-ethynyl-cyclohexylamine and cyclohexyl-methylamine in place of $N^1$-methyl-$N^1$-phenyl-propane-1,3-diamine.

Example 40

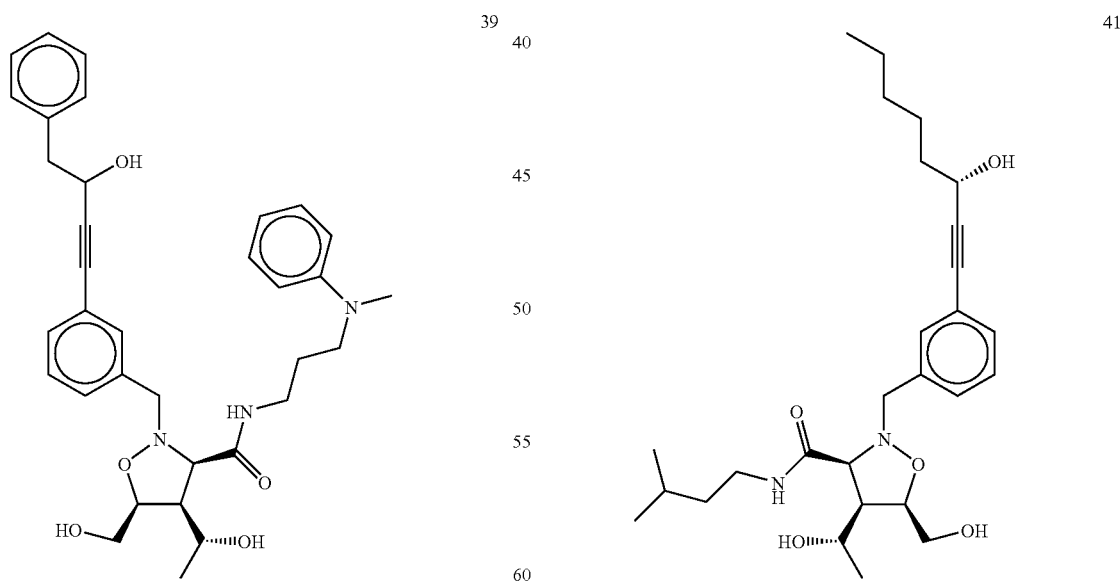

39

Compound 39 was synthesized according to the procedure described in Example 29 using isoxazolidine 18 in place of isoxazolidine 15, 1-phenyl-but-3-yn-2-ol in place of 1-ethynyl-cyclohexylamine and $N^1$-methyl-$N^1$-phenyl-propane-1, 3-diamine.

Example 42

41

Compound 41 was synthesized according to the procedure described in Example 29 using isoxazolidine 15, oct-1-yn-3-ol in place of 1-ethynyl-cyclohexylamine and 3-methyl-butylamine in place of $N^1$-methyl-$N^1$-phenyl-propane-1,3-diamine.

Example 43

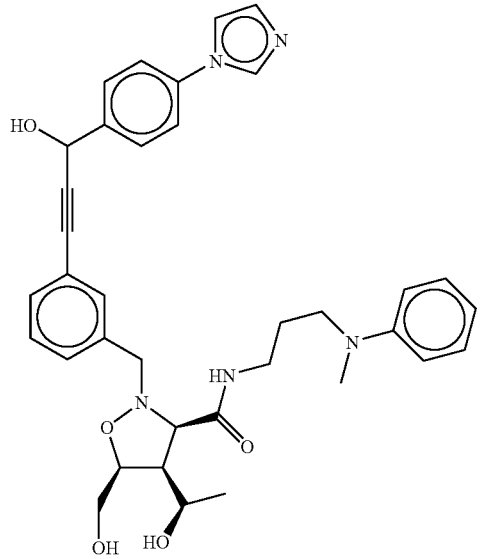

42

Compound 42 was synthesized according to the procedure described in Example 29 using isoxazolidine 18 in place of isoxazolidine 15, 1-(4-imidazol-1-yl-phenyl)-prop-2-yn-1-ol in place of 1-ethynyl-cyclohexylamine and $N^1$-methyl-$N^1$-phenyl-propane-1,3-diamine. MS (ESI(+)) m/e 624.4 (M+H)$^+$.

Example 44

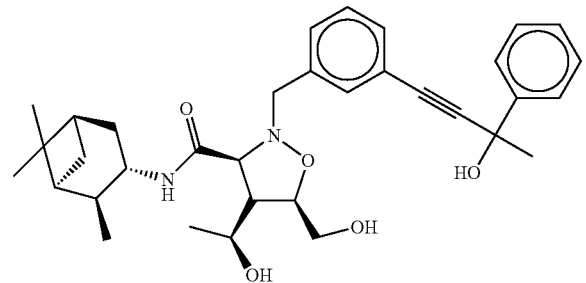

43

Compound 43 was synthesized according to the procedure described in Example 29 using isoxazolidine 15, 2-phenyl-but-3-yn-2-ol in place of 1-ethynyl-cyclohexylamine and (+)-isopinocampheylamine in place of $N^1$-methyl-$N^1$-phenyl-propane-1,3-diamine. MS (ESI(+)) m/e 561.3 (M+H)$^+$.

Example 45

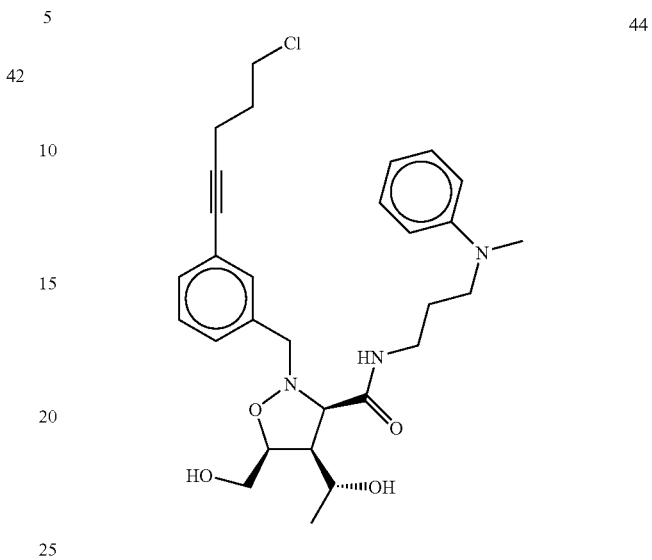

44

Compound 44 was synthesized according to the procedure described in Example 29 using isoxazolidine 18 in place of isoxazolidine 15, 5-chloro-pent-1-yne in place of 1-ethynyl-cyclohexylamine and $N^1$-methyl-$N^1$-phenyl-propane-1,3-diamine.

Example 46

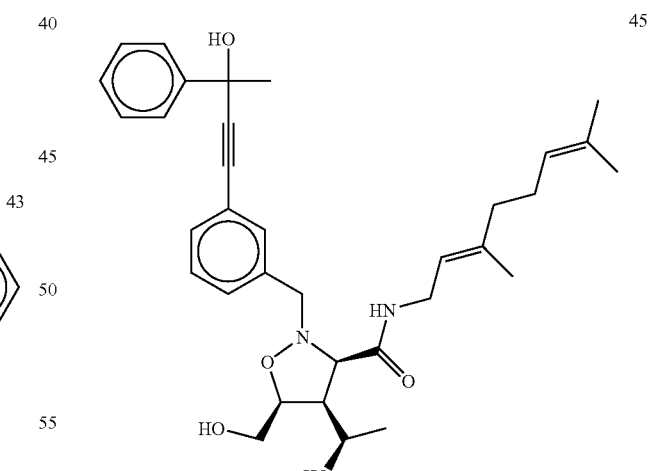

45

Compound 45 was synthesized according to the procedure described in Example 29 using isoxazolidine 18 in place of isoxazolidine 15, 2-phenyl-but-3-yn-2-ol in place of 1-ethynyl-cyclohexylamine and geranylaamine in place of $N^1$-methyl-$N^1$-phenyl-propane-1,3-diamine. MS (ESI(+)) m/e 561.7 (M+H)$^+$.

Example 47

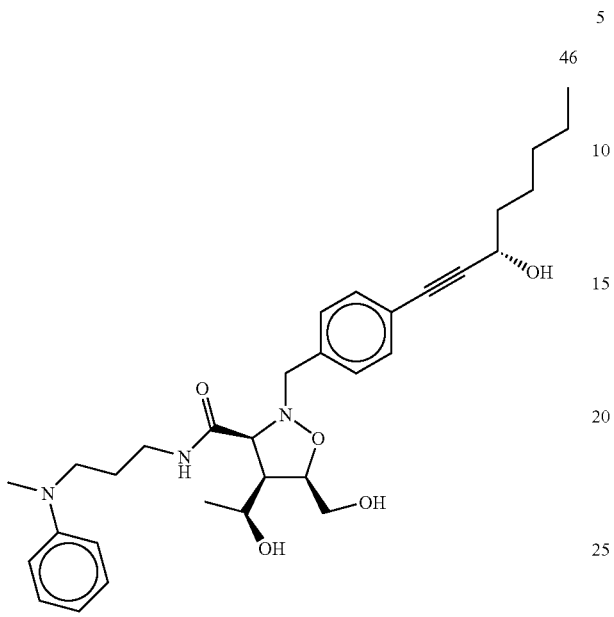

Compound 46 was synthesized according to the procedure described in Example 29 using isoxazolidine 15, oct-1-yn-3-ol in place of 1-ethynyl-cyclohexylamine and $N^1$-methyl-$N^1$-phenyl-propane-1,3-diamine.

Example 48

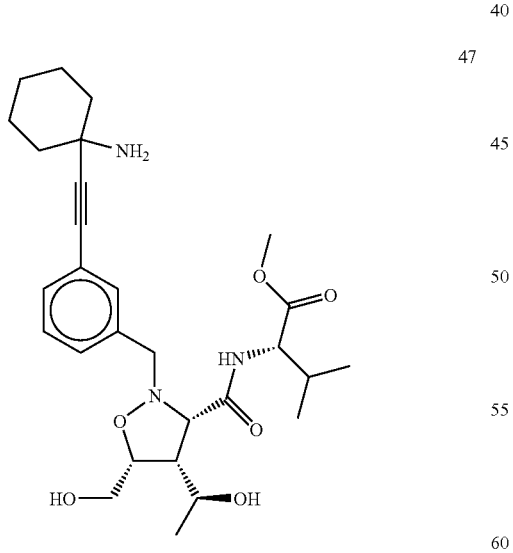

Compound 47 was synthesized according to the procedure described in Example 29 using isoxazolidine 15, 1-ethynyl-cyclohexylamine and valine methyl ester in place of $N^1$-methyl-$N^1$-phenyl-propane-1,3-diamine.

Example 49

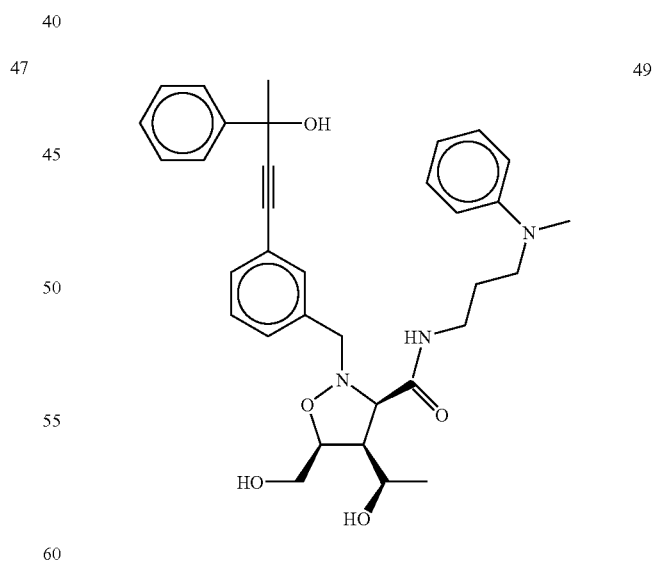

Compound 48 was synthesized according to the procedure described in Example 29 using isoxazolidine 18 in place of isoxazolidine 15, 1-phenyl-prop-2-yn-1-ol in place of 1-ethynyl-cyclohexylamine and $N^1$-methyl-$N^1$-phenyl-propane-1, 3-diamine. MS (ESI(+)) m/e 558.2 (M+H)$^+$.

Example 50

Compound 49 was synthesized according to the procedure described in Example 29 using isoxazolidine 18 in place of isoxazolidine 15, 2-phenyl-but-3-yn-2-ol in place of 1-ethynyl-cyclohexylamine and $N^1$-methyl-$N^1$-phenyl-propane-1, 3-diamine. MS (ESI(+)) m/e 572.3 (M+H)$^+$.

Example 51

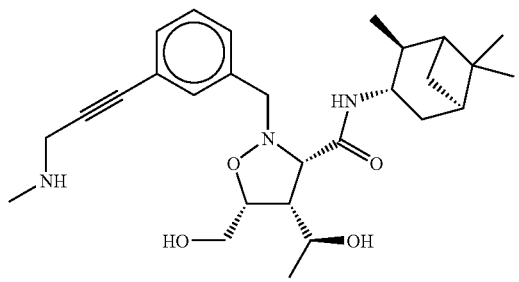

50

Compound 50 was synthesized according to the procedure described in Example 29 isoxazolidine 15, methyl-prop-2-ynyl-amine in place of 1-ethynyl-cyclohexylamine and (+)-isopinocampheylamine in place of $N^1$-methyl-$N^1$-phenyl-propane-1,3-diamine. MS (ESI(+)) m/e 484.2 (M+H)$^+$.

Example 52

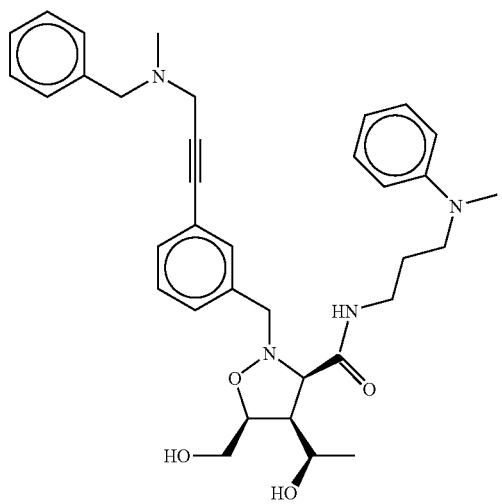

51

Compound 51 was synthesized according to the procedure described in Example 29 using isoxazolidine 18 in place of isoxazolidine 15, benzyl-methyl-prop-2-ynyl-amine in place of 1-ethynyl-cyclohexylamine and $N^1$-methyl-$N^1$-phenyl-propane-1,3-diamine. MS (ESI(+)) m/e 585.3 (M+H)$^+$.

Example 53

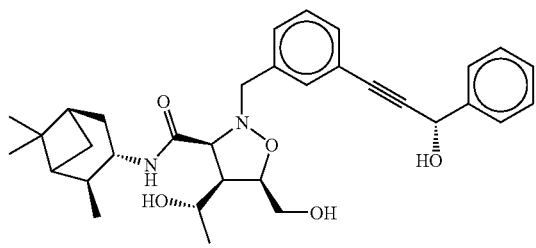

52

Compound 52 was synthesized according to the procedure described in Example 29 isoxazolidine 15, 1-phenyl-prop-2-yn-1-ol in place of 1-ethynyl-cyclohexylamine and (+)-isopinocampheylamine in place of $N^1$-methyl-$N^1$-phenyl-propane-1,3-diamine. MS (ESI(+)) m/e 547.3 (M+H)$^+$.

Example 54

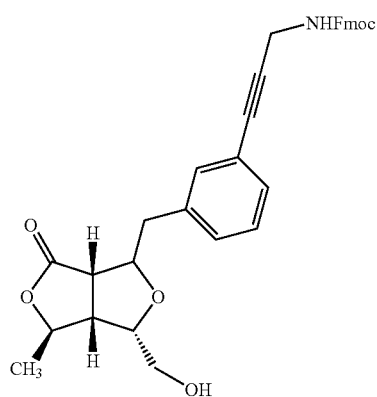

53

Part A

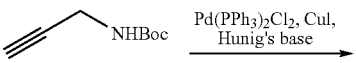

18

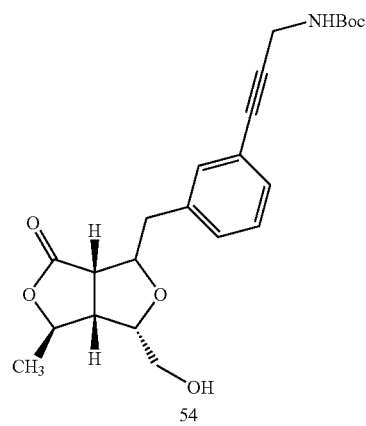

54

To a solution of isoxazolidine 18 (0.1 g, 0.26 mmol) were added N-Boc-propargyl amine (0.08 g, 0.51 mmol) in DMF (3 mL),Pd(PPh₃)₂Cl₂) (54 mg, 0.3 mmol), and CuI (20 mg, 0.1 mmol), diisopropylethylamine (0.14 mL, 0.77 mmol). This reaction mixture was maintained at rt for 12 h. It was then partitioned between EtOAc-Sat aqueous NH₄Cl (60 mL, 1:1). The aqueous layer was extracted with EtOAc (2×30 mL) and all organic fractions were combined and washed with sat aqueous NH₄Cl (2×50 mL). The organic layer was dried (MgSO₄), filtered and concentrated in vacuo. Purification of the crude material by silica gel chromatography (Hexane-EtOAc, 1:1) gave the desired product. Yield 90%.

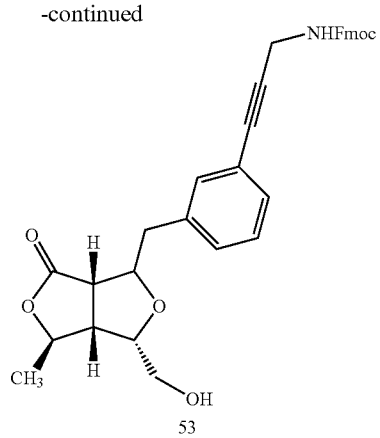

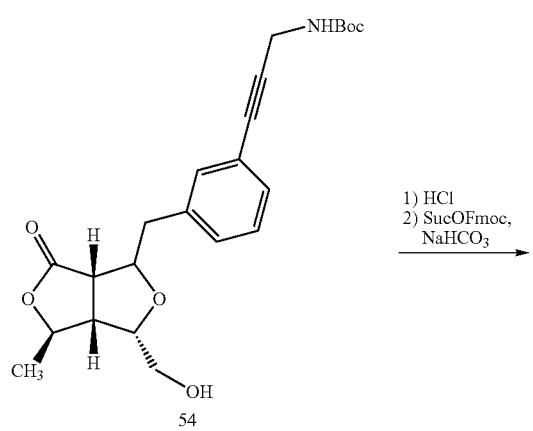

To a solution of the Boc-protected propargylamine 54 in EtOAc (6 mL) was added HCl (0.12 mL, of a 4 M solution in 1,4-dioxane, 0.24 umol) at 0° C. The solution was stirred at rt for 30 min when a precipitate formed, the resulting mixture was stirred at rt for 2 h (TLC indicated existence of SM). Additional HCl (120 mL) was added; reaction was maitained at rt for 24 h. TLC showed reaction was not completed; it was then concentrated to dryness; residue was dissolved in CH₂Cl₂ (6 mL), cooled to 0° C. and TFA (1 mL) was added dropwise. The solution was stirred at rt for 10 min and concentrated in vacuo. The resulting residue was combined with Fmoc-succinamide (0.13 g, 0.39 mmol), 1:1 CH₂Cl₂-water (3 mL) and NaHCO₃ (220 mg, 2.60 mmol). This mixture was stirred vigorously at rt for 14 h. The organic phase was separated and the aqueous phase extracted with CH₂Cl₂, the organic extracts were combined, dried (Na₂SO₄), filtered and concentrated in vacuo. The residue was purified by column chromatography (silica gel, gradient EtOAc-hexane 1:1 to 5:1) to afford the desired product (89 mg, 60%).

Example 55

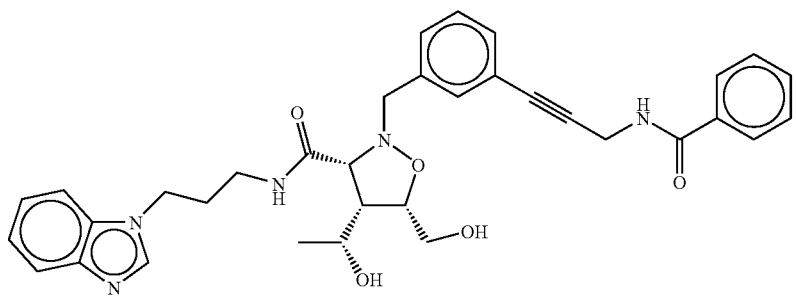

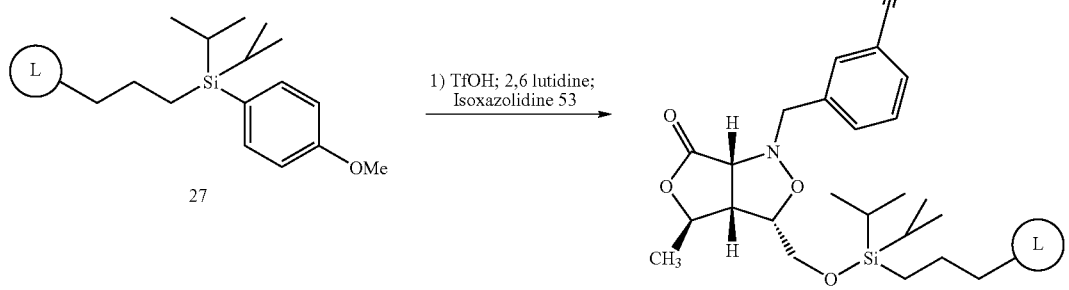

1808 lanterns were placed in a flame dried 2 L flask. A stir bar was added and the flask was purged with nitrogen and capped with a rubber septa. Anhydrous CH₂Cl₂ (1.2 L) was added to the flask and the lanterns were allowed to sit in this solution for 10 min and then the solvent was removed. A 3% triflic acid solution in anhydrous CH₂Cl₂ (1.2 L, 393 mmnol, 3% v/v) was added and the lanterns were stirred gently for 20 min The triflic acid solution was then removed via canula. Anhydrous CH₂Cl₂ (1.2 L) and 2,6-lutidine (62 mL, 532 mmol) were added. The lanterns were stirred in this solution for 10 min isoxazolidine 53 (10 g, 38 mmol) was then added. The resulting mixture was stirred for 18 h, at which point the reaction solution was decanted and the lanterns were washed according to the following protocol: (2×10 min) CH₂Cl₂ (1.5 L), THF (1.5 L), THF:IPA (3:1, 1.5 L), THF:water (3:1, 1.5 L), THF:IPA (3:1, 1.5 L), and THF (1.5 L). The lanterns were dried in vacuo overnight. Loading level determination: 5 lanterns were each placed into 5 mL polypropylene containers. To each container was added THF (300 µL) and HF-pyridine (50 µL). The lanterns were allowed to sit in this solution for 6 h. At which point TMSOMe (500 µL)was added and the lanterns were allowed to sit in this solution for an additional 15 min The reaction solution was then transferred to a tared glass round-bottomed flask and concentrated under reduced pressure to afford isoxazolidine 53. This material was weighed and the average loading level was calculated to 10 µmol/lantern.

(2×10 min) CH₂Cl₂ (9 mL), THF (9 mL), THF:IPA (3:1, 9 mL), THF:water (3:1, 9 mL), THF:IPA (3:1, 9 mL), and THF (9 mL). Reaction conversion determination: 1 lantern was placed into a 5 mL polypropylene container and treated with THF (300 µL) and HF-pyridine (50 µL). The lantern was allowed to sit in this solution for 6 h. At which point TMSOMe (500 µL)was added and the lantern was allowed to sit in this solution for an additional 15 min The reaction solution was then transferred to a glass round-bottomed flask and concentrated under reduced pressure to afford the free amine.

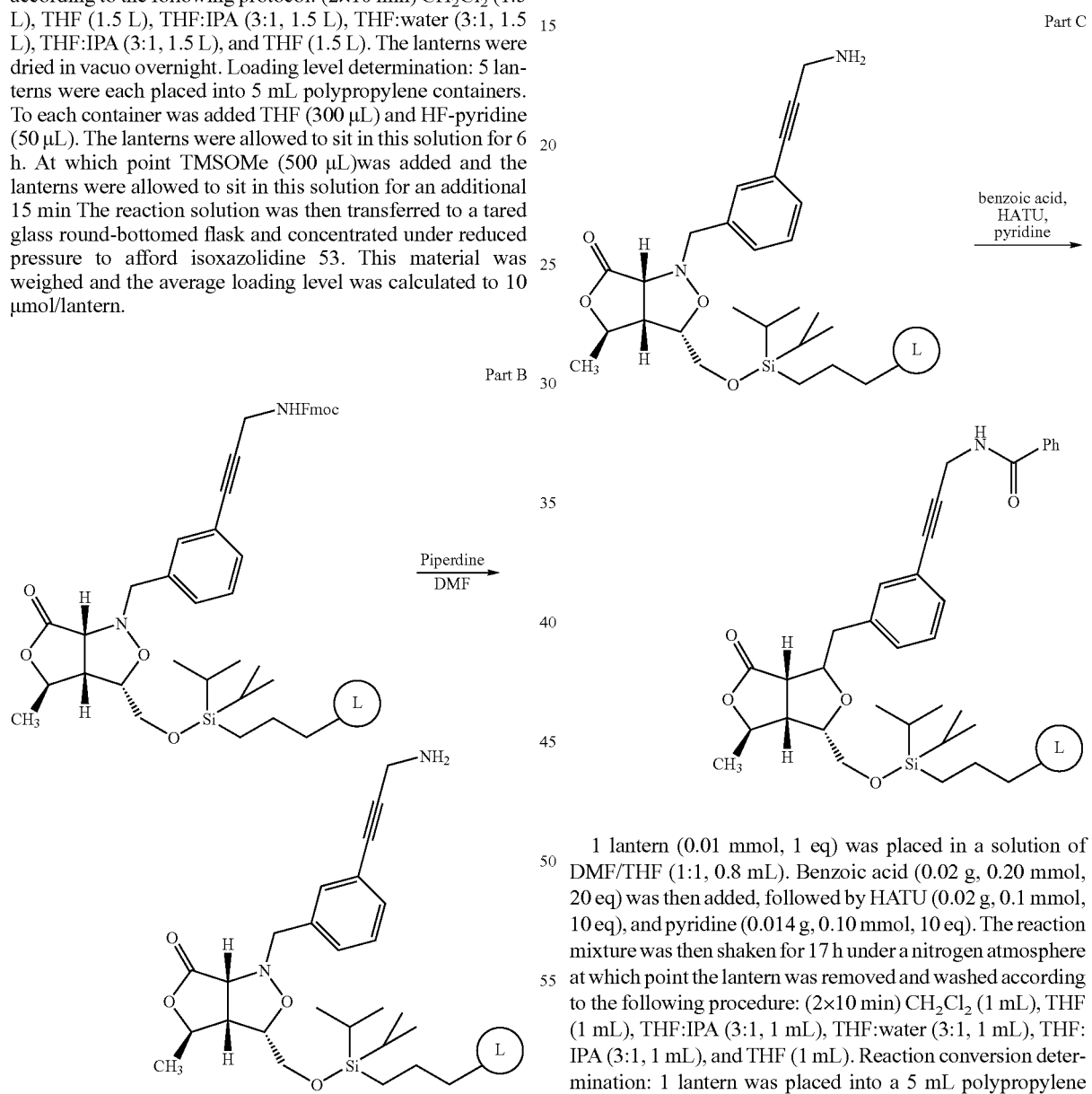

Part B

Part C 9 lanterns (0.09 mmol, 1 eq) were suspended in a 20% solution of piperdine in DMF (9 mL). The reaction mixture was shaken for 1 h at which point the reaction solution was draine 20% piperdine in DMF (9 mL) was added. The reaction mixture was shaken for 1 h. The lanterns were then removed and washed according to the following protocol:

1 lantern (0.01 mmol, 1 eq) was placed in a solution of DMF/THF (1:1, 0.8 mL). Benzoic acid (0.02 g, 0.20 mmol, 20 eq) was then added, followed by HATU (0.02 g, 0.1 mmol, 10 eq), and pyridine (0.014 g, 0.10 mmol, 10 eq). The reaction mixture was then shaken for 17 h under a nitrogen atmosphere at which point the lantern was removed and washed according to the following procedure: (2×10 min) CH₂Cl₂ (1 mL), THF (1 mL), THF:IPA (3:1, 1 mL), THF:water (3:1, 1 mL), THF:IPA (3:1, 1 mL), and THF (1 mL). Reaction conversion determination: 1 lantern was placed into a 5 mL polypropylene container and treated with THF (300 µL) and HF-pyridine (50 µL). The lantern was allowed to sit in this solution for 6 h. At which point TMSOMe (500 µL) was added and the lantern was allowed to sit in this solution for an additional 15 min The reaction solution was then transferred to a glass round-bottomed flaskand concentrated under reduced pressure to afford the desired product.

Part D

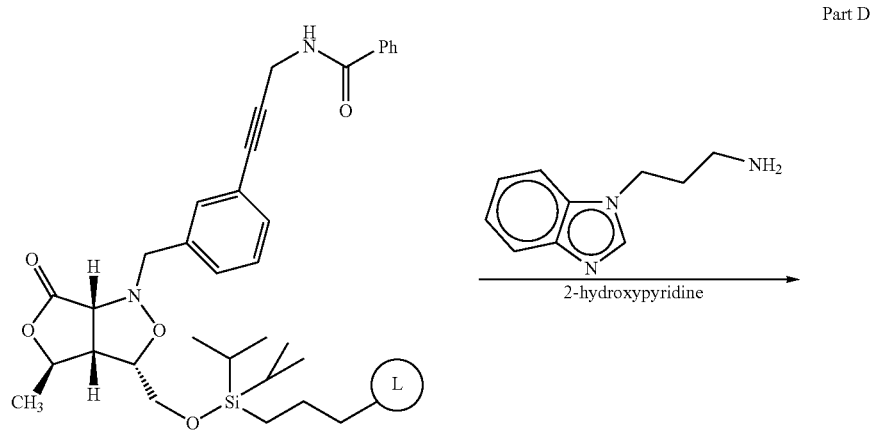

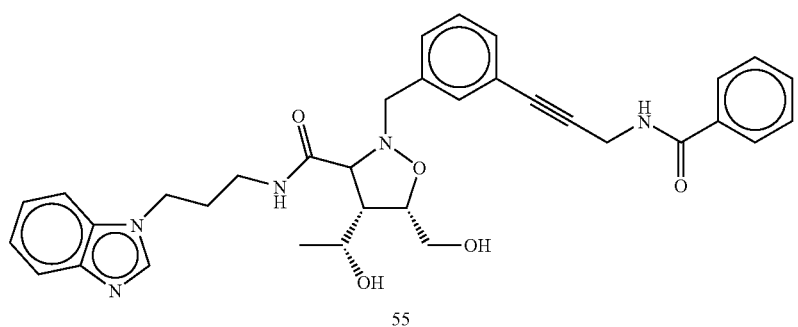

55

52 lanterns (0.52 mmol, 1 eq) were placed in a sealed flask and flushed with nitrogen. To the flask was added 2-hydroxypyridine (30 mL of a 0.35 M solution in THF; 20 eq) and 3-benzoimidazol-1-yl-propylamine (6.38 g, 36.4 mmol, 70 eq). The reaction mixture was shaken for 27 h at 50° C. under an atmosphere of nitrogen, at which point a lantern was removed and washed according to the following procedure: (2×10 min) CH$_2$Cl$_2$ (57 mL), THF (57 mL), THF:IPA (3:1, 57 mL), THF:water (3:1, 57 mL), THF:IPA (3:1, 57 mL), and THF (57 mL). Reaction conversion determination: 1 lantern was placed into a 5 mL polypropylene container. and treated with THF (300 µL) and HF-pyridine (50 µL). The lantern was allowed to sit in this solution for 6 hs. At which point TMSOMe (500 µL) was added and the lantern was allowed to sit in this solution for an additional 15 min The reaction solution was then transferred to a glass round-bottomed flask and concentrated under reduced pressure to afford the desired product.

Example 56

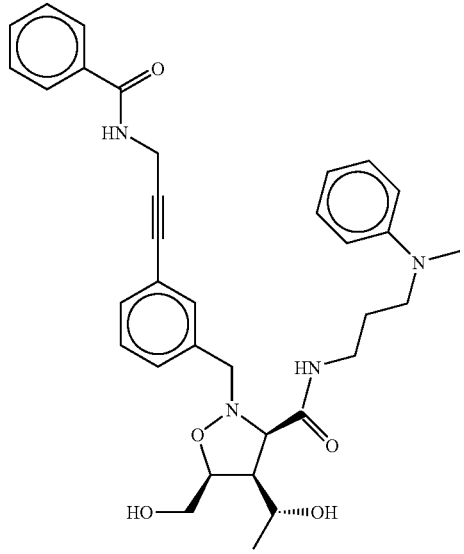

56

Compound 56 was synthesized according to the procedure described in Example 55 using N¹-methyl-N¹-phenyl-propane-1,3-diaamine in place of 3-benzoimidazol-1-yl-propylamine. MS (ESI(+)) m/e 585.4 (M+H)⁺.

Example 57

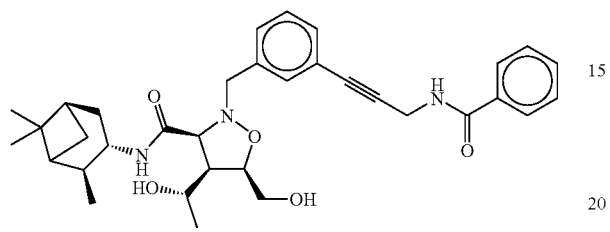

Compound 57 was synthesized according to the procedure described in Example 55 using isoxazolidine core 15 in place of isoxazolidine core 18 and (+)-isopinocampheylamine in place of 3-benzoimidazol-1-yl-propylamine. MS (ESI(+)) m/e 574.4 (M+H)⁺.

Example 58

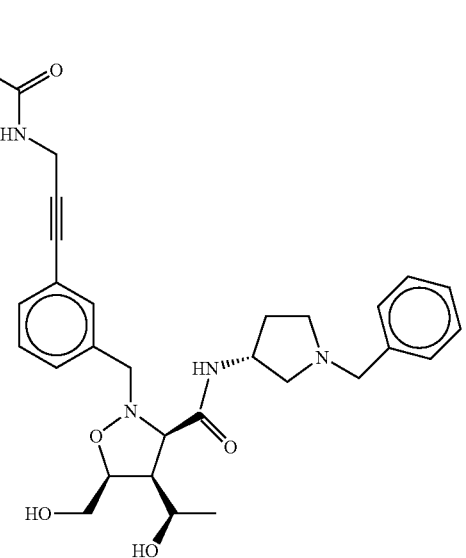

Compound 58 was synthesized according to the procedure described in Example 55 using 1-benzyl-pyrrolidin-3-ylamine in place of 3-benzoimidazol-1-yl-propylamine. MS (ESI(+)) m/e 597.4 (M+H)⁺.

Example 59

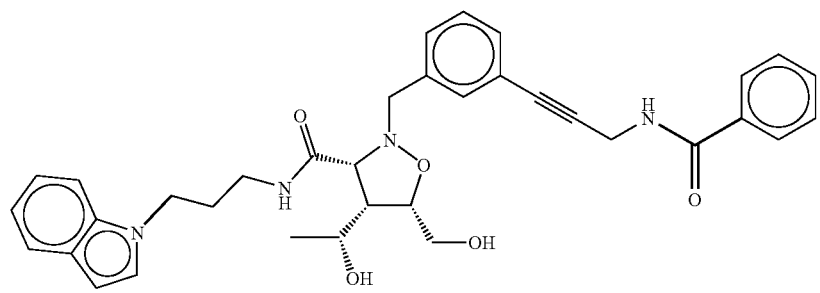

Compound 59 was synthesized according to the procedure described in Example 55 using isoxazolidine core 15 in place of isoxazolidine core 18 and 3-indol-1-yl-propylamine in place of 3-benzoimidazol-1-yl-propylamine. MS (ESI(+)) m/e 574.4 (M+H)⁺.

Example 60

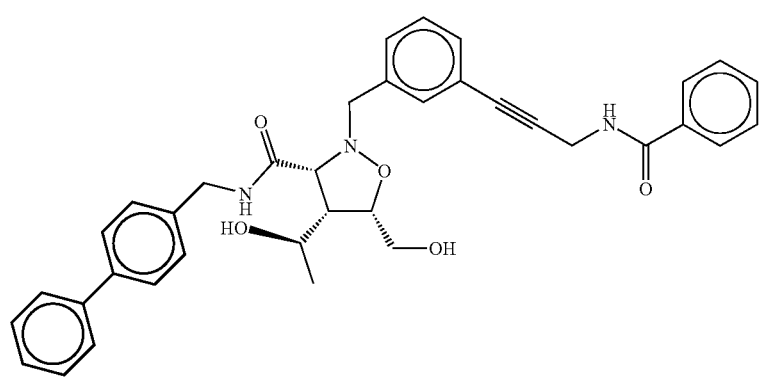

Compound 60 was synthesized according to the procedure described in Example 55 using 4-phenylbenzyl amine in place of 3-benzoimidazol-1-yl-propylamine.

Example 61

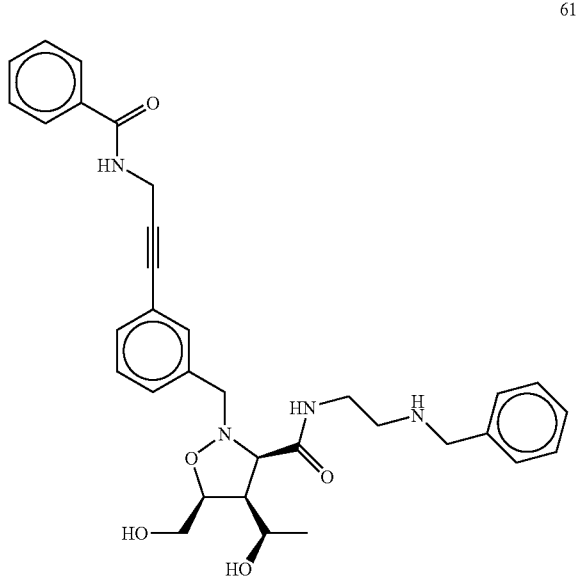

Compound 61 was synthesized according to the procedure described in Example 55 using $N^1$-Benzyl-ethane-1,2-diamine in place of 3-benzoimidazol-1-yl-propylamine.

Example 62

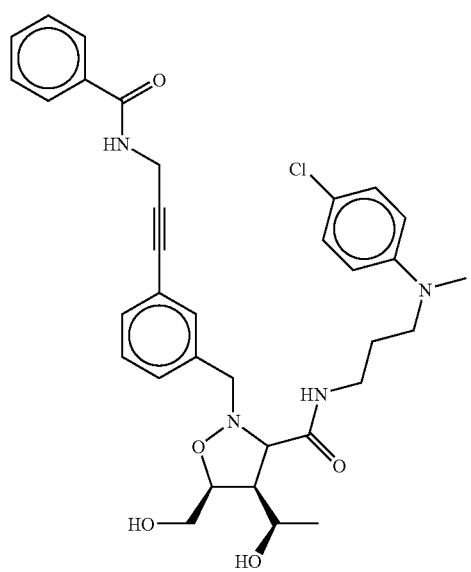

Compound 62 was synthesized according to the procedure described in Example 55 using $N^1$-(4-chloro-phenyl)-$N^1$-methyl-propane-1,3-diamine in place of 3-benzoimidazol-1-yl-propylamine.

Example 63

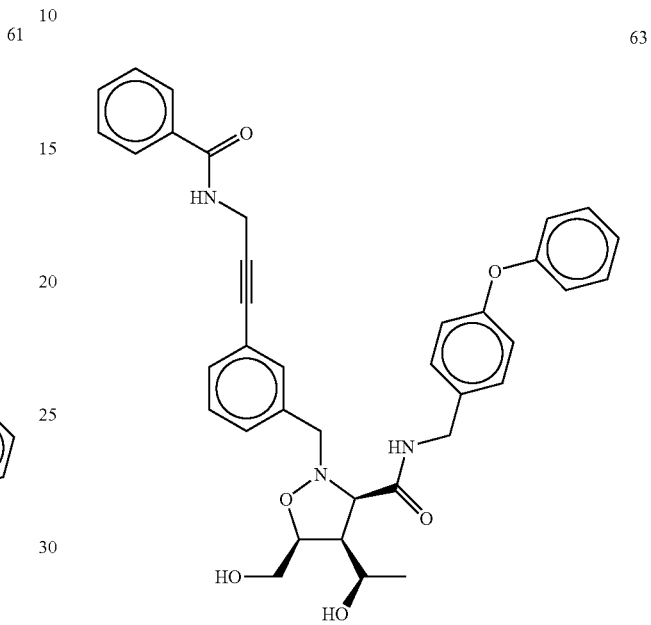

Compound 63 was synthesized according to the procedure described in Example 55 using 4-phenoxybenzylamine in place of 3-benzoimidazol-1-yl-propylamine.

Example 64

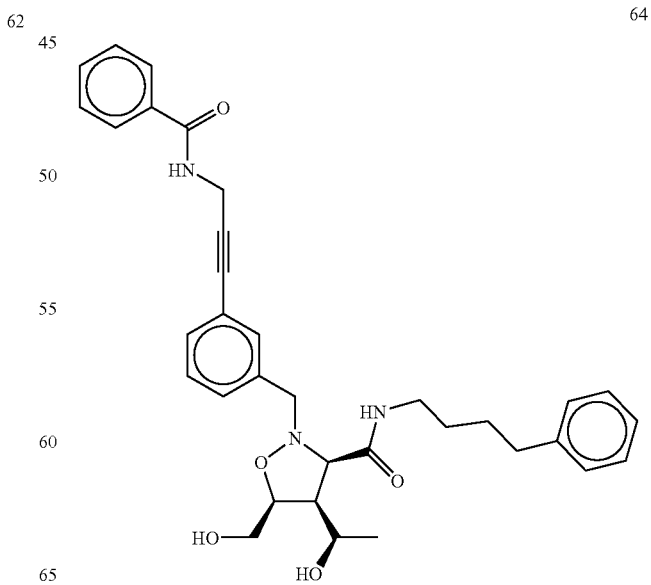

Compound 64 was synthesized according to the procedure described in Example 55 using 4-phenyl-butylamine in place of 3-benzoimidazol-1-yl-propylamine.

Example 65

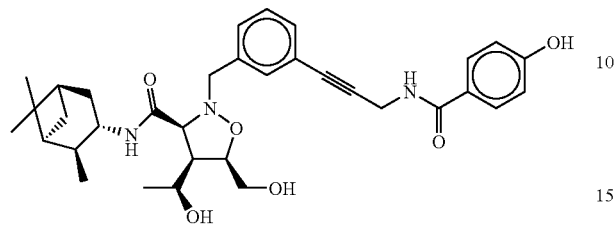

65

Compound 65 was synthesized according to the procedure described in Example 55 using isoxazolidine core 15 in place of isoxazolidine core 18, (+)-isopinocampheylamine in place of 3-benzoimidazol-1-yl-propylamine, and 4 hydroxybenzoic acid in place of benzoic acid. MS (ESI(+)) m/e 590.5 (M+H)⁺.

Example 66

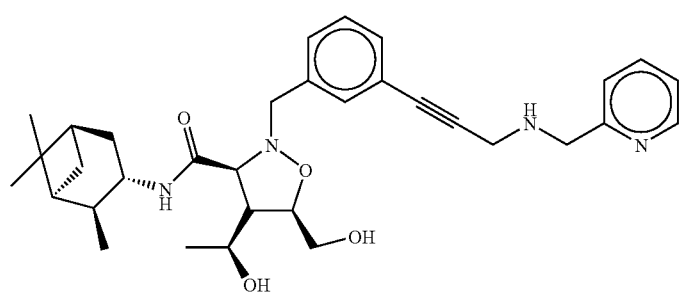

66

Part A

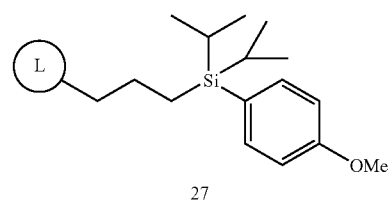

27

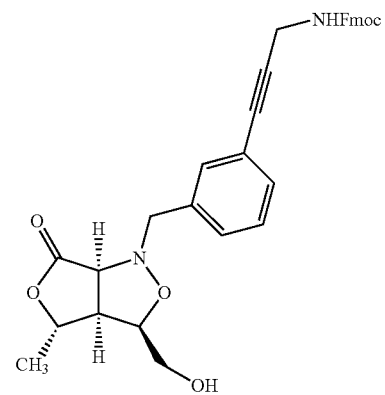

67

1) TfOH; 2,6 lutidine;

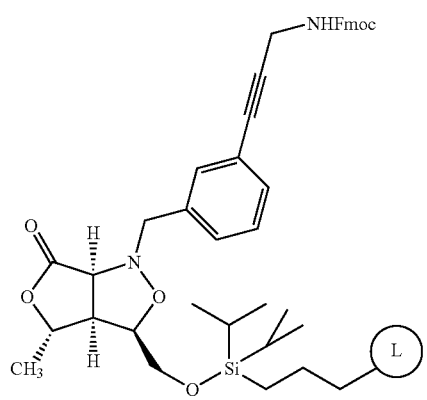

1808 lanterns were placed in a flame dried 2 L flask. A stir bar was added and the flask was purged with nitrogen and capped with a rubber septa. CH$_2$Cl$_2$ (1.2 L) was added to the flask and the lanterns were allowed to sit in this solution for 10 min, when the solvent was removed. A triflic acid solution in anhydrous CH$_2$Cl$_2$ (1.2 L, 393 mmol, 3% v/v) was added and the lanterns were stirred gently for 20 min The triflic acid solution was then removed via cannula. Anhydrous CH$_2$Cl$_2$ (1.2 L) and 2,6-lutidine were added (62 mL, 532 mmol). The lanterns were stirred in this solution for 10 min Isoxazolidine 67 (made according to the procedure described in example 54) (10 g, 38 mmol) was then added. The resulting mixture was stirred for 18 h. At which point the reaction solution was decanted and the lanterns were washed according to the following protocol: (2×10 min) CH$_2$Cl$_2$ (1.5 L), THF (1.5 L), THF:IPA (3:1, 1.5 L), THF:water (3:1, 1.5 L), THF:IPA (3:1, 1.5 L), and THF (1.5 L). The lanterns were then dried under reduced pressure. Loading level determination: 5 lanterns were each placed into 5 mL polypropylene containers. To each container was added THF (300 µL) and HF-pyridine (50 µL). The lanterns were allowed to sit in this solution for 6 h. At which point TMSOMe (500 µL) was added and the lanterns were allowed to sit in this solution for an additional 15 min The reaction solution was then transferred to a tared flask and concentrated in vacuo to afford isoxazolidine 67. This material was massed and the average loading level was calculated to 10 µmol/lantern.

Part B

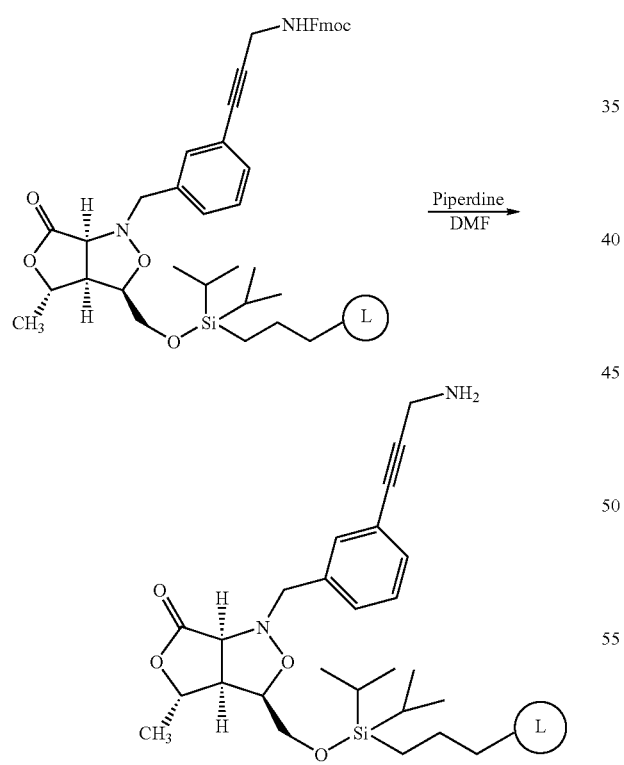

Fix as in above examples 9 lanterns (0.09 mmol, 1 eq) were suspended in a 20% solution of piperdine in DMF (9 mL). The reaction mixture was shaken for 1 h at which point the reaction solution was drained and additional piperdine in DMF (20% v/v, 9 mL) was added. The reaction mixture was shaken for 1 h. The lanterns were then removed and washed according to the following protocol: (2×10 min) CH$_2$Cl$_2$ (9 mL), THF (9 mL), THF:IPA (3:1, 9 mL), THF:water (3:1, 9 mL), THF:IPA (3:1, 9 mL), and THF (9 mL). Reaction conversion determination: 1 lantern was placed into a 5 mL polypropylene container and treated with THF (300 µL) and HF-pyridine (50 µL). The lantern was allowed to sit in this solution for 6 h. At which point TMSOMe (500 µL) was added and the lantern was allowed to sit in this solution for an additional 15 min The reaction solution was then transferred to a glass round-bottomed flask and concentrated in vacuo to afford the free amine.

Part C

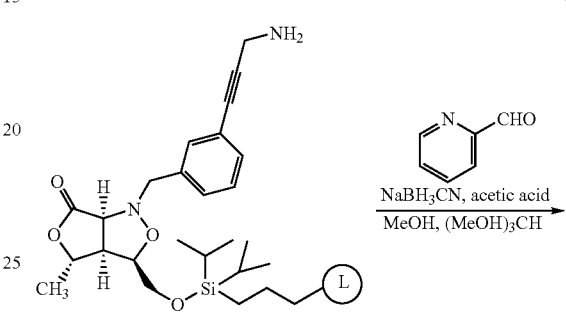

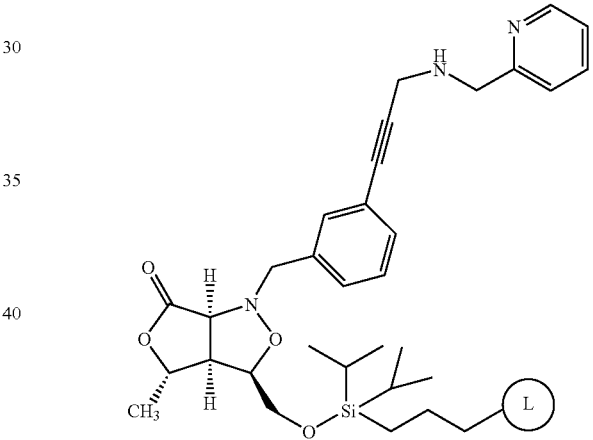

Fix as in examples above 4 lanterns (0.04 mmol, 1 eq) were placed in a glass vial. Pyridine-2-carboxaldehyde (0.08 g, 0.8 mmol, 20 eq) was added, followed by trimethylorthoformate (4 mL). The lanterns were allowed to sit in this solution for 45 min with gentle shaking. NaBH$_3$CN (0.13 g, 2.1 mmol, 30 eq), acetic acid (one drop) and MeOH (one drop) were added and the reaction mixture was shaken under a nitrogen atmosphere for 36 h. The lanterns were then removed and washed according to the following protocol: (2×10 min) CH$_2$Cl$_2$ (4 mL), THF (4 mL), THF:IPA (3:1, 4 mL), THF:water (3:1, 4 mL), THF:IPA (3:1, 4 mL), and THF (4 mL). Reaction conversion determination: 1 lantern was placed into a 5 mL polypropylene container and treated with THF (300 µL) and HF-pyridine (50 µL). The lantern was allowed to sit in this solution for 6 hs. At which point TMSOMe (500 µL) was added and the lantern was allowed to sit in this solution for an additional 15 min The reaction solution was then transferred to a glass round-bottomed flask and concentrated under reduced pressure to afford the desired product.

Part D

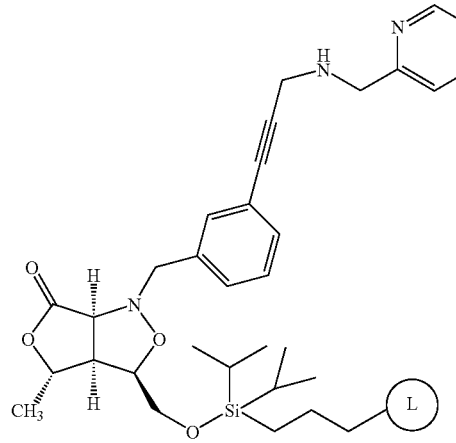

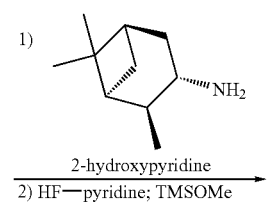

2-hydroxypyridine
2) HF—pyridine; TMSOMe

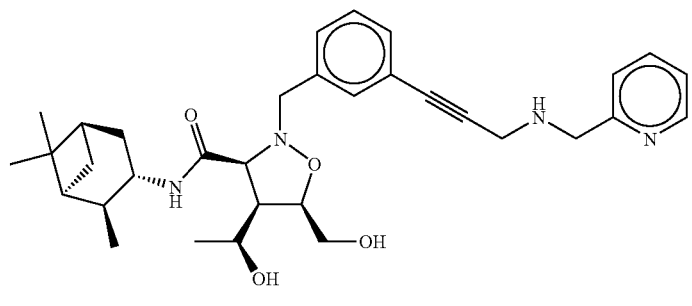

66

52 lanterns (0.52 mmol, 1 eq.) were placed in a pressure flask and flushed with nitrogen. To the flask were added 2-hydroxypyridine (30 mL of a 0.35 M solution in THF; 20 eq.) and (+)-isopinocampheylamine (5.57 g, 36.4 mmol, 70 eq.) The reaction mixture was shaken for 27 h at 50° C. under an atmosphere of nitrogen. At which point a lantern was removed and washed according to the following procedure: (2×10 min) $CH_2Cl_2$ (57 mL), THF (57 mL), THF:IPA (3:1, 57 mL), THF:water (3:1, 57 mL), THF:IPA (3:1, 57 mL), and THF (57 mL). Reaction conversion determination: 1 lantern was placed into a 5 mL polypropylene container and treated with THF (300 µL) and HF-pyridine (50 µL). The lantern was allowed to sit in this solution for 6 h. At which point TMSOMe (500 µL) was added and the lantern was allowed to sit in this solution for an additional 15 min The reaction solution was then transferred to a glass round-bottomed flask and concentrated under reduced pressure to afford the desired product. MS (ESI(+)) m/e 561.5 (M+H)$^+$.

Example 67

68

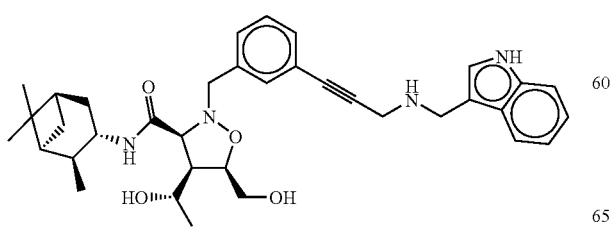

Compound 68 was synthesized according to the procedure described in example 66 using indole-3-carboxaldehyde in place of pyridine-2-carbaldehyde. MS (ESI(+)) m/e 599.0 (M+H)$^+$.

Example 68

69

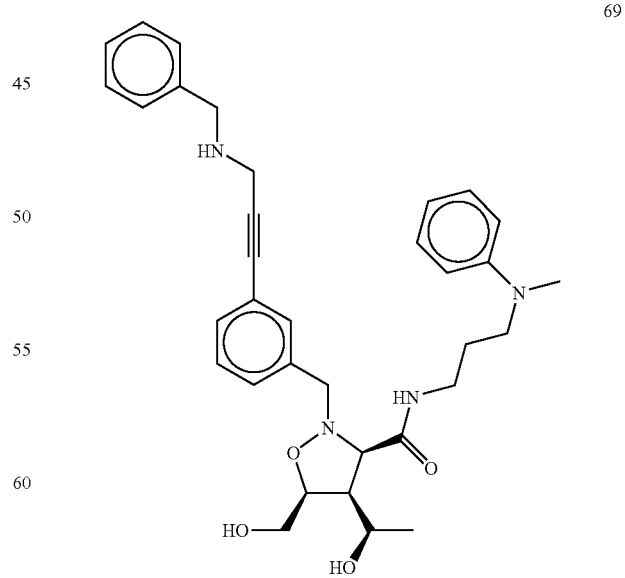

Compound 69 was synthesized according to the procedure described in example 66 using isoxazolidine core 18 in place of isoxazolidine core 15, and benzaldehyde in place of pyridine-2-carboxaldehyde and $N^1$-methyl-$N^1$-phenyl-propane-1,3-diaamine in place of (+)-isopinocampheylamine. MS (ESI(+)) m/e 607.0 (M+H)⁺.

Example 69

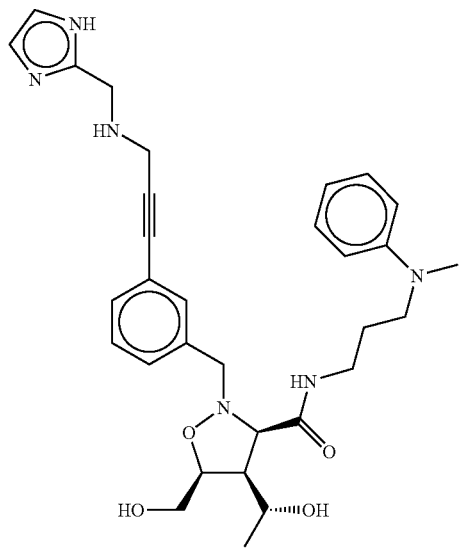

Compound 70 was synthesized according to the procedure described in Example 66 using isoxazolidine core 18 in place of isoxazolidine core 15, and imidazole-2-carbaldehyde in place of pyridine-2-carboxaldehyde and $N^1$-methyl-$N^1$-phe-nyl-propane-1,3-diamine in place of (+)-isopinocampheylamine. MS (ESI(+)) m/e 607.5 (M+H)⁺.

Example 70

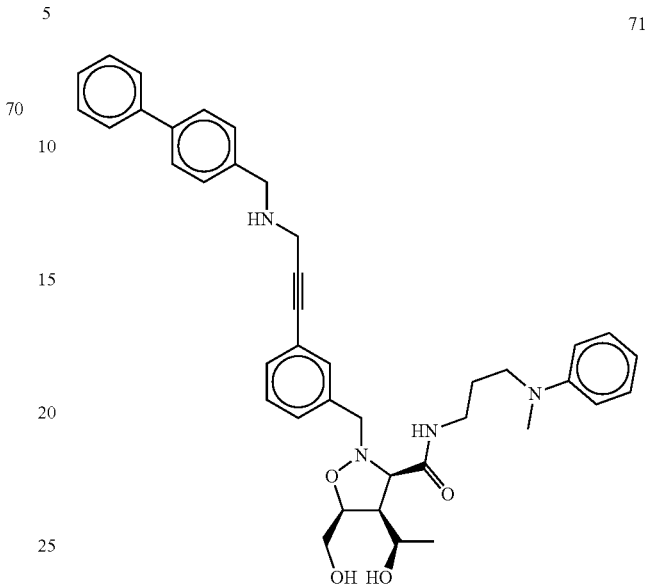

Compound 71 was synthesized according to the procedure described in Example 66 using isoxazolidine core 18 in place of isoxazolidine core 15, and 4-phenylbenzaldehyde in place of pyridine-2-carboxaldehyde and $N^1$-methyl-$N^1$-phenyl-propane-1,3-diamine in place of (+)-isopinocampheylamine. MS (ESI(+)) m/e 647.5 (M+H)⁺.

Example 71

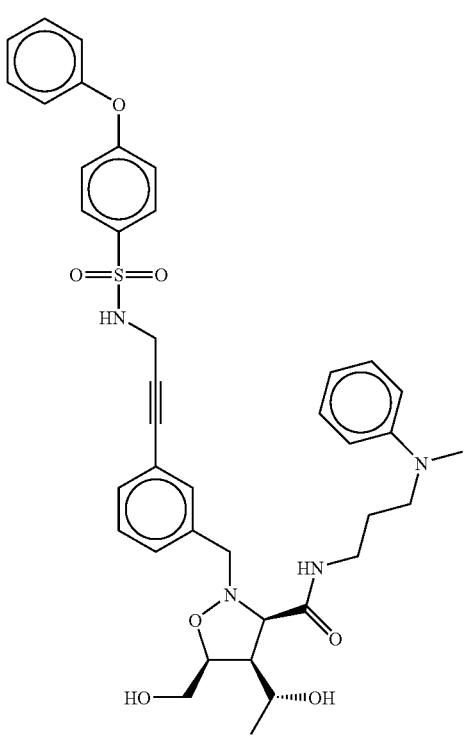

-continued

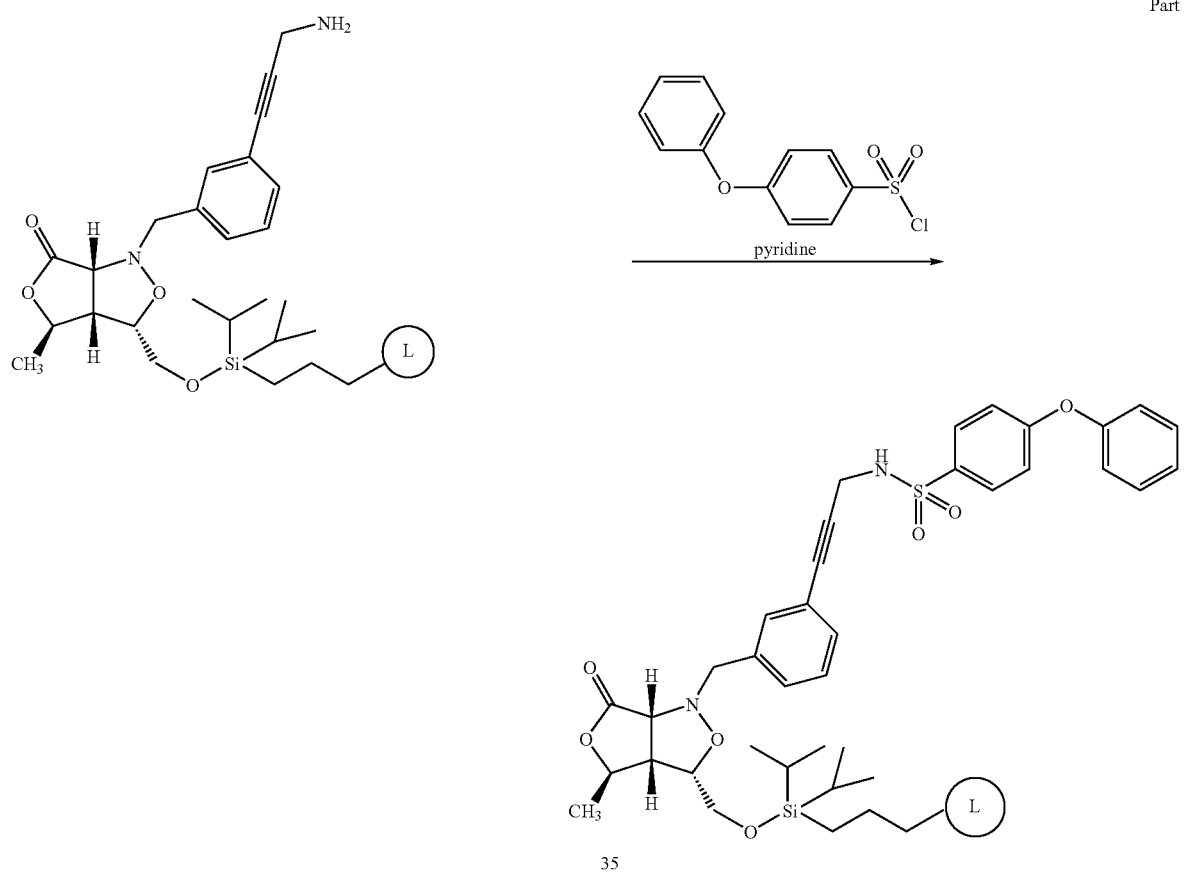

Part A

Fix as in examples abovel lantern was added to a glass vial followed by 4-phenoxybenzene sulfonyl chloride (0.22 g, 20 eq), CH$_2$Cl$_2$ (0.4 mL), and pyridine (18 µL, 20 eq). The reaction mixture was shaken gently for 5 days under nitrogen. At which point the lantern was removed and washed according to the following procedure: (2×10 min) CH$_2$Cl$_2$ (1 mL), THF (1 mL), THF:IPA (3:1, 1 mL), THF:water (3:1, 1 mL), THF:IPA (3:1, 1 mL), and THF (1 mL). Reaction conversion determination: 1 lantern was placed into a 5 mL polypropylene container and treated with THF (300 µL) and HF-pyridine (50 µL). The lantern was allowed to sit in this solution for 6 h. At which point TMSOMe (500 µL) was added and the lantern was allowed to sit in this solution for an additional 15 min The reaction solution was then transferred and concentrated under reduced pressure to afford the desired product.

Part B

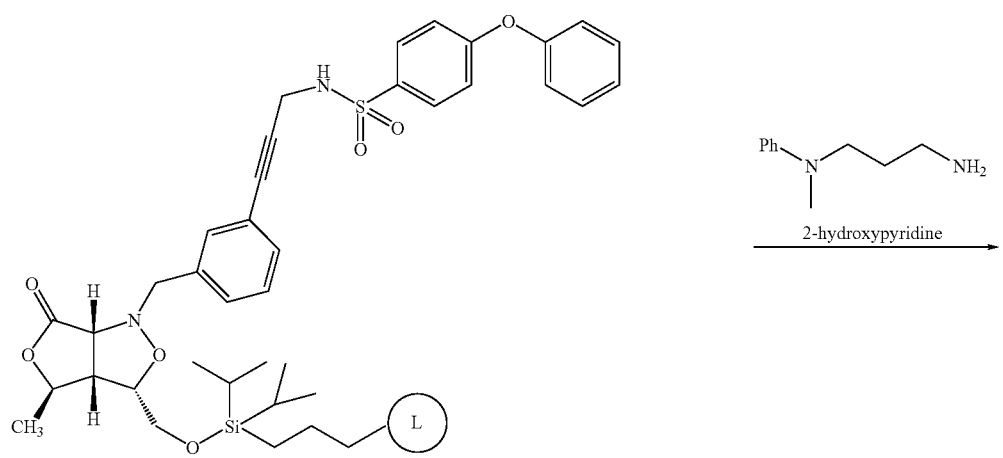

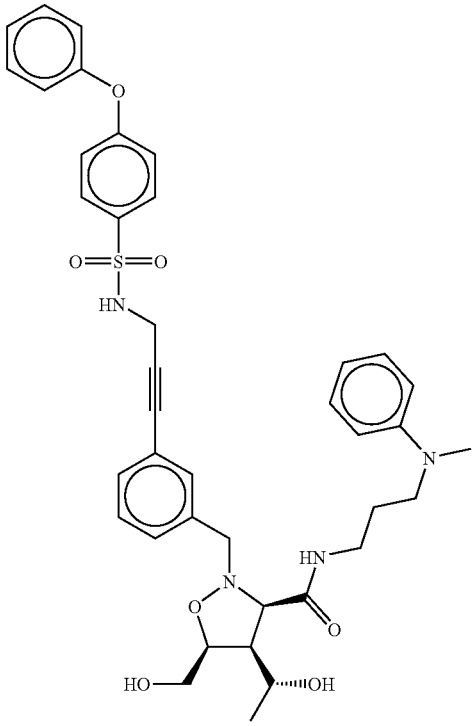

52 lanterns (0.52 mmol, 1 eq) were placed in a pressure flask and flushed with nitrogen. To the flask were added 2-hydroxypyridine (30 mL of a 0.35 M solution in THF; 20 eq.) and $N^1$-methyl-$N^1$-phenyl-propane-1,3-diamine (5.97 g, 36.4 mmol, 70 eq.) The reaction mixture was shaken for 27 h at 50° C. under an atmosphere of nitrogen. At which point a lantern was removed and washed according to the following procedure: (2×10 min) CH$_2$Cl$_2$ (57 mL), THF (57 mL), THF:IPA (3:1, 57 mL), THF:water (3:1, 57 mL), THF:EPA (3:1, 57 mL), and THF (57 mL). Reaction conversion determination: 1 lantern was placed into a 5 mL polypropylene container and treated with THF (300 µL) and HF-pyridine (50 µL). The lantern was allowed to sit in this solution for 6. At which point TMSOMe (500 µL) was added and the lantern was allowed to sit in this solution for an additional 15 min The reaction solution was then transferred to a glass round-bottomed flask and concentrated under reduced pressure to afford the desired product. MS (ESI(+)) m/e 713.3 (M+H)$^+$.

Example 72

Compound 73 was synthesized according to the procedure described in Example 71 using isoxazolidine core 15 in place of isoxazolidine core 18, (+)-isopinocampheylamine in place of $N^1$-methyl-$N^1$-phenyl-propane-1,3-diamine, and biphenyl-4-sulfonyl chloride in place of 4-phenoxybenzene sulfonyl chloride. MS (ESI(+)) m/e 686.5 (M+H)$^+$.

Example 73

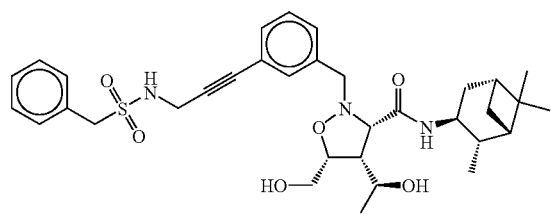

74

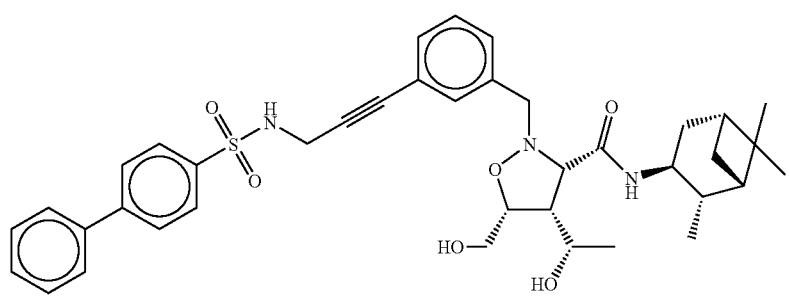

73

Compound 74 was synthesized according to the procedure described in Example 71 using isoxazolidine core 15 in place of isoxazolidine core 18, (+)-isopinocampheylamine in place of N¹-methyl-N¹-phenyl-propane-1,3-diaamine, and phenyl-methanesulfonyl chloride in place of 4-phenoxybenzene sulfonyl chloride. MS (ESI(+)) m/e 624.5 (M+H)⁺.

Example 74

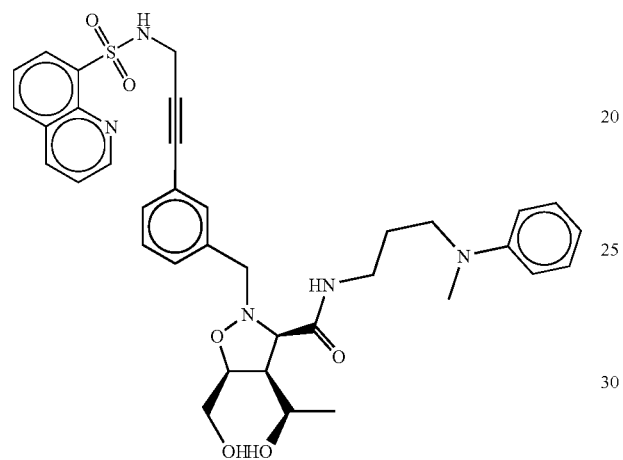

75

Compound 75 was synthesized according to the procedure described in Example 71 using quinoline-8-sulfonyl chloride in place of 4-phenoxybenzene sulfonyl chloride. MS (ESI(+)) m/e 672.5 (M+H)⁺.

Example 75

76

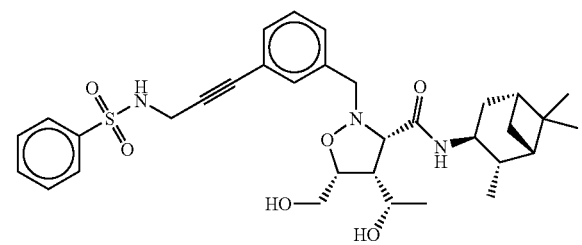

Compound 76 was synthesized according to the procedure described in Example 71, using isoxazolidine core 15 in place of isoxazolidine core 18, (+)-isopinocampheylamine in place of N¹-methyl-N¹-phenyl-propane-1,3-diamine, and phenyl-sulfonyl chloride in place of 4-phenoxybenzene sulfonyl chloride. MS (ESI(+)) m/e 610.5 (M+H)⁺.

Example 76

77

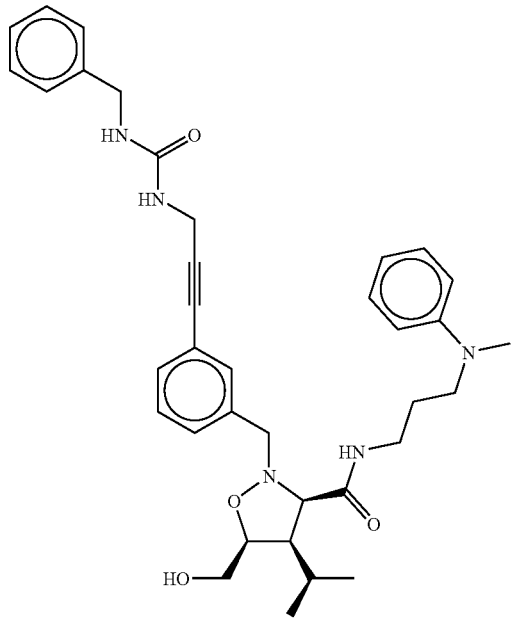

Part A

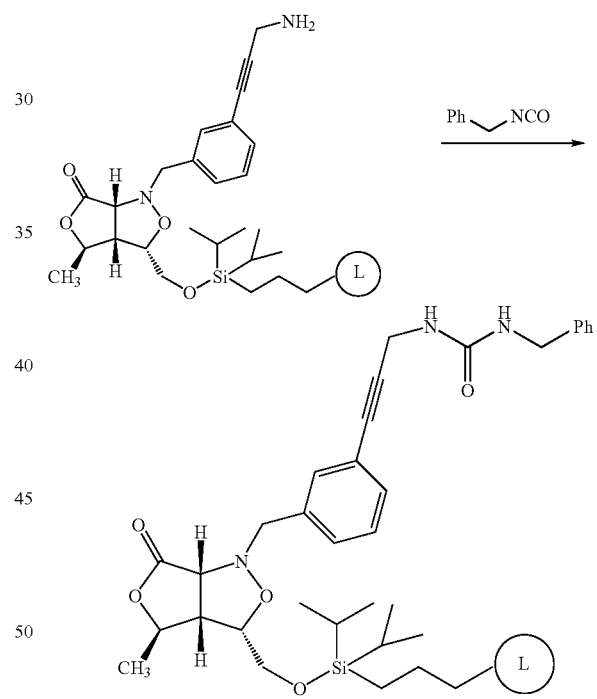

1 lantern was added to a glass vial followed by isocyanatomethyl-benzene (26 mg, 10 eq) and CH₂Cl₂ (0.8 mL). The reaction mixture was shaken gently for 24 h. At which point the lantern was removed and washed according to the following procedure: (2×10 min) CH₂Cl₂ (1 mL), THF (1 mL), THF:IPA (3:1, 1 mL), THF:water (3:1, 1 mL), THF:IPA (3:1, 1 mL), and THF (1 mL). Reaction conversion determination: 1 lantern was placed into a 5 mL polypropylene container and treated with THF (300 µL) and HF-pyridine (50 µL). The lantern was allowed to sit in this solution for 6 h. At which point TMSOMe (500 µL) was added and the lantern was allowed to sit in this solution for an additional 15 min The reaction solution was then transferred to a glass round-bottomed flask and concentrated under reduced pressure to afford the desired product.

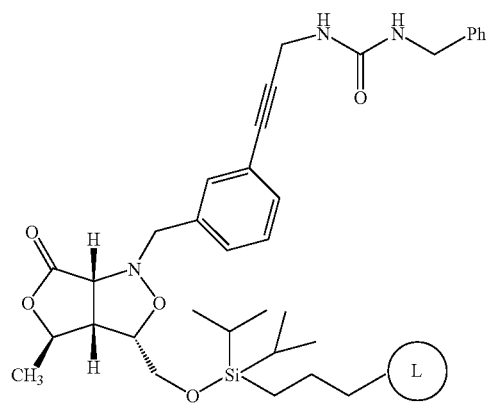
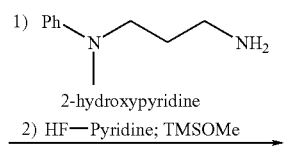

2-hydroxypyridine
2) HF—Pyridine; TMSOMe

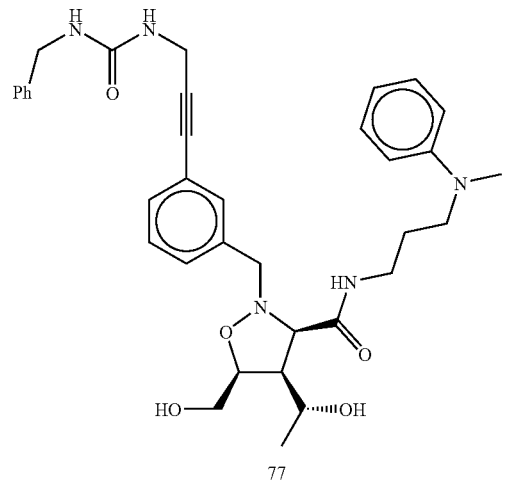

77

Fix as in examples above52 lanterns (0.52 mmol, 1 eq.) were placed in a pressure flask and flushed with nitrogen. To the flask were added 2-hydroxypyridine (0.35 M in THF; 30 mL, 20 eq.) and $N^1$-methyl-$N^1$-phenyl-propane-1,3-diamine (5.97 g, 36.4 mmol, 70 eq.) The reaction mixture was shaken for 27 hs at 50° C. under an atmosphere of nitrogen. At which point a lantern was removed and washed according to the following procedure: (2×10 min) $CH_2Cl_2$ (57 mL), THF (57 mL), THF:IPA (3:1, 57 mL), THF:water (3:1, 57 mL), THF:IPA (3:1, 57 mL), and THF (57 mL). Reaction conversion determination: 1 lantern was placed into a 5 mL polypropylene container and treated with THF (300 µL) and HF-pyridine (50 µL). The lantern was allowed to sit in this solution for 6 hs. At which point TMSOMe (500 µL) was added and the lantern was allowed to sit in this solution for an additional 15 min The reaction solution was then transferred and concentrated under reduced pressure to afford the desired product. MS (ESI(+)) m/e 614.5 (M+H)$^+$.

Example 77

78

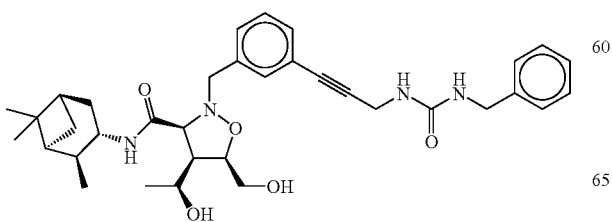

Part B

Compound 78 was synthesized according to the procedure described in example 76, using isoxazolidine core 18 in place of isoxazolidine core 15, (+)-isopinocampheylamine in place of $N^1$-methyl-$N^1$-phenyl-propane-1,3-diamine, and isocyanatomethyl-benzene. MS (ESI(+)) m/e 603.5 (M+H)$^+$.

Example 78

79

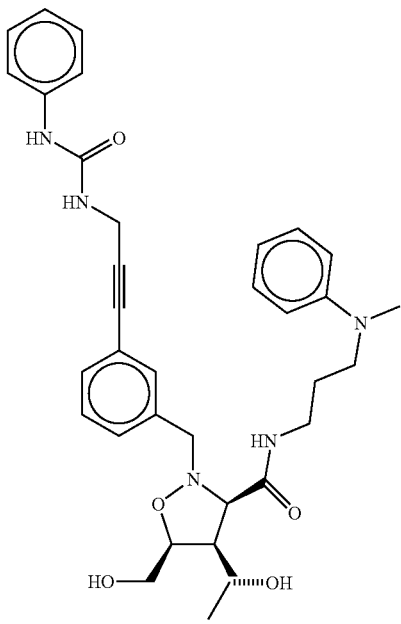

Compound 79 was synthesized according to the procedure described in example 76, using phenyl isocyanate in place of isocyanatomethyl-benzene. MS (ESI(+)) m/e 600.5 (M+H)+.

Example 79

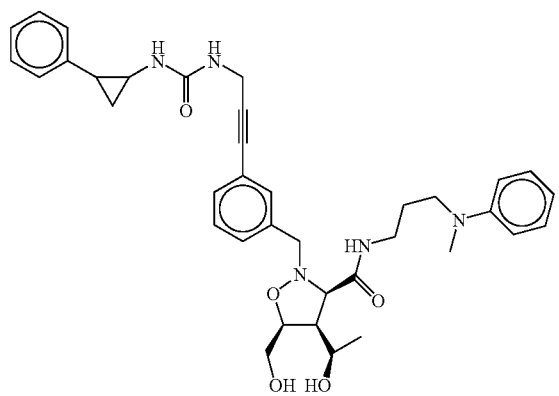

80

Compound 80 was synthesized according to the procedure described in Example 76, using 1-isocyanato-2-phenyl-cyclopropane in place of isocyanatomethyl-benzene. MS (ESI(+)) m/e 640.5 (M+H)+.

Example 80

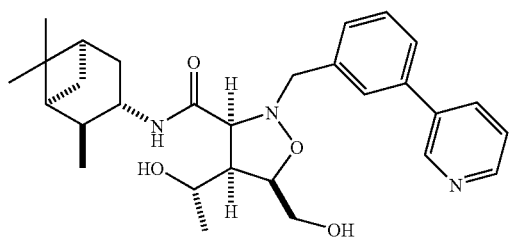

81

Part A

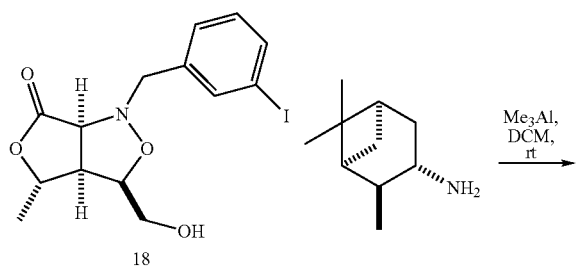

-continued

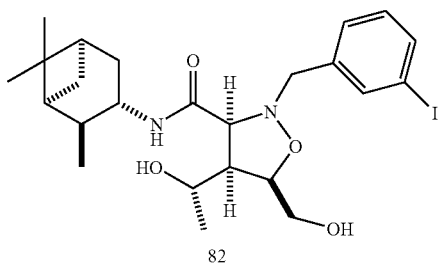

82

To a solution of (+) isopinocampheylamine (0.2 g, 1.3 mmol) in CH$_2$Cl$_2$ (10 mL) at rt was added AlMe$_3$ (0.85 mL of a 2 M solution in toluene, 1.7 mmol) dropwise over 2.5 min The solution was stirred at rt for 10 min prior to the dropwise addition of a solution of lactone 18 (0.5 g, 0.02 mmol) in CH$_2$Cl$_2$ (10 mL). The reaction was stirred for 1 h, diluted with CH$_2$Cl$_2$ (125 mL) and a saturated aqueous solution of Rochell salt (125 mL). The mixture was vigorously stirred for 2 h until the two phases formed. The layers were separated and the organic phase was washed with water, brine, dried (MgSO$_4$), filtered and concentrated in vacuo to afford a solid. T his material was used in the following step without purification. Crude yield: 0.7 g (100%).

Part B

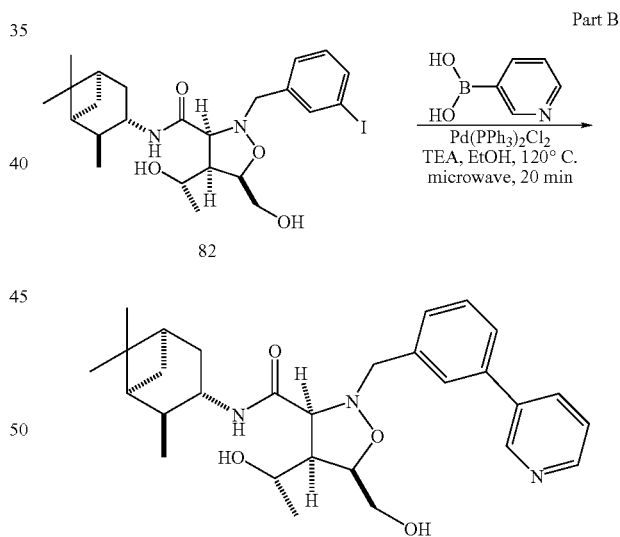

Isoxazolidine 82 (30 mg, 0.06 mmol), 3-pyridylboronic acid (7 mg, 0.06 mmol), Pd(PPh$_3$)$_2$Cl$_2$ (39 mg, 0.06 mmol), Et$_3$N (17 mg, 0.18 mmol), and EtOH (0.5 mL) were combined at rt. This mixture was then heated to 120° C. using a microwave for 30 min The reaction mixture was concentrated in vacuo and resulting residue was purified by flash chromatography to give 81 (10 mg, 30%) as a pale-yellow oil. MS (ESI(+)) m/e 494.3 (M+H)+.

Example 81

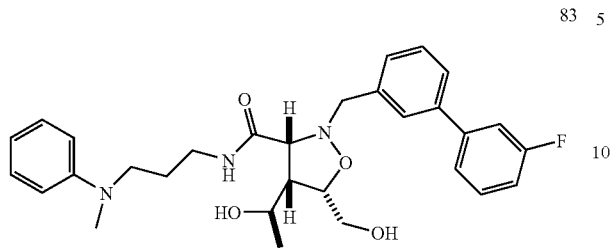

83

Compound 83 was synthesized according to the procedure described in Example 80, using isoxazolidine core 15 in place of isoxazolidine core 18, $N^1$-methyl-$N^1$-phenyl-propane-1,3-diamine in place of (+)-isopinocampheylamine, and 3-flurorophenyl boronic acid. 25% overall yield. MS (ESI(+)) m/e 522.3 (M+H)$^+$.

Example 82

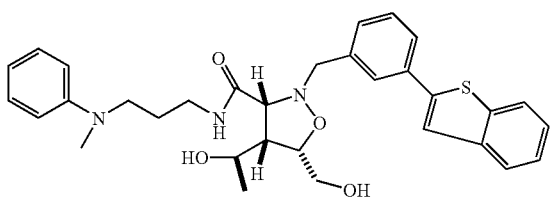

84

Compound 84 was synthesized according to the procedure described in Example 80, using isoxazolidine core 15 in place of isoxazolidine core 18, $N^1$-methyl-$N^1$-phenyl-propane-1,3-diamine in place of (+)-isopinocampheylamine, and benzothiophenyl-2-boronic acid. 17% overall yield.

Example 83

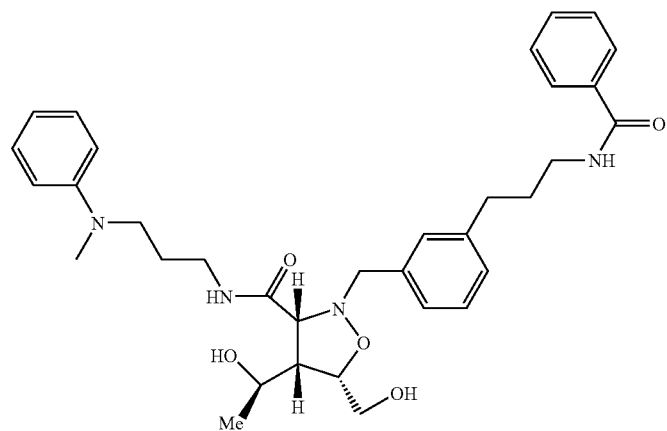

85

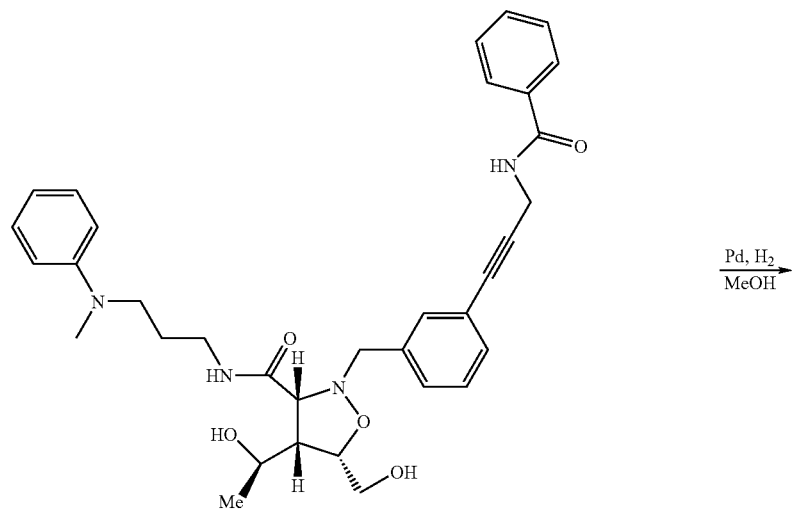

56

Pd, H$_2$ / MeOH →

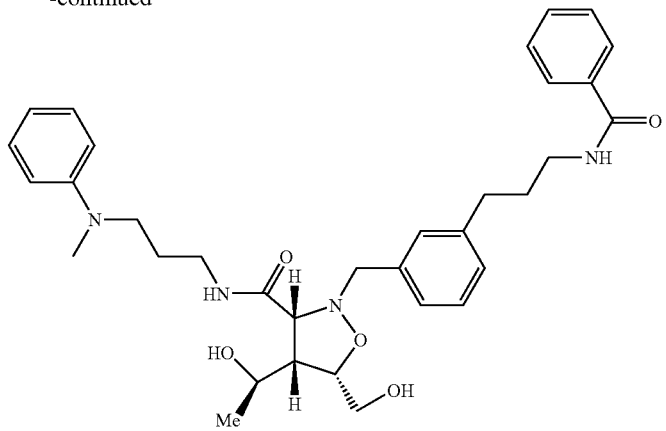
85
Isoxazolidine 56 (20 mg, 0.05 mmol) was dissolved in MeOH (10 mL) and placed under an atomsphere of hydrogen in the presence of Pd on carbon 5 wt % (11 mg, 0.095 mmol) for 12 h, the solution was filtered through celite and concentrated in vacuo to afford an oil. The oil was subjected to preparative plate chromatography (CH$_2$Cl$_2$-MeOH, 9:1) to afford 85 (18 mg, 62%) as a clear oil. MS (ESI(+)) m/e 589.3 (M+H)$^+$.
Example 84
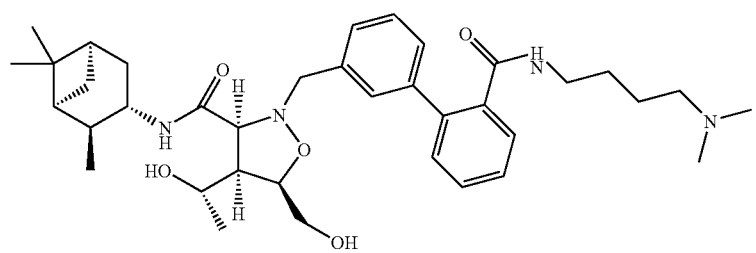
86
Part A
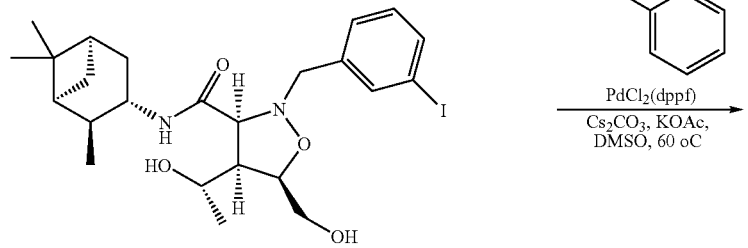 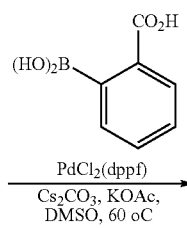
82
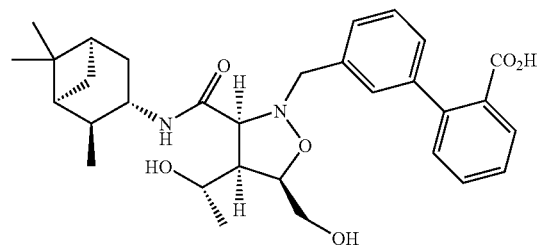
87

To a flask was added 82 (0.33 g, 0.6 mmol ), 2-carboxyphenyl-boronic acid (0.2 g, 1.2 mmol), Cs$_2$CO$_3$ (0.62 g, 1.9 mmol), KOAc (60 mg, 0.6 mmol 1.0 eq.), and PdCl$_2$(dppf) (34.2 mg, 4.2 mol %). The flask was purged with argon and degassed DMSO (30 min with argon, 10 mL) was added and heated to 60° C. under atmosphere of argon. After 5.5 h, another portion of PdCl$_2$(dppf) (34 mg, 4.1 mol %) was added and heating was continued for 12 h, the reaction was judged to be complete by LCMS and TLC analysis (30/70/0.5 Hexane/EtOAc/AcOH, Rf=0.38). The reaction mixture was diluted with CH$_2$Cl$_2$/water (2:1, 45 mL) and acidified to a pH 2 with 6 M HCl (0.5 mL). The aqueous layer was separated and extracted with CH$_2$Cl$_2$ (3×10 mL). The combined organics were washed with water (15 mL) and brine (15 mL), dried (Na$_2$SO$_4$), filtered, and concentrated in vacuo to afford an oil. The oil was purified chromatographed (silica gel, load 75/25, elute 50/50/0.5, 25/75/0.5 (2×), 0/100/0.5 Hexane/EtOAc/AcOH 200 mL) to afford 87 (265 mg, 80%) as an orange-tinted amorphous solid.

Part B

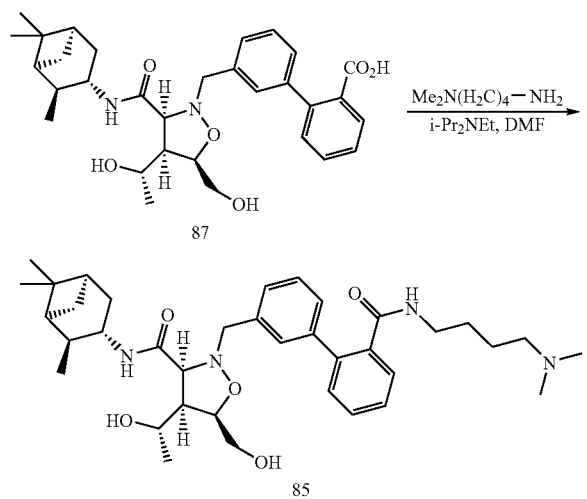

To a DMF solution (0.7 mL) of 87 (15 mg, 0.03 mmol) was added the amine (13 mg, 0.12 mmol), diisopropylethylamine (15 mg, 20 µL, 0.12 mmol) and HBTU (23 mg, 0.06 mmol,). The reaction was stirred at ambient temperature. After 90 min, additional portions of amine (6 mg, 0.03 mmol,), HBTU (11 mg, 0.03 mmol) and diisopropylethylamine (7 mg, 10 µL) were added. After 2 h, the reaction was diluted with MeOH (0.7 mL), and purified by HPLC to afford 85 (10 mg, 52%). MS (ESI(+)) m/e 635.4 (M+H)$^+$.

Example 85

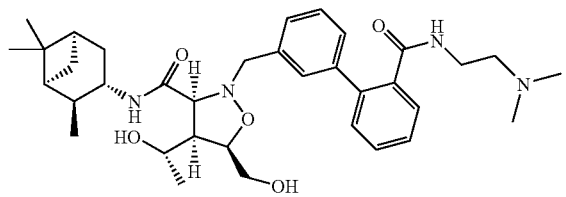

Compound 88 was synthesized according to the procedure described in Example 84, using N,N-dimethyl ethyl amine in place of N,N-dimethyl butylamine 40-70% overall yield. MS (ESI(+)) m/e 635.4 (M+H)$^+$.

Example 86

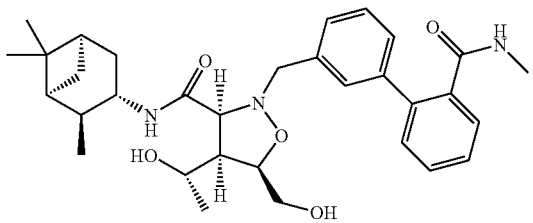

Compound 89 was synthesized according to the procedure described in Example 84, using methylamine in place of N,N-dimethyl butylamine 40-70% overall yield. MS (ESI(+)) m/e 550.2 (M+H)$^+$.

Example 87

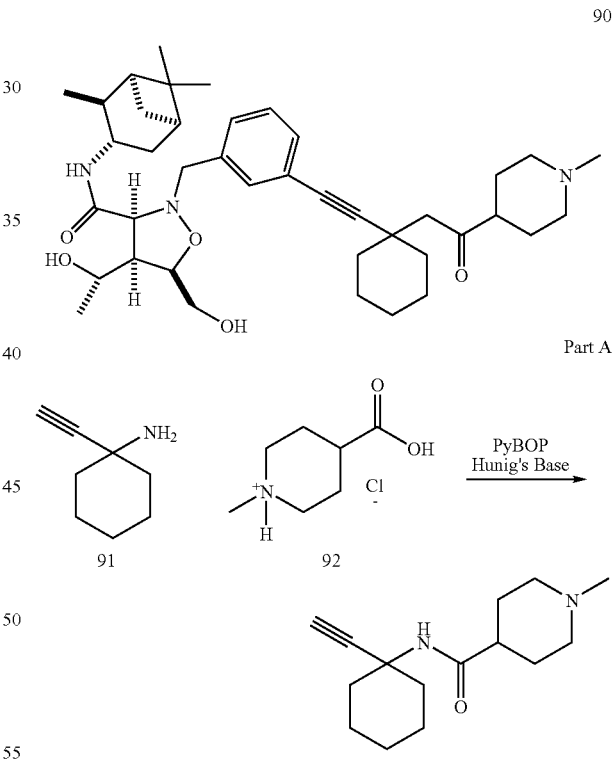

Part A

To a solution of 91 (0.5 g, 4.1 mmol) in DMF (37 mL) was added diisopropylethylamine (2.54 mL, 14.6 mmol) 92 (0.5 g, 4.1 mmol) and PyBOP (2.53 g, 4.87 mmol). The mixture was stirred at rt for 17 h, TLC (MeOH) showed two major components. The reaction solution was diluted with water and the aqueous layer was extracted with EtOAc. The organic extracts were combined, dried (MgSO$_4$), filtered and concentratetd in vacuo to afford an oil. The crude was purified by flash column chromatography to afford 93 (0.9 g, 90%).

Part B

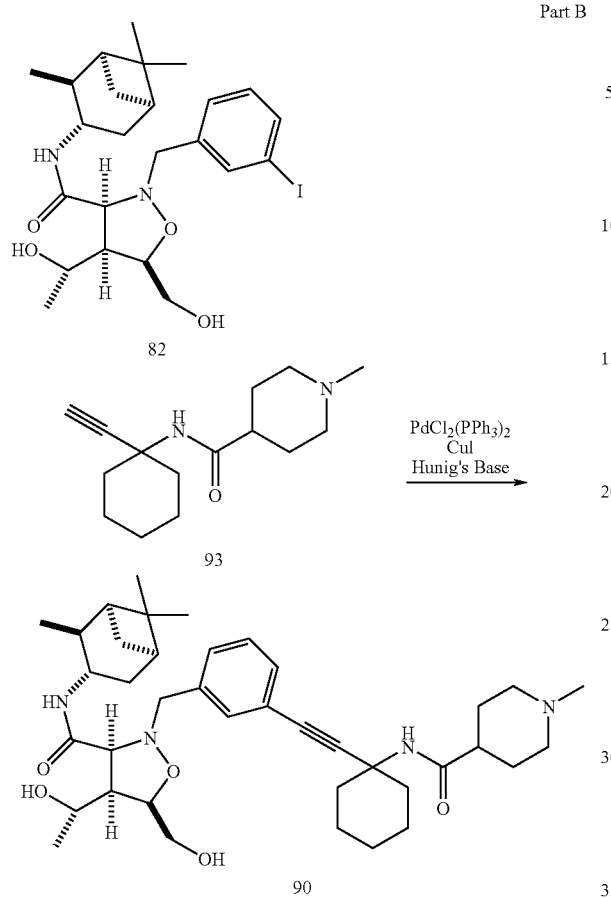

To a mixture of 82 (70 mg, 0.1 mmol), CuI (8 mg, 0.04 mmol), Pd(PPh$_3$)$_2$Cl$_2$ (22 mg, 0.03 mmol) in DMF (3 mL) was added 93 (50 mg, 0.21 mmol) followed by diisopropylethylamine (40 mg, 54.8 µL, 0.32 mmol). The resulting dark brown mixture was stirred at ambient temperature in the dark for 2 days. The reaction was diluted with EtOAc/water (6 mL, 1:1) and the solution was neutralized to a pH 7 using 1 M HCl. The aqueous phase was separated and extracted with EtOAc (2×4 mL). The organic extracts were combined, dried (Na$_2$SO4), filtered and concentrated in vacuo to afford an oil. The crude material was purified column chromatography to afford 90 (48 mg, 70%). MS (ESI(+)) m/e 663.5 (M+H)$^+$.

Example 88

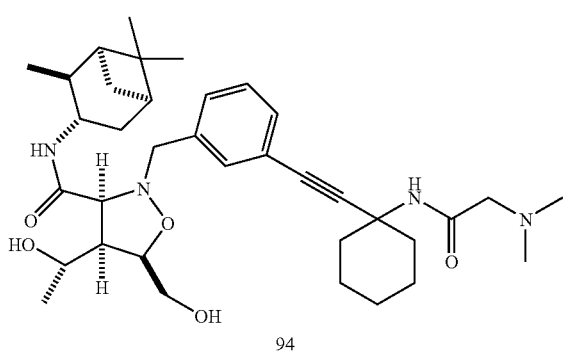

-continued

Part A

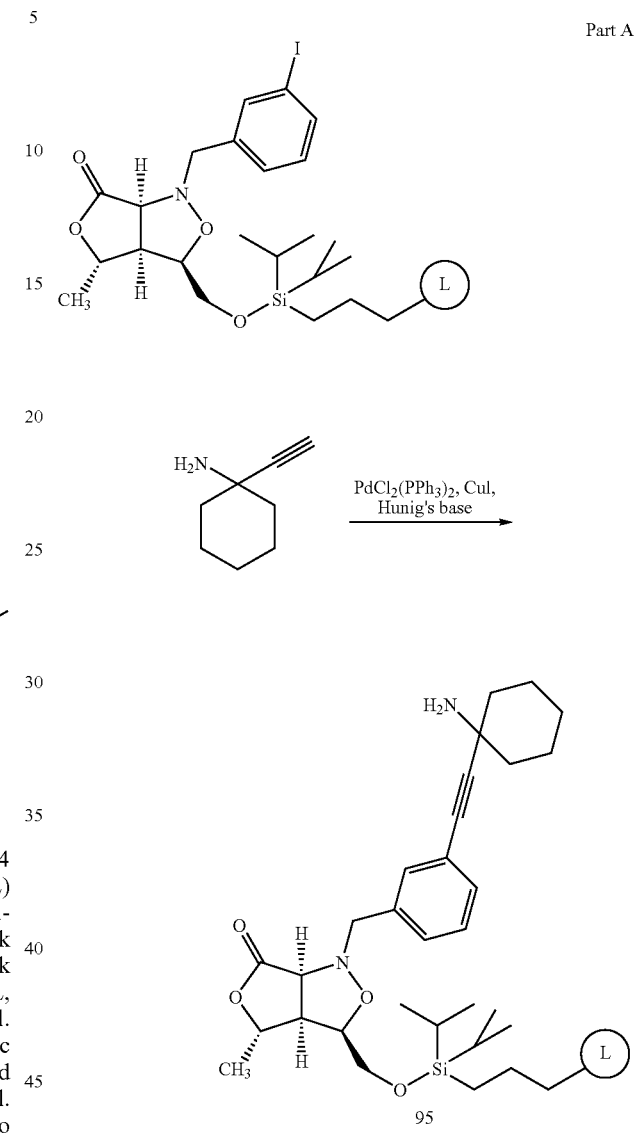

110 lanterns containing the isoxazolidine core (loading 12 µmol/lantern) were placed in a reaction vessel and flushed with nitrogen. To the reaction vessel was added DMF (77 mL) Pd(PPh$_3$)$_2$Cl$_2$ (1.9 g, 2.6 mmol, 2 eq), CuI (0.75 g, 4 mmol, 3 eq), 1-ethynylcyclohexylamine (3.7 g, 3.9 mL, 29 mmol) and diisopropylethylamine (5 g, 6 mL, 40 mmol, 30 eq). The reaction vessel was then flushed with nitrogen, capped and shaken gently for 48 h. At which point the lanterns were removed from the reaction mixture and washed according to the following procedure: wash with CH$_2$Cl$_2$ (2×100 mL), THF (2×100 mL), THF/IPA (2×100 mL, 3:1), DMF (2×100 mL), THF (2×100 mL), CH$_2$Cl$_2$ (2×100 mL). The lanterns were dried under reduced pressure.

Part B

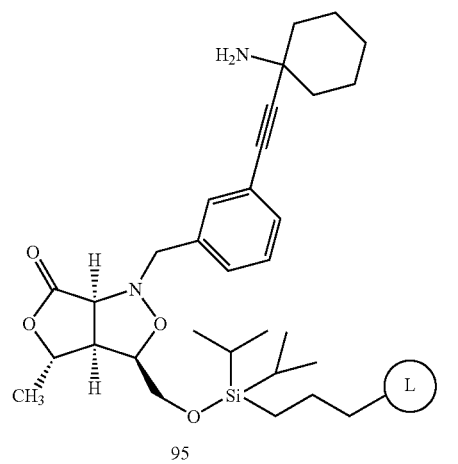
95

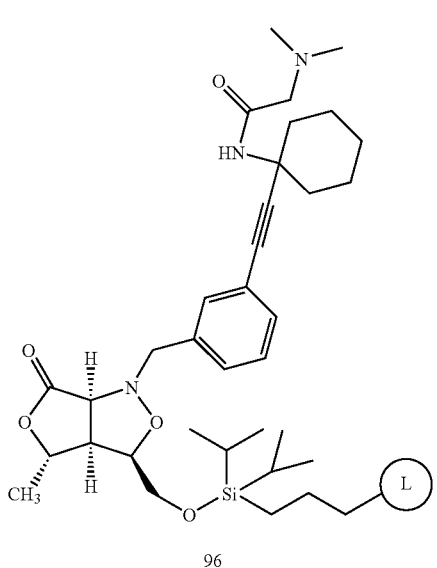
96

To 95 (5 Lanterns) in a solution of THF/DMF(1:1, 3 mL) in a vail was added HATU (76 mg, 2 mmol), pyridine (162 µL, 2 mmol), N,N-dimethyl glycine (0.2 g, 20 mmol) and diisopropylethylamine (0.5 g, 0.7 mL, 4 mmol). The mixture was stirred at rt for 3 days. At which point the lanterns were removed and washed according to the following procedure: wash with CH$_2$Cl$_2$ (2×100 mL), THF (2×100 mL), THF/IPA (3:1, 2×100 µL), DMF (2×100 THF (2×100 mL), CH$_2$Cl$_2$ (2×100 mL). The lanterns were dried under reduced pressure.

Part C

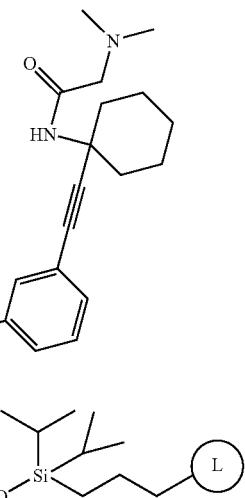
96

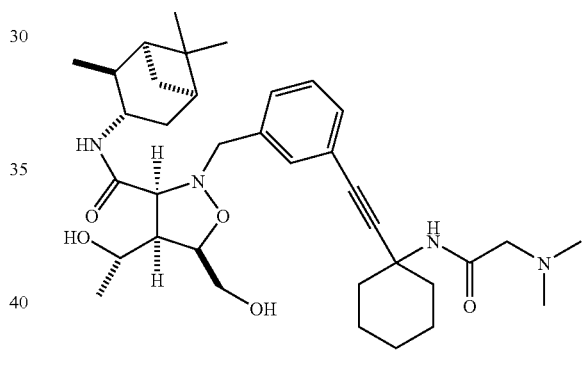
94

To a solution of (+)-isopinocampheylamine (1 g, 1.1 mL, 80 eq.,) in CH$_2$Cl$_2$ (4 mL) was added AlMe$_3$ (0.4 mL of a 2.0 M solution in hexane, 0.8 mmol, 10 eq) and stirred for 15 min To the flask was added 4 L anterns containing compound 96 and shaken gently at rt for 24 h. At which point the lanterns were removed from the reaction solution and washed according to the following protocol: wash with CH$_2$Cl$_2$ (2×100 mL), THF (2×100 mL), THF/IPA (3:1, 2×100 mL), DMF (2×100 mL), THF (2×100 mL), CH$_2$Cl$_2$ (2×100 mL). The lanterns were dried under reduced pressure. The lanterns were then placed in a plastic tube and treated with THF (1.5 mL) and HF/pyridine (0.25 mL) was added and the lanterns were allowed to sit in this solution with gentle shaking for 30 min At which point, TMSOMe (0.5 mL) was added and the resulting mixture was shaken for 30 min The solution was collected and evaporated to yield the product, MS (ESI(+)) m/e 623.4 (M+H)$^+$.

Example 89

Example 90

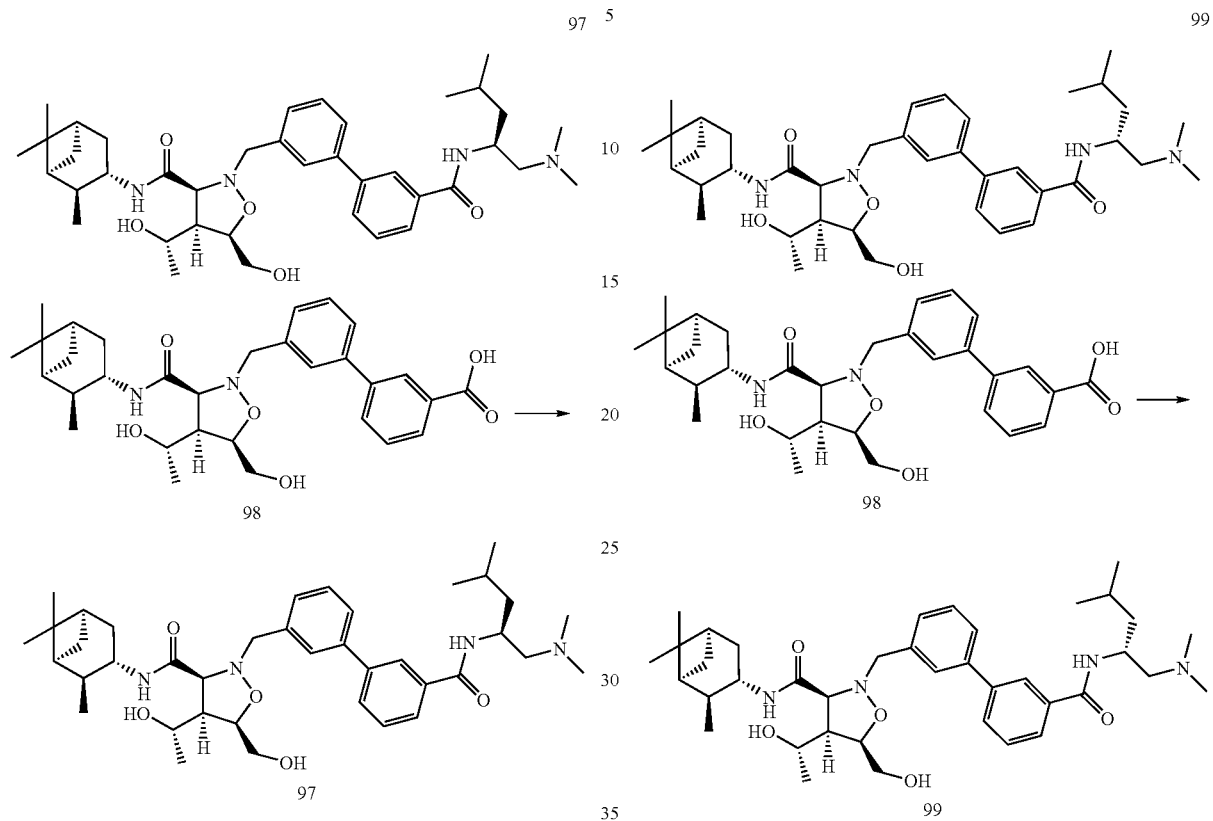

A solution of (S)-Boc-Leu-OH monohydrate (1 g, 4.1 mmol), DMF (5 mL), and N,N dimethylamine (4.1 mL of a 2.0 M solution in THF, 8.6 mmol) was treated with HBTU (2 g, 5.2 mmol) and stirred at ambient temperature overnight. The reaction mixture was added to saturated NaHCO$_3$ (25 mL) and water (25 mL). The layers were separated and the aqueous layer was extracted with Et$_2$O (3×40 mL). The combined organic extracts, along with the white insoluble material, were stripped of solvent and treated with TFA (10 mL) for 3 h, at which point the TFA was evaporated in vacuo. The residue was co-evaporated with toluene, dissolved in THF (50 mL), treated with LiAlH$_4$ (1.6 g, 42 mmol), and the suspension held at reflux overnight. The reaction mixture was cooled in an ice bath and treated with IPA (10 mL) and 6M NaOH (5 mL); after stirring for 2 h, the suspension was filtered and concentrated in vacuo. The resisdue was suspended in brine (50 mL) and extracted with CH$_2$Cl$_2$ (3×15 mL). The combined organic extracts were dried (MgSO$_4$), filtered and concentrated in vacuo to afford (2S)-1-dimethylamino-2-amino-4-methyl-pentane which was used without further purification.

A solution of this crude amine (25 mg, 0.17 mmol) and crude 98 (25 mg, 0.05 mmol) in DMF (0.7 mL) was treated with HBTU (40 mg, 0.1 mmol). After shaking for 1 h, the reaction mixture was diluted with MeOH (0.8 mL) and purified by HPLC. Concentration of the appropriate fractions gave a 97 (20 mg, 25%) as a white solid. MS (ESI(+)) m/e 663.5 (M+H)$^+$.

A solution of (R)-Boc-D-Leu-OH (1 g, 4.1 mmol), DMF (5 mL), and dimethylamine (4.3 mL of a 2M solution in THF, 8.6 mmol) was treated with HBTU (2 g, 5.2 mmol) and stirred at ambient temperature overnight. The reaction mixture was added to saturated NaHCO$_3$ (25 mL) and water (25 mL). The layers were separated and the aqueous layer was extracted with Et$_2$O (3×40 mL). The combined organic extracts along with the white insoluble material, were stripped of solvent and treated with TFA (10 mL) during 3 h, at which point the TFA was evaporated in vacuo. The residue was coevaporated with toluene, dissolved in THF (50 mL), treated with LiAlH$_4$ (1.6 g, 42 mmol), and the suspension held at reflux overnight. The reaction mixture was cooled in an ice bath and treated successively with IPA (10 mL) and 6M NaOH (5 mL); after stirring for 2 h, the suspension was filtered, concentrated in vacuo. The residue was suspended in brine (50 mL) and extracted with CH$_2$Cl$_2$ (3×15 mL). The combined organic extracts were dried (MgSO$_4$), filtered and concentration in vacuo to afford an oil of (2R)-1-dimethylamino-2-amino-4-methyl-pentane which was used without further purification.

A solution of this crude amine (25 mg, 0.17 mmol) and crude 98 (25 mg, 0.04 mmol) in DMF (0.7 mL) was treated with HBTU (40 mg, 0.1 mmol). After shaking for 1 h, the reaction mixture was diluted with MeOH (0.8 mL) and purified by HPLC. Concentration of the appropriate fractions gave a 99 (18 mg, 23%) as a white solid. MS (ESI(+)) m/e 663.5 (M+H)$^+$.

Example 91

Example 94

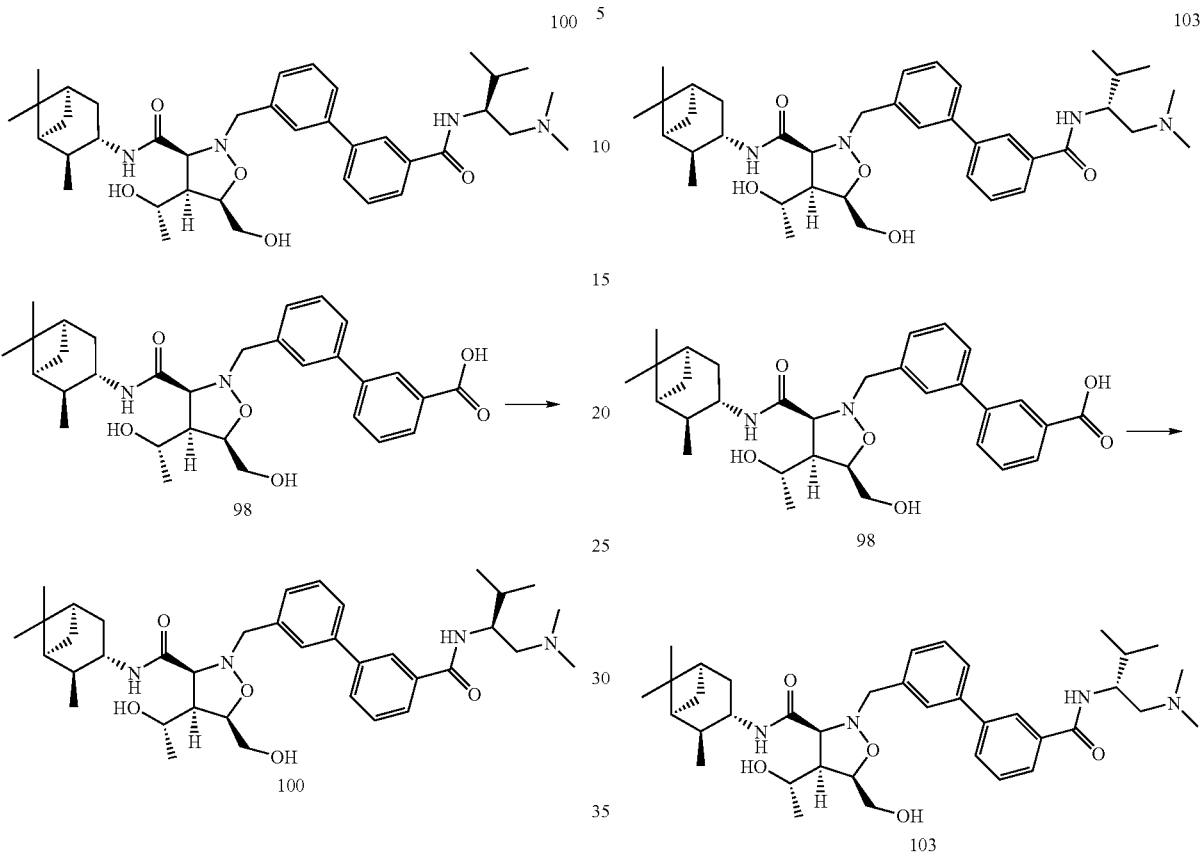

A solution of (S)-Boc-Val-OH (1 g, 4.1 mmol), DMF (5 mL), and dimethylamine (4.3 ml of a 2 M solution in THF, 8.6 mmol) was treated with HBTU (2 g, 5.3 mmol) and stirred at ambient temperature overnight. The reaction mixture was added to saturated $NaHCO_3$ (25 mL) and water (25 mL). The layers were separated and the aqueous layer was extracted with $Et_2O$ (3×40 μL). The combined organics, along with the white insoluble material, were stripped of solvent and treated with TFA (10 mL) during 3 h, at which point the TFA was evaporated in vacuo. The residue was coevaporated with toluene, dissolved in THF (50 mL), treated with $LiAlH_4$ (1.6 g, 42 mmol), and the suspension held at reflux overnight. The reaction mixture was cooled in an ice bath and treated successively with IPA (10 mL) and 6M NaOH (5 mL); after stirring for 2 h, the suspension was filtered, concentrated in vacuo. The residue was suspended in brine (50 mL) and extracted with $CH_2Cl_2$ (3×15 mL), The combined organic extracts were dried ($MgSO_4$), filtered and concentration in vacuo to afford a yellow oil of (2S)-1-dimethylamino-2-amino-3-methyl-butane which was used without further purification.

A solution of crude amine (22 mg, 0.17 mmol) and crude 98 (25 mg, 0.04 mmol) in DMF (0.7 mL) was treated with HBTU (40 mg, 0.1 mmol). After shaking for 1 h, the reaction mixture was diluted with MeOH (0.8 mL) and purified by HPLC. Concentration of the appropriate fractions gave a 100 (20 mg, 26%) as a white solid. MS (ESI(+)) m/e 649.4 $(M+H)^+$.

A solution of Boc-D-Val-OH (940 mg), DMF (5 mL), and 2.0 M dimethylamine in THF (4.3 mL) was treated with HBTU (2.0 g) and stirred at ambient temperature overnight. The reaction mixture was added to saturated NaHCO3 (25 mL) and water (25 mL), then extracted 3×40 mL Et2O. The combined organics, along with the white insoluble material, were stripped of solvent and treated with TFA (10 mL) during 3 h, at which point the TFA was evaporated in vacuo. The residue was coevaporated with toluene, dissolved in THF (50 mL), treated with $LiAlH_4$ (1.6 g), and the suspension held at reflux overnight. The reaction mixture was cooled in an ice bath and treated successively with IPA (10 mL) and 6M NaOH (5 mL); after stirring for 2h, the suspension was filtered, concentrated, and brine (50 mL) added. Extraction with DCM (3×15 mL), drying of the combined organics on MgSO4, and concentration gave a foμL-smelling yellow oil of (2R)-1-dimethylamino-2-amino-3-methyl-butane which was used without further purification.

A solution of this crude amine (22 μL) and crude 98 (25 mg) in DMF (700 μL) was treated with HBTU (40 mg). After shaking for 1 h, the reaction mixture was diluted with MeOH (800 μL) and purified by HPLC. Concentration of the appropriate fractions gave 103 as a white solid, 20 mg. MS (ESI(+)) m/e 649.4 $(M+H)^+$.

Example 95
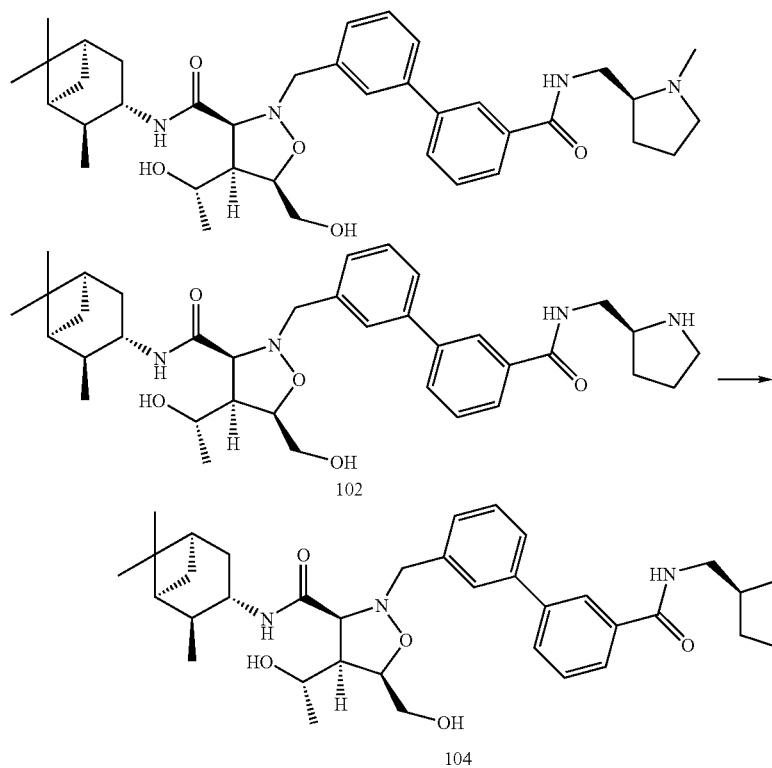
To a vial containing crude 102 (8 mg) in DCM (2 mL) were added 37% aqueous formaldehyde (6 μL) and NaHB(OAc)$_3$ (12 mg). The vial was shaken at ambient temperature during 1.5 h; the reaction mixture was then concentrated, taken up in MeOH, and purified by HPLC, giving 104 as a white solid, 8 mg. MS (ESI(+)) m/e 633.4 (M+H)$^+$.
Example 96
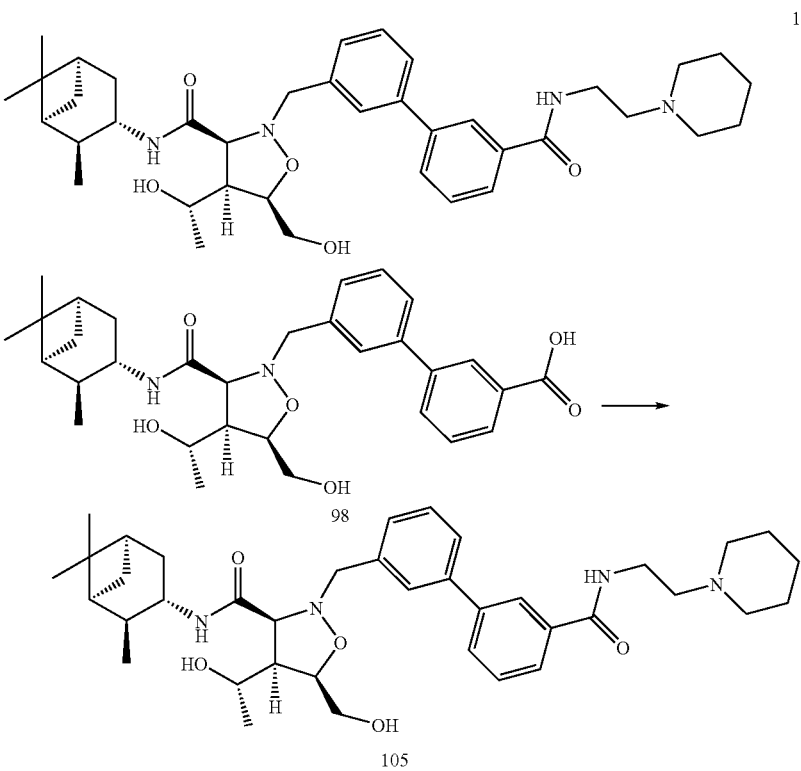

To a solution of crude 98 (25 mg) and 1-(2-aminoethyl)
piperidine (23 µL) in DMF (700 µL) was added HBTU (25
mg). After shaking for 1 h, the reaction mixture was diluted
with MeOH (800 µL) and purified by HPLC. Concentration
of the appropriate fractions gave a 105 as a white solid, 20 mg.
MS (ESI(+)) m/e 647.3 (M+H)⁺.

Example 97

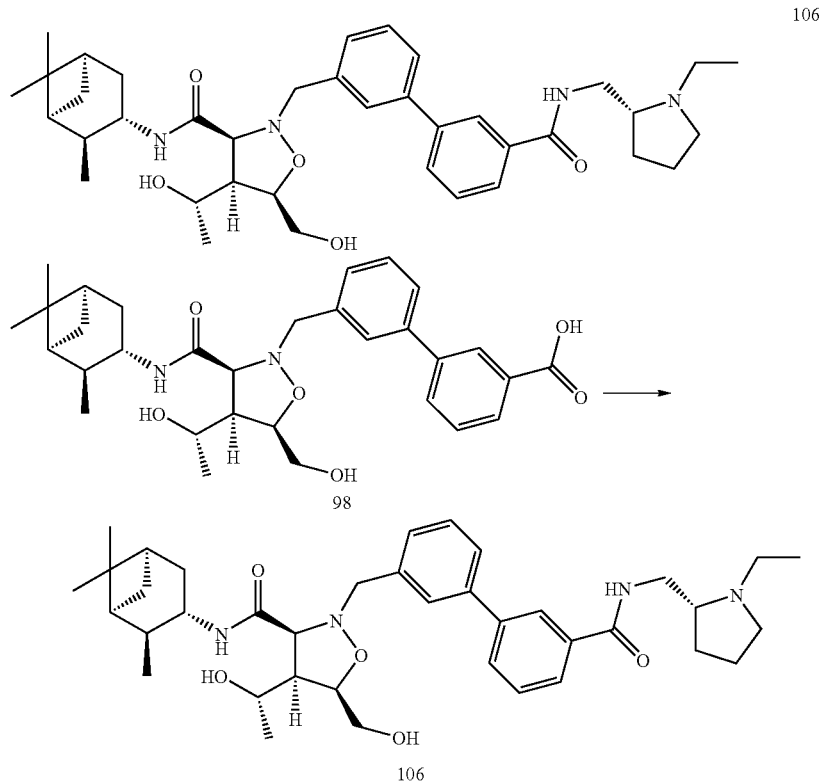

106

To a solution of crude 98 (25 mg) and (2R)-1-ethyl-2-
aminomethylpyrrolidine (25 µL) in DMF (700 µL) was added
HBTU (40 mg). After shaking for 1 h, the reaction mixture
was diluted with MeOH (800 µL) and purified by HPLC.
Concentration of the appropriate fractions gave a 106 as a
white solid, 20 mg. MS (ESI(+)) m/e 647.3 (M+H)⁺.

Example 98

107

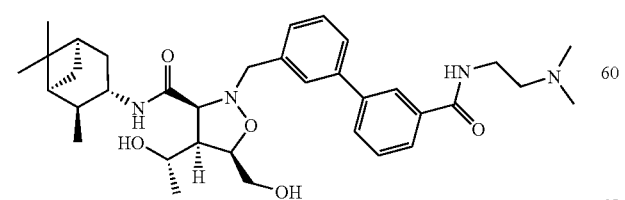

-continued

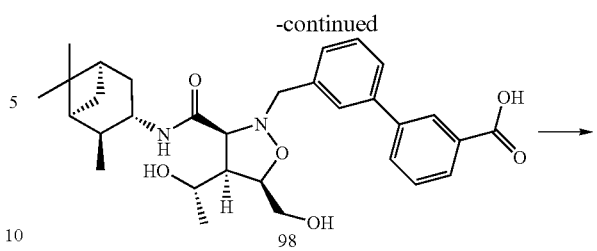

106

-continued

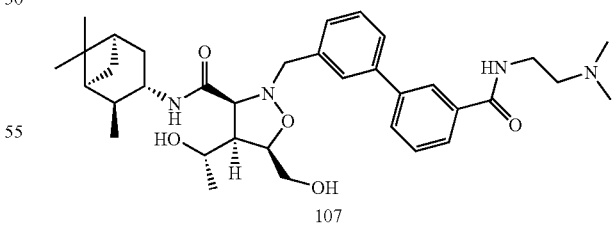

107

To a solution of crude 98 (25 mg) and N,N-dimethylethyl-
enediamine (18 µL) in DMF (700 µL) was added HBTU (25
mg). After shaking for 1 h, the reaction mixture was diluted
with MeOH (800 µL) and purified by HPLC. Concentration
of the appropriate fractions gave a 107 as a white solid, 23 mg.
MS (ESI(+)) m/e 607.3 (M+H)⁺.

Example 99

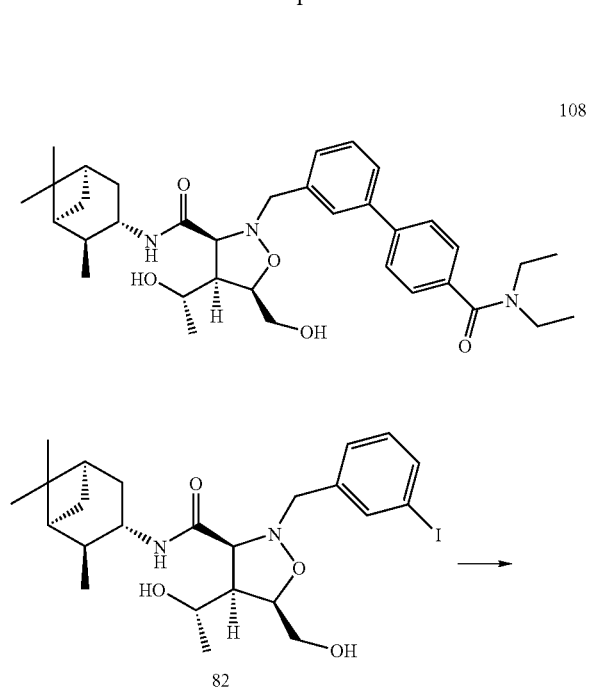

82

108

A tube containing 82 (30 mg), 4-(diethylaminocarbonyl) phenylboronic acid (25 mg), Pd(Ph₃P)₂Cl₂ (2 mg) and NEt₃ (31 µL) in ETOH (900 µL) was sealed and heated in the microwave at 120° C. during 20 mins. The reaction mixture was added to silica gel (1 g) and the solvent allowed to evaporate; purification of the residue by silica gel chromatography (50->100% EtOAc/hexanes) gave 108 as a clear colorless oil, 17 mg. MS (ESI(+)) m/e 592.4 (M+H)⁺.

Example 100

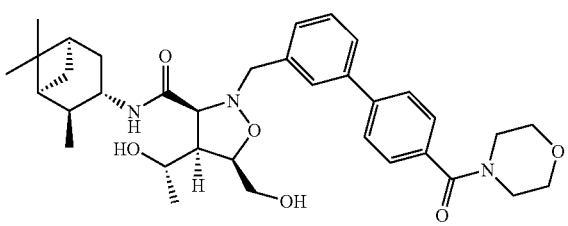

109

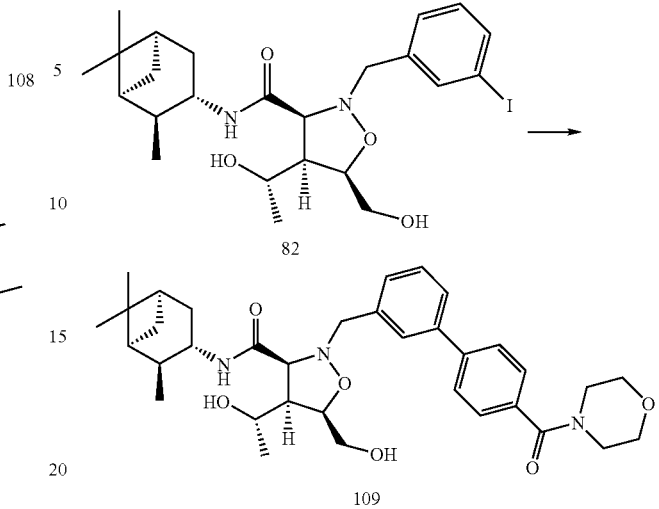

82

109

A tube containing 82 (30 mg), 4-(4-morpholinocarbonyl) phenylboronic acid (263 mg), Pd(Ph₃P)₂Cl₂ (2 mg) and NEt₃ (31 µL) in EtOH (900 µL) was sealed and heated in the microwave at 120° C. during 20 mins. The reaction mixture was added to silica gel (1 g) and the solvent allowed to evaporate; purification of the residue by silica gel chromatography (50->100% EtOAc/hexanes) gave 109 as a clear colorless oil, 14 mg. MS (ESI(+)) m/e 606.4 (M+H)⁺.

Example 101

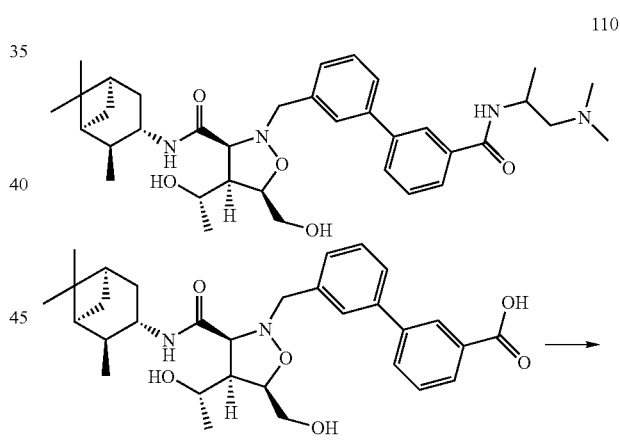

110

98

110

To a solution of crude 98 (25 mg) and racemic 1-dimethylamino-2-propylamine (19 µL) in DMF (700 µL) was added HBTU (40 mg). After shaking for 1 h, the reaction mixture was diluted with MeOH (800 µL) and purified by HPLC. Concentration of the appropriate fractions gave 110 as a white solid, 21 mg. MS (ESI(+)) m/e 621.2 (M+H)⁺.

Example 102

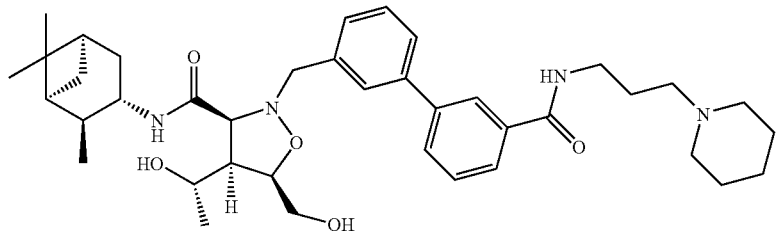

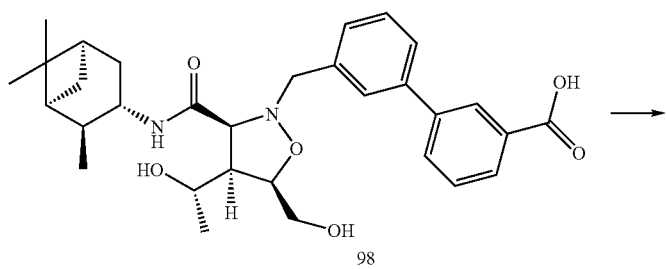

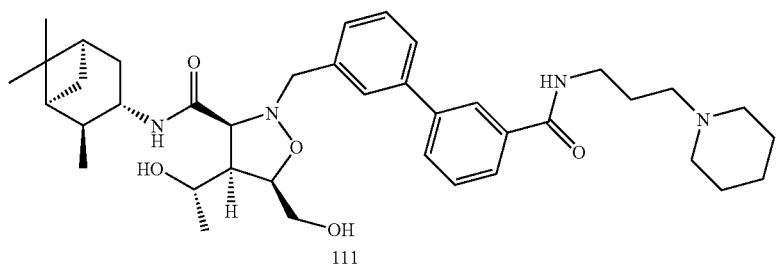

To a solution of crude 98 (25 mg) and 1-(3-aminopropyl)piperidine (26 μL) in DMF (700 μL) was added HBTU (40 mg). After shaking for 1 h, the reaction mixture was diluted with MeOH (800 μL) and purified by HPLC. Concentration of the appropriate fractions gave 111 as a white solid, 14 mg. MS (ESI(+)) m/e 661.4 (M+H)$^+$.

Example 103

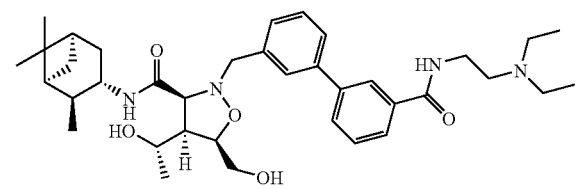

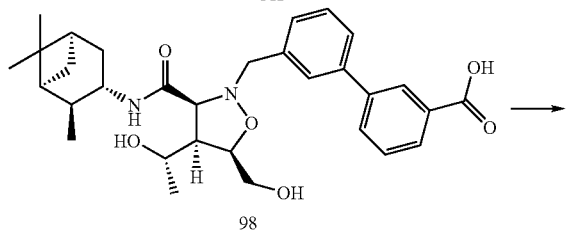

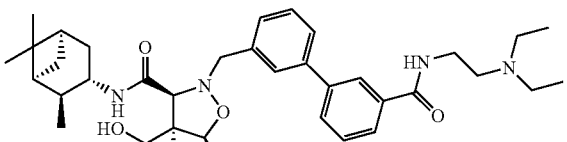

To a solution of crude 98 (25 mg) and N,N-diethylethylenediamine (21 μL) in DMF (700 μL) was added HBTU (40 mg). After shaking for 1 h, the reaction mixture was diluted with MeOH (800 μL) and purified by HPLC. Concentration of the appropriate fractions gave 112 as a white solid, 22 mg. MS (ESI(+)) m/e 635.3 (M+H)$^+$.

Example 104

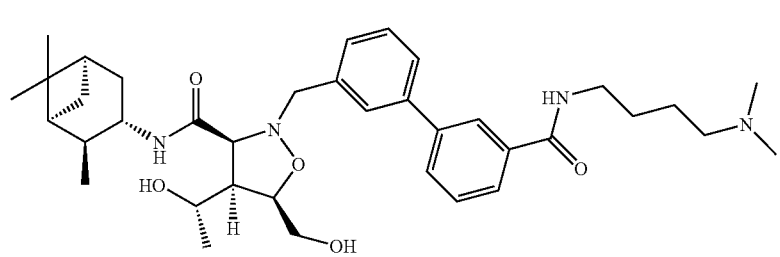

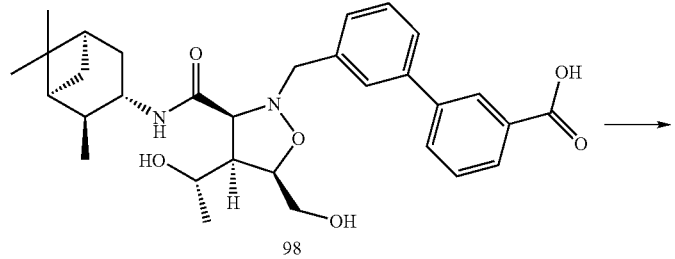

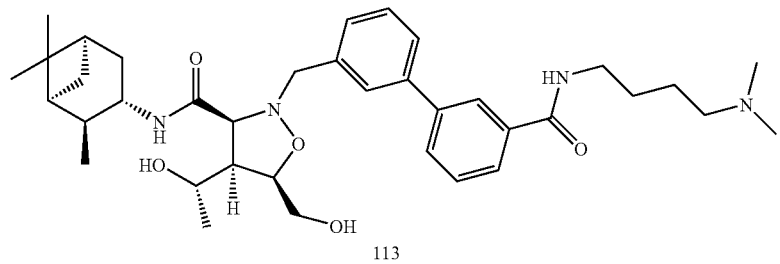

To a solution of crude 98 (25 mg) and 4-dimethylaminobutylamine (25 μL) in DMF (700 μL) was added HBTU (25 mg). After shaking for 1 h, the reaction mixture was diluted with MeOH (800 μL) and purified by HPLC. Concentration of the appropriate fractions gave 113 as a white solid, 25 mg. MS (ESI(+)) m/e 635.3 (M+H)$^+$.

Example 105

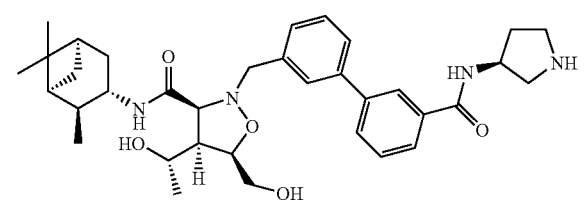

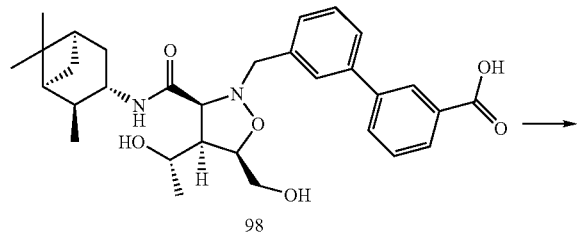

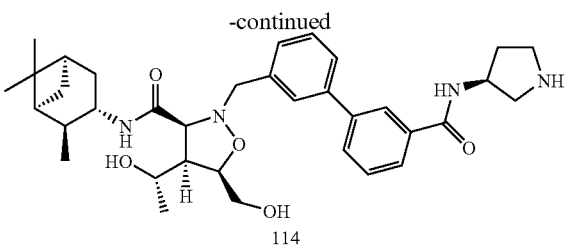

To a solution of (3S)-3-tert-butoxycarbonylamino-pyrrolidine (204 mg) in DCM (5 mL) was added DIEA (286 μL) and benzyl chloroformate (188 μL). The solution was stirred overnight at ambient temperature, then added to saturated NaHCO$_3$ and extracted with DCM (3×20 mL). The combined organic phases were dried on MgSO$_4$ and concentrated to give a white solid. This material was dissolved in TFA (4 mL), stirred for two hours, and the solution concentrated in vacuo to give a clear oil.

To a solution of this crude oil (139 mg), crude 98 (25 mg), and DIEA (80 μL) in DMF (1.4 mL) was added HBTU (80 mg). After shaking for 1 h, the reaction mixture was diluted with MeOH (1.5 mL) and purified by HPLC. Concentration of the appropriate fractions gave a white solid.

Half of this solid was dissolved in EtOH (2 mL), to which were added HOAc (5 μL) and wet 20% Pd on carbon (5 mg). H$_2$ was bubbled through the mixture, which was then allowed to stir under an atmosphere of H$_2$ for 4 h. The reaction mixture was passed through a 0.2-micron filter and purified by HPLC to give 114 as a white solid, 6 mg. MS (ESI(+)) m/e 605.2 (M+H)+.

Example 106

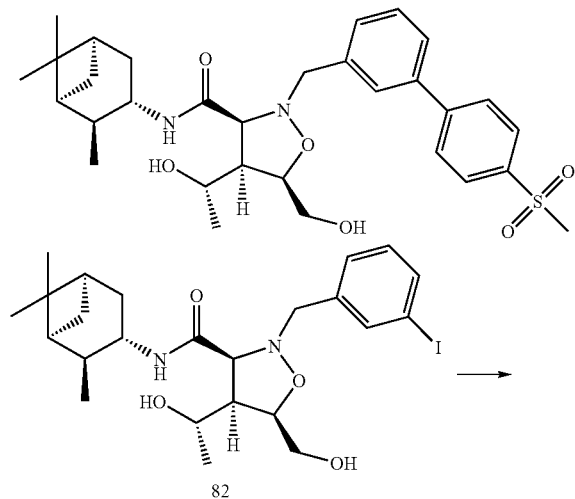

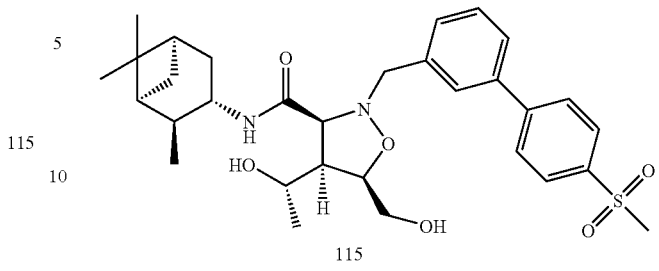

A tube containing 82 (30 mg), 4-(methanesμLfonyl)phenylboronic acid (22 mg), Pd(Ph₃P)₂Cl₂ (2 mg) and NEt₃ (31 μL) in EtOH (1 mL) was sealed and heated in the microwave at 120° C. during 20 mins. The reaction mixture was added to silica gel (1 g) and the solvent allowed to evaporate; purification of the residue by silica gel chromatography (50->100% EtOAc/hexanes) gave 115 as a clear colorless oil, 30 mg. MS (ESI(+)) m/e 571.3 (M+H)+.

Example 107

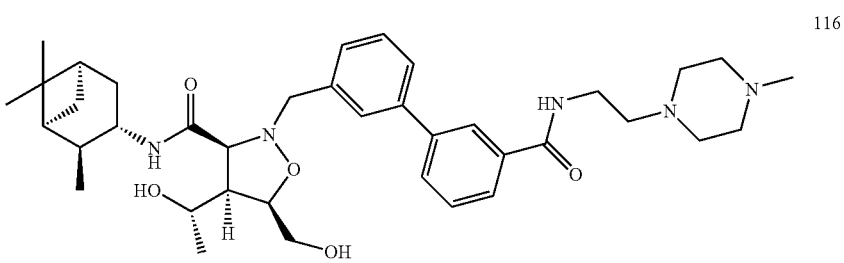

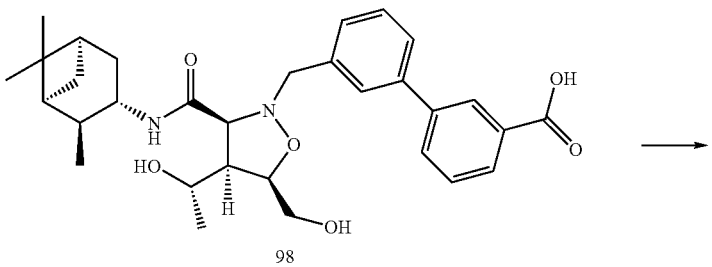

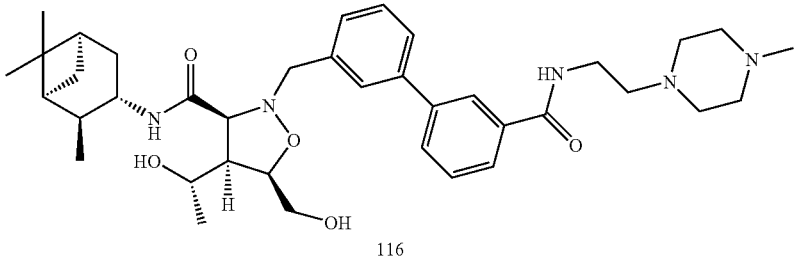

To a solution of crude 98 (25 mg) and 1-(2-aminoethyl)-4-methylpiperazine (23 μL) in DMF (700 μL) was added HBTU (30 mg). After shaking for 1 h, the reaction mixture was diluted with MeOH (800 μL) and purified by HPLC. Concentration of the appropriate fractions gave 116 as a white solid, 26 mg. MS (ESI(+)) m/e 662.3 (M+H)$^+$.

Example 108

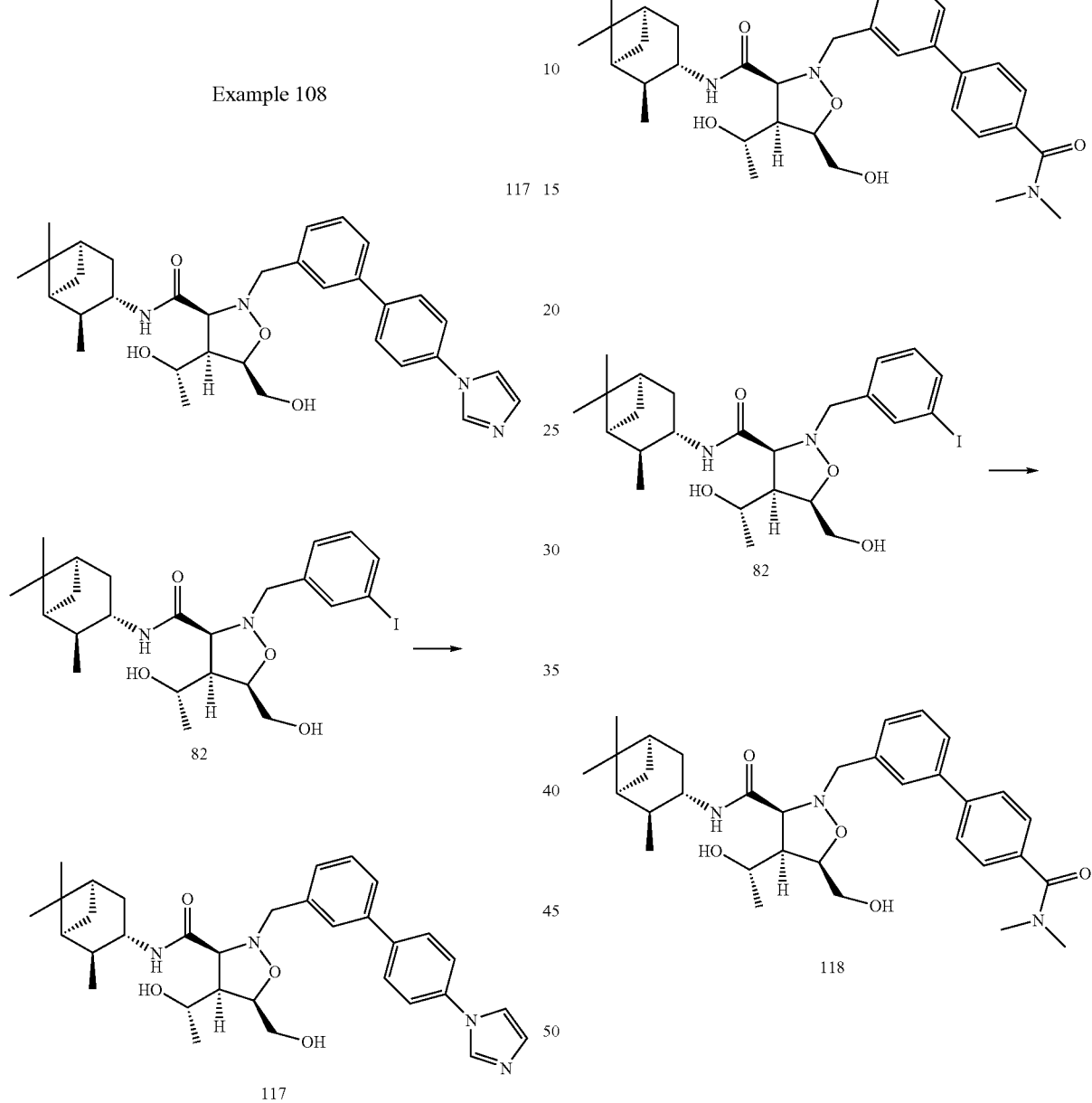

Example 109

A flask was charged with 1-(4-bromophenyl)imidazole (25 mg), Pd(dppf)Cl$_2$ (4 mg), KOAc (33 mg), and bis(pinacolato)diboron (28 mg), flushed with a stream of Ar, and DMSO (3 mL) was added. The mixture was heated at 80° C. during 1 h, then 82 (30 mg) and Cs$_2$CO$_3$ (35 mg) were added and heating continued at 60° C. for 4 h. The reaction mixture was then purified by HPLC. Concentration of the appropriate fractions gave 117 as a white solid, 6.5 mg. MS (ESI(+)) m/e 559.2 (M+H)$^+$.

In a flask were combined 82 (100 mg), 4-(dimethylaminocarbonyl)phenylboronic acid (71 mg), Cs$_2$CO$_3$ (120 mg), KOAc (20 mg), and Pd(dppf)Cl$_2$ (10 mg). The flask was flushed with Ar, and DMSO (6 mL) added; the material was then heated at 60° C. during 3 h, with the more Pd(dppf)Cl$_2$ (5 mg) added after 2.5 h. The reaction mixture was cooled and added to DCM (25 mL) and 1% NaS$_2$CNMe$_2$ (75 mg); the laters were separated and the aqueous phase extracted 3×25 mL DCM. The combined organics were washed with water (25 mL) and brine (25 mL), then dried on Na$_2$SO$_4$. Concentration and HPLC putification of the material gave 118 as a white solid, 64. mg. MS (ESI(+)) m/e 564.3 (M+H)$^+$.

Example 110

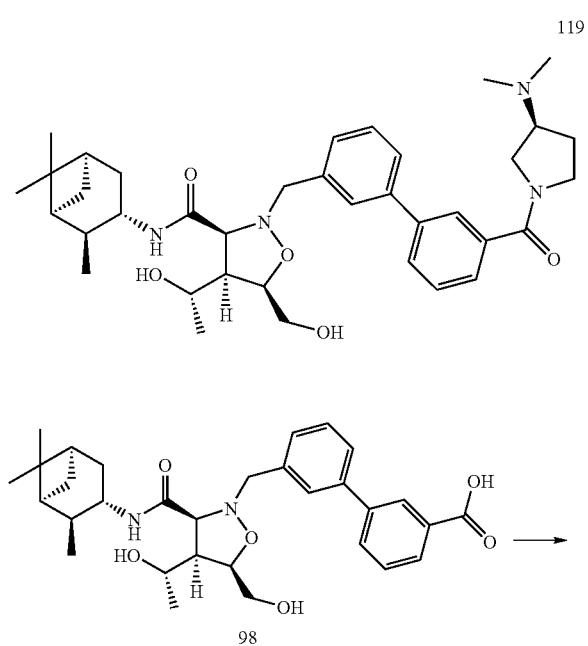
119

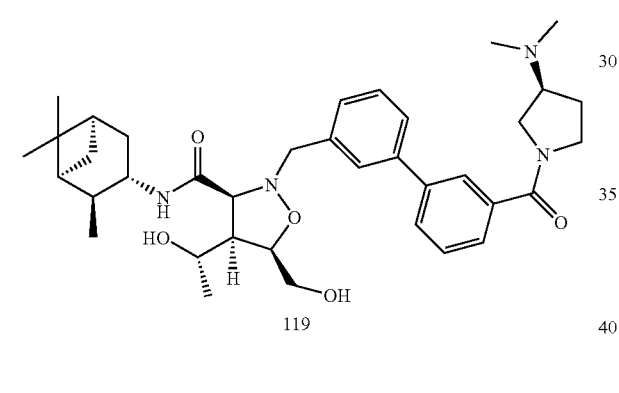
98

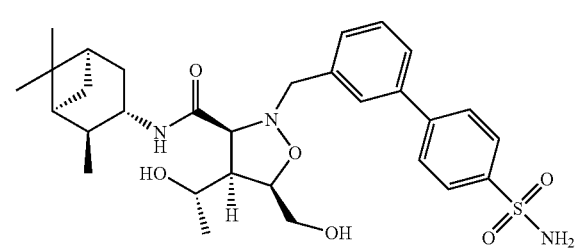
119

To a solution of crude 98 (19 mg) and (3S)-3-(dimethylamino)pyrrolidine (18 μL) in DMF (525 μL) was added HBTU (25 mg). After shaking for 1 h, the reaction mixture was diluted with MeOH (1 mL) and purified by HPLC. Concentration of the appropriate fractions gave 119 as a white solid, 18 mg. MS (ESI(+)) m/e 633.3 (M+H)+.

Example 111

120

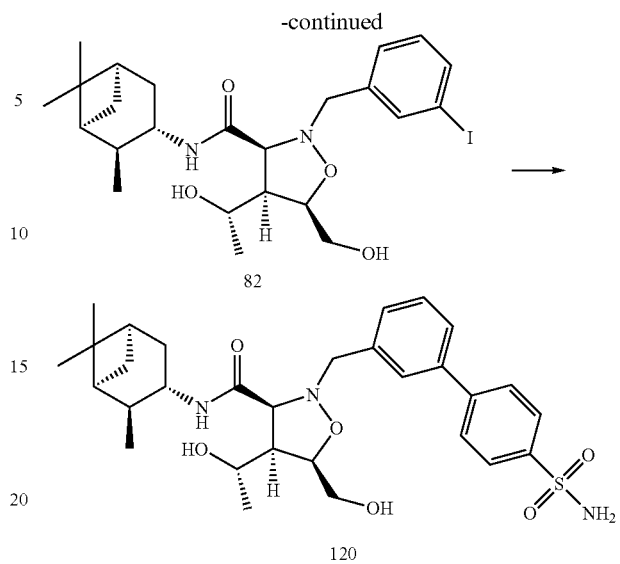
82

120

In a small flask were combined 82 (25 mg), 4-(sulfonylamino)phenylboronic acid (19 mg), Cs$_2$CO$_3$ (40 mg), KOAc (5 mg) and Pd(dppf)Cl$_2$ (4 mg). The flask was flushed with Ar and DMSO (3 mL) added. After heating at 60° C. during 2 h, the reaction mixture was purified by HPLC to give 120 as a white solid, 11 mg. MS (ESI(+)) m/e 572.2 (M+H)+.

Example 112

121

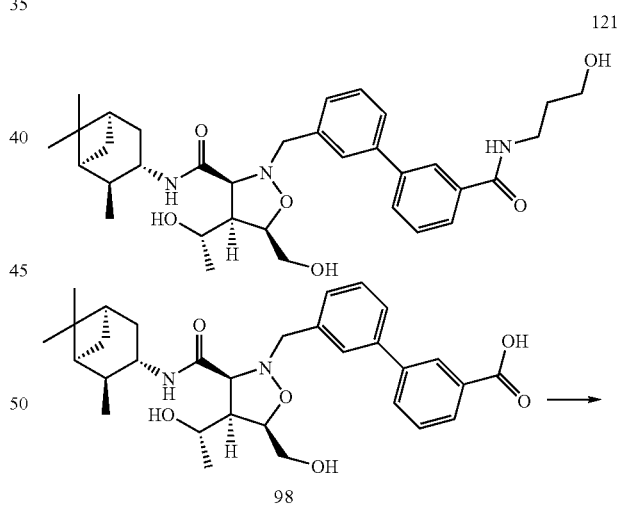
98

121

To a solution of crude 98 (25 mg) and 3-propanolamine (12 μL) in DMF (700 μL) was added HBTU (30 mg). After shaking for 1 h, the reaction mixture was diluted with MeOH (800 μL) and purified by HPLC. Concentration of the appropriate fractions gave 121 as a white solid, 23 mg. MS (ESI(+)) m/e 594.3 (M+H)⁺.

Example 113

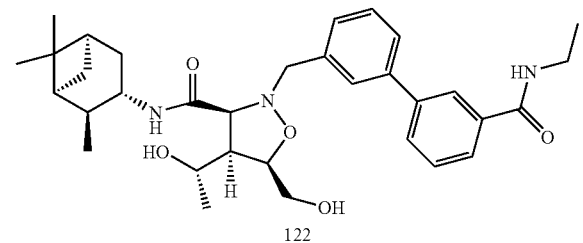
122

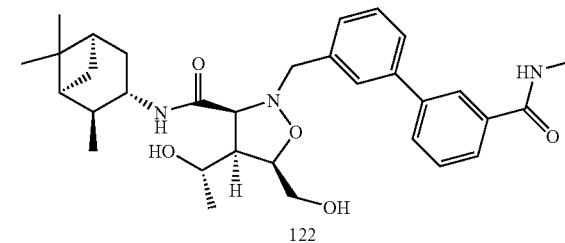
98

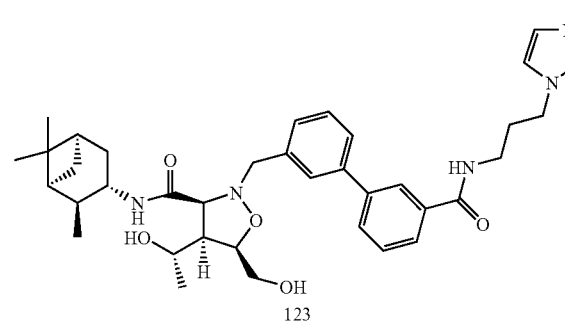
122

To a solution of crude 98 (25 mg) and 2.0M ethylamine in THF (74 μL) in DMF (700 μL) was added HBTU (40 mg). After shaking for 1 h, the reaction mixture was diluted with MeOH (800 μL) and purified by HPLC. Concentration of the appropriate fractions gave 122 as a white solid, 15 mg. MS (ESI(+)) m/e 564.3 (M+H)⁺.

Example 114

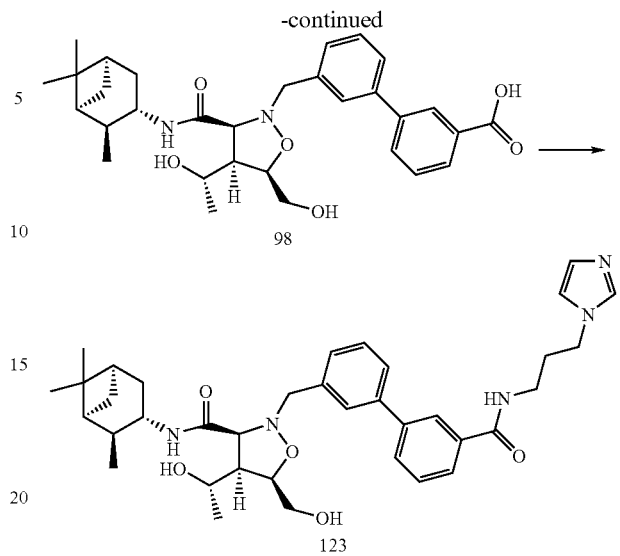
98

123

To a solution of crude 98 (25 mg) and 1-(3-aminopropyl)imidazole (19 μL) in DMF (700 μL) was added HBTU (25 mg). After shaking for 1 h, the reaction mixture was diluted with MeOH (800 μL) and purified by HPLC. Concentration of the appropriate fractions gave 123 as a white solid, 17 mg. MS (ESI(+)) m/e 644.3 (M+H)⁺.

Example 115

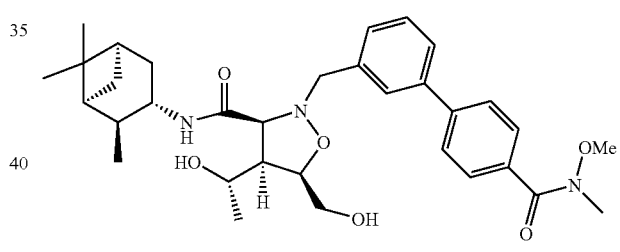
124

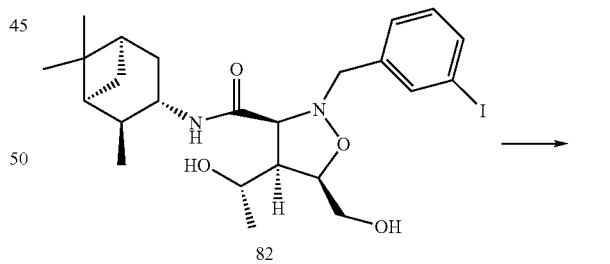
82

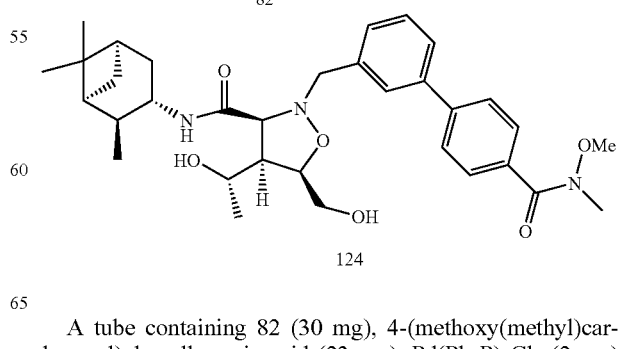
124

A tube containing 82 (30 mg), 4-(methoxy(methyl)carbamoyl)phenylboronic acid (23 mg), Pd(Ph₃P)₂Cl₂ (2 mg)

and NEt$_3$ (31 μL) in EtOH (900 μL) was sealed and heated in the microwave at 120° C. during 20 mins. The reaction mixture was added to silica gel (1 g) and the solvent allowed to evaporate; purification of the residue by silica gel chromatography (50->100% EtOAc/hexanes) gave 124 as a clear colorless oil, 22 mg. MS (ESI(+)) m/e 580.4 (M+H)$^+$.

Example 116

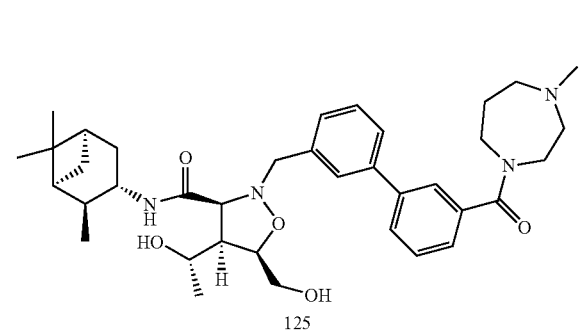
125

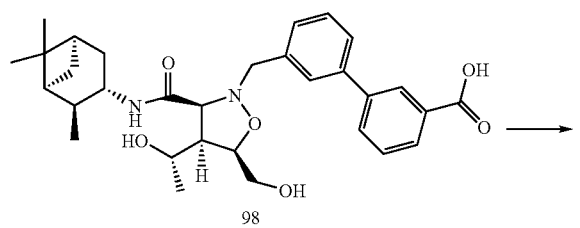
98

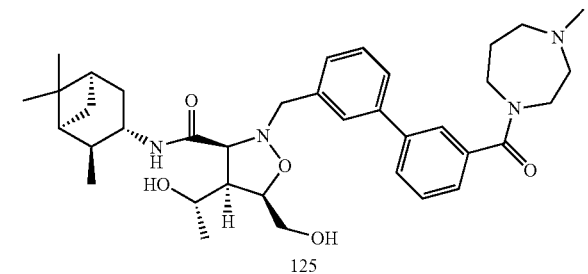
125

To a solution of crude 98 (25 mg) and 1-methylhomopiperazine (20 μL) in DMF (700 μL) was added HBTU (30 mg). After shaking for 1 h, the reaction mixture was diluted with MeOH (800 μL) and purified by HPLC. Concentration of the appropriate fractions gave 125 as a white solid, 20 mg. MS (ESI(+)) m/e 633.3 (M+H)$^+$.

Example 117

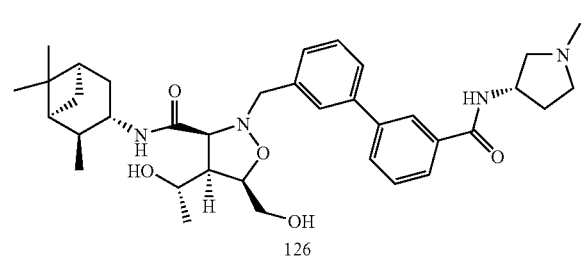
126

-continued

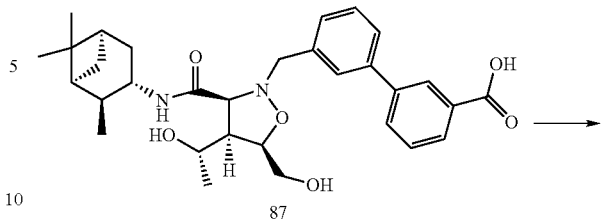
87

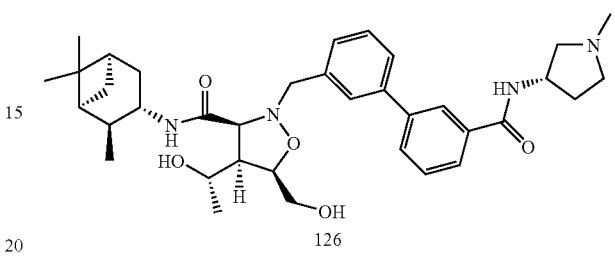
126

To a solution of crude 98 (25 mg), (3S)-3-amino-1-methylpyrrolidine dihydrochloride (25 mg), and DIEA (50 μL) in DMF (700 μL) was added HBTU (30 mg). After shaking for 1 h, the reaction mixture was diluted with MeOH (800 μL) and purified by HPLC. Concentration of the appropriate fractions gave 126 as a white solid, 15 mg. MS (ESI(+)) m/e 619.4 (M+H)$^+$.

Example 118

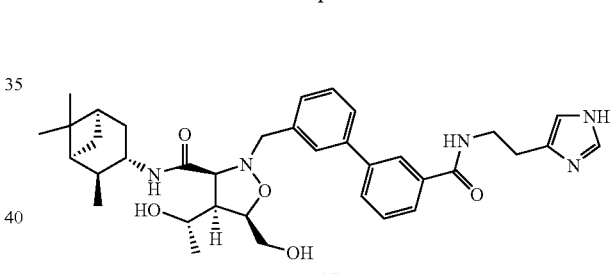
127

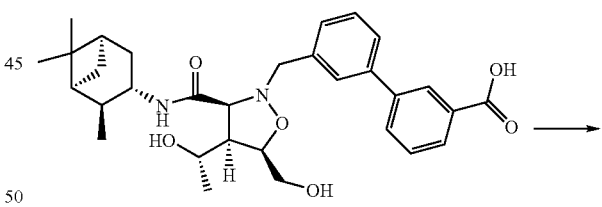
98

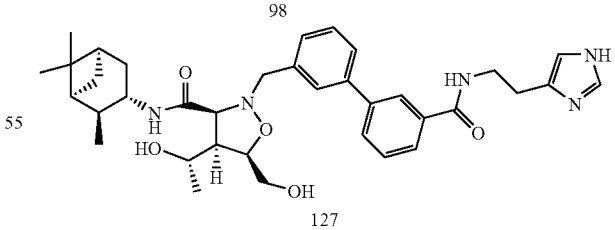
127

To a solution of crude 98 (25 mg) and histamine (18 mg) in DMF (700 μL) was added HBTU (25 mg). After shaking for 1 h, the reaction mixture was diluted with MeOH (800 μL) and purified by HPLC. Concentration of the appropriate fractions gave 127 as a white solid, 10 mg. MS (ESI(+)) m/e 630.2 (M+H)$^+$.

Example 119

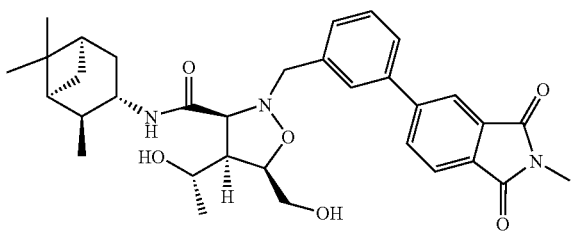
128

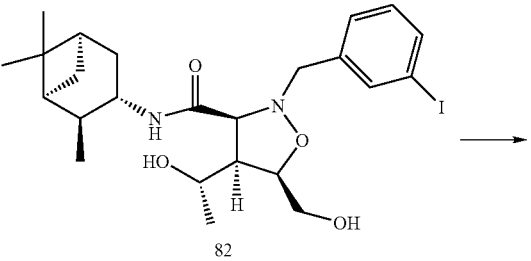
82

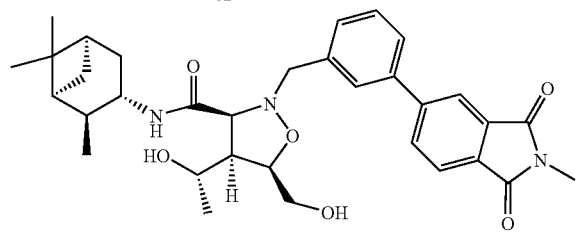
128

A solution of 4-bromophthalic anhydride (2.0 g) in toluene (20 mL) was treated with 33% methylamine in EtOH (1.65 mL) and a crystal of DMAP. After stirring for 1 h at ambient temperature, the mixture was heated to reflux under a dean-stark trap during 14 h. The reaction mixture was cooled to −20° C., and the resulting white crystals collected and washed with hexanes to give N-methyl-3-bromophthalimide (1.32 g) m.p. 149-151. Concentration of the mother liquor and recrystalization from benzene (3 mL) gave a second crop, 430 mg.

A flask was charged with this N-methyl-3-bromophthalimide (27 mg), Pd(dppf)Cl$_2$ (3 mg), KOAc (33 mg), and bis(pinacolato)diboron (28 mg), flushed with a stream of Ar, and DMSO (3 mL) was added. The mixture was heated at 80° C. during 1 h, then 82 (30 mg) and Cs$_2$CO$_3$ (35 mg) were added and heating continued at 80° C. for 2.5 h. The reaction mixture was then purified by HPLC. Concentration of the appropriate fractions gave 128 as a white solid, 12 mg. MS (ESI(+)) m/e 576.3 (M+H)$^+$.

Example 120

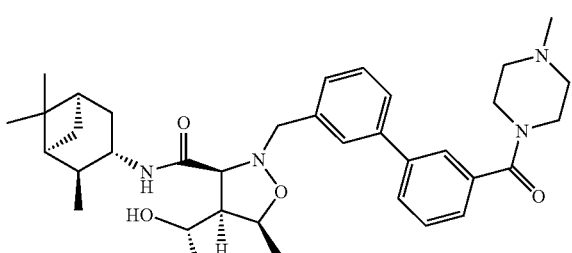
129

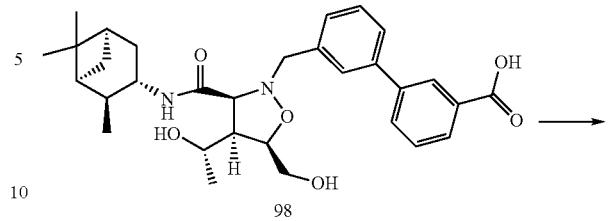
98

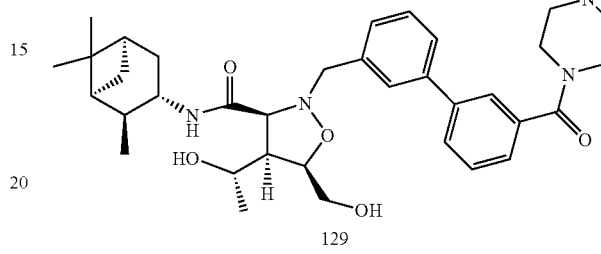
129

To a solution of crude 98 (25 mg) and 1-methylpiperazine (18 μL) in DMF (700 μL) was added HBTU (30 mg). After shaking for 1 h, the reaction mixture was diluted with MeOH (800 μL) and purified by HPLC. Concentration of the appropriate fractions gave 129 as a white solid, 21 mg. MS (ESI(+)) m/e 619.3 (M+H)$^+$.

Example 121

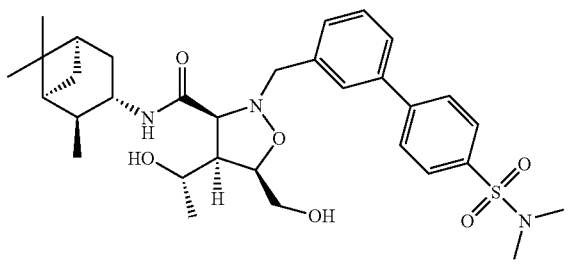
130

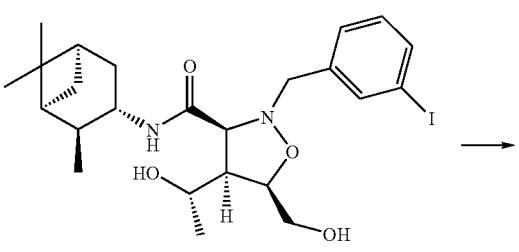
82

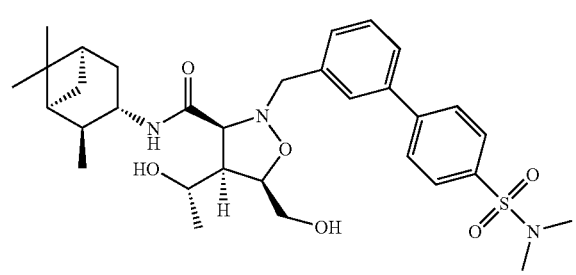
130

A tube containing 82 (30 mg), 4-(dimethylaminosulfonyl)phenylboronic acid (33 mg), Pd(Ph₃P)₂Cl₂ (2 mg) and NEt₃ (31 μL) in EtOH (900 μL) was sealed and heated in the microwave at 120° C. during 20 mins. The reaction mixture was added to silica gel (1 g) and the solvent allowed to evaporate; purification of the residue by silica gel chromatography (50->75% EtOAc/hexanes) gave 130 as a clear colorless oil, 5 mg. MS (ESI(+)) m/e 600.4 (M+H)⁺.

Example 122

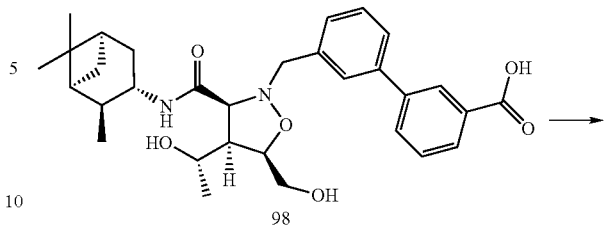

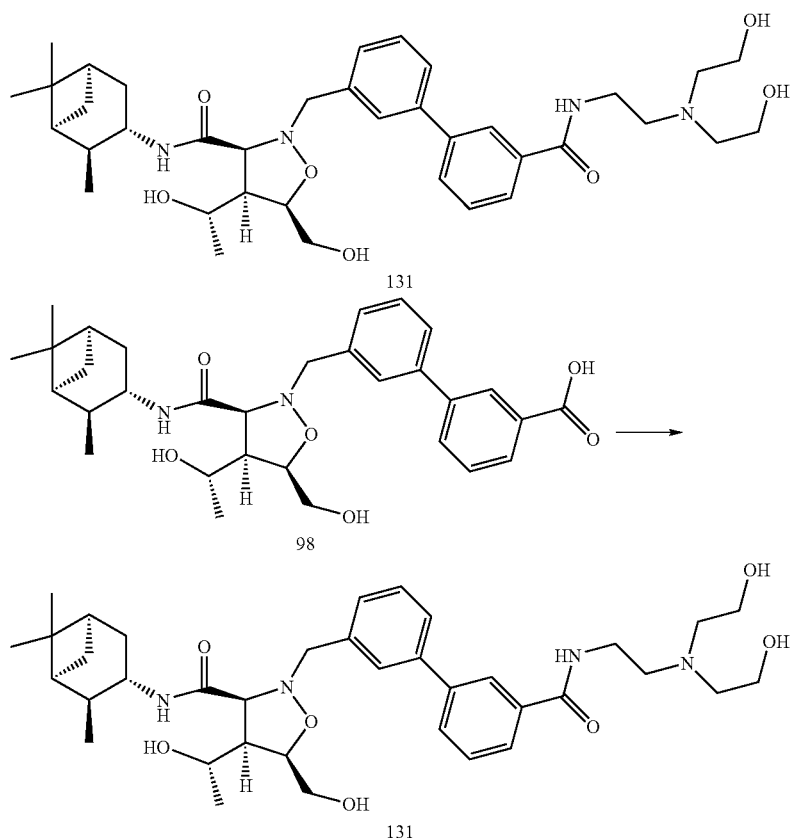

To a solution of crude 98 (25 mg) and N,N-bis(2-hydroxyethyl)ethylenediamine (20 μL) in DMF (700 μL) was added HBTU (40 mg). After shaking for 1 h, the reaction mixture was diluted with MeOH (800 μL) and purified by HPLC. Concentration of the appropriate fractions gave 131 as a white solid, 16 mg. MS (ESI(+)) m/e 667.4 (M+H)⁺.

Example 123

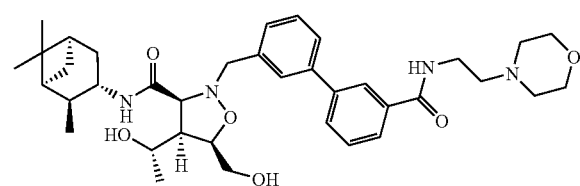

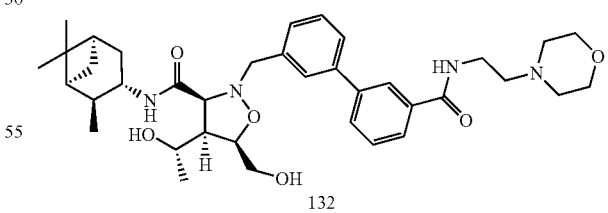

To a solution of crude 98 (25 mg) and 4-(2-aminoethyl)morpholine (21 μL) in DMF (700 μL) was added HBTU (30 mg). After shaking for 1 h, the reaction mixture was diluted with MeOH (800 μL) and purified by HPLC. Concentration of the appropriate fractions gave 132 as a white solid, 21 mg. MS (ESI(+)) m/e 649.3 (M+H)⁺.

Example 124

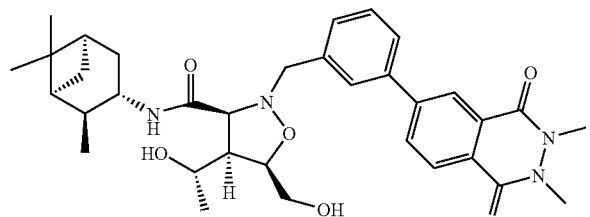

133

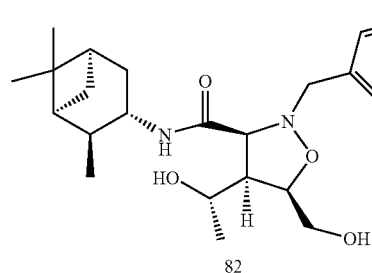

82

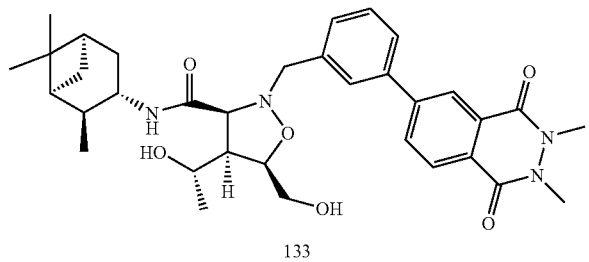

133

A suspension of 4-bromophthalic anhydride (1.0 g) in EtOH (10 mL) was treated with 1,2,-dimethylhydrazine dihydrochloride (650 mg) and NEt₃ (1.35 mL) and heated at reflux during 16 h. The reaction mixture was cooled and diluted into 0.1M HCl (100 mL). The resµLting white solid was collected by filtration, washed with water, and dried in vacuo to give 6-bromo-2,3-dimethyl-2,3-dihydrophthalazine-1,4-dione (516 mg), m.p. 207-209.

A flask was charged with this bromide (30 mg), Pd(dppf)Cl₂ (4 mg), KOAc (33 mg), and bis(pinacolato)diboron (28 mg), flushed with a stream of Ar, and DMSO (3 mL) was added. The mixture was heated at 60° C. during 1 h, then 82 (30 mg) and Cs₂CO₃ (35 mg) were added and heating continued for 1 h. The reaction mixture was then purified by HPLC. Concentration of the appropriate fractions gave 133 as a white solid, 16.5 mg. MS (ESI(+)) m/e 605.2 (M+H)⁺.

Example 125

134

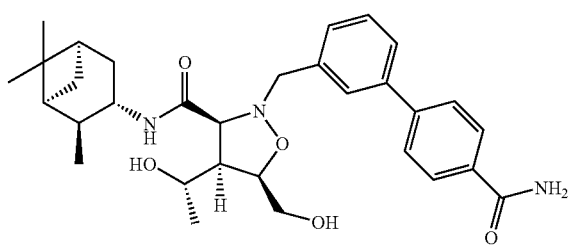

-continued

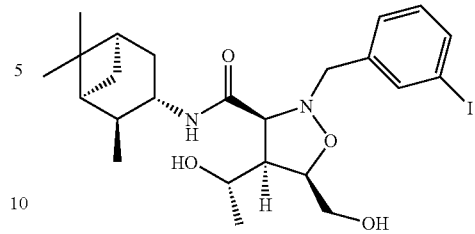

82

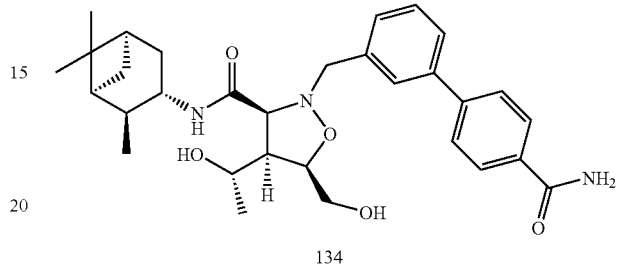

134

A tube containing 82 (30 mg), 4-(aminocarbonyl)phenylboronic acid (33 mg), Pd(Ph₃P)₂Cl₂ (2 mg) and NEt₃ (31 µL) in EtOH (1 mL) was sealed and heated in the microwave at 120° C. during 20 mins. The reaction mixture was added to silica gel (1 g) and the solvent allowed to evaporate; purification of the residue by silica gel chromatography gave 134 as a white solid, 8 mg. MS (ESI(+)) m/e 536.3 (M+H)⁺.

Example 126

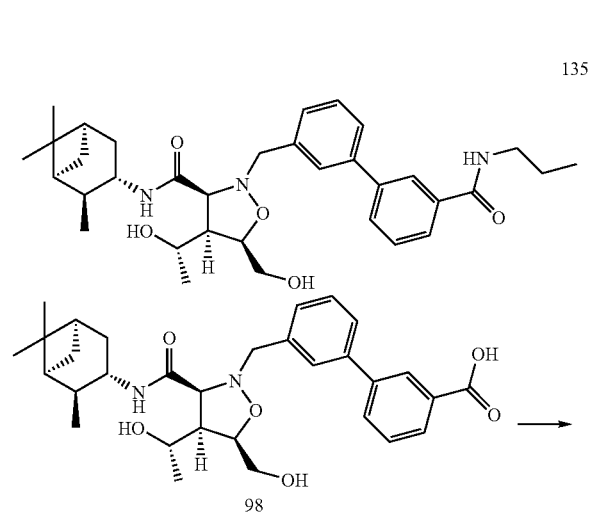

135

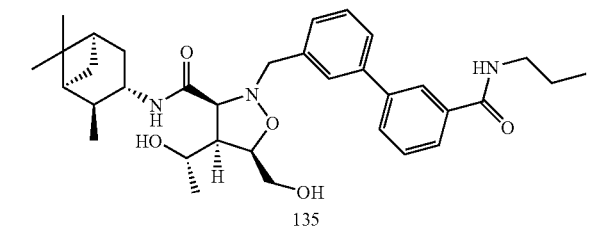

98

135

To a solution of crude 98 (25 mg) and propylamine (12 µL) in DMF (700 µL) was added HBTU (40 mg). After shaking for 1 h, the reaction mixture was diluted with MeOH (800 µL)

and purified by HPLC. Concentration of the appropriate fractions gave 135 as a white solid, 19 mg. MS (ESI(+)) m/e 578.3 (M+H)+.

Example 127

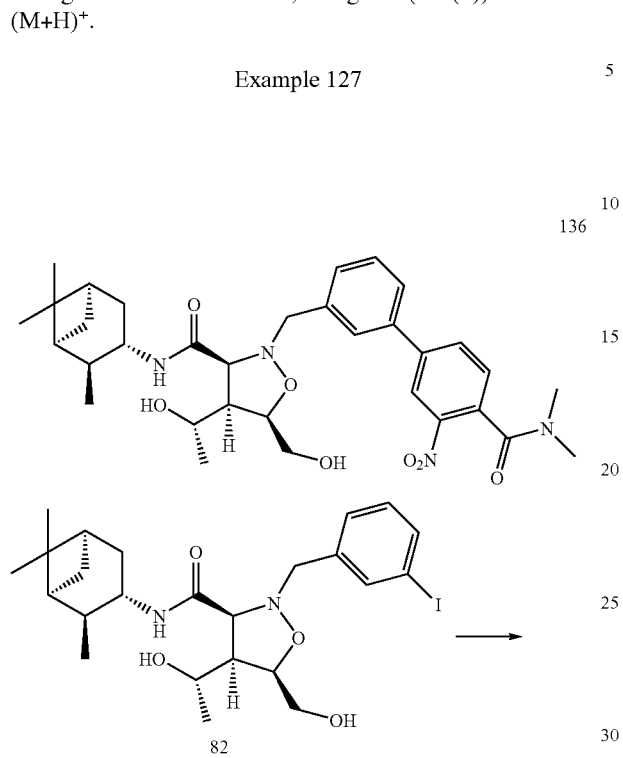

A flask containing 4-bromo-2-nitrobenzoic acid (500 mg) and a stir bar was treated with SOCl$_2$ (3 mL) and heated under reflux during 1 h. The SOCl$_2$ was allowed to distill off; benzene (5 mL) was added and allowed to distill as well. The residue was cooled in an ice bath, dissolved in DCM (3 mL), and treated with 2.0M dimethylamine in THF (4 mL). After stirring at ambient temperature overnight, the reaction mixture was diluted with EtOAc (80 mL), then washed with 20 mL each 2M HCl, 2M NaOH, and water. The organic layer was dried on MgSO$_4$, filtered and the residue recrystalized from hexanes (50 mL) to give fine off yellow needles of N,N-dimethyl-4-bromo-2-nitrobenzamide (453 mg), m.p. 104.5-105.5° C.

A flask was charged with this bromide (30 mg), Pd(dppf)Cl$_2$ (4 mg), KOAc (33 mg), and bis(pinacolato)diboron (28 mg), flushed with a stream of Ar, and DMSO (3 mL) was added. The mixture was heated at 80° C. during 1 h, then 82 (30 mg) and Cs$_2$CO$_3$ (36 mg) were added and heating continued for 3.5 h. The reaction mixture was then purified by HPLC. Concentration of the appropriate fractions gave 136as a white solid, 10 mg. MS (ESI(+)) m/e 609.3 (M+H)+.

Example 128

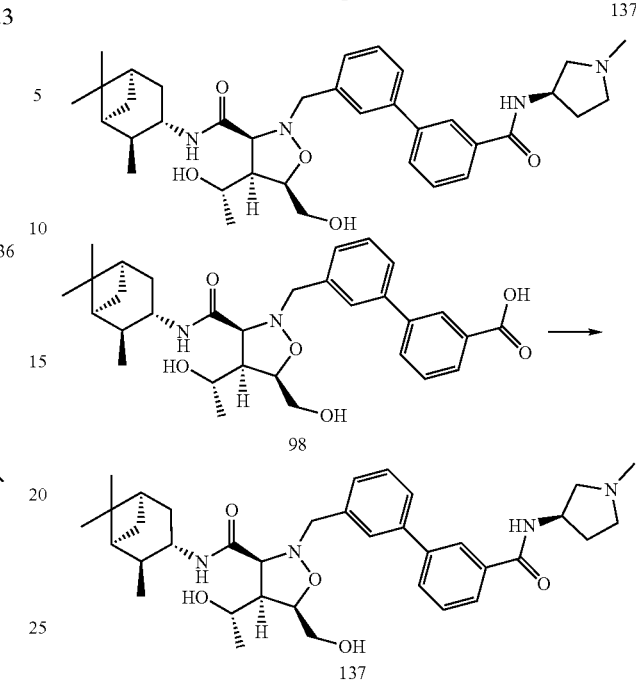

To a solution of crude 98 (25 mg), (3R)-3-amino-1-methylpyrrolidine dihydrochloride (25 mg), and DIEA (50 µL) in DMF (700 µL) was added HBTU (40 mg). After shaking for 1 h, the reaction mixture was diluted with MeOH (800 µL) and purified by HPLC. Concentration of the appropriate fractions gave 137 as a white solid, 14 mg. MS (ESI(+)) m/e 619.4 (M+H)+.

Example 129

Part A.

Compound 140 was made in 94% according to the procedure described in S. T Pickard and H. E. Smith *JACS* 1990, 112, 5741-5747.

Part B

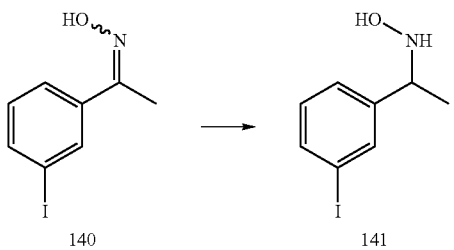

Compound 141 was made in 94% according to the procedure described in M. Ueda et al. *Tet. Lett.* 2002, 43, 4369-4371.

Part C

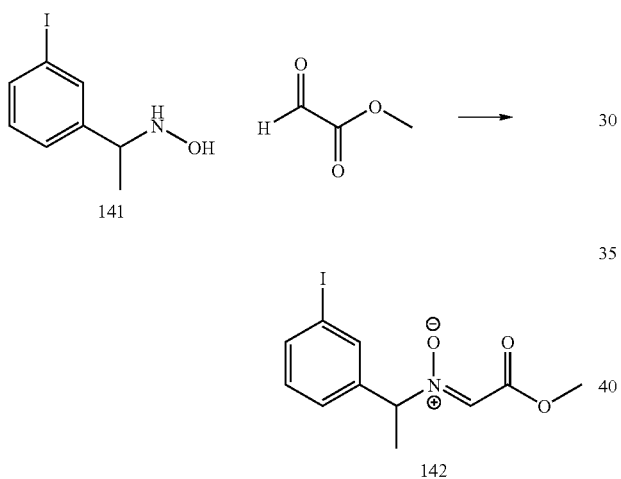

To a solution of the methyl gyloxate (0.29 g, 3.3 mmol, 1.5 equiv) was added the hydroxylamine (0.58 g, 2.2 mmol, 1 equiv) in benzene (15 mL) the solution was heated to reflux for 72 h in a round-bottomed flask equipped with a heating mantle and a Dean-Stark trap. The solution was allowed to cool to rt and concentrated in vacuo. After concentration NMR showed full convertion to the desired nitrone the product was isolated as an orange solid Part D

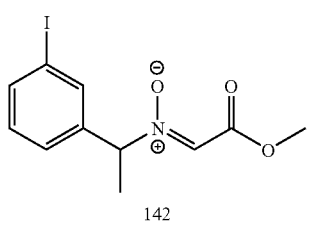

142

-continued

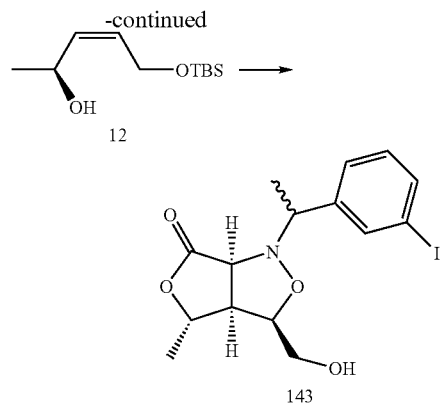

To a solution of racemic methyl 2-(1-(3-iodophenyl)ethylimino)acetate N-oxide (142)( 429 mg) and (S,Z)-5-(tert-butyldimethylsilyloxy)pent-3-en-2-ol (12) (275 mg) in toluene (10 mL) was added Ti(Oi-Pr)$_4$ (570 µL). The solution was heated in the microwave at 140° C. for 15 minutes, then treated with 3-(dimethylamino)propylene glycol (1 mL) and water (20 mL). Extraction, 3×30 mL EtOAc, followed by washing the combined organic layers with water (25 mL) and drying on MgSO$_4$, gave a residue which was purified by column chromatography on silica (5->20% EtOAc/hexanes) to give two diastereomeric materials. The faster-eluting material weighed 179 mg.

This material was dissolved in THF (5 mL) and 6M HCl (1 mL) was added. After stirring at ambient temperature for 30 minutes, EtOAc (30 mL) was added, followed by 1M NaOH (5 mL), saturated NaHCO$_3$ (13 mL), and water (13 mL). The aqueous layer was separated and extracted 2×30 mL EtOAc. The combined organic layers were washed with brine (20 mL), dried on MgSO4 and concentrated to a yellow solid. Hexanes (20 mL) were added to this residue and decanted off, leaving a white solid, 102 mg.

Part E

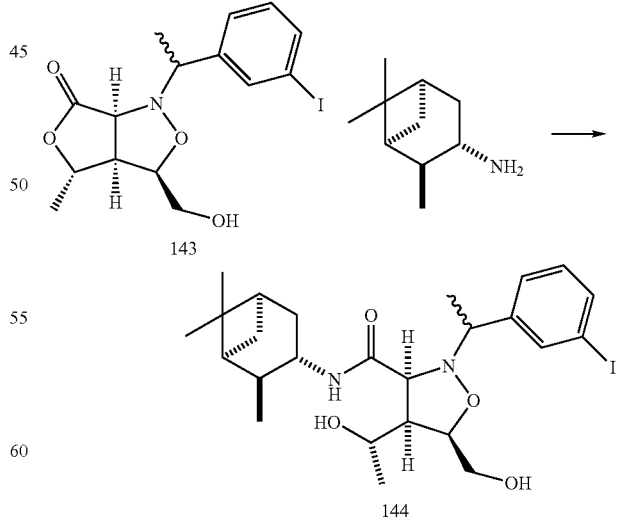

A flame-dried flask containing (+)-isopinocampheylamine (111 mg) and DCM (2 mL) was treated with 2.0M AlMe$_3$ in hexanes (360 µL) and stirred for 15 minutes, at which point the compound 143, suspended in DCM (4 mL), was added. After stirring 18 h at ambient temperature, the reaction mixture was treatew with saturated Rochelle salt solution (10 mL), and stirred for 1 h. Separation and extraction (3×10 mL DCM), followed by drying the organic phases on Na₂SO₄ and purification of the residue by column chromatography gave product, 205 mg.

Part F

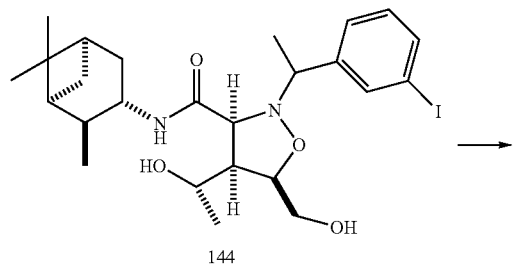
144

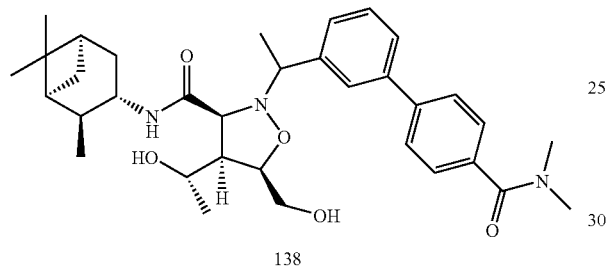
138

Compound 144 (30 mg), along with 4-(dimethylaminocarbonyl)phenylboronic acid (21 mg), Pd(Ph₃P)₂Cl₂ (2 mg), and NEt₃ (31 μL), was dissolved in EtOH (900 μL), which was heated in the microwave at 120° C. during 20 minutes. The reaction mixture was added to silica gel (1 g) and the solvent allowed to evaporate; purification of the residue by silica gel chromatography gave a single diastereomer of 138 as a white solid, 30 mg. MS (ESI(+)) m/e 578.3 (M+H)⁺.

Example 130

145

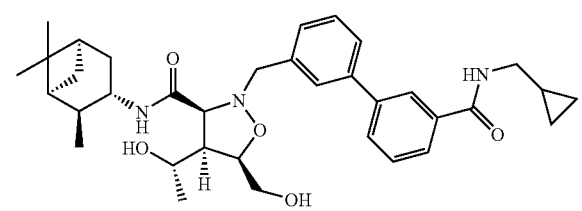

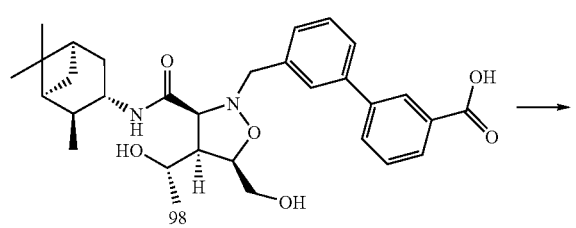
98

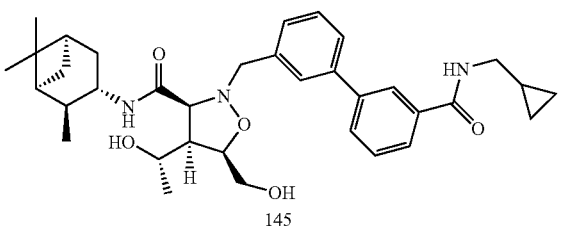
145

To a solution of crude 98 (25 mg) and methylaminocyclopropane (13 μL) in DMF (700 μL) was added HBTU (40 mg). After shaking for 1 h, the reaction mixture was diluted with MeOH (800 μL) and purified by HPLC. Concentration of the appropriate fractions gave 145 as a white solid, 21 mg. MS (ESI(+)) m/e 590.3 (M+H)⁺.

Example 131

146

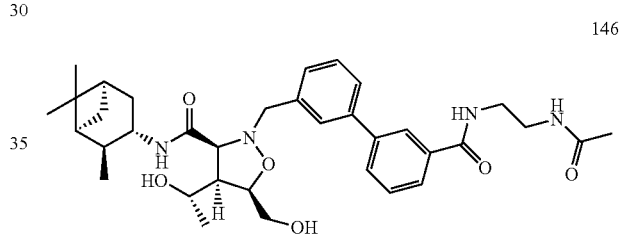

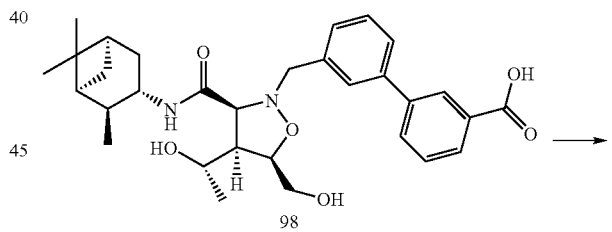
98

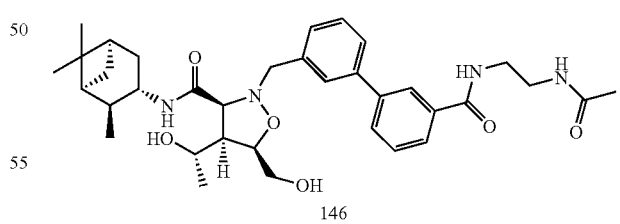
146

To a solution of crude 98 (25 mg) and N-(2-aminoethyl)acetamide (16 μL) in DMF (700 μL) w as added HBTU (25 mg). After shaking for 1 h, the reaction mixture was diluted with MeOH (800 μL) and purified by HPLC. Concentration of the appropriate fractions gave 146 as a white solid, 18 mg. MS (ESI(+)) m/e 621.2 (M+H)⁺.

Example 132

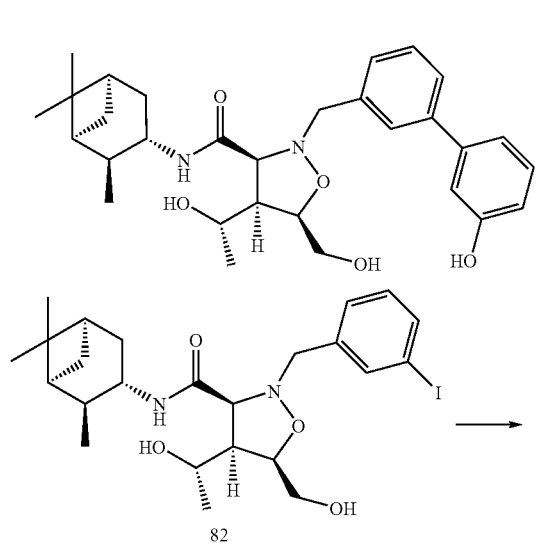

In a small flask were combined 82 (25 mg), 3-hydroxyphenylboronic acid (13 mg), Cs₂CO₃ (40 mg), KOAc (5 mg) and Pd(dppf)Cl₂ (4 mg). The flask was flushed with Ar and DMSO (3 mL) added. After heating at 60° C. during 1.5 h, the reaction mixture was purified by HPLC to give 147 as a white solid, 9 mg. MS (ESI(+)) m/e 509.2 (M+H)⁺.

Example 133

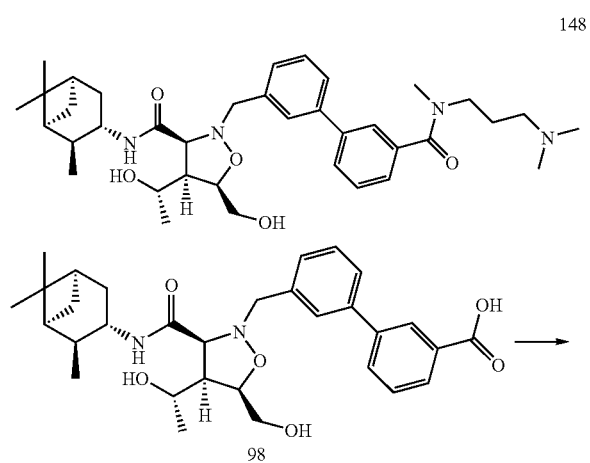

-continued

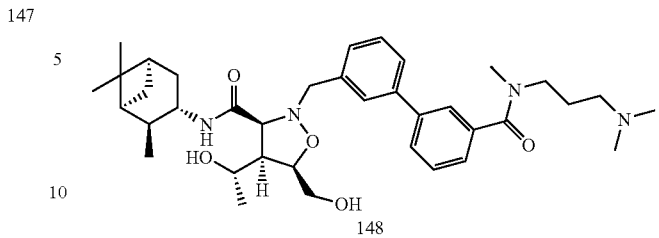

To a solution of crude 98 (23 mg) and N,N,N'-trimethyl-1,3-propanediame (19 µL) in DMF (700 µL) was added HBTU (35 mg). After shaking for 4 h, the reaction mixture was diluted with MeOH (1.5 mL) and purified by HPLC. Concentration of the appropriate fractions gave 148 as a yellowish solid, 6 mg. MS (ESI(+)) m/e 635.5 (M+H)⁺.

Example 134

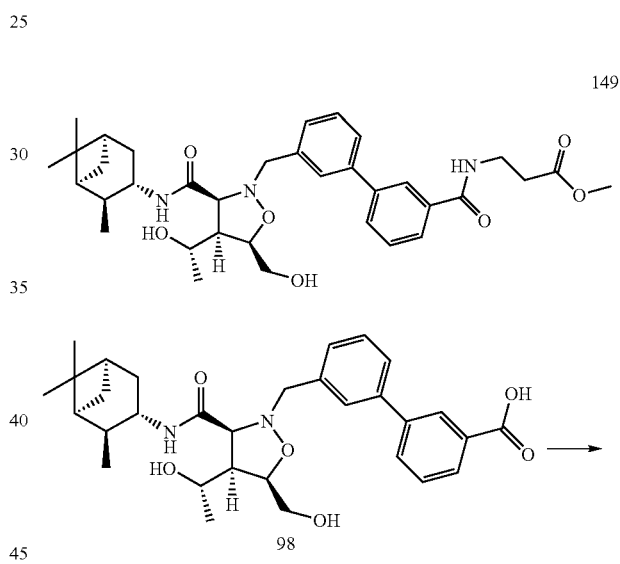

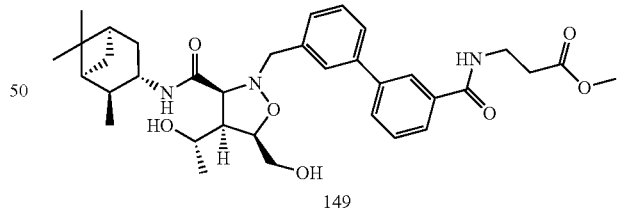

To a solution of crude 98 (25 mg) and methyl 3-aminopropionate (20 mg) in DMF (700 µL) was added HBTU (35 mg) and NEt₃ (18 µL). After shaking for 2 h, the reaction mixture was added to sat NaHCO₃ (5 mL) and water (5 mL), and extracted 3×10 mL DCM. The organic phases were dried on Na₂SO₄, partially concentrated, and added to silica gel (1 g) and the solvent allowed to evaporate; purification of the residue by silica gel chromatography gave 149 as a yellowish solid, 20 mg. MS (ESI(+)) m/e 622.3 (M+H)⁺.

Example 135

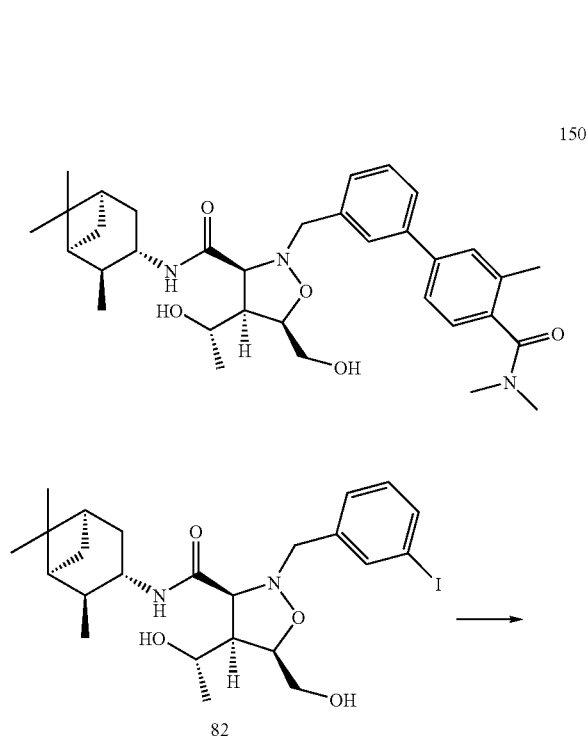

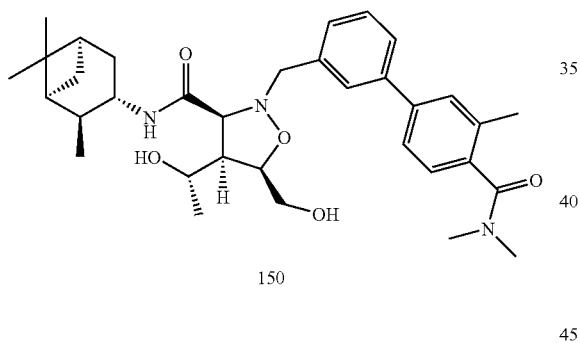

A flask containing 4-bromo-2-methylbenzoic acid (495 mg) and a stir bar was treated with SOCl$_2$ (3 mL) and heated under reflux during 1 h. The SOCl$_2$ was allowed to distill off; benzene (5 mL) was added and allowed to distill as well. The residue was cooled in an ice bath, dissolved in DCM (3 mL), and treated with 2.0M dimethylamine in THF (4 mL). After stirring at ambient temperature overnight, the reaction mixture was diluted with EtOAc (80 mL), then washed with 20 mL each 2M HCl, 2M NaOH, and water. The organic layer was dried on MgSO$_4$ and the residue concentrated to give N,N,2-trimethyl-4-bromobenzamide (460 mg) as a yellowish oil.

A flask was charged with this crude bromide (27 mg), Pd(dppf)Cl$_2$ (3 mg), KOAc (38 mg), and bis(pinacolato)diboron (34 mg), flushed with a stream of Ar, and DMSO (3 mL) was added. The mixture was heated at 80° C. during 1.5 h, then 82 (30 mg) and Cs$_2$CO$_3$ (36 mg) were added and heating continued for 2.5 h. The reaction mixture was then purified by HPLC. Concentration of the appropriate fractions gave 150 as a white solid, 8 mg. MS (ESI(+)) m/e 578.4 (M+H)$^+$.

Example 136

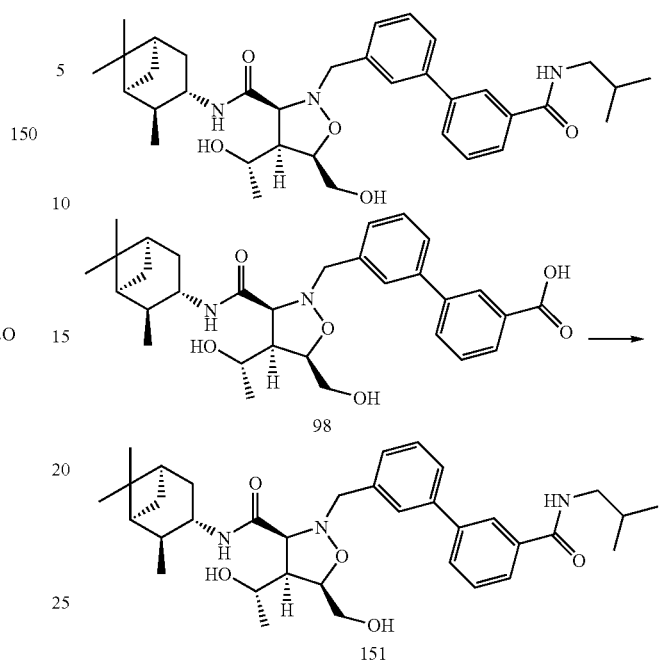

To a solution of crude 98 (25 mg) and isobutylamine (16 µL) in DMF (700 µL) was added HBTU (30 mg). After shaking for 1 h, the reaction mixture was diluted with MeOH (800 µL) and purified by HPLC. Concentration of the appropriate fractions gave 151 as a white solid, 24 mg. MS (ESI(+)) m/e 592.2 (M+H)$^+$.

Example 137

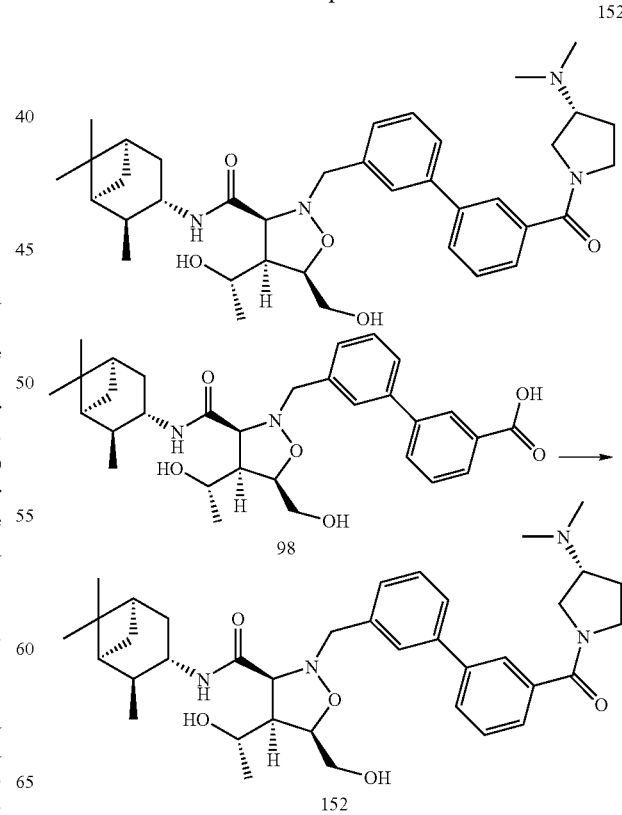

To a solution of crude 98 (19 mg) and (3R)-3-(dimethylamino)pyrrolidine (18 µL) in DMF (525 µL) was added HBTU (25 mg). After shaking for 1 h, the reaction mixture was diluted with MeOH (1 mL) and purified by HPLC. Concentration of the appropriate fractions gave 152 as a white solid, 17 mg. MS (ESI(+)) m/e 633.3 (M+H)+.

Example 138

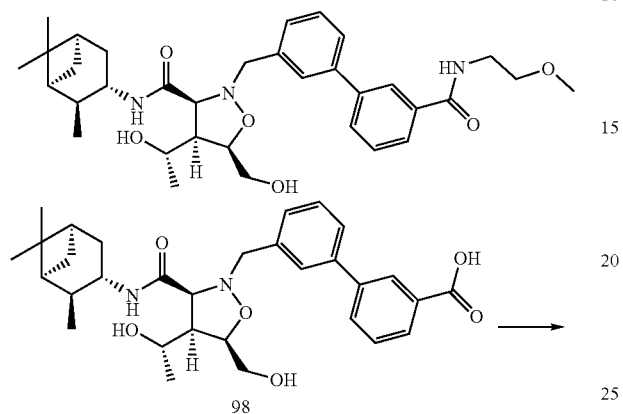

98

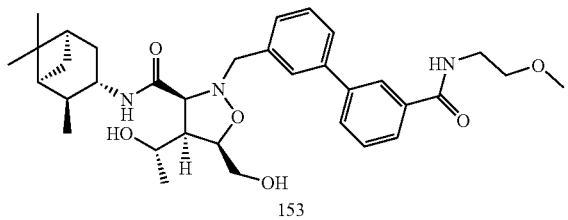

-continued

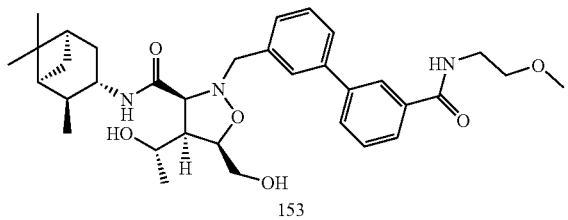

153

To a solution of crude 98 (25 mg) and 2-methoxyethylamine (13 µL) in DMF (700 µL) was added HBTU (40 mg). After shaking for 1 h, the reaction mixture was diluted with MeOH (800 µL) and purified by HPLC. Concentration of the appropriate fractions gave 153 as a white solid, 20 mg. MS (ESI(+)) m/e 594.3 (M+H)+.

Example 139

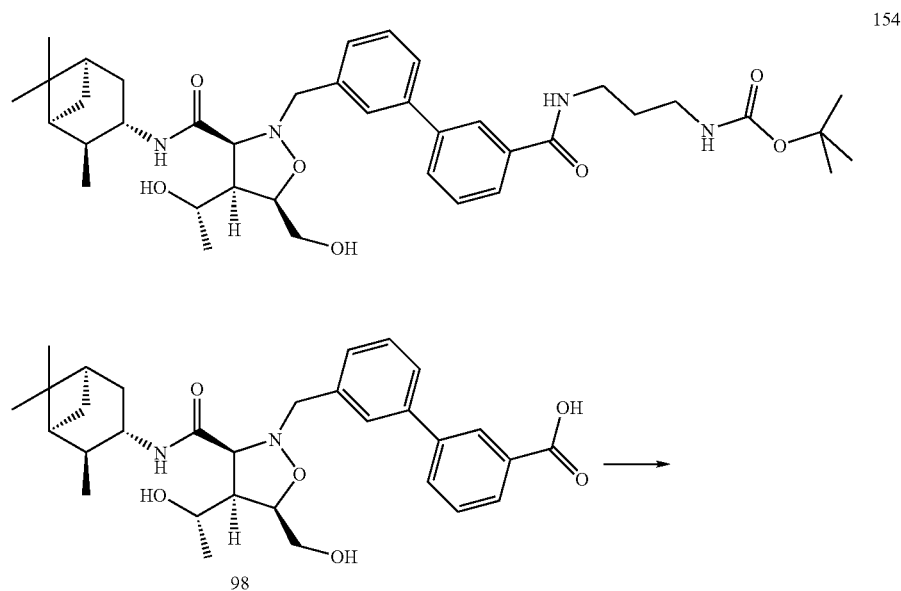

98

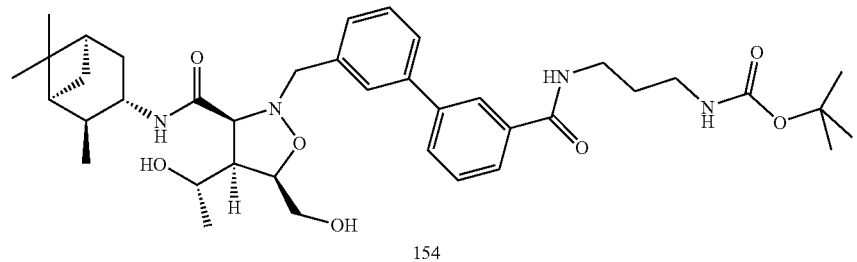

154

To a solution of crude 98 (25 mg) and N-(tert-butoxycarbonyl)-1,3-diaminopropane (28 mg) in DMF (700 μL) was added HBTU (30 mg). After shaking for 1 h, the reaction mixture was diluted with MeOH (800 μL) and purified by HPLC. Concentration of the appropriate fractions gave 154 as a white solid, 26 mg. MS (ESI(+)) m/e 693.3 (M+H)+.

Example 140

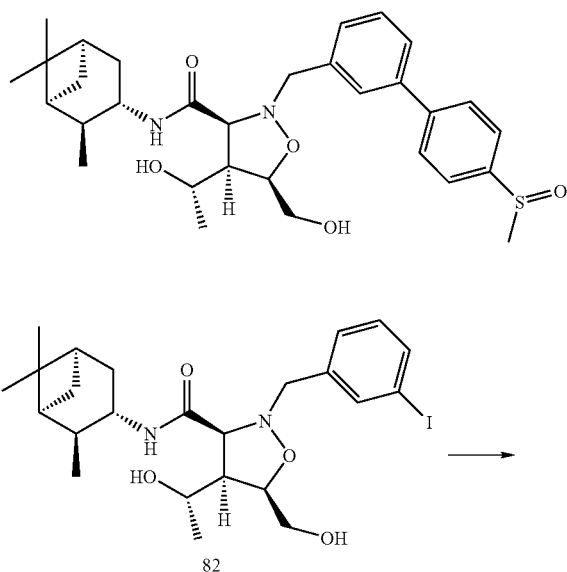

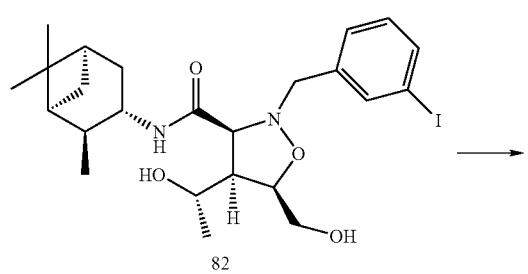

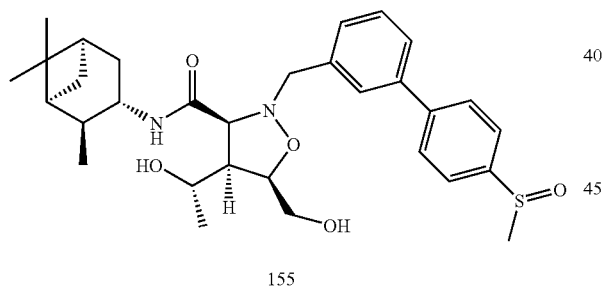

In a small flask were combined 82 (50 mg), 3-methylthiophenylboronic acid (31 mg), Cs₂CO₃ (60 mg), KOAc (10 mg) and Pd(dppf)Cl₂ (7 mg). The flask was flushed with Ar and DMSO (5 mL) added. After heating at 60° C. during 1.5 h, the reaction mixture was purified by HPLC to give a white solid, 45 mg.

A portion of this solid (35 mg) was dissolved in MeOH (1 mL), and a solution of oxone (20 mg) in water (130 μL) was added. After 30 min, the reaction mixture was added to 10% Na₂S₂O₃ (500 μL), diluted with water (10 mL), and extracted 3×10 mL DCM. The combined organic phases were concentrated and purified by HPLC. Concentration of the appropriate fractions gave 155 as a white solid, 28 mg. MS (ESI(+)) m/e 555.1 (M+H)+.

Example 141

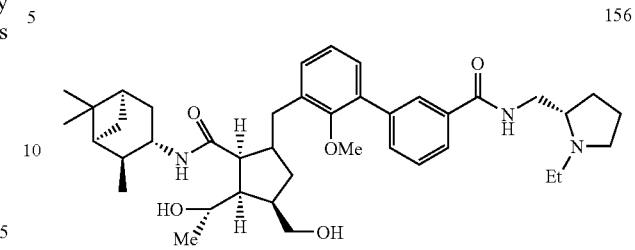

Part A

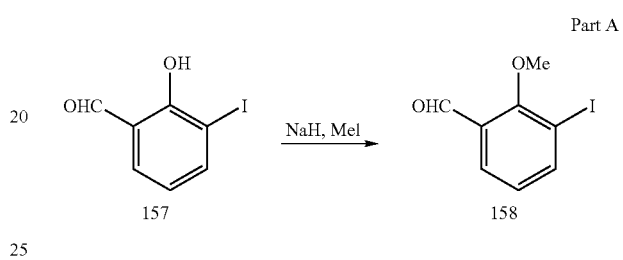

To a solution of phenol 157 (750 mg, 3 mmol) in DMF (5 mL) at 0° C. was added NaH (130 mg, 3.6 mmol) followed by MeI (280 μL, 4.5 mmol). The reaction mixture was stirred at rt for 24 h and then quenched with water. The mixture was diluted with EtOAc and washed with water (2×) then brine. The solution was dried over MgSO₄, filtered and concentrated to afford 795 mg (100%) of crude product 157.

Part B

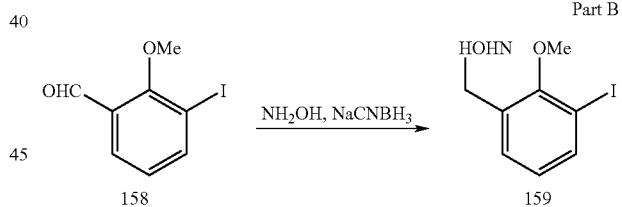

Aldehyde 158 (795 mg, 3.03 mmol) and hydroxylamine hydrochloride (253 mg, 3.64 mmol) were dissolved in THF/MeOH (3:2, 10 mL). Water (2 mL) was added and the pH was adjusted to 9 with 6.0 N KOH. The reaction mixture was stirred at rt overnight. After 16 h, sodium cyanoborohydride (381 mg, 6.07 mmol) was added followed by a crystal of methyl orange. The pH was adjusted to 2 and the resulting ruby red color was maintained for the duration of the reaction by the frequent addition of 1 N HCl. After stirring for 2 h another portion of sodium cyanoborohydride (381 mg) was added. After stirring for a total of 16 h, the pH of the reaction mixture was brought to 7 and DCM was added. The mixture was washed with water (3×), brine and then dried over MgSO₄. The crude product was purified by flash chromatography (50% EtOAc in hexanes then 100% EtOAc) to afford 706 mg (83%) of hydroxylamine 159.

Part C

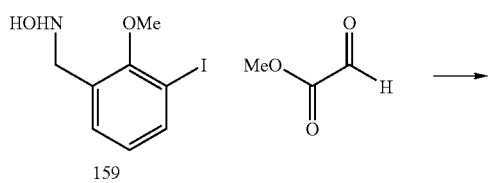

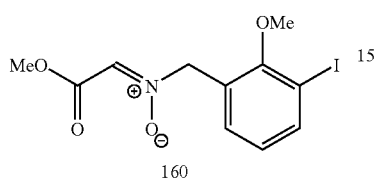

A solution of hydroxylamine 159 (705 mg, 2.53 mmol) and methyl glyoxylate (445 mg, 5.05 mmol) in benzene (15 mL) was heated at reflux with a Dean Stark trap overnight. Excess solvent was removed under reduced pressure and the resulting nitrone (160) was taken on crude in the next step.

Part D

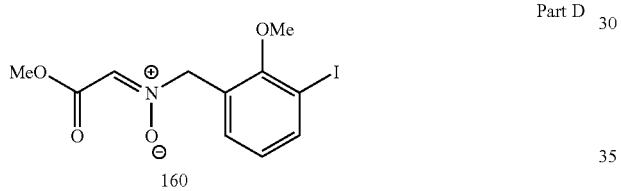

Nitrone 160 (882 mg, 2.53 mmol), allylic alcohol 6 (820 mg, 3.79 mmol) and Ti(iOPr)$_4$ (1.12 mL, 3.79 mmol) were dissolved in toluene (5 mL) and heated in the microwave at 120° C. for 10 min The reaction mixture was diluted with EtOAc (15 mL) and 3-(dimethylamino)-1,2-propanediol (500 µL) was added. After stirring for 2 h, EtOAc was added and the mixture was washed with water (3×) then brine, dried over MgSO$_4$, filtered over Celite and concentrated. The crude residue was purified by flash chromatography (5:1 hexanes/EtOAc) to afford 575 mg (43%) of lactone 161.

Part E

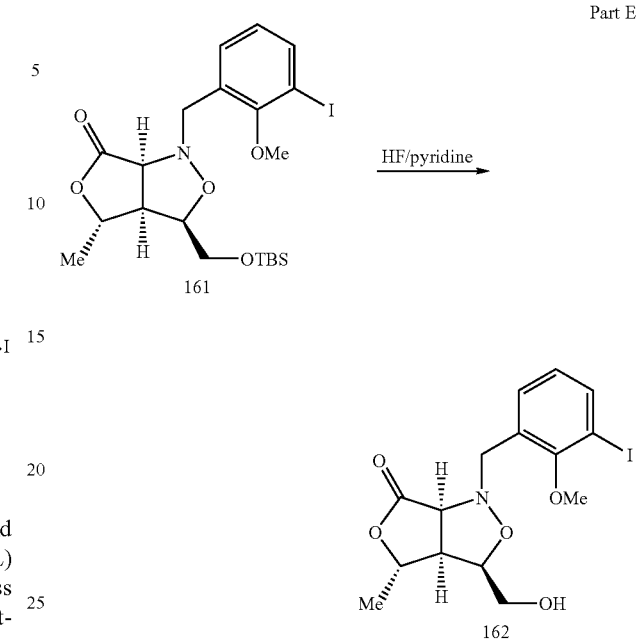

To a solution of 161 (225 mg, 0.042 mmol) in THF (6 mL) was added pyridine (2 mL) and HF/pyridine (2 mL). The mixture was stirred at rt for 4 hrs then TMSOMe (8 mL) was added. Solvent was removed under reduced pressure and the crude product was purified by flash chromatography (EtOAc) to afford 128 mg (72%) of 162 as a white foam.

Part F

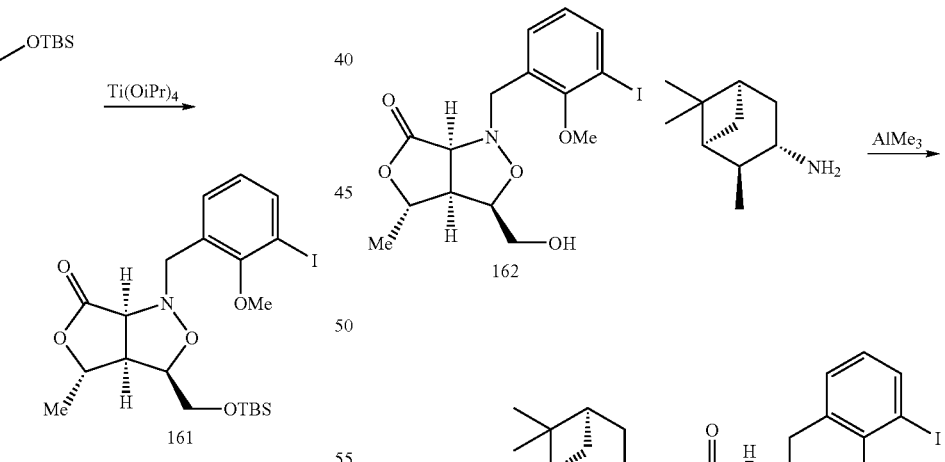

To a flame-dried 10-mL round bottom flask containing (+)-isopinocampheylamine (108 µL, 0.611 mmol) and DCM (2.0 mL) was added trimethylaluminum in hexanes (2.0 M, 305 µL, 0.611 mmol ). After stirring for 15 min, a solution of lactone 162 (128 mg, 0.305 mmol) in DCM (4 mL) was added and the mixture was stirred at rt overnight. The reaction was quenched by the addition of saturated aqueous Rochelle salt (5 mL) and the mixture was stirred rapidly for 2 h. DCM was added and the mixture washed with water (3×) then brine. The solution was dried over MgSO$_4$, filtered and concentrated under reduced pressure. Purification of the crude residue by flash chromatography (EtOAc) afforded 160 mg (91%) of 163.

Part G

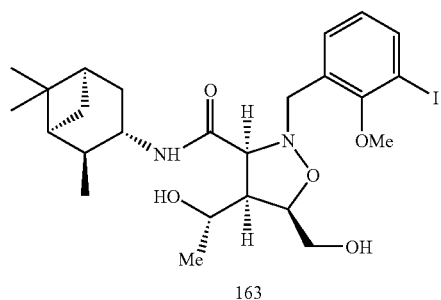

163

-continued

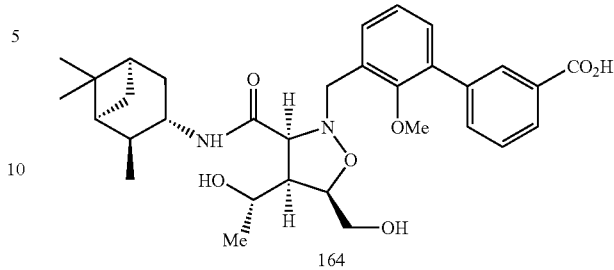

164

To a mixture of iodide 163 (45 mg, 0.079 mmol), 3-carboxyphenyl boronic acid (26 mg, 0.160 mmol), Cs$_2$CO$_3$ (100 mg, 0.31 mmol), KOAc (8 mg, 0.079 mmol) and Pd(dppf)Cl$_2$ (6 mg 0.008 mmol) under argon was added DMSO (2 mL, degassed). The reaction mixture was stirred at 60° C. for 12 h. LCMS analysis of the reaction mixture showed some remaining starting material, thus another 6 mg (0.008 mmol) of Pd(dppf)Cl$_2$ was added, and the mixture was stirred at 60° C. for 6 h. The mixture was diluted with DCM and washed with water (3×) then brine and dried over MgSO$_4$ and concentrated. The crude product (164) was used in the next step without purification.

Part H

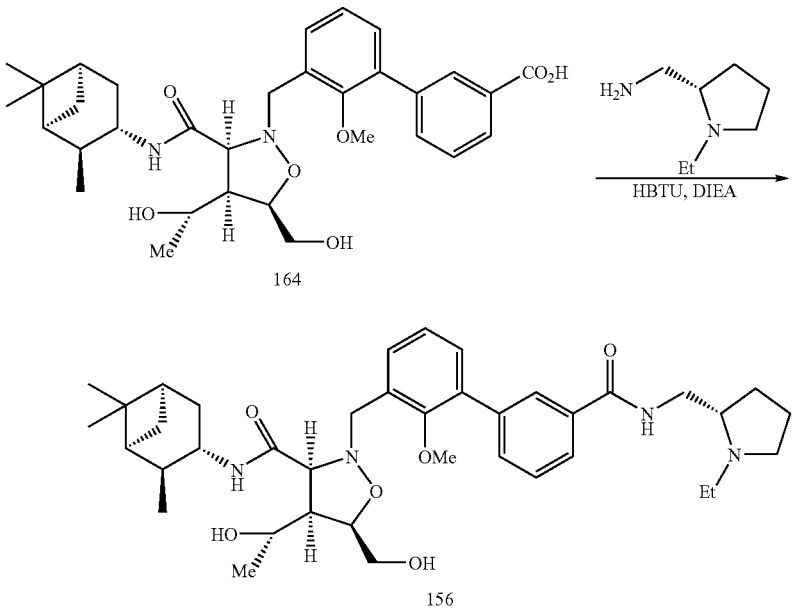

164

156

-continued

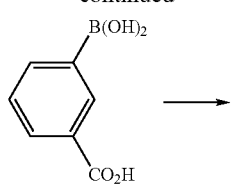

To 22 mg (0.039 mmol) of acid 164 dissolved in DMF (700 µL) was added (S)-2-aminoethyl)-1-ethylpyrrolidine (20 mg, 0.16 mmol), DIEA (27 µL, 0.16 mmol) and HBTU (44 mg, 0.12 mmol). The reaction mixture was stirred at rt for 3 h and then diluted with methanol (800 µL). The crude product was purified by HPLC and fractions containing the desired product were combined and lyophilized to afford 5 mg (20%) of 156 as a fluffy white solid. MS (ESI(+)) m/e 677.4 (M+H)$^+$.

Example 142

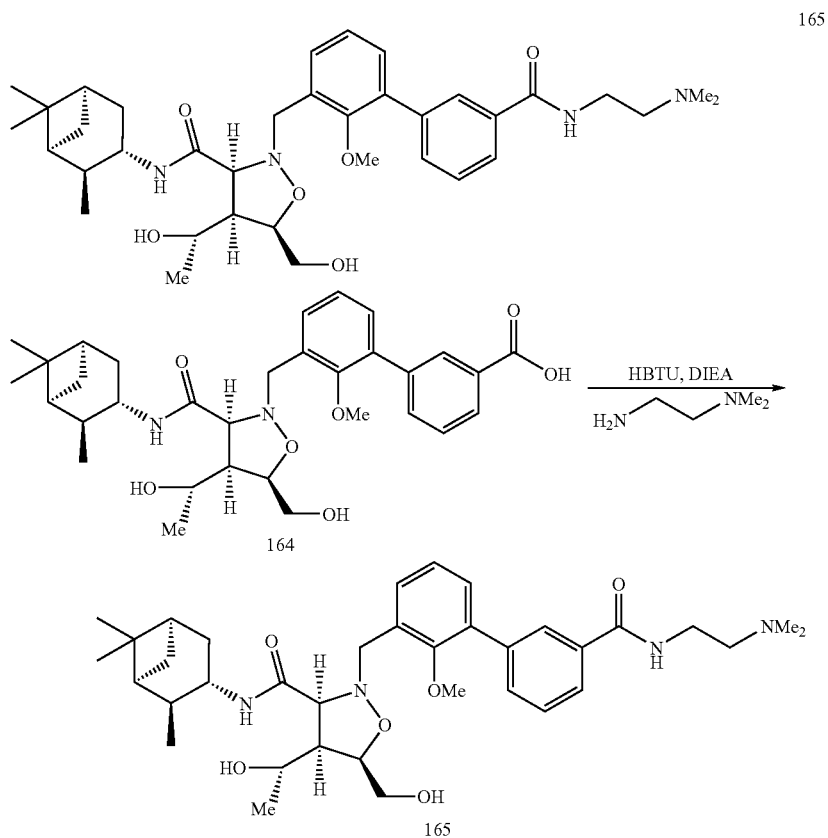

To 22 mg (0.039 mmol) of acid 164 dissolved in DMF (700 µL) was added dimethylethylenediamine (17 µL, 0.16 mmol), DIEA (27 µL, 0.16 mmol) and HBTU (44 mg, 0.12 mmol). The reaction mixture was stirred at rt for 3 h and then diluted with methanol (800 µL). The crude product was purified by HPLC and fractions containing the desired product were combined and lyophilized to afford 5 mg (20%) of 165 as a fluffy white solid.

Example 143

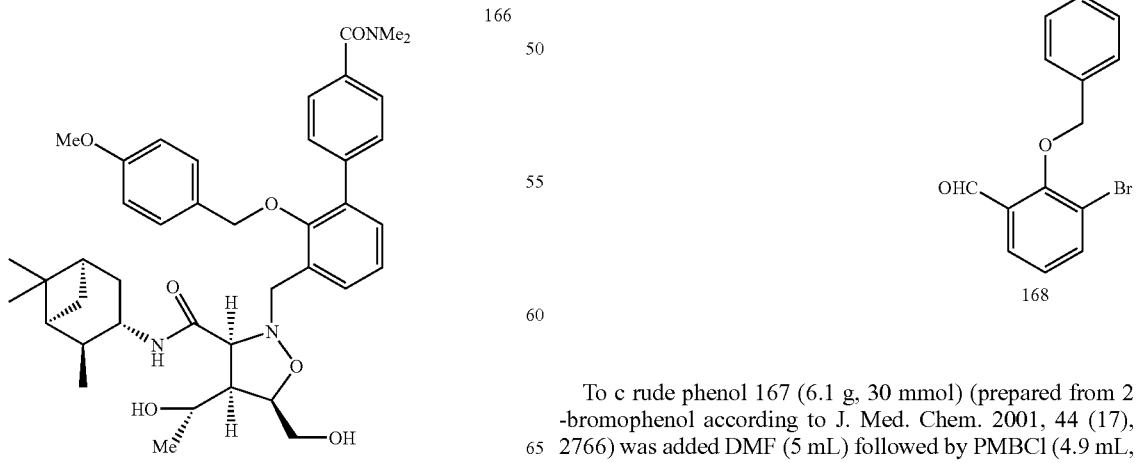

To c rude phenol 167 (6.1 g, 30 mmol) (prepared from 2-bromophenol according to J. Med. Chem. 2001, 44 (17), 2766) was added DMF (5 mL) followed by PMBCl (4.9 mL, 36 mmol) and $K_2CO_3$ (6.3 g, 46 mmol). The reaction mixture was stirred at 60° C. for 5. After cooling to rt, the mixture was diluted with water and extracted with EtOAc (2×). The EtOAc layer was washed with brine, dried over MgSO₄, filtered and concentrated. Purification of the crude material (yellow oil) by flash chromatography (9:1 hexanes/EtOAc) afforded 5.7 g (58% over two steps) of 168 as a white solid.

Part B

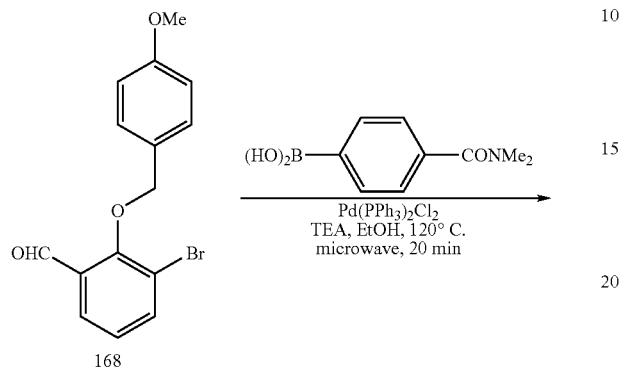

168

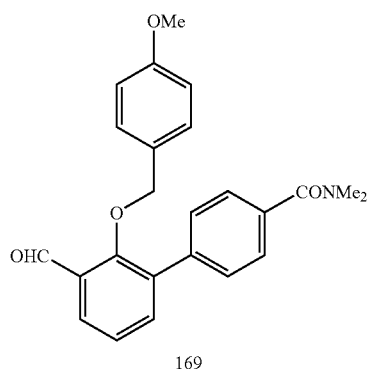

169

To a solution of aryl bromide 168 (500 mg, 2 mmol) in EtOH (5 mL) was added Et₃N (651 μL, 5 mmol), [4-(N,N-dimethylaminocarbony)phenyl]boronic acid (391 mg, 2 mmol) and Pd(PPh₃)₃Cl₂ (109 mg, 0.2 mmol). The mixture was heated by microwave at 120° C. for 20 min and then concentrated and purified by flash chromatography to yield 320 mg (53%) of 169.

Part C

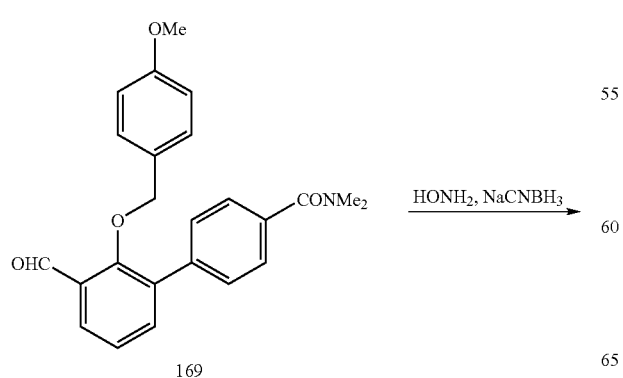

169

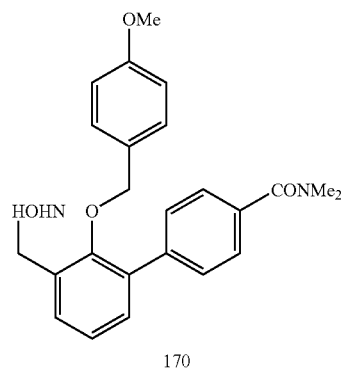

170

Aldehyde 169 (640 mg, 1.64 mmol) and hydroxylamine hydrochloride (136 mg, 1.97 mmol) were dissolved in THF/MeOH (3:2, 10 mL). Water (2 mL) was added and the pH was adjusted to 9 with 6.0 N KOH. The reaction mixture was stirred at rt overnight. After 16 h, sodium cyanoborohydride (207 mg, 3.29 mmol) was added followed by a crystal of methyl orange. The pH was adjusted to 2 and the resulting ruby red color was maintained for the duration of the reaction by the frequent addition of 1 N HCl. After stirring for 2 h another portion of sodium cyanoborohydride (207 mg) was added. After stirring for a total of 16 h, the pH of the reaction mixture was brought to 7 and DCM was added. The mixture was washed with water (3×), brine and then dried over MgSO₄. The crude product was purified by flash chromatography (50% EtOAc in hexanes then 100% EtOAc) to afford 500 mg (75%) of hydroxylamine 170.

Part D

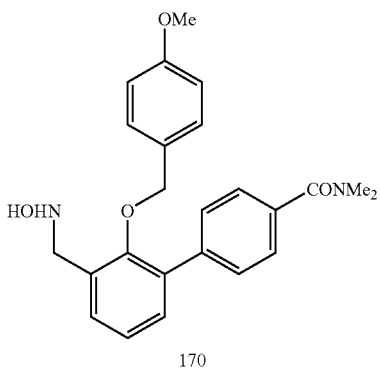

170

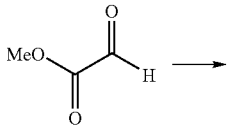

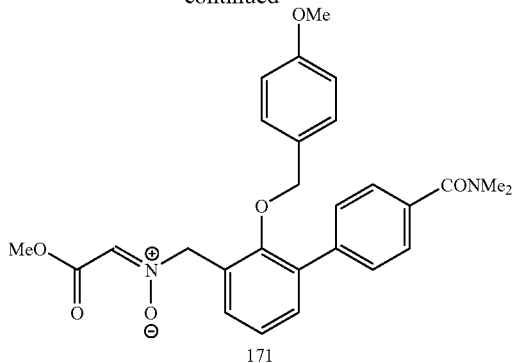
171

A solution of hydroxylamine 170 (500 mg, 1.23 mmol) and methyl glyoxylate (217 mg, 2.46 mmol) in benzene (15 mL) was heated at reflux with a Dean Stark trap overnight. Excess solvent was removed under reduced pressure and the resulting nitrone (171) was taken on crude in the next step.

Part E

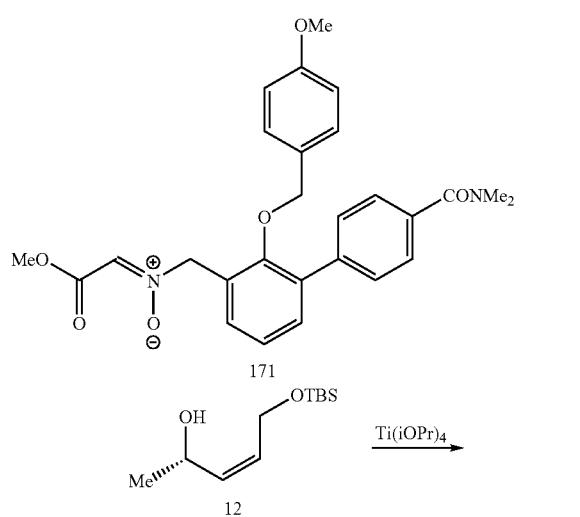

Nitrone 171 (586 mg, 1.23 mmol), allylic alcohol 12 (399 mg, 1.84 mmol) and Ti(iOPr)$_4$ (544 μL, 1.84 mmol) were dissolved in toluene (5 mL) and heated in the microwave at 120° C. for 10 min The reaction mixture was diluted with EtOAc (10 mL) and 3-(dimethylamino)-1,2-propanediol (200 μL) was added. After stirring for 2 h, EtOAc was added and the mixture was washed with water (3×) then brine, dried over MgSO$_4$, filtered over Celite and concentrated. The crude residue was purified by flash chromatography (DCM then 10% MeOH in DCM) to afford 438 mg (54%) of lactone 172.

Part F

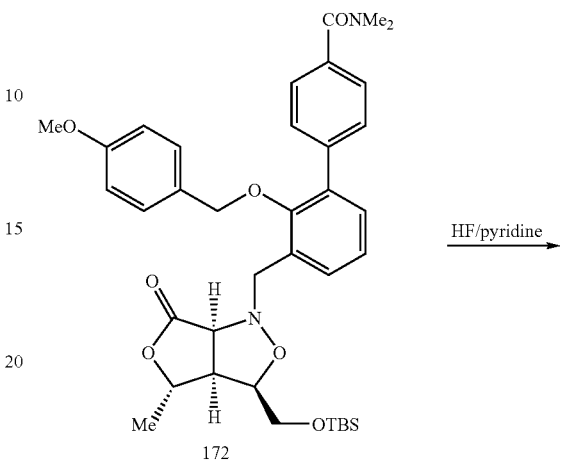
172

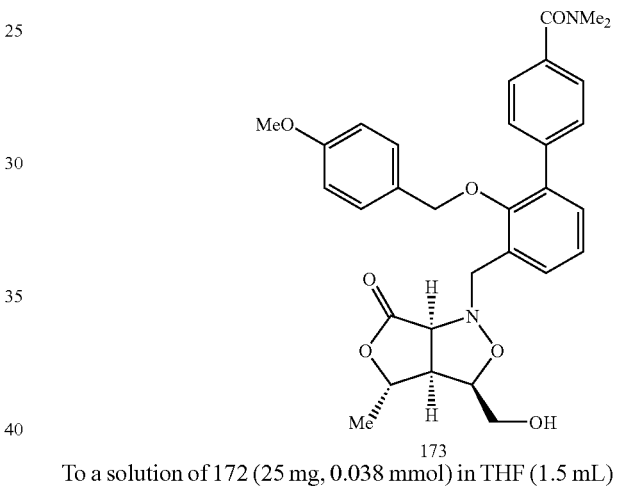
173

To a solution of 172 (25 mg, 0.038 mmol) in THF (1.5 mL) at 0° C. was added pyridine (1.5 mL) and HF/pyridine (450 μL). After stirring for 2 h TMSOMe (1 mL) was added and the mixture was concentrated under reduced pressure. The crude material (173) was used in the next step without purification.

Part G

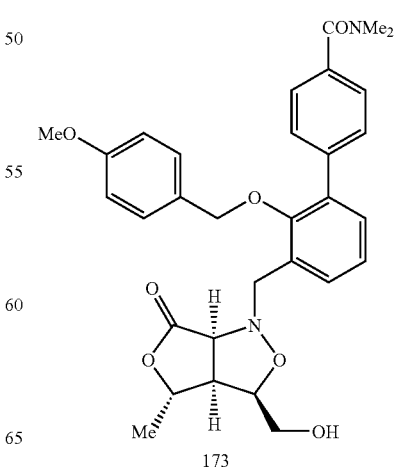
173

-continued

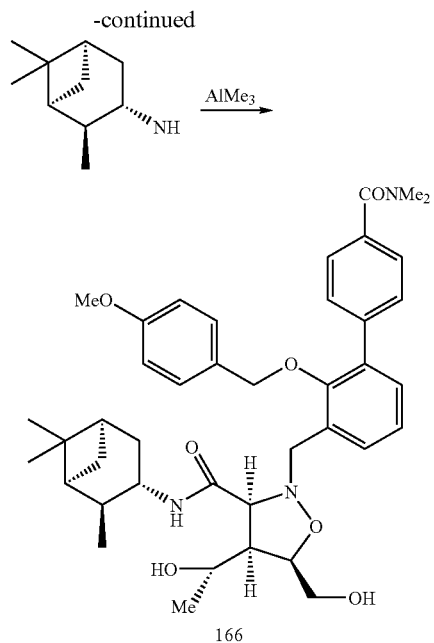

166

To a small, flame-dried vial containing (+)-isopinocampheylamine (16 μL, 0.096 mmol) and DCM (500 μL) was added trimethylaluminum in hexanes (2.0 M, 38 μL, 0.077 mmol). After stirring for 15 min, a solution of lactone 173 (21 mg, 0.038 mmol) in DCM (1 mL) was added and the mixture was stirred at rt overnight. The reaction was quenched by the addition of saturated aqueous Rochelle salt (2 mL) and DCM (3 mL) and the mixture was stirred rapidly for 2 h. DCM was added and the mixture washed with water (3×) then brine. The solution was dried over MgSO$_4$, filtered and concentrated under reduced pressure. Purification of the crude residue by flash chromatography (2% MeOH in DCM) afforded 18 mg (67%) of 166. MS (ESI(+)) m/e 700.3 (M+H)$^+$.

Example 144

0174

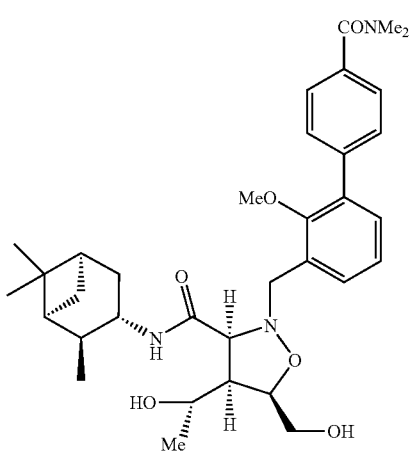

-continued

Part A

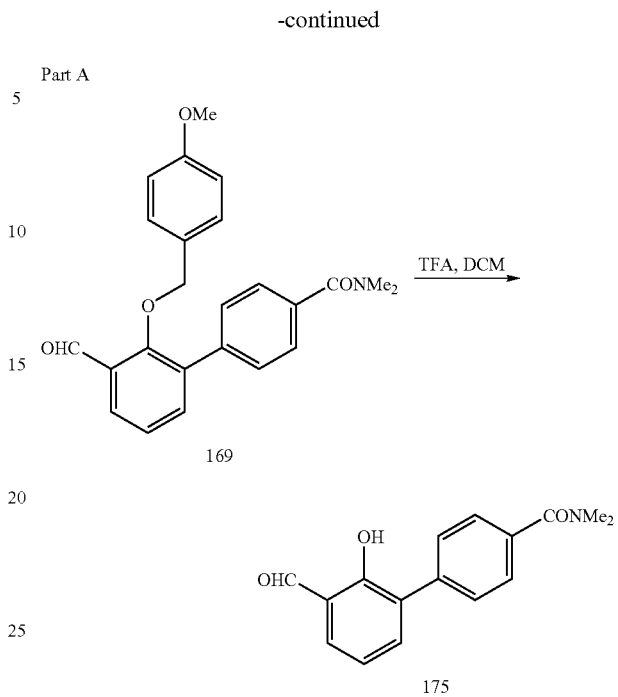

To a solution of 169 in DCM (100 mL) was added TFA (2 mL). The reaction mixture was stirred for 3 h at rt and then diluted with DCM. The mixture was washed with saturated aqueous NaHCO3 (2×) and water, and then dried over MgSO4 and concentrated. The crude residue was purified by flash chromatography (2:1 to 1:1 hexanse/EtOAc) to afford 1.8 g (87%) of 175 as a yellow oil.

Part B

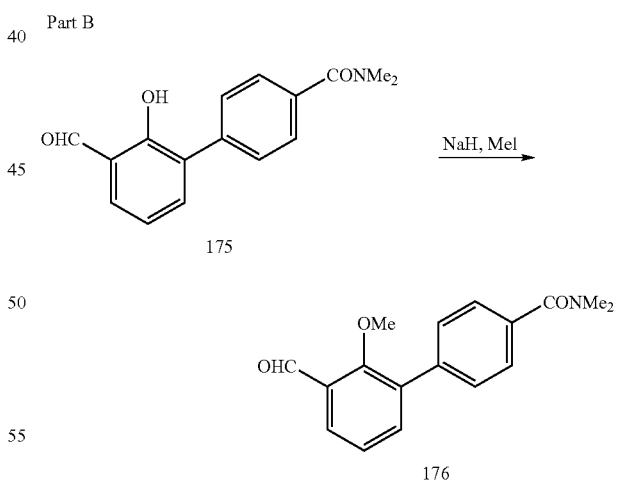

To a solution of phenol 175 (490 mg, 1.8 mmol) in DMF (8 mL) was added NaH (90 mg, 2.2 mmol, 60%) followed by MeI (170 μL, 2.7 mmol). The reaction mixture was stirred at rt for 3 h and then diluted with water and extracted with EtOAc. The EtOAc layer was washed with water then brine, dried over MgSO$_4$ and concentrated. The crude residue was purified by flash chromatography (2:1 then 1:1 hexanes/EtOAc) to afford 453 mg (88%) of 176.

Part C

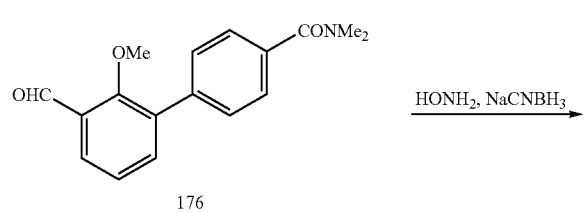

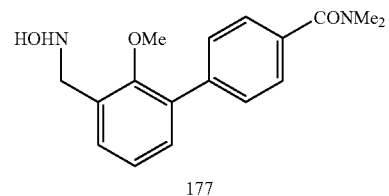

Part E

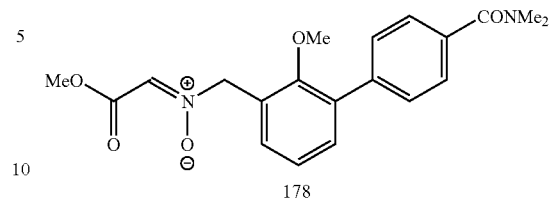

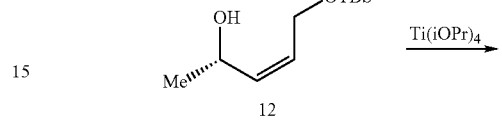

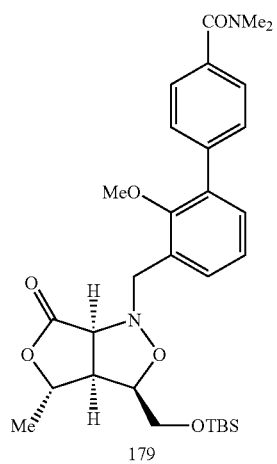

Aldehyde 176 (453 mg, 1.60 mmol) and hydroxylamine hydrochloride (133 mg, 1.92 mmol) were dissolved in THF/MeOH (3:2, 10 mL). Water (2 mL) was added and the pH was adjusted to 9 with 6.0 N KOH. The reaction mixture was stirred at rt overnight. After 16 h, sodium cyanoborohydride (201 mg, 3.20 mmol) was added followed by a crystal of methyl orange. The pH was adjusted to 2 and the resulting ruby red color was maintained for the duration of the reaction by the frequent addition of 1 N HCl. After stirring for 2 h another portion of sodium cyanoborohydride (201 mg) was added. After stirring for a total of 16 h, the pH of the reaction mixture was brought to 7 and DCM was added. The mixture was washed with water (3×), brine and then dried over MgSO₄. The crude product was purified by flash chromatography (50% EtOAc in hexanes then 100% EtOAc) to afford 402 mg (84%) of hydroxylamine 177.

Nitrone 178 (496 mg, 2.53 mmol), allylic alcohol 6 (435 mg, 2.01 mmol) and Ti(iOPr)₄ (0.593 mL, 2.01 mmol) were dissolved in toluene (5 mL) and heated in the microwave at 120° C. for 10 min The reaction mixture was diluted with EtOAc (10 mL) and 3-(dimethylamino)-1,2-propanediol (200 µL) was added. After stirring for 2 h, EtOAc was added and the mixture was washed with water (3×) then brine, dried over MgSO₄, filtered over Celite and concentrated. The crude residue was purified by flash chromatography (DCM then 10% MeOH in DCM) to afford 575 mg (77%) of lactone 179.

Part D

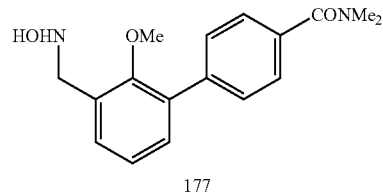

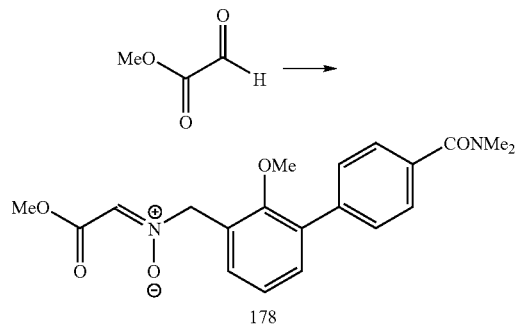

A solution of hydroxylamine 177 (402 mg, 1.34 mmol) and methyl glyoxylate (236 mg, 2.68 mmol) in benzene (15 mL) was heated at reflux with a Dean Stark trap overnight. Excess solvent was removed under reduced pressure and the resulting nitrone (178) was taken on crude in the next step.

Part F

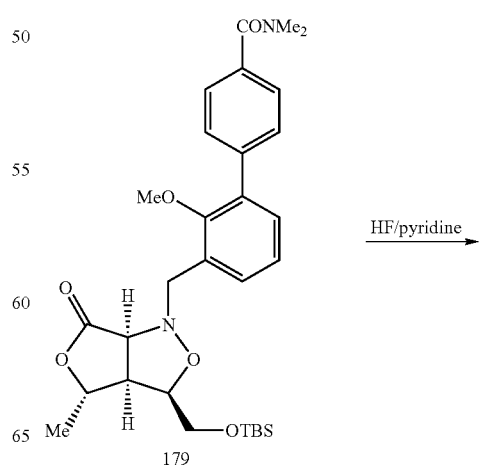

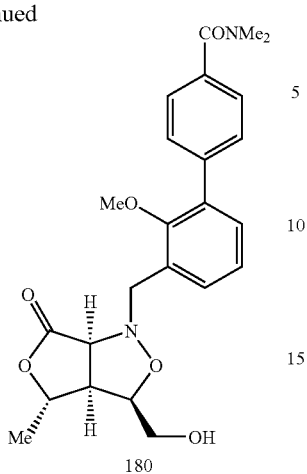

180

To a solution of 179 (510 mg), 919 mmol) in THF (10 mL) at 0° C. was added pyridine (5 mL) followed by HF/pyridine (2 mL). The reaction mixture was stirred for 5 h and then quenched by the addition of TMSOMe (15 mL) and concentrated. The crude residue was purified by flash chromatography (2% MeOH in DCM) to afford 267 mg (66%) of 180.

Part G

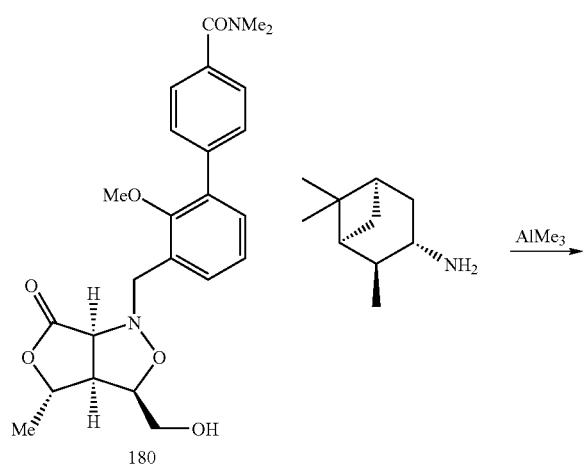

180

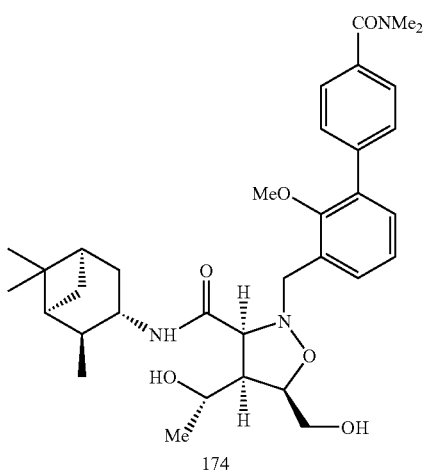

174

To flame-dried 25-mL round bottom flask containing (+)-isopinocampheylamine (160 μL, 0.98 mmol) and DCM (2 mL) was added trimethylaluminum in hexanes (2.0 M, 490 μL, 0.98 mmol ). After stirring for 20 min, a solution of lactone 180 (215 mg, 0.490 mmol) in DCM (8 mL) was added and the mixture was stirred at rt overnight. The reaction was quenched by the addition of saturated aqueous Rochelle salt (10) and DCM (10 mL) and the mixture was stirred rapidly for 2 h. DCM was added and the mixture washed with water (3×) then brine. The solution was dried over MgSO$_4$, filtered and concentrated under reduced pressure. Purification of the crude residue by flash chromatography (EtOAc then 1% MeOH in EtOAc) afforded 170 mg (59%) of 174. MS (ESI(+)) m/e 594.2 (M+H)$^+$.

Example 145

181

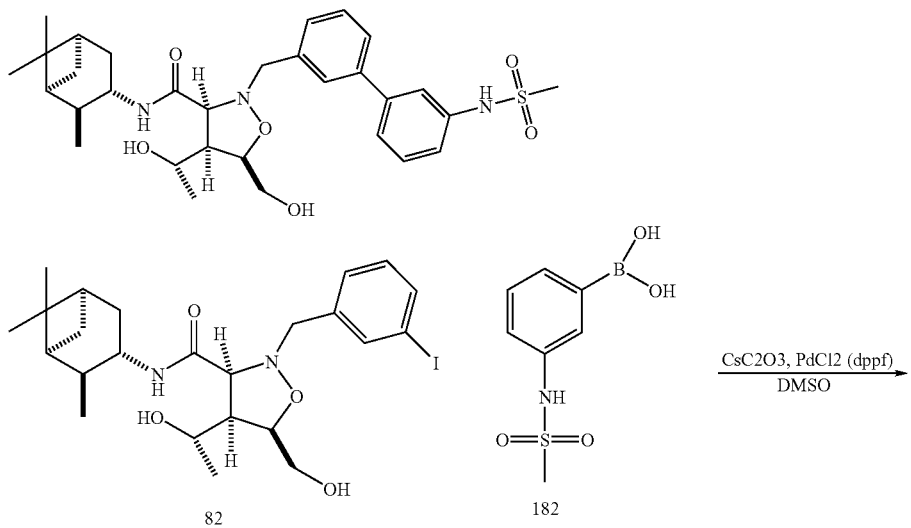

82                                           182

CsC2O3, PdCl2 (dppf)
———————————→
DMSO

-continued

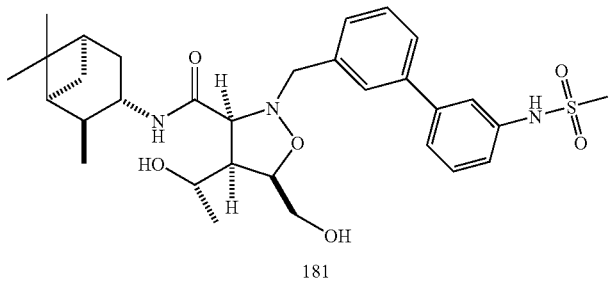
181

Aryl iodide (82)(0.04 mmol), boronic acid (182)(0.08 mmol), cesium carbonate (0.08 mmol) and palladium catalyst (0.008 mmol) are combined in a reaction vial and flushed with argon. DMSO (1 mL) is then added to reaction mixture and stirred under nitrogen at 60° C. for 4 hours. The reaction solution was cooled to rt and diluted with water and extracted 3×5 mL of EtOAc. The organic layers were collected, dried over MgSO$_4$, and concentrated. The crude material was purified byd HPLC. 65% yield. MS (ESI(+)) m/e 586.1 (M+H)$^+$.

Example 146

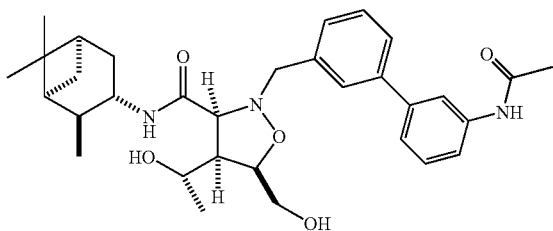
183

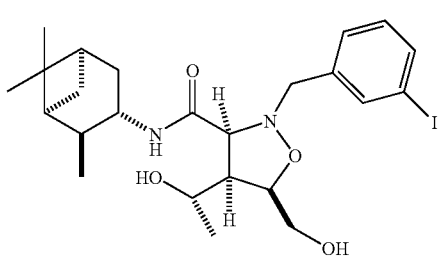
82

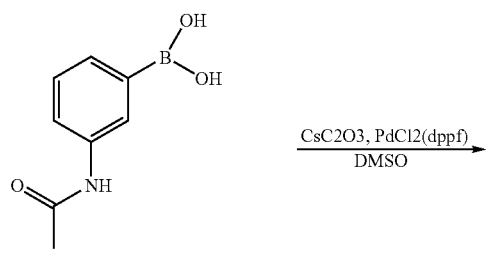
184

CsC2O3, PdCl2(dppf)
―――――――――→
DMSO

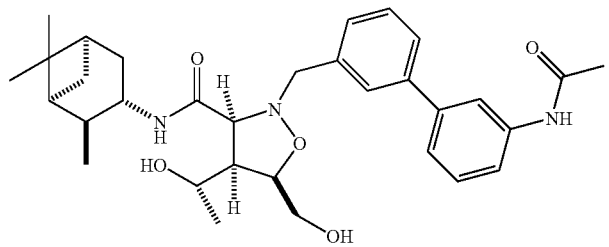
183

Aryl iodide (82)(0.04 mmol), boronic acid (184)(0.08 mmol), cesium carbonate (0.08 mmol) and palladium catalyst (0.008 mmol) are combined in a reaction vial and flushed with argon. DMSO (1 mL) is then added to reaction mixture and stirred under nitrogen at 60 degrees for 4 hours. The reaction solution was cooled to rt and diluted with water and extracted 3×5 mL of EtOAc. The organic layers were collected, dried over MgSO$_4$, and concentrated. The crude material was purified byd HPLC. 60 % yield. MS (ESI(+)) m/e 550.2 (M+H)$^+$.

Example 147

To a solution of biaryl acid (186; made according to the procedure described in the synthesis of 87)(0.03 mmol) in 0.6 ml DMF was added HBTU (0.06 mmol) followed by amine (187)(0.10 mmol). The reaction solution was then capped and stirred at rt for 1 hour under an atmosphere of nitrogen. The reaction solution was cooled to rt and diluted with water and extracted 3×5 mL of EtOAc. The organic layers were collected, dried over MgSO$_4$, and concentrated. The crude material was purified by HPLC. 85% yield. MS (ESI(+)) m/e 697.5 (M+H)$^+$.

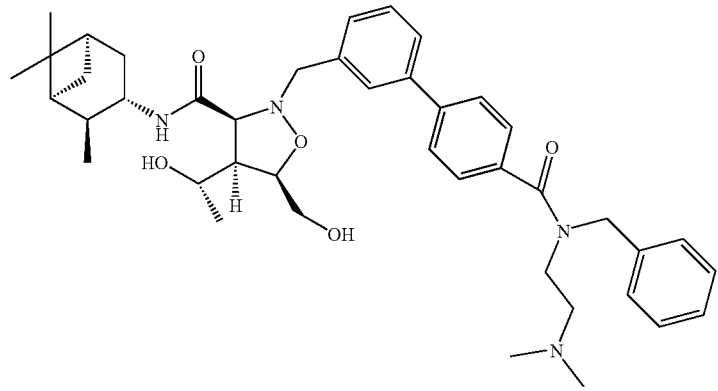

185

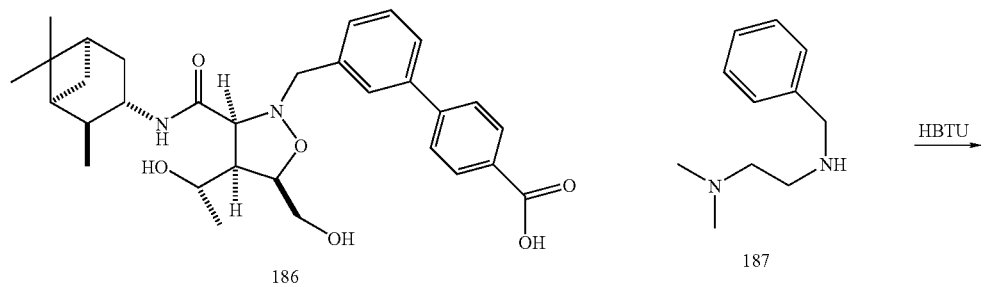

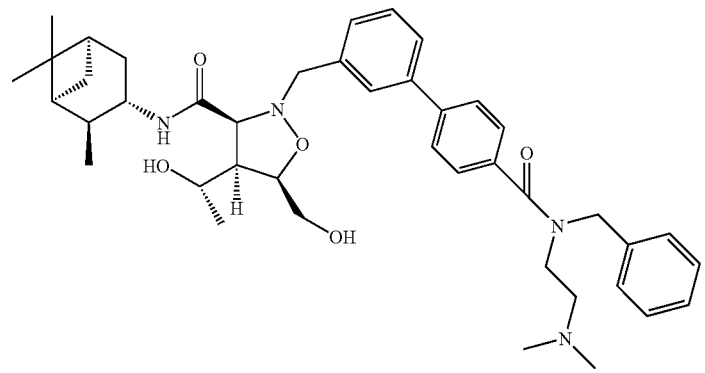

185

257
Example 148

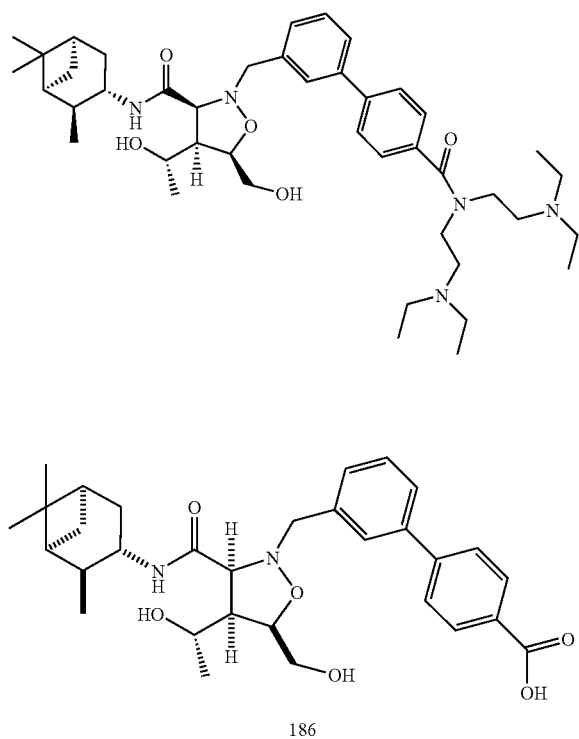

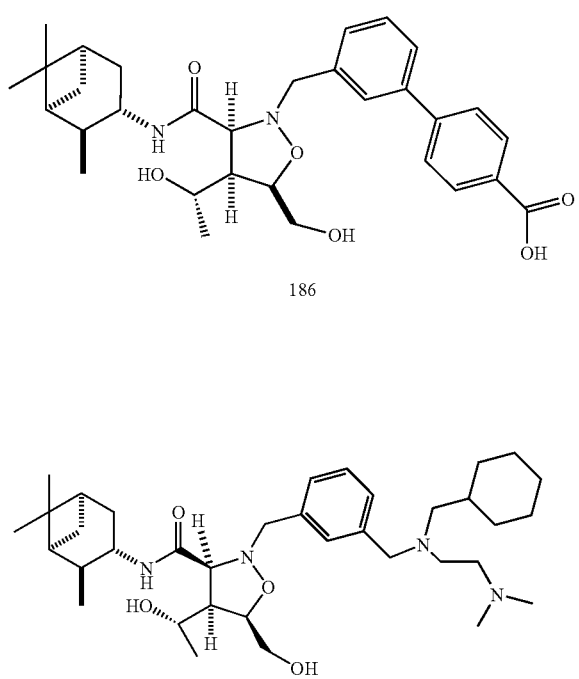

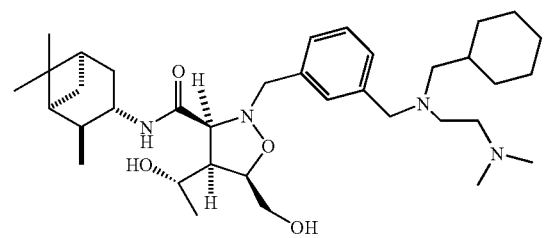

258

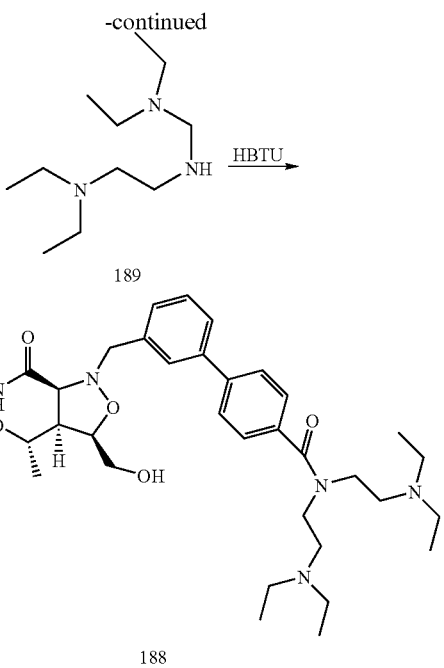

To a solution of biaryl acid (186)(0.03 mmol) in 0.6 ml DMF was added HBTU (0.06 mmol) followed by amine (189)(0.10 mmol). The reaction solution was then capped and stirred at rt for 1 hour under an atmosphere of nitrogen. The reaction solution was diluted with water and extracted 3×5 mL of EtOAc. The organic layers were collected, dried over MgSO$_4$, and concentrated. The crude material was purified by HPLC. 82% yield. MS (ESI(+)) m/e 735.6 (M+H)$^+$.

Part A

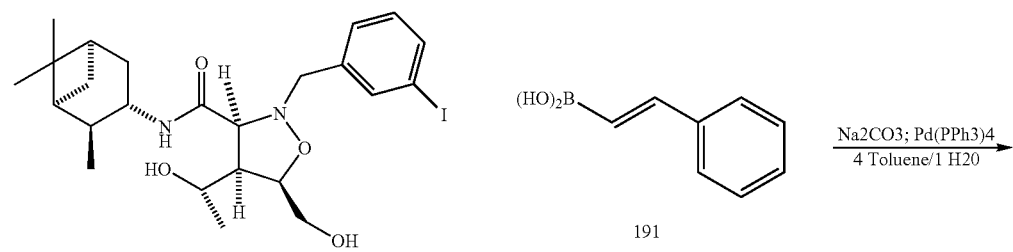

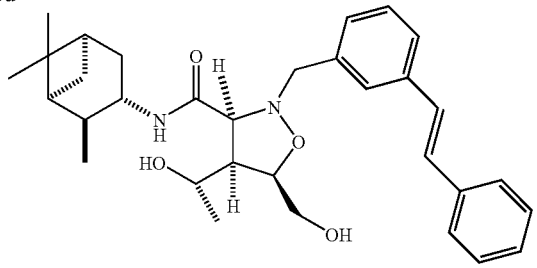

192

Aryl iodide 82 (2.65 mmol), vinyl boronic acid 191 (10.62 mmol), sodium carbonate (10.62 mmol) and palladium tetrakis (0.530 mmol) were weighed into a 100 ml flask. Flask was then purged with argon and content were dissolved in a 4:1 ratio of toluene/water (30 mL). This mixture was then heated at 65° for three hours. The oraganic layer was then collected. The aqueous layer was extracted 3×20 mL of EtOAc. The organic layers were pooled, washed with brine, dried over MgSO$_4$ and concentrated under reduced pressure. The crude material was purified by flash chromatography. Yield 85%.

Part B

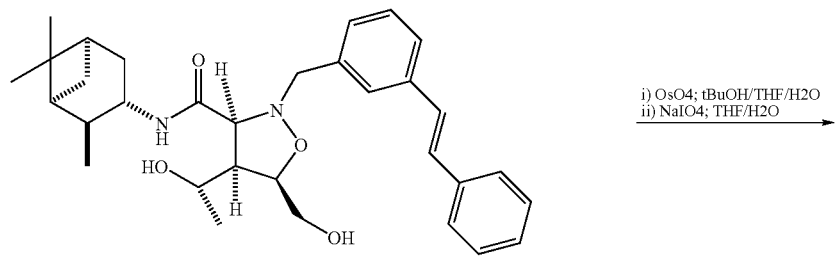

192 i) OsO4; tBuOH/THF/H2O
ii) NaIO4; THF/H2O

Compound 192 (0.110 g, 0.205 mmol) was placed in a 200 ml RB flask to which was added NMO (0.111 g, 0.820 mmol) dissolved in 16 ml tBuOH, 8 ml THF, 2 ml H2O. To this stirring solution was added 2.9 ml of OSO$_4$ (0.210 g, 0.0205 mmol; 2.5% in tBuOH) solution dropwise. The reaction was checked by TLC after 4 h and SM had been completely consumed. Quenched with Na$_2$S$_2$O$_3$ solution and partitioned in ethyl acetate/brine. Washed aqueous layer, dried organics with MgSO$_4$, filtered and concentrated.

This crude product (0.010 g) was then taken up in THF (0.2 mL), to which was added water (20 µL), and sodium periodate (0.0041 g) and stiired overnight. The reaction was quenched with Na$_2$S$_2$O$_3$, washed with brine, dried over MgSO$_4$ and concentrated under reduced pressure. The crude material was purified by flash chromatography. 85% yield.

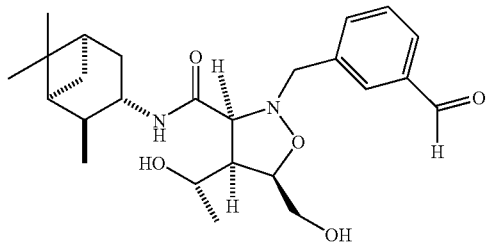

193

Part C

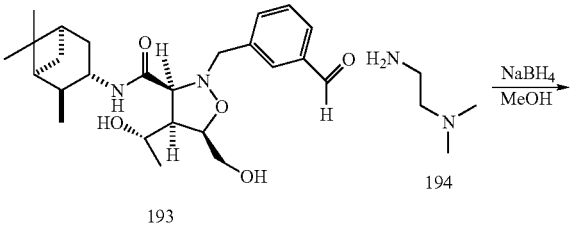

193    194

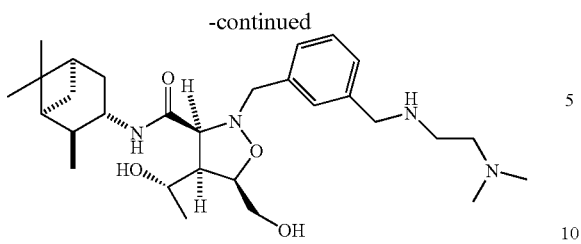

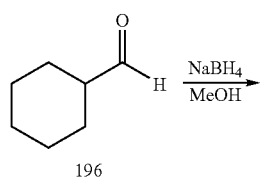

Aldehyde 193 (0.274 mmol) was weighed and transferred to a 25 ml RB flask and dissolved in methanol (6 mL). Amine 194 (0.549 mmol) was then added to this solution and stirred for 1 h. Reaction went from cloudy to clear. To this solution was added sodium borohydride (0.549 mmol) in one portion. Another equivalent of amine was added and the reaction was stirred for 20 minutes. Then another 0.5eq borohydride was added and left to stir. The reaction was quenched with acetic acid (40 µL). Benzene (2 mL) was added the reaction solution was concentrated under reduced pressure. The crude material was azeotroped one more time with 3 ml benzene to a white solid and placed on high vac overnight. This material was used without purification in the next step.

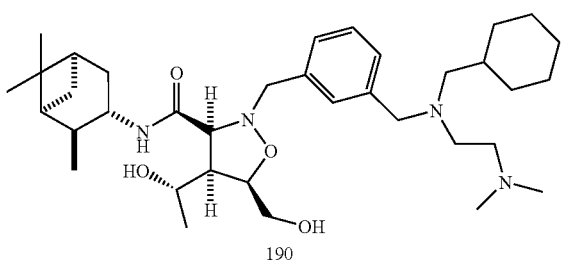

Part D

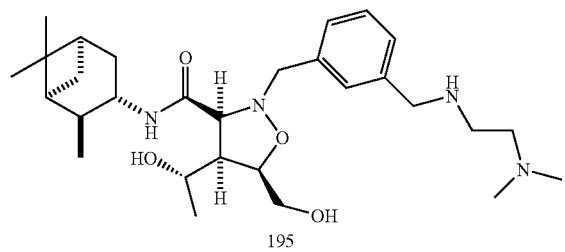

Compound 195 (18 mgs, 0.035 mmol) was added to a ⅛ oz vial to which was added 1 ml DCM followed by the aldehyde 196 (0.070 mmol). Sodium triacetoxyborohydride (0.052 mmol) was then added in one portion and reaction was stirred at rt. Crude material purified by HPLC. 77 % yield. MS (ESI(+)) m/e 613.5 (M+H)$^+$.

Example 150

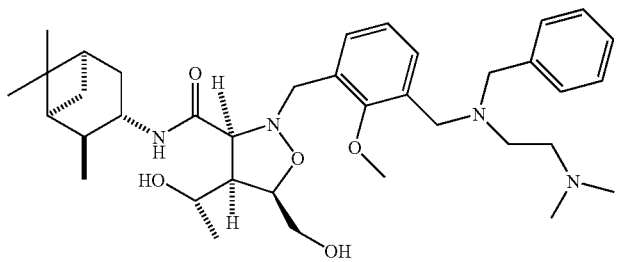

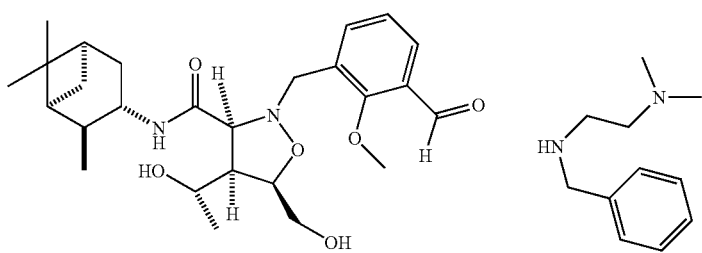

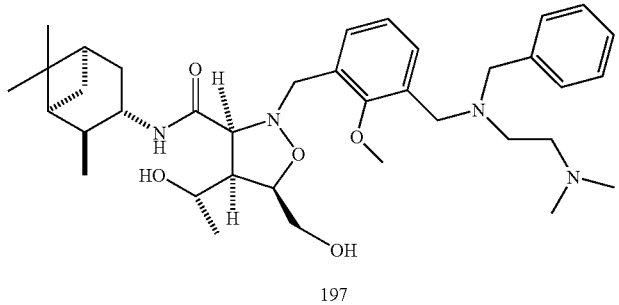

197

Aldehyde 198 was made according to the procedure described in example 149, using aryl iodide 163 in place of aryl iodide 82. 88 % yield.

Aldehyde 198 (0.02 mmol) was added to a flask, dissolved in 0.4 ml DCM, and the amine 199 (0.08 mmol) was added. Sodium triacetoxyborohydride (0.03 mmol) was then added to this mixture and stirred overnight. The crude reaction solution was purified directly on HPLC. 91% yield. MS (ESI(+)) m/e 637.5 (M+H)$^+$.

Example 151

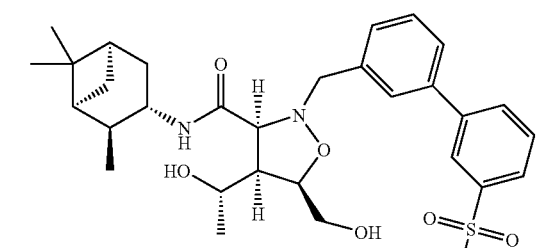

200

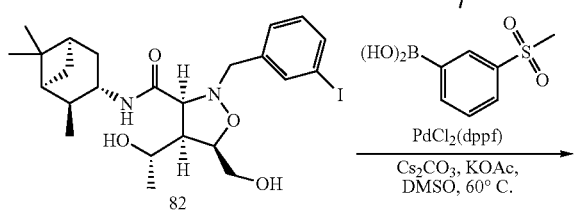

82

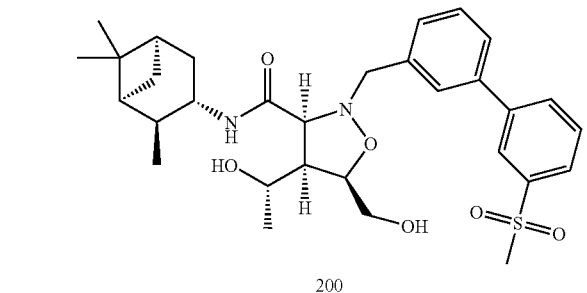

200

To a round-bottomed flask was added 82 (20 mg, 0.035 mmol), 3-methylsulfone-phenylboronic acid (14 mg, 0.070 mmol.), cesium carbonate (34 mg, 0.11 mmol), potassium acetate (3.5 mg, 0.035 eq.), and PdCl$_2$(dppf) (2.9 mg, 0.0035 mmol.). The flask was purged with argon and degassed DMSO (30 min with argon, 1 mL) was added. The reaction was then heated in a 6° C. oil bath under argon for 3 h, cooled and allowed to stir at 23° C. for an additional 12 h. The mixture was diluted with CH$_2$Cl$_2$ (5 mL), saturated brine solution (5 mL) and extracted with CH$_2$Cl$_2$ (2×25 mL). The combined organics were dried (Na$_2$SO$_4$), filtered and concentrated in vacuo. The crude oil was purified by gradient flash chromatography (5 g SiO$_2$, 90-100% EtOAc/Hex) to yield 13 mgs (65%) of the biphenyl methylsulfone 200 as a colorless oil. MS (ESI(+)) m/e 571.2 (M+H)$^+$.

Example 152

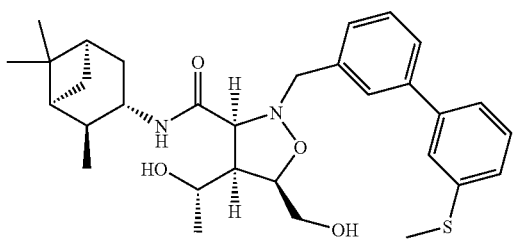

201

Compound 201 was prepared according to the procedure described in example 151 using 3-methylsulfide-phenylboronic acid in place of 3-methylsulfone-phenylboronic acid. Yield 70%. MS (ESI(+)) m/e 539.2 (M+H)$^+$.

Example 153

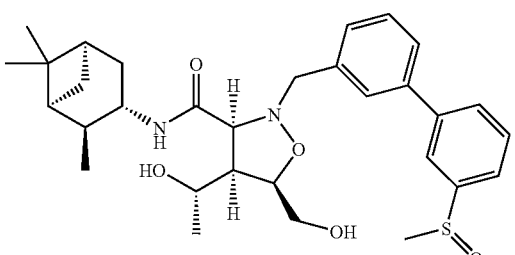

202

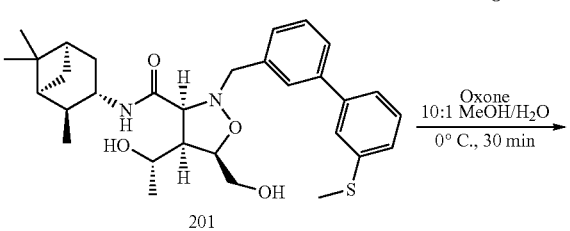

201

-continued

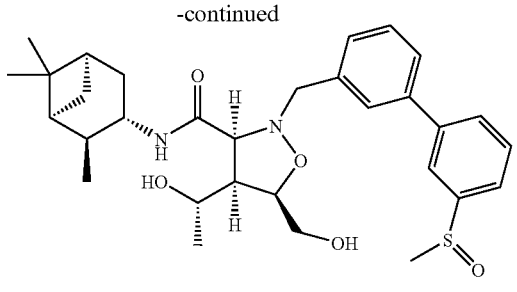

202

To a 0° C. solution of 201 (22 mg, 0.041 mmol) in 10:1 MeOH/THF (2 mL) was added oxone in a single portion (13 mg, 0.02 eq.). After stirring at 0° C. for 1 h, the reaction mixture was diluted with $CH_2Cl_2$ (5 mL), saturated brine solution (5 mL) and extracted with $CH_2Cl_2$ (2×10 mL). The combined organics were dried ($Na_2SO_4$), filtered and concentrated in vacuo. The crude oil was purified by preparative thin layer chromatography (20×20 cm plate, 250 um thickness, 5% MeOH/$CH_2Cl_2$) to yield 18 mg (79%) of a 1:1 diastereomeric mixture of sulfoxides as a white foam. MS (ESI(+)) m/e 555.2 (M+H)$^+$.

Example 154

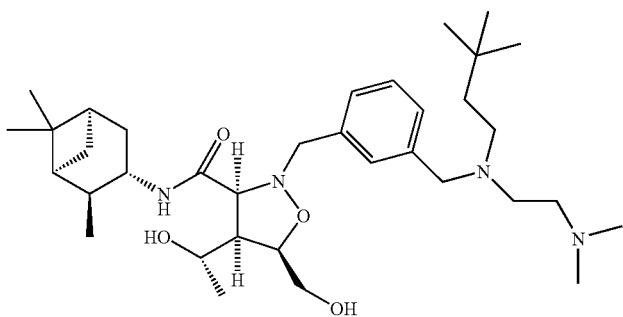

203

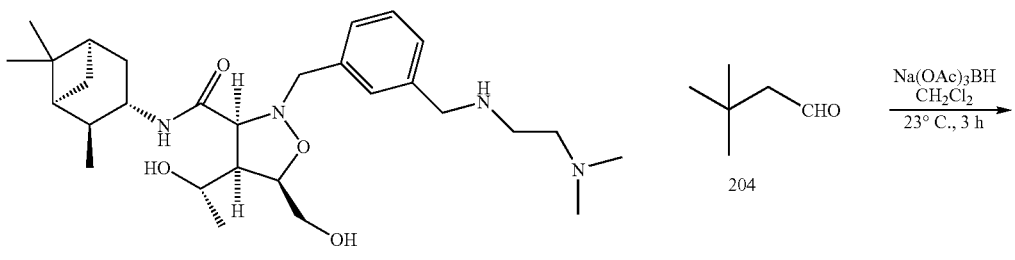

195

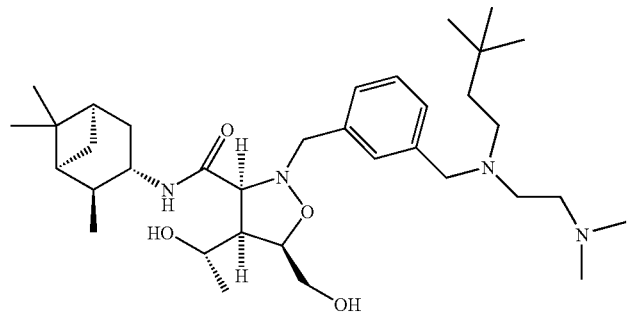

203

To a 23° C. solution of 195 (20 mg, 0.04 mmol) in CH$_2$Cl$_2$ (1 mL) was added 3,3-dimethyylbutyraldehyde (0.08 mmol) followed by Na(OAc)$_3$BH (10 mg, 0.06 eq.). After stirring at 23° C. for 3 h the reaction mixture was filtered through a plug of glass wool and purified directly by HPLC to provide between 5-10 mg (20-50%) of final product. MS (ESI(+)) m/e 601.5 (M+H)$^+$.
Example 155
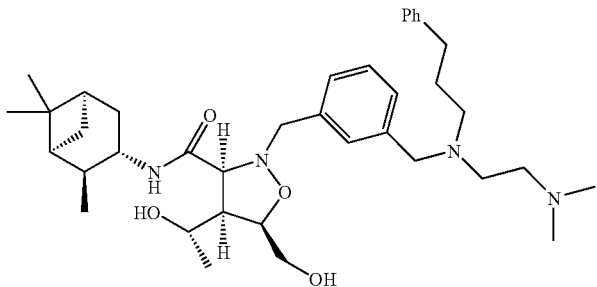
205
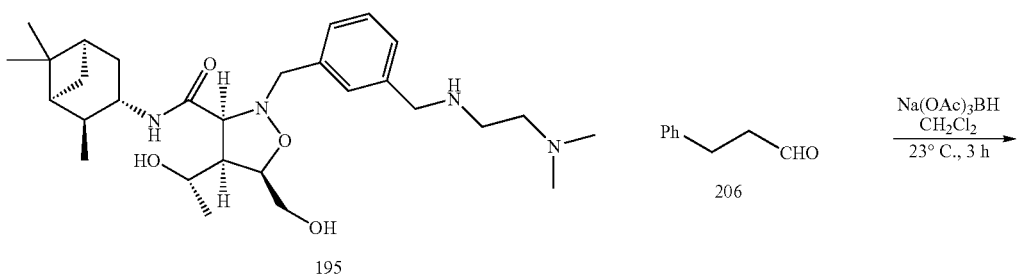
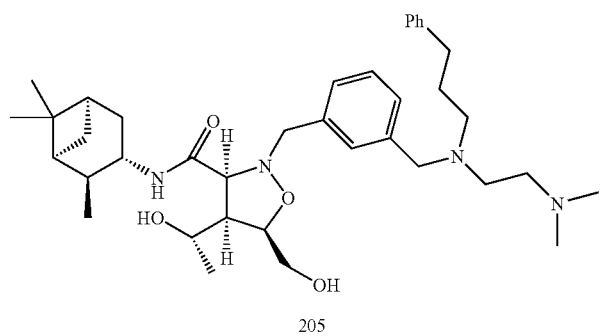
205

To a 23° C. solution of 195 (20 mg, 0.04 mmol) in CH₂Cl₂ (1 mL) was added hydrocinnamaldehyde (0.08 mmol) followed by Na(OAc)₃BH (10 mg, 0.06 eq.). After stirring at 23° C. for 3 h the reaction mixture was filtered through a plug of glass wool and purified directly by HPLC to provide between 5-10 mg (20-50%) of final product. MS (ESI(+)) m/e 635.4 (M+H)⁺.

Example 156

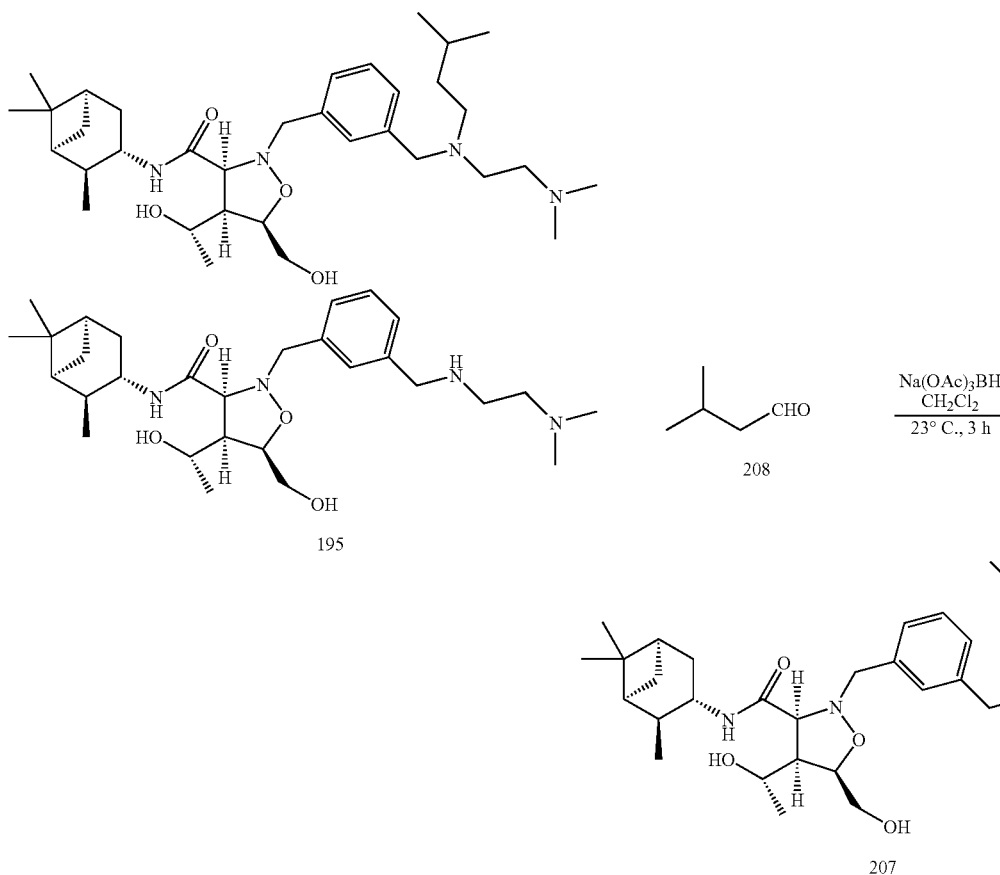

To a 23° C. solution of 195 (20 mg, 0.04 mmol) in CH₂Cl₂ (1 mL) was added isobutyraldehyde (0.08 mmol) followed by Na(OAc)₃BH (10 mg, 0.06 eq.). After stirring at 23° C. for 3 h the reaction mixture was filtered through a plug of glass wool and purified directly by HPLC to provide between 5-10 mg (20-50%) of final product. MS (ESI(+)) m/e 587.5 (M+H)⁺.

Example 157

-continued

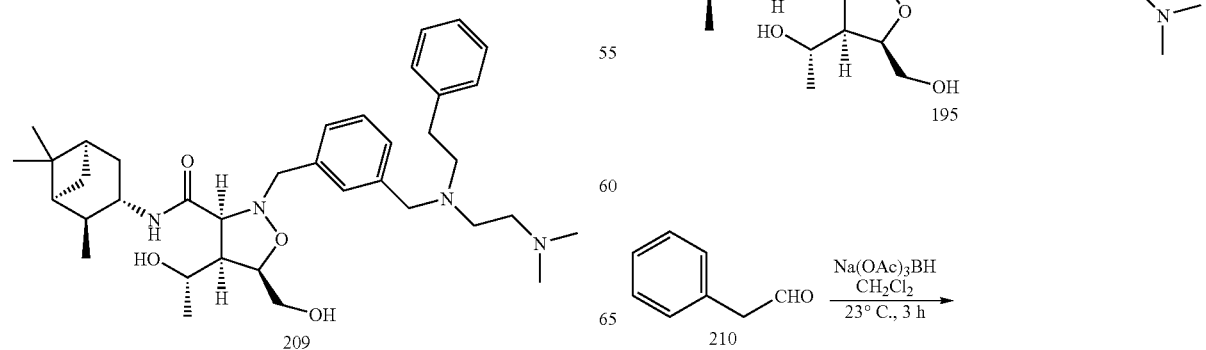

-continued

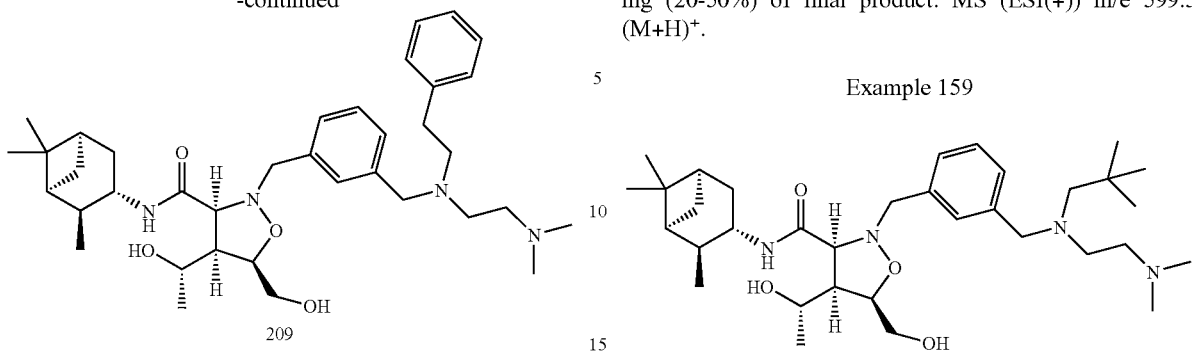
209

To a 23° C. solution of 195 (20 mg, 0.04 mmol) in CH$_2$Cl$_2$ (1 mL) was added phenylacetaldehyde (0.08 mmol) followed by Na(OAc)$_3$BH (10 mg, 0.06 eq.). After stirring at 23° C. for 3 h the reaction mixture was filtered through a plug of glass wool and purified directly by HPLC to provide between 5-10 mg (20-50%) of final product. MS (ESI(+)) m/e 621.5 (M+H)$^+$.

Example 158

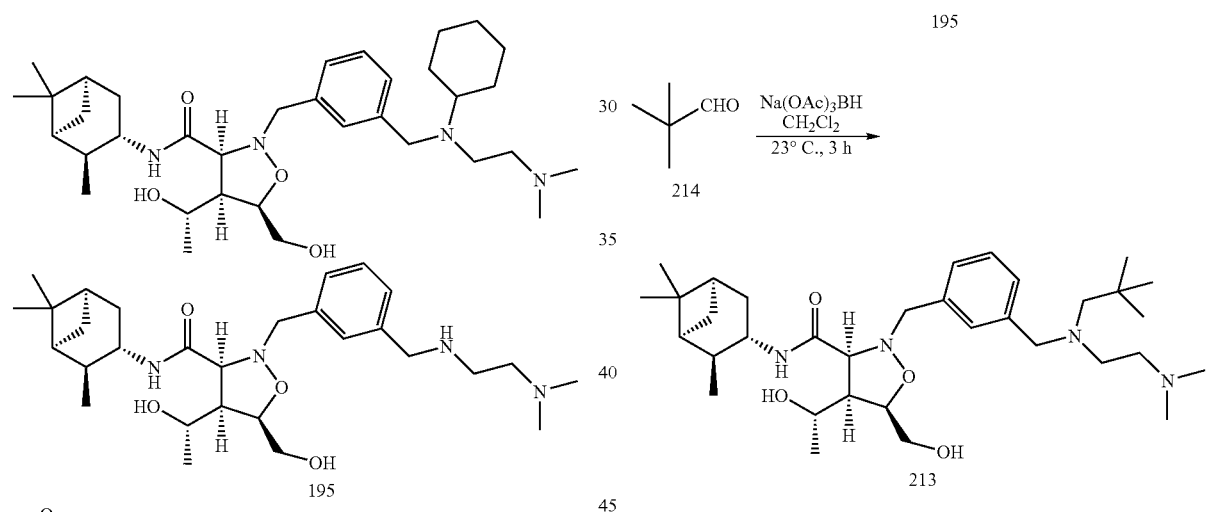
195

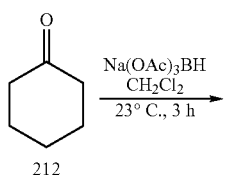
212

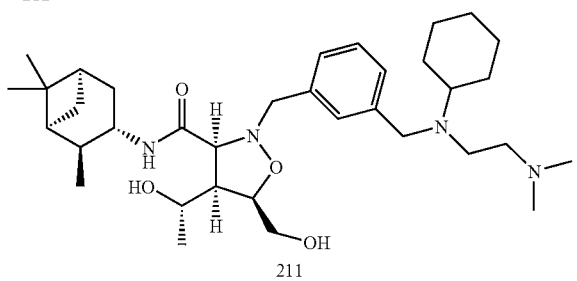
211

To a 23° C. solution of 195 (20 mg, 0.04 mmol) in CH$_2$Cl$_2$ (1 mL) was added cyclohexanone (0.08 mmol) followed by Na(OAc)$_3$BH (10 mg, 0.06 eq.). After stirring at 23° C. for 3 h the reaction mixture was filtered through a plug of glass wool and purified directly by HPLC to provide between 5-10 mg (20-50%) of final product. MS (ESI(+)) m/e 599.5 (M+H)$^+$.

Example 159

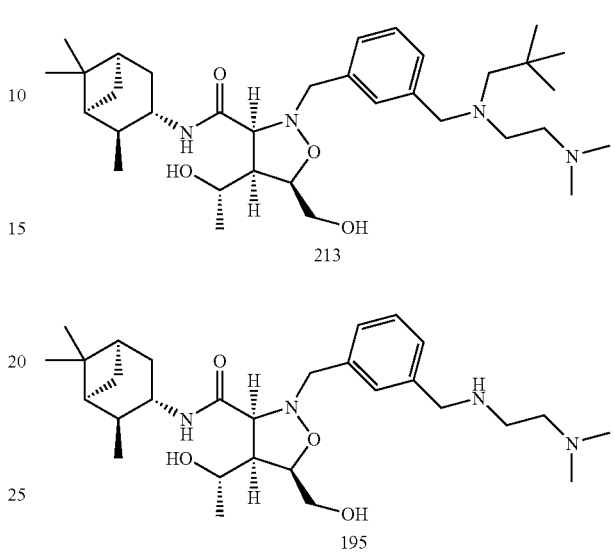
213
195

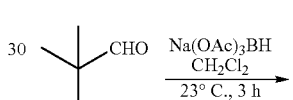
214

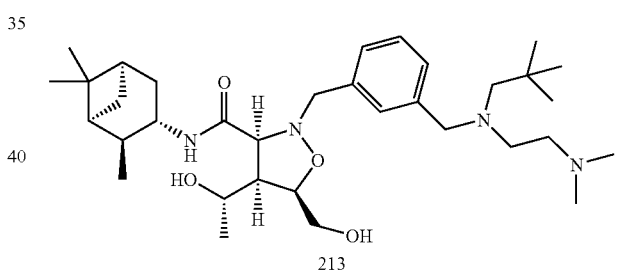
213

To a 23° C. solution of 195 (20 mg, 0.04 mmol) in CH$_2$Cl$_2$ (1 mL) was added pivaldehyde (0.08 mmol) followed by Na(OAc)$_3$BH (10 mg, 0.06 eq.). After stirring at 23° C. for 3 h the reaction mixture was filtered through a plug of glass wool and purified directly by HPLC to provide between 5-10 mg (20-50%) of final product. MS (ESI(+)) m/e 587.5 (M+H)$^+$.

Example 160

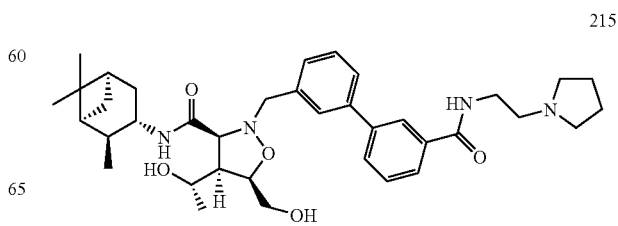
215

-continued

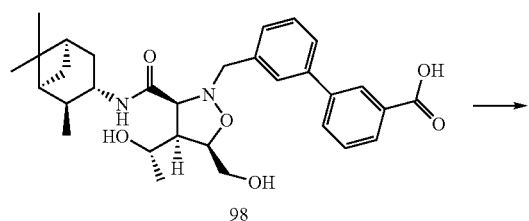
98

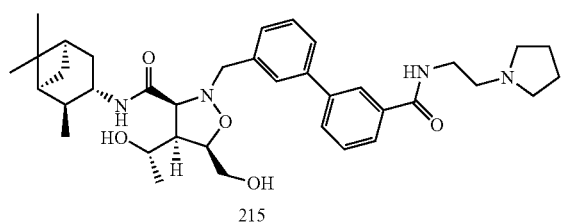
215

To a solution of crude 98 (25 mg) and 1-(2-aminoethyl)pyrrolidine (16 µL) in DMF (700 µL) was added HBTU (30 mg). After shaking for 1 h, the reaction mixture was diluted with MeOH (800 µL) and purified by HPLC. Concentration of the appropriate fractions gave 215 as a white solid, 14 mg. MS (ESI(+)) m/e 633.3 (M+H)⁺.

Example 161

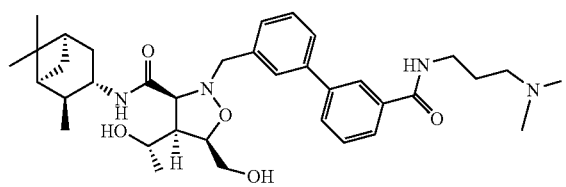
216

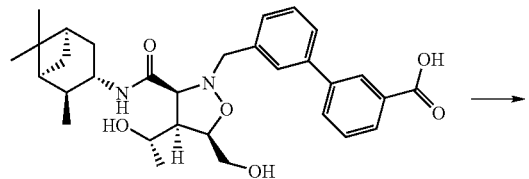
98

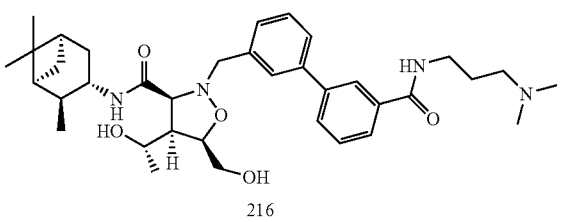
216

To a solution of crude 98 (25 mg) and N,N-dimethyl-1,3-propanediamine (19 µL) in DMF (700 µL) was added HBTU (30 mg). After shaking for 1 h, the reaction mixture was diluted with MeOH (800 µL) and purified by HPLC. Concentration of the appropriate fractions gave 216 as a white solid, 13 mg. MS (ESI(+)) m/e 621.3 (M+H)⁺.

Example 162

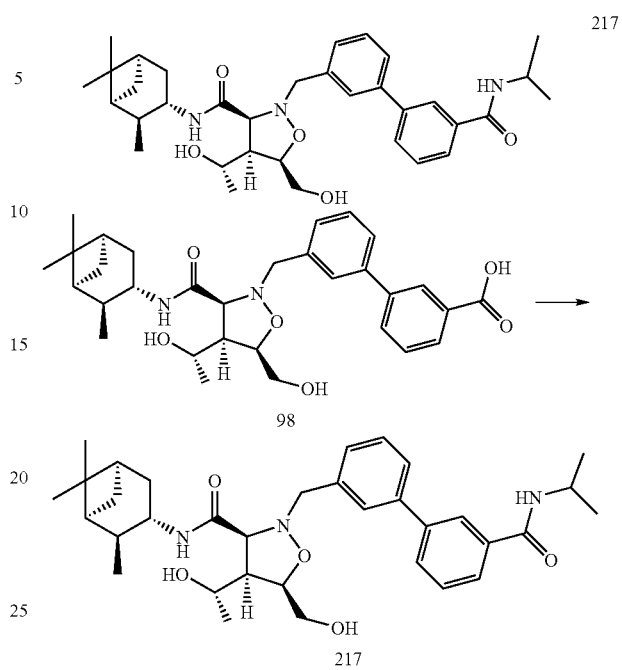

To a solution of crude 98 (25 mg) and isopropylamine (13 µL) in DMF (700 µL) was added HBTU (30 mg). After shaking for 1 h, the reaction mixture was diluted with MeOH (800 µL) and purified by HPLC. Concentration of the appropriate fractions gave 217 as a white solid, 14 mg. MS (ESI(+)) m/e 578.3 (M+H)⁺.

Example 163

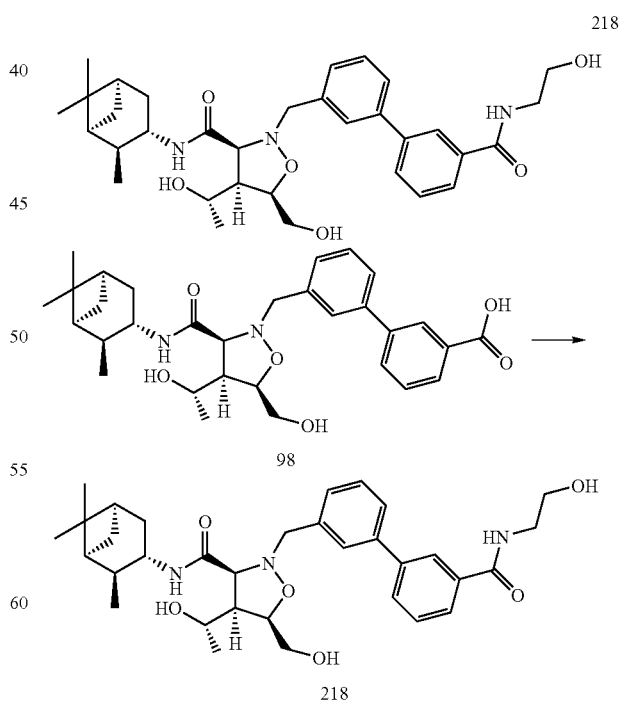

To a solution of crude 98 (25 mg) and ethanolamine (9 µL) in DMF (700 µL) was added HBTU (30 mg). After shaking for 1 h, the reaction mixture was diluted with MeOH (800 μL) and purified by HPLC. Concentration of the appropriate fractions gave 218 as a white solid, 14 mg. MS (ESI(+)) m/e 580.3 (M+H)⁺.

Example 164

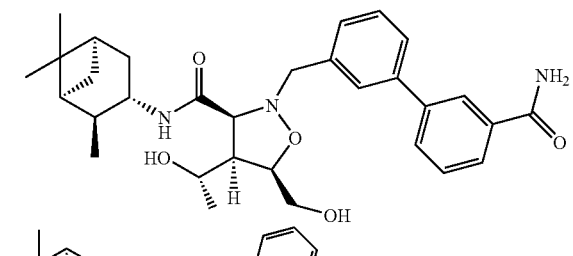
219

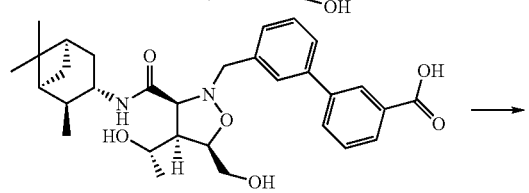
98

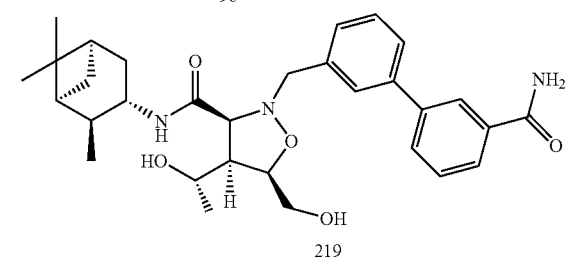
219

To a solution of crude 98 (25 mg), NH₄Cl (8 mg), and DIEA (40 μL) in DMF (700 μL) was added HBTU (30 mg). After shaking for 1 h, the reaction mixture was diluted with MeOH (800 μL) and purified by HPLC. Concentration of the appropriate fractions gave 219 as a white solid, 16 mg. MS (ESI(+)) m/e 536.2 (M+H)⁺.

Example 165

220

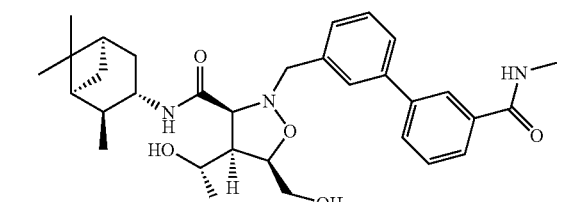

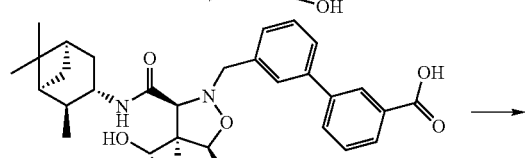
87

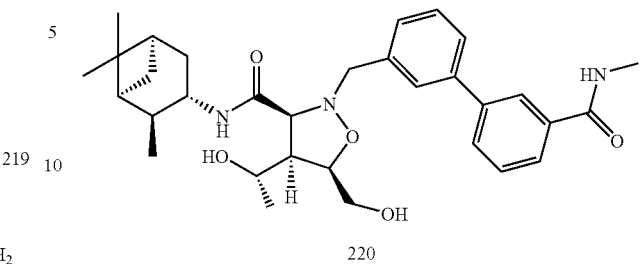
220

To a solution of crude 98 (25 mg) and 2.0M methylamine in THF (74 μL) in DMF (700 μL) was added HBTU (30 mg). After shaking for 1 h, the reaction mixture was diluted with MeOH (800 μL) and purified by HPLC. Concentration of the appropriate fractions gave 220 as a white solid, 14 mg. MS (ESI(+)) m/e 550.2 (M+H)⁺.

Example 166

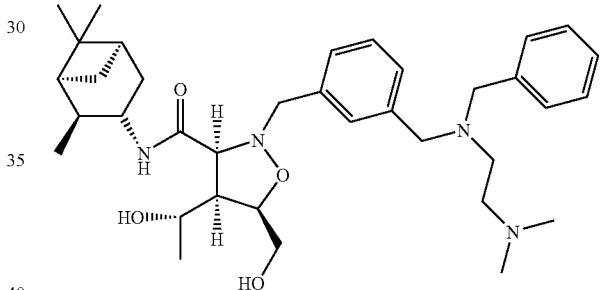
221

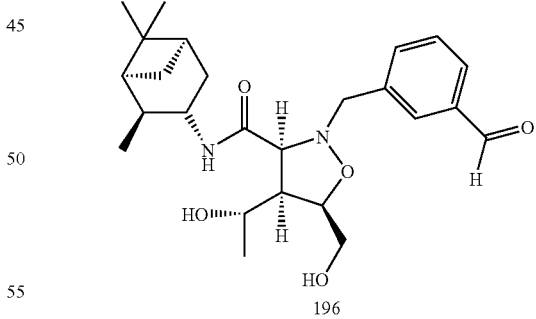
196

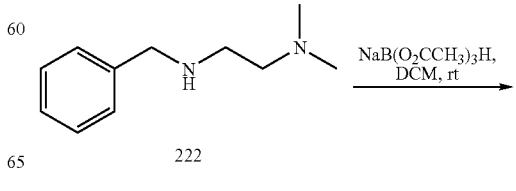
222

$\xrightarrow{\text{NaB(O}_2\text{CCH}_3)_3\text{H,}}_{\text{DCM, rt}}$

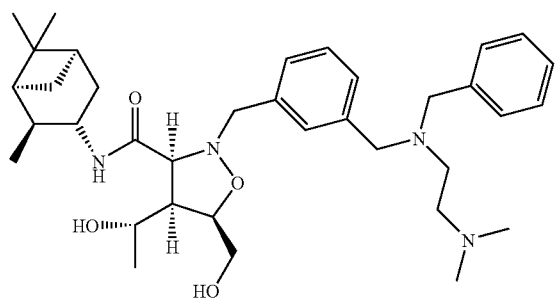

221

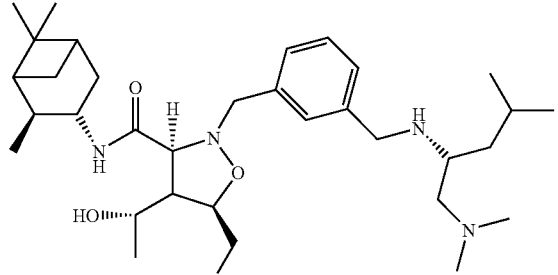

223

To a DCM solution (17 mL) of 196 (0.65 mmol) at 0° C. was added 222 (0.92 mmol) followed by Na(OAc)$_3$BH (1.30 mmol) in one portion. The solution was allowed to warm to rt and stirred for 2 h; it was diluted with water (20 mL), the organic phase was separated, washed with brine (10 mL), dried (Na$_2$SO$_4$), filtered and concentrated in vacuo to afford a white solid. The solid was dissolved in THF (15 mL) and subjected to purification by reverse phase chromatography C18 column and 40% acetonitrile/water containing 0.01% formic acid to afford the desire product. MS (ESI(+)) m/e 607.7 (M+H)$^+$.

To a MeOH (0.5 mL) solution of 196 (0.03 mmol) was added 224 (0.05 mmol). This solution was stirred for 2 h at rt before NaBH$_4$ (0.07 mmol) was added in one portion. The solution was maintained at rt for 1 h; diluted with water (3 mL) and extracted with EtOAc (2×2 mL). The combined organic extracts were washed with brine (4 mL), dried (Na$_2$SO$_4$), filtered and concentrated in vacuo to afford a oil. The oil was purified reverse phase chromatography C18 column and 20% acetronitile/water containing 0.01% formic acid to afford the desired product. MS (ESI(+)) m/e 573.8 (M+H)$^+$.

Example 167

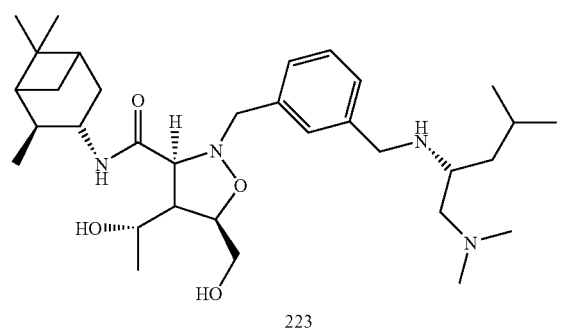

223

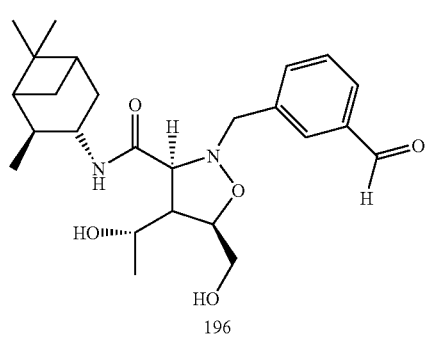

196

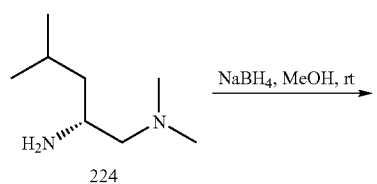

224

Example 168

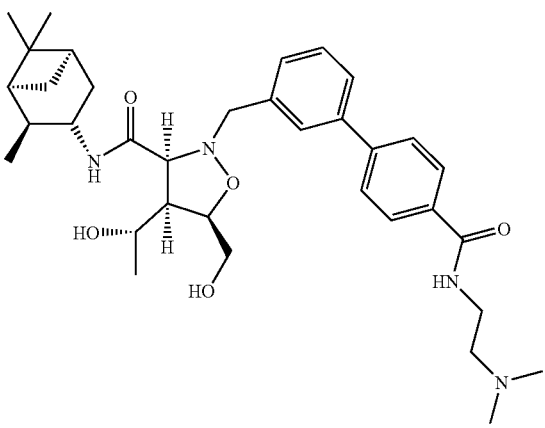

225

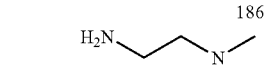

226

-continued

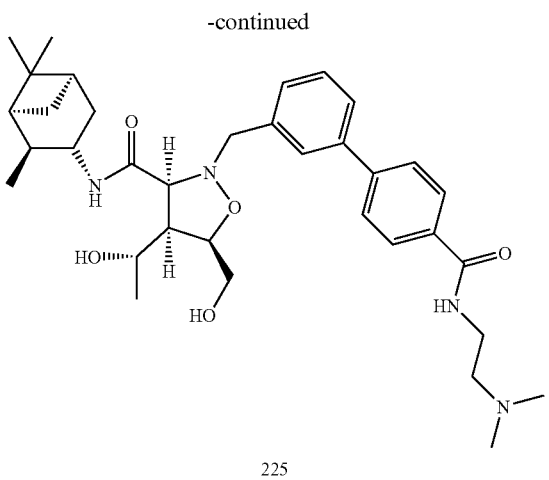

225

To a DMF solution (0.5 mL) of acid 186(0.028 mmol) at rt was added the N,N-dimethylethylenediamine 226 (0.11 mmol) and HBTU (0.084 mmol). The solution was stirred for 2 h, diluted with water (1 mL) and extracted with EtOAc (1 mL), the organic was dried ($Na_2SO_4$), filtered and concentrated in vacuo to afford an oil. The oil was purified by reverse phase chromatography C 18 column and 10% acetonitrile/water containing 0.1% ammonium bicarbonate to afford the desired product.

Example 169

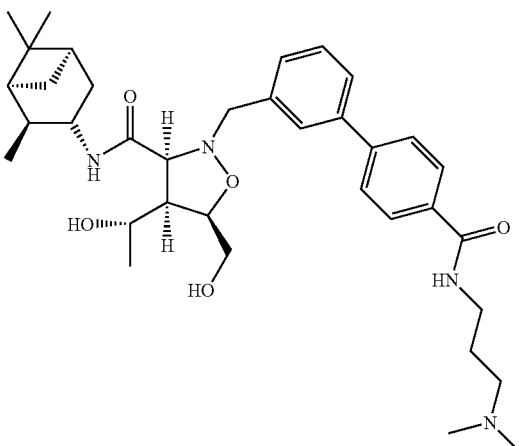

227

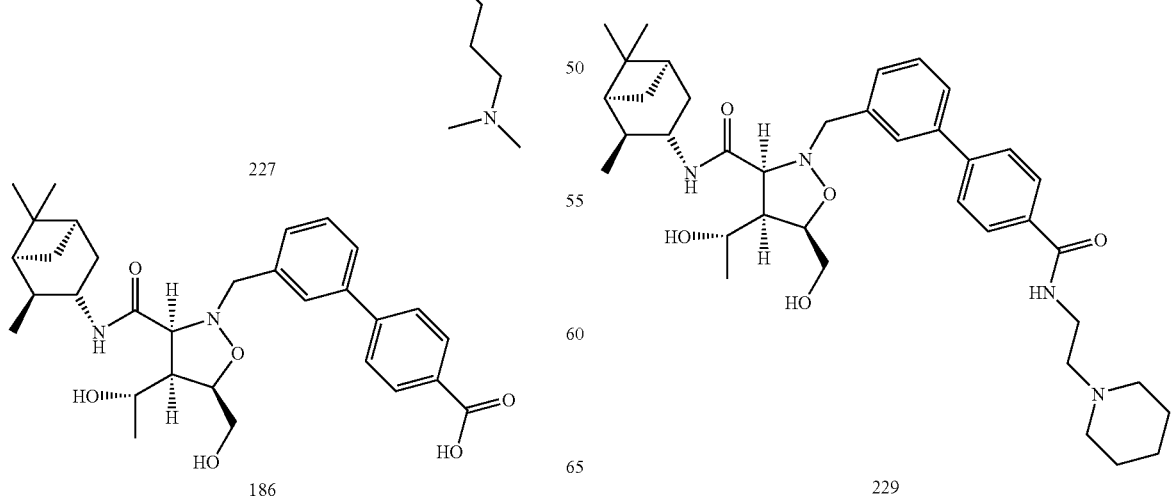

186

-continued

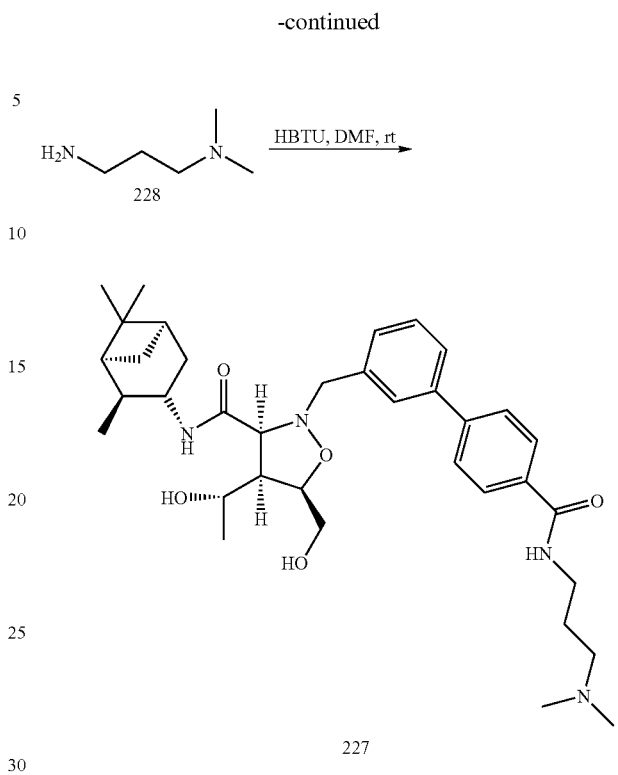

To a DMF solution (0.5 mL) of acid 186(0.028 mmol) at rt was added the N,N-dimethyl-1,3-propanediamine 228(0.11 mmol) and HBTU (0.084 mmol). The solution was stirred for 2 h, diluted with water (1 mL) and extracted with EtOAc (1 mL), the organic extracts were dried ($Na_2SO_4$), filtered and concentrated in vacuo to afford an oil. The oil was purified by reverse phase chromatography C 18 column and 10% acetonitrile/water containing 0.1% ammonium bicarbonate to afford the desired product.

Example 170

229

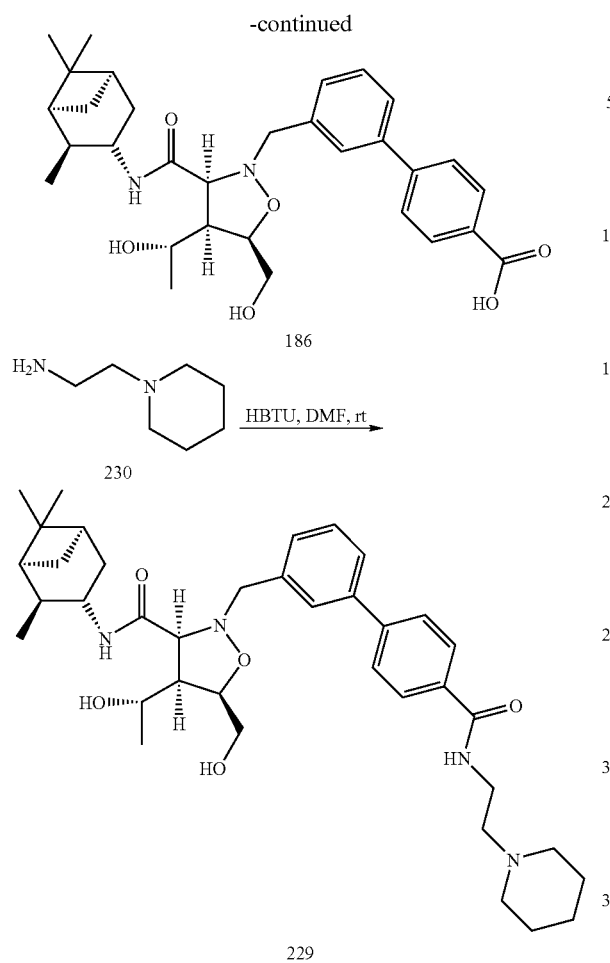

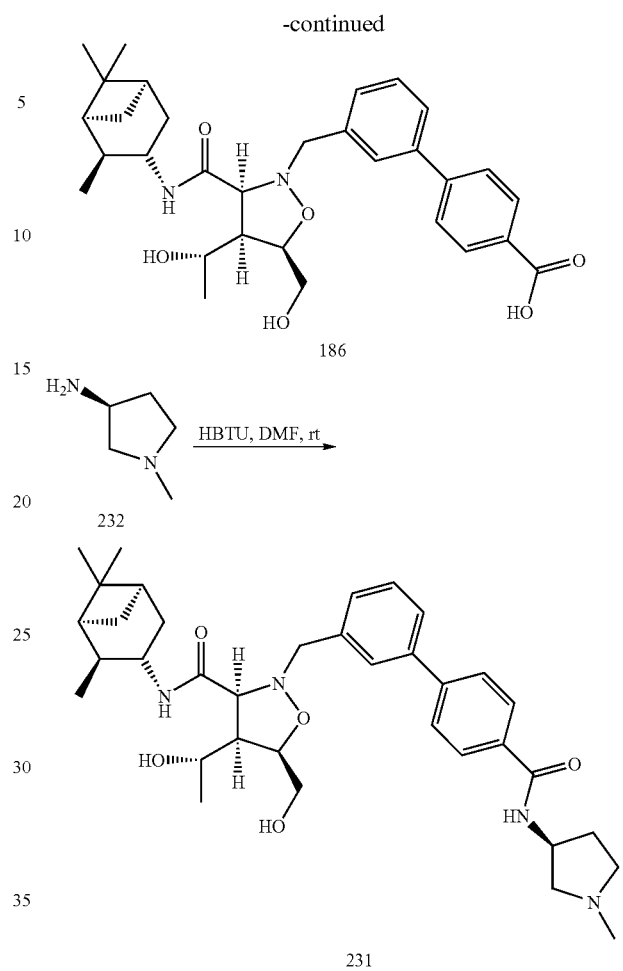

To a DMF solution (0.5 mL) of acid 186(0.028 mmol) at rt was added the 1-(2-aminoethyl)piperidine 230(0.11 mmol) and HBTU (0.084 mmol). The solution was stirred for 2 h, diluted with water (1 mL) and extracted with EtOAc (1 mL), the extracts were dried (Na₂SO₄), filtered and concentrated in vacuo to afford an oil. The oil was purified by reverse phase chromatography C 18 column and 10% acetonoitrile/water containing 0.1% ammonium bicarbonate to afford the desired product.

Example 171

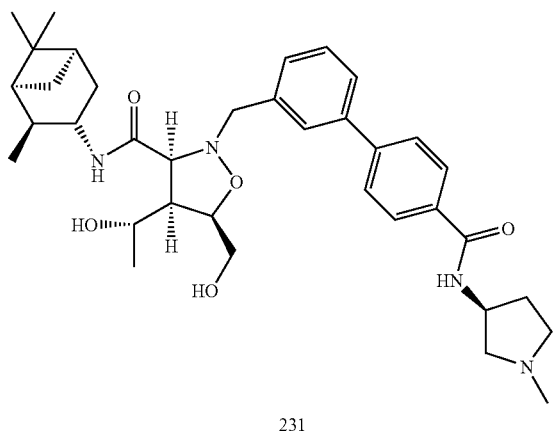

To a DMF solution (0.5 mL) of acid 186(0.028 mmol) at rt was added the (S) N-methyl-3-aminopyrrolidine 232(0.11 mmol) and HBTU (0.084 mmol). The solution was stirred for 2 h, diluted with water (1 mL) and extracted with EtOAc (1 mL), the organic phase was dried (Na₂SO₄), filtered and concentrated in vacuo to afford an oil. The oil was purified by reverse phase chromatography C 18 column and 10% acetonitrile/water containing 0.1% ammonium bicarbonate to afford the desired product. MS (ESI(+)) m/e 619.4 (M+H)⁺.

Example 172

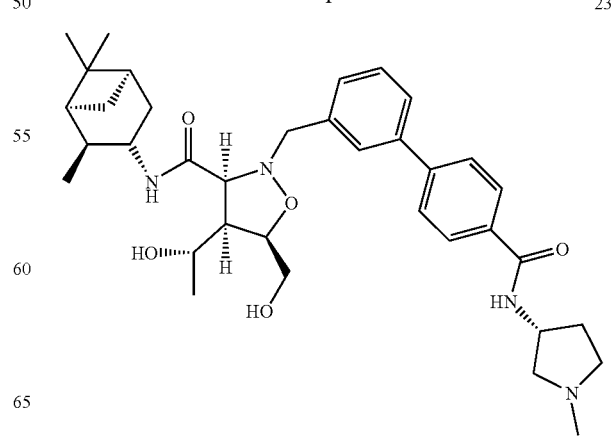

-continued

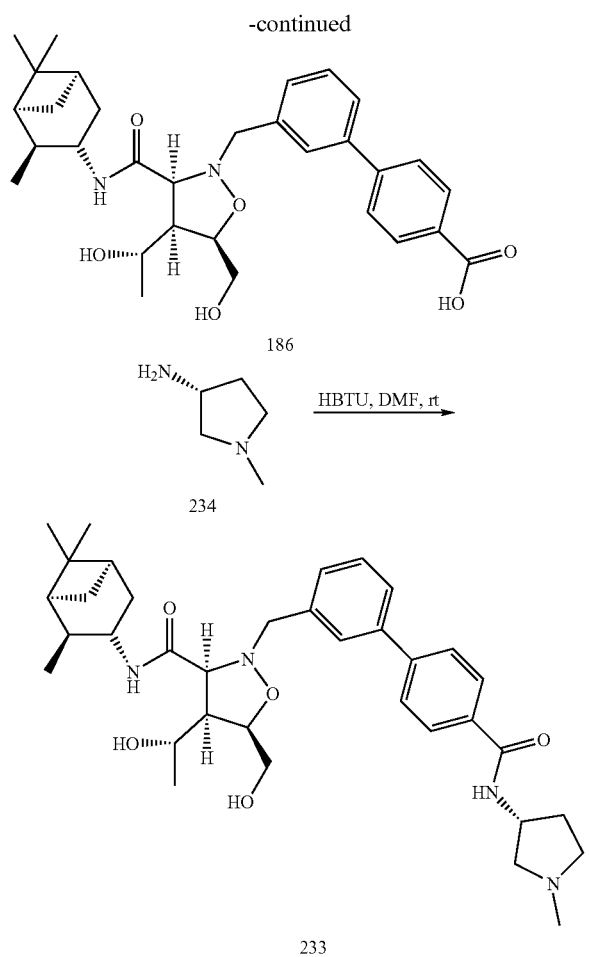

To a DMF solution (0.5 mL) of acid 186(0.028 mmol) at rt was added the (R) N-methyl-3-aminopyrrolidine 234(0.11 mmol) and HBTU (0.084 mmol). The solution was stirred for 2 h, diluted with water (1 mL) and extracted with EtOAc (1 mL), the organic phase was dried (Na$_2$SO$_4$), filtered and concentrated in vacuo to afford an oil. The oil was purified by reverse phase chromatography C 18 column and 10% acetonitrile/water containing 0.1% ammonium bicarbonate to afford the desired product.

Example 173

Part A

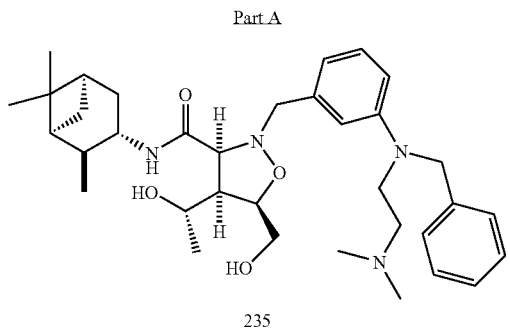

-continued

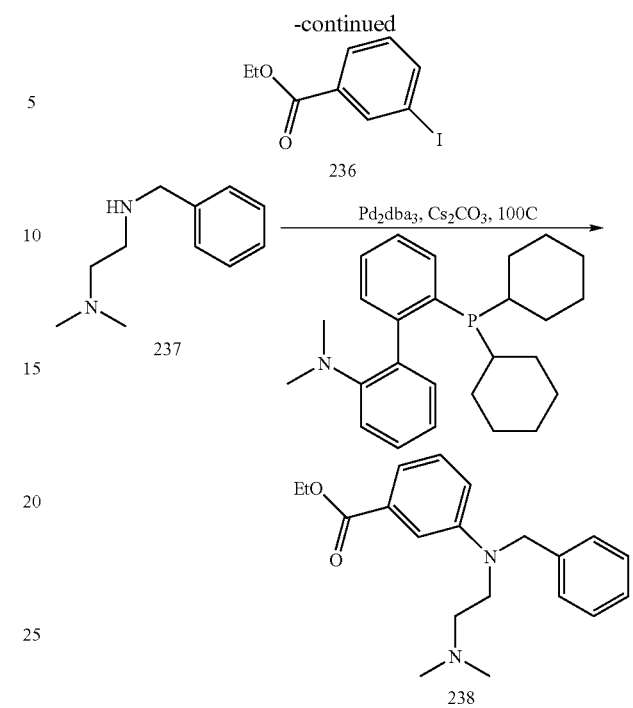

Ethyl 3-iodobenzoate (20 g, 0.077 mol), N-benzyl-N,N-dimethylethylenediamine (18 g, 1.4 equiv.), Pd$_2$DBA$_3$ (3.3 g, 5%), Cs$_2$CO$_3$ (33g, 1.4 equiv.) and 2- dicyclohexylphosphino-2'-(N,N-dimethylamino)biphenyl (2.9 g, 10%) were mixed together in a dry flask under N$_2$. Dioxane (45 mL) and triethyl amine were added to the flask. The reaction mixture was purged under Argon for 5 min before heated to 100 C for 14 h. The mixture was cooled to rt and diluted with EtOAc (200 mL) and filtered through a plug of celite. The crude mixture was concentrated to give crude mixture 32 g. LC-MS showed the desired product. Purification (hexane, 20% followed with 60% EtOAc in hexane and ethyl acetate mixture) gave desired pd. 10 g.

Part B

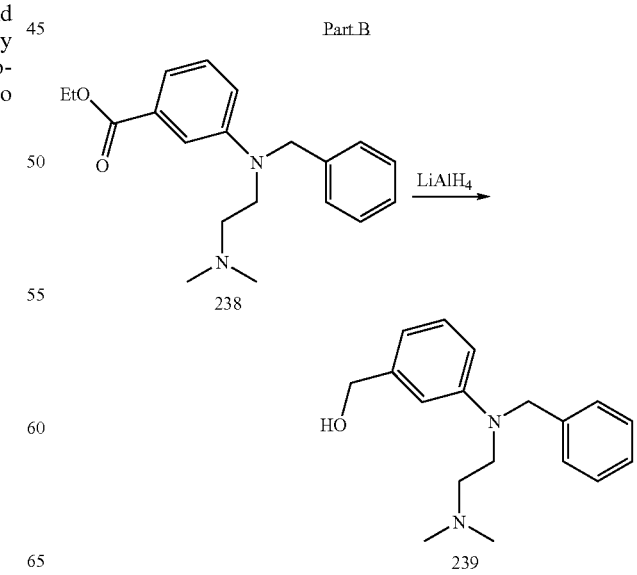

Compound 238 was dissolved in 30 mL THF, and LAH (18 mL, 1 M, 0.6 equiv) was added at 0 C. The reaction mixture was then warmed to rt. After 5 h the reaction was quenched with water (5 mL), washed/extracted with ethyl acetate, dried (Na₂SO₄) and concentrated to give crude product 8 g. Purification on silica gel (50% ethyl acetate in hexane and ethyl acetate mixture, followed with 5% MeOH in DCM) gave desired product 6 g Part C

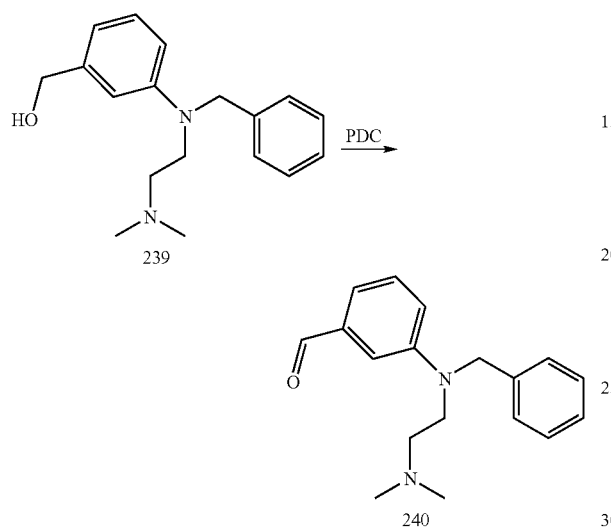

Compound 239 was dissolved in DCM (20 mL). PDC (16 g, 2 equiv.) was added to the solution. The reaction mixture was stirred at rt for 14 h. The crude mixture was filtered through a short plug of celite, and washed with ethyl acetate. The combined organic solution was concentrated and purified on silica gel (DCM, 5% MeOH in DCM) to give desired pd. 2.8 g plus 3 g of starting alcohol.

Part D

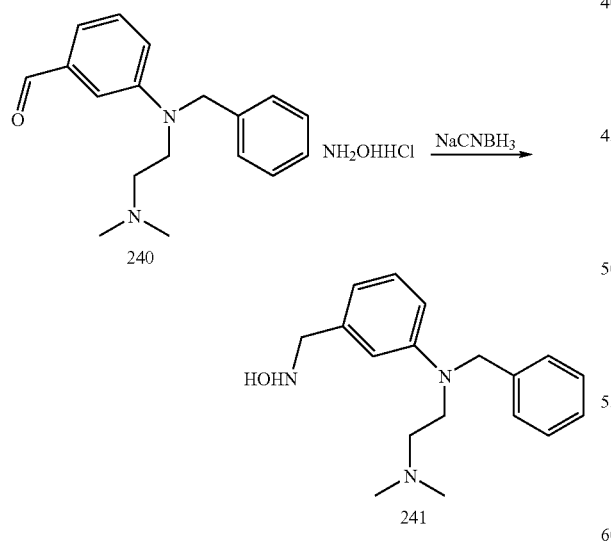

To a solution of benzylaldehyde 240 (2.8 g) in MeOH-THF (3:1, 40 mL) was added an aqueous solution of hydroxylamine (0.9 g in 3 mL water) in one portion. The pH was adjusted to 9 with 6N KOH, and stirred at rt for 2 h, after the disappearance of the aldehyde by TLC. NaBH₃CN (2 eq) was added to the solution. The pH of the solution was adjusted to ph 2-3 using HCl in MeOH (20 V/V) and the solution was allowed to stir over night. Then basified with 2N KOH to a ph of 11 and extracted with CH₂Cl₂ (3 times), dried, concentrated in vacuo to afford 2.8 g yellow solid, which was used without purification in the next step.

Part E

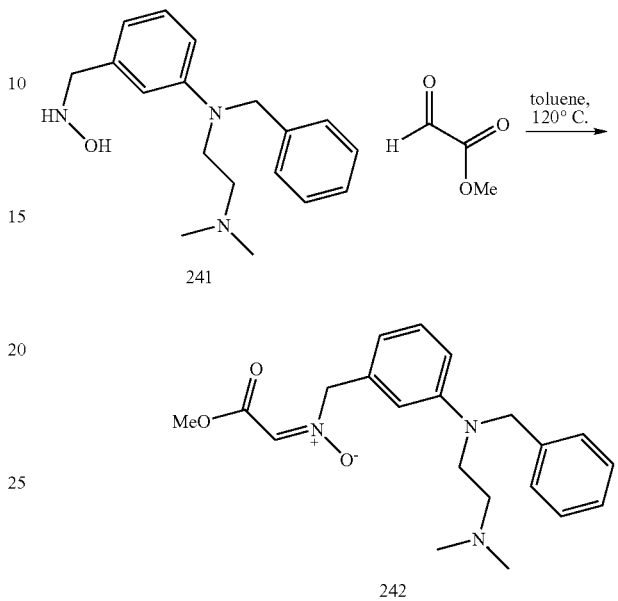

Compound 241 and methyl glyoxylate ester (1 g) were dissolved in 100 mL toluene. The mixture was heated to 120 C for 3 h. The mixture was concentrated to 15 mL for next step Part F

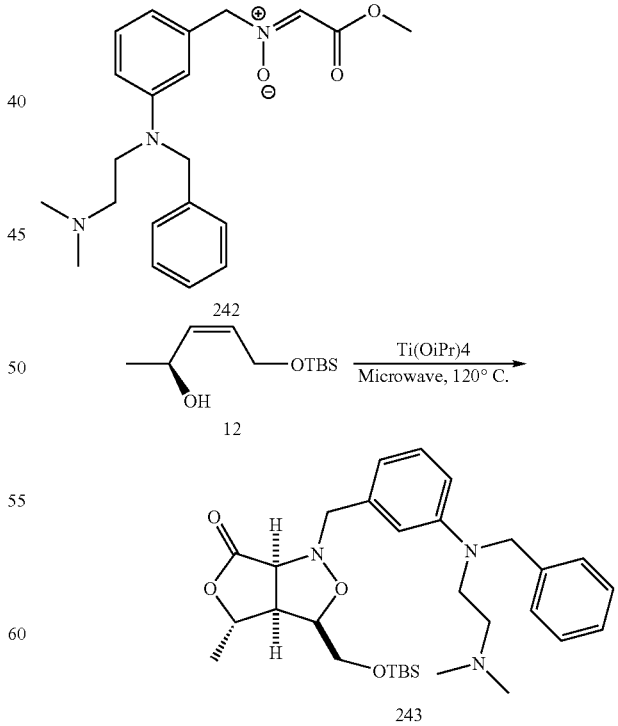

The toluene solution of 242 from previous the step was split between 5 vials (3 mL each). To each vial was added 0.4 g TBS allylic alcohol 12 and 0.6 g of titanium isopropoxide.

287

The mixtures were heated to 140° C. for 10 min in a microwave. The reaction mixtures were cooled to rt and combined. Ethyl acetate was added to the pooled fractions and the organic layer was washed with water, brine, dried over Mg$_2$SO$_4$, filtered and concentrated. Flash chromatography on silica gel ( 3% MeOH in DCM) gave partially pure product 900 mg.

Part G

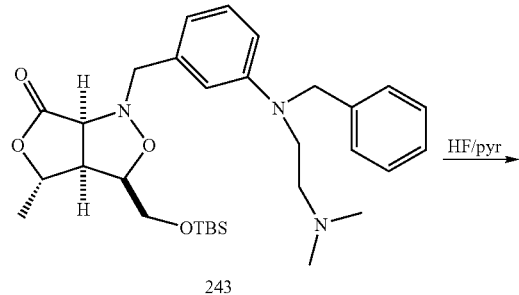

243

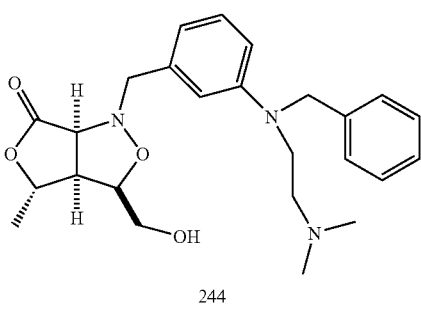

244

The partially pure product from previous step 243 (0.90g) was dissolved in 3 mL of dry THF; HF-Pyr (0.5 mL) was added dropwise. After 1 h, the mixture was concentrated in vacuo to give 180 mg of the desired product plus a major impurity (inseparable on column).

Part H

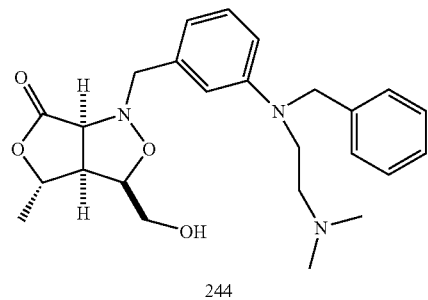

244

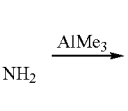

288

-continued

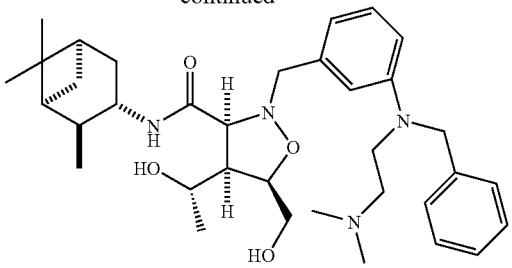

235

Isopinocampheylamine (0.18 g, 0.41 mmol) was dissolved 3 mL dry DCM, Al (Me)$_3$ (2 M, 0.41 mL, 0.82 mmol)was added in a dropwise manner to the solution. The mixture was stirred at rt for 20 min Compound 244 was dissolved in 1 mL of DCM, and the resulting solution was added slowly to the amine and Al(Me)$_3$ solution. The reaction mixture was stirred at rt for 12 h, and then diluted with DCM (25 mL), Rochelle salt (5 mL) (potassium sodium tartrate) aqueous solution and the two layer mixture was stirred at rt for 2 h. The organic layer was separated and washed with water and brine, dried (Na$_2$SO$_4$), filtered and concentrated to give crude product 80 mg. Flash chromatography on silica gel (DCM, 2% MeOH in DCM, 5% MeOH in DCM) gave desired product 40 mg. MS (ESI(+)) m/e 593.4 (M+H)$^+$.

Example 174

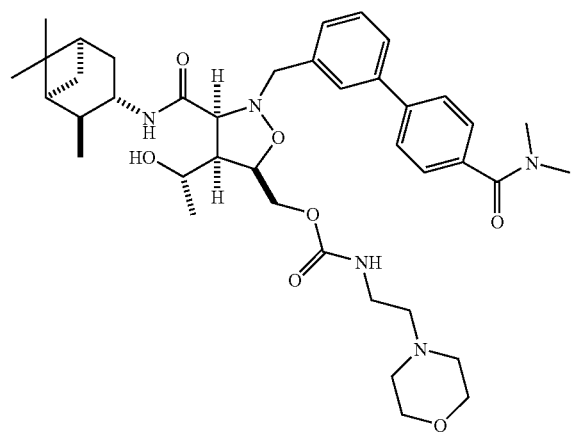

245

Part A

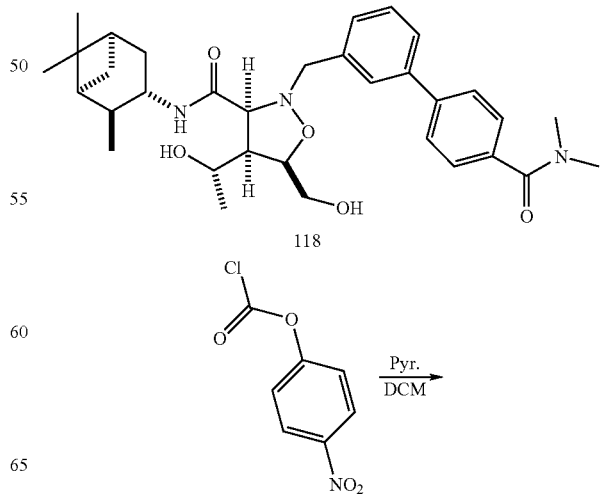

118

-continued

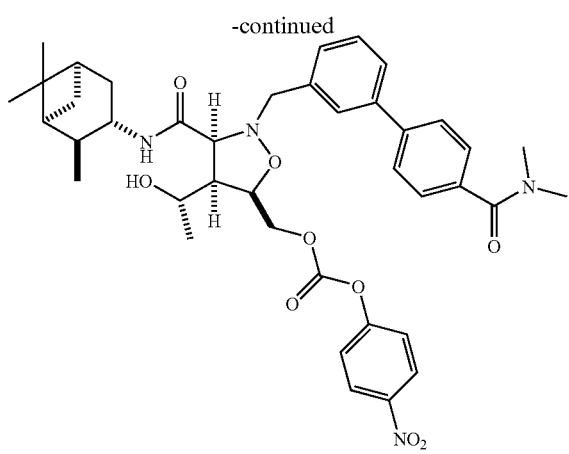

246 p-Nitrophenyl chloroformate (40 mg) was dissolved in 2 mL DCM and pyridine (20 ul, xx mmol, xx eq). The resulting white slurry was cooled to 0 degree symbol C and treated with 118 (80 mg, xx mmol, xx eq) in 1 mL DCM. The reaction mixture was stirred at rt for 14 h, diluted with DCM (30 mL), washed with water, brine and dried over Na$_2$SO$_4$, filtered and concentrated to give 77 mg crude product. Flash chromatography (Hexanes/ EtOAc 10:1 to 1:2) gave desired product 60 mg.

Part B

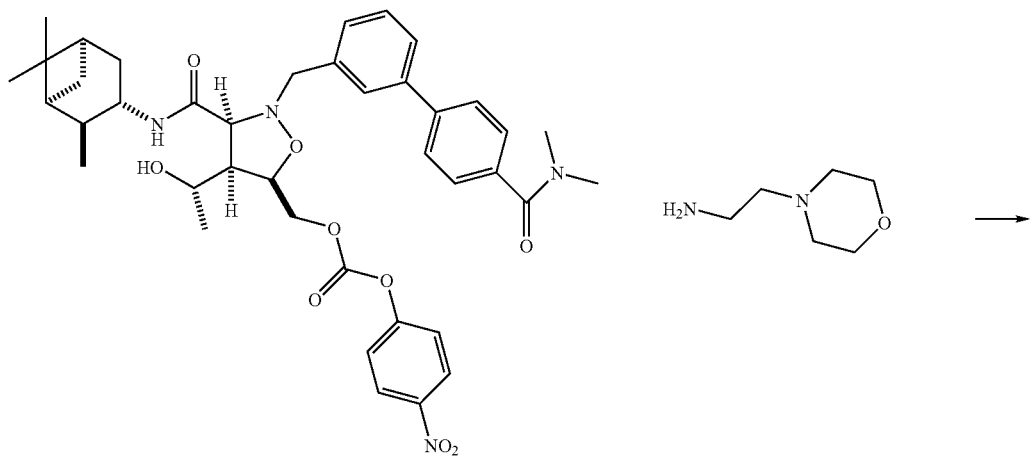

246

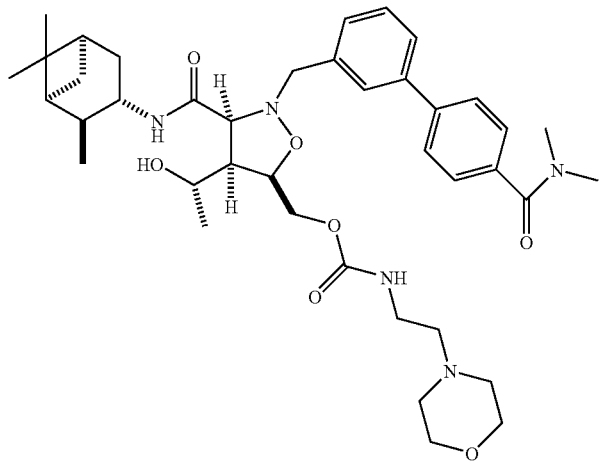

245

Compound 246 (8 mg) and the morpholine amine (6 mg, 4 equiv.) were dissolved in 1 mL DCM, and the mixture was stirred at rt for overnight. The reaction mixture was diluted with 30 mL DCM, washed with water, brine, dried, filtered and concentrated. The crude product was purified on silica gel. (EtOAc to EtOAc-MeOH 10:1) gave pure product 7 mg. MS (ESI(+)) m/e 720.6 (M+H)$^+$.

Example 175

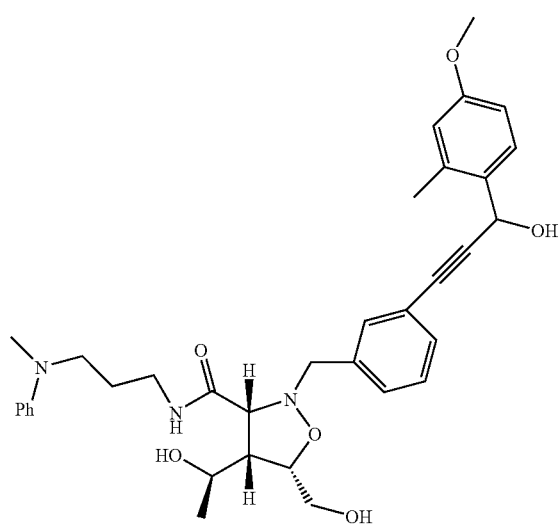

247

Part A

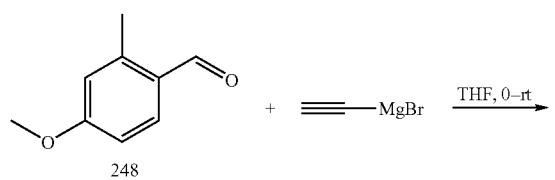

248

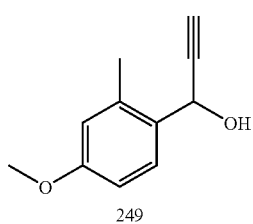

249

Ethynylmagnesium bromide (0.5 M, 8 mL) was cooled to 0 degree symbol C under N2. The aldehyde 248 (0.4 g) was dissolved in 3 mL of dry THF under N$_2$ and the solution was added in a dropwise manner to the Grignard reagent. The mixture was stirred at 0 for 10 min, then rt for 4 h. Sat. NH$_4$Cl was added to quench the reaction and EtOAc was used to extract the desired product. The organic extracts were washed with brine, dried and filtered to give the desired product 0.41 g.

Part B

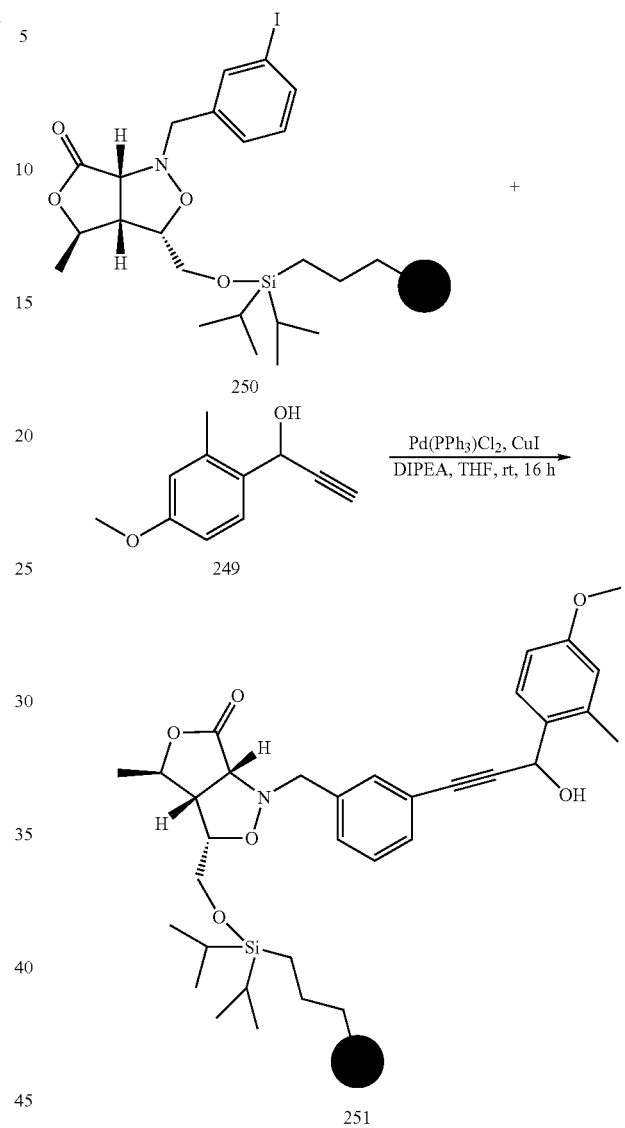

Isoxazolidine 18 was loaded onto lanterns according to the procedure described in Example 29, part A.

In a glass vial three lanterns 250 (loading level is 18 micromole/lantern) were dried under vacuum (18 h) and then purged with nitrogen. To this vial, DMF (xx mL) dichlorobis(triphenylphosphine)palladium(II) (63 mg, 2 equiv.) and copper iodide (26 mg, 3 equiv.) were added sequentially followed by DIPEA(0.3 mL, 40 equiv.). The propargyl alcohol 249 (0.32 g, xx mmol, 40 equiv.) was dissolved in 2 mL of dry DMF and added to the vial. The vial was shaked under nitrogen for 16 h and the excess reagent was decanted. The lanterns were washed with DMF, THF. 3:1 THF/H$_2$O, 3:1 THF/IPA, THF, CH$_2$Cl$_2$. The lanterns were transferred into a round-bottomed flask and the remaining solvent was evaporated under reduced pressure. The lanterns were dried under high vacuum overnight.

The product was cleaved from the lantern with 20 ul HF/Pyr in 200 ul THF followed with 100 ul TMSOMe to afford the desired product.

Part C

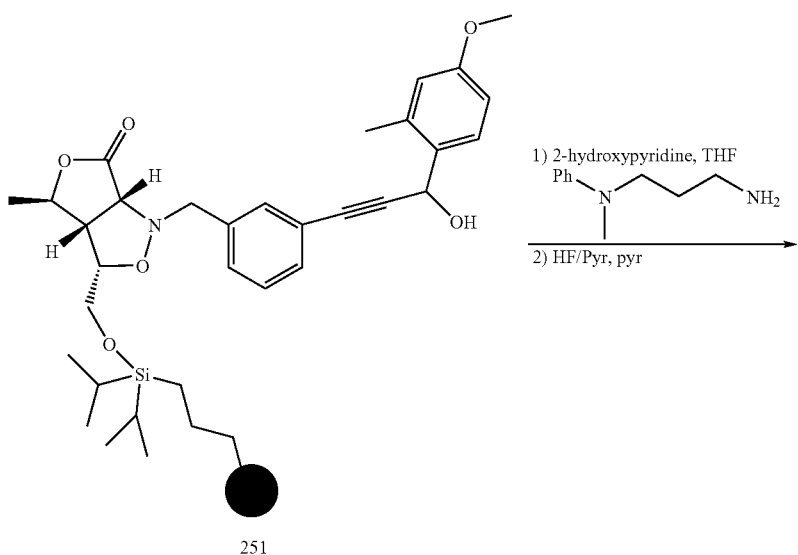

251

251 (2 Lanterns) were added to a small nitrogen purged round-bottomed flask followed by THF (2 mL), 2-hydroxy-pyridine (40 mg, 10 equiv.) and amine (660 mg, 100 equiv.). The reaction flask was agitated at 50 degrees C for 12 h. The excess reagent was decanted the lanterns were washed with DMF, THF. 3:1 THF/H$_2$O, 3:1 THF/IPA, THF, CH$_2$Cl$_2$ and transferred to a round-bottomed flask. The remaining solvent was evaporated under reduced pressure overnight.

The product was cleaved from the lanterns with HF/Pyr (80 µL) in THF (400 µL) followed by 1 mL of TMSOMe to afford 4 mg product. LC-MS and NMR showed the desired product. MS (ESI(+)) m/e 602.2 (M+H)$^+$.

247

Example 176

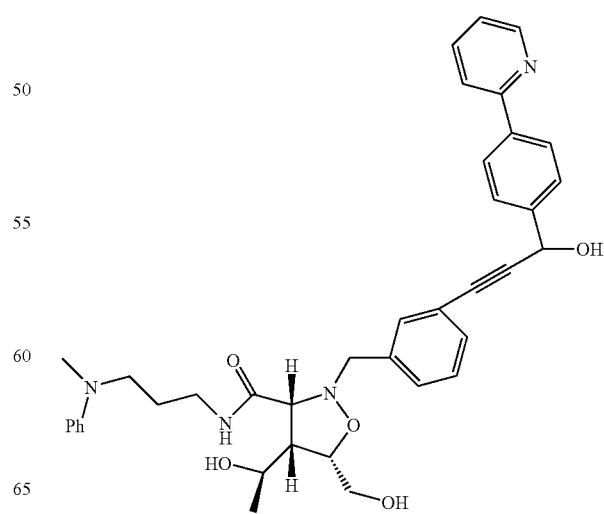

252

Compound 252 was made according to the procedure described in example 186, using 4-(pyridin-2-yl)benzaldehyde in place of 4-methoxy-2-methylbenzaldehyde. MS (ESI (+)) m/e 635.4 (M+H)+.

Example 177

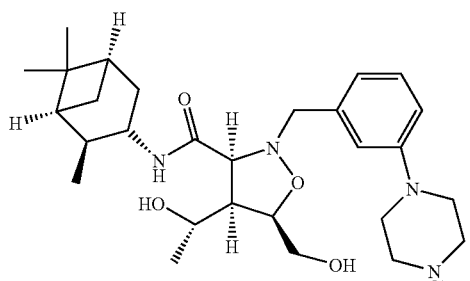
253

Part A

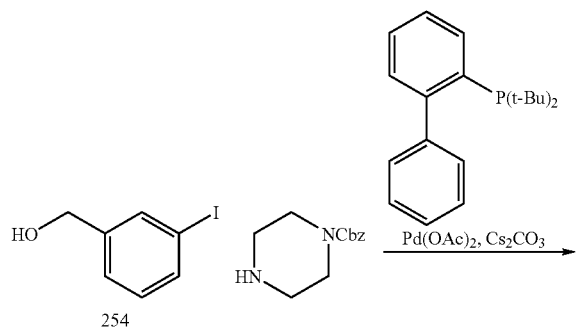
254
255

N-Cbz piperazine (8.24 g, 37.4 mmol), 3-iodobenzyl alcohol 265 (7g, 29.9 mmol), 2-bis(tert-butyl)phosphinobiphenyl (1.8 g, 6.0 mmol), palladium acetate (1.34 g, 6.0 mmol) and cesium carbonate (14.6 g, 44.9 mmol) were combined with benzene (72 mL) at ambient temperature. This mixture was purged with argon and heated to 70° C. for 14 h. The reaction mixture was cooled to ambient and diluted with EtOAc (40 mL); the resulting mixture was stirred vigorously for 10 min Solids were removed by filtration, washed with EtOAc (2×20 mL) and the filtrate was concentrated in vacuo. The residue was purified by silica gel chromatography (4:1 Hex/EtOAc) to afford 255 (2.29 g, 24%) as a light-yellow semi-solid.

Part B

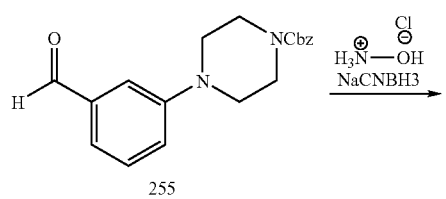
255

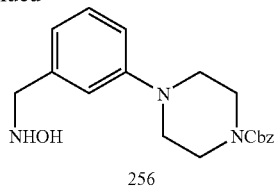
256

To a stirred solution of aldehyde 255 in MeOH (100 mL) and THF (40 mL) was added at 15° C. dropwise over 2 min an aqueous solution of hydroxylamine hydrochloride (5 mL). This solution was stirred at 15° C. for 0.5 h at which time TLC (silica gel, Hex/EtOAc, 2:1) showed no starting material. The pH was adjusted to 10 with 1N NaOH (14 mL) and NaCNBH₃ (1.5 g) was added in one portion. A solution of HCl in MeOH (6 M, 14 mL) was added dropwise to the reaction, which had been cooled to 0° C., until the pH reached 2-4. Cooling bath was removed after the addition of HCl was complete, and the reaction was stirred at 23° C. for 16 h. The reaction was judged to be complete after 16 h. (TLC silica gel, Hex/EtOAc, 2:1); and the pH was adjusted to 8 with sat. aqueous NaHCO₃ (40 mL). DCM/H₂O (1:1, 400 mL) was added and the layers were separated. The aqueous layer was extracted with DCM (2×200 mL) dried (MgSO₄), filtered and concentrated in vacuo to give the desired product as a pale-yellow oil (5.4 g, >100%).

Part C

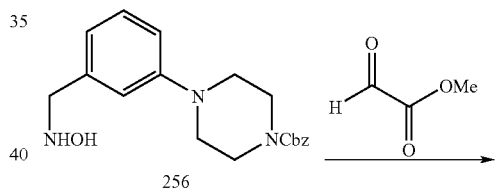
256

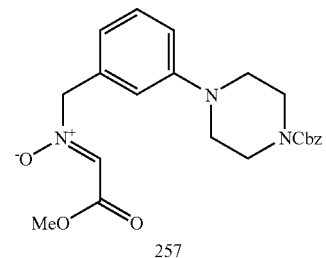
257

Hydroxylamine 256 (5.1 g, 15 mmol), and methyl gyloxylate (1.3 g, 15 mmol) were combined with anhydrous toluene (100 mL). This mixture was heated to 100° C. for 6 h. The mixture was cooled to ambient and concentrated in vacuo to give the desired product (6.2 g, 100%) as a thick yellow oil.

Part D

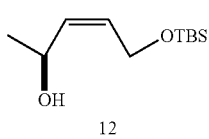
12

-continued

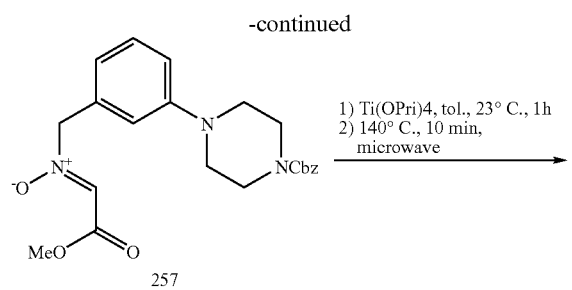
257

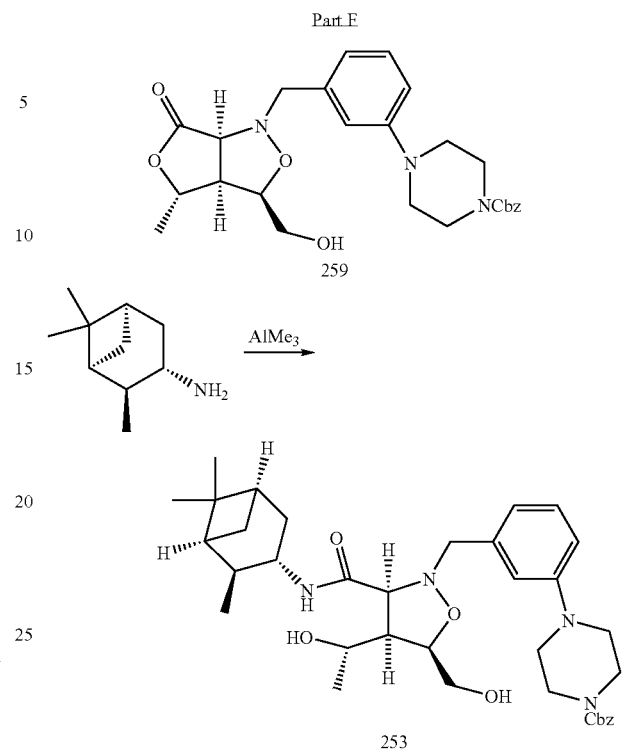

To allylic alcohol 12 (3.2 g, 15 mmol) and nitrone 257 (6.2 g, 15 mmol) in anhydrous toluene (40 mL) was added Ti(O-iPr)$_4$ dropwise over 3 min at ambient temperature. This solution was stirred at ambient temperature for 1 h. The solution was then transferred to 8 mircomave vessels (~6 mL/vessel); each vessel was heated individually at 140° C. in mcrowave oven for 10 min The solutions were pooled, diluted with 200 mL of EtOAc and 3-(dimethylamino)-1,2-propanediol (3.6 g, 30.0 mmol) and stirred at ambient temperature for 14 h. Purification of the crude product using silica gel chromatography Hex/EtOAc (3: 1) afforded the desired product (3.4 g, 38%) as a light-yellow oil.

Part E

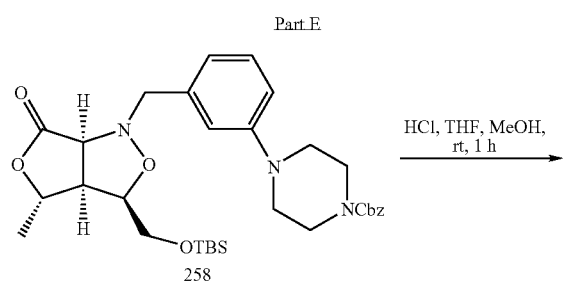
258

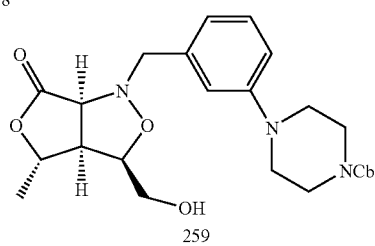
259

To a MeOH solution (20 mL) of 258 (3.4 g, 5.7 mmol) at ambient temperature was added 1:1 HCl/MeOH (8 mL) in four portions over 5 min This solution was stirred for 1 h at which time TLC indicated disappearance of the starting material. With vigorous stirring aqueous sat NaHCO3 (100 mL) was added in five portions over 30 min The layers were separated and the aqueous layer was extracted with DCM (3×250 mL) The combined organic extracts were dried over NaSO$_4$, filtered and concentrated. The residue was purified by silica gel chromatography (25:1 DCM/MeOH) to provide the desired product (2.45 g, 89%) as a yellow color solid.

(+)-Isopinocampheylamine (0.2 mmol) was dissolved in 0.3 mL of DCM at rt, trimethylaluminum (2.0 M in hexane, 0.2 mmol) was added and the solution was stirred for 10 min A DCM solution (0.2 m) of 259 (0.1 mmol) was added and the reaction was stirred for 16 h. The solution was diluted with 15 mL of sat. aqueous Rochelle Salt. This mixture was stirred for 2 h until a biphasic mixture appeared. The aqueous layer was separated and extracted with DCM (2×15 mL)the combined organic extracts were washed with water (15 mL), dried over MgSO$_4$, filtered and concentrated in vacuo. The residue was purified using silica gel chromatography to give the desired product (60%) as a pale-yellow oil. MS (ESI(+)) m/e 635.4 (M+H)$^+$.

Example 178

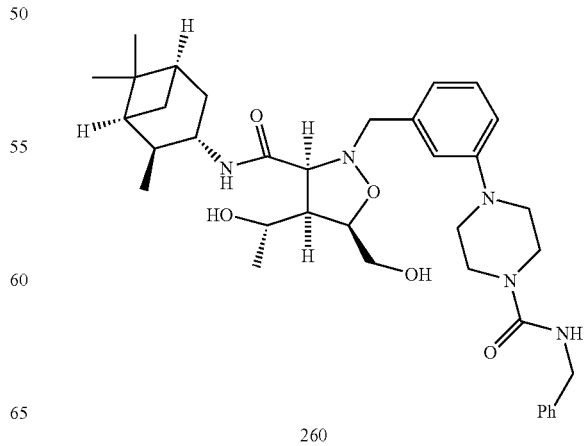
260

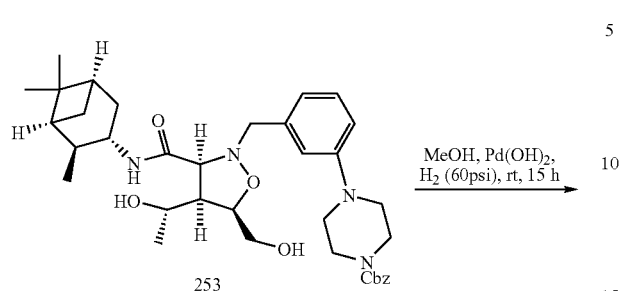

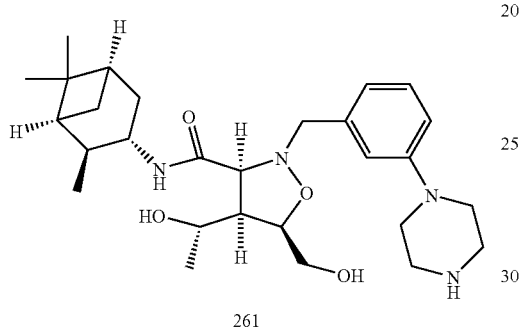

Compound 253 (2.1 g, 3.3 mmol) in MeOH (20 mL) was added to thick walled glass vessel designed to fit on a Parr hydrogenolysis apparatus followed by a suspension of palladium hydroxide (850 mg) in methanol (20 mL). The vessel was placed on the hydrogenolysis apparatus and subjected to a series of gas evacuation and hydrogen purge cycles using vacuum and hydrogen gas to remove any oxygen in the solvent. The vessel was then brought to 60 psi with hydrogen gas for 15 h with shaking. The catalyst was removed by filtration and the filtrate was concentrated in vacuo. The resulting crude product was purified by silica gel chromatography, eluting with DCM/MeOH (30:1, 20:1 then 10:1) to give the desired product (1.1 g, 66%) as a light-yellow colored foam.

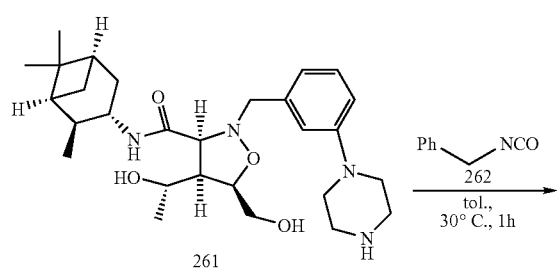

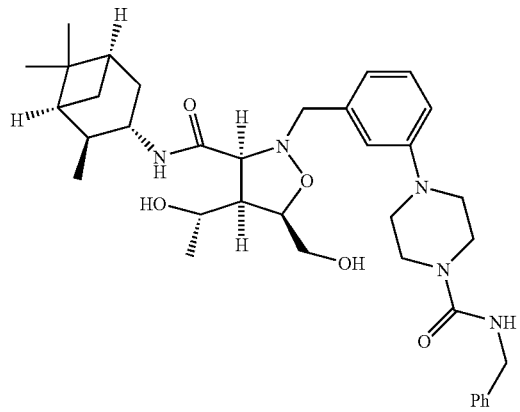

261 (25 mg, 0.05 mmol) and benzylisocyanate 262(7 mg, 0.05 mmol) were combined with 0.3 mL of anhydrous tolueneand heated at 90° C. for 1 h. The solution was cooled to ambient and concentrated in vacuo; the crude product was purified by silica gel chromatography eluting with 40:1 DCM/MeOH to give the desired product (10 mg, 33%) as a pale-yellow foam. MS (ESI(+)) m/e 634.3 (M+H)$^+$.

Example 179

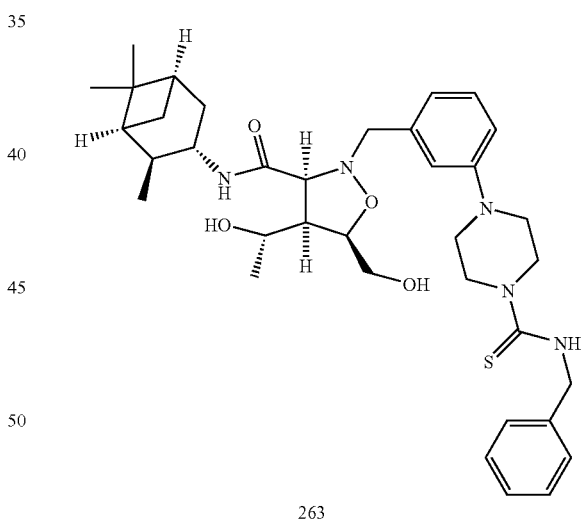

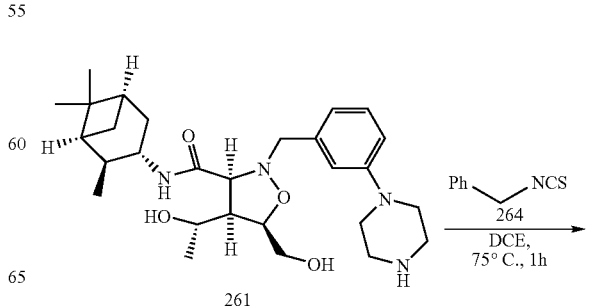

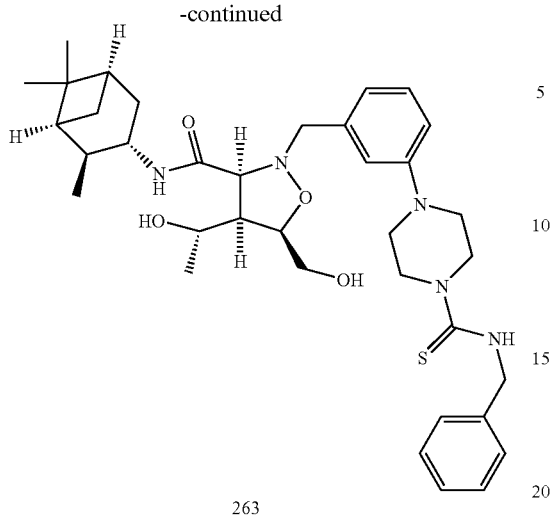
263
Compound 263 was synthesized according to the procedure described in example 189 in using 264 in place of 262. 36% yield. MS (ESI(+)) m/e 650.4 (M+H)$^+$.
Example 180
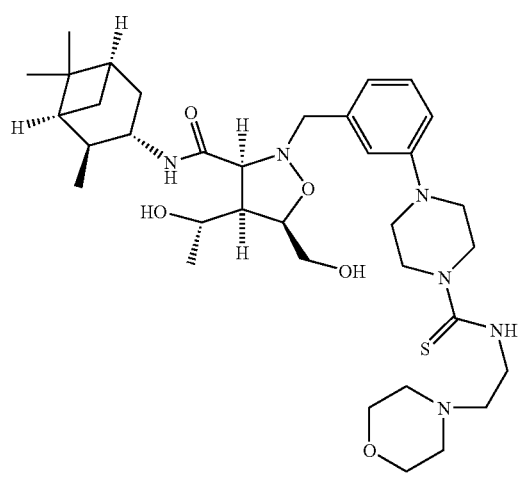
264
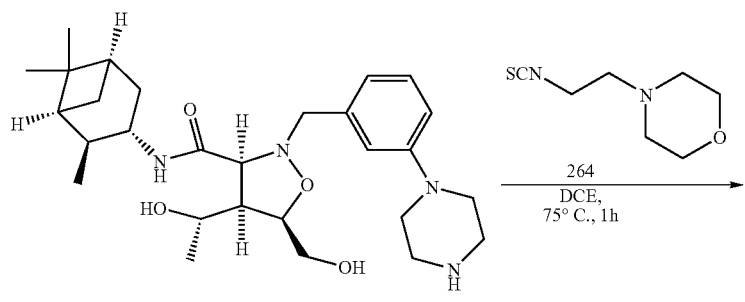

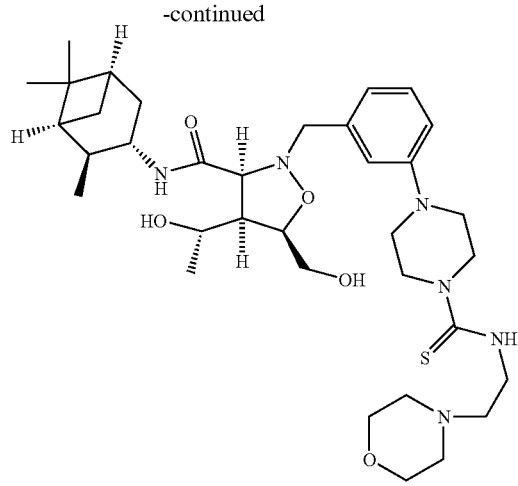
264
Compound 264 was synthesized according to the procedure described in example 189 in using 265 in place of 262. 34% yield. MS (ESI(+)) m/e 673.5 (M+H)+.
Example 181
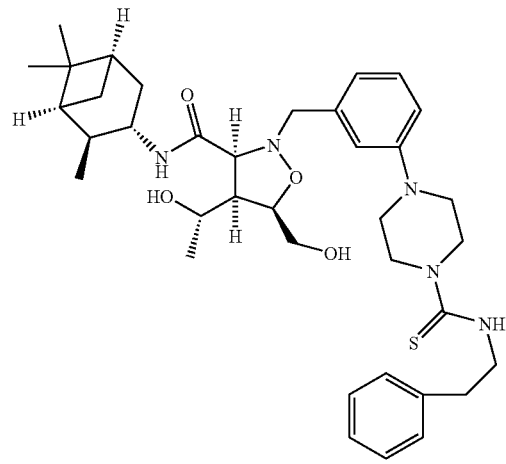
266
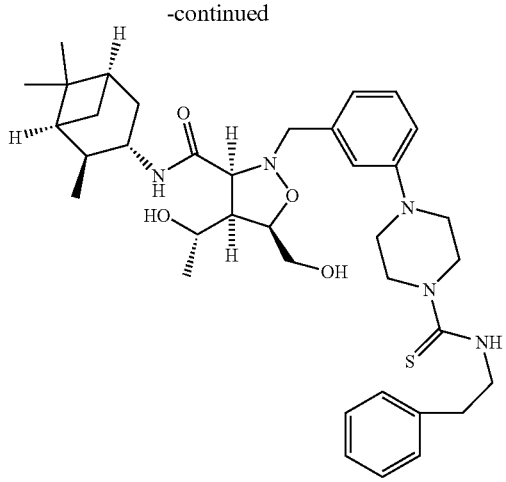
266
Compound 266 was synthesized according to the procedure described in example 189 in using 267 in place of 222. 30% yield. MS (ESI(+)) m/e 664.5 (M+H)+.
Example 182
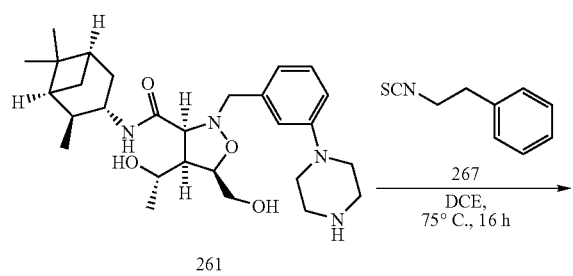
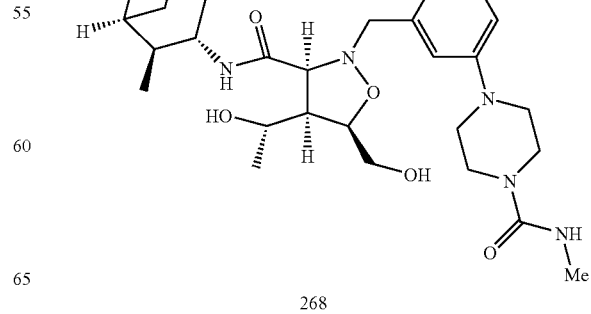
268

-continued

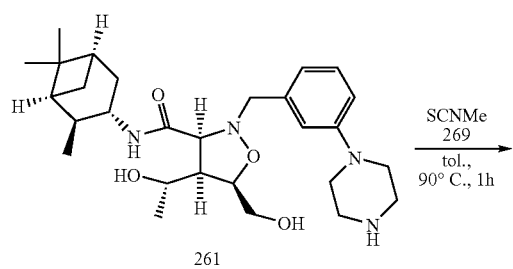
261

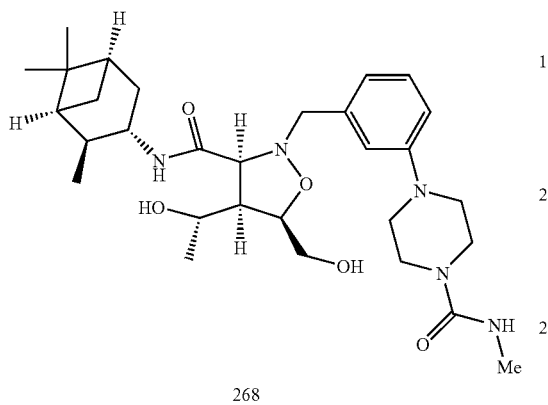
268

Compound 268 was synthesized according to the procedure described in example 189, using 269 in place of 262. 35% yield. MS (ESI(+)) m/e 574.3 (M+H)+.

Example 183

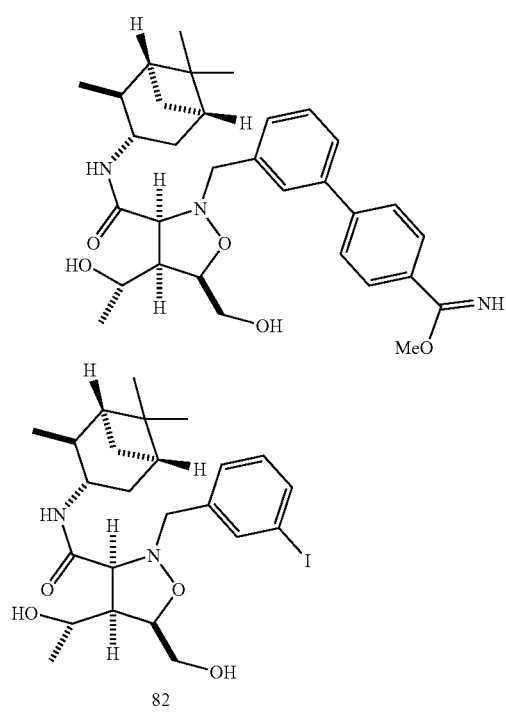
270

82

-continued

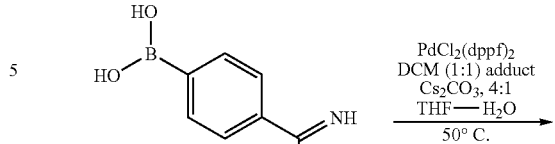
277

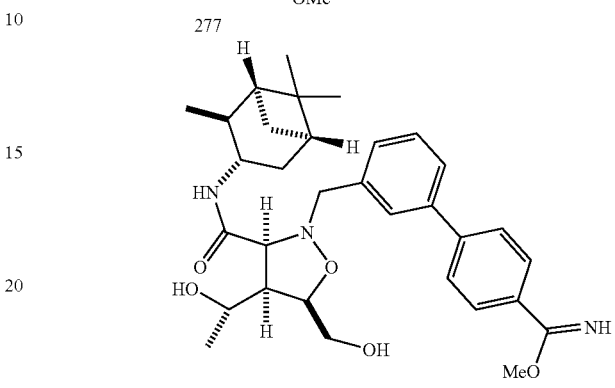
270

Aryl iodide 82 (0.03 mmol), boronic acid 271 (0.03 mmol), PdCl$_2$(dppf)$_2$, 1:1 DCM adduct (0.006 mmol), cesium carbonate (0.03 mmol) were combined with 4:1 THF-H$_2$O (0.3 mL) at ambient temperature. This mixture was then degassed (freeze/pump/thaw X 3). It was then heated to 50° C. for 12 h. The reaction mixture was concentrated in vacuo at 50° C. and the residue was purified by silica gel chromatography to give biaryl (75% yield). MS (ESI(+)) m/e 550.3 (M+H)+.

Example 184

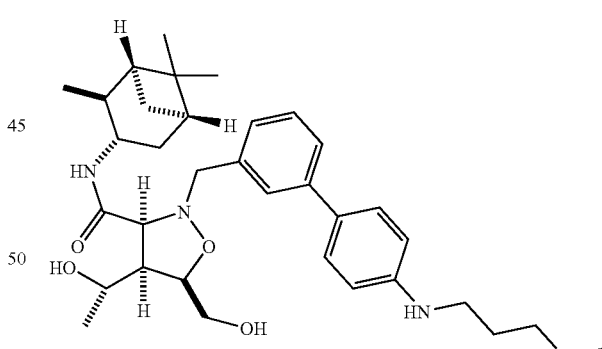
272

Part A

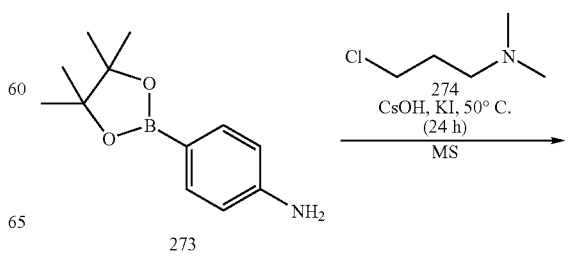
273

-continued

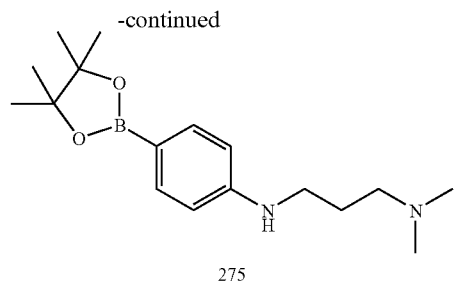

275

273 (300 mg, 1.0 mmol), alkylchloride 274 (2 g, 14 mmol), cesium hydroxide (200 mg, 1.0 mmol), KI (one crystal), and 4 Å molecular sieves (500 mg) were combined with 1.5 mL of anhydrous DMF. This mixture was heated at 50° C. for 24 h. It was cooled to ambient and diluted with 100 mL of EtOAc. Solids were removed by filtration. The residue was purified by silica gel chromatography (25:1 DCM/MeOH) to give biaryl (8.5 mg, 2%) as a pale-yellow solid.

Part B

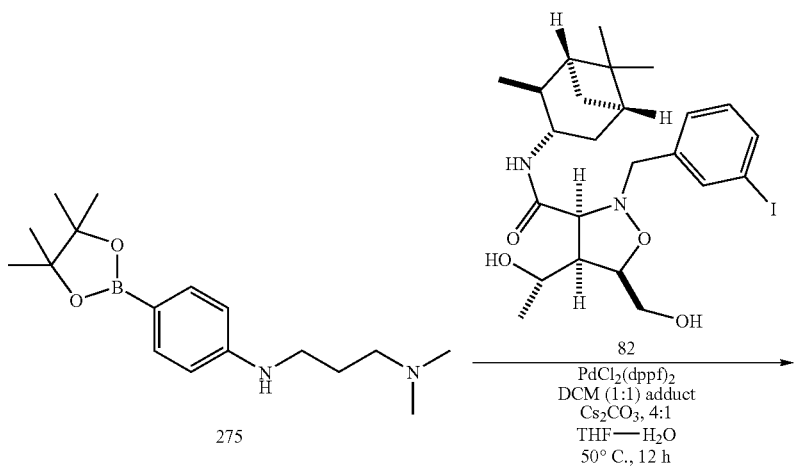

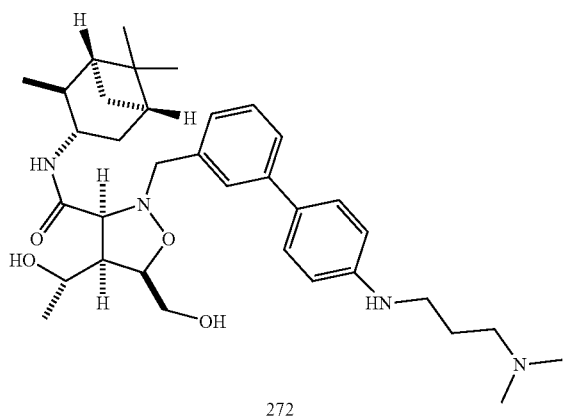

82(15 mg, 0.03 mmol), 275(8 mg, 0.03 mmol), PdCl₂(dppf)₂, 1:1 DCM adduct (5 mg, 0.006 mmol), cesium carbonate (9 mg, 0.03 mmol) were combined with of 4:1 THF-H₂O (0.3 mL) at ambient temperature. This mixture was then degassed (vac/purged with argon 3×) and heated at 50° C. for 12 h. The reaction mixture was concentrated in vacuo at 50° C. and the residue was purified by silica gel chromatography (15:1 DCM-MeOH) to give 272 (5 mg, 31%) as a pale-yellow foam. MS (ESI(+)) m/e 593.6 (M+H)⁺.

Example 185

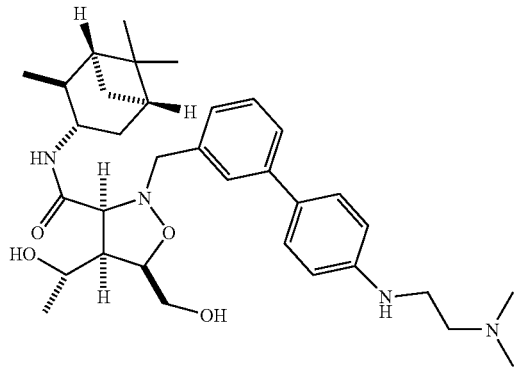

276

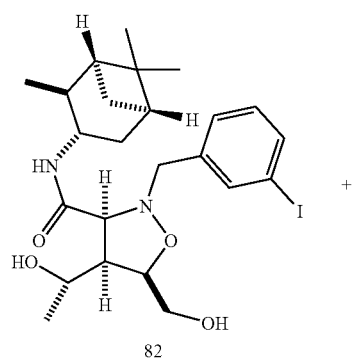

82

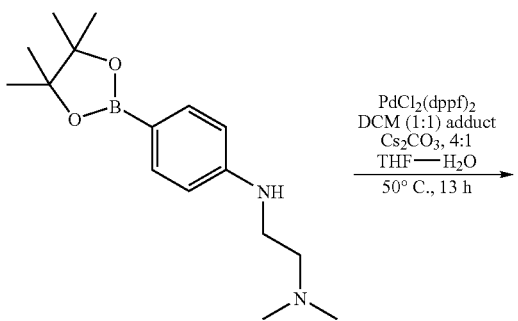

277

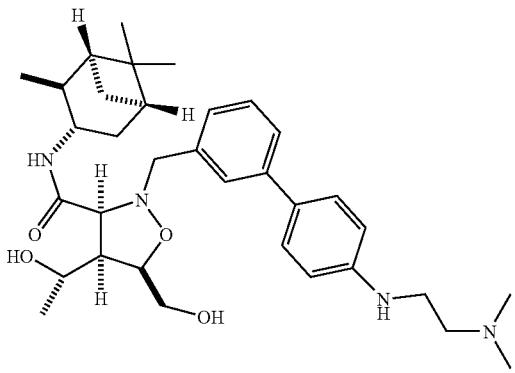

276

Compound 277 was synthesized according to the procedure described in Part A, example 184; using 2-chloro-N,N-dimethylethanamine in place of 2-chloro-N,N-dimethylpropanamine Compound 276 was synthesized according to the procedure described in example 184. 38% yield. MS (ESI(+)) m/e 579.3 (M+H)⁺.

Example 186

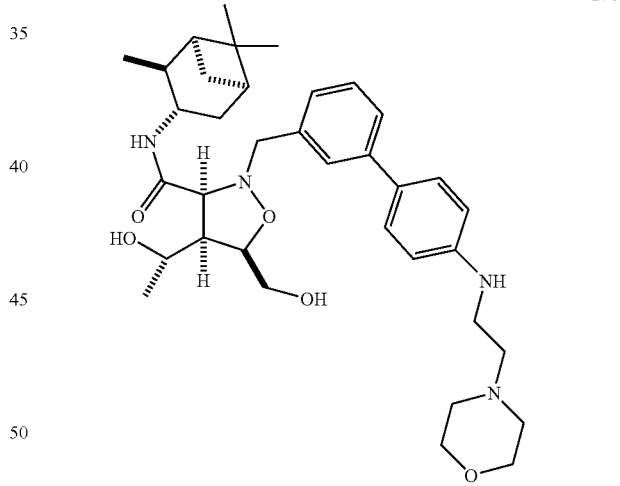

278

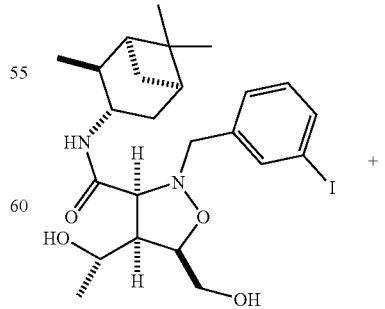

82

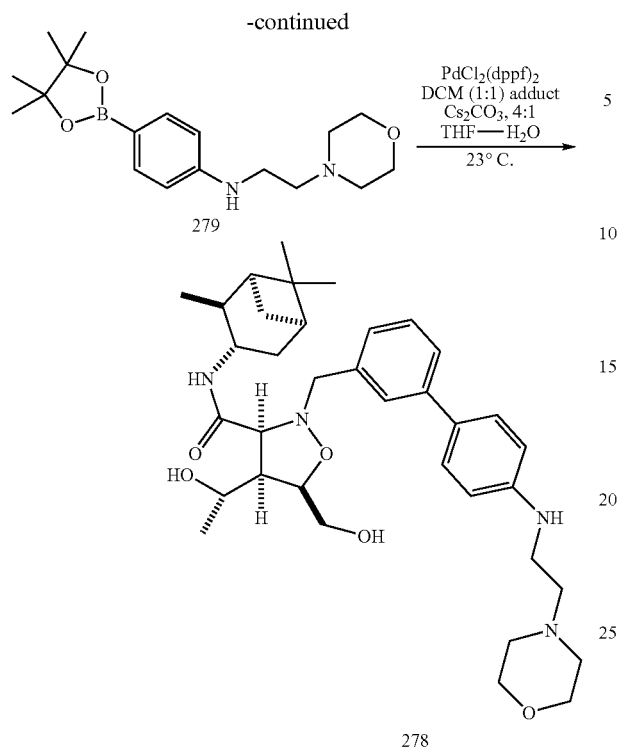

Compound 279 was made according to the proecudere described in example 184, Part A. Using 4-(2-chloroethyl)morpholine in place of 2-chloro-N,N-dimethylpropanamine. Compound 278 was synthesized according to the procedure described in example 184, using 279 in place of 275. 23% yield. MS (ESI(+)) m/e 621.5 (M+H)+.

Example 187

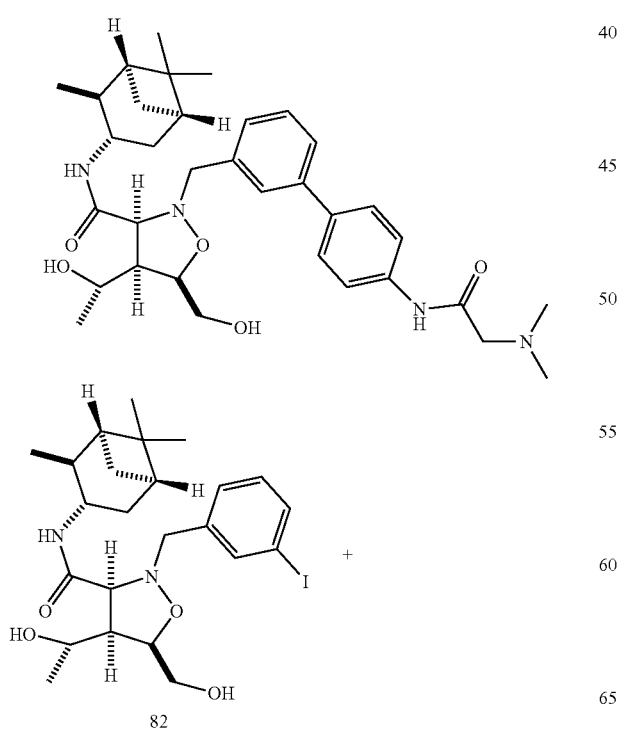

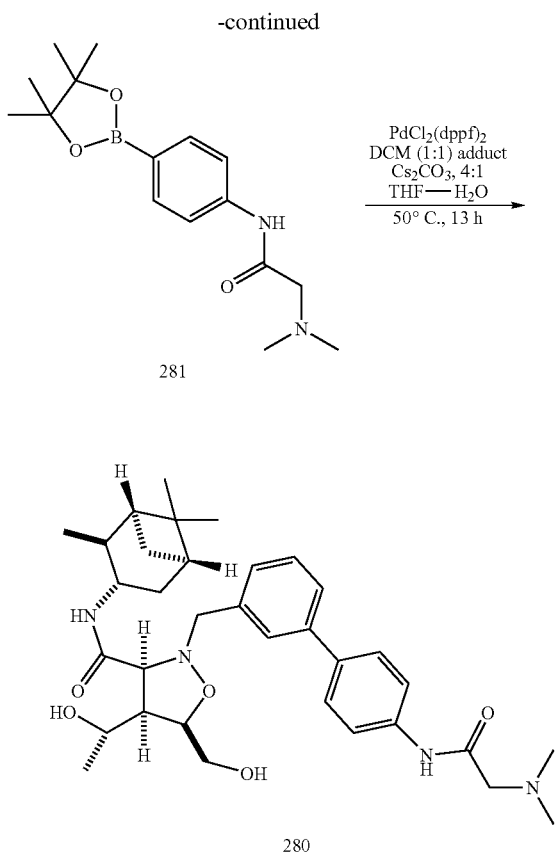

Compound 290 was synthesized according to the procedure described in example 183, using boronic ester 281 in place of boronic acid 271 15% yield.

Example 188

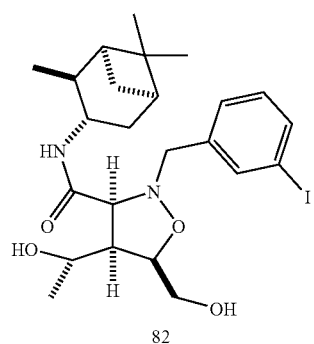
82
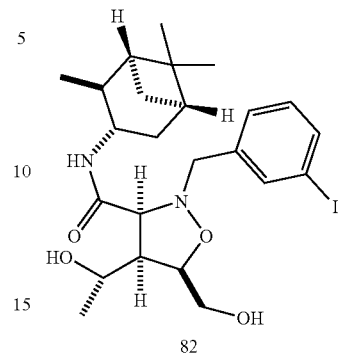
82
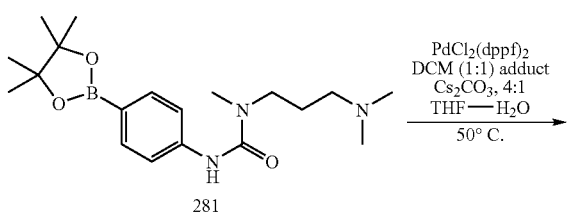
281
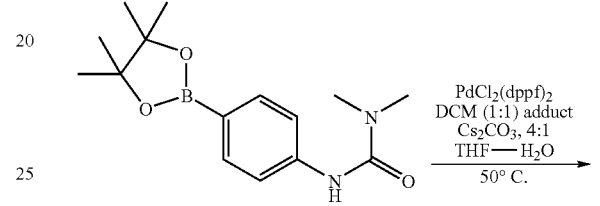
284
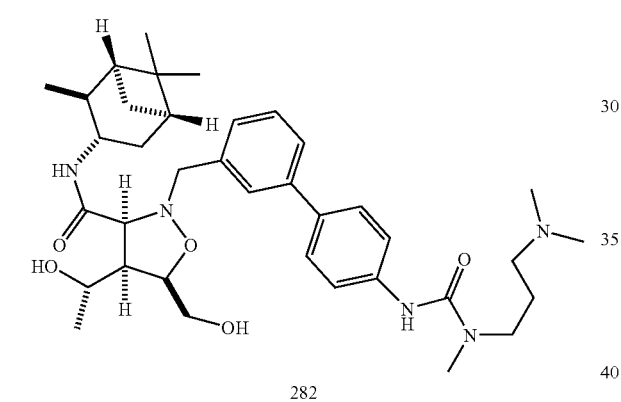
282
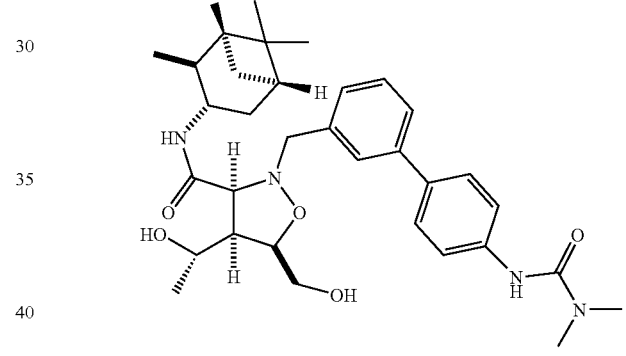
283
Compound 82 was synthesized according to the procedure described in example 183, using boronic ester 281 in place of boronic acid 271. 70% yield. MS (ESI(+)) m/e 650.4 (M+H)+.
Example 189
Compound 82 was synthesized according to the procedure described in example 183, using boronic ester 284 in place of boronic acid 271. 47% yield. MS (ESI(+)) m/e 579.3 (M+H)+.
Example 190
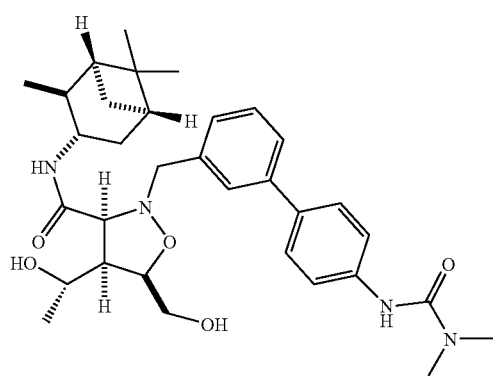
283
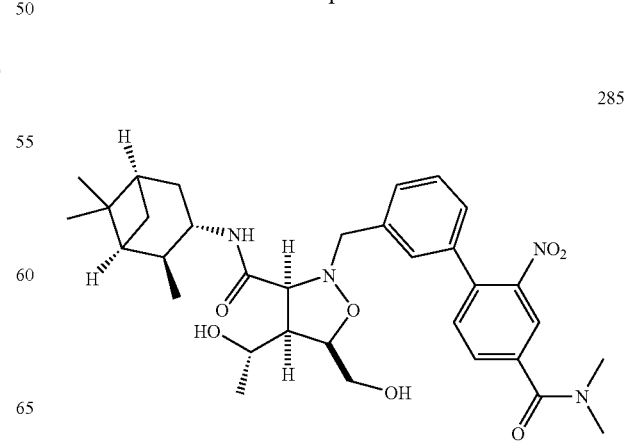
285

Part A

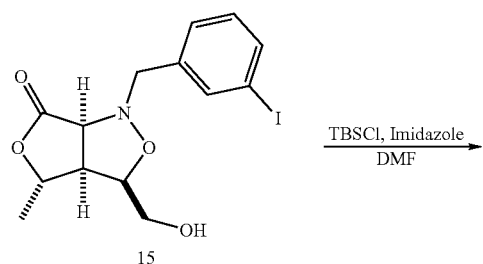

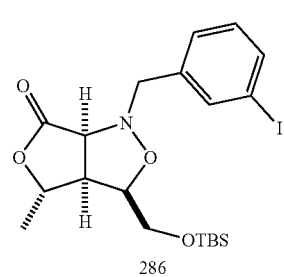

15 (1 mmol) was added to anhydrous DMF (1 mL) followed by TBSCI (1.6 mmol) and imidazole (2.0 mmol). This solution was stirred under an argon for 8 h. Water (5 mL) was then added) and the was aqueous layer was separated and extracted with EtOAc (3×10 mL). The organic extracts were pooled, dried over MgSO₄, filteredand concentrated. The crude material was purified by silica gel chromatigraphy to afford 286 (98%).

Part B

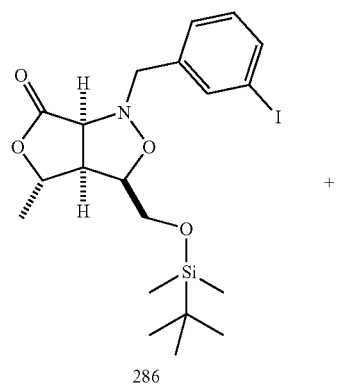

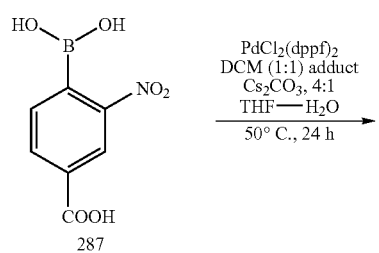

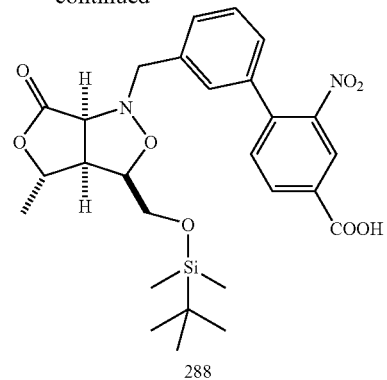

Compound 288 was synthesized according to the procedure described in example 183, using boronic acid 287 in place of boronic acid 271. 56% yield.

Part C

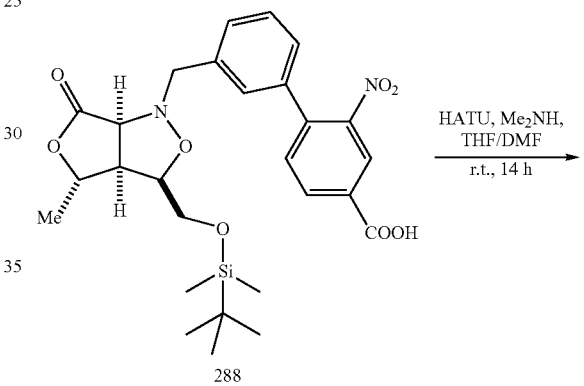

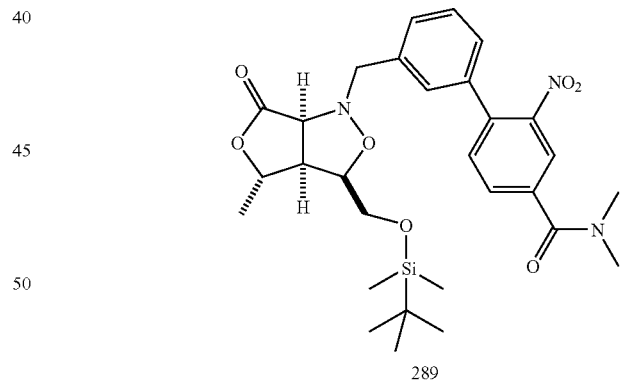

To a DMF (2mL) solution of 288 (0.33 g, 0.60 mmol) and HATU (0.68 g, 1.8 mmol) was added dimethylamine in (2 M in THF 1 mL) at rt. This soution was stirred for 14 h. It was partitioned between water/EtOAc (1:1, 200 mL) the separated organic layer was washed with H₂O (2×50 mL) and the combined aqueous layers were back extracted with EtOAc (2×50 mL).The combined organic extracts were dried over MgSO₄, filtered and concentrated in vacuo The residue was purified via silica gel chromatography (DCM, then 2:1 DCM/EtOAc) to give the desired product (Rf=0.4, 4:1 DCMI-EtOAc, 67 mg, 20%) as a brown-colored semi-solid.

Part D

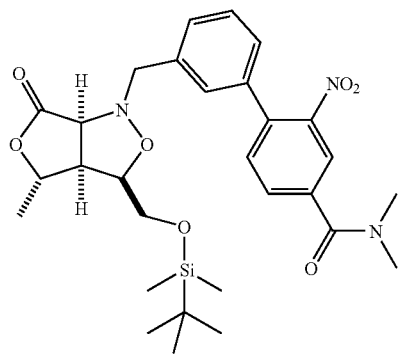

289

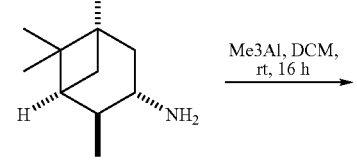

Me3Al, DCM,
rt, 16 h

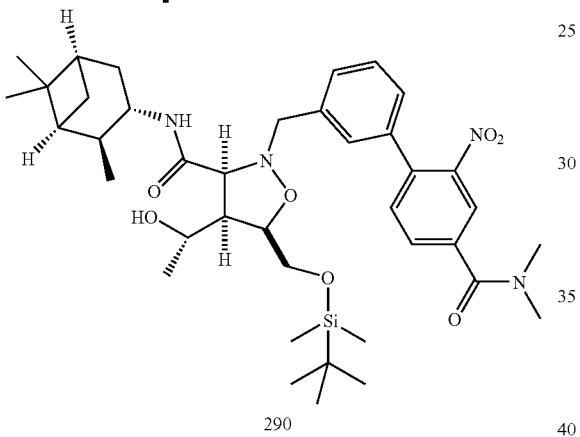

290

Amine (30 mg, 0.2 mmol) was dissolved in 0.3 mL of DCM; at rt trimethylaluminum hexanes solution (2.0 M, 0.1 mL) was added; this solution was stirred at rt for 10 min; a DCM solution (0.2 m) of lactone 289 (56 mg, 0.1 mmol) was added; reaction was maintained at rt fot 16 h. It was diluted with 15 mL; sat. aq pottasium sodium tartarate (Rochelle Salt) solution (15 mL) was added in one portion. This mixture was vigorously stirred at rt for 2 h until a clear two-phase mixture was given. Separated aqueous layer was extracted with DCM (2×15 mL); combined organic phases were washed with water (15 mL), dried over MgSO4 and concentrated in vacuo. The residue was purified using SGC (1:1 Hex-EtOAc) to give the desired product (40 mg, 56%) as a pale-yellow oil.

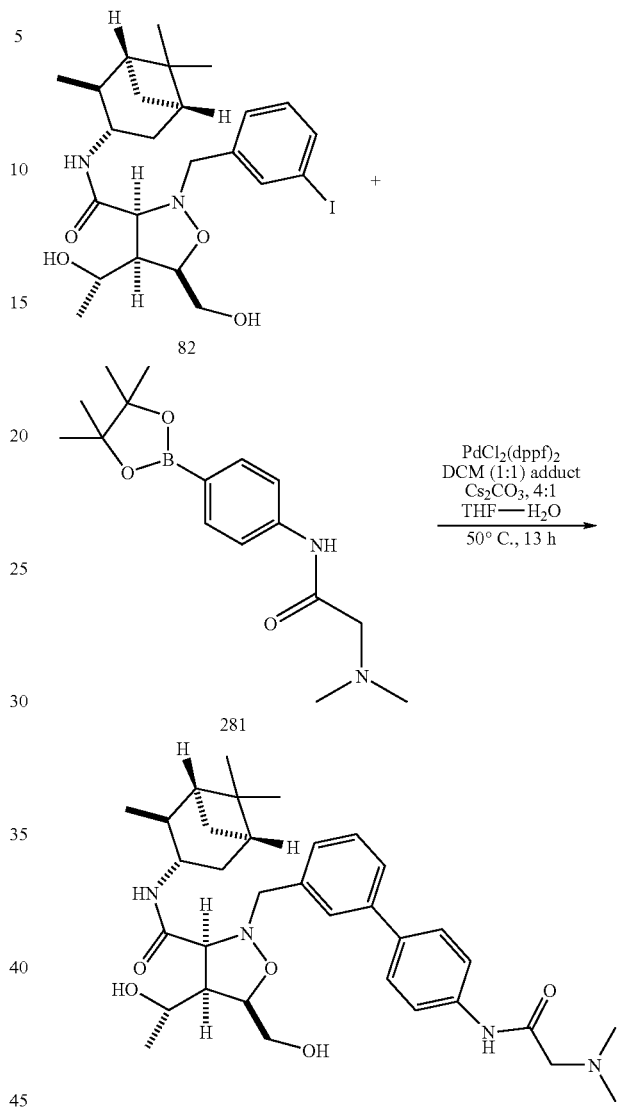

Compound 290 was synthesized according to the procedure described in example 183, using boronic ester 281 in place of boronic acid 271 15% yield.

Example 191

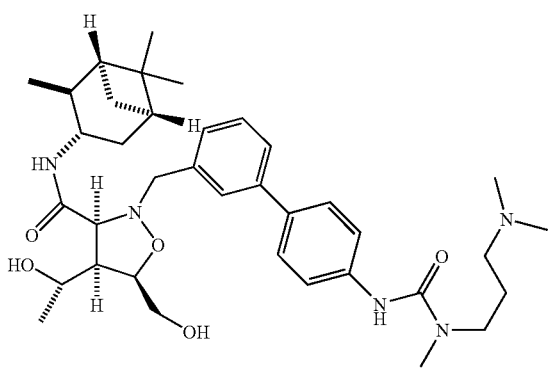

282

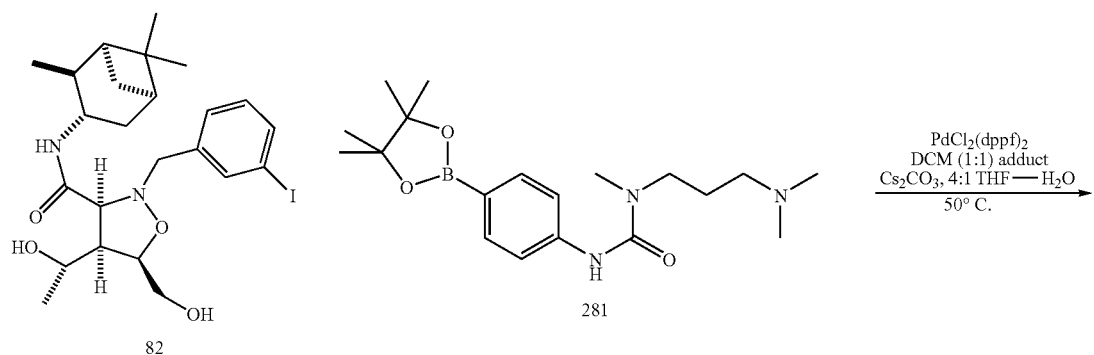
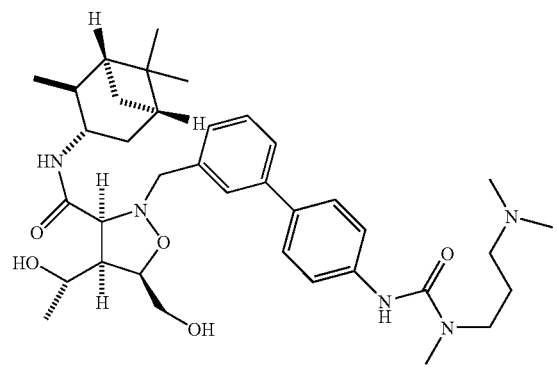
Compound 82 was synthesized according to the procedure described in example 183, using boronic ester 281 in place of boronic acid 271. 70% yield. MS (ESI(+)) m/e 650.4 (M+H)⁺.
Example 192
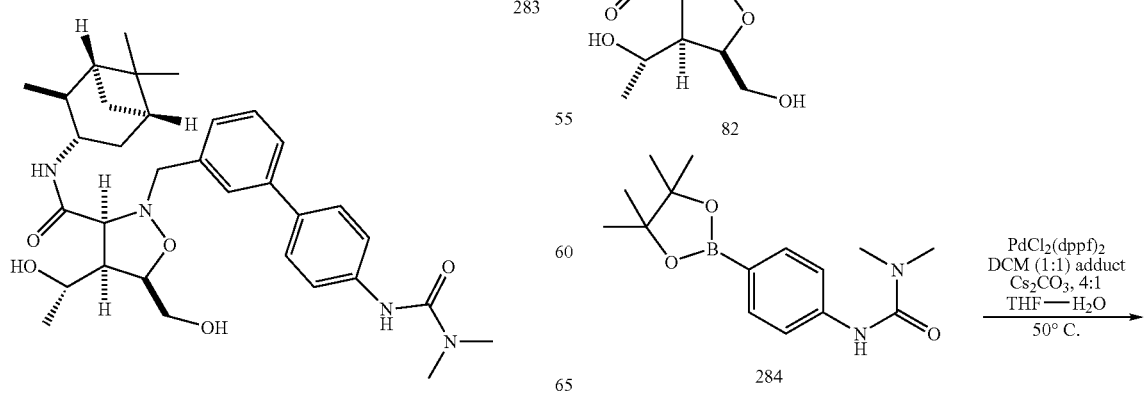

-continued

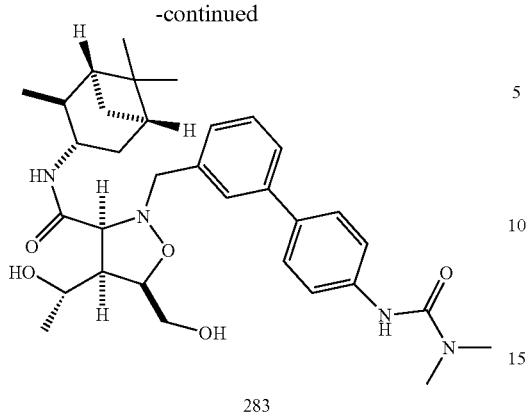

283

Compound 82 was synthesized according to the procedure described in example 183, using boronic ester 284 in place of boronic acid 271. 47% yield. MS (ESI(+) m/e 579.3 (M+H)$^+$.

Example 193

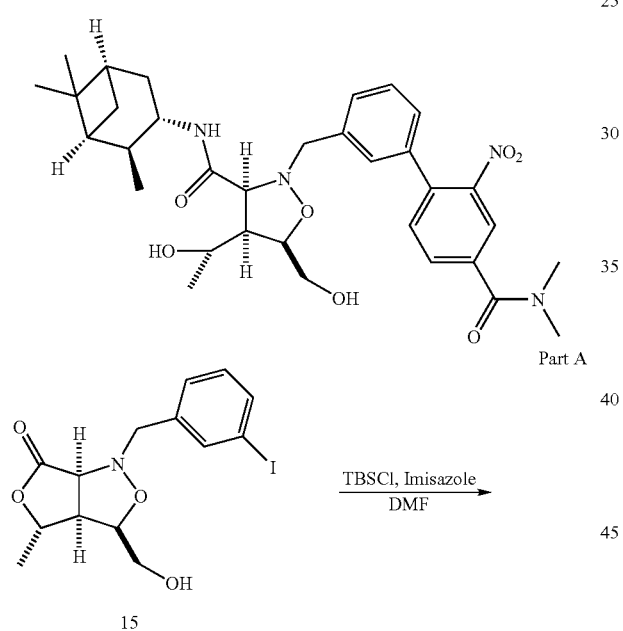

285

Part A

Alcohol 15 (0.4 g, 1 mmol) was added to DMF (1 mL) followed by TBSCI (0.24 g, 1.6 mmol) and imidazole (0.13 g, 2.0 mmol). This solution was stirred under an argon for 8 h. Water (5 mL) was then added and the was aqueous layer was separated and extracted with EtOAc (3×10 mL). The organic extracts were pooled, dried (MgSO$_4$), filtered and concentrated in vacuo. The crude material was purified by silica gel chromatigraphy (Et$_2$O/CH$_2$Cl$_2$, 1:29) to afford 286 (4.9 g, 98%).

Part B

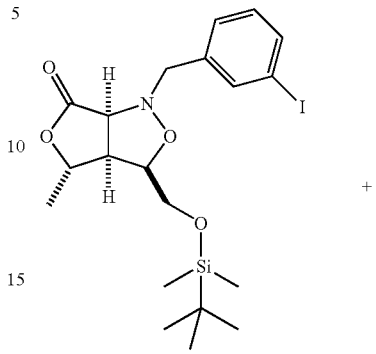

286

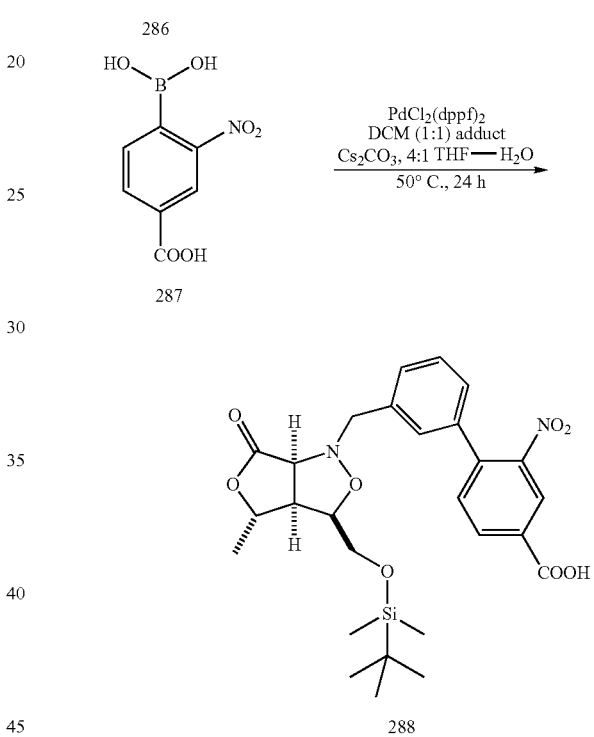

287

288

Compound 288 was synthesized according to the procedure described in example 183, using boronic acid 287 in place of boronic acid 271. 56% yield.

Part C

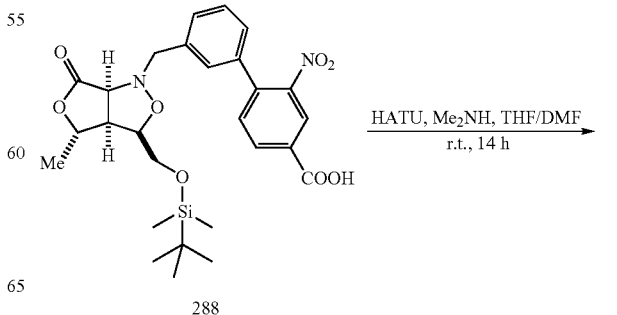

288

-continued

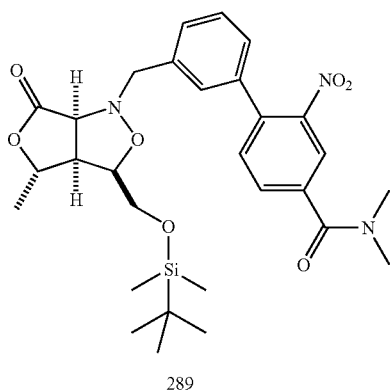

289

To a DMF (2mL) solution of 288 (0.33 g, 0.6 mmol) and HATU (0.68 g, 1.8 mmol) was added dimethylamine in (1 mL in a 2 M solution of THF, 3.1 mmol). This soution was stirred at rt for 14 h. Diluted with water/EtOAc (1:1, 200 mL) and the aqueous layer was extracted with EtOAc (2×50 mL). The combined organic extracts were washed with water (2×50 mL), dried (MgSO$_4$), filtered and concentrated in vacuo. The residue was purified by silica gel chromatography (CH$_2$Cl$_2$/EtOAc, 2:1) to give 289 (67 mg, 20%) as a brown-colored semi-solid.

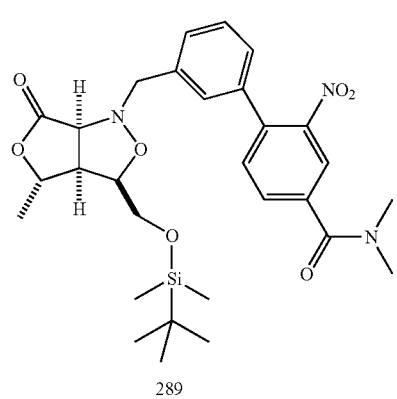

289

To a solution of (+) isopinocampheylamine (30 mg, 0.2 mmol) in CH$_2$Cl$_2$ (0.3 mL) was added AlMe$_3$ (0.1 mL of a 2 M solution in hexane, 0.2 mmol). After stirring for 10 min a solution of lactone 289 (56 mg, 0.1 mmol) in CH$_2$Cl$_2$ (0.2 mL) was added and the mixture was stirred for 16 h. with the reaction was quenched with saturated aqueous Rochelle Salt (15 mL) and vigorously stirred at rt for 2 h until a clear biphasic mixture appeared. The aqueous layer was separated and extracted with CH$_2$Cl$_2$ (2×15 mL), the combined organicextracts were washed with water (15 mL), dried (MgSO$_4$), filtered and concentrated in vacuo. The residue was purified using silica gel chromatography (Hexane/EtOAc, 1:1) to give 290 (40 mg, 56%) as a pale-yellow oil.

Part E

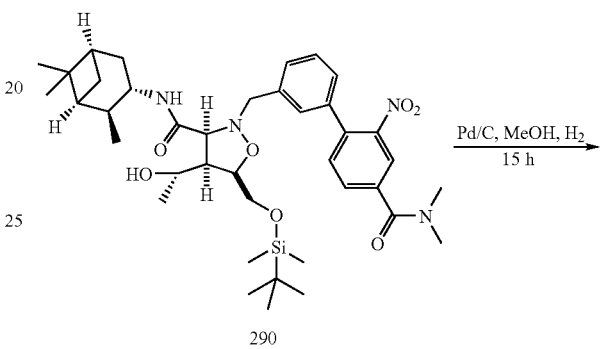

290

Part D

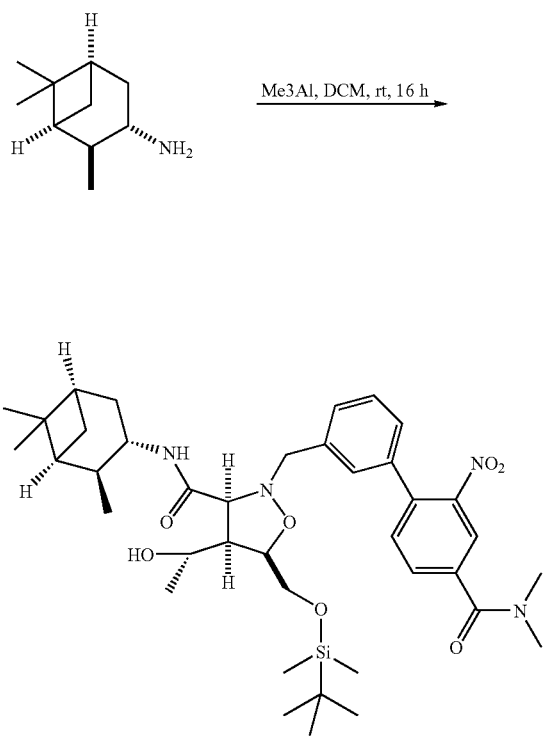

290

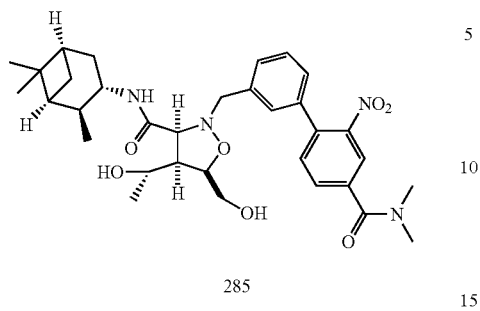

285

Solid sample of Pd/C (1.5 mg) was added under argon in one portion to a solution of 290 (15 mg, 0.02 mmol) in MeOH (0.4 mL). This mixture was treated with hydrogen gas (1 atm) at rt for 15 h. Solids were removed by filtration and the filtrate was concentrated in vacuo. The crude product was purified via silica gel chromatograhy (EtOAc) to give 285 (8 mg, 63%) as a pale-yellow oil. MS (ESI(+)) m/e 609.3 (M+H)$^+$.

Example 194

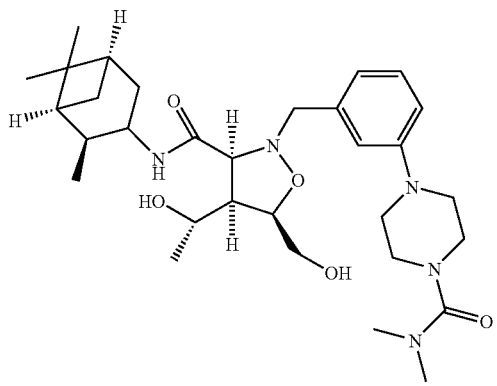

291

Compound 261 (3 mg, 0.006 mmol), acyl chloride 292 (1.2 μL, 0.012 mmol), DMAP (one crystal), and Et$_3$N (0.012 mmol) were combined with CH$_2$Cl$_2$ (0.2 mL) at rt. This solution was stirred for 20 h. and concentrated in vacuo. The resulting residue was purified by silica gel chromatography (CH$_2$Cl$_2$/MeOH, 30:1) to give 291 (2 mg, 58%) as a light-yellow solid. MS (ESI(+)) m/e 572.3 (M+H)$^+$.

Example 195

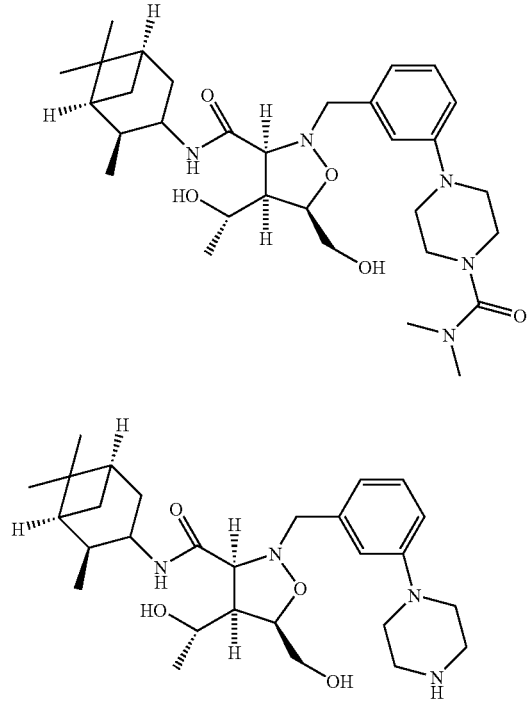

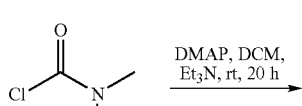

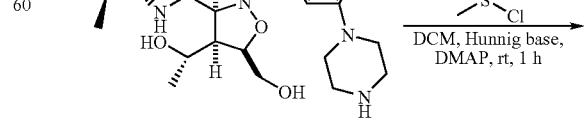

-continued

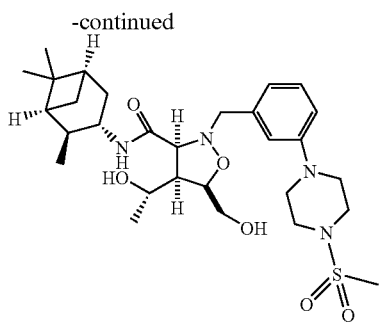

293

To a solution of amine 261 (3 mg, 0.006 mmol) in CH$_2$Cl$_2$ (0.2 mL) was added methanesulfonylchloride (2.6 mg, 0.012 mmol), DMAP (one crystal), and diisopropylethylamine (1.5 mg, 2 μL, 0.012 mmol. The solution was stirred for 20 h. and concentrated in vacuo. The resulting residue was purified by chromatography to afford 293 (1.2 mg, 37%). MS (ESI(+)) m/e 579.2 (M+H)$^+$.

Example 196

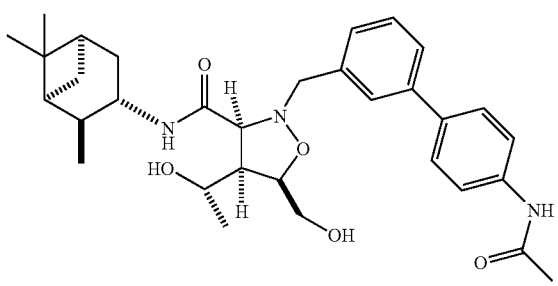

294

-continued

Part A

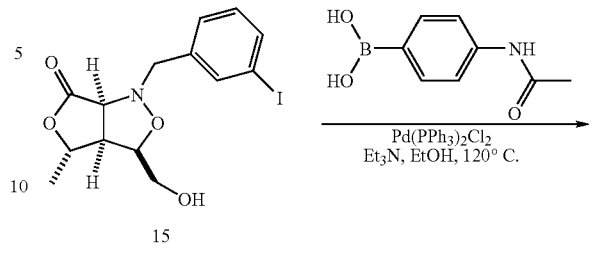

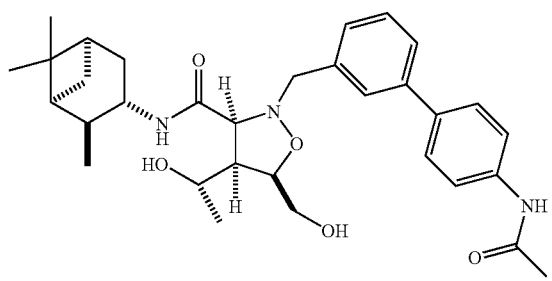

295

To a mixture of aryl iodide 15 (100 mg, 0.26 mmol), boronic acid (46 mg, 0.26 mmol), Et$_3$N (77 mg, 0.11 mL, 0.77 mmol), Pd(PPh$_3$)$_2$Cl$_2$ (4 mg, 2 mol %) was added EtOH (1.5 mL). The resulting mixture was heated to 80° C. for 10 min until it became an almost homogeneous. It was then heated to 12° C. in a microwave oven for 30 min The reaction mixture was concentrated in vacuo and the residue was purified by silica gel chromatography (CH$_2$Cl$_2$/MeOH, 60:1 to 10:1) to afford 295 (86 mg, 84%) as a pale-yellow oil.

Part B

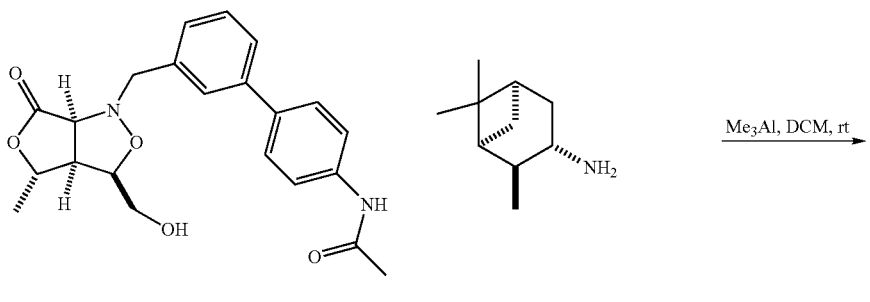

295

294

To a solution of (+) Isopinocampheylamine (3 mg, 0.02 mmol) in CH$_2$Cl$_2$ (0.4 mL) was added AlMe$_3$ (42 μL of a 2 M solution in hexane, 0.042 mmol). After stirring for 10 min, a solution of lactone 295 (8 mg, 0.02 mmol) in CH$_2$Cl$_2$ (0.4 mL) was added and the reaction was stirred for 1 h. The solution was diluted with CH$_2$Cl$_2$ and quenched by the addition of saturated aqueous Rochell salt (25 mL). The solution was vigorously stirred for 2 h until two phases became clear and the layers were separated. The organic phase was dried (Na$_2$SO$_4$), filtered and concentrated in vacuo. The residue was purified via silica gel chromatography (CH$_2$Cl$_2$/MeOH, 40:1 to 15:1) to give 294 (3 mg, 27%) as a semi-solid. MS (ESI(+)) ni/e 550.4 (M+H)$^+$.

the aqueous phase was separated and extracted with EtOAc (0.5 mL). The combined organic extracts were dried (Na$_2$SO$_4$), filtered and concentrated in vacuo to afford an oil. The oil was purified by reverse phase chromatography C 18 column containing 20% acetonitrile/water containing 0.1% ammonium bicarbonate to afford 296 (1.5 mg, 24%). MS (ESI(+)) m/e 627.4 (M+H)$^+$.

Example 198

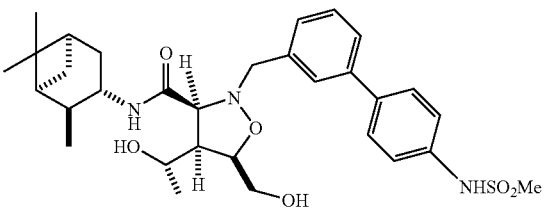

298

Example 197

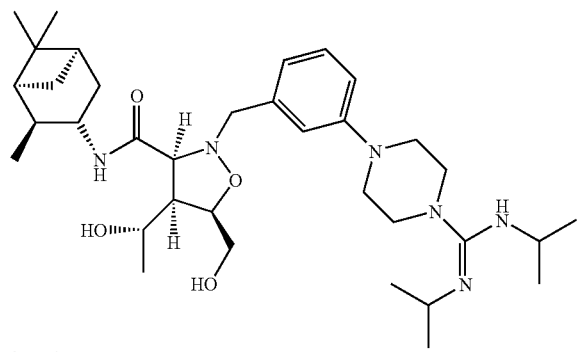

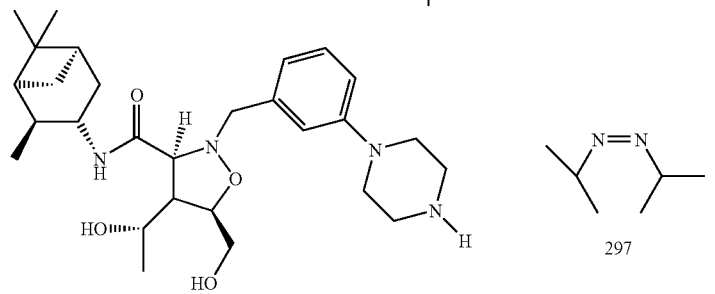

261

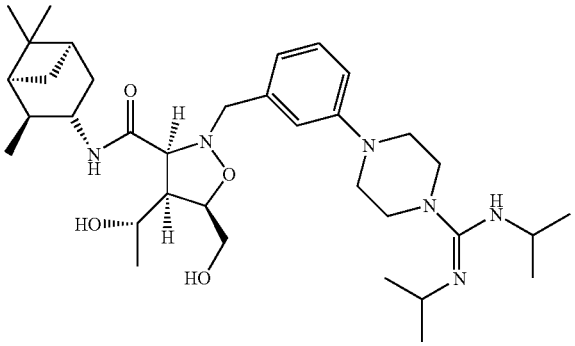

296

To a solution of amine 261 (7 mg, 0.01 mmol) in DMF (0.2 mL) was added diisopropylcarbodimide 297 (2 mg, 0.02 mmol). The reaction was heated to 110° C. for 12 h. The solution was cooled to ambient, diluted with water (0.5 mL), Compound 298 was synthesized according to the procedure decribed in example 183, using 4-(methylsulfonamido) phenylboronic acid in place of 4-acetamidophenylboronic acid. Yield 78%. MS (ESI(+)) m/e 586.3 (M+H)$^+$.

Example 199
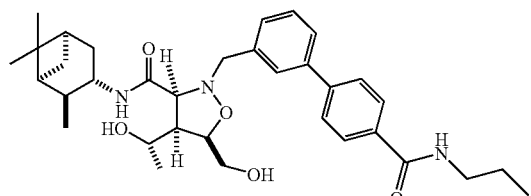
299
Compound 299 was synthesized according to the procedure decribed in example 148, using propylamine in place of 189. Yield 50%. MS (ESI(+)) m/e 578.4 (M+H)$^+$.
Example 200
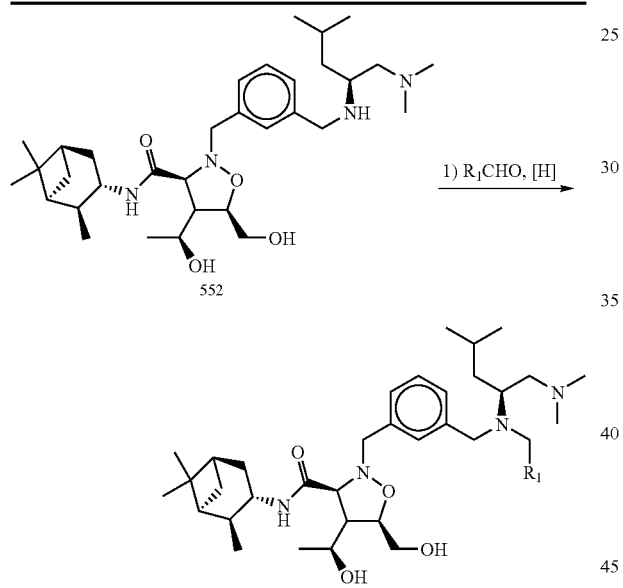
| Compound | R$_1$ |
|---|---|
| 300 | 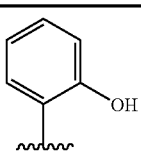 |
| 301 | 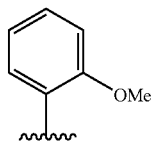 |
| 302 | 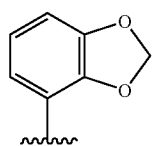 |
-continued
| | |
|---|---|
| 303 | 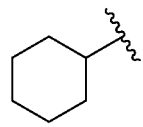 |
| 304 | 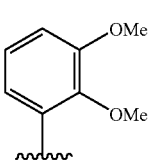 |
| 305 | 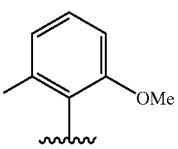 |
| 306 | 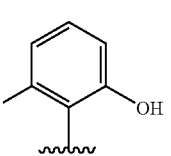 |
| 307 | 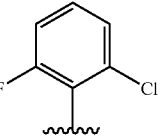 |
| 308 | 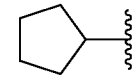 |
| 309 | 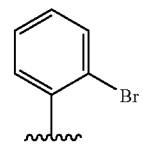 |
| 310 | 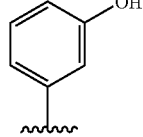 |
| 311 | 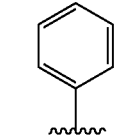 |
| 312 | 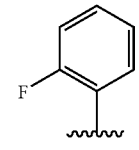 |
| 313 | 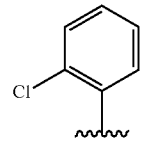 |

-continued
| | | | | |
|---|---|---|---|---|
| 314 | 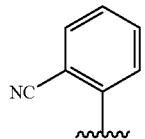 | | 322 | 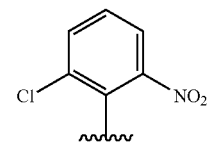 |
| 315 | 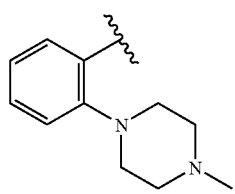 | | 323 | 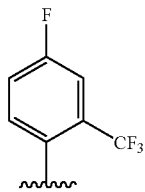 |
| Compound | R₁CHO |
|---|---|
| 324 | 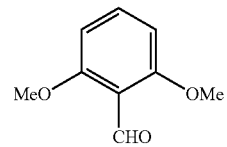 |
| | | | | |
|---|---|---|---|---|
| 316 | 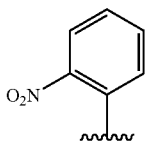 | | 325 | 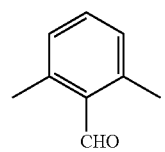 |
| 317 | 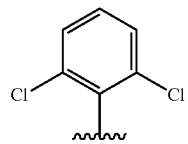 | | 326 | 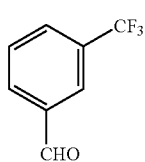 |
| 318 | 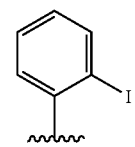 | | 327 | 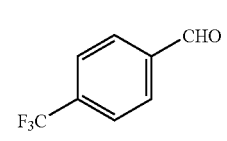 |
| 319 | 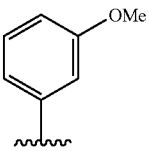 | | 328 | 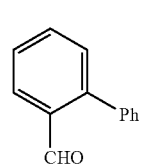 |
| 320 | 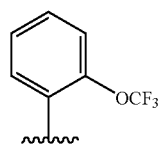 | | 329 | 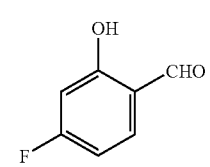 |
| 321 | 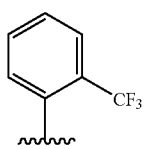 | | 330 | 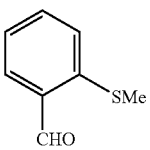 |

-continued
| | |
|---|---|
| 331 | 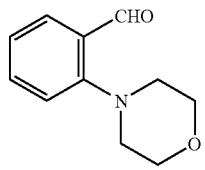 |
| 332 | 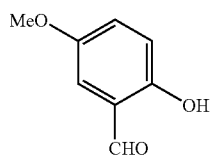 |
| 333 | 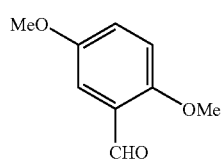 |
| 334 | 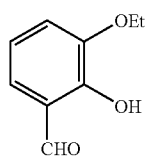 |
| 335 | 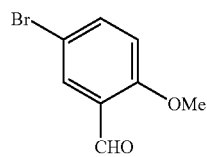 |
| 336 | 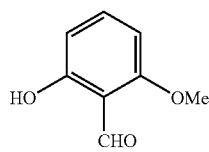 |
| 337 | 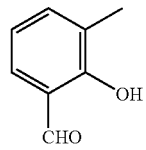 |
| 338 | 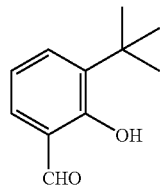 |
-continued
| | |
|---|---|
| 339 | 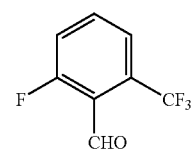 |
Compounds 300-339 were synthesized according to the procedure described in Example 149. MS data is presented in the following table for compounds 300-339.
| Compound | MS (ESI(+)) m/e (M + H)$^+$ |
|---|---|
| 300 | 679.75 |
| 301 | 693.5 |
| 302 | 707.29 |
| 303 | 669.56 |
| 304 | 724.23 |
| 305 | 711.52 |
| 306 | 697.84 |
| 307 | 716.95 |
| 308 | 655.76 |
| 309 | 743.27 |
| 310 | 679.75 |
| 311 | 686.08 (M + Na) |
| 312 | 681.72 |
| 313 | 698.89 |
| 314 | 688.54 |
| 315 | 761.93 |
| 316 | 708.53 |
| 317 | 733.46 |
| 318 | 789.61 |
| 319 | 693.78 |
| 320 | 747.7 |
| 321 | 731.65 |
| 322 | 743.17 |
| 323 | 749.5 |
| 324 | 723.76 |
| 325 | 691.84 |
| 326 | 731.53 |
| 327 | 731.51 |
| 328 | 740.77 |
| 329 | 697.75 |
| 330 | 710.23 |
| 331 | 748.83 |
| 332 | 709.84 |
| 333 | 724.17 |
| 334 | 724.08 |
| 335 | 772.61 |
| 336 | 709.78 |
| 337 | 693.66 |
| 338 | 735.83 |
| 339 | 749.52 |

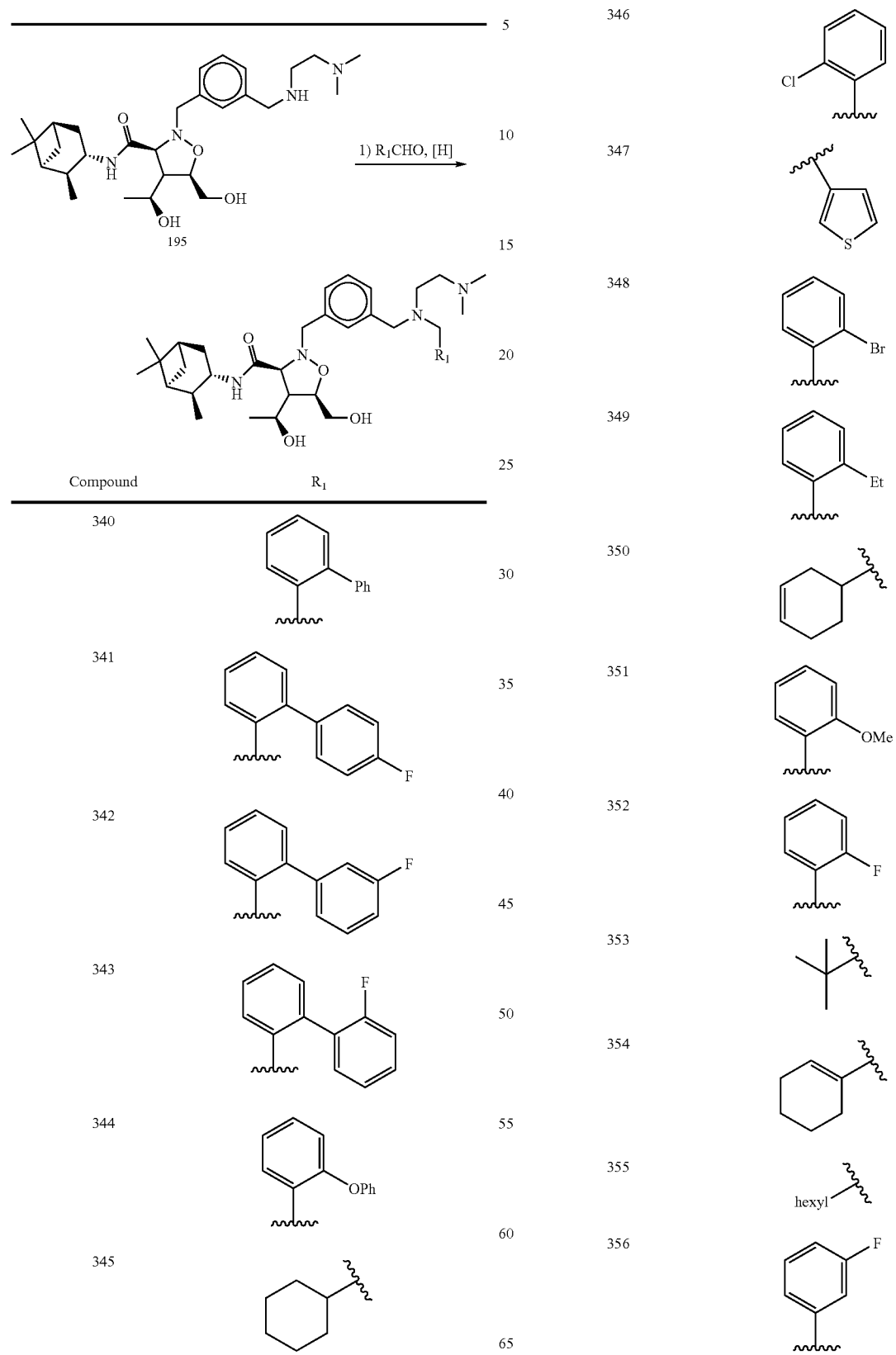

-continued
| | | | | |
|---|---|---|---|---|
| 357 | 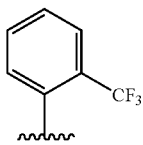 | 5 | 367 | 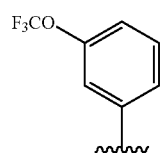 |
| 358 | 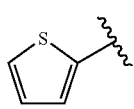 | 10 | 368 | 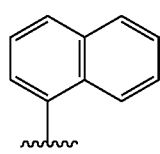 |
| 359 |  | 15 | | |
| 360 | 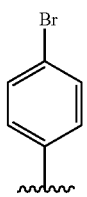 | 20 | 369 | 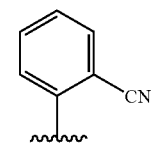 |
| 361 | 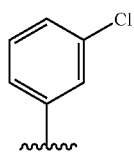 | 25 | 370 | 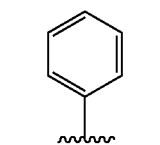 |
| 362 | 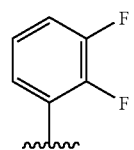 | 30 | 371 | 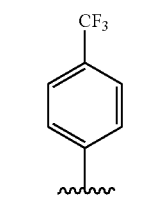 |
| 363 | 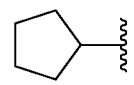 | 35 | | |
| 364 | 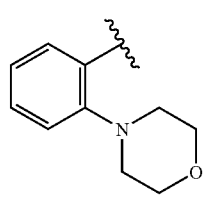 | 40 | 372 | 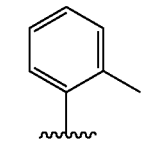 |
| | | 45 | 373 | 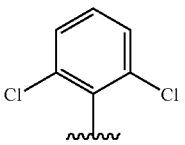 |
| 365 | 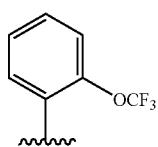 | 50 | | |
| | | 55 | 374 | 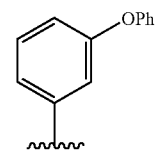 |
| 366 | 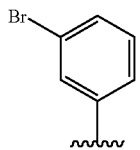 | 60 | 375 | 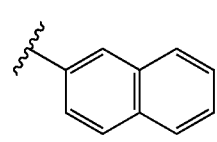 |
| | | 65 | | |

| | | | | |
|---|---|---|---|---|
| 376 | 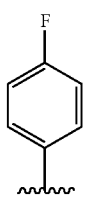 | | 386 | 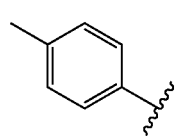 |
| 378 | 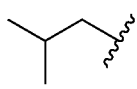 | | 387 | 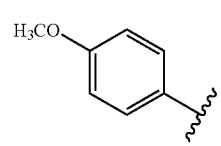 |
| 378 | 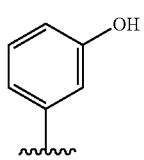 | | 388 | 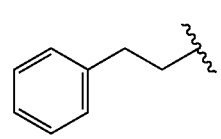 |
| 379 |  | | 389 | 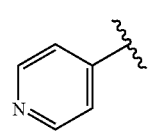 |
| 380 | 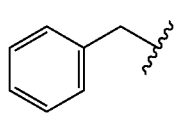 | | 390 | 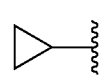 |
| 381 | 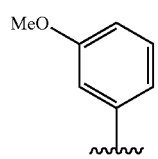 | | 391 | 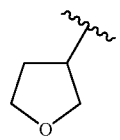 |
| 382 | 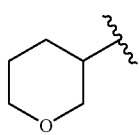 | | 392 | 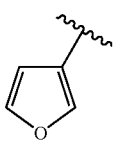 |
| 383 | 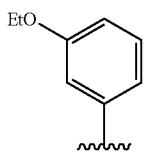 | | 393 | 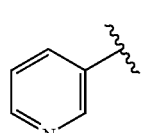 |
| 384 | 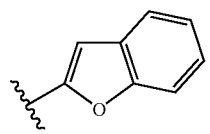 | | | |
| 385 | 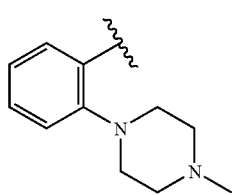 | | | |
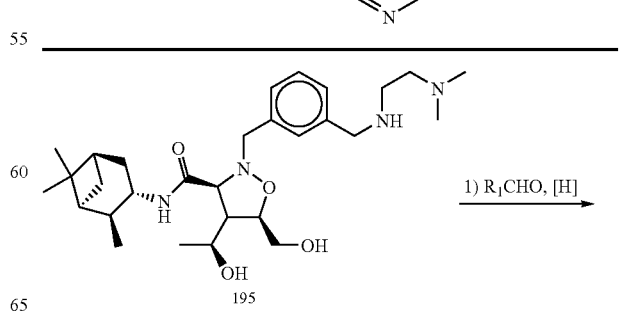
1) R₁CHO, [H] →

-continued

| Compound | R₁ |
|---|---|
| 394 | 2-iodophenyl |
| 395 | thiazol-2-yl |
| 396 | 4-nitrophenyl |
| 397 | 4-(dimethylamino)phenyl |
| 398 | 3-(trifluoromethyl)phenyl |
| 399 | 3-methylphenyl |
| 400 | 4-Ph-phenyl |
| 401 | norbornenyl |
| 402 | 3-Ph-phenyl |
| 403 | tetrahydropyran-3-yl |
| 404 | 3,5-dimethoxyphenyl |
| 405 | 3-AcO-phenyl |
| 406 | 3-(2-methoxyethoxy)phenyl |
| 407 | 3-(2-(2-methoxyethoxy)ethoxy)phenyl |
| 408 | norbornyl |
| 409 | 4'-chlorobiphenyl-2-yl |
| 410 | 2-(piperidin-1-yl)phenyl |
| 411 | 3-formylphenyl |
| 412 | 2-fluoro-3-(trifluoromethyl)phenyl |

-continued
413 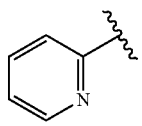
Compounds 340-413 were synthesized according to the procedure described in Example 149. MS data is presented in the following table for compounds 340-413.
| Compound | MS (ESI(+)) m/e (M + H)+ |
|---|---|
| 340 | 683.51 |
| 341 | 701.72 |
| 342 | 701.52 |
| 343 | 701.79 |
| 344 | — |
| 345 | 613.76 |
| 346 | 641.65 |
| 347 | 613.38 |
| 348 | 685.34 |
| 349 | 635.47 |
| 350 | 611.47 |
| 351 | 637.44 |
| 352 | 625.46 |
| 353 | 587.48 |
| 354 | 611.46 |
| 355 | 615.48 |
| 356 | 625.7 |
| 357 | 675.42 |
| 358 | 613.38 |
| 359 | 601.48 |
| 360 | 685.27 |
| 361 | 641.67 |
| 362 | 643.42 |
| 363 | 599.44 |
| 364 | 692.47 |
| 365 | 691.43 |
| 366 | 685.33 |
| 367 | 691.43 |
| 368 | 657.47 |
| 369 | 632.45 |
| 370 | 607.44 |
| 371 | 675.46 |
| 372 | 621.44 |
| 373 | 675.36 |
| 374 | 699.52 |
| 375 | 657.47 |
| 376 | 625.39 |
| 377 | 587.48 |
| 378 | 623.45 |
| 379 | 573.7 |
| 380 | 621.47 |
| 381 | 637.44 |
| 382 | 615.48 |
| 383 | 651.51 |
| 384 | 647.42 |
| 385 | 705.4 |
| 386 | 621.47 |
| 387 | 637.44 |
| 388 | 635.5 |
| 389 | 608.41 |
| 390 | 571.41 |
| 391 | 601.41 |
| 392 | 597.39 |
| 393 | 608.41 |
| 394 | 733.29 |
| 395 | 614.37 |
| 396 | 652.39 |
| 397 | 650.47 |
| 398 | 675.43 |
| 399 | 621.44 |
-continued
| Compound | MS (ESI(+)) m/e (M + H)+ |
|---|---|
| 400 | 683.46 |
| 401 | 623.5 |
| 402 | 683.46 |
| 403 | 615.48 |
| 404 | 667.47 |
| 405 | 665.45 |
| 406 | 681.75 |
| 407 | 724.96962 |
| 408 | 625.52 |
| 409 | 717.73 |
| 410 | 690.65 |
| 411 | 635.71 |
| 412 | 693.42 |
| 413 | 608.41 |
Example 202
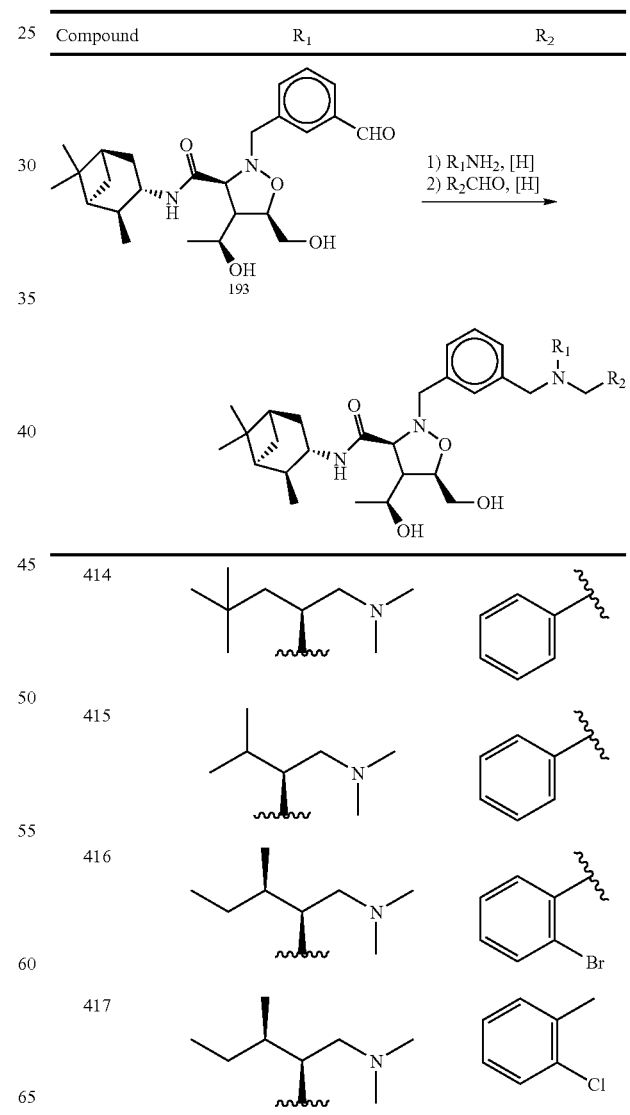
| Compound | R1 | R2 |
|---|---|---|
| 414 | | |
| 415 | | |
| 416 | | |
| 417 | | |

-continued

| Compound | R₁ | R₂ |
|---|---|---|
| 418 | CH(Ph)CH₂N(CH₃)₂ | phenyl |
| 419 | CH₂CH₂N(Et)₂ | cyclohexyl |
| 420 | CH(CH₂CH₂Ph)CH₂N(CH₃)₂ | phenyl |
| 421 | CH(C(CH₃)₃)CH₂N(CH₃)₂ | 2-chlorophenyl |
| 422 | CH(C(CH₃)₃)CH₂N(CH₃)₂ | 2-bromophenyl |
| 423 | CH(CH₂Ph)CH₂N(CH₃)₂ | phenyl |
| 424 | 1-ethylpyrrolidin-2-yl-CH₂ | phenyl |
| 425 | CH₂CH₂-pyrrolidin-1-yl | cyclohexyl |
| 426 | 1-ethylpyrrolidin-2-yl-CH₂ | phenyl |
| 427 | CH₂CH₂-azepan-1-yl | phenyl |
| 428 | CH₂CH₂N(Et)₂ | phenyl |
| 429 | 1-methylpyrrolidin-3-yl | phenyl |
| 430 | CH₂CH₂-pyrrolidin-1-yl | phenyl |
| 431 | CH(CH₃)CH₂N(CH₃)₂ | phenyl |
| 432 | 1-methylpyrrolidin-3-yl | phenyl |
| 433 | CH₂CH₂-piperidin-1-yl | phenyl |
| 434 | CH₂CH₂-morpholin-4-yl | phenyl |
| 435 | CH(CH₂CH(CH₃)₂)CH₂N(CH₃)₂ | phenyl |
| 436 | CH(CH(CH₃)₂)CH₂N(CH₃)₂ | phenyl |
| 437 | CH(CH₂-cyclohexyl)CH₂N(CH₃)₂ | phenyl |
| 438 | CH(CH₂CH₂CH₃)CH₂N(CH₃)₂ | 2-chlorophenyl |

-continued

| Compound | R₁ | R₂ |
|---|---|---|
| 439 | pyrrolidine-CH₂- with N-Cbz | phenyl |
| 440 | Me₂N-CH₂-CH(Et)-CH(Me)- | 3-fluoro-2-hydroxyphenyl |

Compounds 414-440 were synthesized according to the procedure described in Example 149. MS data is presented in the following table for compounds 414-440.

| Compound | MS (ESI(+)) m/e (M + H)⁺ |
|---|---|
| 414 | 677.55 |
| 415 | — |
| 416 | 743.2 |
| 417 | 698.05 |
| 418 | 683.46 |
| 419 | 641.46 |
| 420 | 711.52 |
| 421 | 698.95 |
| 422 | 743.29 |
| 423 | 697.45 |
| 424 | 647.43 |
| 425 | 639.46 |
| 426 | 647.42 |
| 427 | 661.46 |
| 428 | 635.44 |
| 429 | 619.43 |
| 430 | 633.43 |
| 431 | 621.48 |
| 432 | 619.43 |
| 433 | 647.42 |
| 434 | 649.42 |
| 435 | — |
| 436 | 649.78 |
| 437 | 703.82 |
| 438 | 683.74 |
| 439 | 753.5 |
| 440 | — |

Example 203

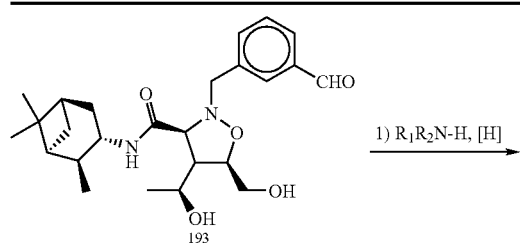

-continued

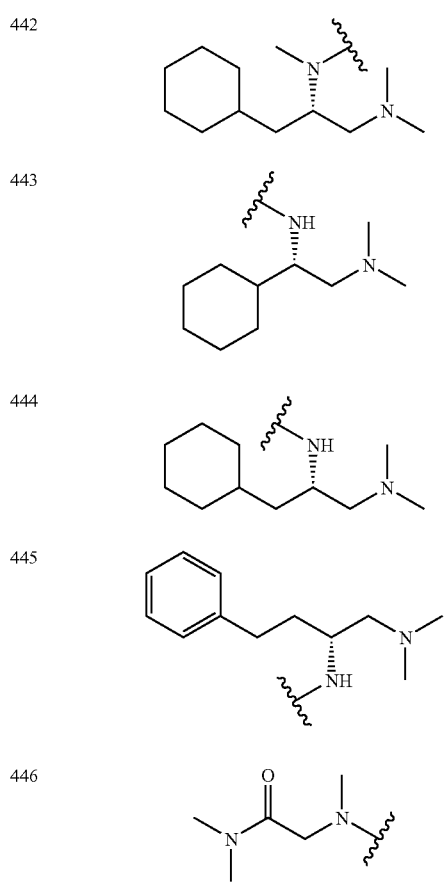

| Compound | R₁R₂N |
|---|---|
| 441 | Ph₂CH-N(CH₂CH₂NMe₂)- |
| 442 | cyclohexyl-CH₂-CH(NMe-)CH₂-NMe- |
| 443 | cyclohexyl-CH(NH-)CH₂-NMe₂ |
| 444 | cyclohexyl-CH₂-CH(NH-)CH₂-NMe₂ |
| 445 | PhCH₂CH₂-CH(NH-)CH₂-NMe₂ |
| 446 | Me₂N-C(O)-CH₂-N(Me)- |
| 447 | 4-methylpiperazinyl |
| 448 | (2-Ph,5-CH₂NMe₂)-pyrrolidinyl |

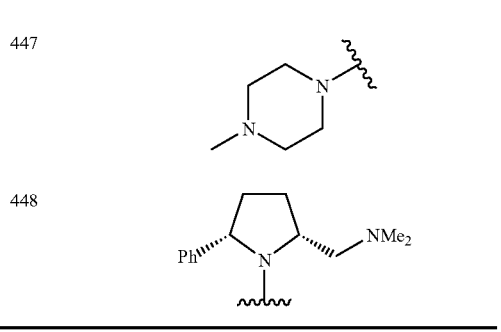

-continued
| Compound | R₁R₂NH |
|---|---|
| 449 | |
| 450 | |
| 451 | |
| 452 | |
| 453 | |
| 454 | |
| 455 | |
| 456 | |
| Compound | R₁R₂N |
|---|---|
| 457 | |
| 458 | |
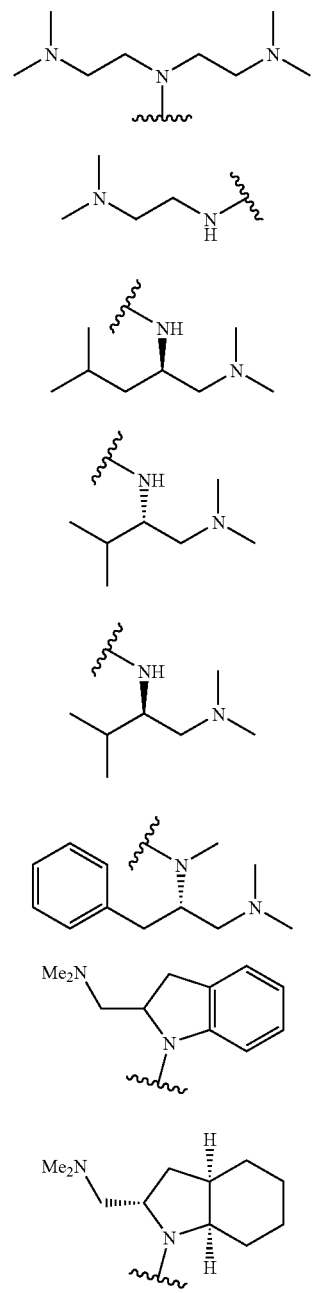
-continued
| Compound | (structures) |
|---|---|
| 459 | |
| 460 | |
| 461 | |
| 462 | |
| 463 | |
| 464 | |
| 465 | |
| 466 | |
| 467 | |
| 468 | |
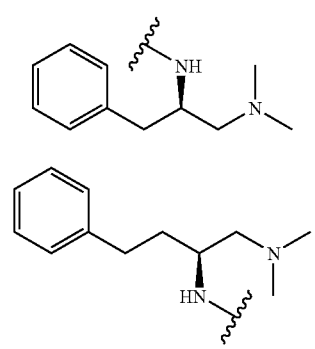

-continued
| | |
|---|---|
| 469 | 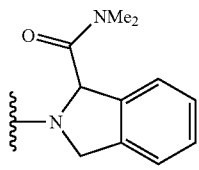 |
| 470 | 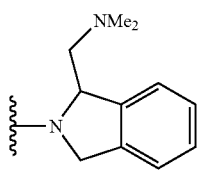 |
| 471 | 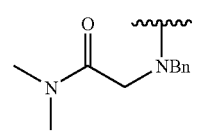 |
| 472 | 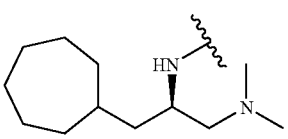 |
| 473 | 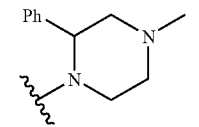 |
| 474 | 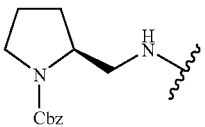 |
| 475 | 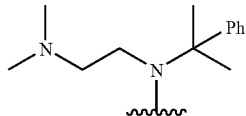 |
| 476 | 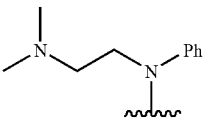 |
Compounds 441-476 were synthesized according to the procedure described in Example 149. MS data presented in the following table for compounds 441-476.
| Compound | MS (ESI(+)) m/e (M + H)+ |
|---|---|
| 441 | 683.75 |
| 442 | 627.51 |
| 443 | 599.4 |
| 444 | 613.47 |
| 445 | 621.44 |
| 446 | 545.35 |
| 447 | 529.35 |
| 448 | 633.43 |
-continued
| Compound | MS (ESI(+)) m/e (M + H)+ |
|---|---|
| 449 | 573.42 |
| 450 | 633.51 |
| 451 | 613.46 |
| 452 | 593.71 |
| 453 | 599.47 |
| 454 | 607.45 |
| 455 | 587.41 |
| 456 | 605.37 |
| 457 | 633.49 |
| 458 | 649.43 |
| 459 | 587.48 |
| 460 | 517.3 |
| 461 | 573.42 |
| 462 | 559.46 |
| 463 | 559.48 |
| 464 | 621.44 |
| 465 | 605.37 |
| 466 | 611.49 |
| 467 | 607.39 |
| 468 | 621.65 |
| 469 | 619.42 |
| 470 | 605.43 |
| 471 | 621.46 |
| 472 | 627.48 |
| 473 | 605.43 |
| 474 | 663.43 |
| 475 | 635.74 |
| 476 | 593.38 |
Example 204
| Compound | $R_1R_2NH$ | $R_3$ |
|---|---|---|
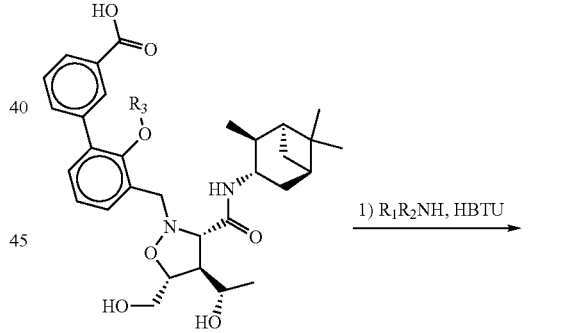
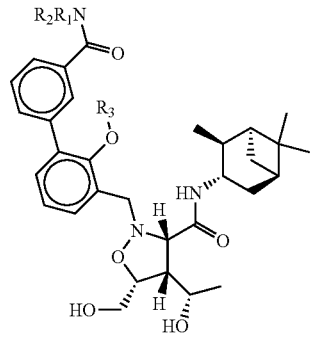
| | | |
|---|---|---|
| 477 | 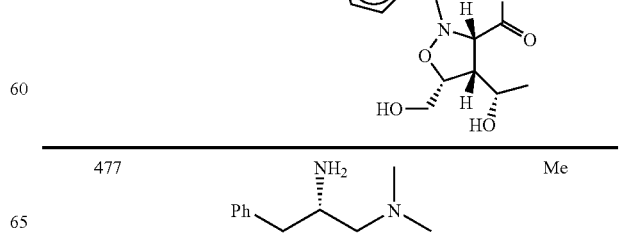 | Me |

-continued

| Compound | R₁R₂NH | R₃ |
|---|---|---|
| 478 | (isobutyl, NH₂, CH₂NMe₂) | Me |
| 479 | (neopentyl, NH₂, CH₂NMe₂) | Me |
| 480 | (cyclohexyl, NH₂, CH₂NMe₂) | Me |
| 481 | (PhCH₂CH₂, NH₂, CH₂NMe₂) | Me |
| 482 | (PhCH₂CH₂, NH₂, CH₂NMe₂) | Me |
| 483 | (isobutyl, NH₂, CH₂-azepane) | Me |
| 484 | (isopropyl, NH₂, CH₂NMe₂) | Me |
| 485 | (isobutyl, NH₂, CH₂NMe₂) | Me |
| 486 | (PhCH₂, NH₂, CH₂NMe₂) | Me |
| 487 | (cyclohexyl-CH₂, NH₂, CH₂NMe₂) | Me |
| 488 | (isopropyl, NH₂, CH₂NMe₂) | Me |
| 489 | (cyclohexyl-CH₂, NH₂, CH₂NMe₂) | Me |
| 490 | (N-methylpyrrolidinyl-CH₂NH₂) | Me |

-continued

| Compound | R₁R₂NH | R₃ |
|---|---|---|
| 491 | (Ph, NH₂, CH₂NMe₂) | Me |
| 492 | (Me₂N-CH₂CH₂-NH₂) | Me |
| 493 | (N-methylpyrrolidinyl-CH₂NH₂) | Et |
| 494 | (isobutyl, NH₂, CH₂NMe₂) | Et |
| 495 | (Me₂N-CH₂CH₂-NH₂) | Et |
| 496 | (N-methylpyrrolidinyl-CH₂NH₂) | CH₂-cyclopropyl |
| 497 | (Me₂N-CH₂CH₂-NH₂) | CH₂-cyclopropyl |

Compounds 477-497 were synthesized according to the procedure described in Example 141. MS data presented in the following table for compounds 477-497.

| Compound | MS (ESI(+)) m/e (M + H)⁺ |
|---|---|
| 477 | 727.39 |
| 478 | 693.44 |
| 479 | 707.44 |
| 480 | 719.42 |
| 481 | 741.46 |
| 482 | 741.46 |
| 483 | 747.48 |
| 484 | 679.43 |
| 485 | 693.44 |
| 486 | 727.4 |
| 487 | 733.45 |
| 488 | 679.44 |
| 489 | 733.49 |
| 490 | 677.37 |
| 491 | 713.4 |
| 492 | 637.31 |
| 493 | 691.43 |
| 494 | 707.47 |
| 495 | 651.38 |
| 496 | 717.44 |
| 497 | 677.41 |

Example 205

| Compound | R₁R₂NH |
|---|---|
| | 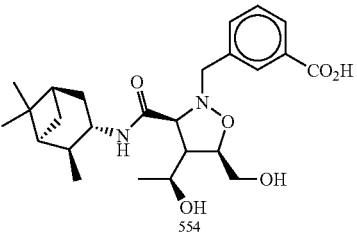 |
| 498 | 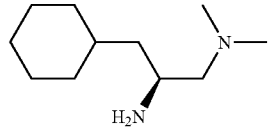 |
| 499 | 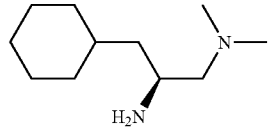 |
| 500 | 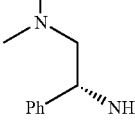 |
| 501 | 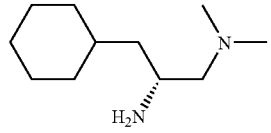 |
| 502 | 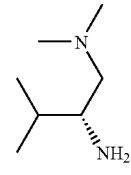 |
| 503 | 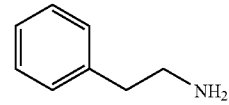 |
| 504 | 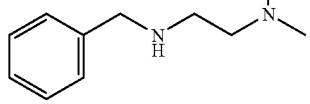 |
| 505 | 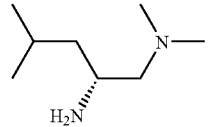 |
| 506 | 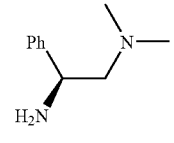 |
| 507 | 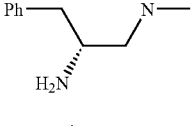 |
| 508 | 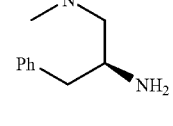 |
| 509 | 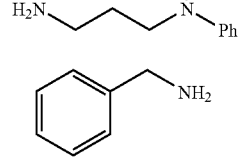 |
| 510 | 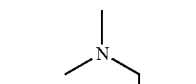 |
| 511 | 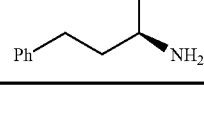 |

Compound 554 was synthesized according to the following procedure:

A solution of aldehyde 554 (60 mg, 1 equiv) in THF (1.5 mL) was placed in a vial with stir bar and isoprene (170 μL, 15 equiv), 2.7M phosphate buffer (225 μL, 4.5 equiv), and NaClO₂ solution (490 μL, 3.6 equiv) were added. The reaction was stirred at rt for 2 hours. At which point the water (30 mL) was added and the resulting solution was acidified to pH 1 with 6M HCl. The solution was then extracted with CH₂Cl₂ (3×15 mL). The organic layers were collected and dried on Na₂SO₄ and concentrated to give a white foam, 74 mg, which is used without further purification in the reactions above.

Compounds 498-511 were synthesized according to the procedure described in example 170. MS data is presented in the following table for compounds 498-511.

| Compound | MS (ESI(+)) m/e (M + H)+ |
|---|---|
| 498 | — |
| 499 | 627.15 |
| 500 | 642.37 |
|  | (M + HCl) |
| 501 | 627.74 |
| 502 | 573.39 |
| 503 | — |
| 504 | 621.29 |
| 505 | 587.41 |
| 506 | 607.68 |
| 507 | 621.41 |
| 508 | 621.39 |
| 509 | 627.46 |
| 510 | — |
| 511 | 635.07 |

Example 206

| Compound | R₁R₂NH |
|---|---|
| 512 | (3-amino-4-methylbiphenyl) |
| 513 | (2-(biphenyl-3-yl)ethylamine) |
| 514 | (2-(3-bromophenyl)ethylamine) |
| 515 | (biphenyl-3-amine) |
| 516 | (tryptamine) |
| 517 | (N,N-dimethyl-1,3-propanediamine) |
| 518 | ((S)-1-benzylpyrrolidin-3-amine) |
| 519 | (4-phenylbutylamine) |
| 520 | (2,2-diphenylethylamine) |
| 521 | (1-(naphthalen-2-yl)ethylamine) |
| 522 | ((S)-1-(naphthalen-2-yl)ethylamine) |
| 523 | (2-(biphenyl-4-yl)ethylamine) |
| 524 | (biphenyl-4-amine) |
| 525 | (3-phenylpropylamine) |

-continued
| Compound | R₁R₂NH |
|---|---|
| 526 | 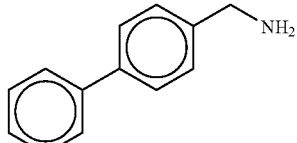 |
| 527 | 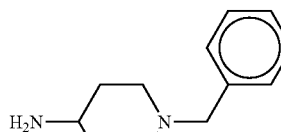 |
| 528 | 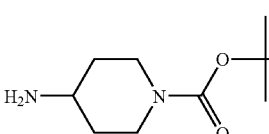 |
Compounds 512-528 were synthesized according to the procedure described in Example 149 and Part F of Example 177. MS data is presented in the following table for compounds 512-528.
| Compound | MS (ESI(+)) m/e (M + H)⁺ |
|---|---|
| 512 | 637.57 |
| 513 | 651.62 |
| 514 | 653.57 |
| 515 | 623.68 |
| 516 | 614.83 |
| 517 | 556.64 |
| 518 | 630.67 |
| 519 | 603.67 |
| 520 | 651.17 |
| 521 | 625.51 |
| 522 | 625.67 |
| 523 | 651.68 |
| 524 | 623.68 |
| 525 | 590.14 |
| 526 | 637.65 |
| 527 | 644.66 |
| 528 | 654.68 |
Example 207
-continued
| Compound | R₁R₂NH |
|---|---|
| |  |
| 529 |  |
| 530 |  |
| 531 |  |
| 532 |  |
| 533 |  |
| 534 |  |
| 535 |  |
| 536 | 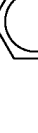 |
| 537 |  |
| 538 | |
| 539 | |

363

-continued

| Compound | R₁R₂NH |
|---|---|
| 540 | (isobutylamine structure) |
| 541 | (aniline structure) |
| 542 | (benzylamine structure) |
| 543 | (Boc-NH-propyl-NH₂ structure) |
| 544 | (N,N-dimethylethylenediamine structure) |

Compounds 529-544 were synthesized according to the procedure described in Example 149 and Part F of Example 177. MS data is presented in the following table for compounds 529-544.

| Compound | MS (ESI(+)) m/e (M + H)⁺ |
|---|---|
| 529 | 635.74 |
| 530 | 709.72 |
| 531 | 674.75 |
| 532 | 667.71 |
| 533 | 597.74 |
| 534 | — |
| 535 | 585.68 |
| 536 | 693.33 |
| 537 | 693.72 |
| 538 | 631.71 |
| 539 | 569.67 |
| 540 | 583.67 |
| 541 | 603.67 |
| 542 | 617.71 |
| 543 | 684.74 |
| 544 | 598.65 |

364

Example 208

553

Part A

To a solution of 4-heptanal (3.2 g) in MeOH-THF (3:1, 16 mL) was added an aqueous solution of hydroxylamine hydrochloride (2.6 g, 4 mL) in one portion. The pH was adjusted to 9 with 6N KOH, and stirred at rt for 2 h, after which the disappearance of the aldehyde was observed by TLC. After the addition of NaBH3CN (3.6 g, 2 eq) was complete the pH of the solution was adjusted to 2-3 using HCl in MeOH (20% V/V) and the solution was allowed to stir over night. The pH of the solution was then adjusted to 11 with 2N KOH. The layers were separated the the aqueous layer was extracted with CH₂Cl₂ (3×50 mL) the combined organic extracts were dried, filtered and concentrated in vacuo to afford the desired hydroxylamine as a white liquid (3 g).

Part B

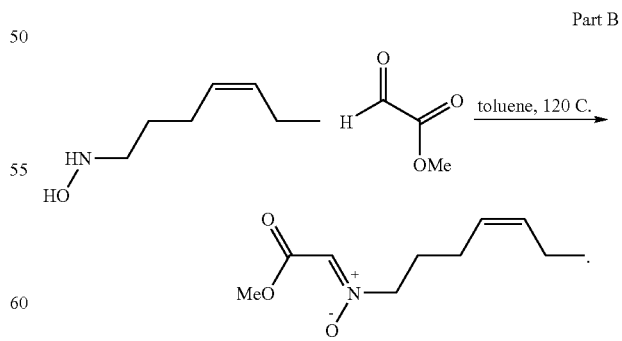

The hydroxyl amine (0.9 g) and methyl glyoxylate ester (0.6 g) were dissolved in toluene (10 mL). The mixture was heated to 120° C. for 3 h. The mixture was concentrated to 6 ml for next step.

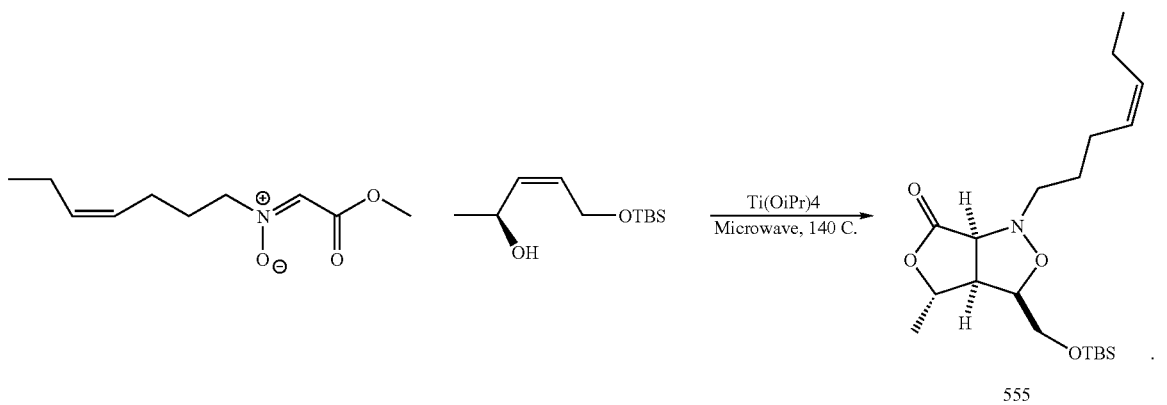

The nitrone ester (0.4 g, 2 mmol) and the TBS allylic alcohol (0.5 g, 2 mmol) and titanium isopropoxide (0.9 g, 3 mmol) were placed in a microwave reaction vial. The mixture was heated to 140° C. for 15 min in the microwave. The mixture was allowed to cool and diluted with ethyl acetate. The mixture was then washed with water, brine, dried and concentrated. Flash chromatography on silica gel (hexanes, 10% EtOAc in Hexanes) gave partially pure product 300 mg.

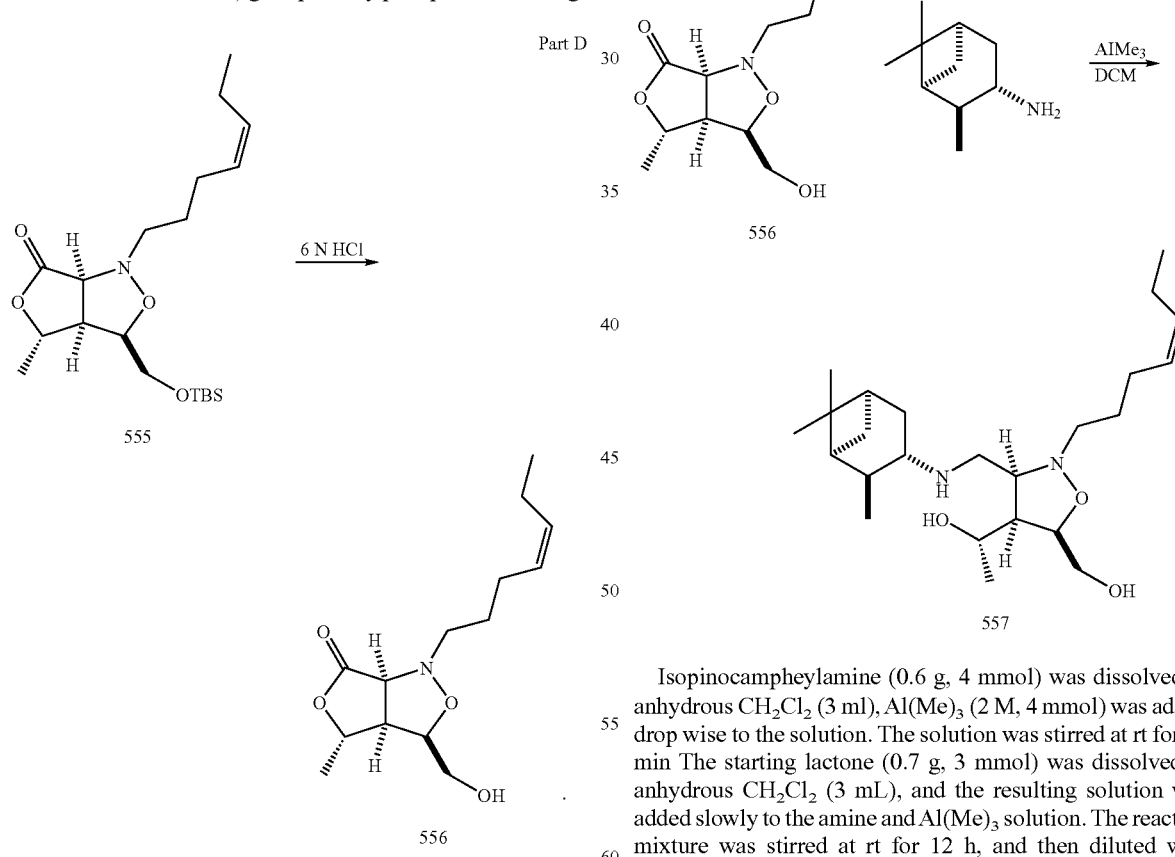

The isoxazolidine was dissolved in THF (14 mL). 6 N HCl (1 mL) was added and the mixture was stirred at rt for 1.5 h. The mixture was diluted with EtOAc (3×50 ml) and the layers were separated. The aqueous layer was extracted with EtOAc and the combined extracts were washed with brine, dried, filtered and concentrated to give desired product 0.2 g.

Isopinocampheylamine (0.6 g, 4 mmol) was dissolved in anhydrous $CH_2Cl_2$ (3 ml), $Al(Me)_3$ (2 M, 4 mmol) was added drop wise to the solution. The solution was stirred at rt for 20 min The starting lactone (0.7 g, 3 mmol) was dissolved in anhydrous $CH_2Cl_2$ (3 mL), and the resulting solution was added slowly to the amine and $Al(Me)_3$ solution. The reaction mixture was stirred at rt for 12 h, and then diluted with $CH_2Cl_2$ (60 mL). A saturated solution of Rochelle's salt (5 mL) was added and the two layers were stirred at rt for 2 h. The organic layer was separated from the aqueous layer and washed with water and brine, dried ($Na_2SO_4$), filtered, and concentrated to give crude product 400 mg. The crude material was purified by flash chromatography (silica gel, 50% EtOAc in Hexanes) to afford 260 mg of the desired product.

Part F

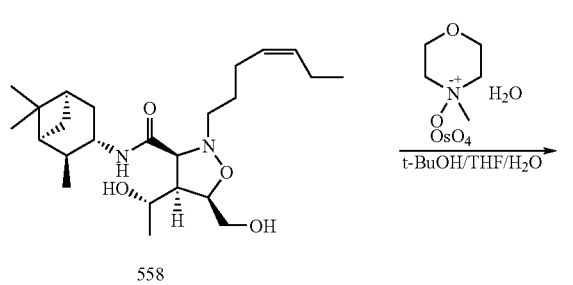

558

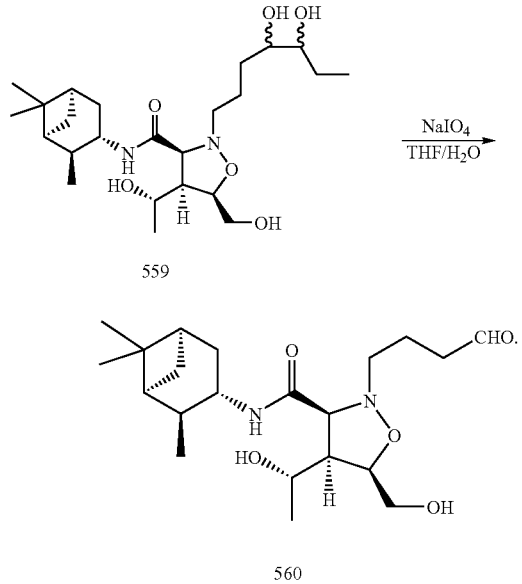

To a solution of the 558 (0.25 g, 0.59 mmol) in 2-methyl-2-propanol (6 mL), THF (3 mL) and H₂O (1 mL) was added NMO (0.1 g, 1.5 eq) was added of OsO₄ (0.37 ml, 2.5% solution in 2-methyl-2-propanol) dropwise. After 1.5 hr the reaction mixture was concentrated to 3 mL, diluted with CH₂Cl₂, brine and 10% Na₂S₂O₃ solution, extracted with CH₂Cl₂ (2×), dried over (MgSO₄), filtered and concentrated to an off white foam. This material was used directly in the next step The off-white foam from above was dissolved in 10:1 THF/H₂O (6 mLs THF, 0.6 mL H₂O). Sodium peridaote (0.19 g) was added in a single portionThe resulting mixture.stirred at rt for 12 hr. The reaction mixture was then diluted with CH₂Cl₂, brine and 10% Na₂S₂O₃ solution, extracted with CH₂Cl₂ (2×), dried over MgSO₄, filtered and concentrated to give an off white foam. The crude product was purified by column (Silica: 20 g SG60, solvent: 80% EtOAc/Hexanes) to give 0.12 g white solid product.

Part G

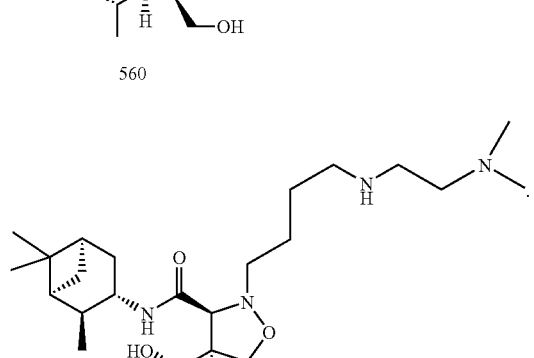

To a solution of the 560 (0.1 g, 0.3 mmol) in MeOH (2 mL) was added the N¹,N¹-dimethylethane-1,2-diamine (0.030 g, 0.36 mmol). The reaction was stired at rt for 3.5 hr. NaBH₄ (0.01 g, 0.3 mmol) was added in one portion and the reaction was stirred for 2 additional hours. Acetic acid (10 μL) was then added to quench the reaction and the reaction solution was concentrated to 0.5 mL. The mixture was then diluted with CH₂Cl₂, saturated NaHCO3 was added and the mixture was extracted with CH₂Cl₂ (2×), dried over MgSO₄, filtered and concentrated to yield the desired product (100 mg).

Part H

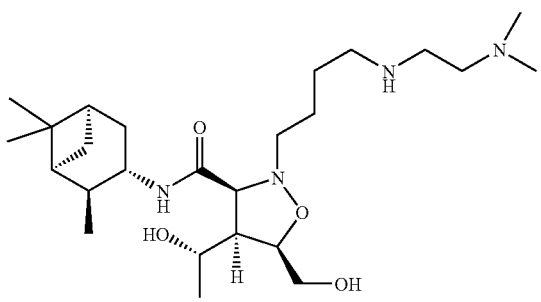

561

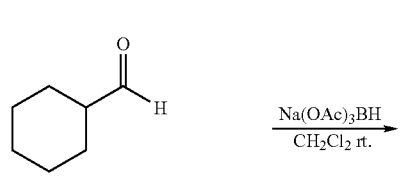

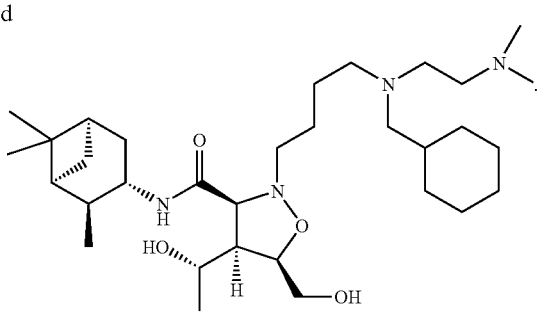

553

561 (15 mg) was dissolved in anhyous DCM (1 mL) and cyclohexanecarbaldehyde (7 mg) was added. This solution was stirred for 15 minutes, at which point sodium triacetoxyborohydride (17 mg) was added to the reaction mixture. After 1 h, methanol (0.5 mL) was added to the reaction mixture and this solution was purified directly on HPLC, using a basic (ammonium bicarbonate-acetonenitrile) gradient. The desired fractions were combined, frozen and lyophilized to afford 7 mg desired product. MS (ESI(+)) m/e 565.75 (M+H)$^+$.

Example 209

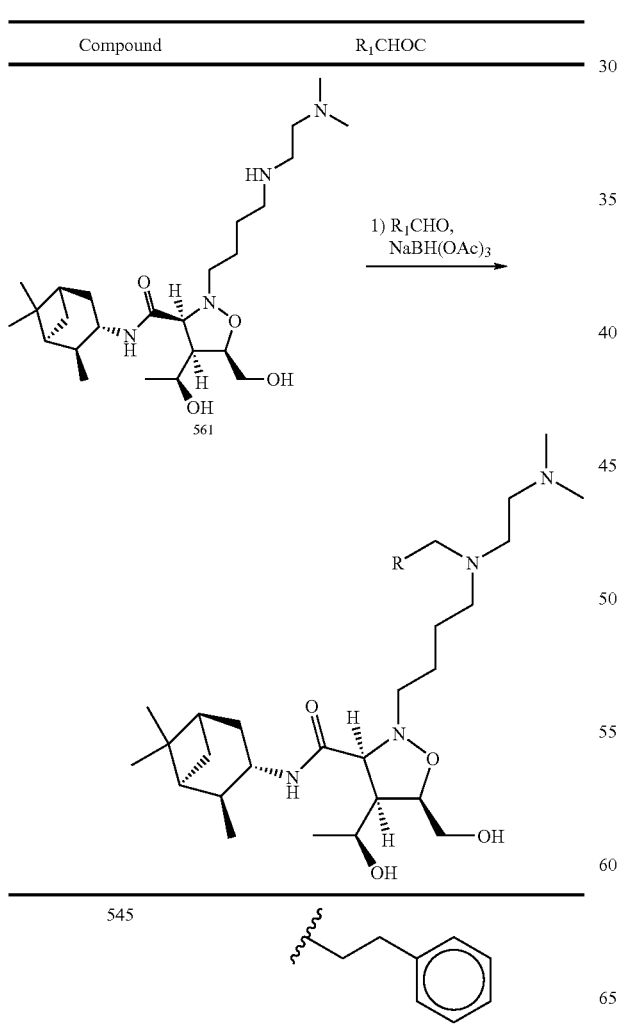

-continued

| Compound | R$_1$CHOC |
|---|---|
| 546 | benzyl |
| 547 | phenyl |
| 548 | cyclohexyl |
| 549 | 2-chlorophenyl |
| 550 | 2-fluorophenyl |
| 551 | 2-biphenyl |

Compounds 545-551 were synthesized according to the procedure described in Example 207. MS data presented in the following table for compounds 545-551.

| Compound | MS (ESI(+)) m/e (M + H)+ |
|---|---|
| 545 | 587.74 |
| 546 | 573.71 |
| 547 | 559.67 |
| 548 | 565.76 |
| 549 | — |
| 550 | — |
| 551 | — |

Example 210

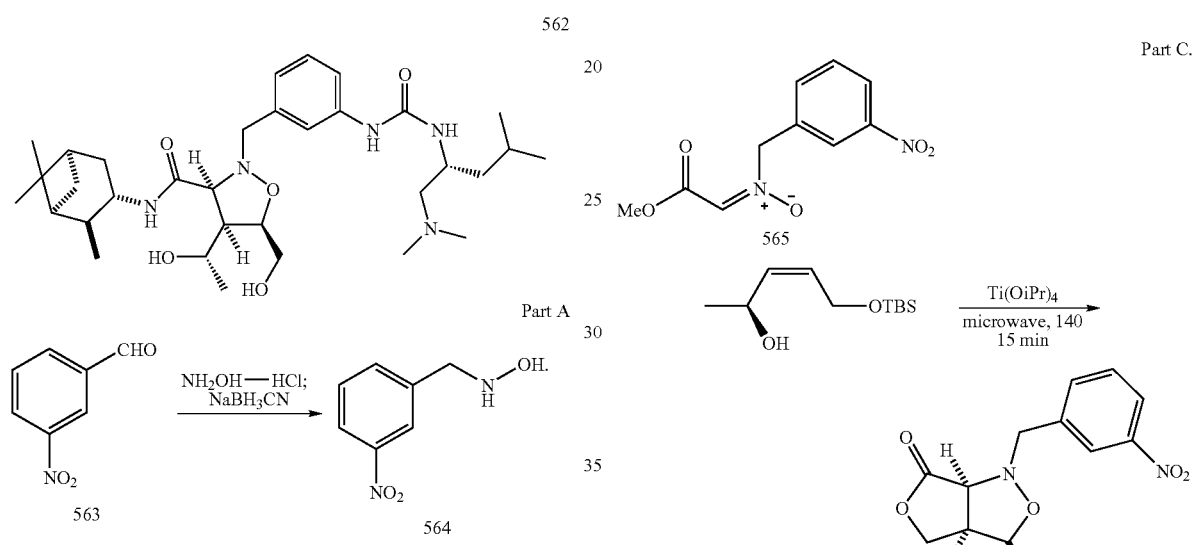

Part A

To a solution of 3-nitrobenzylaldehyde (20 g) in MeOH-THF (3:1, 400 mL) was added an aqueous solution of hydroxylamine (13 g in 60 mL of water) in one portion. The pH was adjusted to 11 with KOH (6N), and stirred at rt for 2 hr NaBH₃CN (17 g, 2 eq) was then added and the solution was acidified to pH 2-3 using HCl in MeOH (20 V/V). The pH of the reaction solution was maintained at pH 3 over the course of the reaction by addition of small amounts of the methanolic HCl solution. The mixture was allowed to stir for 12 hr. The methanolic HCl solution was added to keep the pH at 3. After another 8 h the solution was basified with an aqueous solution of KOH (2 N) to a pH of 11 and extracted with CH₂Cl₂ (3 times), dried over MgSO₄, concentrated in vacuo to afford 564 (20 g, 91%).

Part B

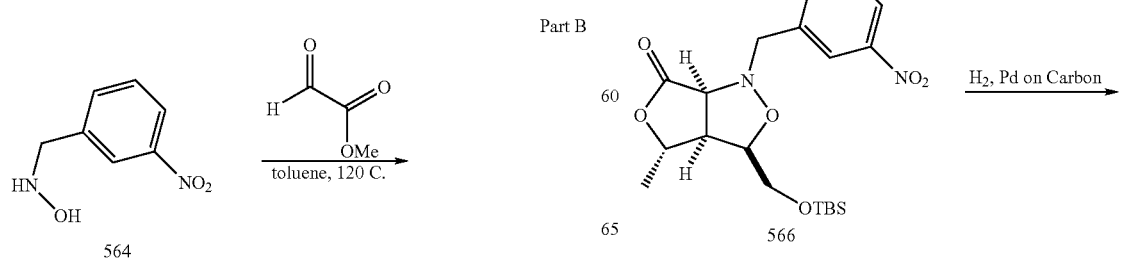

-continued

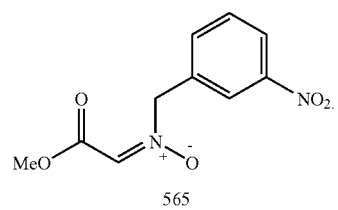

564 (7 g) and glyoxylate ester (4 g) were dissolved in 100 ml of toluene. The mixture was heated to 120° C. with stirring. After 3 hr, the solvent was evaporated to 15 ml. This solution was used directly in the in Part C.

Part C.

A solution of 565 (5 mL from Part A.) was added to a microwave tube. The allylic alcohol (1 g) and Ti(OiPr)₄ (2 g) were added. The microwave tube was then heated at 140° C. for 15 min The mixture was allowed to cool to rt. The crude mixture was diluted with ethyl acetate and washed with water, brine, dried over MgSO₄ and concentrated. The crude material was purified by column chromatography (silica gel, 0% EtOAc in Hexanes) to afford 0.8 g of 566.

Part D.

-continued

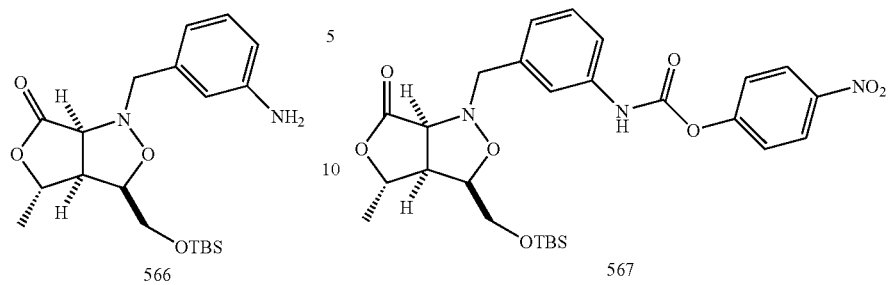

566 (1 g) was dissolved in MeOH (10 mL). The reaction solution was purged with N$_2$, palladium on carbon (10%, 0.7 g) was added, and a balloon full of H$_2$ was attached to the reaction flask. The reaction was stired at rt for 45 min and then the mixture was filtered through a short plug of celite. The celite plug was washed with 2 portions of EtOAc. The organic solutions were combined and concentrated to give crude product 0.9 g. Flash chromatography (silica gel, Hexane, 30% EtOAc in Hexane) afforded 0.8 g of 566.

Part E.

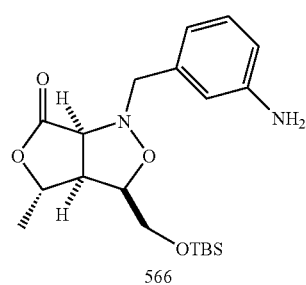

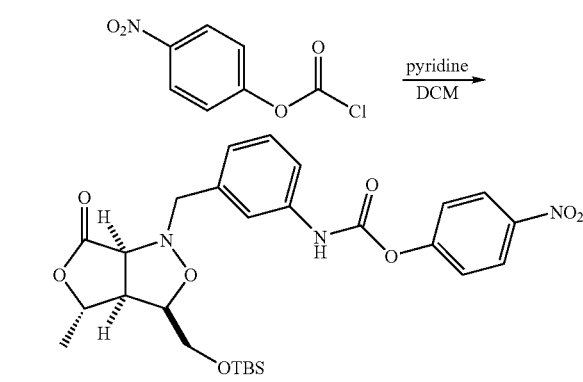

p-Nitrophenyl Chloroformate (300 mg) was dissolved in CH$_2$Cl$_2$ (2 mL). Pyridine (0.1 ml) was added to the reaction solution. The resulting white slurry was cooled to 0 C and a solution of 566 (450 mg) in CH$_2$Cl$_2$ (1 mL) was added in one portion. The reaction mixture was stirred at rt for 14 hr. The mixture was diluted with CH$_2$Cl$_2$, washed with water, brine and dried over MgSO$_4$, and concentrated to afford crude 567 (0.65 g). This material was used without further purification in Part E.

Part E.

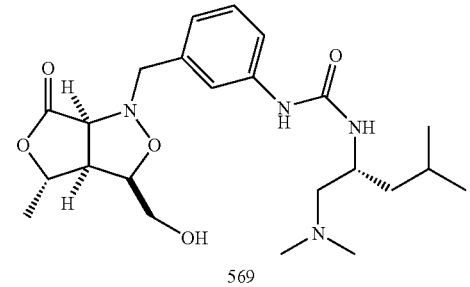

567 (20 mg) was dissolved in CH$_2$Cl$_2$ (1 mL). 568 (10 mg) and DIPEA (10 μl) were added to the reaction solution. The solution was stirred at rt for 12 h. The solution was then concentrated and redissolved in 1 mL of dry THF. HF/pyr (150 μl) was added and the mixture was stirred at rt for 1.5 h. TMSOMe (1.5 ml) was added to quench the reaction and the mixture was concentrated. The crude material was purifed using HPLC to afford 569 (15 mg).

Part F.

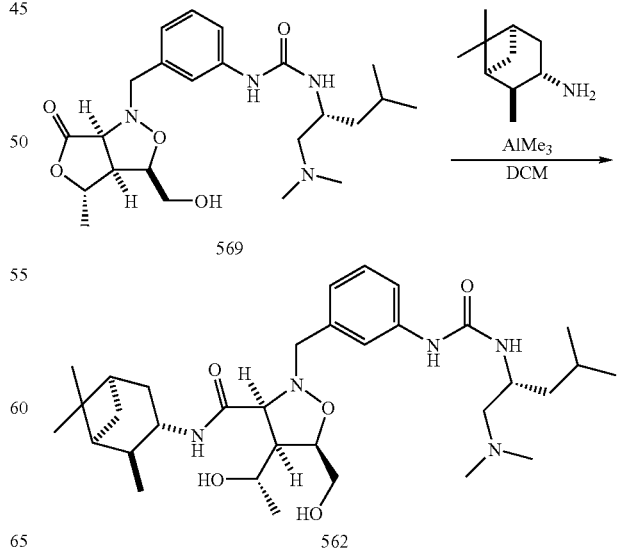

Isopinocampheylamine (5 mg) was dissolved anhydrous $CH_2Cl_2$ (1 mL). $AlMe_3$ (2 M, 20 µl) was added drop wise to the reaction solution. This mixture was stirred at rt for 20 min A solution of 569 (7 mg, in anhydrous $CH_2Cl_2$ (1 mL)) was slowly added to the reaction solution. The reaction mixture was stirred at rt for 12 h, and then diluted $CH_2Cl_2$ (25 mL). A saturated aqueous solution of Rochelle's salt (5 mL) was added and the resulting mixture was stirred at rt for 2 hr. The organic layer was separated from the aqueous layer and washed with water, brine, dried over $Na_2SO_4$, and concentrated to give the crude product (10 mg). The crude material was purified by HPLC to afford 562 (3 mg). MS (ESI(+)) m/e 602.45 $(M+H)^+$.

Example 211

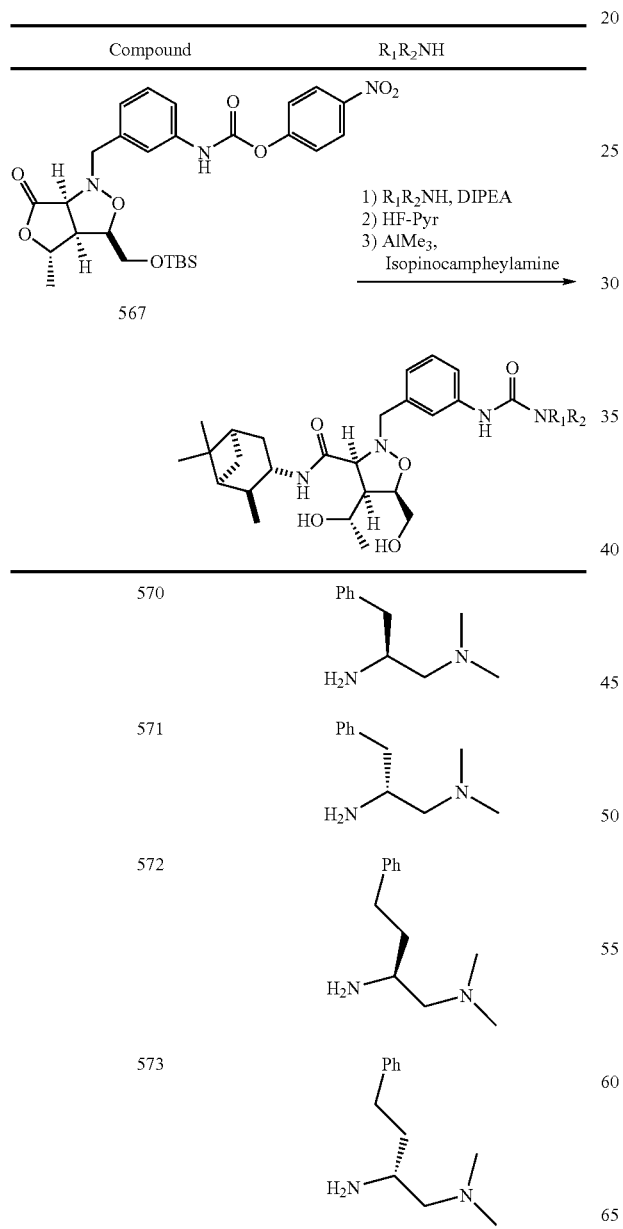

Compounds 570-577 were synthesized according to the procedure described in Example 208. MS data is presented in the following table for compounds 570-577.

| Compound | MS (ESI(+)) m/e $(M + H)^+$ |
|---|---|
| 570 | 636.73 |
| 571 | 636.41 |
| 572 | 650.42 |
| 573 | 650.44 |
| 574 | 642.49 |
| 575 | 656.5 |
| 576 | 656.5 |
| 577 | 642.7 |

Example 212

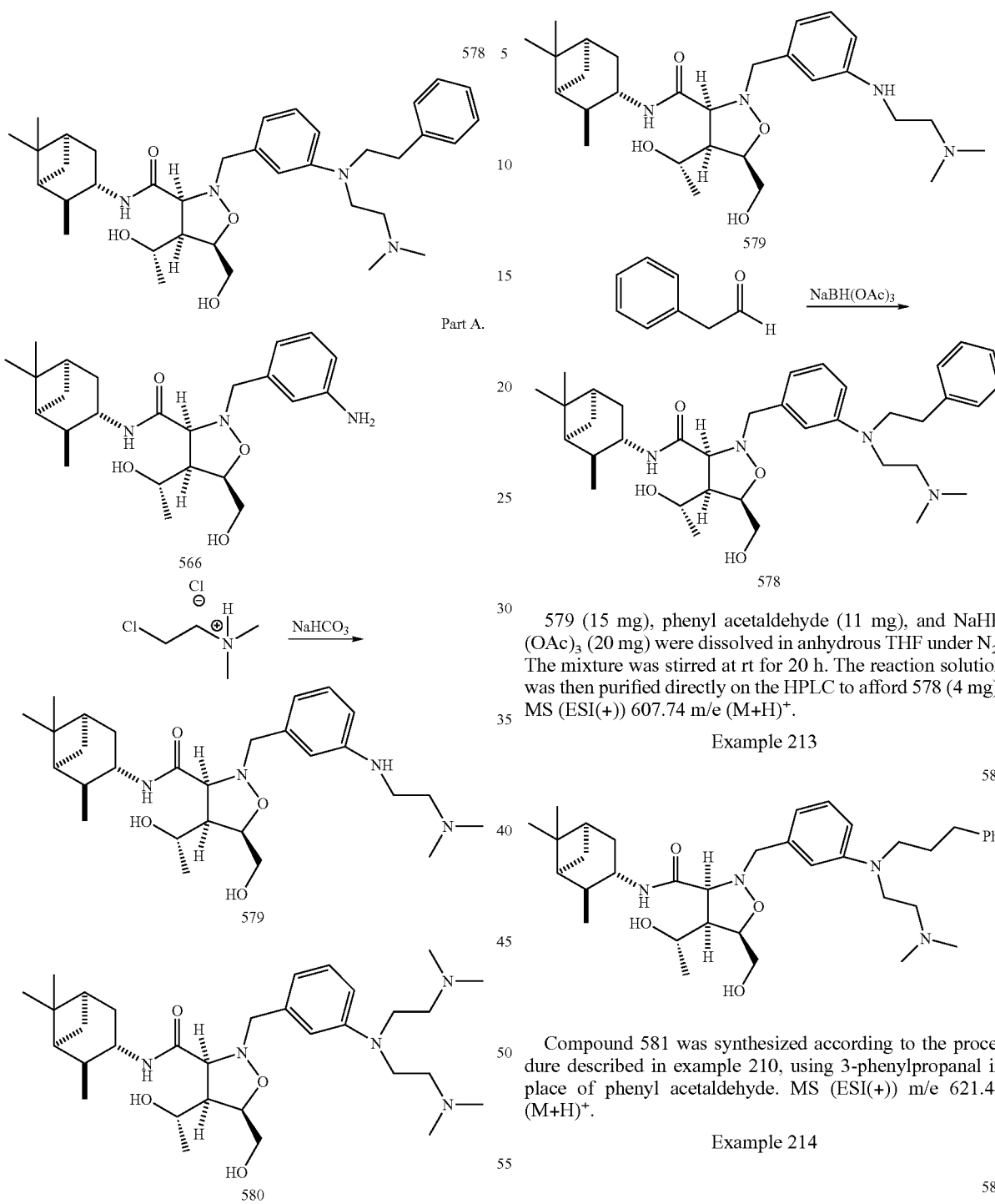

579 (15 mg), phenyl acetaldehyde (11 mg), and NaHB(OAc)₃ (20 mg) were dissolved in anhydrous THF under N₂. The mixture was stirred at rt for 20 h. The reaction solution was then purified directly on the HPLC to afford 578 (4 mg). MS (ESI(+)) 607.74 m/e (M+H)⁺.

Example 213

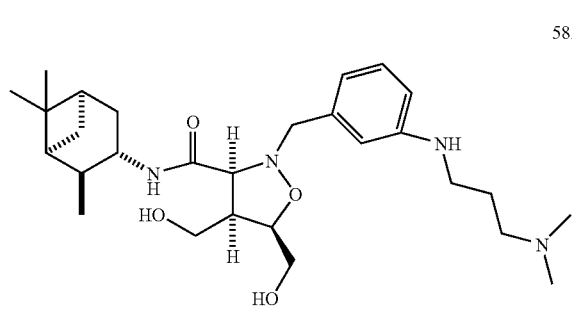

Compound 581 was synthesized according to the procedure described in example 210, using 3-phenylpropanal in place of phenyl acetaldehyde. MS (ESI(+)) m/e 621.44 (M+H)⁺.

Example 214

Sodium bicarbonate (200 mg), 2-chloro-N,N-dimethyl-ethanamine (200 mg) were added to a solution of 566 (200 mg) in EtOH (1 mL) under N₂. The reaction mixture was stirred at 60° C. for 14 h. The reaction mixture was diluted with EtOAc (50 ml), washed with brine, dried over Na₂SO₄, and concentrated to afford the crude product 300 mg. Th crude product was purifed using HPLC to afford 568 (20 mg) and 567 (90 mg).

Compound 582 was synthesized according to the procedure described in example 210, using 3-chloro-N,N-dimethylpropanamine in place of 2-chloro-N,N-dimethylethanamine. MS (ESI(+)) m/e 517.3 (M+H)+.

Example 215

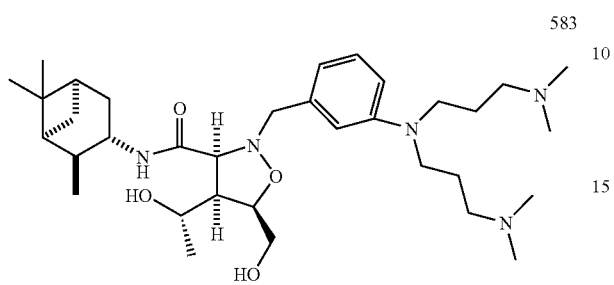

583

Compound 583 was synthesized according to the procedure described in example 210, using 3-chloro-N,N-dimethylpropanamine in place of 2-chloro-N,N-dimethylethanamine. MS (ESI(+)) m/e 602.43 (M+H)+.

Example 216

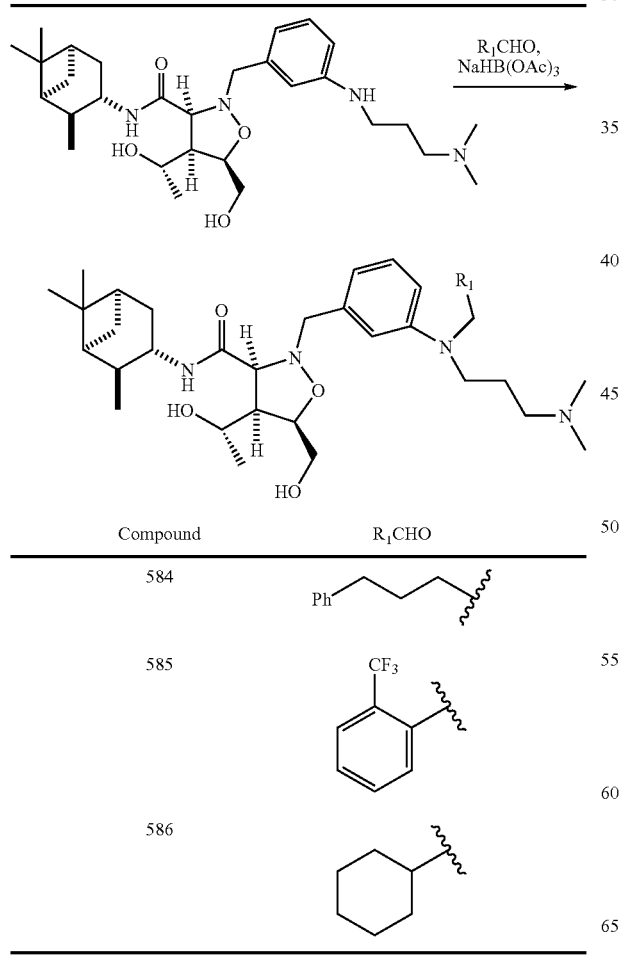

| Compound | MS (ESI(+)) m/e (M + H)+ |
|---|---|
| 584 | 635.74 |
| 585 | 675.69 |
| 586 | 613.77 |

Example 217

Bcl-2 and Bcl-xL binding affinity analysis data is presented below for various compounds of the invention. Note that "**" indicates that the Ki is <0.8 μM, "*" indicates that the Ki is 0.8-6 μM, "**" indicates that the Ki is 6-50 μM, "*" indicates that the Ki is >50 μM. Note that "†" indicates that the Ki is >100 μM, and "††" indicates that the Ki is >200 μM. Note that "ND" indicates that the value was not determined.

| Compound | Bcl-2 | Bcl-XL |
|---|---|---|
| 28 | ** | † |
| 29 | *** | † |
| 30 | *** | †† |
| 31 | *** | † |
| 32 | *** | † |
| 33 | *** | †† |
| 34 | * | † |
| 35 | * | † |
| 36 | *** | †† |
| 37 | ** | † |
| 38 | * | †† |
| 39 | *** | †† |
| 40 | * | † |
| 41 | * | † |
| 42 | *** | †† |
| 43 | *** | †† |
| 44 | ** | † |
| 45 | ** | † |
| 46 | * | † |
| 47 | * | †† |
| 48 | *** | † |
| 49 | *** | † |
| 50 | *** | † |
| 51 | *** | † |
| 52 | *** | † |
| 55 | * | †† |
| 56 | *** | †† |
| 57 | *** | † |
| 58 | *** | † |
| 59 | ** | † |
| 60 | * | †† |
| 61 | ** | † |
| 62 | ** | †† |
| 63 | *** | † |
| 64 | *** | † |
| 66 | *** | ND |
| 68 | *** | ND |
| 69 | *** | ND |
| 71 | ** | ND |
| 72 | ** | ND |
| 73 | *** | ND |
| 74 | *** | ND |
| 75 | *** | ND |
| 76 | *** | ND |
| 77 | *** | ND |
| 78 | *** | ND |
| 79 | *** | ND |
| 80 | *** | ND |
| 97 | *** | †† |
| 99 | *** | †† |
| 100 | **** | † |
| 101 | **** | † |

-continued

| Compound | Bcl-2 | Bcl-XL |
|---|---|---|
| 102 | **** | ‡ |
| 103 | **** | ‡ |
| 104 | **** | ‡ |
| 105 | **** | ‡ |
| 106 | **** | ‡ |
| 107 | **** | ‡ |
| 108 | **** | ‡ |
| 109 | **** | ‡ |
| 110 | **** | ‡ |
| 111 | **** | ‡ |
| 112 | **** | ‡ |
| 113 | **** | ‡ |
| 114 | **** | ‡ |
| 115 | **** | ‡ |
| 116 | **** | ‡ |
| 117 | **** | ♯ |
| 118 | **** | ‡ |
| 119 | **** | ♯ |
| 120 | **** | ♯ |
| 121 | **** | ♯ |
| 122 | **** | ♯ |
| 123 | **** | ‡ |
| 124 | **** | ‡ |
| 125 | **** | ♯ |
| 126 | **** | ‡ |
| 127 | **** | ♯ |
| 128 | **** | ‡ |
| 129 | **** | ♯ |
| 130 | **** | ♯ |
| 131 | **** | ‡ |
| 132 | **** | ♯ |
| 133 | **** | ‡ |
| 134 | **** | ‡ |
| 135 | **** | ♯ |
| 136 | **** | ‡ |
| 137 | **** | ‡ |
| 138 | **** | ‡ |
| 145 | **** | ♯ |
| 146 | **** | ‡ |
| 147 | **** | ♯ |
| 148 | **** | ‡ |
| 149 | **** | ‡ |
| 150 | **** | ♯ |
| 151 | **** | ♯ |
| 152 | **** | ♯ |
| 153 | **** | ‡ |
| 154 | **** | ♯ |
| 155 | **** | ♯ |
| 156 | **** | ‡ |
| 165 | **** | ‡ |
| 166 | **** | ‡ |
| 174 | **** | ‡ |
| 181 | **** | ♯ |
| 183 | **** | ♯ |
| 185 | **** | ‡ |
| 188 | **** | ‡ |
| 190 | **** | ‡ |
| 197 | **** | ‡ |
| 200 | **** | ‡ |
| 201 | **** | ‡ |
| 202 | **** | ‡ |
| 203 | **** | ‡ |
| 205 | **** | ‡ |
| 207 | **** | ‡ |
| 209 | **** | ‡ |
| 211 | **** | ‡ |
| 213 | **** | ‡ |
| 215 | **** | ‡ |
| 216 | **** | ‡ |
| 217 | **** | ‡ |
| 218 | **** | ‡ |
| 219 | **** | ‡ |
| 220 | **** | ‡ |
| 221 | **** | ‡ |
| 223 | **** | ‡ |
| 225 | ND | ND |
| 227 | ND | ND |

-continued

| Compound | Bcl-2 | Bcl-XL |
|---|---|---|
| 229 | ND | ND |
| 231 | **** | ‡ |
| 233 | ND | ND |
| 235 | **** | ♯ |
| 245 | **** | ‡ |
| 247 | **** | ‡ |
| 252 | **** | ‡ |
| 253 | **** | ‡ |
| 260 | **** | ‡ |
| 263 | **** | ‡ |
| 264 | **** | ‡ |
| 266 | **** | ‡ |
| 268 | **** | ‡ |
| 270 | **** | ‡ |
| 272 | **** | ‡ |
| 276 | **** | ‡ |
| 278 | **** | ‡ |
| 280 | ND | ND |
| 282 | **** | ♯ |
| 283 | **** | ♯ |
| 285 | **** | ‡ |
| 291 | **** | ‡ |
| 293 | **** | ‡ |
| 294 | **** | ‡ |
| 296 | **** | ‡ |
| 298 | **** | ♯ |
| 299 | **** | ‡ |
| 300 | **** | ‡ |
| 301 | **** | ‡ |
| 302 | **** | ‡ |
| 303 | **** | ‡ |
| 304 | **** | ‡ |
| 305 | **** | ‡ |
| 306 | **** | ‡ |
| 307 | **** | ‡ |
| 308 | **** | ‡ |
| 309 | **** | ‡ |
| 310 | **** | ‡ |
| 311 | **** | ‡ |
| 312 | **** | ‡ |
| 313 | **** | ‡ |
| 314 | **** | ‡ |
| 315 | **** | ‡ |
| 316 | **** | ‡ |
| 317 | **** | ‡ |
| 318 | **** | ‡ |
| 319 | **** | ‡ |
| 320 | **** | ‡ |
| 321 | **** | ‡ |
| 322 | **** | ‡ |
| 323 | **** | ‡ |
| 324 | **** | ‡ |
| 325 | **** | ‡ |
| 326 | **** | ‡ |
| 339 | **** | ‡ |
| 340 | **** | ‡ |
| 341 | **** | ‡ |
| 342 | **** | ‡ |
| 343 | **** | ‡ |
| 345 | **** | ‡ |
| 346 | **** | ‡ |
| 347 | **** | ‡ |
| 348 | **** | ‡ |
| 349 | **** | ‡ |
| 350 | **** | ‡ |
| 351 | **** | ‡ |
| 352 | **** | ‡ |
| 353 | **** | ‡ |
| 354 | **** | ‡ |
| 355 | **** | ‡ |
| 356 | **** | ‡ |
| 357 | **** | ‡ |
| 358 | **** | ‡ |
| 359 | **** | ‡ |
| 360 | **** | ‡ |
| 361 | **** | ‡ |
| 362 | **** | ‡ |

-continued

| Compound | Bcl-2 | Bcl-XL |
|---|---|---|
| 363 | **** | ‡ |
| 364 | **** | ‡ |
| 365 | **** | ‡ |
| 366 | **** | ‡ |
| 327 | **** | ‡ |
| 328 | **** | ‡ |
| 329 | **** | ‡ |
| 330 | **** | ‡ |
| 331 | **** | ‡ |
| 332 | **** | ‡ |
| 333 | **** | ‡ |
| 334 | **** | ‡ |
| 335 | **** | ‡ |
| 336 | **** | ‡ |
| 337 | **** | ‡ |
| 338 | **** | ‡ |
| 367 | **** | ‡ |
| 368 | **** | ‡ |
| 369 | **** | ‡ |
| 370 | **** | ‡ |
| 371 | **** | ‡ |
| 372 | **** | ‡ |
| 373 | **** | ‡ |
| 374 | **** | ‡ |
| 375 | **** | ‡ |
| 376 | **** | ‡ |
| 377 | **** | ‡ |
| 378 | **** | ‡ |
| 379 | **** | ‡ |
| 380 | **** | ‡ |
| 381 | **** | ‡ |
| 382 | **** | ‡ |
| 383 | **** | ‡ |
| 384 | **** | ‡ |
| 385 | **** | ‡ |
| 386 | **** | ‡ |
| 387 | **** | ‡ |
| 388 | **** | ‡ |
| 389 | **** | ‡ |
| 390 | **** | ‡ |
| 391 | **** | ‡ |
| 392 | **** | ‡ |
| 393 | **** | ‡ |
| 394 | **** | ‡ |
| 395 | **** | ‡ |
| 396 | **** | ‡ |
| 397 | **** | ‡ |
| 398 | **** | ‡ |
| 399 | **** | ‡ |
| 400 | **** | ‡ |
| 401 | **** | ‡ |
| 402 | **** | ‡ |
| 403 | **** | ‡ |
| 404 | **** | ‡ |
| 405 | **** | ‡ |
| 406 | **** | ‡ |
| 407 | **** | ‡ |
| 408 | **** | ‡ |
| 409 | **** | ‡ |
| 410 | **** | ‡ |
| 411 | **** | ‡ |
| 412 | **** | ‡ |
| 413 | **** | ‡ |
| 414 | **** | ‡ |
| 415 | **** | ‡ |
| 416 | **** | ‡ |
| 417 | **** | ‡ |
| 418 | **** | ‡ |
| 419 | **** | ‡ |
| 420 | **** | ‡ |
| 421 | **** | ‡ |
| 422 | **** | ‡ |
| 423 | **** | ‡ |
| 424 | **** | ‡ |
| 425 | **** | ‡ |
| 426 | **** | ‡ |
| 427 | **** | ‡ |

-continued

| Compound | Bcl-2 | Bcl-XL |
|---|---|---|
| 428 | **** | ‡ |
| 429 | **** | ‡ |
| 430 | **** | ‡ |
| 431 | **** | ‡ |
| 432 | **** | ‡ |
| 433 | **** | ‡ |
| 434 | **** | ‡ |
| 435 | **** | ‡ |
| 436 | **** | ‡ |
| 437 | **** | ‡ |
| 438 | **** | ‡ |
| 439 | *** | ‡ |
| 440 | **** | ‡ |
| 441 | **** | ‡ |
| 442 | **** | ‡ |
| 443 | **** | ‡ |
| 444 | **** | ‡ |
| 445 | **** | ‡ |
| 446 | **** | ‡ |
| 447 | **** | ‡ |
| 448 | **** | ‡ |
| 449 | **** | ‡ |
| 450 | **** | ‡ |
| 451 | **** | ‡ |
| 452 | **** | ‡ |
| 453 | **** | ‡ |
| 454 | **** | ‡ |
| 455 | **** | ‡ |
| 456 | **** | ‡ |
| 457 | **** | ‡ |
| 458 | *** | ‡ |
| 459 | **** | ‡ |
| 460 | **** | ‡ |
| 461 | **** | ‡ |
| 462 | **** | ‡ |
| 463 | **** | ‡ |
| 464 | **** | ‡ |
| 465 | **** | ‡ |
| 466 | **** | ‡ |
| 467 | **** | ‡ |
| 468 | **** | ‡ |
| 469 | **** | ‡ |
| 470 | **** | ‡ |
| 471 | **** | ‡ |
| 472 | **** | ‡ |
| 473 | **** | ‡ |
| 474 | **** | ‡ |
| 475 | **** | ‡ |
| 476 | **** | ‡ |
| 477 | **** | ‡ |
| 478 | **** | ‡ |
| 479 | **** | ‡ |
| 480 | **** | ‡ |
| 481 | **** | ‡ |
| 482 | **** | ‡ |
| 483 | **** | ‡ |
| 484 | **** | ‡ |
| 485 | **** | ‡ |
| 486 | **** | ‡ |
| 487 | **** | ‡ |
| 488 | **** | ‡ |
| 489 | **** | ‡ |
| 490 | **** | ‡ |
| 491 | **** | ‡ |
| 492 | **** | ‡ |
| 493 | **** | ‡ |
| 494 | **** | ‡ |
| 495 | **** | ‡ |
| 496 | **** | ‡ |
| 497 | **** | ‡ |
| 498 | **** | ‡ |
| 499 | **** | ‡ |
| 500 | **** | ‡ |
| 501 | **** | ‡ |
| 502 | **** | ‡ |
| 503 | **** | ‡ |
| 504 | **** | ‡ |

-continued

| Compound | Bcl-2 | Bcl-XL |
|---|---|---|
| 505 | **** | ‡ |
| 506 | **** | ‡ |
| 507 | **** | ‡ |
| 508 | **** | ‡ |
| 509 | **** | ‡ |
| 510 | **** | ‡ |
| 511 | **** | ‡ |
| 513 | *** | ‡ |
| 514 | *** | ‡ |
| 515 | **** | ‡ |
| 516 | ** | ‡ |
| 517 | ** | ‡ |
| 518 | ** | ‡ |
| 519 | *** | ‡ |
| 520 | *** | ‡ |
| 521 | *** | ‡ |
| 522 | *** | ‡ |
| 525 | ** | ‡ |
| 526 | **** | ‡ |
| 527 | ** | ‡ |
| 528 | ** | ‡ |
| 529 | ** | ‡ |
| 530 | *** | ‡ |
| 531 | *** | ‡ |
| 532 | *** | ‡ |
| 533 | *** | ‡ |
| 535 | ** | ‡ |
| 536 | *** | ‡ |
| 537 | *** | ‡ |
| 539 | ** | ‡ |
| 540 | ** | ‡ |
| 542 | *** | ‡ |
| 543 | ** | ‡ |
| 545 | *** | ‡ |
| 546 | *** | ‡ |
| 547 | *** | ‡ |
| 548 | *** | ‡ |
| 549 | *** | ‡ |
| 550 | *** | ‡ |
| 551 | **** | ‡ |
| 552 | *** | ‡ |
| 553 | *** | ‡ |
| 562 | **** | ‡ |
| 570 | **** | ‡ |
| 571 | **** | ‡ |
| 572 | **** | ‡ |
| 573 | **** | ‡ |
| 574 | **** | ‡ |
| 575 | **** | ‡ |
| 576 | **** | ‡ |
| 577 | **** | ‡ |
| 578 | **** | ‡ |
| 582 | **** | ‡ |
| 583 | **** | ‡ |
| 584 | **** | ‡ |
| 585 | **** | ‡ |
| 586 | **** | ‡ |

Example 218

Cytotoxicity Data for RL Human Follicular Lymphoma Cell Line

1) Using 96 well plates, compounds were serially diluted in DMSO from 9 mM to 4 uM
2) Assay plates were prepared by diluting samples 310 fold into 150 ul of medium containing 30,000 cells/well resulting in a final DMSO concentration of 0.3% and a concentration range from 29 uM to 0.013 uM for each compound.
3) Plates were incubated at 37 C and 5% $CO_2$ for 72 h
4) After 72 h, Alamar blue reagent was added to each well and plates read according to manufacturer's instructions In vitro cytotoxicity data for RL cells is presented below for various compounds of the invention. Note that "*" indicates that the IC50 is <2 µM, "" indicates that the IC50 is 2-5 µM, and "*" indicated that the IC50 is >5. Note that "nd" indicates that the value was not determined.

| Example | Bcl RL Alamar Blue IC50 |
|---|---|
| 149 | ** |
| 166 | * |
| 173 | * |
| 300 | *** |
| 301 | *** |
| 309 | *** |
| 311 | ** |
| 312 | *** |
| 313 | *** |
| 314 | *** |
| 316 | * |
| 320 | *** |
| 321 | *** |
| 322 | ** |
| 323 | * |
| 324 | *** |
| 325 | *** |
| 326 | ** |
| 327 | *** |
| 339 | *** |
| 340 | ** |
| 346 | ** |
| 348 | * |
| 349 | *** |
| 351 | ** |
| 352 | ** |
| 354 | *** |
| 355 | ** |
| 356 | * |
| 357 | ** |
| 360 | * |
| 361 | ** |
| 362 | ** |
| 363 | * |
| 365 | *** |
| 366 | ** |
| 367 | ** |
| 368 | ** |
| 369 | ** |
| 371 | ** |
| 373 | ** |
| 374 | ** |
| 375 | * |
| 378 | ** |
| 379 | * |
| 380 | ** |
| 383 | ** |
| 384 | ** |
| 386 | ** |
| 390 | * |
| 391 | * |
| 392 | * |
| 393 | * |
| 394 | *** |
| 395 | * |
| 396 | * |
| 397 | * |
| 398 | * |
| 399 | ** |
| 400 | *** |
| 402 | *** |
| 404 | ** |
| 405 | ** |
| 408 | ** |
| 412 | *** |
| 413 | * |
| 414 | ** |
| 415 | ** |
| 418 | ** |

-continued

| Example | Bcl RL Alamar Blue IC50 |
|---|---|
| 420 | *** |
| 424 | *** |
| 425 | *** |
| 428 | * |
| 429 | ** |
| 431 | * |
| 432 | *** |
| 435 | ** |
| 436 | * |
| 436 | * |
| 437 | * |
| 442 | ** |
| 444 | ** |
| 447 | * |
| 448 | ** |
| 456 | * |
| 465 | * |
| 466 | * |
| 470 | * |
| 471 | * |
| 472 | ** |
| 473 | * |
| 474 | ** |
| 477 | *** |
| 480 | ** |
| 481 | ** |
| 482 | *** |
| 483 | ** |
| 484 | ** |
| 485 | ** |
| 486 | ** |
| 487 | ** |
| 488 | ** |
| 491 | ** |
| 498 | * |
| 502 | * |
| 505 | * |
| 507 | * |
| 562 | * |
| 570 | * |
| 571 | * |
| 572 | ** |
| 573 | ** |
| 574 | ** |
| 575 | ** |
| 576 | ** |
| 577 | ** |
| 584 | ** |
| 585 | ** |
| 586 | ** |

Example 219

Cell Death Assay with Human Pancreatic Cancer Cell Line Panc1

1) Compounds were serially diluted in DMSO from a 9 mM stock to a final concentration of 0.004 mM in a 96 well plate.
2) Assay plates were prepared by diluting compounds 310 fold into 150 ul of medium containing 10,000 cells/well, with or without 3 uM Camptothecin, resulting in a final DMSO concentration of 0.3% and a compound concentration range from 29 uM to 0.13 uM for each compound.
3) Assay plates were incubated at 37 C, 5% CO2 for 72 hours.
4) After 72 hours, propidium iodide and Hoechst dye were added to each well according to manufacturer's instruction.
5) Plates were imaged on a fluorescence microscope at wavelengths Ex560/Em650 (Propidium iodide) and Ex360/Em465 (Hoechst)
6) MetaMorph imaging software was used to determine % cell death by dividing the number of propidium iodide stained cells (dead cells) by the number of Hoechst stained cells (all cells), multiplied by 100, in each field.

Panc1 invitro cellular data is presented below for various compounds of the invention. Note that "**" indicates that the IC50 is <1.3 µM, "*" indicates that the IC50 is 1.3-1.8 µM, "**" indicates that the IC50 is 1.8-2.5 µM, "*" indicates that the IC50 is >2.5 µM. Note that "nd" indicates that the value was not determined.

| Compound | Panc1 – Cpt IC50 | Panc1 + Cpt IC50 |
|---|---|---|
| 89 | ** | *** |
| 90 | * | *** |
| 91 | * | ** |
| 96 | * | * |
| 149 | * | ** |
| 160 | * | * |
| 166 | * | **** |
| 300 | * | ** |
| 301 | * | * |
| 303 | * | * |
| 305 | *** | **** |
| 306 | * | *** |
| 307 | * | * |
| 309 | * | *** |
| 310 | * | ** |
| 311 | * | ** |
| 312 | * | * |
| 313 | *** | *** |
| 314 | * | * |
| 316 | * | * |
| 317 | * | * |
| 318 | * | * |
| 319 | ** | *** |
| 320 | * | ** |
| 321 | **** | **** |
| 325 | **** | **** |
| 339 | * | * |
| 346 | * | * |
| 347 | * | * |
| 348 | * | * |
| 354 | ** | *** |
| 357 | * | * |
| 358 | * | * |
| 360 | * | * |
| 363 | * | * |
| 366 | ** | ** |
| 375 | * | * |
| 376 | ** | *** |
| 380 | ** | *** |
| 387 | * | * |
| 389 | ** | *** |
| 390 | * | * |
| 391 | * | * |
| 392 | * | * |
| 393 | * | * |
| 394 | * | * |
| 395 | * | * |
| 396 | * | * |
| 399 | * | * |
| 402 | * | * |
| 412 | * | *** |
| 413 | * | * |
| 414 | * | ** |
| 415 | * | * |
| 416 | * | * |
| 417 | * | * |
| 418 | ** | ** |
| 421 | * | * |
| 422 | * | *** |

-continued

| Compound | Panc1 − Cpt IC50 | Panc1 + Cpt IC50 |
|---|---|---|
| 423 | * | * |
| 424 | * | ** |
| 425 | * | * |
| 426 | * | * |
| 427 | * | * |
| 428 | * | * |
| 430 | * | * |
| 431 | * | * |
| 433 | * | * |
| 434 | * | * |
| 435 | * | * |
| 436 | * | * |
| 442 | * | * |
| 443 | * | * |
| 444 | * | * |
| 451 | * | * |
| 452 | * | * |
| 454 | * | * |
| 455 | * | * |
| 462 | * | * |
| 463 | * | * |
| 464 | * | * |
| 470 | * | * |
| 471 | * | * |
| 472 | * | * |
| 478 | * | * |
| 479 | ** | *** |
| 480 | * | *** |
| 483 | * | ** |
| 484 | * | * |
| 485 | ** | *** |
| 486 | * | * |
| 487 | * | * |
| 488 | * | * |
| 489 | * | ** |
| 493 | * | * |
| 494 | * | * |
| 495 | * | * |
| 496 | * | * |
| 497 | * | * |
| 498 | * | * |
| 501 | ** | *** |
| 505 | * | * |
| 508 | * | * |
| 578 | * | ** |
| 584 | * | * |

Example 217

In Vivo Analysis

The effects of the compound 221 in Example 166 were studied in a human follicular lymphoma cell line RL xenograft in female SCID/NOD mice. In this study, SCID/NOD female mice were implanted subcutaneously with RL cells ($2\times10^6$ cells in a 1:1 matrigel). When the average tumor size reached 150 mm$^3$, animals were randomly assigned to treatment groups (N=8/group) to receive either vehicle, the test compound using the below mentioned dose regiment. The test article or vehicle was administered intravenously (IV) via the tail vein in a volume of 0.1 mL over approximately 10 seconds (sec). The animals were sacrificed after 38 days and tumor volumes compared.

Mice: Female SCID/NOD Mice n=8/Group

Dosing Groups:

1. Compound 221 50 mg/kg i.v. (3 Consecutive Days MTW)
2. Compound 221 50 mg/kg i.v. (Every Other Day MWF)
3. Compound 221 50 mg/kg i.p. (Daily 7×/ week MTWRF-SSu)
4. Vehicle i.v. (3 Consecutive Days MTW)

Vehicle: 10% cyclodextrin in 0.1M NaPhO3 pH 6.0

Dosing Schedule:

M—Monday

T—Tuesday

W—Wednesday

R—Thursday

F—Friday

S—Saturday

Su—Sunday

Drug administration: Compound 221 (pH 6.8) was administered via the tail vein i.v. or intraperitoneally i.p. at (5 ml/kg or 125-ul per 25 g mouse) over approximately 20 sec Animal observation: Mice were inoculated subcutaneously (SC) with the human follicular lymphoma cell line RL ($2\times10^6$ cells 1:1 matrigel) into the dorsal side of the right rear leg using a 25 gauge needle. When tumors reached an average volume of ~150 mm$^3$, animals were randomly assigned to one of the treatment groups. Animals are divided into 4 groups (n=8 mice per group). The animals were carefully monitored for 30 min after dosing and observed daily for clinical signs. Tumors and bodyweight were measured and recorded 2× per week. Tumor dimensions were measured twice weekly with digital calipers and tumor volumes were calculated with the formula (width$^2$×length)/2. Mice were followed until tumor volumes in the vehicle group reached IACUC guidelines.

Study Duration: Animals were dosed for 4 weeks or until the vehicle reached 3500 mm$^3$. At this point 50% of the surviving animals were euthanized and tumors were removed, flash frozen and stored in −80° C. The remaining 50% were used to evaluate re-growth and durability of the anti-tumor response.

Take Down

Post 4 hour dosing:

4 mice per group were sacrificed

Blood and tumors collected

Groups: Vehicle, (MWF) iv, every day i.p

Post 24 hour dosing:

4 mice per group were sacrificed.

Blood and tumors collected

Groups: Vehicle, (MWF) iv, every day i.p.

The results from the biological activity analysis of the compounds of the invention are presented in FIG. 1.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound of formula 1:

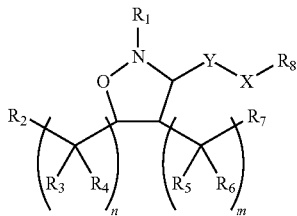

or a pharmaceutically acceptable salt thereof,
wherein
Y is —C(O)—;
X is —N($R_{11}$)—;
X' represents independently for each occurrence O, N($R_{10}$), or S;
m is 1;
n represents 1;
$R_1$ has the formula 1b:

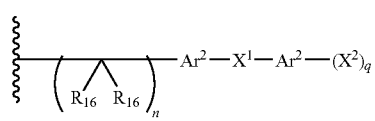

wherein
$R_{16}$ represents independently for each occurrence H, alkyl, cycloalkyl, heterocycloalkyl, aryl, aralkyl, halide, hydroxyl, alkoxyl, aryloxy, acyloxy, amino, alkylamino, arylamino, acylamino, aralkylamino, nitro, acylthio, carboxamide, carboxyl, nitrile, —COR$_{10}$, —CO$_2$R$_{10}$, —N(R$_{10}$)CO$_2$R$_{10}$, —OC(O)N(R$_{10}$)$_2$, —N(R$_{10}$)SO$_2$R$_{10}$, or —N(R$_{10}$)C(X')N(R$_{10}$)$_2$; wherein any two instances of $R_{16}$ may be connected by a covalent bond to form a ring;
$Ar^2$ represents independently for each occurrence monocyclic or bicyclic aryl with 6-14 ring atoms;
$X^1$ represents a bond;
$X^2$ represents independently for each occurrence halide, hydroxyl, alkoxyl, aryloxy, acyloxy, amino, alkylamino, arylamino, acylamino, aralkylamino, nitro, acylthio, carboxamide, carboxyl, nitrile, —COR$_{10}$, —CO$_2$R$_{10}$, —N(R$_{10}$)CO$_2$R$_{10}$, —OC(O)N(R$_{10}$)$_2$, —N(R$_{10}$)SO$_2$R$_{10}$, —N(R$_{10}$)C(X')N(R$_{10}$)$_2$, or —CH$_2$O-heterocyclyl; and
q represents independently for each occurrence 1, 2, 3, 4, or 5;
$R_2$ and $R_7$ are independently hydroxyl, alkoxyl, amino, alkylamino, or acylamino;
$R_3$, $R_4$, $R_5$ and $R_6$ represent independently for each occurrence H or alkyl;
$R_8$ is H, a branched or unbranched alkyl or alkenyl, cycloalkyl, heterocycloalkyl, bicycloalkyl, heterocycloalkyl substituted with an aralkyl group, or has the formula 1c:

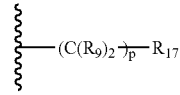

wherein
p is 0, 1, 2, 3, 4, 5, or 6; and
$R_{17}$ is aryl, cycloalkyl, cycloalkenyl, heterocyclyl, alkoxyl, heteroaryl, —OR$_{18}$, —SR$_{18}$, —N(R$_{18}$)$_2$, —N(R$_{10}$)CO$_2$-alkyl, —CO$_2$R$_{10}$, —C(O)N(R$_{10}$)aryl, or a polycyclic ring containing 8-14 carbon atoms; wherein $R_{18}$ is independently for each occurrence H, alkyl, aryl, aralkyl, acyl, -A$^1$-A$^2$-A$^3$, or —CR$_9$=CR$_9$(C(R$_9$)$_2$)$_n$CR$_9$=C(R$_9$)$_2$; or two $R_{18}$ taken together form a ring;
$R^9$ represents independently for each occurrence H or alkyl;
$R_{10}$ and $R_{11}$ represent independently for each occurrence H, alkyl, aryl, cycloalkyl, aralkyl, heteroaryl, or heteroaralkyl;
$R_{19}$ represents independently for each occurrence H, alkyl, aryl, cycloalkyl, aralkyl, heteroaryl, heteroaralkyl, or -A$^1$ A$^2$-A$^3$;
A$^1$ and A$^3$ represent independently for each occurrence alkyl, cycloalkyl, heterocycloalkyl, aryl, heteroaryl, aralkyl, or heteroaralkyl;
A$^2$ represents independently for each occurrence O, N(R$_{10}$), S, or a bond; and
the stereochemical configuration at any stereocenter of a compound represented by 1 is R, S, or a mixture of these configurations.

2. The compound of claim 1, wherein $R_2$ and $R_7$ are hydroxyl; $R_6$ is methyl, ethyl, or propyl; and $R_3$, $R_4$, and $R_5$ are H.

3. A compound represented by formula 5:

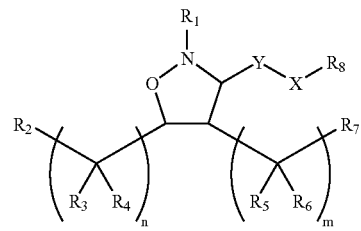

or a pharmaceutically acceptable salt thereof,
wherein:
Y is —C(O)—;
X is —N($R_{11}$)—;
m is 1;
n represents 1;
$R_1$ has the formula 5a:

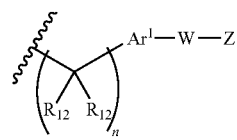

wherein:
R$_{12}$ represents independently for each occurrence H or alkyl; wherein any two instances of R$_{12}$ may be connected by a covalent bond;
Ar$^1$ is represented by formula 5c:

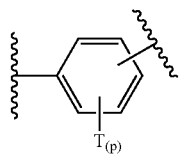

5c wherein,
T independently for each occurrence is H, halide, branched or unbranched alkyl, alkenyl, allyl, alkoxy, aryl, aralkyl, hydroxyl, amino, aminoalkyl, amido, carboxamide, cycloalkyl, cycloalkene, bicycloalkyl, bicycloalkene, cycloalkalkyl, heteroaromatic, heteroaralkyl, heterocyclyl, heterocyclalkyl, haloalkyl, ester; carboxylic, bis aryl, bis aryl ether, heterocyclic substituted aryl, or two T taken together form an aromatic or nonaromatic ring; and
p is 1;
W is aryl;
Z is —SR; —S(O)$_2$R; —NRSO$_2$R; —S(O)R; —N(R)$_2$; —C(O)R; —CO$_2$R; —C(O)N(R)$_2$; —C(S)N(R)$_2$; —CH$_2$C(O)heterocyclyl; —NRC(O)R; —NRCO$_2$R; —OC(O)N(R)$_2$; —NRC(O)(C(R$_9$)$_2$)$_n$N(R)$_2$; —NC(O)CH(R)$_2$; —C(=NR)N(R)$_2$; —C(=NR)R; hydroxyalkyl; or mono or bicyclic aryl, heteroaryl, or heterocyclyl;
wherein:
R is independently for each occurrence H, branched or unbranched alkyl, alkenyl, allyl, alkoxy, haloalkyl, acyl, mesylate, tosylate, aralkyl, ester, —(C(R$_9$)$_2$)$_n$T, —CH((C(R$_9$)$_2$)$_n$T)$_2$, or two R taken together form an aromatic or nonaromatic ring;
R$_2$ and R$_7$ are independently hydroxyl, alkoxyl, amino, or alkylamino;
R$_3$ and R$_6$ represent independently for each occurrence H, alkyl, or perhaloalkyl;
R$_4$ and R$_5$ represent independently for each occurrence H or alkyl;
R$_8$ is H, a branched or unbranched alkyl or alkenyl, cycloalkyl, heterocycloalkyl, bicycloalkyl, a branched or unbranched aminoalkyl, or heterocycloalkyl substituted with an aralkyl group;
R$_9$, R$_{10}$, and R$_{11}$ represent independently for each occurrence H, alkyl, aryl, aralkyl, cycloalkyl, cycloalkalkyl, heteroaryl, or heteroaralkyl;
providing that Ar$^1$, W and Z may be further substituted with one or more groups selected from the following: halide, aryl, alkamino, amido, alkoxy, ether, —NO$_2$, hydroxyl, —NR$_2$, or —CN;
that where applicable Ar$^1$, W, and Z, may be bonded to each other at the ortho, meta, or para positions; and
the stereochemical configuration at any stereocenter of a compound represented by 5 is R, S, or a mixture of these configurations.

4. The compound of claim 3, wherein R$_2$ is OH.
5. The compound of claim 3, wherein R$_6$ is methyl or ethyl and R$_7$ is hydroxyl.
6. The compound of claim 3, wherein R$_8$ is bicycloalkyl.
7. The compound of claim 3, wherein R$_{12}$ is H or methyl.
8. The compound of claim 3, wherein Ar$^1$ is a benzene ring.
9. The compound of claim 3, wherein W is a benzene ring.
10. A compound represented by formula 5d:

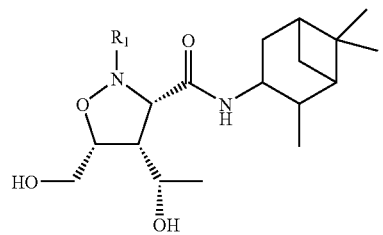

5d wherein:
R$_1$ has formula 5f:

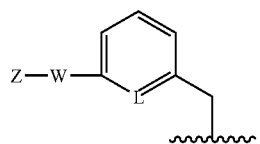

5f wherein:
L is CR;
W is aryl;
Z is —SR; —S(O)$_2$R; —NRSO$_2$R; —S(O)R; —N(R)$_2$; —C(O)R; —CO$_2$R; —C(O)N(R)$_2$; —C(S)N(R)$_2$; —CH$_2$C(O)heterocyclyl; —NRC(O)R; —NRCO$_2$R; —OC(O)N(R)$_2$; —NRC(O)(C(R$_9$)$_2$)$_n$N(R)$_2$; —NC(O)CH(R)$_2$; —C(=NR)N(R)$_2$; —C(=NR)R; hydroxyalkyl; or mono or bicyclic aryl, heteroaryl, or heterocyclyl; and
R is independently for each occurrence H, branched or unbranched alkyl, alkenyl, allyl, alkoxy, haloalkyl, acyl, mesylate, tosylate, aralkyl, ester, —(C(R$_9$)$_2$)$_n$T, —CH((C(R$_9$)$_2$)$_n$T)$_2$, or two R taken together form an aromatic or nonaromatic ring,
provided that when L is CH, Z is —C(O)N(R)$_2$, C(S)N(R)$_2$, —NRCO$_2$R, —OC(O)N(R)$_2$, or —NRC(O)(C(R$_9$)$_2$)$_n$N(R)$_2$.

11. The compound of claim 10, wherein L is CH, W is a benzene ring, and Z is —C(O)N(R)$_2$.
12. The compound of claim 10, wherein L is CR, R is alkoxy, W is a benzene ring, and Z is —C(O)N(R)$_2$.
13. The compound of claim 10, wherein L is COMe, W is a benzene ring, and Z is —C(O)N(R)$_2$.
14. The compound of claim 10, wherein L is COEt, W is a benzene ring, and Z is —C(O)N(R)$_2$.
15. The compound of claim 10, wherein L is COCH$_2$(cyclopropyl), W is a benzene ring, and Z is —C(O)N(R)$_2$.

16. A compound of formula 5g:
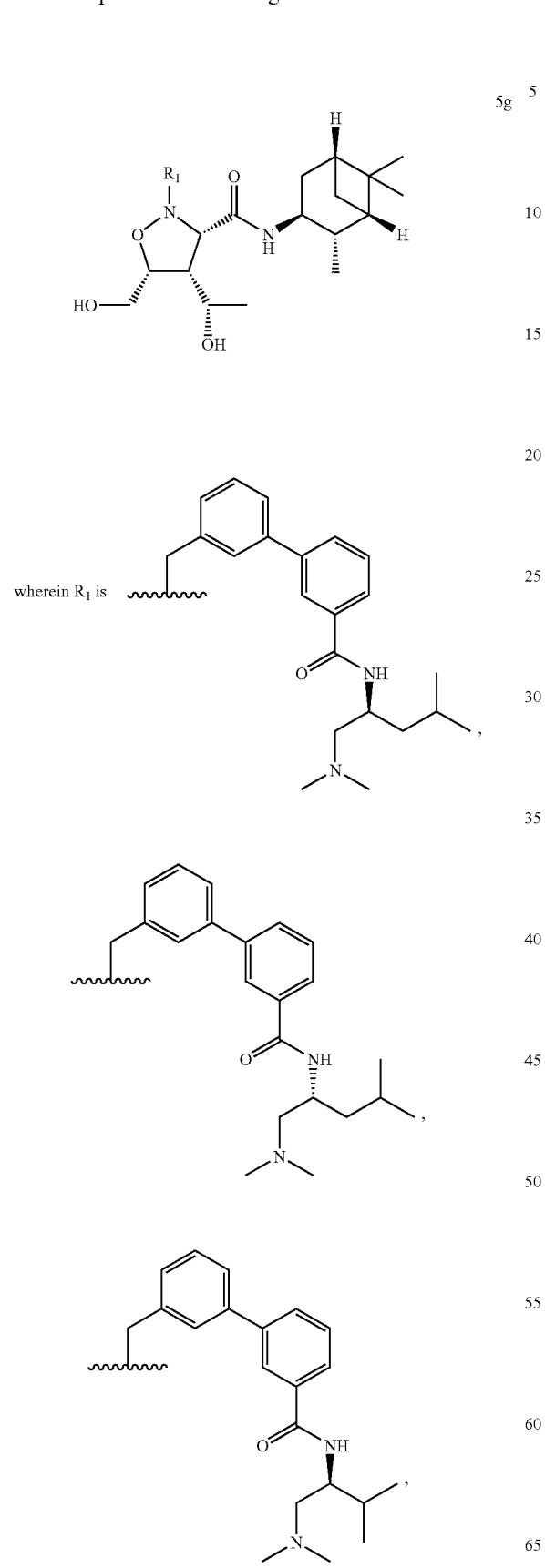
wherein $R_1$ is
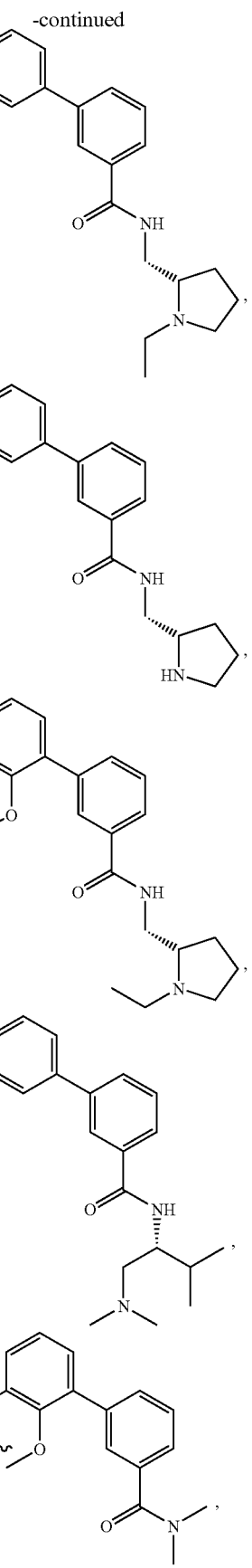

397
-continued
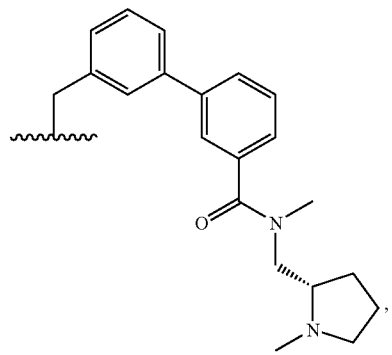
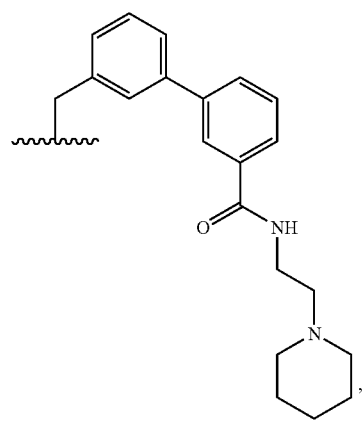
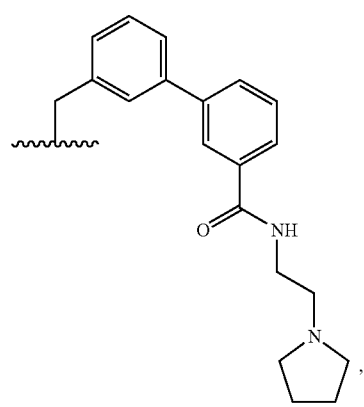
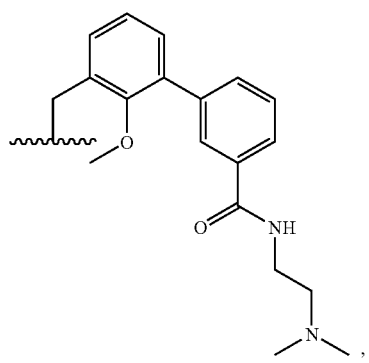
398
-continued
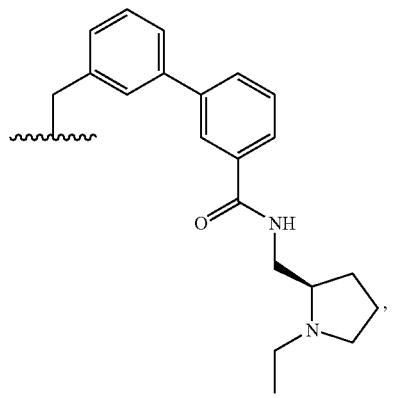
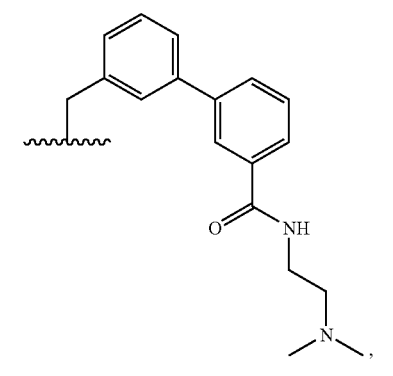
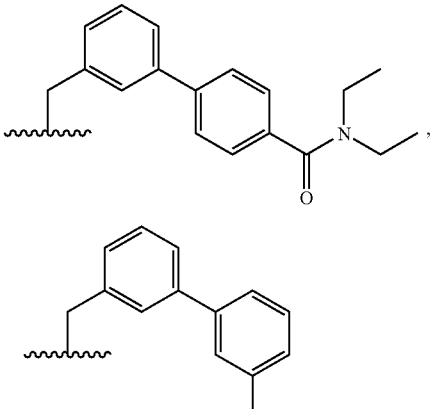
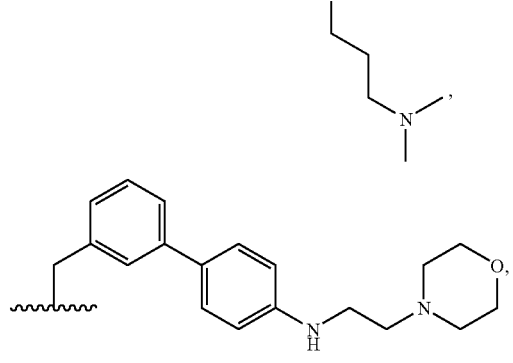

399
-continued
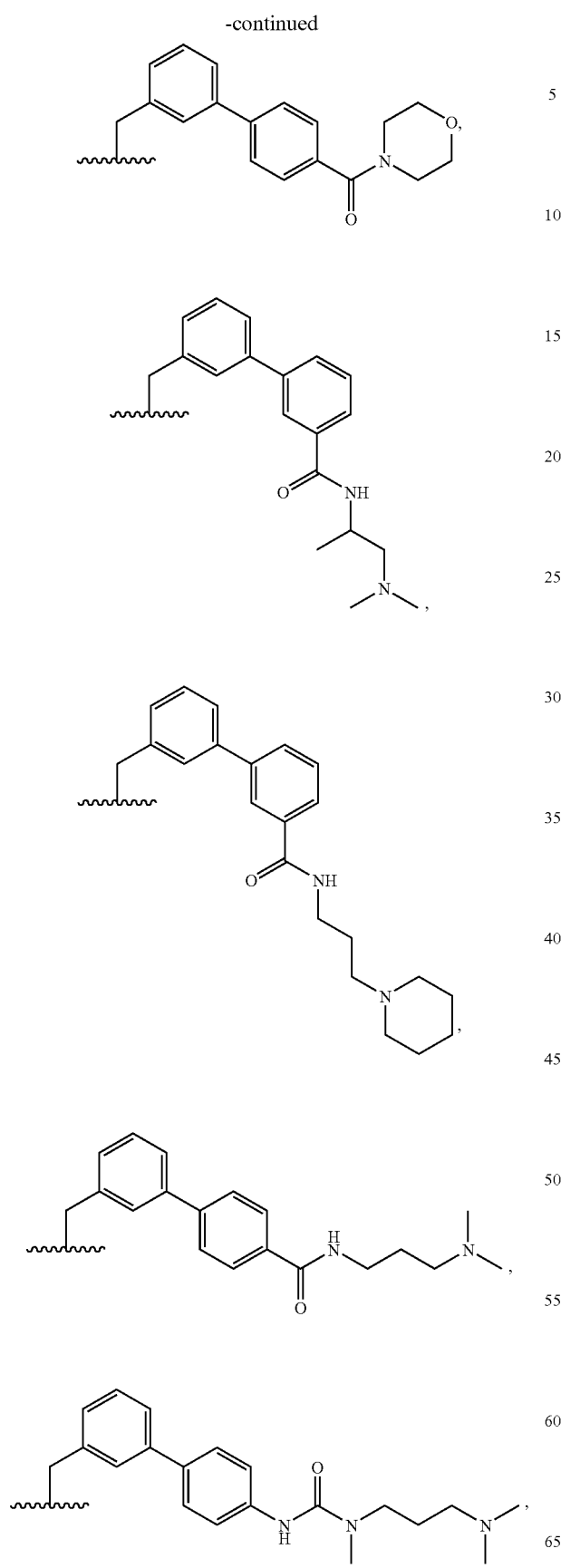
400
-continued
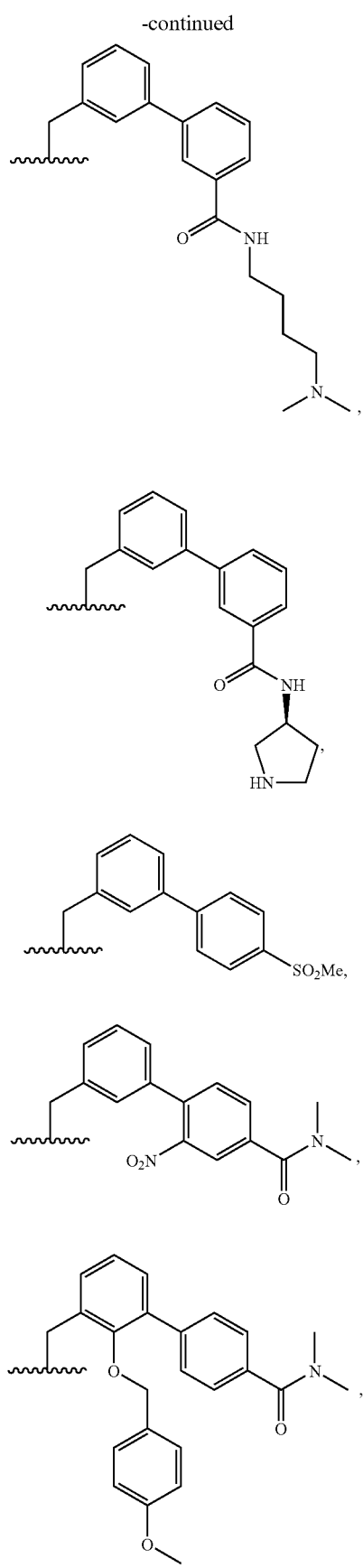

401
-continued
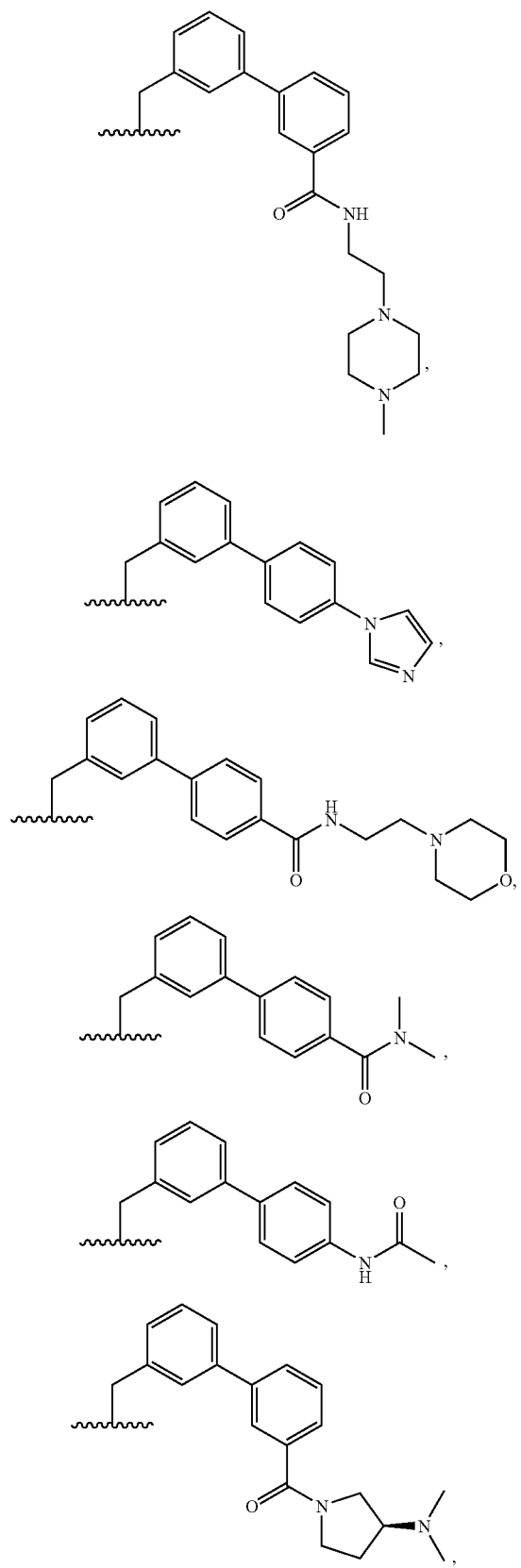
402
-continued
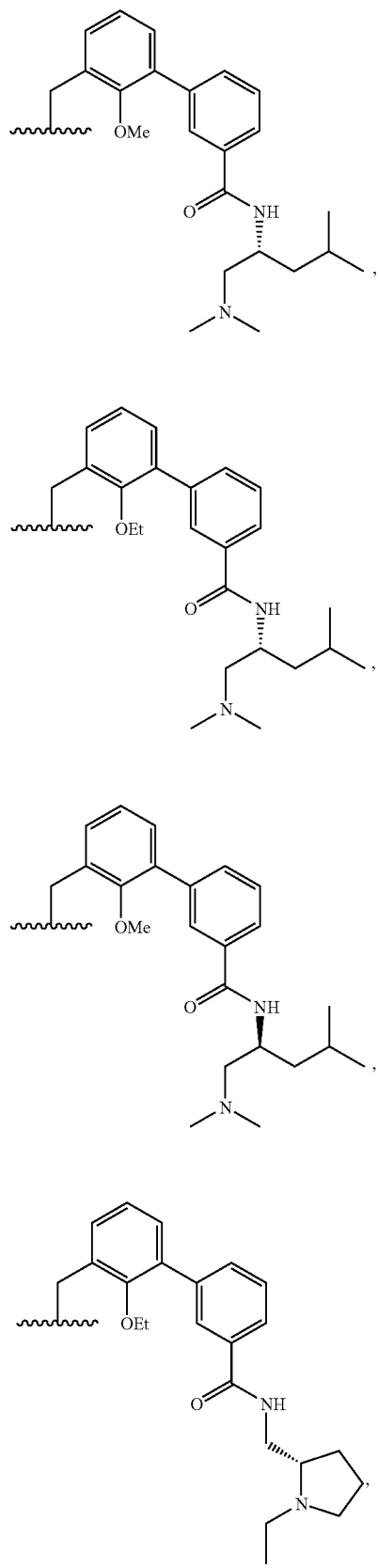

403
-continued
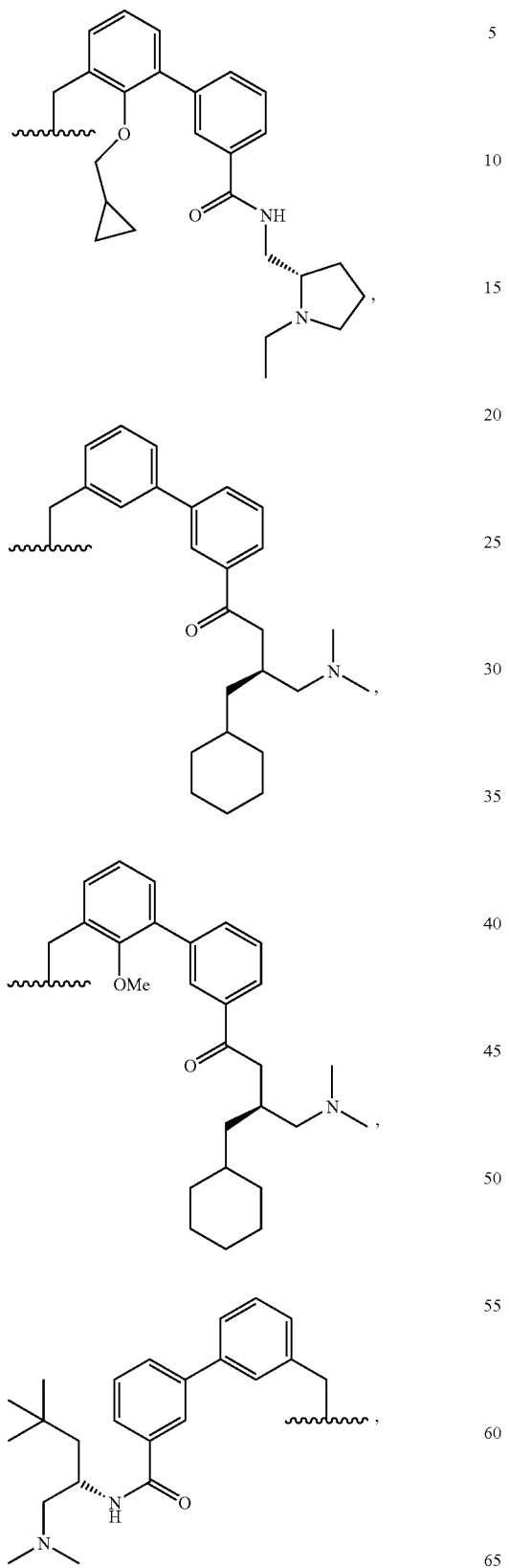
404
-continued
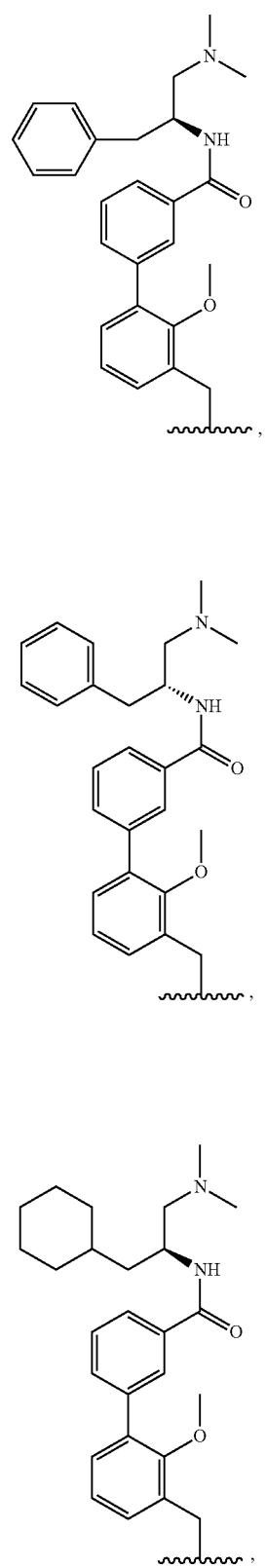

405
-continued
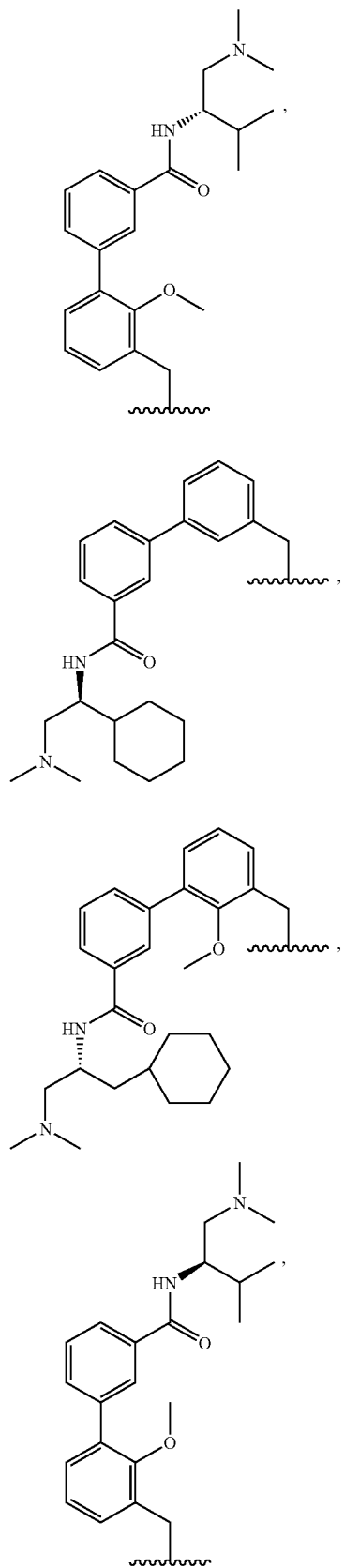
406
-continued
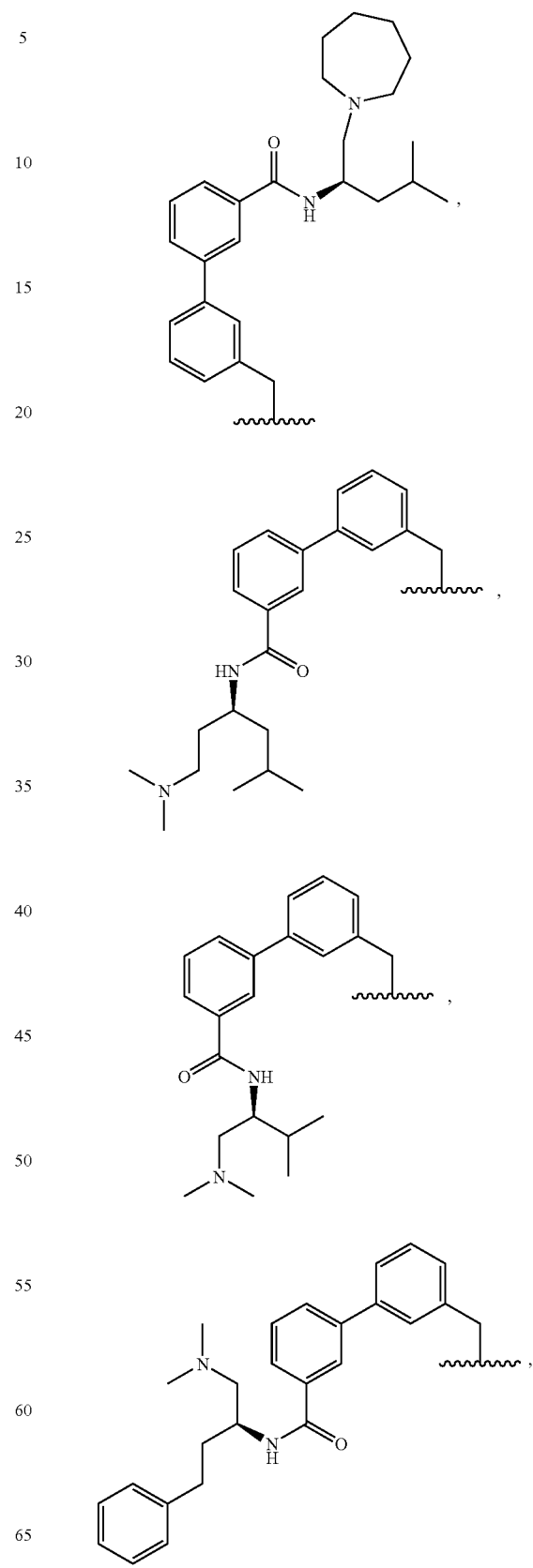

407
-continued
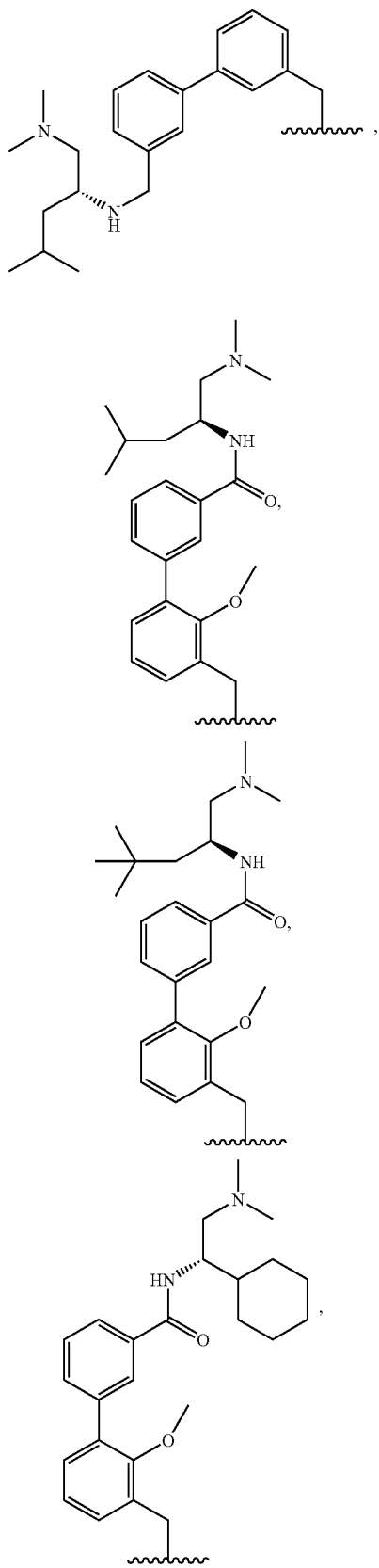
408
-continued
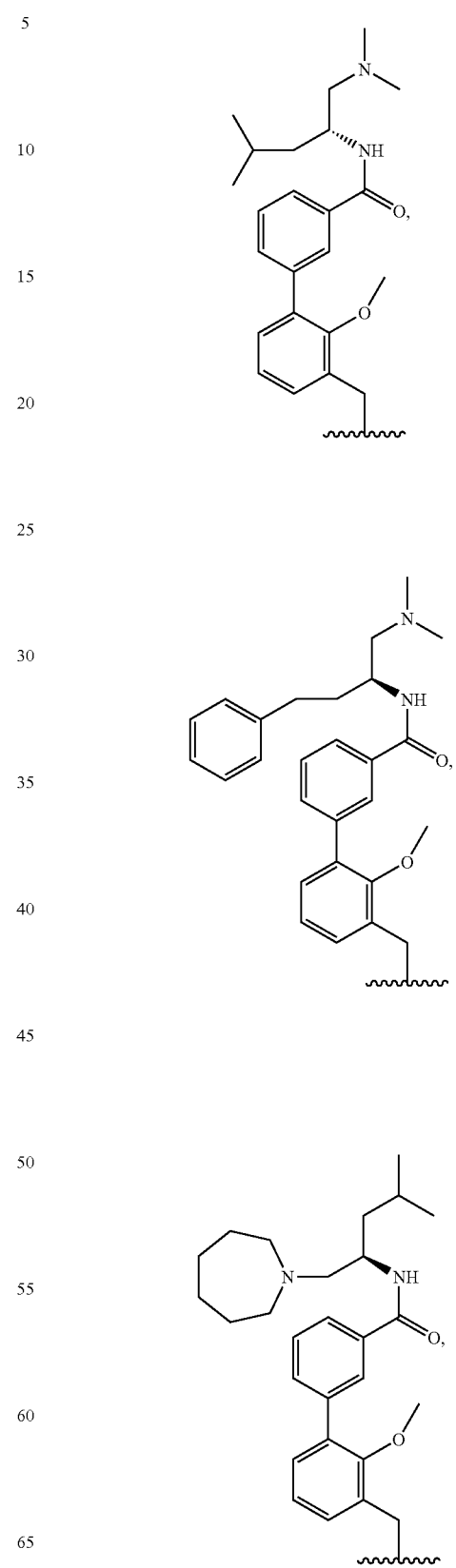

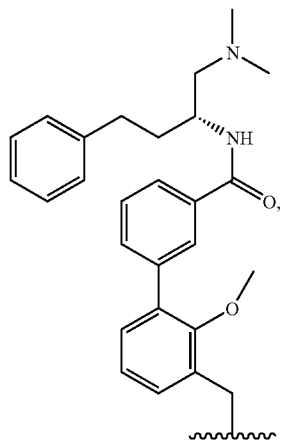
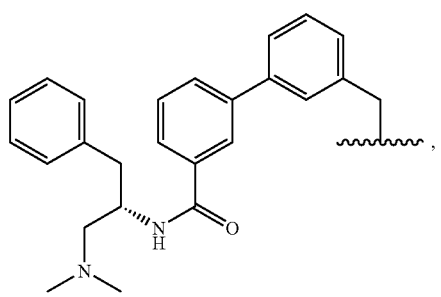
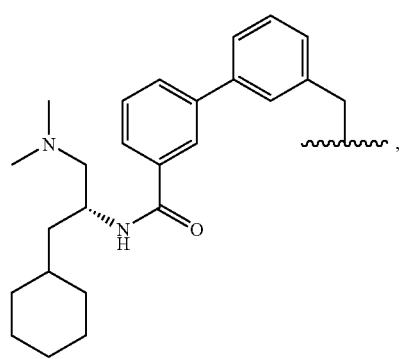
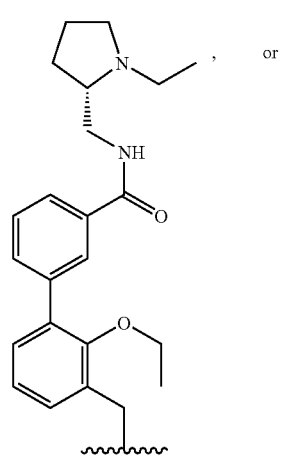
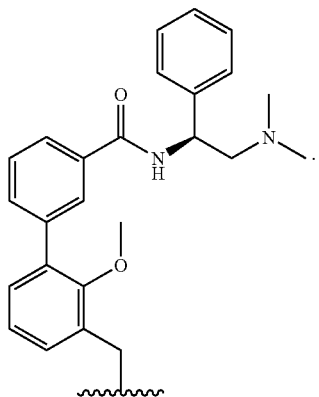
17. A compound selected from the group consisting of:
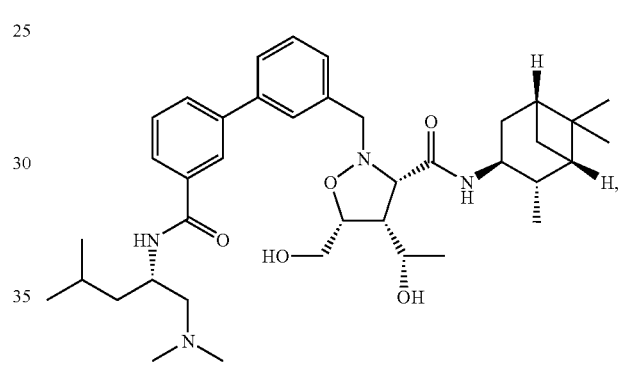
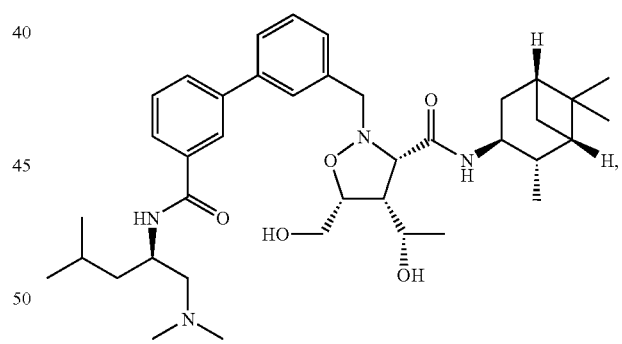
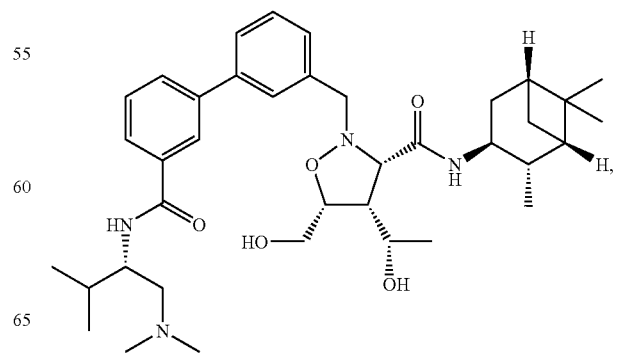

411 412
-continued -continued
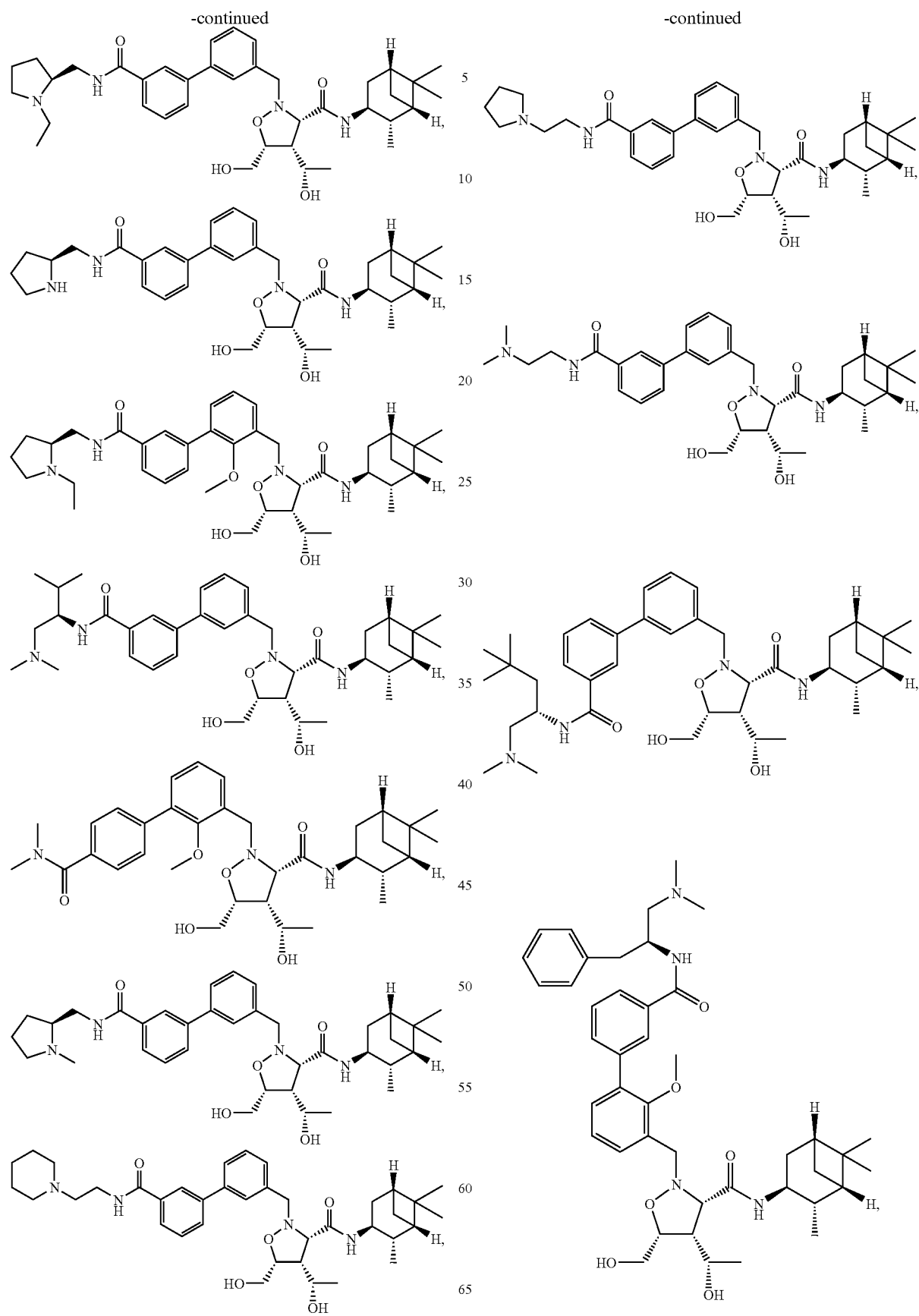

413
-continued
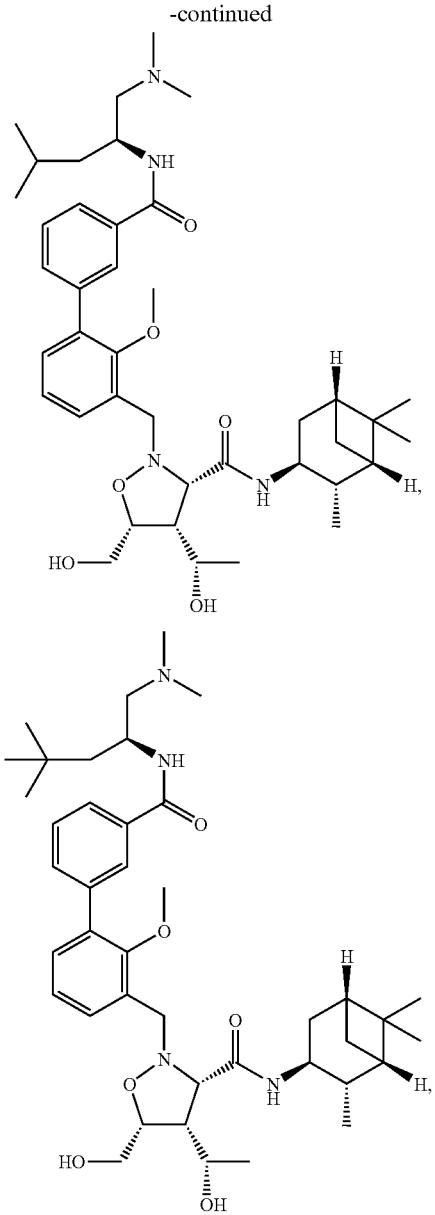
414
-continued
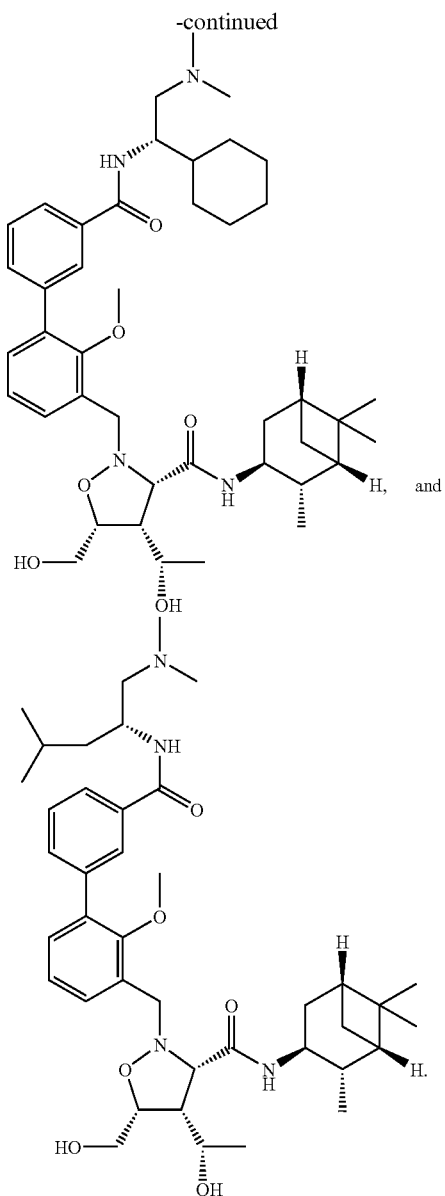 and
* * * * *